United States Patent
Lanter et al.

(10) Patent No.: US 11,230,526 B1
(45) Date of Patent: Jan. 25, 2022

(54) CYLCOALKENYL DERIVATIVES USEFUL AS AGONISTS OF THE GPR120 AND/OR GPR40 RECEPTORS

(71) Applicants: Janssen Pharmaceutica NV, Beerse (BE); James C. Lanter, Cambridge, MA (US)

(72) Inventors: James C. Lanter, Cambridge, MA (US); Mark J. Macielag, Gwynedd Valley, PA (US); Mark Wall, Lansdale, PA (US); Michael P. Winters, Morgantown, PA (US); Yue-Mei Zhang, Wellesley, MA (US); Zhihua Sui, Norristown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/977,828

(22) PCT Filed: Mar. 5, 2019

(86) PCT No.: PCT/IB2019/051779
§ 371 (c)(1),
(2) Date: Sep. 3, 2020

(87) PCT Pub. No.: WO2019/171277
PCT Pub. Date: Sep. 12, 2019

Related U.S. Application Data

(60) Provisional application No. 62/639,027, filed on Mar. 6, 2018.

(51) Int. Cl.
| | |
|---|---|
| *C07D 213/55* | (2006.01) |
| *C07C 255/46* | (2006.01) |
| *C07D 307/40* | (2006.01) |
| *C07C 57/46* | (2006.01) |
| *C07D 277/24* | (2006.01) |
| *C07C 57/38* | (2006.01) |

(52) U.S. Cl.
CPC ............ *C07D 213/55* (2013.01); *C07C 57/38* (2013.01); *C07C 57/46* (2013.01); *C07C 255/46* (2013.01); *C07D 277/24* (2013.01); *C07D 307/40* (2013.01)

(58) Field of Classification Search
CPC .. C07D 213/55; C07D 277/24; C07D 307/40; C07C 57/38; C07C 255/46; C07C 57/46
See application file for complete search history.

(56) References Cited

U.S. PATENT DOCUMENTS

| 4,939,171 A | 7/1990 | Moeller et al. |
|---|---|---|
| 7,005,538 B1 | 2/2006 | Malm et al. |
| 2017/0210731 A1* | 7/2017 | Kumar ................ C07D 213/30 |

FOREIGN PATENT DOCUMENTS

| CN | 104293877 A | 1/2015 |
|---|---|---|
| WO | WO 2016012965 A2 | 1/2016 |
| WO | WO 2019171277 A1 | 9/2019 |

OTHER PUBLICATIONS

International Search Report relating to International Patent Application No. PCT/IB2019/051779, filed Mar. 5, 2019. Date of Mailing of International Search Report: dated May 23, 2019.
Written Opinion of the International Searching Authority relating to International Patent Application No. PCT/IB2019/051779, filed Mar. 5, 2019. Date of Mailing of Written Opinion: dated May 23, 2019.
Brisco, et al., "The Orphan G Protein-coupled Receptor GPR40 Is Activated by Medium and Long Chain Fatty Acids.", *J. Biol. Chem.*, 2003, pp. 11303-11311, vol. 278(13).
Edfalk, et al., "GPR40 Is Expressed in Enteroendocrine Cells and Mediates Free Fatty Acid Stimulation of Incretin Secretion.", *Diabetes*, Sep. 2008, pp. 2280-2287, vol. 57.
Gardner et al., "3,7-Dicarbethoxy-5-hydroxytropolone. A Convenient Synthesis of Pimelic Acid.", *J. Am. Chem. Soc.*, Jul. 20, 1956, pp. 3425-3427, vol. 78.
Han, C., et al., "Negishi Coupling of Secondary Alkylzinc Halides with Aryl Bromides and Chlorides", *JACS*, 2009, pp. 7532, vol. 131(22).
Itoh, et al., "Free Fatty Acids Regulate Insulin Secretion From Pancreatic β Cells Through GPR40.", *Nature*, Mar. 2003, pp. 173-176, vol. 422.
Kotarsky, et al., "A human cell surface receptor activated by free fatty acids and thiazolidinedione drugs.", *Biochem. Biophys. Res. Commun.*, 2003, pp. 406-410, vol. 301.
Smith III, A.B., et al., "Preparation, reactivity, and spectral properties of 1,3-dioxin vinylogous esters: versatile beta.-ketovinyl cation equivalents", *JOC*, 1988, pp. 4314-4325, vol. 53(18).

* cited by examiner

*Primary Examiner* — Matthew P Coughlin

(57) ABSTRACT

The present invention is directed to cycloalkenyl derivatives, pharmaceutical compositions containing them and their use in the treatment of disorders and conditions modulated by the GPR120 and/or GPR40 receptors. More particularly, the compounds of the present invention are agonists of GPR120 and/or GPR40, useful in the treatment of, for example, obesity, Type II Diabetes Mellitus, dyslipidemia, etc.

25 Claims, No Drawings

CYLCOALKENYL DERIVATIVES USEFUL AS AGONISTS OF THE GPR120 AND/OR GPR40 RECEPTORS

CROSS-REFERENCE TO RELATED APPLICATIONS

This application is a U.S. national stage of PCT Application No. PCT/IB2019/051779, filed on Mar. 5, 2019, and claims the benefit of U.S. Provisional Application 62/639,027, filed on Mar. 6, 2018, which is incorporated by reference herein in its entirety.

FIELD OF THE INVENTION

The present invention is directed to cycloalkenyl derivatives, pharmaceutical compositions containing them and their use in the treatment of disorders and conditions modulated by the GPR120 and/or GPR40 receptors. More particularly, the compounds of the present invention are agonists of GPR120 and/or GPR40, useful in the treatment of, for example, obesity, Type II Diabetes Mellitus, dyslipidemia, etc.

BACKGROUND OF THE INVENTION

A diabetes mellitus epidemic is unfolding across the globe with the World Health Organization (WHO) reporting a worldwide prevalence of 177 million patients with diabetes. It is estimated that the incidence of all forms of diabetes totals approximately 2.8% of the world population. The number of newly diagnosed diabetic patients is increasing by 4-5% per year. The total number of people with diabetes worldwide is projected to rise to 366 million (4.4% prevalence) in 2030. Type 2 diabetes accounts for approximately 95% of all diabetes cases. Long-term complications of type 2 diabetes include atherosclerosis, heart disease, stroke, end-stage renal disease, retinopathy leading to blindness, nerve damage, sexual dysfunction, frequent infections, and difficult-to-treat foot ulcers, sometimes resulting in lower limb amputation. Diabetics are twice as likely to develop cardiovascular disease or have a stroke, 2 to 6 times more likely to have transient ischemic attacks, and 15 to 40 times more likely to require lower-limb amputation compared with the general population. The total estimated cost of diabetes in 2007 in the US was $174 billion, including $116 billion in medical expenditures. The largest components of medical expenditures attributed to diabetes are hospital inpatient care (50% of total cost), diabetes medication and supplies (12%), retail prescriptions to treat complications of diabetes (11%), and physician office visits (9%). This may be related to the lack of durable efficacy of current drug therapies for Type 2 diabetes (>50% Type 2 patients are not reaching the targeted blood glucose control with current oral medications after 5 years of treatment). There is a general consensus that a considerable need exists for improved awareness, diagnosis and new, more effective, drug therapies for diabetes.

Agents that reduce hepatic glucose production, the so-called biguanides, such as metformin or phenformin, are generally preferred as the first-line of treatment for newly-diagnosed patients. Glitazones, such as rosiglitazone and pioglitazone function as insulin sensitizers (i.e., enhance insulin action) through the activation of peroxisome proliferator-activated receptor-gamma. (PPAR-gamma). These agents can provide the benefit of enhanced insulin action in tissues such as muscle, liver and adipose, but their use is frequently accompanied by increased weight and edema. In addition, rosiglitazone has recently been linked to heart attacks and its use has subsequently been more restricted. The insulin secretagogue sulfonylureas (such as tolbutamide, chlorpropamide, glipizide or glyburide) enhance insulin secretion from functional beta cells and are often combined with biguanide or glitazone therapy. However, because their effects on stimulating insulin release are independent of glucose levels, the sulfonylureas bear the risk of inducing incidences of hypoglycemia. Weight gain is also a common side-effect from this compound class.

Dipeptidyl-peptidase-4 (DPP-4) inhibitors (the so-called, "gliptins" such as sitagliptin, saxagliptin, linagliptin, vildagliptin, anagliptin or alogliptin) inhibit the metabolic degradation of endogenous incretins and thereby provide indirect increases in insulin secretion in response to elevations in circulating glucose levels.

GLP-1 is secreted from specific cells in the colon according to a meal and is a key regulator of glucose homeostasis, linking the gut, brain and pancreas. GLP-1 potentiates insulin secretion, reduces glucagon secretion and preserves β-cell function whilst also improving satiety. Levels of post-prandial GLP-1 are reduced in type 2 diabetics and dramatically elevated according to gastric by-pass surgery, contributing to the amelioration of type 2 diabetes in these patients. Approaches that prolong the half-life of GLP-1 (JANUVIA (Merck), GALVUS (Novartis)) or activate the GLP-1 receptor (BYETTA (Amylin)) have been recently approved for use in type 2 diabetes.

Hyperinsulinemia in patients with type 2 diabetes mellitus results from peripheral insulin resistance, coupled with inadequate pancreatic insulin secretion and elevated glucagon levels. There is a strong correlation between obesity and peripheral insulin resistance and hyperinsulinemia. Accumulation of free fatty acids in insulin responsive tissues other than fat (i.e. muscle and liver) results in tissue insulin resistance. Additionally, free fatty acids have a direct effect on the pancreas and in the colon and further stimulate glucose-dependent insulin secretion and GLP-1 release with acute exposure whereas chronic exposure of free fatty acids impairs insulin secretion and becomes toxic to the β-cell. In the liver, hyperinsulinemia per se has been linked to exacerbating insulin resistance by increasing liver fatty acid accumulation and hepatic glucose output creating a vicious cycle of disease progression. Current therapeutic strategies only partially address the complex pathology of free fatty acids in the exacerbation of diabetes. Agents that target both liver and pancreas function, directly or indirectly via GLP-1 release, either individually or in combination with current treatment, could significantly improve blood glucose control while maintaining β-cell function. Agents that potentiate GLP-1 release also have the ability to reduce weight, providing additional benefits.

A decade ago, the discovery of the G-protein coupled receptor GPR40 as a fatty acid receptor specifically expressed in beta cells and which stimulates glucose-dependent insulin secretion, sparked interest in the pharmaceutical industry as a potential therapeutic target to enhance insulin secretion in type 2 diabetes. The recognition of GPR40 as a receptor whose activation enhances glucose-dependent insulin secretion has led to the search for selective agonists for this putative therapeutic target. GPR40, also known as free fatty acid receptor 1 (FFR1), is one of a family of G-protein coupled receptors that, through receptor deorphanization studies, was shown to be endogenously activated by medium- to long-chain saturated and unsaturated fatty acids (~$C_{12-20}$) (BRISCO, et al., *J. Biol. Chem.,* 2003, pp 11303-11311, Vol. 278; ITOH, et al., *Nature,* 2003, pp 173-176, Vol. 422: KOTARSKY, et al., *Biochem. Biophys. Res. Commun.*, 2003, pp 406-410, Vol. 301). In humans and rodents, although present in brain and enteroendocrine cells, its expression is particularly high in pancreatic beta cells and enteroendocrine cells in the gut. Operating primarily through GC signaling, GPR40 activation of the beta cell leads to an increase in intracellular calcium levels, which in the presence of glucose, ultimately results in augmented insulin secretion. In enteroendocrine cells, GPR40 activation by fatty acids leads to stimulation of incretin secretion (EDFALK, et al., *Diabetes*, 2008, pp 2280-2287, Vol. 57). Thus, in addition to directly promoting GSIS from islet beta cells, GPR40 activation in enteroendocrine cells provides an indirect means of stimulating GSIS through the actions of released incretins.

Because of the hyperglycemic dependency of GPR40-mediated effects on insulin secretion, activation (including selective activation) of this receptor provides a unique potential therapeutic mechanism by which to treat the diabetic state with minimal risk of hypoglycemic incidents. Given the relatively restricted tissue expression pattern of GPR40, selective GPR40 agonists may offer the additional advantage of providing an improved safety profile relative to the other therapeutic agents. Thus, GPR40 receptor agonists may provide a therapeutic benefit for the treatment of diabetes, particularly Type II Diabetes Mellitus, as well as related disorders and conditions such as obesity, impaired glucose tolerance, insulin resistance, metabolic syndrome (also known as Syndrome X), etc.

GPR120 is a seven transmembrane g-protein coupled receptor (GPCR) that is predominantly expressed in the intestine and adipose. GPR120 functions as a receptor for long chain free fatty acids (FFAs). Acute FFA stimulation of GPR120 in GLP-1 expressing cell-lines amplifies GLP-1 release. Administration of α-linolenic acid into the colon of mice increases GLP-1 and potentiates insulin release according to a glucose challenge. In contrast to agonists of GPR40, the existing literature suggests that a GPR120 agonist would potentiate insulin secretion and reduce glucagon indirectly via GLP-1 release. GPR120 is also expressed in adipose, with expression induced during differentiation. Inhibition of GPR120 expression in 3T3-L1 adipocytes has been shown to reduce adipocyte differentiation. The role of the receptor in the adipose or in the taste cells of the tongue where it has also been Measured: remains unclear.

GPR120 is a Gq coupled GPCR that acts a receptor for long chain fatty acids. It belongs to a family of lipid binding GPCRs that include GPR 40, 41, 43. Functionally, GPR120s closest homolog is GPR40. The cloned rat and mouse GPR120 receptors have been cloned and have >85% homology with the human receptor. GPR120 signals through Gq to elevate intracellular Ca+2 levels as well as activate MAP kinase signal transduction cascades. GPR120's activation of calcium flux and PKC activation is most likely how FFAs contribute to the release GLP-1 in the L-cell.

Although relatively little is known about GPR120 due to lack of potent, selective pharmacological tools or a documented metabolic phenotype of GPR120 knockout mice, the potential to elevate GLP-1 from a small-molecule perspective is attractive as a novel approach to unmet medical need in the treatment of type 2 diabetes mellitus and related disorders. The beneficial effects of elevating GLP-1 are already well validated in the clinic and in addition to improved glucose homeostasis, offer the potential of weight loss. Thus it is theorized that GPR120 agonists may be complementary to existing diabetes therapies that affect liver insulin sensitivity and those that preserve β-cell function.

KUMAR, S., et al., in PCT Patent Publication WO2016/012965 A2, published Jan. 28, 2016 describe substituted phenyl alkanoic acid compounds as GPR120 agonists and uses thereof.

MALM, J., et al., in U.S. Pat. No. 7,005,538 B1, Issued Feb. 28, 2006 describe thyroid receptor ligands, preferably antagonists, useful for the treatment of cardiac arrhythmias, thyrotoxicosis and subclinical hyperthyroidism.

MOELLER, H. M., et al., in U.S. Pat. No. 4,939,171, issued Jul. 3, 1990 describe alkyl and alkenyl aryl ether derivatives useful as sebosuppressive agents in cosmetic or pharmaceutical preparations for topical application to the hair and to the skin.

There remains a need for GPR120, GPR40 and dual GPR120/GPR40 agonists for the treatment of disorders including, but not limited to obesity, Type II Diabetes Mellitus, dyslipidemia, and the like.

SUMMARY OF THE INVENTION

The present invention is directed to compounds of formula (I)

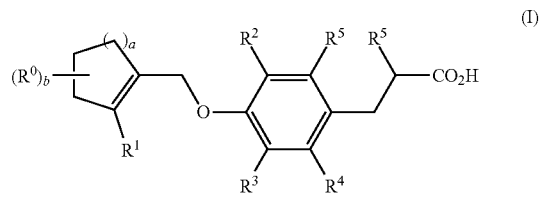

wherein
a is an integer from 1 to 3;
b is an integer from 0 to 2;
each $R^0$ is independently selected from the group consisting of halogen, oxo, hydroxy, cyano, $C_{1-4}$alkyl, fluorinated $C_{1-2}$alkyl, $C_{1-4}$alkoxy and fluorinated $C_{1-2}$alkoxy;
$R^1$ is selected from the group consisting of $C_{1-6}$alkyl, $C_{2-8}$alkynyl, $C_{3-6}$cycloalkyl, —($C_{1-2}$alkyl)-$C_{3-6}$cycloalkyl, $C_{5-6}$cycloalkenyl, bicyclo[3.1.0]hexy-2-yl, (1S,4S)-2-methyl-bicyclo[2.2.1]hept-2-yl, (1R,2R,4S)-bicyclo[2.2.1]heptan-2-yl, 2,2-difluoro-benzo[d][1,3]dioxol-4-yl, phenyl, —($C_{1-2}$alkyl)-phenyl, —C(=CH)-phenyl, —C(O)-phenyl, tetrahydropyranyl, furanyl, pyrimidinyl, pyridyl, thienyl, thiazolyl, —($C_{1-2}$alkyl)-thiazolyl, 3,6-dihydro-pyran-4-yl and 1-methyl-imidazol-4-yl;
wherein the $C_{3-6}$cycloalkyl or $C_{5-6}$cycloalkenyl, whether alone or as part of a substituent group is optionally substituted with one or more (preferably one to two) substituents independently selected from the group consisting of halogen, $C_{1-4}$alkyl and fluorinated $C_{1-2}$alkyl;
and wherein the phenyl, furanyl, pyrimidinyl, pyridyl, thienyl, thiazolyl, or 3,6-dihydro-pyran-4-yl, whether alone or as part of a substituent group is optionally substituted with one or more (preferably one to three) substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$alkyl), —SO$_2$—($C_{1-2}$alkyl), nitro, —NR$^A$R$^B$, —NH—C(O)—($C_{1-4}$alkyl) and phenyl; wherein R$^A$ and R$^B$ are each independently selected from the group consisting of hydrogen and $C_{1-4}$alkyl;
$R^2$ is selected from the group consisting of hydrogen, halogen, $C_{1-4}$alkyl, fluorinated $C_{1-2}$alkyl, —($C_{1-4}$alkyl)-S—($C_{1-2}$alkyl), —($C_{1-4}$alkyl)-SO—($C_{1-2}$alkyl) and —($C_{1-4}$alkyl)-SO$_2$—($C_{1-2}$alkyl);

R³ is selected from the group consisting of hydrogen, halogen, $C_{1-4}$alkyl and fluorinated $C_{1-2}$alkyl;

R⁴ is selected from the group consisting of hydrogen, halogen, $C_{1-4}$alkyl and fluorinated $C_{1-2}$alkyl;

R⁵ is selected from the group consisting of hydrogen, cyano, halogen, $C_{1-4}$alkyl, fluorinated $C_{1-2}$alkyl, vinyl, halogen substituted vinyl, ethynyl, hydroxy substituted $C_{1-2}$alkyl, $C_{1-4}$alkoxy, fluorinated $C_{1-2}$alkoxy, cyclopropyl, cyclopropyl-methyl- and phenyl;

alternatively, R² and R⁵ or R³ and R⁴ are taken together with the carbon atoms to which they are bound to form cyclopenten-1-yl;

provided that when a is 3, then at least one of R², R³ R⁴ or R⁵ is other than hydrogen;

R⁶ is selected from the group consisting of hydrogen and methyl;

and isotopologues and pharmaceutically acceptable salts thereof.

The present invention is further directed to processes for the preparation of the compounds of formula (I). The present invention is further directed to a compound prepared according to any of the process(es) described herein.

Illustrative of the invention is a pharmaceutical composition comprising a pharmaceutically acceptable carrier and the compound prepared according to the process described herein. An illustration of the invention is a pharmaceutical composition made by mixing the compound prepared according to the process described herein and a pharmaceutically acceptable carrier. Illustrating the invention is a process for making a pharmaceutical composition comprising mixing the compound prepared according to the process described herein and a pharmaceutically acceptable carrier.

Exemplifying the invention are methods of treating a disorder modulated by GPR120 such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD) or liver fibrosis, comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder modulated by GPR120 such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD) or liver fibrosis.

In another embodiment, the present invention is directed to a composition comprising a compound of formula (I) for the treatment of a disorder modulated by GPR120 such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD) or liver fibrosis.

Another example of the invention is the use of any of the compounds described herein in the preparation of a medicament for treating: (a) obesity, (b) obesity induced inflammation, (c) impaired glucose tolerance, (d) elevated fasting glucose, (e) insulin resistance, (f) hyperglycemia, (g) hyperinsulinemia, (h) Type II Diabetes Mellitus, (j) metabolic syndrome (also known as Syndrome X), (j) gestational diabetes, (k) diabetic retinopathy, (l) kidney disease, (m) ketoacidosis, (n) diabetic nephropathy, (o) dyslipidemia, (p) elevated LDL, (q) hyperlipidemia, (r) hyperlipoproteinemia, (s) hypertriglyceridemia (i.e. elevated triglycerides), (t) non-alcoholic steatohepatitis (NASH), (u) non-alcoholic fatty liver disease (NAFLD) and (v) liver fibrosis, in a subject in need thereof.

In another example, the present invention is directed to a compound as described herein for use in a methods for treating a disorder selected from the group consisting of obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD) and liver fibrosis, in a subject in need thereof.

Exemplifying the invention are methods of treating a disorder modulated by GPR40 such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis or cardiovascular disorders (including but not limited to hypertension, atherosclerosis, thrombotic disorders, and cardiac fibrosis), comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder modulated by GPR40 such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis or cardiovascular disorders (including but not limited to hypertension, atherosclerosis, thrombotic disorders, and cardiac fibrosis).

In another embodiment, the present invention is directed to a composition comprising a compound of formula (I) for the treatment of a disorder modulated by GPR40 such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis or cardiovascular disorders (including but not limited to hypertension, atherosclerosis, thrombotic disorders, and cardiac fibrosis).

Another example of the invention is the use of any of the compounds described herein in the preparation of a medicament for treating: (a) obesity, (b) obesity induced inflammation, (c) impaired glucose tolerance, (d) elevated fasting glucose, (e) insulin resistance, (f) hyperglycemia, (g) hyperinsulinemia, (h) Type II Diabetes Mellitus, (i) metabolic syndrome (also known as Syndrome X), (j) gestational diabetes, (k) diabetic retinopathy, (l) kidney disease, (m) ketoacidosis, (n) diabetic nephropathy, (o) dyslipidemia, (p) elevated LDL, (q) hyperlipidemia, (r) hyperlipoproteinemia, (s) hypertriglyceridemia (i.e. elevated triglycerides), (t) non-alcoholic steatohepatitis (NASH), (u) non-alcoholic fatty liver disease (NAFLD), (v) liver fibrosis and (w) cardiovascular disorders (including but not limited to hypertension, atherosclerosis, thrombotic disorders, and cardiac fibrosis), in a subject in need thereof.

In another example, the present invention is directed to a compound as described herein for use in a methods for treating a disorder selected from the group consisting of obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis and cardiovascular disorders (including but not limited to hypertension, atherosclerosis, thrombotic disorders, and cardiac fibrosis), in a subject in need thereof.

Exemplifying the invention are methods of treating a disorder which responds to dual agonism of the GPR120 and GP40 receptors such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis or cardiovascular disorders (including but not limited to hypertension, atherosclerosis, thrombotic disorders, and cardiac fibrosis), comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder which responds to dual agonism of the GPR120 and GP40 receptors such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis or cardiovascular disorders (including but not limited to hypertension, atherosclerosis, thrombotic disorders, and cardiac fibrosis).

In another embodiment, the present invention is directed to a composition comprising a compound of formula (I) for the treatment of a disorder which responds to dual agonism of the GPR120 and GP40 receptors such as obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis or cardiovascular disorders (including but not limited to hypertension, atherosclerosis, thrombotic disorders, and cardiac fibrosis).

Another example of the invention is the use of any of the compounds described herein in the preparation of a medicament for treating: (a) obesity, (b) obesity induced inflammation, (c) impaired glucose tolerance, (d) elevated fasting glucose, (e) insulin resistance, (f) hyperglycemia, (g) hyperinsulinemia, (h) Type II Diabetes Mellitus, (i) metabolic syndrome (also known as Syndrome X), (j) gestational diabetes, (k) diabetic retinopathy, (l) kidney disease, (m) ketoacidosis, (n) diabetic nephropathy, (o) dyslipidemia, (p) elevated LDL, (q) hyperlipidemia, (r) hyperlipoproteinemia, (s) hypertriglyceridemia (i.e. elevated triglycerides), (u) non-alcoholic steatohepatitis (NASH), (u) non-alcoholic fatty liver disease (NAFLD), (v) liver fibrosis and (w) cardiovascular disorders (including but not limited to hypertension, atherosclerosis, thrombotic disorders, and cardiac fibrosis), in a subject in need thereof.

In another example, the present invention is directed to a compound as described herein for use in a methods for treating a disorder selected from the group consisting of obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis and cardiovascular disorders (including but not limited to hypertension, atherosclerosis, thrombotic disorders, and cardiac fibrosis), in a subject in need thereof.

DETAILED DESCRIPTION OF THE INVENTION

The present invention is directed to compounds of formula (I)

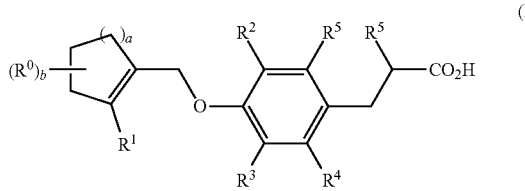

(I)

wherein a, b, $R^0$, $R^1$, $R^2$, $R^3$, $R^4$, $R^5$ and $R^6$ are as herein defined. The compounds of the present invention are agonists of the GPR120 and/or GPR40 receptors, useful in the treatment of disorders and diseases which are modulated by said receptors, including for example, obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis and cardiovascular disorders (including but not limited to hypertension, atherosclerosis, thrombotic disorders, and cardiac fibrosis). Preferably, the disorder or disease is selected from the group consisting of obesity, impaired glucose tolerance, elevated fasting glucose, insulin resistance, hyperglycemia, hyperinsulinemia, Type II Diabetes Mellitus, metabolic syndrome (also known as Syndrome X), diabetic retinopathy, diabetic nephropathy, dyslipidemia, elevated LDL, hyperlipidemia, hypertriglyceridemia (i.e. elevated triglycerides), non-alcoholic steatohepatitis (NASH) and non-alcoholic fatty liver disease (NAFLD). More preferably, the disorder or disease is selected from the group consisting of obesity, Type II diabetes, metabolic syndrome (also known as Syndrome X), dyslipidemia. hypertriglyceridemia (i.e. elevated triglycerides), non-alcoholic steatohepatitis (NASH) and non-alcoholic fatty liver disease (NAFLD). More preferably, the disorder or disease is selected from the group consisting of obesity, Type II diabetes, metabolic syndrome (also known as Syndrome X), dyslipidemia and hypertriglyceridemia.

In an embodiment, the present invention is directed to compounds of formula (A)

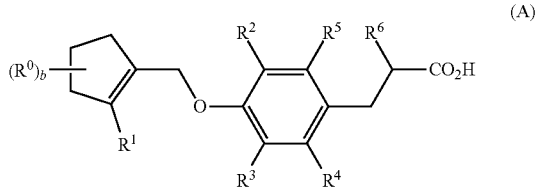

(A)

(compounds of formula (I) wherein a is 1) and isotopologues and pharmaceutically acceptable salts thereof.

In another embodiment, the present invention is directed to compounds of formula (B)

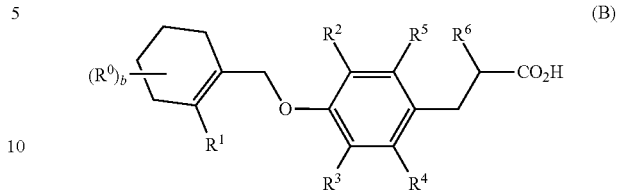

(B)

(compounds of formula (I) wherein a is 2) and isotopologues and pharmaceutically acceptable salts thereof.

In another embodiment, the present invention is directed to compounds of formula (C)

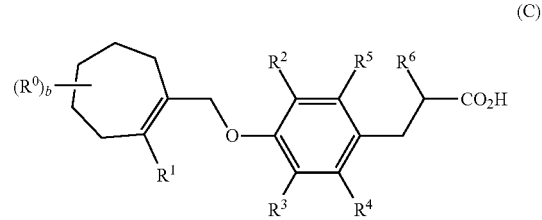

(C)

(compounds of formula (I) wherein a is 3) and isotopologues and pharmaceutically acceptable salts thereof.

In certain embodiments, the present invention is directed to compounds of formula (I) wherein a is an integer from 1 to 3. In certain embodiments, the present invention is directed to compounds of formula (I) wherein a is an integer from 1 to 2. In certain embodiments, the present invention is directed to compounds of formula (I) wherein a is 1. In certain embodiments, the present invention is directed to compounds of formula (I) wherein a is 2. In certain embodiments, the present invention is directed to compounds of formula (I) wherein a is 3.

In certain embodiments, the present invention is directed to compounds of formula (I) wherein b is an integer from 0 to 2. In certain embodiments, the present invention is directed to compounds of formula (I) wherein b is an integer from 1 to 2. In certain embodiments, the present invention is directed to compounds of formula (I) wherein b is 0 or 2. In certain embodiments, the present invention is directed to compounds of formula (I) wherein b is 0. In certain embodiments, the present invention is directed to compounds of formula (I) wherein b is 1. In certain embodiments, the present invention is directed to compounds of formula (I) wherein b is 2. In certain embodiments, the present invention is directed to compounds of formula (I) wherein b is 2 and the two $R^0$ groups are the same.

In certain embodiments, the present invention is directed to compounds of formula (I) wherein each $R^0$ is independently selected from the group consisting of halogen, oxo, hydroxy, cyano, $C_{1-4}$alkyl, fluorinated $C_{1-2}$alkyl, $C_{1-4}$ alkoxy and fluorinated $C_{1-2}$alkoxy.

In certain embodiments, the present invention is directed to compounds of formula (I) wherein each $R^0$ is independently selected from the group consisting of halogen, hydroxy, oxo, cyano, $C_{1-4}$alkyl, fluorinated $C_{1-2}$alkyl and $C_{1-4}$alkoxy.

In certain embodiments, the present invention is directed to compounds of formula (I) wherein each $R^0$ is independently selected from the group consisting of 4-fluoro, 5-fluoro, 4-chloro, 5-hydroxy, 5-oxo, 3-methyl, 5-methyl, 3-ethyl, 4-ethyl, 5-ethyl, 3-isopropyl, 4-isopropyl, 5-isopropyl, 5-trifluoromethyl, 4-methoxy, 5-methoxy and 4-cyano.

In certain embodiments, the present invention is directed to compounds of formula (I) wherein each $R^o$ is independently selected from the group consisting of 4-fluoro, 4-chloro, 5-hydroxy, 5-oxo, 3-methyl, 5-methyl, 3-ethyl, 3-isopropyl, 5-trifluoromethyl, 4-methoxy and 4-cyano. In certain embodiments, the present invention is directed to compounds of formula (I) wherein each $R^o$ is independently selected from the group consisting of 4-fluoro, 5-fluoro, 5-methyl, 3-ethyl, 4-ethyl, 5-ethyl, 3-isopropyl, 4-isopropyl, 5-isopropyl, and 5-methoxy. In certain embodiments, the present invention is directed to compounds of formula (I) wherein each $R^o$ is independently selected from the group consisting of 4-fluoro, 5-fluoro, 4-chloro, 3-methyl, 5-methyl, 5-ethyl, 5-isopropyl, 5-trifluoromethyl, 4-methoxy, 5-methoxy and 4-cyano. In certain embodiments, the present invention is directed to compounds of formula (I) wherein each $R^o$ is independently selected from the group consisting of 4-fluoro, 5-fluoro, 4-chloro, 5-methyl, 5-ethyl, 4-methoxy and 5-methoxy.

In certain embodiments, the present invention is directed to compounds of formula (I) wherein each $R^o$ is independently selected from the group consisting of 4-fluoro, 5-fluoro and 5-methyl. In certain embodiments, the present invention is directed to compounds of formula (I) wherein each $R^o$ is independently selected from the group consisting of 4-fluoro, 5-fluoro and 4-methoxy. In certain embodiments, the present invention is directed to compounds of formula (I) wherein each $R^o$ is independently selected from the group consisting of 4-fluoro and 5-fluoro. In certain embodiments, the present invention is directed to compounds of formula (I) wherein the two $R^o$ groups are the same and are selected from the group consisting of 4-fluoro and 5-fluoro. In certain embodiments, the present invention is directed to compounds of formula (I) wherein each $R^o$ is 4-fluoro. In certain embodiments, the present invention is directed to compounds of formula (I) wherein each $R^o$ is 5-methyl.

In certain embodiments, the present invention is directed to compounds of formula (I) wherein $R^1$ is selected from the group consisting of $C_{1-6}$alkyl, $C_{2-6}$alkynyl, $C_{3-6}$cycloalkyl, —($C_{1-2}$alkyl)-$C_{3-6}$cycloalkyl, $C_{5-6}$cycloalkenyl, bicyclo[3.1.0]hexy-2-yl, (1 S,4S)-2-methyl-bicyclo[2.2.1]hept-2-yl, (1R,2R,4S)-bicyclo[2.2.1]heptan-2-yl, phenyl, —($C_{1-2}$alkyl)-phenyl, —C(=CH)-phenyl, —C(O)— phenyl, tetrahydropyran-4-yl, furanyl, pyrimidinyl, pyridyl, thienyl, thiazolyl, —($C_{1-2}$ alkyl)-thiazolyl, 3,6-dihydro-pyran-4-yl and 1-methyl-imidazol-4-yl; wherein the $C_{3-6}$cycloalkyl or $C_{5-6}$ cycloalkenyl, whether alone or as part of a substituent group is optionally substituted with one to two substituents independently selected from the group consisting of halogen, $C_{1-2}$alkyl and fluorinated $C_{1-2}$ alkyl; and wherein the phenyl, furanyl, pyrimidinyl, pyridyl, thienyl, thiazolyl, or 3,6-dihydro-pyran-4-yl, whether alone or as part of a substituent group is optionally substituted with one to three substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$alkyl), —SO$_2$—($C_{1-2}$alkyl), nitro, —NR$^A$R$^B$, —NH—C(O)—($C_{1-4}$alkyl) and phenyl; wherein R$^A$ and R$^B$ are each independently selected from the group consisting of hydrogen and $C_{1-2}$ alkyl.

In certain embodiments, the present invention is directed to compounds of formula (I) wherein $R^1$ is selected from the group consisting of $C_{1-6}$alkyl, $C_{2-6}$alkynyl, $C_{3-6}$cycloalkyl, —($C_{1-2}$alkyl)-$C_{3-6}$cycloalkyl, $C_{5-6}$cycloalkenyl, bicyclo[3.1.0]hex-2-yl, (1R,2R,4S)-bicyclo[2.2.1]heptan-2-yl, (1 S,4S)-2-methyl-bicyclo[2.2.21]hept-2-yl, phenyl, —($C_{1-2}$alkyl)-phenyl, —C(O)-phenyl, pyridyl, pyrimidinyl, furanyl, thienyl, thiazolyl, —($C_{1-2}$alkyl)-thiazolyl, 1-methyl-imidazol-4-yl, 3,6-dihydro-pyran-4-yl and tetrahydro-pyran-4-yl; wherein the $C_{3-6}$cycloalkyl or $C_{5-6}$cycloalkenyl is optionally substituted with one to two substituents independently selected from the group consisting of halogen and $C_{1-2}$alkyl; wherein the phenyl, pyridyl, furanyl, thienyl or thiazolyl, whether alone or as part of a substituent group is optionally substituted with one to three substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$alkyl), —SO$_2$—($C_{1-2}$alkyl), cyano, nitro, —NR$^A$R$^B$, —NH—C(O)—($C_{1-4}$alkyl) and phenyl; wherein R$^A$ and R$^B$ are each independently selected from the group consisting of hydrogen and $C_{1-2}$alkyl.

In certain embodiments, the present invention is directed to compounds of formula (I) wherein $R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, n-pentyn-1-yl, cyclopropyl, cyclobutyl, 1-fluoro-cyclobut-1-yl, cyclopentyl, cyclopentyl-methyl-, cyclohexyl, cyclohexyl-methyl-, bicyclo[3.1.0]hex-2-yl, (1R,2R,4S)-bicyclo[2.2.1]heptan-2-yl, (1 S,4S)-2-methyl-bicyclo[2.2.21]hept-2-yl, cyclopenten-3-yl, cyclohex-1-en-1-yl, 4,4-difluoro-cyclohex-1-yl, phenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 2-iodophenyl, 4-iodophenyl, 2-methylphenyl, 3-methylphenyl, 4-methylphenyl, 4-ethylphenyl, 4-isopropyl-phenyl, 4-n-propyl-phenyl, 4-isopropyl-phenyl, 4-trifluoromethyl-phenyl, 3-methoxyphenyl, 4-methoxyphenyl, 4-ethoxyphenyl, 4-trifluoromethoxy-phenyl, 2,4-difluorophenyl, 3,4-difluorophenyl, 2,4-dichlorophenyl, 3,4-dichlorophenyl, 3,5-dichlorophenyl, 2-fluoro-4-chloro-phenyl, 2-fluoro-4-methyl-phenyl, 2-fluoro-5-chloro-phenyl, 2-fluoro-5-methyl-phenyl, 3-fluoro-4-chloro-phenyl, 3-fluoro-4-methyl-phenyl, 3-fluoro-5-methoxy-phenyl, 2-methyl-4-chloro-phenyl, 2-methyl-4-methoxy-phenyl, 2,4-dimethylphenyl, 3,4-dimethylphenyl, 2-isopropyl-4-methyl-phenyl, 2-methoxy-4-methyl-phenyl, 3-methoxy-4-methyl-phenyl, 2-hydroxy-4-methyl-phenyl, 3-hydroxy-4-methyl-phenyl, 4-cyanophenyl, 3-nitro-4-methyl-phenyl, 3-amino-4-methyl-phenyl, 3-(dimethylamino)-phenyl, 4-dimethylamino-phenyl, 4-(methyl-thio)-phenyl, 4-(methyl-sulfinyl)-phenyl, 4-(methyl-sulfonyl)-phenyl, 4-(methyl-carbonyl-amino)-phenyl, 2-phenyl-4-methyl-phenyl, 3-phenyl-4-methyl-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, phenyl-carbonyl-, pyrid-2-yl, pyrid-3-yl, pyrid-4-yl, 6-chloro-pyrid-3-yl, 6-methyl-pyrid-3-yl, 6-methoxy-pyrid-3-yl, 6-ethoxy-pyrid-3-yl, 5-fluoro-6-methoxy-pyrid-3-yl, pyrimidin-2-yl, furan-2-yl, 5-methyl-furan-2-yl, thien-2-yl, thien-3-yl, 5-chloro-thien-2-yl, 5-cyano-thien-2-yl, 5-methyl-thien-2-yl, thiazol-2-yl, thiazol-5-yl, 2-methyl-thiazol-5-yl, thiazol-2-yl-methyl-, thiazol-5-yl-methyl-, 1-methyl-imidazol-4-yl, 3,6-dihydro-pyran-4-yl and tetrahydro-pyran-4-yl.

In certain embodiments, the present invention is directed to compounds of formula (I) wherein $R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, n-pentyn-1-yl, cyclopropyl, cyclobutyl, 1-fluoro-cyclobut-1-yl, cyclopentyl, cyclopentyl-methyl-, cyclohexyl-methyl-, bicyclo[3.1.0]hex-2-yl, (1S,4S)-2- methyl-bicyclo[2.2.21]hept-2-yl, cyclopenten-3-yl, cyclohex-1-en-1-yl, 4,4-difluoro-cyclohex-1-yl, phenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 4-iodophenyl, 2-methylphenyl, 3-methylphenyl, 4-methylphenyl, 4-ethylphenyl, 4-isopropyl-phenyl, 4-n-propyl-phenyl, 4-trifluoromethyl-phenyl, 3-methoxyphenyl, 4-methoxyphenyl, 4-ethoxyphenyl, 4-trifluoromethoxyphenyl, 2,4-difluorophenyl, 3,4-difluorophenyl, 2,4-dichlorophenyl, 3,4-dichlorophenyl, 3,5-dichlorophenyl, 2-fluoro-4-chloro-phenyl, 2-fluoro-4-methyl-phenyl, 2-fluoro-5-chloro-phenyl, 2-fluoro-5-methyl-phenyl, 3-fluoro-4-chloro-phenyl, 3-fluoro-4-methyl-phenyl, 3-fluoro-5-methoxy-phenyl, 2-methyl-4-chloro-phenyl, 2-methyl-4-methoxy-phenyl, 2,4-dimethylphenyl, 3,4-dimethylphenyl, 2-isopropyl-4-methyl-phenyl, 2-methoxy-4-methyl-phenyl, 3-methoxy-4-methyl-phenyl, 2-hydroxy-4-methyl-phenyl, 3-hydroxy-4-methyl-phenyl, 4-cyanophenyl, 3-nitro-4-methyl-phenyl, 3-amino-4-methyl-phenyl, 3-(dimethylamino)-phenyl, 4-(methyl-thio)-phenyl, 4-(methyl-sulfinyl)-phenyl, 4-(methyl-sulfonyl)-phenyl, 4-(methyl-carbonyl-amino)-phenyl, 2-phenyl-4-methyl-phenyl, 3-phenyl-4-methyl-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, phenyl-carbonyl-, pyrid-2-yl, pyrid-3-yl, pyrid-4-yl, 6-chloro-pyrid-3-yl, 6-methyl-pyrid-3-yl, 6-methoxy-pyrid-3-yl, 6-ethoxy-pyrid-3-yl, 5-fluoro-6-methoxy-pyrid-3-yl, pyrimidin-2-yl, furan-2-yl, 5-methyl-furan-2-yl, thien-2-yl, thien-3-yl, thiazol-2-yl, thiazol-5-yl, 2-methyl-thiazol-5-yl, thiazol-2-yl-methyl-, 3,6-dihydro-pyran-4-yl and tetrahydro-pyran-4-yl.

In certain embodiments, the present invention is directed to compounds of formula (I) wherein $R^1$ is selected from the group consisting of n-propyl, isopropyl, n-butyl, isobutyl, cyclobutyl, cyclopentyl, cyclohexyl, (1R,2R,4S)-bicyclo[2.2.1]heptan-2-yl, phenyl, 4-cyanophenyl, 4-fluorophenyl, 2-chlorophenyl, 3-chlorophenyl, 4-chlorophenyl, 4-bromophenyl, 2-iodophenyl, 2-methylphenyl, 4-methylphenyl, 4-n-propy-phenyl, 4-isopropyl-phenyl, 4-trifluoromethyl-phenyl, 4-ethoxyphenyl, 4-trifluoromethoxy-phenyl, 2,4-difluorophenyl, 3,4-difluorophenyl, 3-fluoro-4-chloro-phenyl, 3-fluoro-4-methyl-phenyl, 4-(methyl-thio)-phenyl, 4-(methyl-sulfinyl)-phenyl, 4-(methyl-sulfonyl)-phenyl, 4-dimethylamino-phenyl, 4-(methyl-carbonyl-amino)-phenyl, benzyl, pyrid-2-yl, pyrid-4-yl, 6-methyl-pyrid-3-yl, pyrimidin-2-yl, furan-2-yl, thien-2-yl, 5-chloro-thien-2-yl, 5-cyano-thien-2-yl, 5-methyl-thien-2-yl, thiazol-5-yl, 2-methyl-thiazol-5-yl, 1-methyl-imidazol-4-yl and thiazol-5-yl-methyl-.

In certain embodiments, the present invention is directed to compounds of formula (I) wherein $R^1$ is selected from the group consisting of n-butyl, isopropyl, cyclobutyl, cyclopentyl, cyclopentyl-methyl-, bicyclo[3.1.0]hex-2-yl, cyclopenten-3-yl, phenyl, 2-fluorophenyl, 3-fluorophenyl, 4-fluorophenyl, 2-chlorophenyl, 3-chlorophenyl, 4-chlorophenyl, 4-bromophenyl, 4-iodophenyl, 4-methylphenyl, 4-ethylphenyl, 4-trifluoromethyl-phenyl, 4-methoxyphenyl, 2,4-difluorophenyl, 3,4-difluorophenyl, 3,4-dichlorophenyl, 2-fluoro-4-chloro-phenyl, 2-fluoro-4-methyl-phenyl, 2-fluoro-5-methyl-phenyl, 3-fluoro-4-chloro-phenyl, 3-fluoro-4-methyl-phenyl, 3-amino-4-methyl-phenyl, 4-dimethylamino-phenyl, 4-(methyl-thio)-phenyl, benzyl, 6-chloro-pyrid-3-yl, 6-methyl-pyrid-3-yl, 6-methoxy-pyrid-3-yl, 5-fluoro-6-methoxy-pyrid-3-yl, furan-2-yl, 5-methyl-furan-2-yl, thien-2-yl, 5-chloro-thien-2-yl, 5-cyano-thien-2-yl, 5-methyl-thien-2-yl, thiazol-2-yl, thiazol-5-yl, 2-methyl-thiazol-5-yl, and 3,6-dihydro-pyran-4-yl.

In certain embodiments, the present invention is directed to compounds of formula (I) wherein $R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, cyclobutyl, 1-fluoro-cyclobut-1-yl, cyclopentyl, cyclopentyl-methyl-, cyclohexyl, cyclohexyl-methyl-, bicyclo[3.1.0]hex-2-yl, (1S,4S)-2-methyl-bicyclo[2.2.21]hept-2-yl, cyclopenten-3-yl, cyclohex-1-en-1-yl, 4,4-difluoro-cyclohex-1-yl, 4-fluorophenyl, 4-chlorophenyl, 4-bromophenyl, 2-fluoro-5-chloro-phenyl, 2-fluoro-5-methyl-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, thiazol-2-yl-methyl- and tetrahydro-pyran-4-yl.

In certain embodiments, the present invention is directed to compounds of formula (I) wherein $R^1$ is selected from the group consisting of cyclopentyl, cyclopentyl-methyl-, cyclopenten-3-yl, phenyl, 2-fluorophenyl, 3-fluorophenyl, 4-fluorophenyl, 3-chlorophenyl, 4-chlorophenyl, 4-bromophenyl, 4-iodophenyl, 4-methylphenyl, 4-ethylphenyl, 2,4-difluorophenyl, 3,4-difluorophenyl, 2-fluoro-4-methyl-phenyl, 3-fluoro-4-chloro-phenyl, 3-fluoro-4-methyl-phenyl, 4-dimethylamino-phenyl, 4-(methyl-thio)-phenyl, benzyl, 6-methoxy-pyrid-3-yl, 5-fluoro-6-methoxy-pyrid-3-yl, furan-2-yl, thien-2-yl, 5-chloro-thien-2-yl, 5-methyl-thien-2-yl and 2-methyl-thiazol-5-yl.

In certain embodiments, the present invention is directed to compounds of formula (I) wherein $R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, cyclobutyl, 1-fluoro-cyclobut-1-yl, cyclopentyl, cyclopentyl-methyl-, cyclohexyl-methyl-, bicyclo[3.1.0]hex-2-yl, (1S,4S)-2-methyl-bicyclo[2.2.21]hept-2-yl, cyclopenten-3-yl, 4,4-difluoro-cyclohex-1-yl, 4-chlorophenyl, 2-fluoro-5-chloro-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, thiazol-2-yl-methyl- and tetrahydro-pyran-4-yl. In certain embodiments, the present invention is directed to compounds of formula (I) wherein $R^1$ is selected from the group consisting of cyclopentyl, phenyl, 2-fluorophenyl, 3-fluorophenyl, 4-fluorophenyl, 4-chlorophenyl, 4-bromophenyl, 4-iodophenyl, 4-methylphenyl, 4-ethylphenyl, 2,4-difluorophenyl, 3,4-difluorophenyl, 3-fluoro-4-chloro-phenyl, 3-fluoro-4-methyl-phenyl, 6-methoxy-pyrid-3-yl, 5-fluoro-6-methoxy-pyrid-3-yl, thien-2-yl, 5-chloro-thien-2-yl and 5-methyl-thien-2-yl.

In certain embodiments, the present invention is directed to compounds of formula (I) wherein $R^1$ is selected from the group consisting of n-propyl, isopropyl, 1-methyl-n-propyl, 2,2-dimethyl-n-propyl, isobutyl, n-pent-3-yl, cyclobutyl, 1-fluoro-cyclobut-1-yl, cyclopentyl, cyclopentyl-methyl-, cyclohexyl-methyl-, bicyclo[3.1.0]hex-2-yl, (1S,4S)-2-methyl-bicyclo[2.2.21]hept-2-yl, cyclopenten-3-yl, 4,4-difluoro-cyclohex-1-yl, benzyl, 4-fluoro-benzyl, 4-chloro-benzyl and 4-methyl-benzyl.

In certain embodiments, the present invention is directed to compounds of formula (I) wherein $R^1$ is selected from the group consisting of cyclopentyl, phenyl, 3-fluorophenyl, 4-fluorophenyl, 4-chlorophenyl, 4-bromophenyl, 4-iodophenyl, 4-methylphenyl, 4-ethylphenyl, 2,4-difluorophenyl, 3,4-difluorophenyl, 3-fluoro-4-chloro-phenyl and 3-fluoro-4-methyl-phenyl. In certain embodiments, the present invention is directed to compounds of formula (I) wherein $R^1$ is selected from the group consisting of isopropyl, isobutyl, cyclobutyl, cyclopentyl, cyclopentyl-methyl-, bicyclo[3.1.0]hex-2-yl, (1S,4S)-2-methyl-bicyclo[2.2.21]hept-2-yl, cyclopenten-3-yl and 4-fluoro-benzyl. In certain embodiments, the present invention is directed to compounds of formula (I) wherein $R^1$ is selected from the group consisting of cyclopentyl and 4-chlorophenyl.

In certain embodiments, the present invention is directed to compounds of formula (I) wherein $R^2$ is selected from the group consisting of hydrogen, halogen, $C_{1-4}$alkyl, fluorinated $C_{1-2}$alkyl, —($C_{1-4}$alkyl)-S—($C_{1-2}$alkyl) and —($C_{1-4}$alkyl)-SO$_2$—($C_{1-2}$alkyl). In certain embodiments, the present invention is directed to compounds of formula (I) wherein $R^2$ is selected from the group consisting of hydrogen, halogen, $C_{1-4}$alkyl, —($C_{1-4}$alkyl)-S—($C_{1-2}$alkyl) and —($C_{1-4}$alkyl)-SO$_2$—($C_{1-2}$alkyl).

In certain embodiments, the present invention is directed to compounds of formula (I) wherein $R^2$ is selected from the group consisting of hydrogen, fluoro, chloro, bromo, iodo, methyl, ethyl 4-(methyl-thio)-n-butyl, and 4-(methyl-sulfonyl)-n-butyl. In certain embodiments, the present invention is directed to compounds of formula (I) wherein $R^2$ is selected from the group consisting of hydrogen, fluoro, methyl, 4-(methyl-thio)-n-butyl and 4-(methyl-sulfonyl)-n-butyl.

In certain embodiments, the present invention is directed to compounds of formula (I) wherein $R^2$ is selected from the group consisting of hydrogen, fluoro, chloro, bromo, iodo and methyl. In certain embodiments, the present invention is directed to compounds of formula (I) wherein $R^2$ is selected from the group consisting of hydrogen, fluoro and methyl. In certain embodiments, the present invention is directed to compounds of formula (I) wherein $R^2$ is selected from the group consisting of hydrogen and methyl.

In certain embodiments, the present invention is directed to compounds of formula (I) wherein $R^3$ is selected from the group consisting of hydrogen, halogen, $C_{1-2}$alkyl and fluorinated $C_{1-2}$alkyl. In certain embodiments, the present invention is directed to compounds of formula (I) wherein $R^3$ is selected from the group consisting of hydrogen, halogen and $C_{1-4}$alkyl.

In certain embodiments, the present invention is directed to compounds of formula (I) wherein $R^3$ is selected from the group consisting of hydrogen, fluoro, chloro, bromo, iodo, and methyl. In certain embodiments, the present invention is directed to compounds of formula (I) wherein $R^3$ is selected from the group consisting of hydrogen, fluoro, chloro, bromo, and methyl. In certain embodiments, the present invention is directed to compounds of formula (I) wherein $R^3$ is selected from the group consisting of hydrogen, fluoro, chloro and bromo. In certain embodiments, the present invention is directed to compounds of formula (I) wherein $R^3$ is selected from the group consisting of hydrogen, fluoro and bromo. In certain embodiments, the present invention is directed to compounds of formula (I) wherein $R^3$ is selected from the group consisting of hydrogen, fluoro and iodo. In certain embodiments, the present invention is directed to compounds of formula (I) wherein $R^3$ is selected from the group consisting of hydrogen and fluoro. In certain embodiments, the present invention is directed to compounds of formula (I) wherein $R^3$ is hydrogen.

In certain embodiments, the present invention is directed to compounds of formula (I) wherein $R^4$ is selected from the group consisting of hydrogen, halogen, $C_{1-2}$alkyl and fluorinated $C_{1-2}$alkyl. In certain embodiments, the present invention is directed to compounds of formula (I) wherein $R^4$ is selected from the group consisting of hydrogen, halogen and fluorinated $C_{1-2}$alkyl.

In certain embodiments, the present invention is directed to compounds of formula (I) wherein $R^4$ is selected from the group consisting of hydrogen, fluoro, chloro, and trifluoromethyl. In certain embodiments, the present invention is directed to compounds of formula (I) wherein $R^4$ is selected from the group consisting of hydrogen, fluoro, and chloro. In certain embodiments, the present invention is directed to compounds of formula (I) wherein $R^4$ is selected from the group consisting of hydrogen and fluoro. In certain embodiments, the present invention is directed to compounds of formula (I) wherein $R^4$ is selected from the group consisting of hydrogen and chloro. In certain embodiments, the present invention is directed to compounds of formula (I) wherein $R^4$ is hydrogen.

In certain embodiments, the present invention is directed to compounds of formula (I) wherein $R^5$ is selected from the group consisting of hydrogen, halogen, cyano, $C_{1-4}$alkyl, fluorinated $C_{1-2}$alkyl, vinyl, halogen substituted vinyl, ethynyl, hydroxy substituted $C_{1-2}$alkyl, $C_{1-4}$alkoxy, fluorinated $C_{1-2}$alkoxy, cyclopropyl and phenyl.

In certain embodiments, the present invention is directed to compounds of formula (I) wherein $R^5$ is selected from the group consisting of hydrogen, fluoro, chloro, bromo, methyl, ethyl, isopropyl, t-butyl, 1-hydroxy-ethyl, trifluoromethyl, 1,1,2,2,2-pentafluorethyl, methoxy, trifluoromethoxy, vinyl, 1-bromo-vinyl, ethynyl, cyano, cyclopropyl and phenyl.

In certain embodiments, the present invention is directed to compounds of formula (I) wherein $R^5$ is selected from the group consisting of hydrogen, fluoro, chloro, bromo, methyl, ethyl, isopropyl, trifluoromethyl, 1,1,2,2,2-pentafluorethyl, methoxy, vinyl, ethynyl and cyclopropyl. In certain embodiments, the present invention is directed to compounds of formula (I) wherein $R^5$ is selected from the group consisting of hydrogen, fluoro, chloro, bromo, methyl, ethyl, isopropyl, trifluoromethyl, methoxy, vinyl and cyclopropyl.

In certain embodiments, the present invention is directed to compounds of formula (I) wherein $R^5$ is selected from the group consisting of fluoro, chloro, bromo, methyl, ethyl, trifluoromethyl, methoxy and vinyl. In certain embodiments, the present invention is directed to compounds of formula (I) wherein $R^5$ is selected from the group consisting of hydrogen, fluoro, chloro, bromo, methyl, trifluoromethyl and methoxy. In certain embodiments, the present invention is directed to compounds of formula (I) wherein $R^5$ is selected from the group consisting of fluoro, chloro, bromo, methyl, trifluoromethyl and vinyl.

In certain embodiments, the present invention is directed to compounds of formula (I) wherein $R^5$ is selected from the group consisting of hydrogen, fluoro, chloro, methyl and trifluoromethyl. In certain embodiments, the present invention is directed to compounds of formula (I) wherein $R^5$ is selected from the group consisting of hydrogen, fluoro, methyl and trifluoromethyl. In certain embodiments, the present invention is directed to compounds of formula (I) wherein $R^5$ is selected from the group consisting of hydrogen, fluoro, chloro and methyl.

In certain embodiments, the present invention is directed to compounds of formula (I) wherein $R^2$ and $R^5$ are taken together with the carbon atoms to which they are bound to form cyclopenten-1-yl. In certain embodiments, the present invention is directed to compounds of formula (I) wherein $R^3$ and $R^4$ are taken together with the carbon atoms to which they are bound to form cyclopenten-1-yl.

In certain embodiments, the present invention is directed to compounds of formula (I) wherein $R^6$ is hydrogen. In certain embodiments, the present invention is directed to compounds of formula (I) wherein $R^6$ is methyl.

In certain embodiments, the present invention is directed to compounds of formula (I) wherein one or more, preferably one to ten, more preferably one to five, for example one to five, one to four, one to three, one to two or one hydrogen atom is replaced with its corresponding isotope, preferably deuterium or tritium, more preferably deuterium.

In certain embodiments, the present invention is directed to compounds of formula (I) which is deuterated with two or more, preferably two deuterium atoms, for example, wherein the —$CH_2CH_2CO_2H$ substituent group (or portion of the structure) is replaced with its corresponding di-deuterated isotopologue, a substituent group of the formula —$CHD$-$CHD$-$CO_2H$.

In certain embodiments, the present invention is directed to compounds of formula (I) which is deuterated with two or more, preferably two deuterium atoms, for example, wherein any one or more, preferably one —$CH_2$— group is replaced with its corresponding di-deuterated isotopologue, a group of the formula —$CD_2$-.

In certain embodiments, the present invention is directed to compounds of formula (I) which is deuterated with three or more, preferably three deuterium atoms, for example, wherein one or more, preferably one —$CH_3$ (methyl) group replaced is replaced with its corresponding tri-deuterated isotopologue, a group of the formula —$CD_3$. In certain embodiments, the present invention is directed to compounds of formula (I) wherein $R^1$ is 4-$CD_3$-phenyl.

In certain embodiments, the present invention is directed to any one or more compounds of formula (I) selected from the group consisting of
3-(4-{[2-(4-Ethylphenyl)cyclopent-1-en-1-yl]methoxy}-2,3-dimethylphenyl)propanoic acid;
3-(2,3-Dimethyl-4-{[2-(4-methylphenyl)cyclopent-1-en-1-yl]methoxy}phenyl)propanoic acid;
3-(4-{[2-(3-Fluoro-4-methylphenyl)cyclopent-1-en-1-yl]methoxy}-2,3-dimethylphenyl)propanoic acid;
3-(4-{[2-(4-Chlorophenyl)cyclopent-1-en-1-yl]methoxy}-3-methylphenyl)propanoic acid;
3-(4-{[2-(4-Chlorophenyl)cyclohex-1-en-1-yl]methoxy}-3-methylphenyl)propanoic acid;
3-(2,3-Dimethyl-4-{[2-(6-methylpyridin-3-yl)cyclopent-1-en-1-yl]methoxy}phenyl)propanoic acid;
3-(4-{[2-(4-Chlorophenyl)-5,5-difluorocyclohex-1-en-1-yl]methoxy}-2,3-dimethylphenyl)propanoic acid;
3-[4-{[2-(4-Chlorophenyl)cyclopent-1-en-1-yl]methoxy}-2-(trifluoromethyl)phenyl]propanoic acid;
3-(4-{[4,4-Difluoro-2-(4-fluorophenyl)cyclopent-1-en-1-yl]methoxy}-2,3-dimethylphenyl)propanoic acid;
3-(4-{[2-(4-Chlorophenyl)-4,4-difluorocyclopent-1-en-1-yl]methoxy}-2,3-dimethylphenyl)propanoic acid;
and pharmaceutically acceptable salts thereof.

In certain embodiments, the present invention is directed to any one or more compounds of formula (I) selected from the group consisting of
3-[4-{[2-(4-Chlorophenyl)cyclopent-1-en-1-yl]methoxy}-2-(trifluoromethyl)phenyl]propanoic acid;
3-(4-([1,1'-bi(cyclopentan)]-1-en-2-ylmethoxy)-2-(trifluoromethyl)phenyl)propanoic acid;
3-(4-([1,1'-bi(cyclopentane)]-1,2'-dien-2-ylmethoxy)-2-chlorophenyl)propanoic acid;
3-(4-((4,4-difluoro-[1,1'-bi(cyclopentan)]-1-en-2-yl)methoxy)-2-(trifluoromethyl)phenyl)propanoic acid;
3-(2-chloro-4-((4,4-difluoro-[1,1'-bi(cyclopentan)]-1-en-2-yl)methoxy)phenyl)propanoic acid;
3-(4-((4,4-difluoro-[1,1'-bi(cyclopentan)]-1-en-2-yl)methoxy)-2-methylphenyl)propanoic acid;
3-(4-((4,4-difluoro-[1,1'-bi(cyclopentan)]-1-en-2-yl)methoxy)-2-(trifluoromethyl)phenyl)propanoic acid;
3-(4-((2-cyclobutylcyclopent-1-en-1-yl)methoxy)-2-(trifluoromethyl)phenyl)propanoic acid;
and pharmaceutically acceptable salts thereof.

In certain embodiments, the present invention is directed to compounds of formula (I) wherein a is an integer from 1 to 2.

In certain embodiments, the present invention is directed to compounds of formula (I) wherein a is 3 and wherein at least one of $R^2$, $R^3$, $R^4$ or $R^5$ is other than hydrogen. In certain other embodiments, the present invention is directed to compounds of formula (I) wherein at least one of $R^2$, $R^3$, $R^4$ or $R^5$ is other than hydrogen.

In certain embodiments, the present invention is directed to compounds of formula (I) wherein a is 3 and wherein $R^1$ is selected from the group consisting of $C_{1-6}$alkyl, $C_{2-8}$alkynyl, $C_{3-6}$cycloalkyl, —($C_{1-2}$alkyl)-$C_{3-6}$cycloalkyl, $C_{5-6}$cycloalkenyl, 5,5-dimethyl-cyclopenten-1-yl, bicyclo[3.1.0]hexy-2-yl, (1S,4S)-2-methyl-bicyclo[2.2.1]hept-2-yl, (1R,2R,4S)-bicyclo[2.2.1]heptan-2-yl, 2,2-difluoro-benzo[d][1,3]dioxol-4-yl, —($C_{1-2}$alkyl)-phenyl, —C(=$CH_2$)-phenyl, —C(O)— phenyl, biphenyl, tetrahydropyranyl, furanyl, pyrimidinyl, pyridyl, thienyl, thiazolyl, —($C_{1-2}$alkyl)-thiazolyl, 3,6-dihydro-pyran-4-yl and 1-methyl-imidazol-4-yl; wherein the $C_{3-6}$cycloalkyl or $C_{5-6}$cycloalkenyl, whether alone or as part of a substituent group is optionally substituted with one or more (preferably one to two) substituents independently selected from the group consisting of halogen, $C_{1-4}$alkyl and fluorinated $C_{1-2}$alkyl; and wherein the furanyl, pyrimidinyl, pyridyl, thienyl, thiazolyl, or 3,6-dihydro-pyran-4-yl, whether alone or as part of a substituent group is optionally substituted with one or more (preferably one to two) substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$ alkoxy, —S—($C_{1-2}$alkyl), —SO—($C_{1-2}$alkyl), —$SO_2$—($C_{1-2}$alkyl), nitro, —$NR^AR^B$ and —NH—C(O)—($C_{1-4}$alkyl); wherein $R^A$ and $R^B$ are each independently selected from the group consisting of hydrogen and $C_{1-4}$alkyl.

In certain embodiments, the present invention is directed to compounds of formula (I) wherein $R^1$ is selected from the group consisting of $C_{1-6}$alkyl, $C_{2-6}$alkynyl, $C_{3-6}$cycloalkyl, —($C_{1-2}$alkyl)-$C_{3-6}$cycloalkyl, $C_{5-6}$cycloalkenyl, 5,5-dimethyl-cyclopenten-1-yl, bicyclo[3.1.0]hexy-2-yl, (1S,4S)-2-methyl-bicyclo[2.2.1]hept-2-yl, (1R,2R,4S)-bicyclo[2.2.1]heptan-2-yl, 2,2-difluoro-benzo[d][1,3]dioxol-4-yl, —($C_{1-2}$alkyl)-phenyl, —C(=$CH_2$)-phenyl, —C(O)-phenyl, biphenyl, tetrahydropyranyl, furanyl, pyrimidinyl, pyridyl, thienyl, thiazolyl, —($C_{1-2}$ alkyl)-thiazolyl, 3,6-dihydro-pyran-4-yl and 1-methyl-imidazol-4-yl; wherein the $C_{3-6}$cycloalkyl or $C_{5-6}$cycloalkenyl, whether alone or as part of a substituent group is optionally substituted with one or more (preferably one to two) substituents independently selected from the group consisting of halogen, $C_{1-4}$ alkyl and fluorinated $C_{1-2}$alkyl; and wherein the furanyl, pyrimidinyl, pyridyl, thienyl, thiazolyl, or 3,6-dihydro-pyran-4-yl, whether alone or as part of a substituent group is optionally substituted with one or more (preferably one to two) substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$ alkoxy, —S—($C_{1-2}$alkyl), —SO—($C_{1-2}$alkyl), —$SO_2$—($C_{1-2}$alkyl), nitro, —$NR^AR^B$ and —NH—C(O)—($C_{1-4}$alkyl); wherein $R^A$ and $R^B$ are each independently selected from the group consisting of hydrogen and $C_{1-4}$alkyl.

In certain embodiments, the present invention is directed to compounds of formula (I) wherein a is 3 and wherein $R^1$ is selected from the group consisting of $C_{1-6}$alkyl, $C_{2-8}$alkynyl, —($C_{1-2}$alkyl)-$C_{3-6}$cycloalkyl, $C_{5-6}$cycloalkenyl, 5,5-dimethyl-cyclopenten-1-yl, bicyclo[3.1.0]hexy-2-yl, (1S,4S)-

2-methyl-bicyclo[2.2.1]hept-2-yl, (1R,2R,4S)-bicyclo[2.2.1]heptan-2-yl, 2,2-difluoro-benzo[d][1,3]dioxol-4-yl, —($C_{1-2}$alkyl)-phenyl, —C(=$CH_2$)-phenyl, —C(O)-phenyl, biphenyl, tetrahydropyranyl, furanyl, pyrimidinyl, thiazolyl, —($C_{1-2}$alkyl)-thiazolyl, 3,6-dihydro-pyran-4-yl and 1-methyl-imidazol-4-yl; wherein the $C_{3-6}$cycloalkyl or $C_{5-6}$cycloalkenyl, whether alone or as part of a substituent group is optionally substituted with one or more (preferably one to two) substituents independently selected from the group consisting of halogen, $C_{1-4}$alkyl and fluorinated $C_{1-2}$ alkyl; and wherein the furanyl, pyrimidinyl, thiazolyl, or 3,6-dihydro-pyran-4-yl, whether alone or as part of a substituent group is optionally substituted with one or more (preferably one to two) substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$alkyl), —$SO_2$—($C_{1-2}$ alkyl), nitro, —$NR^AR^B$ and —NH—C(O)—($C_{1-4}$alkyl); wherein $R^A$ and $R^B$ are each independently selected from the group consisting of hydrogen and $C_{1-4}$alkyl.

In certain embodiments, the present invention is directed to compounds of formula (I) wherein $R^1$ is selected from the group consisting of $C_{1-6}$alkyl, $C_{2-6}$alkynyl, —($C_{1-2}$alkyl)-$C_{3-6}$cycloalkyl, $C_{5-6}$cycloalkenyl, 5,5-dimethyl-cyclopenten-1-yl, bicyclo[3.1.0]hexy-2-yl, (1S,4S)-2-methyl-bicyclo[2.2.1]hept-2-yl, (1R,2R,4S)-bicyclo[2.2.1]heptan-2-yl, 2,2-difluoro-benzo[d][1,3]dioxol-4-yl, —($C_{1-2}$ alkyl)-phenyl, —C(=$CH_2$)-phenyl, —C(O)-phenyl, biphenyl, tetrahydropyranyl, furanyl, pyrimidinyl, thiazolyl, —($C_{1-2}$alkyl)-thiazolyl, 3,6-dihydro-pyran-4-yl and 1-methyl-imidazol-4-yl; wherein the cycloalkyl or cycloalkenyl, whether alone or as part of a substituent group is optionally substituted with one or more (preferably one to two) substituents independently selected from the group consisting of halogen, $C_{1-4}$alkyl and fluorinated $C_{1-2}$alkyl; and wherein the furanyl, pyrimidinyl, thiazolyl, or 3,6-dihydro-pyran-4-yl, whether alone or as part of a substituent group is optionally substituted with one or more (preferably one to two) substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$alkyl), —$SO_2$—($C_{1-2}$alkyl), nitro, —$NR^AR^B$ and —NH—C(O)—($C_{1-4}$alkyl); wherein $R^A$ and $R^B$ are each independently selected from the group consisting of hydrogen and $C_{1-4}$alkyl.

In certain embodiments, the present invention is directed to compounds of formula (I) wherein $R^1$ is selected from the group consisting of $C_{1-6}$alkyl and $C_{2-6}$alkynyl.

In certain embodiments, the present invention is directed to compounds of formula (I) wherein at least one of $R^2$, $R^3$, $R^4$ or $R^5$ is fluorinated $C_{1-2}$alkyl. In certain embodiments, the present invention is directed to compounds of formula (I) wherein $R^2$ is fluorinated $C_{1-2}$alkyl. In certain embodiments, the present invention is directed to compounds of formula (I) wherein $R^3$ is fluorinated $C_{1-2}$alkyl. In certain embodiments, the present invention is directed to compounds of formula (I) wherein $R^4$ is fluorinated $C_{1-2}$alkyl. In certain embodiments, the present invention is directed to compounds of formula (I) wherein $R^5$ is fluorinated $C_{1-2}$alkyl.

In certain embodiments, the present invention is directed to compounds of formula (I) wherein at least one of $R^2$ is selected from the group consisting of fluorinated $C_{1-2}$alkyl, —($C_{1-4}$alkyl)-S—($C_{1-2}$alkyl), —($C_{1-4}$alkyl)-SO—($C_{1-2}$alkyl) and —($C_{1-4}$alkyl)-$SO_2$—($C_{1-2}$alkyl). In certain embodiments, the present invention is directed to compounds of formula (I) wherein $R^5$ is selected from the group consisting of fluorinated $C_{1-2}$alkyl, vinyl, halogen substituted vinyl, ethynyl, hydroxy substituted $C_{1-2}$alkyl, $C_{1-4}$alkoxy, fluorinated $C_{1-2}$alkoxy and cyclopropyl-methyl-.

Additional embodiments of the present invention, include those wherein the substituents selected for one or more of the variables defined herein (i.e. a, b, $R^0$, $R^1$, $R^2$, $R^3$, $R^4$, $R^5$, etc.) are independently selected to be any individual substituent or any subset of substituents selected from the complete list as defined herein.

In another embodiment of the present invention is any single compound or subset of compounds selected from the representative compounds listed in Tables 1-3 below.

Representative compounds of the present invention are as listed in Tables 1-3 below. Unless otherwise noted, wherein a stereogenic center is present in the listed compound, the compound was prepared as a mixture of stereo-isomers.

TABLE 1

Representative Compounds of Formula (I)

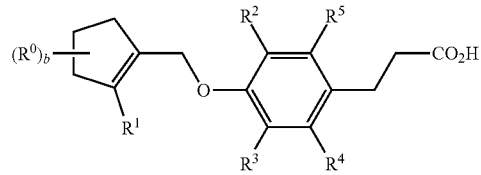

| ID No. | $(R^0)_b$ | $R^1$ | $R^2$ | $R^5$ | $R^3$ | $R^4$ |
|---|---|---|---|---|---|---|
| 4 | b = 0 | 4-fluoro-phenyl | methyl | methyl | H | H |
| 6 | 3-ethyl | 4-chloro-phenyl | methyl | methyl | H | H |
| 8 | b = 0 | 4-chloro-phenyl | methyl | H | H | H |
| 10 | 4,4-difluoro | 4-fluoro-phenyl | methyl | methyl | H | H |
| 12 | 5-trifluoromethyl | 4-chloro-phenyl | methyl | methyl | H | H |
| 15 | b = 0 | 4-chloro-phenyl | methyl | methyl | H | H |
| 16 | b = 0 | 4-ethyl-phenyl | fluoro | H | fluoro | H |
| 19 | b = 0 | phenyl | H | H | H | H |
| 20 | b = 0 | 4-trifluoromethoxy-phenyl | methyl | methyl | H | H |
| 21 | b = 0 | 4-methoxy-phenyl | methyl | methyl | H | H |
| 22 | b = 0 | thien-3-yl | methyl | methyl | H | H |
| 23 | b = 0 | phenyl | methyl | methyl | H | H |
| 25 | b = 0 | 4-ethyl-phenyl | fluoro | fluoro | H | H |
| 27 | b = 0 | 4-ethyl-phenyl | methyl | methyl | H | H |

TABLE 1-continued

Representative Compounds of Formula (I)

| | | | | | | |
|---|---|---|---|---|---|---|
| 30 | b = 0 | 4-chloro-phenyl | methyl | H | bromo | H |
| 32 | 5-trifluoromethyl | 4-chloro-phenyl | fluoro | fluoro | H | H |
| 33 | 5-trifluoromethyl | 4-chloro-phenyl | fluoro | H | fluoro | H |
| 39 | b = 0 | 4-chloro-phenyl | H | trifluoromethyl | H | H |
| 42 | b = 0 | 4-fluoro-phenyl | methyl | H | H | H |
| 43 | b = 0 | 4-fluoro-phenyl | H | H | H | H |
| 45 | 5-hydroxy | 4-chloro-phenyl | fluoro | fluoro | H | H |
| 46 | 3-isopropyl | 4-chloro-phenyl | methyl | methyl | H | H |
| 47 | b = 0 | 4-chloro-phenyl | H | fluoro | H | H |
| 49 | b = 0 | 4-fluoro-phenyl | fluoro | H | H | H |
| 50 | b = 0 | 4-methyl-thio-phenyl | methyl | methyl | H | H |
| 51 | b = 0 | 4-(methyl-carbonyl-amino)-phenyl | methyl | methyl | H | H |
| 52 | b = 0 | 4-methyl-phenyl | methyl | methyl | H | H |
| 55 | b = 0 | 4-isopropyl-phenyl | methyl | methyl | H | H |
| 56 | b = 0 | 4-bromo-phenyl | methyl | methyl | H | H |
| 57 | b = 0 | 4-iodo-phenyl | methyl | methyl | H | H |
| 58 | b = 0 | 3-chloro-phenyl | methyl | methyl | H | H |
| 60 | b = 0 | 4-chloro-phenyl | fluoro | H | fluoro | H |
| 62 | b = 0 | 4-chloro-phenyl | methyl | H | H | H |
| 65 | b = 0 | 3-fluoro-5-methoxy-phenyl | methyl | methyl | H | H |
| 66 | b = 0 | 3,4-dicloro-phenyl | methyl | methyl | H | H |
| 67 | b = 0 | 4-chloro-phenyl | H | methyl | bromo | H |
| 68 | b = 0 | 4-chloro-phenyl | bromo | methyl | bromo | H |
| 69 | 5-hydroxy-5-trifluoro-methyl | 4-chloro-phenyl | methyl | methyl | H | H |
| 70 | b = 0 | 4-chloro-phenyl | fluoro | fluoro | H | H |
| 72 | b = 0 | 2,4-dimethyl-phenyl | fluoro | fluoro | H | H |
| 74 | b = 0 | 4-methyl-sulfonyl-phenyl | methyl | methyl | H | H |
| 75 | b = 0 | 4-trifluoromethyl-phenyl | methyl | methyl | H | H |
| 76 | b = 0 | 2-chloro-phenyl | methyl | methyl | H | H |
| 77 | b = 0 | thien-2-yl | methyl | methyl | H | H |
| 78 | b = 0 | 3-fluoro-4-methyl-phenyl | fluoro | fluoro | H | H |
| 79 | b = 0 | thiazol-2-yl | methyl | methyl | H | H |
| 80 | b = 0 | 3-fluoro-4-methyl-phenyl | methyl | methyl | H | H |
| 82 | b = 0 | 2,4-dimethyl-phenyl | methyl | methyl | H | H |
| 83 | b = 0 | 3,4-dimethyl-phenyl | fluoro | fluoro | H | H |
| 84 | b = 0 | 3,4-dimethyl-phenyl | fluoro | H | fluoro | H |
| 85 | b = 0 | 6-methyl-pyrid-3-yl | methyl | methyl | H | H |
| 87 | b = 0 | 6-methyl-pyrid-3-yl | fluoro | fluoro | H | H |
| 88 | b = 0 | thiazol-5-yl | methyl | methyl | H | H |
| 89 | b = 0 | 4-chloro-phenyl | H | 1,1,2,2,2-penta-fluoroethyl | H | H |
| 91 | b = 0 | 4-chloro-phenyl | fluoro | H | H | trifluoromethyl |
| 92 | b = 0 | 3-nitro-4-methyl-phenyl | fluoro | fluoro | H | H |
| 93 | b = 0 | 3-amino-4-methyl-phenyl | fluoro | fluoro | H | H |
| 94 | b = 0 | 4-methyl-phenyl | fluoro | fluoro | H | H |
| 95 | b = 0 | 4-methyl-phenyl | fluoro | H | fluoro | H |
| 96 | b = 0 | 4-chloro-phenyl | H | trifluoromethoxy | H | H |
| 97 | b = 0 | 4-chloro-phenyl | H | methoxy | H | H |
| 98 | b = 0 | 4-chloro-phenyl | methyl | H | H | trifluoromethyl |
| 99 | b = 0 | 4-chloro-phenyl | chloro | chloro | H | H |
| 100 | 4-fluoro | 4-fluoro-phenyl | methyl | methyl | H | H |
| 101 | b = 0 | 4-chloro-phenyl | bromo | trifluoromethyl | bromo | H |
| 102 | b = 0 | 6-methyl-pyrid-3-yl | methyl | H | H | H |
| 103 | b = 0 | 3,4-difluoro-phenyl | H | H | H | H |
| 105 | b = 0 | pyrimidin-2-yl | methyl | methyl | H | H |
| 106 | b = 0 | 3,4-dimethyl-phenyl | methyl | methyl | H | H |
| 107 | b = 0 | 4-chloro-phenyl | H | H | H | H |
| 108 | b = 0 | pyrid-3-yl | methyl | methyl | H | H |
| 109 | b = 0 | 3-nitro-4-methyl-phenyl | fluoro | H | fluoro | H |
| 111 | b = 0 | 2-bromo-phenyl | methyl | methyl | H | H |
| 112 | b = 0 | 3,5-dichloro-phenyl | methyl | methyl | H | H |
| 113 | b = 0 | 3-methoxy-4-methyl-phenyl | methyl | methyl | H | H |
| 114 | b = 0 | 3-dimethyl-amino-phenyl | methyl | methyl | H | H |
| 115 | b = 0 | 3-nitro-4-methyl-phenyl | methyl | methyl | H | H |
| 116 | b = 0 | 3-fluoro-4-chloro-phenyl | methyl | H | H | H |
| 117 | b = 0 | 3,4-difluoro-phenyl | methyl | methyl | H | H |
| 119 | b = 0 | 4-chloro-phenyl | H | methyl | methyl | H |
| 120 | b = 0 | 4-methyl-sulfinyl-phenyl | methyl | methyl | H | H |
| 122 | b = 0 | 4-chloro-phenyl | fluoro | fluoro | fluoro | fluoro |
| 124 | b = 0 | 2-fluoro-phenyl | methyl | methyl | H | H |
| 126-D[a] | b = 0 | 4-chloro-phenyl | methyl | H | H | H |
| 127 | b = 0 | 4-chloro-phenyl | methyl | methyl | H | H |
| 129 | b = 0 | 4-chloro-phenyl | bromo | H | H | H |
| 130 | b = 0 | 4-chloro-phenyl | iodo | H | H | H |

TABLE 1-continued

Representative Compounds of Formula (I)

| | | | | | |
|---|---|---|---|---|---|
| 131 | b = 0 | 4-chloro-phenyl | H | methyl | H | H |
| 132 | b = 0 | 2-methyl-phenyl | methyl | methyl | H | H |
| 133 | b = 0 | 2,4-dichloro-phenyl | methyl | methyl | H | H |
| 134 | b = 0 | 3-amino-4-methyl-phenyl | methyl | methyl | H | H |
| 135 | b = 0 | 3-amino-4-methyl-phenyl | fluoro | H | fluoro | H |
| 136 | b = 0 | 4-chloro-phenyl | H | phenyl | H | H |
| 137 | 4,4-difluoro | 4-chloro-phenyl | methyl | methyl | H | H |
| 139 | b = 0 | pyrid-4-yl | methyl | methyl | H | H |
| 140 | b = 0 | 4-n-propyl-phenyl | methyl | methyl | H | H |
| 141 | b = 0 | 3-methoxy-phenyl | methyl | methyl | H | H |
| 142 | b = 0 | 4-chloro-phenyl | ethyl | H | H | trifluoromethyl |
| 143 | b = 0 | 4-chloro-phenyl | H | chloro | H | H |
| 145 | 5-oxo | 4-chloro-phenyl | methyl | methyl | H | H |
| 146 | b = 0 | 4-cyano-phenyl | methyl | methyl | H | H |
| 147 | b = 0 | pyrid-2-yl | methyl | methyl | H | H |
| 149 | b = 0 | 4-chloro-phenyl | fluoro | H | H | H |
| 151 | b = 0 | 4-ethoxy-phenyl | methyl | methyl | H | H |
| 152 | b = 0 | 3-fluoro-4-methyl-phenyl | methyl | H | H | H |
| 153 | b = 0 | 4-chloro-phenyl | H | H | H | H |
| 157 | b = 0 | 3-fluoro-4-chloro-phenyl | methyl | methyl | H | H |
| 158 | b = 0 | 6-chloro-pyrid-3-yl | methyl | methyl | H | H |
| 159 | b = 0 | 3-fluoro-4-chloro-phenyl | methyl | H | H | H |
| 161 | b = 0 | 4-chloro-phenyl | H | ethyl | H | H |
| 166 | 4,4,-difluoro | 4-chloro-phenyl | methyl | H | H | H |
| 167 | b = 0 | 4-chloro-phenyl | H | isopropyl | H | H |
| 168 | b = 0 | 4-chloro-phenyl | H | t-butyl | H | H |
| 169 | b = 0 | 4-methyl-phenyl | bromo | H | H | H |
| 171 | 4,4-difluoro | 3-fluoro-4-chloro-phenyl | methyl | methyl | H | H |
| 172 | 4,4-difluoro | 3-fluoro-4-methyl-phenyl | methyl | methyl | H | H |
| 173 | 4,4-difluoro | 2,4-difluoro-phenyl | methyl | methyl | H | H |
| 177 | 4,4-difluoro | 3,4-difluoro-phenyl | methyl | methyl | H | H |
| 179 | 4,4-difluoro | 3,4-difluoro-phenyl | methyl | H | H | H |
| 180 | 4,4-difluoro | 4-fluoro-phenyl | methyl | H | H | H |
| 181 | b = 0 | 4-chloro-phenyl | 4-(methyl-sulfonyl)-n-butyl | H | H | H |
| 182 | 4,4-difluoro | 2,4-difluoro-phenyl | methyl | H | H | H |
| 183 | 4,4-difluoro | 4-fluoro-phenyl | fluoro | H | fluoro | H |
| 184 | 4,4-difluoro | 3,4-difluoro-phenyl | fluoro | H | fluoro | H |
| 185 | 4-cyano | 4-chloro-phenyl | fluoro | H | fluoro | H |
| 186 | 4-fluoro | 4-fluoro-phenyl | H | trifluoromethyl | H | H |
| 187 | 4-methoxy | 4-chloro-phenyl | fluoro | H | fluoro | H |
| 188 | 4,4-difluoro | 4-fluoro-phenyl | H | trifluoromethyl | H | H |
| 189 | 4-methoxy | 4-chloro-phenyl | methyl | methyl | H | H |
| 190 | 4,4-difluoro | thiazol-5-yl | methyl | H | H | H |
| 191 | 4,4-difluoro | 3-fluoro-phenyl | methyl | H | H | H |
| 192 | 4,4-difluoro | 3-fluoro-phenyl | methyl | methyl | H | H |
| 193 | 4,4-difluoro | phenyl | methyl | H | H | H |
| 194 | 4,4-difluoro | phenyl | methyl | methyl | H | H |
| 195 | 4-chloro | 4-chloro-phenyl | methyl | methyl | H | H |
| 196 | 4-cyano | 4-chloro-phenyl | methyl | methyl | H | H |
| 198 | b = 0 | 4-chloro-phenyl | 4-(methyl-thio)-n-butyl | H | H | H |
| 199 | 4,4-difluoro | 2-methyl-thiazol-5-yl | methyl | H | H | H |
| 200 | 4,4-difluoro | thien-2-yl | methyl | methyl | H | H |
| 201 | 4,4-difluoro | thien-2-yl | fluoro | H | fluoro | H |
| 202 | 4,4-difluoro | thien-2-yl | methyl | H | H | H |
| 203 | 4,4-difluoro | 4-fluoro-phenyl | chloro | H | H | H |
| 204 | 4,4-difluoro | 4-fluoro-phenyl | methyl | H | fluoro | H |
| 205 | 4,4-difluoro | 4-fluoro-phenyl | chloro | H | chloro | H |
| 207 | 4,4-difluoro | 4-fluoro-phenyl | H | cyano | H | H |
| 208 | b = 0 | furan-2-yl | methyl | H | H | H |
| 209 | b = 0 | furan-2-yl | fluoro | H | fluoro | H |
| 210 | b = 0 | furan-2-yl | methyl | methyl | H | H |
| 211 | b = 0 | 5-methyl-furan-2-yl | methyl | H | H | H |
| 212 | b = 0 | 5-methyl-furan-2-yl | fluoro | H | fluoro | H |
| 213 | b = 0 | 2-hydroxy-4-methyl-phenyl | H | H | H | H |
| 214 | 4,4-difluoro | 4-fluoro-phenyl | fluoro | H | H | H |
| 215 | 4,4-difluoro | 3-fluoro-phenyl | fluoro | H | fluoro | H |
| 216 | 4,4-difluoro | 3,4-difluoro-phenyl | fluoro | H | fluoro | H |
| 218 | b = 0 | 6-methoxy-pyrid-3-yl | methyl | H | H | H |
| 219 | b = 0 | 6-ethoxy-pyrid-3-yl | methyl | methyl | H | H |
| 220 | b = 0 | 6-methoxy-pyrid-3-yl | methyl | methyl | H | H |
| 221 | b = 0 | 6-methoxy-pyrid-3-yl | fluoro | H | fluoro | H |
| 222 | b = 0 | 5-fluoro-6-methoxy-pyrid-3-yl | methyl | H | H | H |
| 223 | b = 0 | 5-fluoro-6-methoxy-pyrid-3-yl | methyl | methyl | H | H |

TABLE 1-continued

Representative Compounds of Formula (I)

| # | | | | | | |
|---|---|---|---|---|---|---|
| 224 | b = 0 | 5-fluoro-6-methoxy-pyrid-3-yl | fluoro | H | fluoro | H |
| 225 | b = 0 | 6-ethoxy-pyrid-3-yl | methyl | H | H | H |
| 226 | b = 0 | 6-ethoxy-pyrid-3-yl | fluoro | H | fluoro | H |
| 227 | b = 0 | 4-fluoro-phenyl | methyl | H | fluoro | H |
| 228 | 4,4-difluoro | 4-fluoro-phenyl | H | H | H | H |
| 229 | 4,4-difluoro | 4-fluoro-phenyl | methyl | H | chloro | H |
| 230 | b = 0 | cyclohex-1-en-1-yl | H | H | H | H |
| 232 | 4,4-difluoro | furan-2-yl | methyl | H | H | H |
| 233 | b = 0 | pent-1-yn-1-yl | H | H | H | H |
| 234 | b = 0 | 3-hydroxy-4-methyl-phenyl | H | H | H | H |
| 235 | b = 0 | 4-fluoro-phenyl | chloro | H | chloro | H |
| 236 | b = 0 | 4-fluoro-phenyl | methyl | H | chloro | H |
| 237 | b = 0 | 4-fluoro-phenyl | H | cyano | H | H |
| 238 | b = 0 | 3,6-dihydro-pyran-4-yl | methyl | H | H | H |
| 239 | b = 0 | 3,6-dihydro-pyran-4-yl | methyl | methyl | H | H |
| 240 | b = 0 | 4-fluoro-phenyl | H | trifluoromethyl | H | H |
| 241 | 4,4-difluoro | phenyl | H | trifluoromethyl | H | H |
| 242 | 4,4-difluoro | phenyl | H | chloro | H | H |
| 243 | b = 0 | 2-methyl-4-chloro-phenyl | H | trifluoromethyl | H | H |
| 244 | b = 0 | 2,4-dimethyl-phenyl | H | methyl | fluoro | H |
| 245 | b = 0 | 2,4-dimethyl-phenyl | H | H | H | H |
| 246 | b = 0 | 2,4-dimethyl-phenyl | H | chloro | H | H |
| 247 | b = 0 | 2,4-dimethyl-phenyl | H | trifluoromethyl | H | H |
| 248 | 4,4-difluoro | 4-chloro-phenyl | H | trifluoromethyl | H | H |
| 249 | 4,4-difluoro | 4-methyl-phenyl | H | trifluoromethyl | H | H |
| 250 | 4,4-difluoro | 4-methyl-phenyl | H | chloro | H | H |
| 251 | 4,4-difluoro | 4-chloro-phenyl | H | chloro | H | H |
| 252 | 4-fluoro | 4-chloro-phenyl | H | chloro | H | H |
| 254 | b = 0 | 4-fluoro-phenyl | methyl | methyl | fluoro | H |
| 255 | b = 0 | 2-methoxy-4-methyl-phenyl | H | H | H | H |
| 257 | b = 0 | 2-methyl-phenyl | H | trifluoromethyl | H | H |
| 258 | b = 0 | phenyl | H | trifluoromethyl | H | H |
| 259 | b = 0 | phenyl | H | chloro | H | H |
| 260 | b = 0 | 4-fluoro-phenyl | H | chloro | H | H |
| 261 | b = 0 | 3-methoxy-4-methyl-phenyl | H | H | H | H |
| 262 | b = 0 | 2-methyl-phenyl | H | methyl | fluoro | H |
| 263 | b = 0 | 3-fluoro-phenyl | H | trifluoromethyl | H | H |
| 264 | b = 0 | 3-fluoro-4-methyl-phenyl | H | methyl | fluoro | H |
| 265 | b = 0 | 2-chloro-phenyl | H | methyl | fluoro | H |
| 268-D$^a$ | b = 0 | 4-methyl-phenyl | H | trifluoromethyl | H | H |
| 269 | b = 0 | 4-bromo-phenyl | H | trifluoromethyl | H | H |
| 270 | b = 0 | 2-fluoro-4-methyl-phenyl | H | methyl | fluoro | H |
| 272 | b = 0 | 4-trifluoromethyl-phenyl | H | chloro | H | H |
| 273 | b = 0 | 2-fluoro-4-methyl-phenyl | H | chloro | H | H |
| 274 | b = 0 | 3-fluoro-4-chloro-phenyl | H | chloro | H | H |
| 275 | b = 0 | 2-fluoro-4-chloro-phenyl | H | chloro | H | H |
| 276 | b = 0 | 4-bromo-phenyl | H | chloro | H | H |
| 277 | b = 0 | phenyl | H | methyl | fluoro | H |
| 278 | b = 0 | 2-methyl-4-methoxy-phenyl | H | methyl | fluoro | H |
| 279 | b = 0 | 4-methoxy-phenyl | H | methyl | fluoro | H |
| 280 | b = 0 | 3-fluoro-4-chloro-phenyl | H | methyl | fluoro | H |
| 281 | b = 0 | 2-fluoro-4-chloro-phenyl | H | methyl | fluoro | H |
| 282 | b = 0 | 3-fluoro-4-methyl-phenyl | H | trifluoromethyl | H | H |
| 283 | b = 0 | 2-fluoro-4-methyl-phenyl | H | trifluoromethyl | H | H |
| 284 | b = 0 | 3-fluoro-4-chloro-phenyl | H | trifluoromethyl | H | H |
| 285 | b = 0 | 2-fluoro-4-chloro-phenyl | H | trifluoromethyl | H | H |
| 286 | b = 0 | 2-methyl-4-chloro-phenyl | H | methyl | fluoro | H |
| 287 | b = 0 | 2-methyl-4-methoxy-phenyl | H | trifluoromethyl | H | H |
| 288 | b = 0 | 4-methoxy-phenyl | H | chloro | H | H |
| 289 | b = 0 | 4-chloro-phenyl | H | methyl | fluoro | H |
| 290 | b = 0 | 4-ethyl-phenyl | H | methyl | fluoro | H |
| 291 | b = 0 | 2-phenyl-4-methyl-phenyl | H | trifluoromethyl | H | H |
| 292 | b = 0 | 3-phenyl-4-methyl-phenyl | H | trifluoromethyl | H | H |
| 293 | b = 0 | 4-ethyl-phenyl | H | chloro | H | H |
| 294 | b = 0 | 4-ethyl-phenyl | H | trifluoromethyl | H | H |
| 295 | b = 0 | 2-chloro-phenyl | H | chloro | H | H |
| 296 | b = 0 | 3-fluoro-4-methyl-phenyl | H | chloro | H | H |
| 297 | b = 0 | 3-fluoro-phenyl | H | chloro | H | H |
| 298 | b = 0 | 3-methyl-phenyl | H | chloro | H | H |
| 299 | b = 0 | 4-bromo-phenyl | H | methyl | fluoro | H |
| 300 | b = 0 | 4-trifluoromethyl-phenyl | H | trifluoromethyl | H | H |
| 301 | b = 0 | 4-methoxy-phenyl | H | trifluoromethyl | H | H |

TABLE 1-continued

Representative Compounds of Formula (I)

| | | | | | | |
|---|---|---|---|---|---|---|
| 302-D[a] | b = 0 | 4-methyl-phenyl | H | chloro | H | H |
| 303-D[a] | b = 0 | 4-methyl-phenyl | H | methyl | fluoro | H |
| 304 | b = 0 | 4-fluoro-phenyl | H | methyl | fluoro | H |
| 305 | b = 0 | 3-fluoro-phenyl | H | methyl | fluoro | H |
| 306 | 3-methyl | phenyl | H | trifluoromethyl | H | H |
| 307 | b = 0 | 4-methyl-phenyl | H | trifluoromethyl | H | H |
| 308 | b = 0 | 4-trifluoromethoxy-phenyl | H | trifluoromethyl | H | H |
| 310 | b = 0 | 4-methyl-phenyl | H | chloro | H | H |
| 311 | b = 0 | 4-trifluoromethoxy-phenyl | H | chloro | H | H |
| 312 | b = 0 | 3-methyl-phenyl | H | trifluoromethyl | H | H |
| 313 | b = 0 | 2-chloro-phenyl | H | trifluoromethyl | H | H |
| 314 | b = 0 | benzyl | H | methyl | fluoro | H |
| 315 | b = 0 | benzyl | m | H | H | H |
| 316 | 3-methyl | 4-chloro-phenyl | H | trifluoromethyl | H | H |
| 317 | 3-methyl | 4-chloro-phenyl | H | methyl | fluoro | H |
| 318 | b = 0 | 3-methyl-phenyl | H | methyl | fluoro | H |
| 319 | b = 0 | benzyl | H | trifluoromethyl | H | H |
| 320 | 3-methyl | phenyl | H | chloro | H | H |
| 321 | 3-methyl | phenyl | H | H | H | H |
| 322 | b = 0 | benzyl | H | H | H | H |
| 323 | 3-methyl | phenyl | H | methyl | fluoro | H |
| 325 | b = 0 | 4-trifluoromethoxy-phenyl | H | methyl | fluoro | H |
| 326 | b = 0 | 4-methyl-phenyl | H | methyl | fluoro | H |
| 327 | 3-methyl | 4-chloro-phenyl | H | chloro | H | H |
| 328 | 3-methyl | 4-chloro-phenyl | H | H | H | H |
| 329 | b = 0 | benzyl | H | chloro | H | H |
| 330 | b = 0 | benzyl | fluoro | H | fluoro | H |
| 331 | b = 0 | 2-isopropyl-4-methyl-phenyl | H | trifluoromethyl | H | H |
| 332 | 5-methyl | 4-chloro-phenyl | H | H | H | H |
| 333 | 5-methyl | 4-chloro-phenyl | H | methyl | fluoro | H |
| 334 | 5-methyl | phenyl | H | chloro | H | H |
| 336 | 5-methyl | 4-chloro-phenyl | H | trifluoromethyl | H | H |
| 337 | 5-methyl | 4-chloro-phenyl | H | chloro | H | H |
| 338 | 5-methyl | phenyl | H | methyl | fluoro | H |
| 339 | b = 0 | 2-fluoro-5-chloro-phenyl | H | methyl | fluoro | H |
| 340 | b = 0 | 2-fluoro-5-methyl-phenyl | H | methyl | fluoro | H |
| 341 | b = 0 | 2-fluoro-5-methyl-phenyl | H | trifluoromethyl | H | H |
| 342 | b = 0 | 2-fluoro-5-chloro-phenyl | H | chloro | H | H |
| 343 | b = 0 | 2-fluoro-5-methyl-phenyl | H | chloro | H | H |
| 344 | b = 0 | 2-fluoro-5-chloro-phenyl | H | trifluoromethyl | H | H |
| 345 | b = 0 | 4-methyl-benzyl | H | trifluoromethyl | H | H |
| 346 | b = 0 | 4-methyl-benzyl | H | H | H | H |
| 347 | b = 0 | 4-methyl-benzyl | H | methyl | fluoro | H |
| 348 | b = 0 | 4-methyl-benzyl | H | chloro | H | H |
| 349 | b = 0 | 4-fluoro-benzyl | H | chloro | H | H |
| 350 | b = 0 | 4-fluoro-benzyl | H | methyl | fluoro | H |
| 351 | b = 0 | cyclopropyl | H | trifluoromethyl | H | H |
| 352 | b = 0 | cyclohex-1-en-1-yl | H | methyl | fluoro | H |
| 353 | b = 0 | 4-fluoro-benzyl | H | trifluoromethyl | H | H |
| 354 | b = 0 | cyclohex-1-en-1-yl | H | trifluoromethyl | H | H |
| 355 | b = 0 | cyclohex-1-en-1-yl | H | chloro | H | H |
| 356 | b = 0 | 4-chloro-benzyl | H | chloro | H | H |
| 357 | 4,4-difluoro | benzyl | H | methyl | fluoro | H |
| 358 | 4,4-difluoro | benzyl | H | trifluoromethyl | H | H |
| 359 | b = 0 | 4-chloro-benzyl | H | trifluoromethyl | H | H |
| 360 | b = 0 | 4-chloro-benzyl | H | methyl | fluoro | H |
| 361 | b = 0 | 3-fluoro-benzyl | H | trifluoromethyl | H | H |
| 362 | b = 0 | 3-fluoro-benzyl | H | chloro | H | H |
| 363 | b = 0 | 3-fluoro-benzyl | H | methyl | fluoro | H |
| 364 | 4,4-difluoro | benzyl | H | chloro | H | H |
| 365 | b = 0 | n-butyl | H | H | H | H |
| 366 | 5-methyl | phenyl | H | H | H | H |
| 367 | 5-methyl | phenyl | H | trifluoromethyl | H | H |
| 369 | b = 0 | cyclohexyl-methyl | H | trifluoromethyl | H | H |
| 370 | b = 0 | n-butyl | H | trifluoromethyl | H | H |
| 372 | b = 0 | phenyl-ethyl | H | trifluoromethyl | H | H |
| 373 | b = 0 | cyclopropyl | H | methyl | fluoro | H |
| 374 | b = 0 | 3-methyl-n-butyl | H | trifluoromethyl | H | H |
| 375 | 4,4-difluoro | 4-chloro-phenyl | H | methyl | fluoro | H |
| 377 | b = 0 | isopropyl | H | trifluoromethyl | H | H |
| 380 | b = 0 | n-pent-3-yl | H | trifluoromethyl | H | H |
| 381 | 4,4-difluoro | isobutyl | H | trifluoromethyl | H | H |
| 382 | 4,4-difluoro | cyclobutyl | H | trifluoromethyl | H | H |
| 384 | b = 0 | isobutyl | H | H | H | H |
| 385 | b = 0 | isobutyl | H | trifluoromethyl | H | H |
| 386 | b = 0 | cyclohexyl-methyl | H | trifluoromethyl | H | H |
| 387 | b = 0 | 2,2-dimethyl-n-propyl | H | trifluoromethyl | H | H |

TABLE 1-continued

Representative Compounds of Formula (I)

| | | | | | | |
|---|---|---|---|---|---|---|
| 388 | b = 0 | 1-methyl-n-propyl | H | trifluoromethyl | H | H |
| 389 | b = 0 | n-propyl | H | trifluoromethyl | H | H |
| 390 | b = 0 | (1S,4S)-2-methyl-bicyclo[2.2.1]hept-2-yl | H | trifluoromethyl | H | H |
| 392 | 4,4-difluoro | 4-bromo-phenyl | H | methyl | fluoro | H |
| 393 | 4,4-difluoro | 4-bromo-phenyl | H | chloro | H | H |
| 394 | b = 0 | isobutyl | H | chloro | H | H |
| 395 | b = 0 | cyclo-pentyl | H | H | H | H |
| 397 | b = 0 | cyclobutyl | H | H | H | H |
| 398 | b = 0 | cyclo-pentyl | H | trifluoromethyl | H | H |
| 399 | b = 0 | cyclobutyl | H | trifluoromethyl | H | H |
| 400 | b = 0 | cyclobutyl | H | chloro | H | H |
| 401 | 4,4-difluoro | 4-fluoro-phenyl | H | chloro | H | H |
| 402 | 4,4-difluoro | 4-fluoro-phenyl | H | methyl | fluoro | H |
| 403 | b = 0 | phenyl-carbonyl- | H | trifluoromethyl | H | H |
| 404 | b = 0 | 2-fluoro-benzyl | H | trifluoromethyl | H | H |
| 405 | b = 0 | 3-methyl-benzyl | H | trifluoromethyl | H | H |
| 406 | b = 0 | 3-methyl-benzyl | H | chloro | H | H |
| 407 | 4,4-difluoro | cyclo-pentyl | H | trifluoromethyl | H | H |
| 409 | 4,4-difluoro | cyclo-pentyl | H | chloro | H | H |
| 410 | b = 0 | cyclo-pentyl | H | isopropyl | H | H |
| 411 | b = 0 | 4,4-difluoro-cyclohex-1-yl | H | chloro | H | H |
| 412 | b = 0 | 4,4-difluoro-cyclohex-1-yl | H | H | H | H |
| 413 | b = 0 | 4,4-difluoro-cyclohex-1-yl | methyl | methyl | H | H |
| 414 | b = 0 | cyclopentyl | H | cyano | H | H |
| 415 | b = 0 | tetrahydro-pyran-4-yl | H | trifluoromethyl | H | H |
| 416 | b = 0 | 4,4-difluoro-cyclohex-1-yl | H | trifluoromethyl | H | H |
| 417 | b = 0 | 4,4-difluoro-cyclohex-1-yl | H | methyl | fluoro | H |
| 418 | b = 0 | tetrahydro-pyran-4-yl | H | chloro | H | H |
| 419 | b = 0 | 4,4-difluoro-cyclohex-1-yl | H | fluoro | H | fluoro |
| 420 | b = 0 | cyclopentyl-methyl- | H | trifluoromethyl | H | H |
| 421 | b = 0 | cyclo-pentyl | H | bromo | H | H |
| 422 | b = 0 | cyclo-pentyl | H | methyl | H | H |
| 423 | b = 0 | cyclo-pentyl | H | ethyl | H | H |
| 424 | b = 0 | cyclo-pentyl | H | methyl | fluoro | H |
| 425 | b = 0 | cyclo-pentyl | fluoro | H | H | H |
| 426 | b = 0 | cyclo-pentyl | H | fluoro | H | H |
| 427 | b = 0 | cyclo-pentyl-methyl- | methyl | methyl | H | H |
| 428 | b = 0 | cyclo-pentyl | H | chloro | H | H |
| 429 | 4,4-difluoro | 1-fluoro-cyclobut-1-yl | H | trifluoromethyl | H | H |
| 430 | 4,4-difluoro | cyclobutyl | H | chloro | H | H |
| 431 | b = 0 | cyclo-pentyl | fluoro | methyl | H | H |
| 432 | b = 0 | cyclo-pentyl | methyl | methyl | H | H |
| 433 | b = 0 | cyclo-pentyl | fluoro | H | H | trifluoromethyl |
| 434 | b = 0 | cyclo-pentyl | H | methoxy | H | H |
| 435 | b = 0 | cyclo-pentyl | fluoro | trifluoromethyl | H | H |
| 436 | b = 0 | cyclo-pentyl | fluoro | H | fluoro | H |
| 438 | b = 0 | 2-fluoro-benzyl | H | chloro | H | H |
| 439 | b = 0 | cyclo-pentyl | H | fluoro | H | trifluoromethyl |
| 440 | b = 0 | thiazol-2-yl-methyl- | H | trifluoromethyl | H | H |
| 441 | 4,4-difluoro | cyclo-pentyl | H | methyl | H | H |
| 442 | b = 0 | cyclo-pentyl | H | vinyl | H | H |
| 443 | b = 0 | cyclo-pentyl | H | 1-hydroxy-ethyl | H | H |
| 444 | b = 0 | cyclo-pentyl | H | cyclopropyl | H | H |
| 445 | b = 0 | thiazol-2-yl-methyl- | H | chloro | H | H |
| 446 | b = 0 | cyclo-pentyl | H | 1,1,2,2,2-pentafluoro-ethyl | H | H |
| 448 | b = 0 | cyclo-pentyl | H | 1-bromo-vinyl | H | H |
| 450 | b = 0 | cyclo-pentyl | fluoro | H | H | chloro |
| 451 | b = 0 | cyclopenten-3-yl | H | chloro | H | H |
| 452 | b = 0 | cyclopenten-3-yl | H | H | H | H |
| 453 | b = 0 | cyclopenten-3-yl | H | trifluoromethyl | H | H |
| 454 | b = 0 | cyclo-pentyl | H | ethynyl | H | H |
| 455 | b = 0 | bicyclo[3.1.0]hex-2-yl | H | H | H | H |
| 456 | b = 0 | bicyclo[3.1.0]hex-2-yl | H | trifluoromethyl | H | H |
| 457 | 4,4-difluoro | cyclo-pentyl | H | fluoro | H | H |

TABLE 1-continued

Representative Compounds of Formula (I)

| ID No. | (R⁰)_b | R¹ | R² | R⁵ | R³ | R⁴ |
|---|---|---|---|---|---|---|
| 34 | b = 0 | 4-chloro-phenyl | fluoro | H | H | H |
| 36 | b = 0 | 4-chloro-phenyl | methyl | H | H | H |
| 144 | b = 0 | 4-chloro-phenyl | fluoro | H | fluoro | H |
| 160 | b = 0 | 4-fluoro-phenyl | methyl | H | H | H |
| 458 | b = 0 | 4-fluoro-phenyl | fluoro | H | H | H |

| ID No. | (R⁰)_b | R¹ | R² and R⁵ taken together | R³ | R⁴ |
|---|---|---|---|---|---|
| 123 | b = 0 | 4-chloro-phenyl | cyclopenten-1-yl | H | H |

*a*Compound #126-D is deuterated with two deuterium atoms on the —CH₂CH₂CO₂H substituent, as -CHD-CHD-CO₂H; Compound #268-D is deuterated with three deuterium atoms on the methyl of the 4-methylphenyl (R¹) substituent group, as 4-CD₃-phenyl; Compound #302-D is deuterated with three deuterium atoms on the methyl of the 4-methylphenyl (R¹) substituent group, as 4-CD₃-phenyl, Compound #303-D is deuterated with three deuterium atoms on the methyl of the 4-methylphenyl (R¹) substituent group, as 4-CD₃-phenyl.

TABLE 2

Representative Compounds of Formula (I)

| ID No. | (R⁰)_b | R¹ | R² | R⁵ | R³ | R⁴ |
|---|---|---|---|---|---|---|
| 460 | b = 0 | 4-trifluoromethyl-phenyl | methyl | methyl | H | H |
| 461 | b = 0 | 4-ethoxy-phenyl | methyl | methyl | H | H |
| 462 | b = 0 | 4-methyl-phenyl | methyl | methyl | H | H |
| 463 | b = 0 | 4-n-propyl-phenyl | methyl | methyl | H | H |
| 464 | b = 0 | 2-chloro-phenyl | methyl | methyl | H | H |
| 465 | b = 0 | pyrid-4-yl | methyl | methyl | H | H |
| 466 | b = 0 | 4-trifluoromethoxy-phenyl | methyl | methyl | H | H |
| 467 | 5,5-difluoro | 4-chloro-phenyl | methyl | H | H | H |
| 468 | 5,5-difluoro | 4-chloro-phenyl | methyl | methyl | H | H |
| 472 | b = 0 | phenyl | methyl | methyl | H | H |
| 474 | b = 0 | 4-chloro-phenyl | methyl | methyl | H | H |
| 475 | b = 0 | pyrimidin-2-yl | methyl | methyl | H | H |
| 476 | b = 0 | 4-iodo-phenyl | methyl | methyl | H | H |
| 477 | b = 0 | 6-methyl-pyrid-3-yl | methyl | H | H | H |
| 478 | 3-ethyl | 4-chloro-phenyl | methyl | methyl | H | H |
| 479 | b = 0 | 4-chloro-phenyl | fluoro | fluoro | fluoro | fluoro |
| 480 | b = 0 | 4-fluoro-phenyl | methyl | methyl | H | H |
| 481 | b = 0 | 4-bromo-phenyl | methyl | methyl | H | H |
| 482 | b = 0 | thien-2-yl | methyl | methyl | H | H |
| 483 | b = 0 | 4-chloro-phenyl | methyl | H | H | H |
| 489 | 5,5-difluoro | 4-fluoro-phenyl | H | trifluoromethyl | H | H |
| 490 | b = 0 | pyrid-2-yl | methyl | methyl | H | H |
| 491 | 5,5-difluoro | 4-chloro-phenyl | fluoro | H | fluoro | H |
| 492 | b = 0 | 4-methyl-thio-phenyl | methyl | methyl | H | H |
| 493 | b = 0 | 3-fluoro-4-methyl-phenyl | fluoro | H | fluoro | H |
| 494 | b = 0 | 3-fluoro-4-methyl-phenyl | fluoro | fluoro | H | H |
| 495 | b = 0 | 4-(methyl-carbonyl-amino)-phenyl | methyl | methyl | H | H |

TABLE 2-continued

Representative Compounds of Formula (I)

| | | | | | | |
|---|---|---|---|---|---|---|
| 496 | b = 0 | 3-fluoro-4-methyl-phenyl | methyl | methyl | H | H |
| 497 | 5,5-difluoro | 4-fluoro-phenyl | methyl | methyl | H | H |
| 498 | 5,5-difluoro | 4-fluoro-phenyl | methyl | H | H | H |
| 499 | 5,5-difluoro | 4-fluoro-phenyl | H | H | H | H |
| 500 | 4-isopropyl | 4-chloro-phenyl | methyl | methyl | H | H |
| 501 | 5-isopropyl | 4-chloro-phenyl | methyl | methyl | H | H |
| 502 | 5-ethyl | 4-chloro-phenyl | methyl | methyl | H | H |
| 503 | 5,5-difluoro | 4-chloro-phenyl | fluoro | fluoro | H | H |
| 504 | b = 0 | 4-chloro-phenyl | H | fluoro | H | H |
| 506 | b = 0 | 4-chloro-phenyl | H | methyl | H | H |
| 507 | b = 0 | 4-methyl-sulfinyl-phenyl | methyl | methyl | H | H |
| 509 | b = 0 | 3-chloro-phenyl | methyl | methyl | H | H |
| 510 | b = 0 | 4-chloro-phenyl | fluoro | H | fluoro | H |
| 511 | b = 0 | 4-chloro-phenyl | fluoro | H | H | H |
| 512 | b = 0 | 4-dimethyl-amino-phenyl | methyl | methyl | H | H |
| 513 | b = 0 | 4-chloro-phenyl | fluoro | fluoro | H | H |
| 515 | b = 0 | 4-methyl-sulfonyl-phenyl | methyl | methyl | H | H |
| 516 | b = 0 | 4-isopropyl-phenyl | methyl | methyl | H | H |
| 517 | b = 0 | 4-chloro-phenyl | H | H | H | H |
| 518 | 5,5,-difluoro | 4-fluoro-phenyl | H | methyl | H | H |
| 519 | 5,5-difluoro | 4-chloro-phenyl | H | methyl | H | H |
| 520 | b = 0 | 4-cyano-phenyl | methyl | methyl | H | H |
| 521 | b = 0 | 6-methyl-pyrid-3-yl | methyl | methyl | H | H |
| 522 | 4-ethyl | 4-chloro-phenyl | methyl | methyl | H | H |
| 523 | 3-isopropyl | 4-chloro-phenyl | methyl | methyl | H | H |
| 524 | b = 0 | 4-iodo-phenyl | methyl | methyl | iodo | H |
| 525 | 5,5-difluoro | 3-fluoro-4-methyl-phenyl | fluoro | H | fluoro | H |
| 526 | 5,5-difluoro | 3-fluoro-4-chloro-phenyl | methyl | methyl | H | H |
| 527 | 5,5-difluoro | 3-fluoro-4-chloro-phenyl | methyl | H | H | H |
| 528 | 5,5-difluoro | 3-fluoro-4-chloro-phenyl | fluoro | H | fluoro | H |
| 529 | 5,5-difluoro | 3-fluoro-4-methyl-phenyl | methyl | methyl | H | H |
| 530 | 5,5-difluoro | 3-fluoro-4-methyl-phenyl | methyl | H | H | H |
| 531 | 5,5-difluoro | 3,4-difluoro-phenyl | methyl | methyl | H | H |
| 532 | 5,5-difluoro | 3,4-difluoro-phenyl | methyl | H | H | H |
| 533 | 5,5-difluoro | 3,4-difluoro-phenyl | fluoro | H | fluoro | H |
| 534 | 5,5-difluoro | 2,4-difluoro-phenyl | methyl | methyl | H | H |
| 535 | 5,5-difluoro | 2,4-difluoro-phenyl | methyl | H | H | H |
| 536 | 5,5-difluoro | 2,4-difluoro-phenyl | fluoro | H | fluoro | H |
| 537 | 5,5-difluoro | phenyl | methyl | methyl | H | H |
| 538 | 5,5-difluoro | phenyl | methyl | H | H | H |
| 539 | 5,5-difluoro | phenyl | fluoro | H | fluoro | H |
| 540 | 5-methoxy | 4-chloro-phenyl | methyl | methyl | H | H |
| 541 | 5,5-dimethyl | 4-chloro-phenyl | methyl | methyl | H | H |
| 542 | 5,5-difluoro | 5-chloro-thien-2-yl | methyl | H | H | H |
| 543 | 5,5-difluoro | 5-chloro-thien-2-yl | fluoro | H | fluoro | H |
| 544 | 5,5-difluoro | 1-methyl-imidazol-4-yl | fluoro | H | fluoro | H |
| 545 | 5,5-difluoro | 1-methyl-imidazol-4-yl | methyl | methyl | H | H |
| 546 | 5,5-difluoro | 1-methyl-imidazol-4-yl | methyl | H | H | H |
| 547 | 5,5-difluoro | thiazol-5-yl | methyl | methyl | H | H |
| 548 | 5,5-difluoro | thiazol-5-yl | methyl | H | H | H |
| 549 | 5,5-difluoro | thiazol-5-yl | fluoro | H | fluoro | H |
| 550 | 5,5-difluoro | 2-methyl-thiazol-5-yl | methyl | H | H | H |
| 551 | 5,5-difluoro | 4-chloro-phenyl | 4-(methyl-sulfonyl)-n-butyl | H | H | H |
| 552 | 5,5-difluoro | furan-2-yl | methyl | methyl | H | H |
| 553 | 5,5-difluoro | 2-methyl-thiazol-5-yl | methyl | methyl | H | H |
| 554 | 5,5-difluoro | 2-methyl-thiazol-5-yl | fluoro | H | fluoro | H |
| 555 | 5,5-difluoro | furan-2-yl | methyl | H | H | H |
| 557 | 5,5-difluoro | thien-2-yl | methyl | methyl | H | H |
| 558 | 5,5-difluoro | 5-cyano-thien-2-yl | methyl | methyl | H | H |
| 559 | 5,5-difluoro | thien-2-yl | fluoro | H | fluoro | H |
| 560 | 5,5-difluoro | thien-2-yl | methyl | H | H | H |
| 561 | 5,5-difluoro | 5-methyl-thien-2-yl | methyl | H | H | H |
| 562 | 5,5-difluoro | 5-methyl-thien-2-yl | fluoro | H | fluoro | H |
| 563 | 5,5-difluoro | 5-chloro-thien-2-yl | methyl | methyl | H | H |
| 564 | 5,5-difluoro | 5-methyl-thien-2-yl | methyl | methyl | H | H |
| 565 | 5,5-difluoro | 4-chloro-phenyl | 4-(methyl-thio)-n-butyl | H | H | H |
| 566 | 4,4-difluoro | 4-chloro-phenyl | methyl | H | H | H |
| 567-D[b] | 5,5-difluoro | 4-chloro-phenyl | methyl | H | H | H |
| 568 | 4,4-difluoro | 4-chloro-phenyl | methyl | methyl | H | H |
| 569 | 5,5-difluoro | furan-2-yl | fluoro | H | fluoro | H |
| 572 | 5,5-difluoro | 5-cyano-thien-2-yl | fluoro | H | fluoro | H |
| 573 | 5,5-difluoro | 5-cyano-thien-2-yl | methyl | H | H | H |
| 574 | 5-methoxy | 4-methyl-phenyl | H | H | H | H |
| 575 | 5-methoxy | 2-methyl-phenyl | H | H | H | H |
| 576 | 5-methoxy | 2-methyl-phenyl | H | trifluoromethyl | H | H |
| 577 | 5-methoxy | 4-methyl-phenyl | H | trifluoromethyl | H | H |
| 578 | b = 0 | isobutyl | H | H | H | H |
| 579 | b = 0 | isobutyl | H | trifluoromethyl | H | H |

TABLE 2-continued

Representative Compounds of Formula (I)

| | | | | | | |
|---|---|---|---|---|---|---|
| 580 | b = 0 | isobutyl | H | chloro | H | H |
| 581 | b = 0 | benzyl | H | H | H | H |
| 582 | b = 0 | benzyl | H | chloro | H | H |
| 583 | b = 0 | n-butyl | H | chloro | H | H |
| 584 | b = 0 | benzyl | H | trifluoromethyl | H | H |
| 585 | b = 0 | isopropyl | H | H | H | H |
| 586 | b = 0 | isopropyl | H | trifluoromethyl | H | H |
| 587 | b = 0 | isopropyl | H | chloro | H | H |
| 588 | b = 0 | n-butyl | H | H | H | H |
| 589 | b = 0 | n-propyl | H | H | H | H |
| 590 | b = 0 | n-propyl | H | trifluoromethyl | H | H |
| 591 | b = 0 | n-propyl | H | chloro | H | H |
| 592 | b = 0 | (1R,2R,4S)-bicyclo[2.2.1]heptan-2-yl | H | trifluoromethyl | H | H |
| 593 | b = 0 | (1R,2R,4S)-bicyclo[2.2.1]heptan-2-yl | H | chloro | H | H |
| 594 | b = 0 | cyclopentyl | H | chloro | H | H |
| 595 | b = 0 | thiazol-5-yl-methyl | H | chloro | H | H |
| 596 | b = 0 | thiazol-5-yl-methyl | H | trifluoromethyl | H | H |
| 598 | b = 0 | n-butyl | H | trifluoromethyl | H | H |
| 599 | b = 0 | cyclobutyl | H | trifluoromethyl | H | H |
| 600 | b = 0 | cyclobutyl | H | chloro | H | H |
| 601 | b = 0 | cyclohexyl | H | trifluoromethyl | H | H |
| 602 | b = 0 | cyclohexyl | H | chloro | H | H |
| 603 | b = 0 | cyclopentyl | H | trifluoromethyl | H | H |
| 604 | 5,5-dimethyl | cyclopentyl | H | trifluoromethyl | H | H |
| 605 | 5,5-dimethyl | cyclopentyl | H | chloro | H | H |
| 606 | 5,5-difluoro | cyclopentyl | H | trifluoromethyl | H | H |
| 607 | 5,5-difluoro | cyclopentyl | H | chloro | H | H |

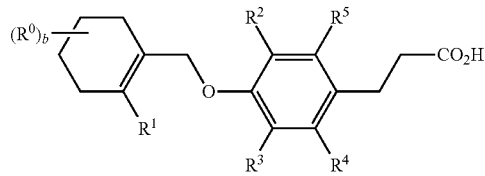

| ID No. | $(R^0)_b$ | $R^1$ | $R^2$ and $R^5$ taken together | $R^3$ | $R^4$ |
|---|---|---|---|---|---|
| 514 | b = 0 | 4-chloro-phenyl | cyclo-penten-1-yl | H | H |

[b]Compound #567-D is deuterated with two deuterium atoms on the —CH$_2$— group bound at the 1-position to the 5,5-difluoro-cyclohexen-1-yl substituent.

TABLE 3

Representative Compounds of Formula (I)

| ID No | $(R^0)_b$ | $R^1$ | $R^2$ | $R^5$ |
|---|---|---|---|---|
| 610 | 5,5-difluoro | cyclopentyl | H | fluoro |
| 611 | 5,5-difluoro | cyclopentyl | H | H |
| 612 | b = 0 | cyclopentyl | H | trifluoromethyl |
| 613 | b = 0 | cyclopentyl | H | fluoro |
| 614 | b = 0 | cyclopentyl | H | H |
| 615 | b = 0 | 4-chloro-phenyl | methyl | methyl |
| 616 | 5,5-difluoro | 4-chloro-phenyl | methyl | methyl |
| 617 | 5,5-difluoro | cyclopentyl | H | trifluoromethyl |
| 618 | 5,5-difluoro | cyclopentyl | methyl | methyl |

In an embodiment, the present invention is directed to a compound of formula (I); wherein the compound of formula exhibits an $EC_{50}$ against GPR120, measured as described in the Biological Examples, which follow herein, of less than about 1.0 μM, preferably less than about 0.500 μM, more preferably less than about 0.250 μM, more preferably less than about 0.100 μM, more preferably less than about 0.050 μM, more preferably less than about 0.025 μM.

In an embodiment, the present invention is directed to a compound of formula (I); wherein the compound of formula exhibits an $EC_{50}$ against GPR40, measured as described in the Biological Examples, which follows herein, of less than about 1.0 μM, preferably less than about 0.500 μM, more preferably less than about 0.250 μM, more preferably less than about 0.100 μM, more preferably less than about 0.050 μM.

Definitions

As used herein, unless otherwise noted, the term "halogen" shall mean chlorine, bromine, fluorine and iodine.

As used herein, unless otherwise noted, the term "oxo" shall mean an oxygen atom bound through a double bond (i.e =O).

As used herein, unless otherwise noted, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. The term "$C_{X-Y}$alkyl" wherein X and Y are integers, whether used alone or as part of a substituent group, include straight and branched chains of between X and Y carbon atoms. For example, the term "$C_{1-4}$alkyl" includes straight and branched chains of between 1 and 4 carbon atoms, including methyl, ethyl, n-propyl, isopropyl, n-butyl, isobutyl and tert-butyl.

One skilled in the art will recognize that the term "—($C_{X-Y}$alkyl)-" shall denote any $C_{1-4}$alkyl carbon chain as herein defined, wherein said $C_{X-Y}$alkyl chain is divalent and is further bound through two points of attachment, preferably through two terminal carbon atoms.

As used herein, unless otherwise noted, the term "fluorinated $C_{X-Y}$alkyl" shall mean any $C_{X-Y}$alkyl group as defined above substituted with at least one fluoro atom. For example, the term fluorinated $C_{1-4}$alkyl shall mean any $C_{1-4}$ alkyl group as defined above substituted with at least one, preferably one to five, more preferably one to three fluoro atoms. Suitable examples of fluorinated $C_{X-Y}$alkyl groups include, but are not limited to —$CF_3$, —$CH_2$—$CF_3$, —$CF_2CF_3$, —$CF_2$—$CF_2$—$CF_2$—$CF_3$, and the like.

As used herein, unless otherwise noted, the term "hydroxy substituted $C_{X-Y}$alkyl" shall mean a $C_{X-Y}$alkyl group as defined above substituted with at least one hydroxy group. Preferably, the $C_{X-Y}$alkyl group is substituted with one hydroxy group. Preferably, the $C_{X-Y}$alkyl group is substituted with a hydroxy group at the terminal carbon. Suitable examples include, but are not limited to, —$CH_2(OH)$, —$CH_2$—$CH_2(OH)$, —$CH_2$—$CH(OH)$—$CH_2$, and the like.

As used herein, unless otherwise noted, the term "halogen substituted vinyl" shall mean a vinyl (i.e —CH=$CH_2$) group substituted with one or more, preferably one to two, more preferably one independently selected halogen atoms as defined above. Preferably, the halogen substituted vinyl is substituted with one fluoro, chloro, bromo or iodo group. More preferably the halogen substituted vinyl is a bromo substituted vinyl.

As used herein, unless otherwise noted, the term "$C_{X-Y}$alkynyl" shall mean a straight or branched chain of between X and Y carbon atoms, wherein the straight or branched chain contains as least one, preferably one, unsaturated triple bond. For example, the term "$C_{2-6}$alkynyl" includes straight and branched chains of between 2 and 6 carbon atoms containing at least one, preferably one, unsaturated triple bond such as ethynyl, n-propyn-1-yl, n-pentyn-1-yl, pentyn-2-yl, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. The term "$C_{X-Y}$alkoxy" wherein X and Y are integers, whether used alone or as part of a substituent group, shall denote an oxygen ether radical of the above described straight or branched chain of between X and Y carbon atoms. For example, the term "$C_{1-4}$alkoxy" includes oxygen ether radicals of straight and branched chains of between 1 and 4 carbon atoms, including methoxy, ethoxy, n-propoxy, isopropoxy, n-butoxy, isobutoxy and tert-butoxy.

As used herein, unless otherwise noted, the term "fluorinated $C_{X-Y}$alkoxy" shall mean any $C_{X-Y}$alkoxy group as defined above substituted with at least one fluoro atom. For example, the term fluorinated $C_{1-4}$alkoxy shall mean any $C_{1-4}$alkoxy group as defined above substituted with at least one, preferably one to five, more preferably one to three fluoro atoms. Suitable examples of fluorinated $C_{X-Y}$alkoxy groups include, but are not limited to —$OCF_3$, —$OCH_2$—$CF_3$, —$CF_2CF_3$, —$OCF_2$—$CF_2$—$CF_2$—$CF_3$, and the like.

As used herein, unless otherwise noted, the term "$C_{3-6}$cycloalkyl" shall mean any stable 3-8 membered monocyclic, saturated ring system, for example cyclopropyl, cyclobutyl, cyclopentyl, cyclohexyl, cycloheptyl and cyclooctyl. Similarly, the term "$C_{5-6}$cycloalkyl" shall mean any stable 5-6 membered monocyclic, saturated ring system, more particularly cyclopentyl and cyclohexyl.

As used herein, unless otherwise noted, the term "$C_{5-6}$cycloalkenyl" shall mean any stable 5-6 membered monocyclic, partially unsaturated ring system, wherein the partially unsaturated ring system contains one to two, preferably one unsaturated double bond. Suitably examples include, but are not limited to cyclopentenyl and cyclohexenyl.

When a particular group is "substituted" (e.g., alkyl, cycloalkyl, phenyl, pyridyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isotopologues" shall mean molecules that differ only in their isotopic composition. More particularly, an isotopologue of a molecule differs from the parent molecule in that it contains at least one atom which is an isotope (i.e. has a different number of neutrons from its parent atom).

For example, isotopologues of water include, but are not limited to, "light water" (HOH or $H_2O$), "semi-heavy water" with the deuterium isotope in equal proportion to protium (HDO or $^1H^2HO$), "heavy water" with two deuterium isotopes of hydrogen per molecule ($D_2O$ or $^2H_2O$), "super-heavy water" or tritiated water ($T_2O$ or $^3H_2O$), where the hydrogen atoms are replaced with tritium ($^3H$) isotopes, two heavy-oxygen water isotopologues ($H_2^{18}O$ and $H_2^{17}O$) and isotopologues where the hydrogen and oxygen atoms may each independently be replaced by isotopes, for example the doubly labeled water isotopologue $D_2{}^{18}O$.

It is intended that within the scope of the present invention, any one or more element(s), in particular when mentioned in relation to a compound of formula (I), shall comprise all isotopes and isotopic mixtures of said element(s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise one or more radioactive isotope(s) selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$ $^{11}C$ and $^{18}F$.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

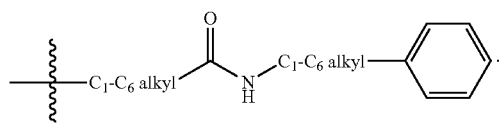

In the definition of the

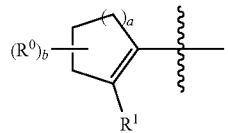

substituent group, wherein the compounds of the present invention b is an integer from 1 to 2, the position at which the $R^0$ groups are bound onto the cycloalkenyl portion of the compound of formula (I) are denoted as indicated below:

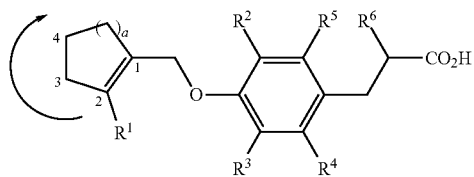

wherein the 1-position is defined as the alkene carbon bound to the —$CH_2$—O— portion of the compound of formula (I), the 2-position is defined as the alkene carbon bound to the $R^1$ group, and the remaining carbon atoms of the cycloalkenyl group are thereafter counted in a clockwise manner.

Abbreviations used in the specification, particularly the Schemes and Examples, are as follows:

| | |
|---|---|
| ADDP = | 1,1'-(Azodicarbonyl)dipiperidine |
| aq. = | Aqueous |
| BAST or Deoxo-Fluor ® = | Bis(2-methoxyethyl)aminosulfur trifluoride |
| $BF_3$•$EtO_2$ = | Boron Trifluoride Diethyl Etherate |
| BSA = | Bovine Serum Albumin |
| $Bu_4N^+F^-$ or TBAF = | Tetra-n-butylammonium fluoride (solution) |
| $Bu_3P$ or n-$Bu_3P$ = | Tri(n-butyl)phosphine |
| DAST = | Diethylaminosulfur trifluoride |
| DCE = | 1,2-Dichloroethane |
| DCM = | Dichloromethane |
| DEAD = | Diethylazodicarboxylate |
| Dess-Martin Periodinane = | 1,1,1-Tris(acetyloxy)-1,1-dihydro-1,2-benziodoxol-3-(1H)-one |
| DIAD = | Diisopropylazodicarboxylate |
| DIBAL or DIBAL-H or DiBAI-H = | Diisobutylaluminum hydride |
| DIO = | Diet-induced obese/obesity |
| DIPEA or DIEA = | Diisopropylethylamine |
| DMAC = | Dimethylacetamide |
| DME = | Dimethoxyethane |
| DMEM = | Dulbecco's Modified Eagle Medium |
| DMF = | N,N-Dimethylformamide |
| DMSO = | Dimethylsulfoxide |
| dppf = | 1,1'-Ferrocenediyl-bis(diphenylphosphine) |
| EA = | Ethyl Acetate |
| ESI = | Electrospray ionization |
| FBS = | Fetal Bovine Serum |
| FLIPR = | Fluorometric Imaging Plate Reader |
| GCMS = | Gas Chromatography Mass Spectroscopy |
| HBSS = | Hank's Balanced Salt Solution |
| HDL = | High Density Lipoproetin |
| HEPES = | 4-(2-Hydroxyethyl)-1-Piperizine Ethane Sulfonic Acid |
| $^1$H NMR = | $^1$Hydrogen Nuclear Magnetic Resonance |
| HPLC = | High Pressure Liquid Chromatography |
| i.p. = | Intra-peritoneal |
| IPGTT = | Intra-peritoneal Glucose Tolerance Test |
| KOt-Bu = | Potassium t-Butoxide |
| LAH = | Lithium Aluminum Hydride |
| LCMS = | Liquid Chromatography Mass Spectroscopy |
| LDL = | Low Density Lipoprotein |
| MeOH = | Methanol |
| Mesyl = | Methylsulfonyl |
| MOM = | Methoxymethyl |
| MOMCl = | Methoxymethyl chloride |
| MS = | Mass Spectroscopy |
| MTBE = | Methyl t-Butyl Ether |
| NASH = | Non-alcoholic Steatohepatitis |
| NAFLD = | Non-alcoholic Fatty Liver Disease |
| NMP = | N-Methyl-2-pyrrolidone |
| OGTT = | Oral Glucose Tolerance Test |
| OTf = | Triflate (i.e $CF_3SO_3$-) |
| $Pd_2(OAc)_2$ = | Palladium(II)acetate |
| $Pd_2(dba)_3$ = | Tris(dibenzylidene acetone)dipalladium(0) |
| Pd(dppf)$Cl_2$ or PdCl$_2$(dppf) = | [1,1'-Bis(diphenylphosphino)ferrocene] dichloropalladium(II) |
| Pd(PPh$_3$)$_4$ = | Tetrakistriphenylphosphine palladium (0) |
| Pd(PPh$_3$)$_2$Cl$_2$ or PdCl$_2$(PPh$_3$)$_2$ or (Ph$_3$P)$_2$PdCl$_2$ = | Bis(triphenylphosphine)palladium (II) chloride |
| PPh$_3$ or TPP = | Triphenyl Phosphine |
| PE = | Petroleum Ether |
| PO or p.o. = | Per os (oral) |
| Rochelle's salt = | Potassium sodium tartrate tetrahydrate |
| sat. = | saturated |
| SPhos = | 2-Dicyclohexylphosphino-2',6'-dimethoxybiphenyl |
| Swern reagent = | oxalyl chloride/DMSO |
| TBDMS = | t-Butyldimethylsilyl |
| TBDMSCl or TBDMS chloride = | t-Butyldimethylsilyl chloride |
| TEA = | Triethylamine |
| TFA = | Trifluoroacetic Acid |
| TfO$_2$ = | Triflic Anhydride |
| THF = | Tetrahydrofuran |
| THP = | Tetrahyropyranyl |
| TLC = | Thin Layer Chromatography |
| TMS = | Trimethylsilyl |
| Tosyl = | p-Toluenesulfonyl |

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein unless otherwise noted, the term "cardiovascular disorders" shall mean any cardiovascular disease, disorder or condition in which obesity and/or diabetes (preferably, Type II Diabetes Mellitus) has a role in the initiation or exacerbation of said disorder or condition. Suitable examples include, but are not limited to, hypertension, atherosclerosis, and cardiac fibrosis.

For purposes of the present invention, the term "modulated by the GPR120 receptor" is used to refer to the condition of being affected by the modulation of the GPR120 receptor, including but not limited to, the state of being mediated by activation or agonism of the GPR120 receptor.

For purposes of the present invention, the term "modulated by the GPR40 receptor" is used to refer to the condition of being affected by the modulation of the GPR40 receptor, including but not limited to, the state of being mediated by activation or agonism of the GPR40 receptor.

As used herein, unless otherwise noted, the term "disorder modulated by the GPR120 receptor" shall mean any disease, disorder or condition characterized in that at least one of its characteristic symptoms is alleviated or eliminated upon treatment with a GPR120 receptor agonist. Suitably examples include, but are not limited to obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD) and liver fibrosis.

Preferably, the disorder modulated by the GPR120 receptor is selected from the group consisting of obesity, impaired glucose tolerance, elevated fasting glucose, insulin resistance, hyperglycemia, hyperinsulinemia, Type II Diabetes Mellitus, metabolic syndrome (also known as Syndrome X), diabetic retinopathy, diabetic nephropathy, dyslipidemia, elevated LDL, hyperlipidemia, hypertriglyceridemia (i.e. elevated triglycerides), non-alcoholic steatohepatitis (NASH) and non-alcoholic fatty liver disease (NAFLD). More preferably, the disorder modulated by the GPR120 receptor is selected from the group consisting of obesity, Type II diabetes, metabolic syndrome (also known as Syndrome X), dyslipidemia. hypertriglyceridemia (i.e. elevated triglycerides), non-alcoholic steatohepatitis (NASH) and non-alcoholic fatty liver disease (NAFLD). More preferably, the disorder modulated by the GPR120 receptor is selected from the group consisting of obesity, Type II diabetes, metabolic syndrome (also known as Syndrome X), dyslipidemia and hypertriglyceridemia.

As used herein, unless otherwise noted, the term "disorder modulated by the GPR40 receptor" shall mean any disease, disorder or condition characterized in that at least one of its characteristic symptoms is alleviated or eliminated upon treatment with a GPR40 receptor agonist. Suitably examples include, but are not limited to obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis and cardiovascular disorders (including but not limited to hypertension, atherosclerosis, thrombotic disorders, and cardiac fibrosis).

Preferably, the disorder modulated by the GPR40 receptor is selected from the group consisting of obesity, impaired glucose tolerance, elevated fasting glucose, insulin resistance, hyperglycemia, hyperinsulinemia, Type II Diabetes Mellitus, metabolic syndrome (also known as Syndrome X), diabetic retinopathy, diabetic nephropathy, dyslipidemia, elevated LDL, hyperlipidemia, hypertriglyceridemia (i.e. elevated triglycerides), non-alcoholic steatohepatitis (NASH) and non-alcoholic fatty liver disease (NAFLD). More preferably, the disorder modulated by the GPR40 receptor is selected from the group consisting of obesity, Type II diabetes, metabolic syndrome (also known as Syndrome X), dyslipidemia. hypertriglyceridemia (i.e. elevated triglycerides), non-alcoholic steatohepatitis (NASH) and non-alcoholic fatty liver disease (NAFLD). More preferably, the disorder modulated by the GPR40 receptor is selected from the group consisting of obesity, Type II diabetes, metabolic syndrome (also known as Syndrome X), dyslipidemia and hypertriglyceridemia For purposes of the present invention, the terms "modulated by the GPR120 and GPR40 receptor", "responds to dual agonism of the GPR120 and GPR40 receptors" and "responds to agonism of both the GPR120 and GPR40 receptors" are used to refer to the condition of being affected by the modulation of both the GPR120 and the GPR40 receptor, including but not limited to, the state of being mediated by the activation or agonism of both the GPR120 and the GPR40 receptor.

As used herein, unless otherwise noted, the terms "modulated by the GPR120 and GPR40 receptor", "responds to dual agonism of the GPR120 and GPR40 receptors" and "responds to agonism of both the GPR120 and GPR40 receptors" shall mean any disease, disorder or condition characterized in that at least one of its characteristic symptoms is alleviated or eliminated upon treatment with a dual GPR120 and GPR40 receptor agonist. Suitably examples include, but are not limited to obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia (i.e. elevated triglycerides), non-alcoholic steatohepatitis (NASH), non-alcoholic fatty liver disease (NAFLD), liver fibrosis and cardiovascular disorders (including but not limited to hypertension, atherosclerosis, thrombotic disorders, and cardiac fibrosis).

Preferably, the disorder modulated by dual agonism of the GPR120 and GPR40 receptors is selected from the group consisting of obesity, impaired glucose tolerance, elevated fasting glucose, insulin resistance, hyperglycemia, hyperinsulinemia, Type II Diabetes Mellitus, metabolic syndrome (also known as Syndrome X), diabetic retinopathy, diabetic nephropathy, dyslipidemia, elevated LDL, hyperlipidemia, hypertriglyceridemia (i.e. elevated triglycerides), non-alcoholic steatohepatitis (NASH) and non-alcoholic fatty liver disease (NAFLD). More preferably, the disorder modulated by dual agonism of the GPR120 and GPR40 receptors is selected from the group consisting of obesity, Type II diabetes, metabolic syndrome (also known as Syndrome X), dyslipidemia. hypertriglyceridemia (i.e. elevated triglycerides), non-alcoholic steatohepatitis (NASH) and non-alcoholic fatty liver disease (NAFLD). More preferably, the disorder modulated by dual agonism of the GPR120 and GPR40 receptors is selected from the group consisting of obesity, Type II diabetes, metabolic syndrome (also known as Syndrome X), dyslipidemia and hypertriglyceridemia In certain embodiments of the present invention, the disorder modulated by a dual GPR120 and GPR40 agonist is selected from the group consisting of obesity, hyperglycemia, impaired glucose tolerance, elevated fasting glucose, insulin resistance, hyperinsulinemia, Type II Diabetes Mellitus, metabolic syndrome (also known as Syndrome X), dyslipidemia, hyperlipoproteinemia, hyperlipidemia, elevated LDL, hypertriglyceridemia (i.e. elevated triglycerides), kidney disease, ketoacidosis, diabetic neuropathy and diabetic retinopathy.

In certain embodiments of the present invention, the disorder modulated by a dual GPR120 and GPR40 agonist is selected from the group consisting of obesity, hyperglycemia, impaired glucose tolerance, elevated fasting glucose, insulin resistance, hyperinsulinemia, Type II Diabetes Mellitus, metabolic syndrome (also known as Syndrome X), kidney disease, ketoacidosis, diabetic neuropathy and diabetic retinopathy. Preferably, the disorder modulated by a dual GPR120 and GPR40 agonist is selected from the group consisting of hyperglycemia, impaired glucose tolerance, elevated fasting glucose, insulin resistance, hyperinsulinemia and Type II Diabetes Mellitus.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications (including, to reduce the frequency or severity of one or more symptoms), or eliminate the disease, condition, or disorder.

As used herein, unless otherwise noted, the term "prevention" shall include (a) the delay or avoidance of the development of additional symptoms; and/or (b) delay or avoidance of the development of the disorder or condition along a known development pathway.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. A subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.W. Greene & P.G.M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be Measured: in texts such as T.W. Greene & P.G.M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be Measured: in texts such as T.W. Greene & P.G.M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max])\times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benetamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthesis Schemes

Compounds of formula (I) may be prepared according to the process outlined in Scheme 1.

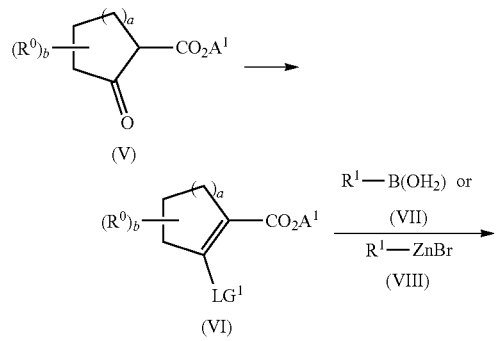

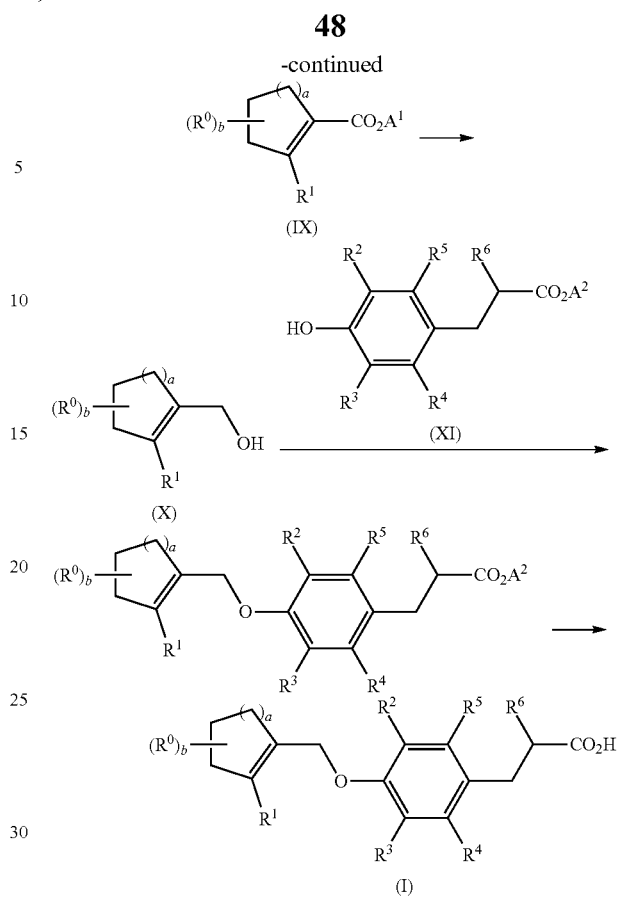

Accordingly, a suitably substituted compound of formula (V), wherein $A^1$ is selected from the group consisting of $C_{1-4}$alkyl, preferably methyl or ethyl, a known compound or compound prepared by known methods, is reacted with a triflating agent such as triflic anhydride, nonaflate (i.e. $SO_2C_4F_9$), and the like, a known compound; in the presence of a suitably selected base such as NaH, and the like; in a suitably selected solvent such as diethyl ether, MTBE, and the like; to yield the corresponding compound of formula (VI), wherein $LG^1$ is —OTf.

Alternatively, the compound of formula (V) is reacted with N-phenyl-bis(trifluoromethanesulfonimide), a known compound; in the presence of a suitably selected base such as DIPEA, TEA, NaH, and the like; in a suitably selected solvent such as THF, diethyl ether, MTBE, and the like; to yield the corresponding compound of formula (VI), wherein $LG^1$ is —OTf.

The compound of formula (VI) is reacted with a suitably substituted boronic acid, a compound of formula (VII), a known compound or compound prepared by known methods; in the presence of a suitably selected catalyst such as $Pd(OAc)_2$, $Pd(PPh_3)_4$, $Pd_2(dba)_3 \cdot CH_2Cl_2$, and the like; in the presence of a suitably selected ligand such as SPhos, $PPh_3$, dppf, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (VIII).

Alternatively, the compound of formula (VI) is reacted with a suitably substituted zinc bromide, a compound of formula (VIII); in the presence of a suitably selected coupling catalyst such as $Pd(PPh_3)_4$, $Pd_2(dba)_3$, $Pd(OAc)_2$; in a suitably selected organic solvent such as THF, 1,4-dioxane, toluene, and the like; to yield the corresponding compound of formula (IX).

The compound of formula (IX), is reacted with a suitably selected reducing agent such as LAH, DIBAL-H, and the like; in a suitably selected solvent such as THF, DCM, toluene, and the like; to yield the corresponding compound of formula (X).

The compound of formula (X), is reacted with a suitably substituted phenol, a compound of formula (XI), wherein $A^2$ is selected from the group consisting of $C_{1-4}$alkyl, preferably methyl or ethyl, a known compound or compound prepared by known methods; in the presence of a suitably selected coupling agent such as DEAD, ADDP, DIAD, and the like; in the presence of a suitably selected ligand such as triph-enylphosphine (TPP), $Bu_3P$, and the like; in a suitably selected solvent such as DCM, toluene, benzene, and the like; to yield the corresponding compound of formula (XII).

The compound of formula (XII) is reacted with a suitably selected base such as KOH, NaOH, LiOH, and the like; in a suitably selected solvent or mixture of solvents such as a mixture of THF:methanol:water, and the like; to yield the corresponding compound of formula (I).

Compounds of formula (I) may alternatively be prepared as described in Scheme 2, below.

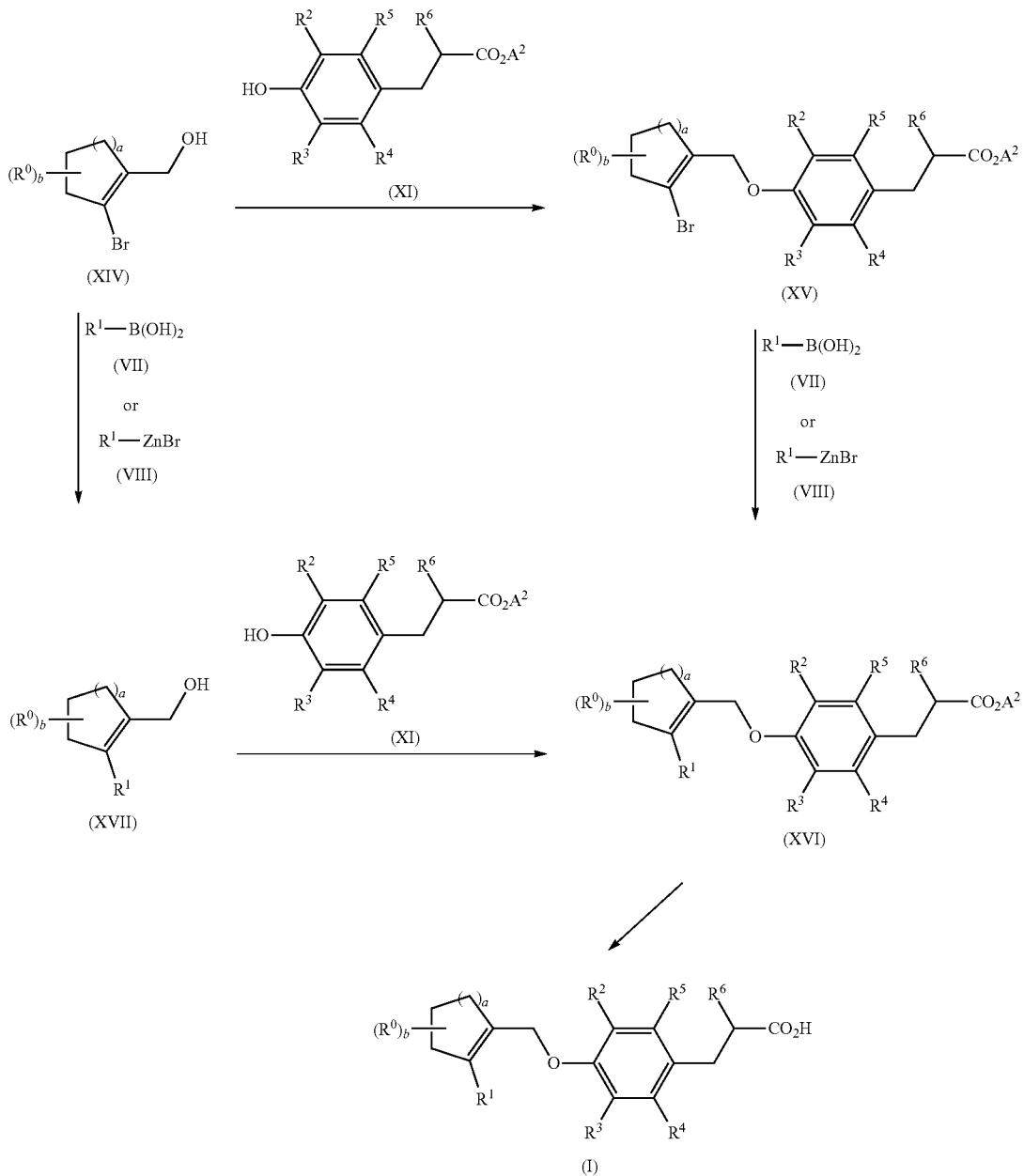

Accordingly, a suitably substituted compound of formula (XIV), a known compound or compound prepared by known methods, is reacted with a suitably substituted compound of formula (XI), wherein $A^2$ is selected from the group consisting of $C_{1-4}$alkyl, preferably methyl or ethyl, a known compound or compound prepared by known methods; in the presence of a suitably selected coupling agent such as DEAD, ADDP, DIAD, and the like; in the presence of a suitably selected ligand such as triphenylphosphine, $Bu_3P$, and the like; in a suitably selected solvent such as DCM, toluene, benzene, and the like; to yield the corresponding compound of formula (XV).

The compound of formula (XV) is reacted with a suitably substituted compound of formula (VI), a known compound or compound prepared by known methods; in the presence of a suitably selected catalyst such as $Pd(OAc)_2$, $Pd(PPh_3)_4$, $Pd_2(dba)_3 \cdot CH_2Cl_2$, and the like; in the presence of a suitably selected ligand such as SPhos, $PPh_3$, dppf, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XVI).

Alternatively, the compound of formula (XV) is reacted with a suitably substituted zinc bromide, a compound of formula (VIII); in the presence of a suitably selected coupling catalyst such as $Pd(PPh_3)_4$, $Pd_2(dba)_3$, $Pd(OAc)_2$; in a suitably selected organic solvent such as THF, 1,4-dioxane, toluene, and the like; to yield the corresponding compound of formula (XVI).

The compound of formula (XVI) is reacted with a suitably selected base such as KOH, NaOH, LiOH, and the like; in a suitably selected solvent or mixture of solvents such as a mixture of THF: methanol: water, and the like; to yield the corresponding compound of formula (I).

Alternatively, the compound of formula (XIV) is reacted with a suitably substituted compound of formula (VI), a known compound or compound prepared by known methods; in the presence of a suitably selected catalyst such as $Pd(OAc)_2$, $Pd(PPh_3)_4$, $Pd_2(dba)_3 \cdot CH_2Cl_2$, and the like; in the presence of a suitably selected ligand such as SPhos, $PPh_3$, dppf, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XVII).

Alternatively, the compound of formula (XIV) is reacted with a suitably substituted zinc bromide, a compound of formula (VIII); in the presence of a suitably selected coupling catalyst such as $Pd(PPh_3)_4$, $Pd_2(dba)_3$, $Pd(OAc)_2$; in a suitably selected organic solvent such as THF, 1,4-dioxane, toluene, and the like; to yield the corresponding compound of formula (XVII).

The compound of formula (XVII) is reacted with a suitably substituted compound of formula (XI) wherein $A^2$ is selected from the group consisting of $C_{1-4}$alkyl, preferably methyl or ethyl, a known compound or compound prepared by known methods; in the presence of a suitably selected coupling agent such as DEAD, ADDP, DIAD, and the like; in the presence of a suitably selected ligand such as triphenyl phosphine, $Bu_3P$, and the like; in a suitably selected solvent such as DCM, toluene, benzene, and the like; to yield the corresponding compound of formula (XVI).

The compound of formula (XVI) is reacted with a suitably selected base such as KOH, NaOH, LiOH, and the like; in a suitably selected solvent or mixture of solvents such as a mixture of THF: methanol: water, and the like; to yield the corresponding compound of formula (I).

Compounds of formula (XIV) may be prepared as described in Scheme 3, below.

Scheme 3

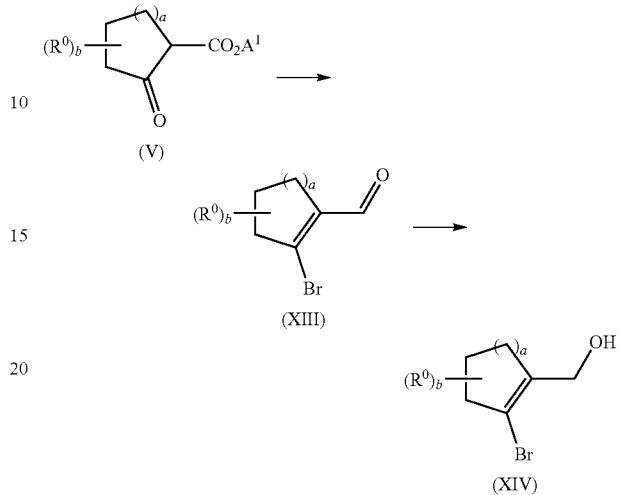

Accordingly, a suitably substituted compound of formula (V), a known compound or compound prepared by known methods, is reacted with a suitably selected brominating agent such as $PBr_3$, bromine-triphenylphosphine, and the like; in a suitably selected organic solvent such as DMF, DMAC, NMP, and the like; to yield the corresponding compound of formula (XIII).

The compound of formula (XIII) is reacted with a suitably selected reducing agent such as $NaBH_4$, in a solvent such as methanol, ethanol, and the like or DIBAL in a solvent such as DCM, toluene, THF, and the like; to yield the corresponding compound of formula (XIV).

Compounds of formula (I) wherein a is 1, and wherein the 4-position on the cyclopenten-1-yl portion of the compound of formula (I) is substituted with one or two $R^0$ groups, may alternatively be prepared as described in Scheme 4, below.

Scheme 4

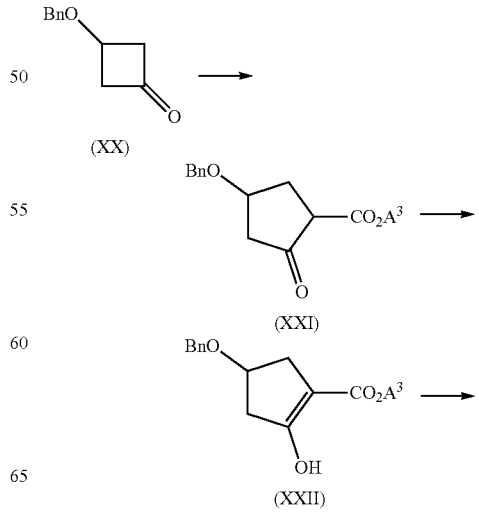

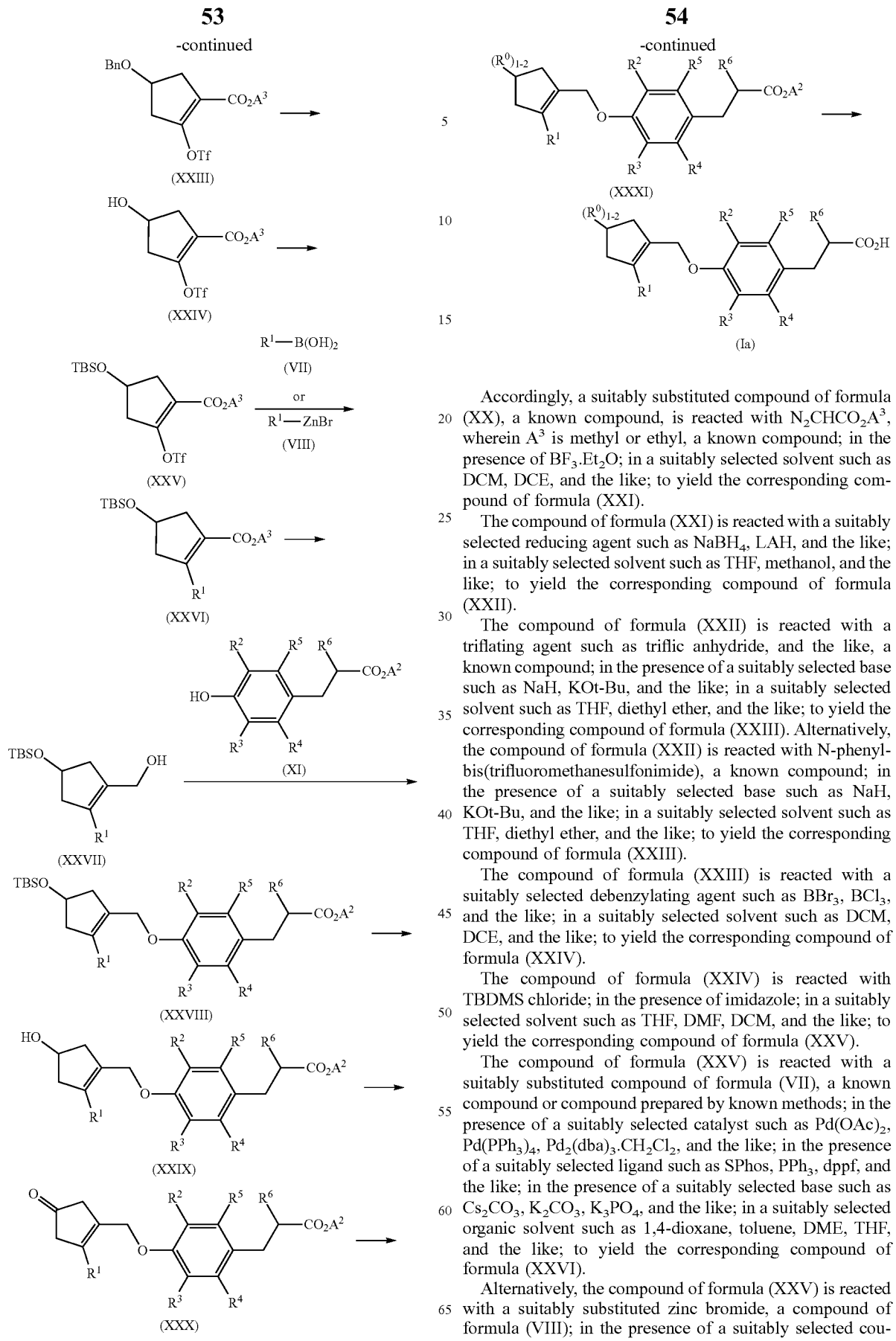

Accordingly, a suitably substituted compound of formula (XX), a known compound, is reacted with $N_2CHCO_2A^3$, wherein $A^3$ is methyl or ethyl, a known compound; in the presence of $BF_3.Et_2O$; in a suitably selected solvent such as DCM, DCE, and the like; to yield the corresponding compound of formula (XXI).

The compound of formula (XXI) is reacted with a suitably selected reducing agent such as $NaBH_4$, LAH, and the like; in a suitably selected solvent such as THF, methanol, and the like; to yield the corresponding compound of formula (XXII).

The compound of formula (XXII) is reacted with a triflating agent such as triflic anhydride, and the like, a known compound; in the presence of a suitably selected base such as NaH, KOt-Bu, and the like; in a suitably selected solvent such as THF, diethyl ether, and the like; to yield the corresponding compound of formula (XXIII). Alternatively, the compound of formula (XXII) is reacted with N-phenyl-bis(trifluoromethanesulfonimide), a known compound; in the presence of a suitably selected base such as NaH, KOt-Bu, and the like; in a suitably selected solvent such as THF, diethyl ether, and the like; to yield the corresponding compound of formula (XXIII).

The compound of formula (XXIII) is reacted with a suitably selected debenzylating agent such as $BBr_3$, $BCl_3$, and the like; in a suitably selected solvent such as DCM, DCE, and the like; to yield the corresponding compound of formula (XXIV).

The compound of formula (XXIV) is reacted with TBDMS chloride; in the presence of imidazole; in a suitably selected solvent such as THF, DMF, DCM, and the like; to yield the corresponding compound of formula (XXV).

The compound of formula (XXV) is reacted with a suitably substituted compound of formula (VII), a known compound or compound prepared by known methods; in the presence of a suitably selected catalyst such as $Pd(OAc)_2$, $Pd(PPh_3)_4$, $Pd_2(dba)_3.CH_2Cl_2$, and the like; in the presence of a suitably selected ligand such as SPhos, $PPh_3$, dppf, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XXVI).

Alternatively, the compound of formula (XXV) is reacted with a suitably substituted zinc bromide, a compound of formula (VIII); in the presence of a suitably selected coupling catalyst such as $Pd(PPh_3)_4$, $Pd_2(dba)_3$, $Pd(OAc)_2$; in a suitably selected organic solvent such as THF, 1,4-dioxane, toluene, and the like; to yield the corresponding compound of formula (XXVI).

The compound of formula (XXVI) is reacted with a suitably selected reducing agent such as DIBAL, LAH, and the like; in a suitably selected organic solvent such as DCM, THF, diethyl ether, and the like; at a reduced temperature of about −78° C. to 0° C.; to yield the corresponding compound of formula (XXVII).

The compound of formula (XXVII) is reacted with a suitably substituted compound of formula (XI), wherein $A^2$ is selected from the group consisting of $C_{1-4}$alkyl, preferably methyl or ethyl, a known compound or compound prepared by known methods; in the presence of a suitably selected coupling agent such as DEAD, ADDP, DIAD, and the like; in the presence of a suitably selected ligand such as triphenyl phosphine, $Bu_3P$, and the like; in a suitably selected solvent such as DCM, THF, toluene, benzene, and the like; to yield the corresponding compound of formula (XXVIII).

The compound of formula (XXVIII) is reacted with a suitably selected TBDMS deprotection agent such as $Bu_4N^+$ $F^-$, HCl, and the like; in a suitably selected solvent such as THF, 1,4-dioxane, and the like; to yield the corresponding compound of formula (XXIX).

The compound of formula (XXIX), is reacted with a suitably selected oxidizing agent such as Dess-Martin periodinane, SWERN reagent, and the like; in a suitably selected solvent such as DCM, THF, and the like; to yield the corresponding compound of formula (XXX).

The compound of formula (XXX), is reacted with a suitably selected fluorintaing agent such as DAST, BAST, Deoxo-Fluor®, and the like; in a suitably selected organic solvent such as DCM, DCE, and the like; to yield the corresponding compound of formula (XXXI); wherein one or more $R^0$ groups are fluoro.

The compound of formula (XXXI) is reacted with a suitably selected base such as KOH, NaOH, and the like; in a suitably selected solvent or mixture of solvents such as a mixture of THF: methanol: water, and the like; to yield the corresponding compound of formula (Ia).

Compounds of formula (IX) wherein a is 2, and wherein the 5-position of the cyclohexenyl is substituted with two fluoro groups (i.e. a compound of formula (IXa) of the structure

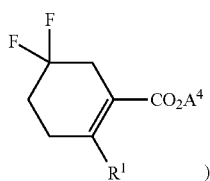

may alternatively be prepared as described in Scheme 5, below.

Scheme 5

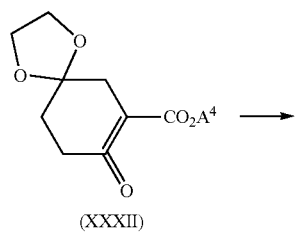

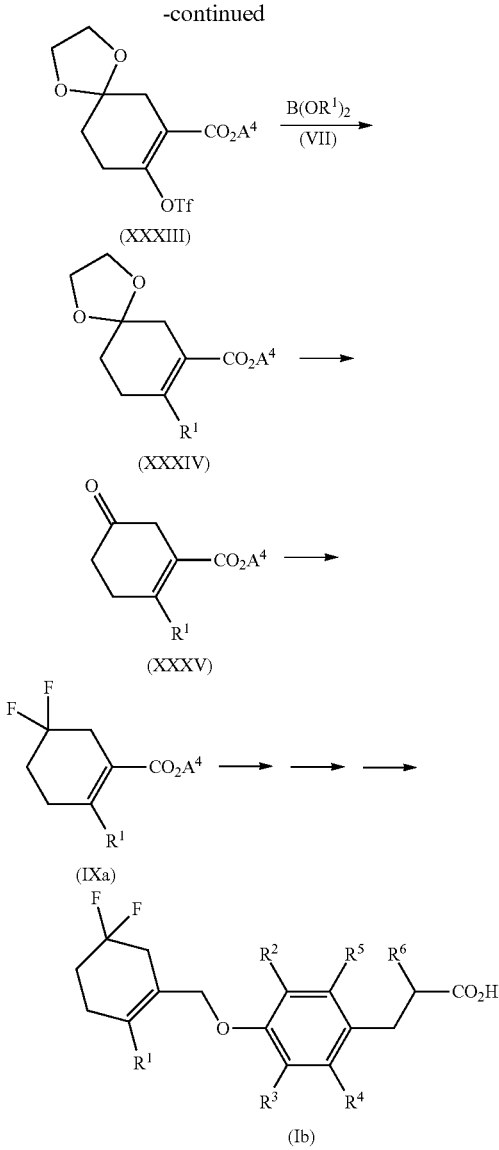

Accordingly, a compound of formula (XXXII) wherein $A^4$ is selected from the group consisting of $C_{1-4}$ alkyl, preferably methyl or ethyl, a known compound or compound prepared by known methods, (for example as described in GARDNER et al., *J. Am. Chem. Soc.*, 1956, pp 3425-3427, Vol. 78) is reacted with a triflating agent such as triflic anhydride, nonaflate (i.e. $SO_2C_4F_9$), and the like, a known compound; in the presence of a suitably selected base such as NaH, and the like; in a suitably selected solvent such as diethyl ether, MTBE, and the like; to yield the corresponding compound of formula (XXXII), wherein $LG^1$ is —OTf.

Alternatively, the compound of formula (XXXII) is reacted with N-phenyl-bis(trifluoromethanesulfonimide), a known compound; in the presence of a suitably selected base such as DIPEA, TEA, NaH, and the like; in a suitably selected solvent such as THF, diethyl ether, MTBE, and the like; to yield the corresponding compound of formula (XXXIII), wherein $LG^1$ is —OTf.

The compound of formula (XXXIII) is reacted with a suitably substituted boronic acid, a compound of formula (VII), a known compound or compound prepared by known methods; in the presence of a suitably selected catalyst such as Pd(PPh$_3$)$_4$, PdCl$_2$(dppf), PdCl$_2$(PPh$_3$)$_2$, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (XXXIV).

The compound of formula (XXXIV) is reacted with a suitably selected acid such as HCl, H$_2$SO$_4$, p-TSOH, and the like; in a suitably selected solvent or mixture of solvents such as a mixture of acetonitrile and water, 1,4-dioxane and water, and the like; to yield the corresponding compound of formula (XXXV).

The compound of formula (XXXV) is reacted with a suitably selected fluorinating agent such as Deoxo-Fluor®, DAST, and the like; in a suitably selected solvent such as DCM, DCE, and the like; to yield the corresponding compound of formula (IXa).

The compound of formula (IXa) is then substituted for the compound of formula (IX) is Scheme 1, and reacted as described in Scheme 1, to yield the corresponding compound of formula (Ib) (the corresponding compound of formula (I) wherein a is 2, and the 5-position of the cyclohexen-1-yl is substituted with two fluoro groups).

Certain compounds of formula (I), particularly compounds of formula (I) wherein b is 1 and wherein R$^0$ is selected from the group consisting of C$_{1-4}$alkoxy and fluorinated C$_{1-2}$alkoxy may be prepared as described in Scheme 6, below.

Accordingly, a suitably substituted compound of formula (XXXVI), wherein A$^5$ is selected from the group consisting of C$_{1-4}$alkyl, preferably methyl or ethyl, a known compound or compound prepared by known methods, a known compound or compound prepared by known methods, is reacted with a suitably selected reducing agent such as SBH, and the like; in a suitably selected organic solvent such as THF, DCM, and the like; to yield the corresponding compound of formula (XXXVII).

The compound of formula (XXXVII) is deprotonated by a suitably selected base such as sodium hydride, cesium carbonate, potassium carbonate and the like, and then reacted with a suitably selected electrophile, a compound of formula (XXXVIII), wherein X is a suitably selected halogen such as bromo, iodo, and the like; and wherein R$^{10}$ is selected from the group C$_{1-4}$alkyl and fluorinated C$_{1-2}$alkyl (to yield the corresponding R$^0$ group selected from the group consisting of C$_{1-4}$alkoxy and fluorinated C$_{1-2}$alkoxy); in a suitably selected organic solvent such as THF, DMF, DMAC, NMP, and the like; to yield the corresponding compound of formula (XXXIX).

The compound of formula (XXXIX) is reacted with a suitably selected reducing agent such as DIBAL, and the like; in a suitably selected organic solvent such as toluene, and the like; at a reduced temperature of about −78° C.; to yield the corresponding compound of formula (XL).

The compound of formula (XL) is reacted with a suitably substituted compound of formula (XI), wherein A$^2$ is selected from the group consisting of C$_{1-4}$alkyl, preferably

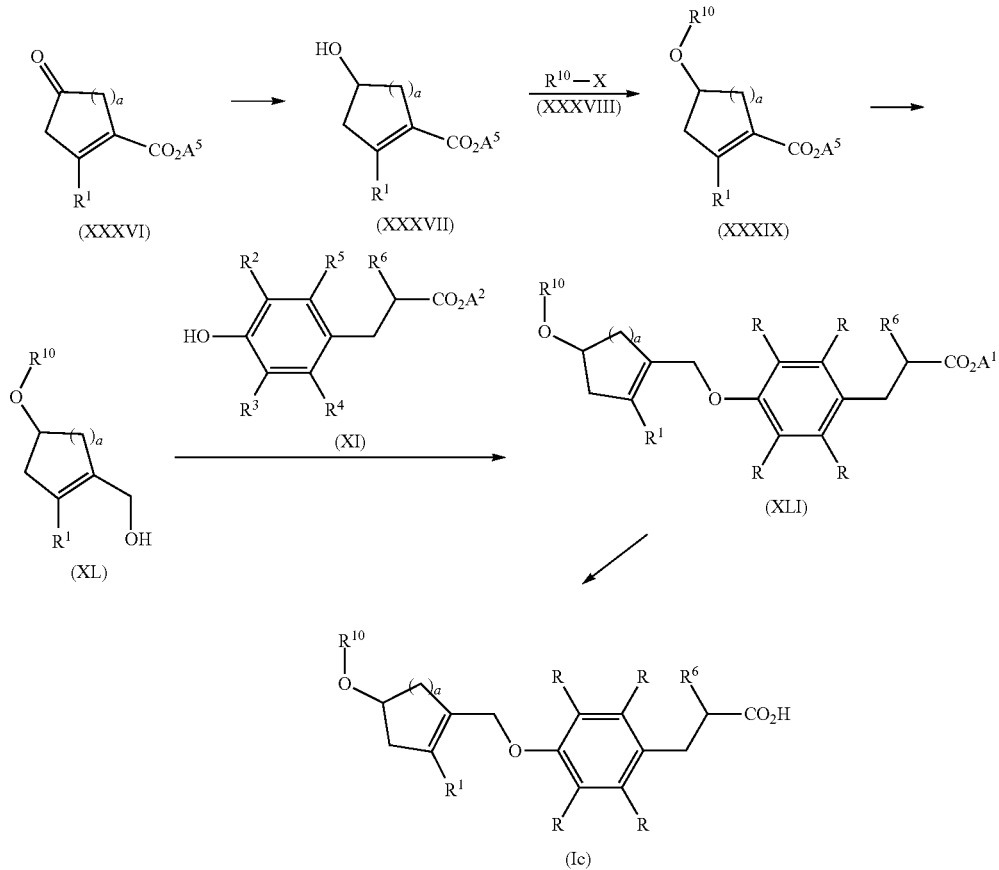

Scheme 6 methyl or ethyl, a known compound or compound prepared by known methods; in the presence of a suitably selected coupling agent such as DEAD, ADDP, DIAD, and the like; in the presence of a suitably selected ligand such as triphenylphosphine (TPP), $Bu_3P$, and the like; in a suitably selected solvent such as DCM, toluene, benzene, and the like; to yield the corresponding compound of formula (XLI).

The compound of formula (XLI) is reacted with a suitably selected base such as KOH, NaOH, LiOH, and the like; in a suitably selected solvent or mixture of solvents such as a mixture of THE: methanol: water, and the like; to yield the corresponding compound of formula (Ic).

Pharmaceutical Compositions

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending upon the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like, for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 100 mg/kg/day, or any amount or range therein, preferably from about 0.5 mg/kg/day to about 50 mg/kg/day, preferably from about 1.0 mg/kg/day to about 25 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method(s) of treating disorders as described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders, as described herein, is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.1 to about 100.0 mg/kg of body weight per day, or any amount or range therein. More preferably, from about 0.5 to about 50.0 mg/kg of body weight per day, or any amount or range therein. More preferably, from about 1.0 to about 25.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

SYNTHESIS EXAMPLES

Representative compounds of formula (I) of the present invention were prepared according to the synthesis methods described herein.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like. Additionally, in the Examples with follow, the "RS" designation in the compound structure indicates that the compound was prepared as a racemic mixture of stereo-isomers (for designated stereo-center.)

Example 1: Compound #185

3-[4-[[2-(4-chlorophenyl)-4-cyano-cyclopenten-1-yl]methoxy]-3,5-difluoro-phenyl]Propanoic Acid

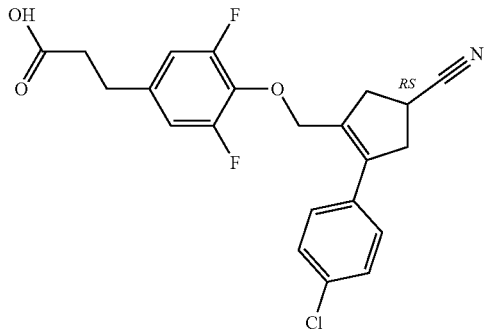 [SMILES: N#CC1CC(COc2c(F)cc(CCC(=O)O)cc2F)=C(c2ccc(Cl)cc2)C1]

$^1$H NMR (300 MHz, CD$_3$OD) δ: 7.36 (d, J=6.6 Hz, 2H), 7.18 (d, J=6.7 Hz, 2H), 6.86 (d, J=9.3 Hz, 2H), 4.68 (s, 2H), 3.40-3.48 (m, 1H), 3.20-3.28 (m, 2H), 3.01-3.09 (m, 2H), 2.87 (t, J=7.5 Hz, 2H), 2.61 (t, J=7.2 Hz, 2H). $^{19}$F NMR (300 MHz, CD$_3$OD) δ: −130.02. Mass spectrum (ESI, m/z): Calculated for C$_{22}$H$_{18}$ClF$_2$NO$_3$, 416.1 [M−H], measured as 416.0

Example 2: Compound #187

3-[4-[[2-(4-chlorophenyl)-4-methoxy-cyclopenten-1-yl]methoxy]-3,5-difluoro-phenyl]Propanoic Acid

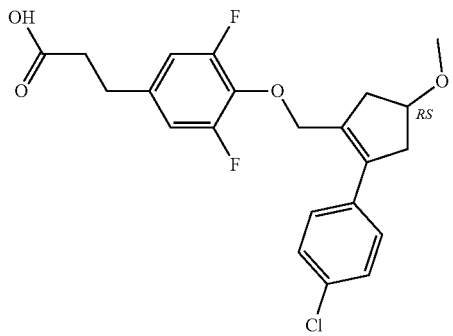 [SMILES: COC1CC(COc2c(F)cc(CCC(=O)O)cc2F)=C(c2ccc(Cl)cc2)C1]

$^1$H NMR (400 MHz, CD$_3$OD) δ: 7.24 (d, J=8.1 Hz, 2H), 7.12 (d, J=8.1 Hz, 2H), 6.75 (d, J=10.2 Hz, 2H), 4.53 (s, 2H), 4.05-4.10 (m, 1H), 3.24 (s, 3H), 2.88-2.98 (m, 2H), 2.71-2.75 (m, 2H), 2.63-2.67 (m, 2H), 2.30 (t, J=7.5 Hz, 2H). $^{19}$F NMR (300 MHz, CD$_3$OD) δ: −130.20. Mass spectrum (ESI, m/z): Calculated for C$_{22}$H$_{21}$ClF$_2$O$_4$, 421.1 [M−H], measured as 421.0.

Example 3: Compound #189

3-[4-[[2-(4-chlorophenyl)-4-methoxy-cyclopenten-1-yl]methoxy]-2,3-dimethyl-phenyl]Propanoic Acid

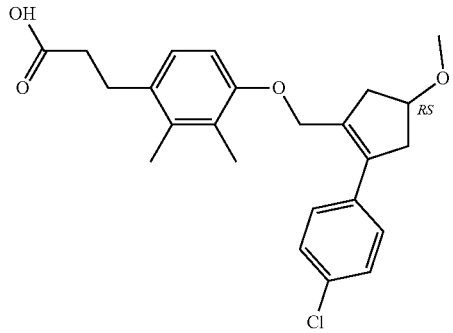 [SMILES: COC1CC(COc2ccc(CCC(=O)O)c(C)c2C)=C(c2ccc(Cl)cc2)C1]

$^1$H NMR (300 MHz, CD$_3$OD) δ 7.38 (d, J=8.1 Hz, 2H), 7.27 (d, J=8.1 Hz, 2H), 6.91 (d, J=8.1 Hz, 1H), 6.52 (d, J=8.1 Hz, 1H), 4.64 (s, 2H), 4.18-4.23 (m, 1H), 3.36 (s, 3H), 3.02-3.15 (m, 1H), 2.89-2.99 (m, 1H), 2.78-2.87 (m, 3H), 2.72-2.77 (m, 1H), 2.35-2.37 (m, 2H), 2.20 (s, 3H), 2.15 (s, 3H). Mass spectrum (ESI, m/z): Calculated for C$_{24}$H$_{27}$ClO$_4$, 413.1[M−H], measured as 413.1

Example 4: Compound #195

3-[4-[[4-chloro-2-(4-chlorophenyl)cyclopenten-1-yl]methoxy]-2,3-dimethyl-phenyl]Propanoic Acid

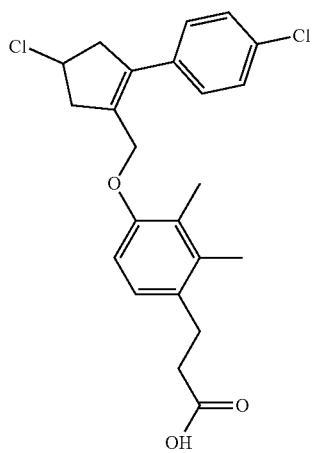 [SMILES: Cc1c(CCC(=O)O)ccc(OCC2=C(c3ccc(Cl)cc3)CC(Cl)C2)c1C]

$^1$H NMR (300 MHz, CD$_3$OD) δ: 7.38 (d, J=8.1 Hz, 2H), 7.27 (d, J=8.1 Hz, 2H), 6.91 (d, J=8.1 Hz, 1H), 6.52 (d, J=8.1 Hz, 1H), 4.65-4.69 (m, 3H), 3.39-3.46 (m, 1H), 3.24-3.26 (m, 1H), 2.82-3.08 (m, 4H), 2.31-2.36 (m, 2H), 2.23 (s, 3H), 2.14 (s, 3H). Mass spectrum (ESI, m/z): Calculated for C$_{23}$H$_{24}$Cl$_2$O$_3$, 417.1 [M−H], measured as 417.0

Example 5: Compound #196

3-[4-[[2-(4-chlorophenyl)-4-cyano-cyclopenten-1-yl]methoxy]-2,3-dimethyl-phenyl]Propanoic Acid

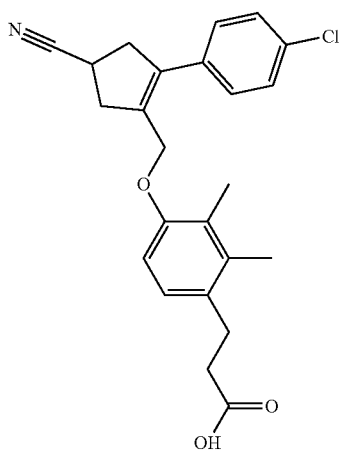 [SMILES: Cc1c(CCC(=O)O)ccc(OCC2=C(c3ccc(Cl)cc3)CC(C#N)C2)c1C]

$^1$H NMR (300 MHz, CD$_3$OD) δ 7.38 (d, J=8.1 Hz, 2H), 7.27 (d, J=8.1 Hz, 2H), 6.91 (d, J=8.1 Hz, 1H), 6.50 (d, J=8.1 Hz, 1H), 4.84 (s, 2H), 3.40-3.46 (m, 1H), 2.96-3.29 (m, 4H), 2.83-2.88 (m, 2H), 2.31-2.37 (m, 2H), 2.23 (s, 3H), 2.14 (s, 3H). Mass spectrum (ESI, m/z): Calculated for C$_{24}$H$_{24}$ClNO$_3$, 408.1 [M−H], measured as 408.0

Example 6: Compound #610

3-[4-[(2-cyclopentyl-5,5-difluoro-cyclohepten-1-yl)methoxy]-2-fluoro-phenyl]Propanoic Acid

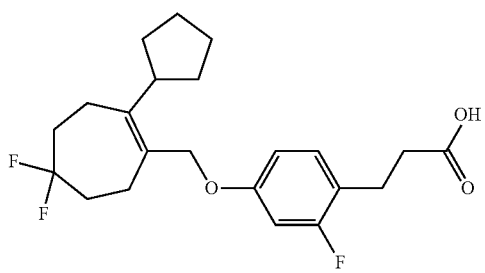 [SMILES: O=C(O)CCc1ccc(OCC2=C(C3CCCC3)CCC(F)(F)CC2)cc1F]

$^1$H NMR (300 MHz, CD$_3$OD) δ: 7.10-7.15 (m, 1H), 6.58-6.65 (m, 2H), 4.55 (s, 2H), 3.09-3.16 (m, 1H), 2.82 (t, J=7.5 Hz, 2H), 2.40 (t, J=7.5 Hz, 2H), 2.24-2.28 (m, 2H), 2.12-2.17 (m, 2H), 1.74-1.87 (m, 4H), 1.61-1.72 (m, 6H), 1.37-1.44 (m, 2H). $^{19}$F NMR (300 MHz, CD$_3$OD) δ: −91.42, −118.90. Mass spectrum (ESI, m/z): Calculated for C$_{22}$H$_{27}$F$_3$O$_3$, 395.2 [M−H], measured as 395.1

Example 7: Compound #611

3-[4-[(2-cyclopentyl-5,5-difluoro-cyclohepten-1-yl)methoxy]phenyl]Propanoic Acid

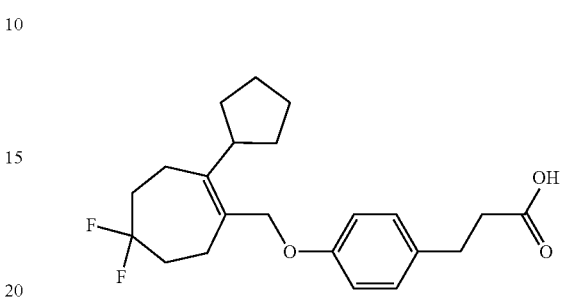

$^1$H NMR (300 MHz, CD$_3$OD) δ: 7.09 (d, J=8.7 Hz, 2H), 6.78 (d, J=8.7 Hz, 2H), 4.54 (s, 2H), 3.03-3.08 (m, 1H), 2.80 (t, J=7.5 Hz, 2H), 2.39 (t, J=7.5 Hz, 2H), 2.25-2.29 (m, 2H), 2.11-2.14 (m, 2H), 1.74-1.87 (m, 4H), 1.64-1.72 (m, 6H), 1.37-1.42 (m, 2H). $^{19}$F NMR (300 MHz, CD3OD) δ: −91.42. Mass spectrum (ESI, m/z): Calculated for C$_{22}$H$_{28}$F$_2$O$_3$, 377.2 [M−H], measured as 377.1

Example 8: Compound #612

3-[4-[(2-cyclopentylcyclohepten-1-yl)methoxy]-2-(trifluoromethyl)phenyl]Propanoic Acid

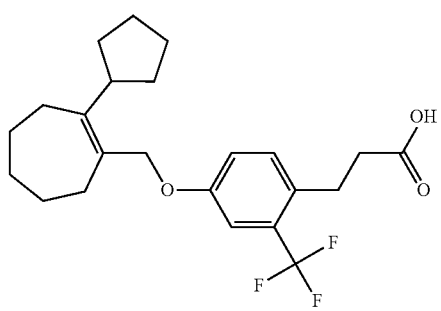 [SMILES: O=C(O)CCc1ccc(OCC2=C(C3CCCC3)CCCCC2)cc1C(F)(F)F]

$^1$H NMR (300 MHz, CD$_3$OD) δ: 7.40 (d, J=8.7 Hz, 1H), 7.08-7.15 (m, 2H), 4.62 (s, 2H), 3.01-3.12 (m, 3H), 2.42-2.47 (m, 2H), 2.34 (t, J=5.1 Hz, 2H), 2.19 (t, J=5.7 Hz, 2H), 1.66-1.82 (m, 8H), 1.38-1.49 (m, 6H). $^{19}$F NMR (300 MHz, CD$_3$OD): δ −61.18. Mass spectrum (ESI, m/z): Calculated for C$_{23}$H$_{29}$F$_3$O$_3$, 409.2 [M−H], measured as 409.1.

Example 9: Compound #613

3-[4-[(2-cyclopentylcyclohepten-1-yl)methoxy]-2-fluoro-phenyl]Propanoic Acid

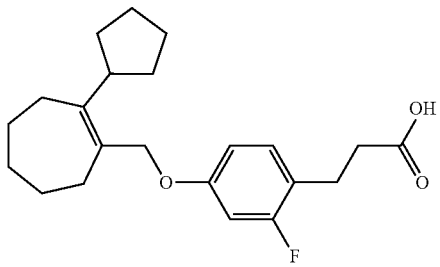 [SMILES: O=C(O)CCc1ccc(OCC2=C(C3CCCC3)CCCCC2)cc1F]

$^1$H NMR (300 MHz, CD$_3$OD) δ: 7.14-7.20 (m, 1H), 6.61-6.68 (m, 2H), 4.55 (s, 2H), 3.04-3.12 (m, 1H), 2.85-2.90 (m, 2H), 2.41-2.46 (m, 2H), 2.33 (t, J=5.4 Hz, 2H), 2.18 (t, J=5.4 Hz, 2H), 1.69-1.83 (m, 8H), 1.32-1.51 (m, 6H). $^{19}$F NMR (300 MHz, CD$_3$OD) δ: −119.13. Mass spectrum (ESI, m/z): Calculated for C$_{22}$H$_{29}$FO$_3$, 359.2 [M−H], measured as 359.1.

Example 10: Compound #614

3-[4-[(2-cyclopentylcyclohepten-1-yl)methoxy]phenyl]Propanoic Acid

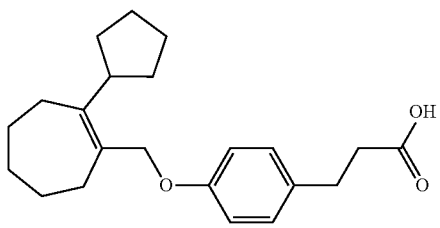 [SMILES: O=C(O)CCc1ccc(OCC2=C(C3CCCC3)CCCCC2)cc1]

$^1$H NMR (300 MHz, CD$_3$OD) δ: 7.13 (d, J=8.7 Hz, 2H), 6.85 (d, J=8.7 Hz, 2H), 4.55 (s, 2H), 3.04-3.12 (m, 1H), 2.86 (t, J=7.5 Hz, 2H), 2.57 (d, J=7.5 Hz, 2H), 2.34 (t, J=5.4 Hz, 2H), 2.18 (t, J=5.4 Hz, 2H), 1.69-1.83 (m, 8H), 1.32-1.51 (m, 6H). Mass spectrum (ESI, m/z): Calculated for C$_{22}$H$_{30}$O$_3$, 341.2 [M−H], measured as 341.1.

Example 11: Compound #615

3-[4-[[2-(4-chlorophenyl)cyclohepten-1-yl]methoxy]-2,3-dimethyl-phenyl]Propanoic Acid

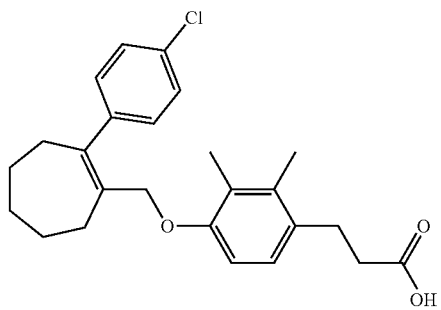 [SMILES: Cc1c(CCC(=O)O)ccc(OCC2=C(c3ccc(Cl)cc3)CCCCC2)c1C]

Step 1: ethyl 2-(trifluoromethylsulfonyloxy)cyclohept-1-enecarboxylate

Into a 250-mL three-necked flask was placed ethyl 2-oxo-cycloheptanecarboxylate (2.8 g, 15.198 mmol, 1.0 eq) and diethyl ether (80 mL). To the reaction mixture was then added sodium hydride (6.5 g, 23.038 mmol, 2.0 eq) in portions at 0° C. The mixture solution was stirred for 1 h at 25° C. To this mixture was then added trifluoromethanesulfonic anhydride (466 mg, 1.652 mmol, 1.5 eq) dropwise at 0° C. The mixture was stirred for 3 h at 25° C. The reaction progress was monitored by TLC (PE/EA=10:1). The reaction was then quenched by the addition of water, the resulting solution was extracted with EA and the organic layers combined. The resulting mixture was concentrated under vacuum. The residue was applied onto a silica gel with PE/EA=20:1 to yield ethyl 2-(trifluoromethylsulfonyloxy)cyclohept-1-enecarboxylate as a colorless oil.

Step 2: ethyl 2-(4-chlorophenyl)cyclohept-1-enecarboxylate

Into a 100-mL round-bottom flask charged and maintained with an inert atmosphere of nitrogen was placed ethyl 2-(trifluoromethylsulfonyloxy)cyclohept-1-enecarboxylate (600 mg, 1.897 mmol, 1.0 eq), 4-chlorophenylboronic acid (355 mg, 2.270 mmol, 1.2 eq), Pd(PPh$_3$)$_4$ (110 mg, 0.095 mmol, 0.05 eq), K$_3$PO$_4$ (1.2 g, 5.687 mmol, 3.0 eq) and 1,4-dioxane (10 mL). The solution was stirred overnight at 90° C., and the reaction progress was monitored by GCMS. The reaction was then quenched by the addition of water, the resulting solution was extracted with EA and the organic layers combined. The resulting mixture was concentrated under vacuum. The residue was applied onto a silica gel with PE/EA=10:1 to yield ethyl 2-(4-chlorophenyl)cyclohept-1-enecarboxylate as a colorless oil.

Step 3: (2-(4-chlorophenyl)cyclohept-1-enyl)methanol

Into a 50-mL round-bottom flask charged and maintained with an inert atmosphere of nitrogen was placed ethyl 2-(4-chlorophenyl)cyclohept-1-enecarboxylate (373 mg, 1.338 mmol, 1.0 eq), and DCM (10 mL). To the mixture was then added DIBAL (4.0 mL, 4.0 mmol, 3.0 eq) dropwise at −78° C. The mixture solution was stirred for 3 h at 25° C.

The reaction progress was monitored by LCMS. The reaction was then quenched by the addition of water, the resulting solution was extracted with EA and organic layers combined. The resulting mixture was washed with brine. The mixture was dried over anhydrous sodium sulfate, the solids were filtered out. The filtrate was concentrated under vacuum. The residue was applied onto a silica gel with PE/EA (20:1) to yield (2-(4-chlorophenyl)cyclohept-1-enyl) methanol as a colorless oil.

Step 4: ethyl 3-(4-((2-(4-chlorophenyl)cyclohept-1-enyl)methoxy)-2,3-dimethylphenyl)Propanoate Into a 50-mL round-bottom flask charged and maintained with an inert atmosphere of nitrogen was placed (2-(4-chlorophenyl)cyclohept-1-enyl)methanol (50 mg, 0.211 mmol, 1.0 eq), ethyl 3-(4-hydroxy-2,3-dimethylphenyl)propanoate (71 mg, 0.319 mmol, 1.5 eq), ADDP (159 mg, 0.636 mmol, 3.0 eq), n-Bu$_3$P (128 mg, 0.634 mmol, 3.0 eq), and toluene (5 mL). The mixture solution was stirred overnight at 80° C., the reaction progress was monitored by TLC (PE/EA=6:1). The resulting mixture was concentrated under vacuum. The residue was applied onto a silica gel with PE/EA=6:1 to yield ethyl 3-(4-((2-(4-chlorophenyl)cyclohept-1-enyl)methoxy)-2,3-dimethylphenyl)propanoate as a colorless oil.

Step 4: 3-[4-[[2-(4-chlorophenyl)cyclohepten-1-yl]methoxy]-2,3-dimethyl-phenyl]Propanoic acid Into a 50-mL round-bottom flask was placed (Z)-ethyl 3-(4-((2-(4-chlorophenyl)cyclohept-1-enyl)methoxy)-2,3-dimethylphenyl)propanoate (65 mg, 0.147 mmol, 1.0 eq), lithium hydroxide (18 mg 0.752 mmol, 5.0 eq), THF (5 mL), and H$_2$O (5 mL). The resulting solution was stirred for 6 h at 25° C. The reaction progress was monitored by LCMS. The pH value of the solution was adjusted to pH6 with hydrogen chloride (2 M). The resulting solution was extracted with ethyl acetate (3×10 mL) and the organic layers combined and concentrated under vacuum. The resulting residue was purified by Prep-HPLC with the following conditions (1 #-Waters 2767-5): Column, SunFire Prep C18, 5 um, 19*100 mm; mobile phase, Water of 0.05% NH$_4$HCO$_3$ and CH$_3$CN (35% CH$_3$CN up to 75% in 8 min, up to 95% in 1 min, down to 35% in 1 min); Detector, UV 220&254 nm to yield 3-[4-[[2-(4-chlorophenyl)cyclohepten-1-yl]methoxy]-2,3-dimethyl-phenyl]propanoic acid as a white solid.

$^1$H NMR (300 MHz, CD$_3$OD) δ: 7.24-7.29 (m, 2H), 7.07-7.11 (m, 2H), 6.82 (d, J=8.4 Hz, 1H), 6.33 (d, J=8.4 Hz, 1H), 4.23 (s, 2H), 2.83 (t, J=7.2 Hz, 2H), 2.40-2.54 (m, 6H), 2.17 (s, 3H), 2.12 (s, 3H), 1.78-1.89 (m, 2H), 1.63-1.65 (m, 4H). Mass spectrum (ESI, m/z): Calculated for C$_{25}$H$_{29}$ClO$_3$, 411.2 [M–H] Measured: 411.1.

Example 12: Compound #616

3-[4-[[2-(4-chlorophenyl)-5,5-difluoro-cyclohepten-1-yl]methoxy]-2,3-dimethyl-phenyl]Propanoic Acid

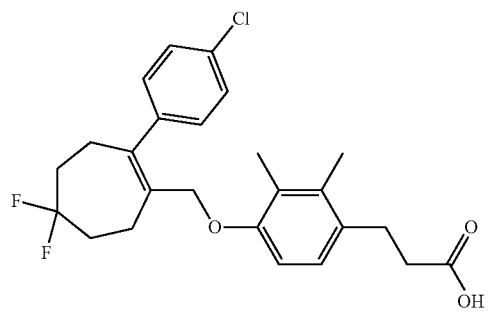 [SMILES: Cc1c(CCC(=O)O)ccc(OCC2=C(c3ccc(Cl)cc3)CCC(F)(F)CC2)c1C]

$^1$H NMR (300 MHz, CD$_3$OD) δ: 7.29-7.32 (m, 2H), 7.12-7.15 (m, 2H), 6.83 (d, J=8.1 Hz, 1H), 6.31 (d, J=8.1 Hz, 1H), 4.30 (s, 2H), 2.81 (t, J=7.5 Hz, 2H), 2.45-2.54 (m, 4H), 2.31 (t, J=7.5 Hz, 2H), 2.29 (s, 3H), 2.18 (s, 3H), 1.95-2.10 (m, 4H). $^{19}$F NMR (300 MHz, CD$_3$OD) δ: −91.34. Mass spectrum (ESI, m/z): Calculated for C$_{25}$H$_{27}$ClF$_2$O$_3$, 447.2 [M−H], measured as 447.0

Example 13: Compound #617

3-[4-[(2-cyclopentyl-5,5-difluoro-cyclohepten-1-yl) methoxy]-2-(trifluoromethyl)phenyl]Propanoic Acid

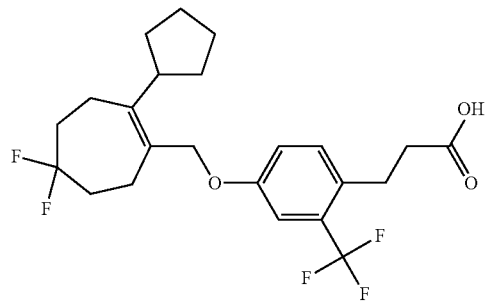 [SMILES: O=C(O)CCc1ccc(OCC2=C(C3CCCC3)CCC(F)(F)CC2)cc1C(F)(F)F]

Step 1: ethyl 5,5-difluoro-2-oxocycloheptanecarboxylate

To a 100-mL round-bottom-flask purged and maintained with an inert atmosphere of nitrogen was placed methyl 4-cyclopentyl-2,5-dihydrofuran-3-carboxylate (500 mg, 3.7 mmol, 1 equiv), DCM (10 mL), ethyl diazoacetate (510 mg, 4.4 mmol, 1.2 equiv), followed by BF$_3$.Et$_2$O (788 mg, 5.5 mmol, 1.5 equiv) at −78° C. The resulting solution was stirred for 30 min at −78° C. The resulting mixture was concentrated under vacuum. The residue was purified by silica gel with ethyl acetate/petroleum ether (2:98). The collected fractions were combined and concentrated under vacuum to yield ethyl 5,5-difluoro-2-oxocycloheptanecarboxylate as yellow oil.

Step 2: ethyl 5,5-difluoro-2-(trifluoromethylsulfonyloxy)cyclohept-1-enecarboxylate To a 100-mL round-bottom-flask purged and maintained with an inert atmosphere of nitrogen was placed ethyl 5,5-difluoro-2-oxocycloheptanecarboxylate (2.2 g, 10 mmol, 1 equiv), Et$_2$O (50 mL), sodium hydride (0.8 g, 20 mmol, 2 equiv), followed by Tf$_2$O (4.23 g, 15 mmol, 1.5 equiv) with stirred at 0° C. The resulting solution was stirred for 2 h at 25° C. The resulting mixture was quenched by H$_2$O and extracted with EA (3×20 mL), the organic layers were concentrated under vacuum. The residue was purified by silica gel with ethyl acetate/petroleum ether (2:98). The collected fractions were combined and concentrated under vacuum to yield ethyl 5,5-difluoro-2-(trifluoromethylsulfonyloxy)cyclohept-1-enecarboxylate as yellow oil.

Step 3: ethyl 2-cyclopentyl-5,5-difluorocyclohept-1-enecarboxylate

To a 250-mL round-bottom-flask purged and maintained with an inert atmosphere of nitrogen was placed ethyl 5,5-difluoro-2-(trifluoromethylsulfonyloxy)cyclohept-1-enecarboxylate (1.5 g, 4.2 mmol, 1 equiv), THF (50 mL), and Pd(PPh$_3$)$_4$ (245 mg, 0.21 mmol, 0.05 equiv), followed by cyclopentylzinc(II) bromide (0.5M) (16 mL, 8 mmol, 2 equiv) at 20° C. The resulting solution was stirred for 16 h. The resulting mixture was concentrated under vacuum. The residue was purified by silica gel with ethyl acetate/petroleum ether (5:95). The collected fractions were combined and concentrated under vacuum to yield ethyl 2-cyclopentyl-5,5-difluorocyclohept-1-enecarboxylate as yellow oil.

Step 4: (2-cyclopentyl-5,5-difluorocyclohept-1-enyl)methanol

Into a 100-mL round-bottom-flask purged and maintained with an inert atmosphere of nitrogen was placed ethyl 2-cyclopentyl-5,5-difluorocyclohept-1-enecarboxylate (0.6 g, 2.2 mmol, 1 equiv), DCM (10 mL), and DIBAL (4.4 mL, 4.4 mmol, 2 equiv) and stirred at −78° C. The resulting solution was stirred for 2 h at 20° C. The resulting mixture was quenched by MeOH, and concentrated under vacuum. The residue was purified by silica gel with ethyl acetate/petroleum ether (10:90). The collected fractions were combined and concentrated under vacuum to yield (2-cyclopentyl-5,5-difluorocyclohept-1-enyl)methanol as a yellow oil.

Step 5: ethyl 3-(4-((2-cyclopentyl-5,5-difluorocyclohept-1-enyl)methoxy)-2-(trifluoromethyl)phenyl)Propanoate Into a 50-mL round-bottle purged and maintained with an inert atmosphere of nitrogen was added (2-cyclopentyl-5,5-difluorocyclohept-1-enyl)methanol (50 mg, 0.21 mmol, 1 equiv), ethyl 3-(4-hydroxy-2-(trifluoromethyl)phenyl)propanoate (68 mg, 0.26 mmol, 1.2 equiv), ADDP (157 mg, 0.62 mmol, 3 equiv), n-Bu$_3$P (127 mg, 0.62 mmol, 3 equiv), and toluene (5 mL). The resulting solution was stirred overnight at 80° C. The resulting mixture was concentrated under vacuum. The residue was applied onto a TLC with ethyl acetate/petroleum ether (1/10). The collected fractions were combined and concentrated under vacuum to yield ethyl 3-(4-((2-cyclopentyl-5,5-difluorocyclohept-1-enyl)methoxy)-2-(trifluoromethyl)phenyl)propanoate as yellow oil.

Step 6: 3-[4-[(2-cyclopentyl-5,5-difluoro-cyclohepten-1-yl)methoxy]-2-(trifluoromethyl)phenyl]Propanoic Acid Into a 50-mL round-bottle was added ethyl 3-(4-((2-cyclopentyl-5,5-difluorocyclohept-1-enyl)methoxy)-2-(trifluoromethyl)phenyl)propanoate (50 mg, 0.105 mmol, 1 equiv), LiOH (50 mg, 2.1 mmol, 20 equiv), THF (3 mL), and H$_2$O (3 mL). The resulting solution was stirred 3 h at 40° C. The pH value was adjust to pH6 with HCl (2M), extracted with EA, the organic layers were concentrated under reduced pressure and the resulting residue was purified by Prep-HPLC with the following conditions (16 #-Waters 2767-5): Column, SunFire Prep C18, 19*100 mm, 5 um; mobile phase, Water with 0.5% trifluoroacetic acid and CH$_3$CN (55% CH$_3$CN up to 95% in 7 min, up to 100% in 0.1 min, hold 100% in 0.9 min, down to 55% in 0.1 min, hold 55% in 1.4 min); Detector, UV 220&254 nm to yield −3-(4-((2-cyclopentyl-5,5-difluorocyclohept-1-enyl) methoxy)-2-(trifluoromethyl)phenyl)propanoic acid as white solid.

$^1$H NMR (300 MHz, CD$_3$OD) δ 7.34 (t, J=8.4 Hz, 1H), 7.04-7.11 (m, 2H), 4.62 (s, 2H), 3.03-3.09 (m, 1H), 2.95-3.00 (m, 2H), 2.36-2.42 (m, 2H), 2.25-2.29 (m, 2H), 2.12-2.16 (m, 2H), 1.72-1.87 (m, 4H), 1.60-1.68 (m, 6H), 1.21-1.37 (m, 2H). $^{19}$F NMR (300 MHz, CD$_3$OD) δ: −61.22, −91.17. Mass spectrum (ESI, m/z): Calculated for C$_{23}$H$_{27}$F$_5$O$_3$, 445.2 [M−H], measured as 445.0

Example 14: Compound #618

3-[4-[(2-cyclopentyl-5,5-difluoro-cyclohepten-1-yl)methoxy]-2,3-dimethyl-phenyl]Propanoic Acid

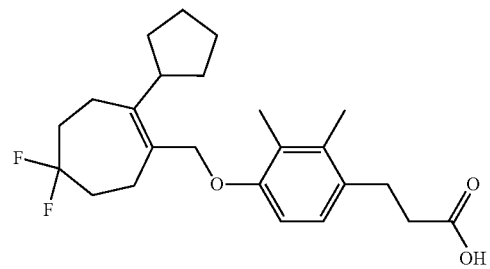 [SMILES: Cc1c(CCC(=O)O)ccc(OCC2=C(C3CCCC3)CCC(F)(F)CC2)c1C]

$^1$H NMR (300 MHz, CD$_3$OD) δ: 6.92 (d, J=8.4 Hz, 1H), 6.66 (d, J=8.4 Hz, 1H), 4.52 (s, 2H), 3.03.3.09 (m, 1H), 2.81-2.86 (m, 2H), 2.29-2.34 (m, 4H), 2.28 (s, 3H), 2.10-2.19 (m, 5H), 1.76-1.98 (m, 4H), 1.53-1.73 (m, 6H), 1.29-1.42 (m, 2H). $^{19}$F NMR (300 MHz, CD3OD) δ: −90.92, −91.81. Mass spectrum (ESI, m/z): Calculated for C$_{24}$H$_{32}$F$_2$O$_3$, 405.2 [M−H], measured as 405.1

Example 15: Compound #478

3-[4-[[2-(4-chlorophenyl)-3-ethyl-cyclohexen-1-yl]methoxy]-2,3-dimethyl-phenyl]Propanoic Acid

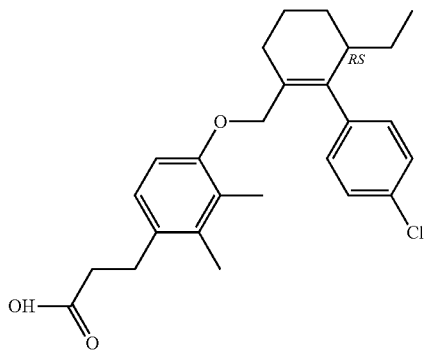 [SMILES: CCC1CCCC(COc2ccc(CCC(=O)O)c(C)c2C)=C1c1ccc(Cl)cc1]

$^1$H NMR (300 MHz, CDCl$_3$) δ: 7.25 (d, J=6.6 Hz, 2H), 7.05 (d, J=6.6 Hz, 2H), 6.85 (d, J=8.4 Hz, 1H), 6.39 (d, J=8.4 Hz, 1H), 4.23 (d, J=10.5 Hz, 1H), 4.13 (d, J=10.2 Hz, 1H), 2.90 (t, J=7.5 Hz, 2H), 2.56 (t, J=8.7 Hz, 2H), 2.16-2.39 (m, 2H), 2.20 (s, 3H), 2.16 (s, 3H), 1.67-1.75 (m, 4H), 1.09-1.03 (m, 3H), 0.769 (t, J=7.2 Hz, 3H). Mass spectrum (ESI, m/z): Calculated for C$_{26}$H$_{31}$ClO$_3$, 425.2 (M–H), measured as 425.2.

Example 16: Compound #500

3-[4-[[2-(4-chlorophenyl)-4-isopropyl-cyclohexen-1-yl]methoxy]-2,3-dimethyl-phenyl]Propanoic Acid

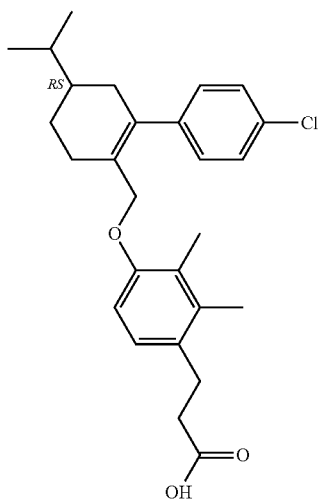 [SMILES: Cc1c(CCC(=O)O)ccc(OCC2=C(c3ccc(Cl)cc3)CC(C(C)C)CC2)c1C]

$^1$H NMR (400 MHz, CD$_3$OD) δ: 7.32 (d, J=8.7 Hz, 2H), 7.15 (d, J=8.7 Hz, 2H), 6.87 (d, J=8.7 Hz, 1H), 6.41 (d, J=8.7 Hz, 1H), 4.23-4.29 (m, 2H), 2.88 (t, J=7.2 Hz, 2H), 2.40-2.48 (m, 3H), 2.25-2.29 (m, 2H), 2.22 (s, 3H), 2.15 (s, 3H), 2.06-2.13 (m, 1H), 1.92-1.96 (m, 1H), 1.51-1.57 (m, 2H), 1.33-1.38 (m, 1H), 0.96 (d, J=6.4 Hz, 6H). Mass spectrum (ESI, m/z): Calculated for C$_{27}$H$_{33}$ClO$_3$, 247.1 (M-C$_{11}$H$_{13}$O$_3$), measured as 247.0.

Example 17: Compound #501

3-[4-[[2-(4-chlorophenyl)-5-isopropyl-cyclohexen-1-yl]methoxy]-2,3-dimethyl-phenyl]Propanoic Acid

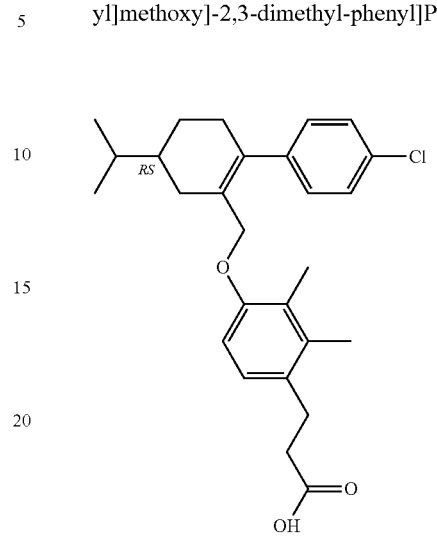

$^1$H NMR (300 MHz, CDCl$_3$) δ: 7.25 (d, J=6.9 Hz, 2H), 7.11 (d, J=6.9 Hz, 2H), 6.87 (d, J=8.4 Hz, 1H), 6.44 (d, J=8.4 Hz, 1H), 4.19-4.27 (m, 2H), 2.91 (t, J=7.5 Hz, 2H), 2.57 (t, J=7.5 Hz, 2H), 2.37-2.43 (m, 3H), 2.21 (s, 3H), 2.18 (s, 3H), 1.86-2.05 (m, 2H), 1.32-1.62 (m, 3H), 0.95 (d, J=6.4 Hz, 6H). Mass spectrum (ESI, m/z): Calculated for C$_{27}$H$_{33}$ClO$_3$, 439.2 [M–H], measured as 439.2.

Example 18: Compound #502

3-[4-[[2-(4-chlorophenyl)-5-ethyl-cyclohexen-1-yl]methoxy]-2,3-dimethyl-phenyl]Propanoic Acid

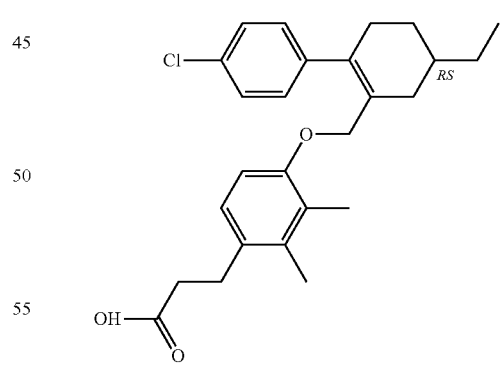

$^1$H NMR (300 MHz, CD$_3$OD) δ: 7.35 (d, J=7.5 Hz, 2H), 7.16 (d, J=6.6 Hz, 2H), 6.87 (d, J=6.0 Hz, 1H), 6.42 (d, J=6.6 Hz, 1H), 4.23-4.30 (m, 2H), 2.88 (t, J=6.0 Hz, 2H), 2.46-2.51 (m, 3H), 2.22-2.39 (m, 2H), 2.20 (s, 3H), 2.12 (s, 3H), 1.90-1.97 (m, 2H), 1.46-1.60 (m, 1H), 1.31-1.39 (m, 3H), 0.99 (t, J=7.5 Hz, 3H). Mass spectrum (ESI, m/z): Calculated for C$_{26}$H$_{31}$ClO$_3$, 425.2 [M–H], measured as 425.2

Example 19: Compound #522

3-[4-[[2-(4-chlorophenyl)-4-ethyl-cyclohexen-1-yl]methoxy]-2,3-dimethyl-phenyl]Propanoic Acid

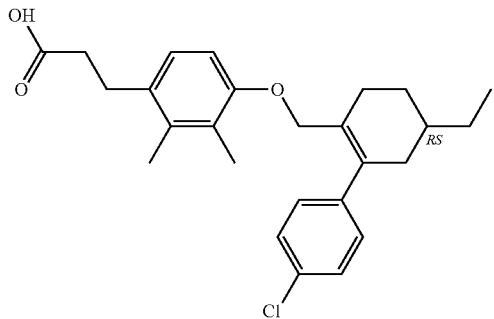 [SMILES: CCC1CCC(COc2ccc(CCC(=O)O)c(C)c2C)=C(c2ccc(Cl)cc2)C1]

$^1$H NMR (300 MHz, CD$_3$OD) δ: 7.19 (d, J=8.4 Hz, 2H), 7.02 (d, J=9.0 Hz, 2H), 6.30 (d, J=7.8 Hz, 1H), 6.27 (d, J=7.8 Hz, 1H), 4.15 (s, 2H), 2.78 (t, J=8.0 Hz, 2H), 2.24-2.39 (m, 5H), 2.10 (s, 3H), 2.03 (s, 3H), 1.82-1.90 (m, 2H), 1.50 (br s, 1H), 1.20-1.33 (m, 3H), 0.86 (t, J=7.5 Hz, 3H). Mass spectrum (ESI, m/z): Calculated for C$_{26}$H$_{31}$ClO$_3$, 425.2 [M−H], measured as 425.2

Example 20: Compound #523

3-[4-[[2-(4-chlorophenyl)-3-isopropyl-cyclohexen-1-yl]methoxy]-2,3-dimethyl-phenyl]Propanoic Acid

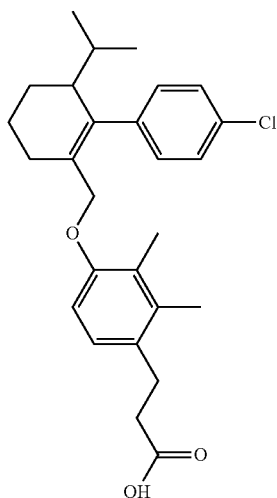 [SMILES: Cc1c(CCC(=O)O)ccc(OCC2=C(c3ccc(Cl)cc3)C(C(C)C)CCC2)c1C]

$^1$H NMR (400 MHz, CDCl$_3$) δ 7.27 (d, J=7.6 Hz, 2H), 7.06 (d, J=7.6 Hz, 2H), 6.88 (d, J=8.4 Hz, 1H), 6.41 (d, J=8.4 Hz, 1H), 4.27 (d, J=10.4 Hz, 1H), 4.16 (d, J=10.4 Hz, 1H), 2.93 (t, J=7.6 Hz, 2H), 2.59 (t, J=7.6 Hz, 2H), 2.47 (s, 1H), 2.27-2.30 (m, 2H), 2.23 (s, 3H), 2.18 (s, 3H), 1.97-1.79 (m, 2H), 1.68-1.73 (m, 2H), 1.61-1.68 (m, 1H), 0.85 (d, J=7.2 Hz, 3H), 0.73 (d, J=6.8 Hz, 3H). Mass spectrum (ESI, m/z): Calculated for C$_{27}$H$_{33}$ClO$_3$, 439.2 [M−H], measured as 439.3.

Example 21: Compound #540

3-[4-[[2-(4-chlorophenyl)-5-methoxy-cyclohexen-1-yl]methoxy]-2,3-dimethyl-phenyl]Propanoic Acid

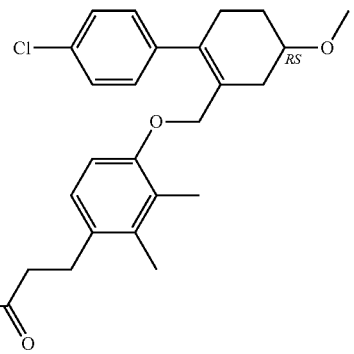

$^1$H NMR (300 MHz, CD$_3$OD) δ: 7.26 (d, J=8.4 Hz, 2H), 7.10 (d, J=8.4 Hz, 2H), 6.87 (d, J=8.4 Hz, 1H), 6.41 (d, J=8.4 Hz, 1H), 4.21-4.27 (m, 2H), 3.61-3.67 (m, 1H), 3.43 (s, 3H), 2.91 (t, J=7.6 Hz, 2H), 2.30-2.68 (m, 6H), 2.28 (s, 3H), 2.21 (s, 3H), 2.00-2.18 (m, 1H), 1.70-1.85 (m, 1H). Mass spectrum (ESI, m/z): Calculated for C$_{25}$H$_{29}$ClO$_4$, 427.2 [M−H], measured as 427.0

Example 22: Compound #541

3-[4-[[2-(4-chlorophenyl)-5,5-dimethyl-cyclohexen-1-yl]methoxy]-2,3-dimethyl-phenyl]Propanoic Acid

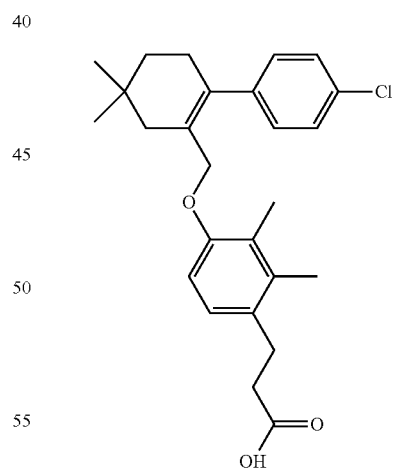

$^1$H NMR (300 MHz, CD$_3$OD) δ: 7.31 (d, J=8.4 Hz, 2H), 7.15 (d, J=8.4 Hz, 2H), 6.85 (d, J=8.8 Hz, 1H), 6.39 (d, J=8.4 Hz, 1H), 4.24 (s, 2H), 2.87 (t, J=7.6 Hz, 2H), 2.47 (t, J=7.6 Hz, 2H), 2.35-2.38 (m, 2H), 2.22 (s, 3H), 2.11 (s, 3H), 2.05 (s, 2H), 1.53 (t, J=6.4 Hz, 2H), 1.00 (s, 6H). Mass spectrum (ESI, m/z): Calculated for C$_{26}$H$_{31}$ClO$_3$, 425.2 [M−H], measured as 425.1

Example 23: Compound #547

3-[4-[(5,5-difluoro-2-thiazol-5-yl-cyclohexen-1-yl)methoxy]-2,3-dimethyl-phenyl]Propanoic Acid

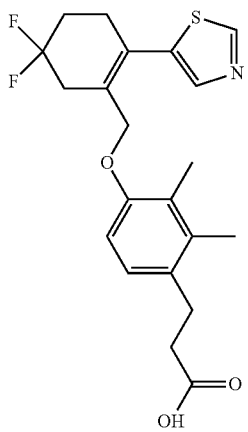 [SMILES: Cc1c(CCC(=O)O)ccc(OCC2=C(c3cncs3)CCC(F)(F)C2)c1C]

$^1$H NMR (300 MHz, CD$_3$OD) δ: 8.99 (s, 1H), 7.73 (s, 1H), 6.90 (d, J=8.4 Hz, 1H), 6.51 (d, J=8.4 Hz, 1H), 4.87 (s, 2H), 2.84-2.93 (m, 4H), 2.73-2.69 (m, 2H), 2.45-2.50 (m, 2H), 2.14-2.27 (m, 8H). $^{19}$F NMR (300 MHz, CD$_3$OD) δ:-98.21. Mass spectrum (ESI, m/z): Calculated for C$_{21}$H$_{23}$F$_2$NO$_3$S, 406.1 [M−H], measured as 406.1

Example 24: Compound #548

3-[4-[(5,5-difluoro-2-thiazol-5-yl-cyclohexen-1-yl)methoxy]-3-methyl-phenyl]Propanoic Acid

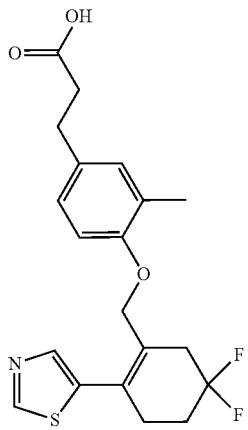 [SMILES: Cc1cc(CCC(=O)O)ccc1OCC1=C(c2cncs2)CCC(F)(F)C1]

$^1$H NMR (300 MHz, CD$_3$OD) δ: 8.99 (s, 1H), 7.76 (s, 1H), 7.00 (d, J=1.5 Hz, 1H), 6.94 (d, J=8.1 Hz, 1H), 6.61 (d, J=8.4 Hz, 1H), 4.87 (s, 2H), 2.69-2.93 (m, 6H), 2.54 (t, J=7.5 Hz, 2H), 2.14-2.28 (m, 5H). $^{19}$F NMR (300 MHz, CD$_3$OD) δ: −98.20. Mass spectrum (ESI, m/z): Calculated for C$_{20}$H$_{21}$F$_2$NO$_3$S, 392.1 [M−H], measured as 392.1

Example 25: Compound #549

3-[4-[(5,5-difluoro-2-thiazol-5-yl-cyclohexen-1-yl)methoxy]-3,5-difluoro-phenyl]Propanoic Acid

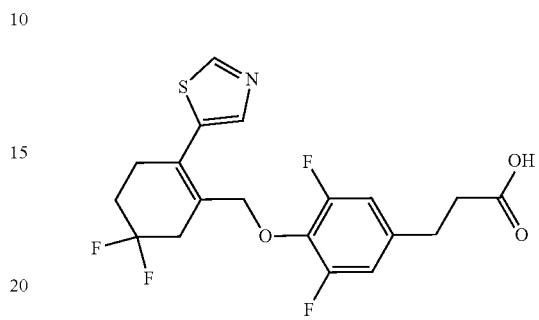

$^1$H NMR (300 MHz, CD$_3$OD) δ: 8.97 (s, 1H), 7.62 (s, 1H), 6.87 (d, J=9.3 Hz, 2H), 4.55 (s, 2H), 2.84-3.02 (m, 4H), 2.58-2.66 (m, 4H), 2.11-2.25 (m, 2H). $^{19}$F NMR (300 MHz, CD$_3$OD) δ: −98.09, −129.81. Mass spectrum (ESI, m/z): Calculated for C$_{19}$H$_{17}$F$_4$NO$_3$S, 414.1 [M−H], measured as 413.8

Example 26: Compound #550

3-[4-[[5,5-difluoro-2-(2-methylthiazol-5-yl)cyclohexen-1-yl]methoxy]-3-methyl-phenyl]Propanoic Acid

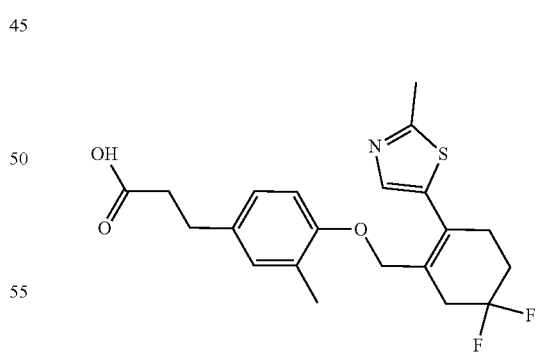

$^1$H NMR (300 MHz, CD$_3$OD) δ: 7.47 (s, 1H), 6.99 (s, 1H), 6.93 (d, J=8.4 Hz, 1H), 6.62 (d, J=8.1 Hz, 1H), 4.52 (s, 2H), 2.77-2.90 (m, 4H), 2.65-2.68 (m, 5H), 2.51-2.56 (m, 2H), 2.11-2.24 (m, 5H). $^{19}$F NMR (300 MHz, CD$_3$OD) δ: −98.04. Mass spectrum (ESI, m/z): Calculated for C$_{21}$H$_{23}$F$_2$NO$_3$S, 406.1 [M−H], measured as 406.1.

Example 27: Compound #552

3-[4-[[5,5-difluoro-2-(2-furyl)cyclohexen-1-yl]methoxy]-2,3-dimethyl-phenyl]Propanoic Acid

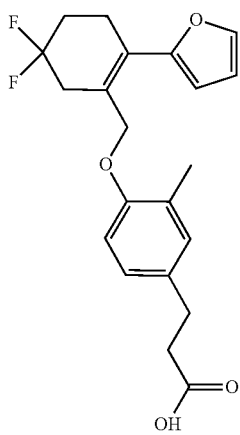 [SMILES: Cc1cc(CCC(=O)O)ccc1OCC1=C(c2ccco2)CCC(F)(F)C1]

$^1$H NMR (300 MHz, CD$_3$OD) δ: 7.53 (s, 1H), 6.90 (d, J=8.4 Hz, 1H), 6.58 (d, J=8.4 Hz, 1H), 6.46 (d, J=8.4 Hz, 1H), 6.40 (d, J=6.6 Hz, 1H), 4.78 (s, 2H), 2.78-2.83 (m, 6H), 2.48-2.51 (m, 2H), 2.23 (s, 3H), 2.17 (s, 3H), 2.03-2.15 (m, 2H). $^{19}$F NMR (300 MHz, CD$_3$OD) δ: −98.094. Mass spectrum (ESI, m/z): Calculated for C$_{22}$H$_{24}$F$_2$O$_4$, 389.2 [M−H], measured as 389.1.

Example 28: Compound #553

3-[4-[[5,5-difluoro-2-(2-methylthiazol-5-yl)cyclohexen-1-yl]methoxy]-2,3-dimethyl-phenyl]Propanoic Acid

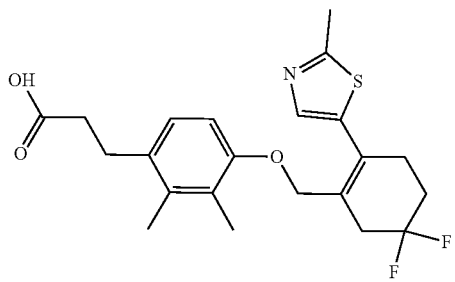 [SMILES: Cc1ncc(C2=C(COc3ccc(CCC(=O)O)c(C)c3C)CC(F)(F)CC2)s1]

$^1$H NMR (300 MHz, CD$_3$OD) δ: 7.43 (s, 1H), 6.91 (d, J=8.4 Hz, 1H), 6.53 (d, J=8.7 Hz, 1H), 4.51 (s, 2H), 2.81-2.29 (m, 4H), 2.60-2.75 (m, 5H), 2.45-2.51 (m, 2H), 2.12-2.25 (m, 8H). $^{19}$F NMR (300 MHz, CD$_3$OD) δ: −98.11. Mass spectrum (ESI, m/z): Calculated for C$_{22}$H$_{25}$F$_2$NO$_3$S, 420.2 [M−H], measured as 420.0.

Example 29: Compound #554

3-[4-[[5,5-difluoro-2-(2-methylthiazol-5-yl)cyclohexen-1-yl]methoxy]-3,5-difluoro-phenyl]Propanoic Acid

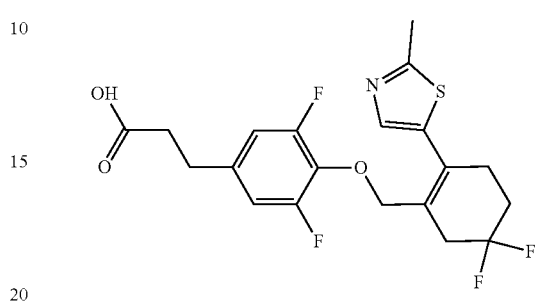

$^1$H NMR (300 MHz, CD$_3$OD) δ: 7.34 (s, 1H), 6.83-6.91 (m, 2H), 4.57 (s, 2H), 2.84-2.99 (m, 4H), 2.68 (s, 3H), 2.58-2.66 (m, 4H), 2.09-2.23 (m, 2H). $^{19}$F NMR (300 MHz, CD$_3$OD) δ: −98.08, −129.76. Mass spectrum (ESI, m/z): Calculated for C$_{20}$H$_{19}$F$_4$NO$_3$S, 428.1 [M−H], measured as 428.0.

Example 30: Compound #555

3-[4-[[5,5-difluoro-2-(2-furyl)cyclohexen-1-yl]methoxy]-3-methyl-phenyl]Propanoic Acid

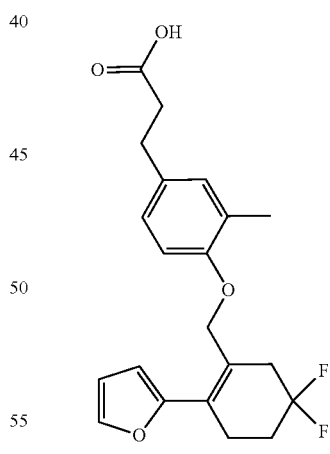

$^1$H NMR (400 MHz, CDCl$_3$) δ: 7.36 (s, 1H), 6.86-6.91 (m, 2H), 6.60 (d, J=8.0 Hz, 1H), 6.34 (s, 1H), 6.24 (d, J=3.2 Hz, 1H), 4.72 (s, 2H), 2.75-2.82 (m, 4H), 2.54 (t, J=7.8 Hz, 2H), 2.54-2.58 (m, 2H), 2.11 (s, 3H), 1.97-2.10 (m, 2H). $^{19}$F NMR (400 MHz, CDCl$_3$) δ: −101.19. Mass spectrum (ESI, m/z): Calculated for C$_{21}$H$_{22}$F$_2$O$_4$, 375.2 [M−H], measured as 375.1.

Example 31: Compound #557

3-[4-[[5,5-difluoro-2-(2-thienyl)cyclohexen-1-yl]methoxy]-2,3-dimethyl-phenyl]Propanoic Acid

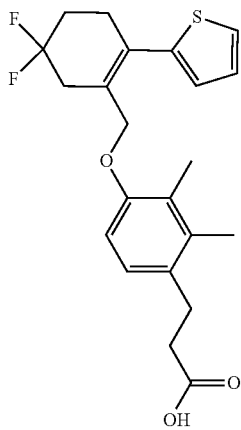 [SMILES: Cc1c(CCC(=O)O)ccc(OCC2=C(c3cccs3)CCC(F)(F)C2)c1C]

$^1$H NMR (300 MHz, CD$_3$OD) δ: 7.41 (d, J=5.1 Hz, 1H), 7.01-7.04 (m, 1H), 6.95-6.97 (m, 1H), 6.87-6.91 (m, 1H), 6.49 (d, J=8.4 Hz, 1H), 4.55 (s, 2H), 2.83-2.91 (m, 4H), 2.69-2.78 (m, 2H), 2.45-2.51 (m, 2H), 2.11-2.23 (m, 8H). $^{19}$F NMR (300 MHz, CD$_3$OD) δ: −98.16. Mass spectrum (ESI, m/z): Calculated for C$_{22}$H$_{24}$F$_2$O$_3$S, 405.1 [M−H], measured as 405.1

Example 32: Compound #558

3-[4-[[2-(5-cyano-2-thienyl)-5,5-difluoro-cyclohexen-1-yl]methoxy]-2,3-dimethyl-phenyl]Propanoic Acid

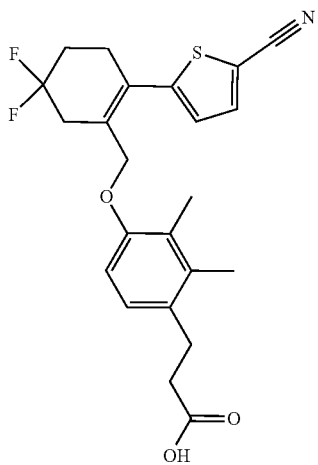 [SMILES: Cc1c(CCC(=O)O)ccc(OCC2=C(c3ccc(C#N)s3)CCC(F)(F)C2)c1C]

$^1$H NMR (300 MHz, CD$_3$OD) δ: 7.66 (d, J=3.9 Hz, 1H), 7.04 (d, J=3.9 Hz, 1H), 6.91 (d, J=8.4 Hz, 1H), 6.51 (d, J=8.4 Hz, 1H), 4.49 (s, 2H), 2.84-2.93 (m, 4H), 2.69-2.73 (m, 2H), 2.39-2.44 (m, 2H), 2.15-2.27 (m, 8H). $^{19}$F NMR (300 MHz, CD$_3$OD) δ: −98.10. Mass spectrum (ESI, m/z): Calculated for C$_{23}$H$_{23}$F$_2$NO$_3$S, 430.1 [M−H], measured as 430.0

Example 33: Compound #559

3-[4-[[5,5-difluoro-2-(2-thienyl)cyclohexen-1-yl]methoxy]-3,5-difluoro-phenyl]Propanoic Acid

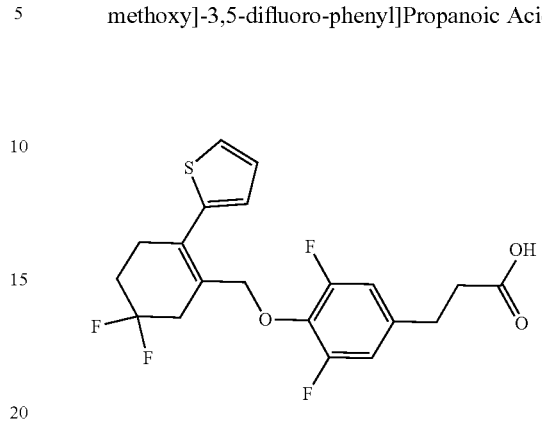

$^1$H NMR (300 MHz, CD$_3$OD) δ: 7.36 (d, J=4.2 Hz, 1H), 6.97 (d, J=5.4 Hz, 1H), 6.77-6.89 (m, 3H), 4.60 (s, 2H), 2.79-2.98 (m, 4H), 2.54-2.66 (m, 4H), 2.09-0.22 (m, 2H). $^{19}$F NMR (300 MHz, CD$_3$OD) δ: −98.05, −129.81. Mass spectrum (ESI, m/z): Calculated for C$_{22}$H$_{24}$F$_2$O$_3$S, 413.1 [M−H], measured as 413.0

Example 34: Compound #560

3-[4-[[5,5-difluoro-2-(2-thienyl)cyclohexen-1-yl]methoxy]-3-methyl-phenyl]Propanoic Acid

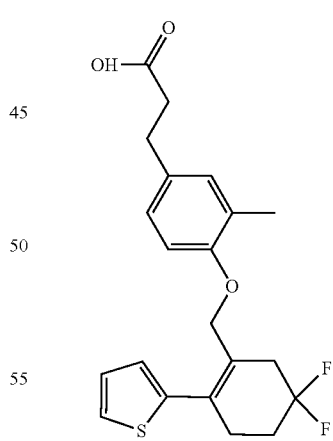

$^1$H NMR (300 MHz, CD$_3$OD) δ: 7.41 (d, J=6.0 Hz, 1H), 6.89-7.04 (m, 4H), 6.58 (d, J=8.1 Hz, 1H), 4.57 (s, 2H), 2.77-2.87 (m, 4H), 2.68-2.73 (m, 2H), 2.51-2.56 (m, 2H), 2.10-2.23 (m, 5H). $^{19}$F NMR (300 MHz, CD$_3$OD) δ: −98.12. Mass spectrum (ESI, m/z): Calculated for C$_{21}$H$_{22}$F$_2$O$_3$S, 391.1 [M−H], measured as 391.1

Example 35: Compound #569

3-[4-[[5,5-difluoro-2-(2-furyl)cyclohexen-1-yl]methoxy]-3,5-difluoro-phenyl]Propanoic Acid

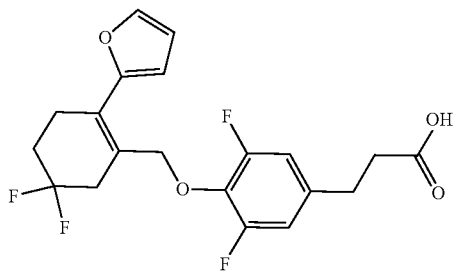 [SMILES: O=C(O)CCc1cc(F)c(OCC2=C(c3ccco3)CCC(F)(F)C2)c(F)c1]

$^1$H NMR (300 MHz, CD$_3$OD) δ: 7.47 (d, J=9 Hz, 1H), 6.83-6.91 (m, 2H), 6.42 (d, J=7.8 Hz, 2H), 4.86 (s, 2H), 2.84-2.99 (m, 4H), 2.66 (t, J=7.8 Hz, 2H), 2.60-2.70 (m, 2H), 2.09-2.20 (m, 2H). $^{19}$F NMR (300 MHz, CD$_3$OD) δ: −98.043, −129.98. Mass spectrum (ESI, m/z): Calculated for C$_{20}$H$_1$SF$_4$O$_4$, 397.1 [M−H], measured as 397.0

Example 36: Compound #572

3-[4-[[2-(5-cyano-2-thienyl)-5,5-difluoro-cyclohexen-1-yl]methoxy]-3,5-difluoro-phenyl]Propanoic Acid

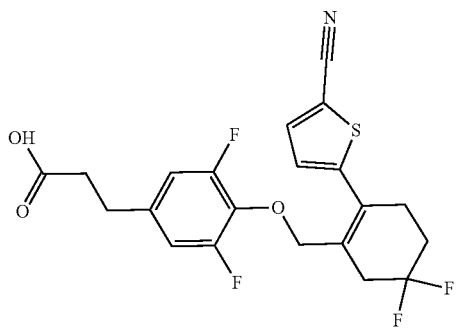 [SMILES: N#Cc1ccc(C2=C(COc3c(F)cc(CCC(=O)O)cc3F)CC(F)(F)CC2)s1]

$^1$H NMR (300 MHz, CD$_3$OD) δ: 7.66 (d, J=3.9 Hz, 1H), 6.84-7.11 (m, 3H), 4.69 (s, 2H), 2.84-3.32 (m, 4H), 2.66 (t, J=7.6 Hz, 2H), 2.29 (t, J=7.6 Hz, 2H), 2.12-2.23 (m, 2H). $^{19}$F NMR (300 MHz, CD$_3$OD) δ: −98.19, −130.06. Mass spectrum (ESI, m/z): Calculated for C$_{21}$H$_{21}$FO$_5$, 438.1 [M−H], measured as 438.1.

Example 37: Compound #573

3-[4-[[2-(5-cyano-2-thienyl)-5,5-difluoro-cyclohexen-1-yl]methoxy]-3-methyl-phenyl]Propanoic Acid

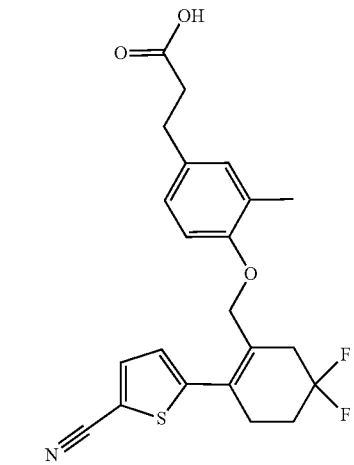 [SMILES: Cc1cc(CCC(=O)O)ccc1OCC1=C(c2ccc(C#N)s2)CCC(F)(F)C1]

$^1$H NMR (300 MHz, CD$_3$OD) δ: 7.66 (d, J=3.9 Hz, 1H), 7.05 (d, J=3.6 Hz, 1H), 6.95 (s, 1H), 6.94 (d, J=8.4 Hz, 1H), 6.61 (d, J=8.4 Hz, 1H), 4.51 (s, 2H), 2.93-2.80 (m, 4H), 2.77 (t, J=7.6 Hz, 2H), 2.46 (t, J=7.6 Hz, 2H), 2.27-2.13 (m, 5H). $^{19}$F NMR (300 MHz, CD$_3$OD) δ: −98.23. Mass spectrum (ESI, m/z): Calculated for C$_{22}$H$_{21}$F$_2$NO$_3$S, 416.1 [M−H], measured as 416.0.

Example 38: Compound #604

3-[4-[(2-cyclopentyl-5,5-dimethyl-cyclohexen-1-yl)methoxy]-2-(trifluoromethyl)phenyl]Propanoic Acid

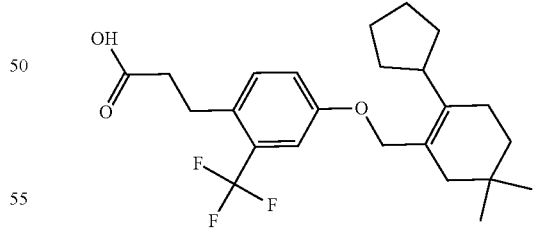

$^1$H NMR (400 MHz, CD$_3$OD) δ: 7.37 (d, J=8.4 Hz, 1H), 7.17 (s, 1H), 7.12 (d, J=8.4 Hz, 1H), 4.58 (s, 2H), 3.01-3.09 (m, 3H), 2.57 (t, J=8.0 Hz, 2H), 2.07-2.09 (m, 2H), 1.93 (s, 2H), 1.60-1.70 (m, 6H), 1.47-1.53 (m, 2H), 1.38 (t, J=6.4 Hz, 2H), 0.90 (s, 6H). $^{19}$FNMR (400 MHz, CD$_3$OD) δ: −61.32. Mass spectrum (ESI, m/z): Calculated for C$_{24}$H$_{31}$F$_3$O$_3$, 423.2 [M−H], measured as 423.1.

Example 39: Compound #605

3-[2-chloro-4-[(2-cyclopentyl-5,5-dimethyl-cyclo-hexen-1-yl)methoxy]phenyl]Propanoic Acid

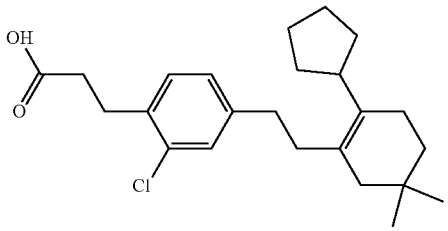 [SMILES: CC1(C)CCC(C2CCCC2)=C(CCc2ccc(CCC(=O)O)c(Cl)c2)C1]

$^1$H NMR (400 MHz, CD$_3$OD) δ: 7.20 (d, J=8.4 Hz, 1H), 6.96 (s, 1H), 6.82 (d, J=8.4 Hz, 1H), 4.51 (s, 2H), 3.02-3.11 (m, 1H), 2.97 (t, J=7.6 Hz, 2H), 2.58 (d, J=7.6 Hz, 2H), 2.01-2.08 (m, 2H), 1.92 (s, 2H), 1.61-1.69 (m, 6H), 1.39-1.48 (m, 2H), 1.36-1.38 (m, 2H), 0.91 (s, 6H). Mass spectrum (EI, m/z): Calculated for C$_{23}$H$_{31}$ClO$_3$, 389.2 [M−H], measured as 389.1.

Example 40: Compound #606

3-[4-[(2-cyclopentyl-5,5-difluoro-cyclohexen-1-yl)methoxy]-2-(trifluoromethyl)phenyl]Propanoic Acid

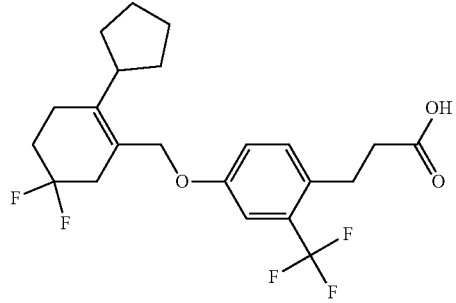 [SMILES: O=C(O)CCc1ccc(OCC2=C(C3CCCC3)CCC(F)(F)C2)cc1C(F)(F)F]

$^1$H NMR (400 MHz, CD$_3$OD) δ: 7.38 (d, J=8.4 Hz, 1H), 7.20 (s, 1H), 7.15 (d, J=8.4 Hz, 1H), 4.63 (s, 2H), 3.02-3.15 (m, 3H), 2.56-2.68 (m, 4H), 2.32-2.36 (m, 2H), 1.96-2.06 (m, 2H), 1.62-1.73 (m, 6H), 1.40-1.50 (m, 2H). $^{19}$FNMR (400 MHz, CD$_3$OD) δ: −61.34, −97.61. Mass spectrum (ESI, m/z): Calculated for C$_{22}$H$_{25}$F$_5$O$_3$, 431.2 [M−H], measured as 431.1.

Example 41: Compound #607

3-[2-chloro-4-[(2-cyclopentyl-5,5-difluoro-cyclohexen-1-yl)methoxy]phenyl]Propanoic Acid

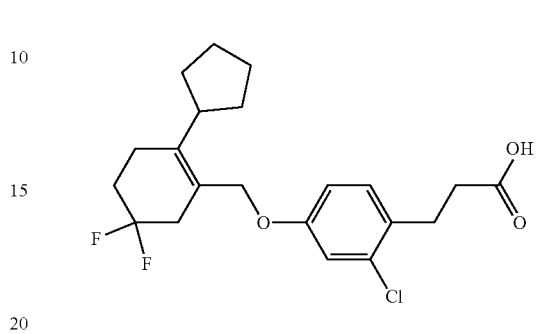

$^1$H NMR (400 MHz, CD$_3$OD) δ: 7.22 (d, J=8.4 Hz, 1H), 7.00 (s, 1H), 6.86 (d, J=8.4 Hz, 1H), 4.57 (s, 2H), 3.03-3.10 (m, 1H), 2.98 (t, J=7.6 Hz, 2H), 2.57-2.67 (m, 4H), 2.31-2.35 (m, 2H), 1.95-2.05 (m, 2H), 1.52-1.74 (m, 6H), 1.44-1.50 (m, 2H). $^{19}$FNMR (400 MHz, CD$_3$OD) δ: −97.55. Mass spectrum (EI, m/z): Calculated for C$_{21}$H$_{25}$ClF$_2$O$_3$, 397.1 [M−H], measured as 397.1.

Example 42: Compound #483

3-[4-[[2-(4-chlorophenyl)cyclohexen-1-yl]methoxy]-3-methyl-phenyl]Propanoic Acid

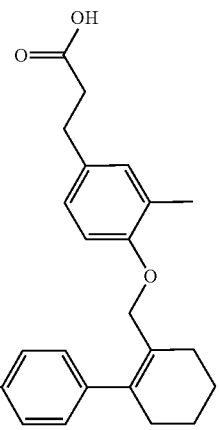

$^1$H NMR (300 MHz, CDCl$_3$) δ: 7.25 (d, J=9.0 Hz, 2H), 7.08 (d, J=8.7 Hz, 2H), 6.93 (s, 1H), 6.85 (d, J=8.4 Hz, 1H), 6.49 (d, J=8.4 Hz, 1H), 4.22 (s, 2H), 2.82 (t, J=7.5 Hz, 2H), 2.61 (t, J=7.5 Hz, 2H), 2.28 (br s, 4H), 2.18 (s, 3H), 1.72 (br s, 4H). Mass spectrum (ESI, m/z): Calculated for C$_{23}$H$_{25}$ClO$_3$, 383.1 [M−H], measured as 383.3

Example 43: Compound #526

3-[4-[[2-(4-chloro-3-fluoro-phenyl)-5,5-difluoro-cyclohexen-1-yl]methoxy]-2,3-dimethyl-phenyl]Propanoic Acid

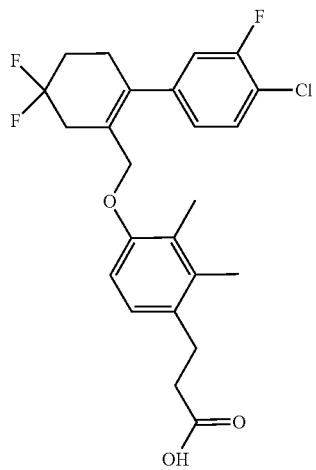 [SMILES: Cc1c(CCC(=O)O)ccc(OCC2=C(c3ccc(Cl)c(F)c3)CCC(F)(F)C2)c1C]

$^1$H NMR (CHLOROFORM-d) δ: 7.34 (td, J=7.1, 2.5 Hz, 1H), 6.97-7.09 (m, 2H), 6.87 (d, J=8.6 Hz, 1H), 6.41 (d, J=8.1 Hz, 1H), 4.24 (br s, 2H), 2.73-3.01 (m, 4H), 2.41-2.70 (m, 4H), 2.18 (d, J=20.7 Hz, 8H). Calculated for $C_{24}H_{24}ClF_3O_3$: 475.1 (M+23); Measured: 475.2.

Example 44: Compound #527

3-[4-[[2-(4-chloro-3-fluoro-phenyl)-5,5-difluoro-cyclohexen-1-yl]methoxy]-3-methyl-phenyl]Propanoic Acid

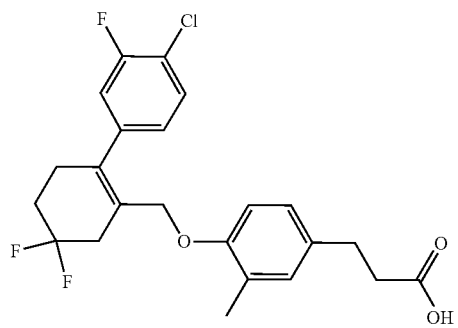 [SMILES: Cc1cc(CCC(=O)O)ccc1OCC1=C(c2ccc(Cl)c(F)c2)CCC(F)(F)C1]

$^1$H NMR (CHLOROFORM-d) δ: 7.35 (td, J=7.1, 2.5 Hz, 1H), 6.99-7.10 (m, 2H), 6.96 (d, J=1.5 Hz, 1H), 6.89 (dd, J=8.3, 1.8 Hz, 1H), 6.48 (d, J=8.6 Hz, 1H), 4.25 (br s, 2H), 2.84 (br t, J=7.6 Hz, 4H), 2.40-2.73 (m, 4H), 2.11-2.28 (m, 5H). Calculated for $C_{23}H_{22}ClF_3O_3$: 461.1 (M+23); Measured: 461.2.

Example 45: Compound #528

3-[4-[[2-(4-chloro-3-fluoro-phenyl)-5,5-difluoro-cyclohexen-1-yl]methoxy]-3,5-difluoro-phenyl]Propanoic Acid

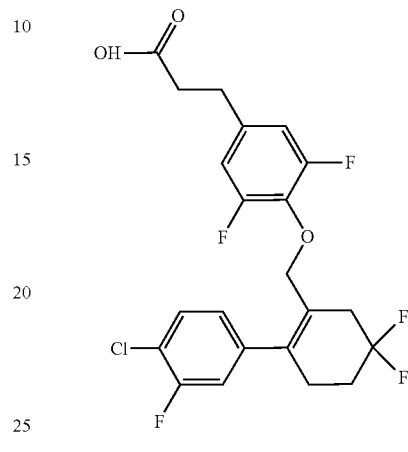

$^1$H NMR (CHLOROFORM-d) δ: 7.33 (td, J=7.6, 1.5 Hz, 1H), 6.97-7.07 (m, 1H), 6.88 (td, J=6.9, 1.8 Hz, 1H), 6.63-6.74 (m, 2H), 4.33 (s, 2H), 2.80-3.13 (m, 4H), 2.34-2.73 (m, 4H), 2.08-2.26 (m, 2H). Calculated for $C_{22}H_{16}ClF_5O_3$: 483.1 (M+23); Measured: 483.1.

Example 46: Compound #529

3-[4-[[5,5-difluoro-2-(3-fluoro-4-methyl-phenyl)cyclohexen-1-yl]methoxy]-2,3-dimethyl-phenyl]Propanoic Acid

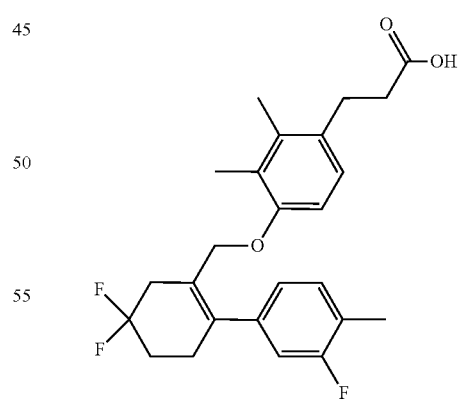

$^1$H NMR (CHLOROFORM-d) δ: 7.08-7.17 (m, 1H), 6.76-6.91 (m, 3H), 6.41 (d, J=8.6 Hz, 1H), 4.30 (s, 2H), 2.87-2.95 (m, 2H), 2.82 (br t, J=14.7 Hz, 2H), 2.51-2.65 (m, 4H), 2.10-2.30 (m, 11H). Calculated for $C_{25}H_{27}F_3O_3$: 455.2 (M+23); Measured: 455.3.

Example 47: Compound #530

3-[4-[[5,5-difluoro-2-(3-fluoro-4-methyl-phenyl)cyclohexen-1-yl]methoxy]-3-methyl-phenyl]Propanoic Acid

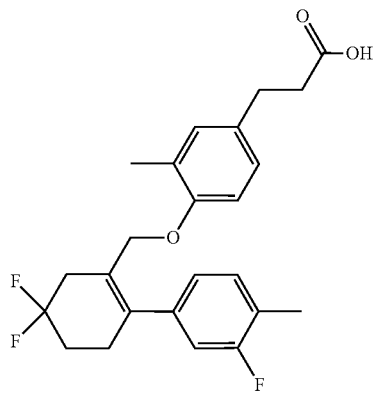 [SMILES: Cc1ccc(C2=C(COc3ccc(CCC(=O)O)cc3C)CC(F)(F)CC2)cc1F]

¹H NMR (CHLOROFORM-d) δ: 7.14 (t, J=8.1 Hz, 1H), 6.97 (d, J=2.0 Hz, 1H), 6.86-6.93 (m, 1H), 6.78-6.86 (m, 2H), 6.49 (d, J=8.1 Hz, 1H), 4.32 (s, 2H), 2.75-2.90 (m, 4H), 2.54-2.67 (m, 4H), 2.27 (s, 3H), 2.09-2.23 (m, 5H). Calculated for $C_{24}H_{25}F_3O_3$: 441.2 (M+23); Measured: 441.1.

Example 48: Compound #525

3-[4-[[5,5-difluoro-2-(3-fluoro-4-methyl-phenyl)cyclohexen-1-yl]methoxy]-3,5-difluoro-phenyl]Propanoic Acid

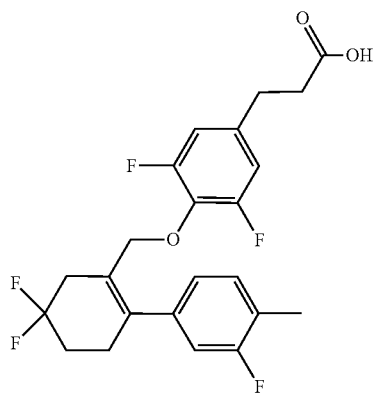 [SMILES: Cc1ccc(C2=C(COc3c(F)cc(CCC(=O)O)cc3F)CC(F)(F)CC2)cc1F]

¹H NMR (CHLOROFORM-d) δ: 7.10 (t, J=7.8 Hz, 1H), 6.66-6.78 (m, 3H), 6.63 (d, J=10.6 Hz, 1H), 4.37 (s, 2H), 2.80-3.02 (m, 4H), 2.66 (br t, J=7.6 Hz, 2H), 2.50-2.60 (m, 2H), 2.26 (s, 3H), 2.15 (tt, J=13.6, 6.8 Hz, 2H). Calculated for $C_{23}H_{21}F_5O_3$: 463.1 (M+23); Measured: 463.2.

Example 49: Compound #531

3-[4-[[2-(3,4-difluorophenyl)-5,5-difluoro-cyclohexen-1-yl]methoxy]-2,3-dimethyl-phenyl]Propanoic Acid

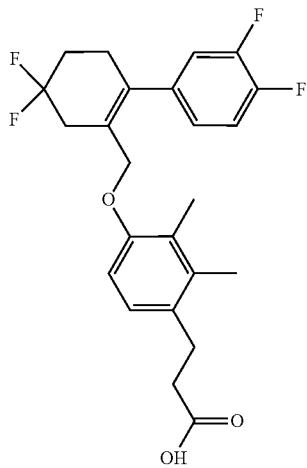 [SMILES: Cc1c(CCC(=O)O)ccc(OCC2=C(c3ccc(F)c(F)c3)CCC(F)(F)C2)c1C]

¹H NMR (CHLOROFORM-d) δ: 7.06-7.18 (m, 1H), 6.94-7.04 (m, 1H), 6.89 (br d, J=8.6 Hz, 2H), 6.41 (br d, J=8.1 Hz, 1H), 4.26 (s, 2H), 2.76-2.98 (m, 4H), 2.58 (br s, 4H), 2.19 (br d, J=19.2 Hz, 8H). Calculated for $C_{24}H_{24}F_4O_3$: 459.2 (M+23); Measured: 459.1.

Example 50: Compound #532

3-[4-[[2-(3,4-difluorophenyl)-5,5-difluoro-cyclohexen-1-yl]methoxy]-3-methyl-phenyl]Propanoic Acid ¹H NMR (CHLOROFORM-d) δ: 7.12 (dt, J=10.1, 8.3 Hz, 1H), 6.94-7.04 (m, 2H), 6.85-6.93 (m, 2H), 6.49 (d, J=8.6 Hz, 1H), 4.28 (s, 2H), 2.75-2.90 (m, 4H), 2.54-2.67 (m, 4H), 2.11-2.26 (m, 5H). Calculated for $C_{23}H_{22}F_4O_3$: 445.2 (M+23); Measured: 445.2.

Example 51: Compound #533

3-[4-[[2-(3,4-difluorophenyl)-5,5-difluoro-cyclohexen-1-yl]methoxy]-3,5-difluoro-phenyl]Propanoic Acid

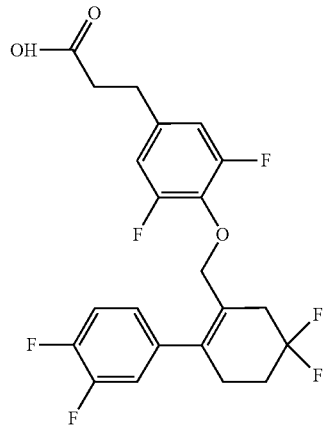 [SMILES: O=C(O)CCc1cc(F)c(OCC2=C(c3ccc(F)c(F)c3)CCC(F)(F)C2)c(F)c1]

$^1$H NMR (CHLOROFORM-d) δ: 7.03-7.16 (m, 1H), 6.77-6.88 (m, 2H), 6.73 (br d, J=8.6 Hz, 2H), 4.33 (s, 2H), 2.82-3.03 (m, 4H), 2.61-2.73 (m, 2H), 2.55 (br s, 2H), 2.08-2.26 (m, 2H). Calculated for $C_{22}H_{18}F_6O_3$: 467.1 (M+23); Measured: 467.0.

Example 52: Compound #534

3-[4-[[2-(2,4-difluorophenyl)-5,5-difluoro-cyclohexen-1-yl]methoxy]-2,3-dimethyl-phenyl]Propanoic Acid

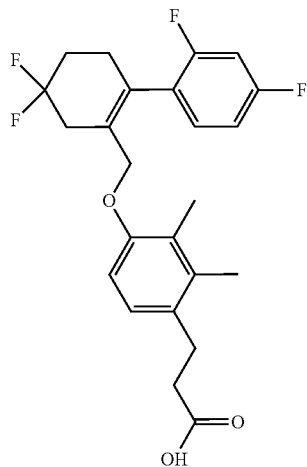 [SMILES: Cc1c(CCC(=O)O)ccc(OCC2=C(c3ccc(F)cc3F)CCC(F)(F)C2)c1C]

$^1$H NMR (CHLOROFORM-d) δ: 7.03-7.14 (m, 1H), 6.78-6.93 (m, 3H), 6.40 (br d, J=8.6 Hz, 1H), 4.23 (br s, 2H), 2.90 (br t, J=7.8 Hz, 4H), 2.43-2.71 (m, 4H), 2.18 (br d, J=20.2 Hz, 8H). Calculated for $C_{24}H_{24}F_4O_3$: 459.2 (M+23); Measured: 459.0.

Example 53: Compound #535

3-[4-[[2-(2,4-difluorophenyl)-5,5-difluoro-cyclohexen-1-yl]methoxy]-3-methyl-phenyl]Propanoic Acid

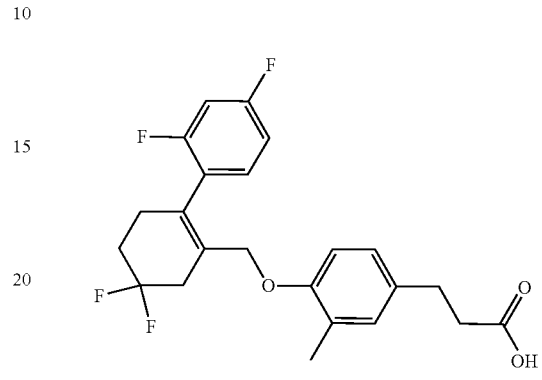

$^1$H NMR (CHLOROFORM-d) δ: 7.05-7.15 (m, 1H), 6.96 (d, J=1.5 Hz, 1H), 6.79-6.92 (m, 3H), 6.48 (d, J=8.6 Hz, 1H), 4.25 (br s, 2H), 2.84 (br t, J=7.8 Hz, 4H), 2.43-2.68 (m, 4H), 2.10-2.26 (m, 5H). Calculated for $C_{23}H_{22}F_4O_3$: 445.2 (M+23); Measured: 445.2.

Example 54: Compound #536

3-[4-[[2-(2,4-difluorophenyl)-5,5-difluoro-cyclohexen-1-yl]methoxy]-3,5-difluoro-phenyl]Propanoic Acid

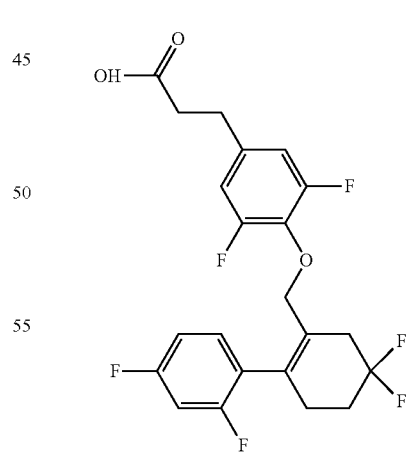

$^1$H NMR (CHLOROFORM-d) δ: 6.91-7.01 (m, 1H), 6.74-6.86 (m, 2H), 6.66-6.74 (m, 2H), 4.31 (br s, 2H), 2.80-3.12 (m, 4H), 2.38-2.70 (m, 4H), 2.08-2.24 (m, 2H). Calculated for $C_{22}H_{18}F_6O_3$: 467.1 (M+23); Measured: 467.0.

Example 55: Compound #537

3-[4-[(5,5-difluoro-2-phenyl-cyclohexen-1-yl)methoxy]-2,3-dimethyl-phenyl]Propanoic Acid

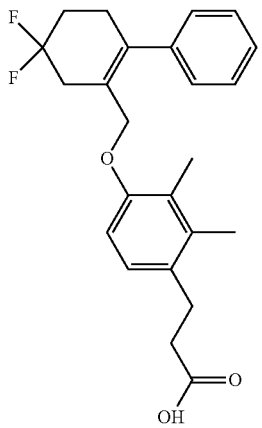 [SMILES: Cc1c(CCC(=O)O)ccc(OCC2=C(c3ccccc3)CCC(F)(F)C2)c1C]

$^1$H NMR (CHLOROFORM-d) δ: 7.27-7.38 (m, 3H), 7.12-7.20 (m, 2H), 6.86 (d, J=8.1 Hz, 1H), 6.39 (d, J=8.6 Hz, 1H), 4.30 (s, 2H), 2.76-2.96 (m, 4H), 2.63 (br t, J=6.6 Hz, 2H), 2.56 (dd, J=8.6, 7.1 Hz, 2H), 2.19 (d, J=13.6 Hz, 8H). Calculated for $C_{24}H_{28}F_2O_3$: 423.2 (M+23); Measured: 423.1.

Example 56: Compound #538

3-[4-[(5,5-difluoro-2-phenyl-cyclohexen-1-yl)methoxy]-3-methyl-phenyl]Propanoic Acid

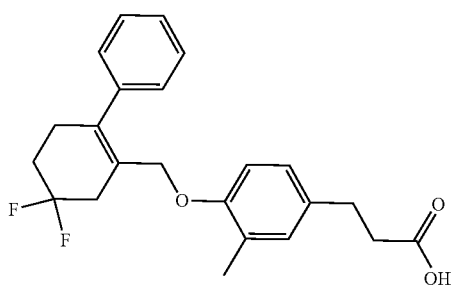 [SMILES: Cc1cc(CCC(=O)O)ccc1OCC1=C(c2ccccc2)CCC(F)(F)C1]

$^1$H NMR (CHLOROFORM-d) δ: 7.26-7.39 (m, 3H), 7.11-7.21 (m, 2H), 6.96 (d, J=1.5 Hz, 1H), 6.87 (dd, J=8.1, 2.0 Hz, 1H), 6.46 (d, J=8.6 Hz, 1H), 4.32 (s, 2H), 2.75-2.91 (m, 4H), 2.54-2.69 (m, 4H), 2.09-2.26 (m, 5H). Calculated for $C_{23}H_{24}F_2O_3$: 409.2 (M+23); Measured: 409.2.

Example 57: Compound #539

3-[4-[(5,5-difluoro-2-phenyl-cyclohexen-1-yl)methoxy]-3,5-difluoro-phenyl]Propanoic Acid

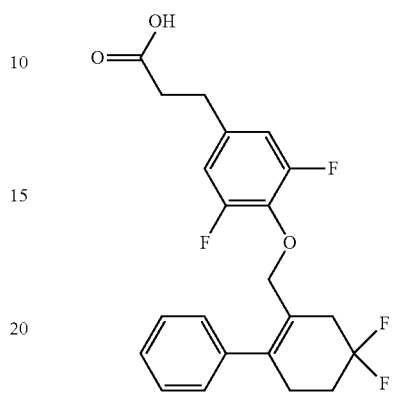

$^1$H NMR (CHLOROFORM-d) δ: 7.19-7.34 (m, 3H), 7.04 (dd, J=7.6, 2.0 Hz, 2H), 6.63-6.75 (m, 2H), 4.37 (s, 2H), 2.95 (br t, J=14.7 Hz, 2H), 2.80-2.89 (m, 2H), 2.55-2.69 (m, 4H), 2.17 (tt, J=13.8, 6.7 Hz, 2H). Calculated for $C_{22}H_{20}F_4O_3$: 431.1 (M+23); Measured: 431.1.

Example 58: Compound #563

3-[4-[[2-(5-chloro-2-thienyl)-5,5-difluoro-cyclohexen-1-yl]methoxy]-2,3-dimethyl-phenyl]Propanoic Acid

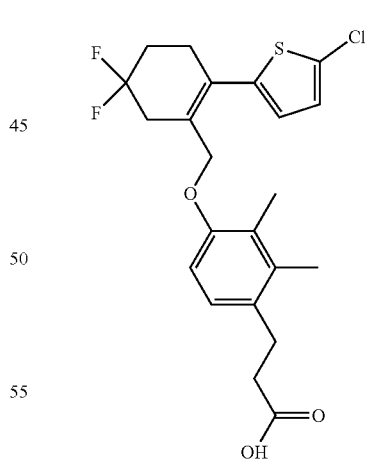

$^1$H NMR (CHLOROFORM-d) δ: 6.92 (d, J=8.6 Hz, 1H), 6.79 (d, J=3.5 Hz, 1H), 6.68 (d, J=3.5 Hz, 1H), 6.51 (d, J=8.1 Hz, 1H), 4.52 (s, 2H), 2.89-2.97 (m, 2H), 2.84 (br t, J=14.4 Hz, 2H), 2.65 (br t, J=6.6 Hz, 2H), 2.54-2.61 (m, 2H), 2.09-2.26 (m, 8H). Calculated for $C_{22}H_{23}ClF_2O_3S$: 463.1 (M+23); Measured: 463.2.

Example 59: Compound #542

3-[4-[[2-(5-chloro-2-thienyl)-5,5-difluoro-cyclohexen-1-yl]methoxy]-3-methyl-phenyl]Propanoic Acid

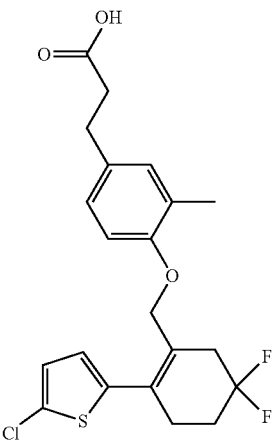 [SMILES: Cc1cc(CCC(=O)O)ccc1OCC1=C(c2ccc(Cl)s2)CCC(F)(F)C1]

$^1$H NMR (CHLOROFORM-d) δ: 6.99 (s, 1H), 6.93 (dd, J=8.6, 2.0 Hz, 1H), 6.80 (d, J=4.0 Hz, 1H), 6.68 (d, J=3.5 Hz, 1H), 6.59 (d, J=8.1 Hz, 1H), 4.53 (s, 2H), 2.76-2.91 (m, 4H), 2.59-2.70 (m, 4H), 2.09-2.25 (m, 5H). Calculated for $C_{21}H_{21}ClF_2O_3S$: 449.1 (M+23); Measured: 449.2.

Example 60: Compound #543

3-[4-[[2-(5-chloro-2-thienyl)-5,5-difluoro-cyclohexen-1-yl]methoxy]-3,5-difluoro-phenyl]Propanoic Acid

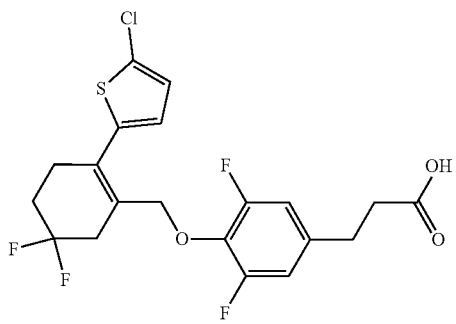 [SMILES: O=C(O)CCc1cc(F)c(OCC2=C(c3ccc(Cl)s3)CCC(F)(F)C2)c(F)c1]

$^1$H NMR (CHLOROFORM-d) δ: 6.71-6.83 (m, 3H), 6.70 (d, J=4.0 Hz, 1H), 4.58 (s, 2H), 2.83-3.01 (m, 4H), 2.55-2.72 (m, 4H), 2.16 (tt, J=13.6, 6.6 Hz, 2H). Calculated for $C_{20}H_{17}ClF_4O_3S$: 471.1 (M+23); Measured: 471.1.

Example 61: Compound #545

3-[4-[[5,5-difluoro-2-(1-methylpyrazol-4-yl)cyclohexen-1-yl]methoxy]-2,3-dimethyl-phenyl]Propanoic Acid

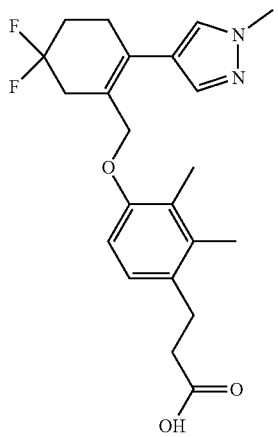 [SMILES: Cc1c(CCC(=O)O)ccc(OCC2=C(c3cnn(C)c3)CCC(F)(F)C2)c1C]

$^1$H NMR (CHLOROFORM-d) δ: 7.42 (s, 1H), 7.24-7.36 (m, 1H), 6.93 (br d, J=8.6 Hz, 1H), 6.53 (br d, J=8.6 Hz, 1H), 4.49 (s, 2H), 3.88 (s, 3H), 2.93 (br t, J=7.8 Hz, 2H), 2.80 (br t, J=14.4 Hz, 2H), 2.54-2.69 (m, 4H), 2.08-2.31 (m, 8H). Calculated for $C_{22}H_{26}F_2N_2O_3$: 427.2 (M+23); Measured: 427.2.

Example 62: Compound #546

3-[4-[[5,5-difluoro-2-(1-methylpyrazol-4-yl)cyclohexen-1-yl]methoxy]-3-methyl-phenyl]Propanoic Acid

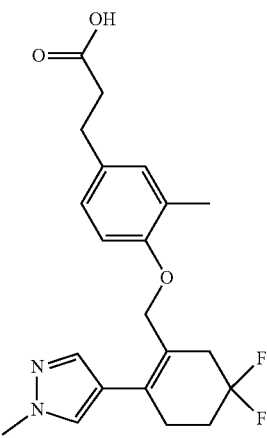 [SMILES: Cc1cc(CCC(=O)O)ccc1OCC1=C(c2cnn(C)c2)CCC(F)(F)C1]

$^1$H NMR (CHLOROFORM-d) δ: 7.27 (d, J=6.6 Hz, 2H), 7.00 (d, J=1.5 Hz, 1H), 6.94 (dd, J=8.6, 2.0 Hz, 1H), 6.60 (d, J=8.1 Hz, 1H), 4.50 (s, 2H), 3.88 (s, 3H), 2.73-2.92 (m, 4H), 2.55-2.68 (m, 4H), 2.07-2.25 (m, 5H). Calculated for $C_{21}H_{24}F_2N_2O_3$: 413.2 (M+23); Measured: 413.3.

Example 63: Compound #544

3-[4-[5,5-difluoro-2-(1-methylpyrazol-4-yl)cyclohexen-1-yl]methoxy]-3,5-difluoro-phenyl]Propanoic Acid

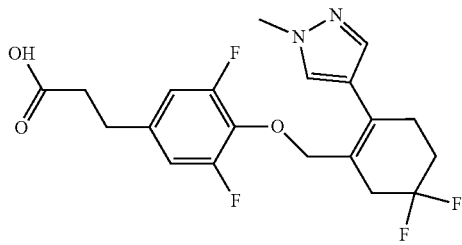 [SMILES: Cn1cc(C2=C(COc3c(F)cc(CCC(=O)O)cc3F)CC(F)(F)CC2)cn1]

$^1$H NMR (CHLOROFORM-d) δ: 7.47 (s, 1H), 7.40 (s, 1H), 6.73-6.82 (m, 2H), 4.50 (s, 2H), 3.91 (s, 3H), 2.83-2.96 (m, 4H), 2.63-2.71 (m, 2H), 2.60 (br t, J=6.6 Hz, 2H), 2.14 (tt, J=13.6, 6.6 Hz, 2H). Calculated for $C_{20}H_{20}F_4N_2O_3$: 435.1 (M+23); Measured: 435.2.

Example 64: Compound #564

3-[4-[[5,5-difluoro-2-(5-methyl-2-thienyl)cyclohexen-1-yl]methoxy]-2,3-dimethyl-phenyl]Propanoic Acid

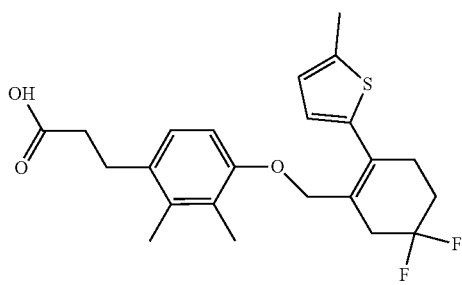 [SMILES: Cc1ccc(C2=C(COc3ccc(CCC(=O)O)c(C)c3C)CC(F)(F)CC2)s1]

$^1$H NMR (CHLOROFORM-d) δ: 6.91 (d, J=8.6 Hz, 1H), 6.69 (d, J=3.5 Hz, 1H), 6.62 (dd, J=3.5, 1.0 Hz, 1H), 6.51 (d, J=8.6 Hz, 1H), 4.57 (s, 2H), 2.88-2.97 (m, 2H), 2.83 (br t, J=14.7 Hz, 2H), 2.67 (br t, J=6.6 Hz, 2H), 2.58 (br t, J=7.8 Hz, 2H), 2.46 (s, 3H), 2.08-2.26 (m, 8H). Calculated for $C_{23}H_{28}F_2O_3S$: 443.2 (M+23); Measured: 443.2.

Example 65: Compound #561

3-[4-[[5,5-difluoro-2-(5-methyl-2-thienyl)cyclohexen-1-yl]methoxy]-3-methyl-phenyl]Propanoic Acid

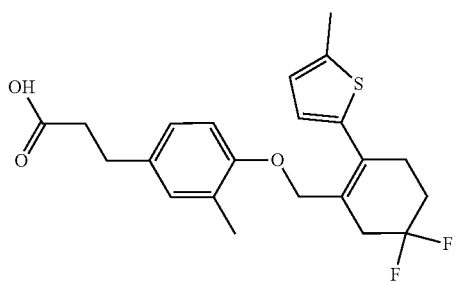 [SMILES: Cc1ccc(C2=C(COc3ccc(CCC(=O)O)cc3C)CC(F)(F)CC2)s1]

$^1$H NMR (CHLOROFORM-d) δ: 6.98 (s, 1H), 6.92 (br d, J=8.6 Hz, 1H), 6.68 (d, J=3.5 Hz, 1H), 6.63 (dd, J=3.5, 1.0 Hz, 1H), 6.59 (d, J=8.1 Hz, 1H), 4.59 (s, 2H), 2.75-2.91 (m, 4H), 2.59-2.71 (m, 4H), 2.47 (s, 3H), 2.08-2.26 (m, 5H). Calculated for $C_{22}H_{24}F_2O_3S$: 429.1 (M+23); Measured: 429.1.

Example 66: Compound #562

3-[4-[[5,5-difluoro-2-(5-methyl-2-thienyl)cyclohexen-1-yl]methoxy]-3,5-difluoro-phenyl]Propanoic Acid

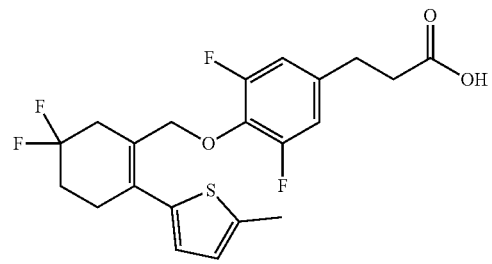 [SMILES: Cc1ccc(C2=C(COc3c(F)cc(CCC(=O)O)cc3F)CC(F)(F)CC2)s1]

$^1$H NMR (CHLOROFORM-d) δ: 6.67-6.81 (m, 3H), 6.62 (dd, J=3.5, 1.0 Hz, 1H), 4.63 (s, 2H), 2.82-3.00 (m, 4H), 2.58-2.73 (m, 4H), 2.45 (d, J=1.0 Hz, 3H), 2.15 (tt, J=13.6, 6.6 Hz, 2H). Calculated for $C_{21}H_{20}F_4O_3S$: 451.1 (M+23); Measured: 451.2.

Example 67: Compound #568

3-[4-[[2-(4-chlorophenyl)-4,4-difluoro-cyclohexen-1-yl]methoxy]-2,3-dimethyl-phenyl]Propanoic Acid

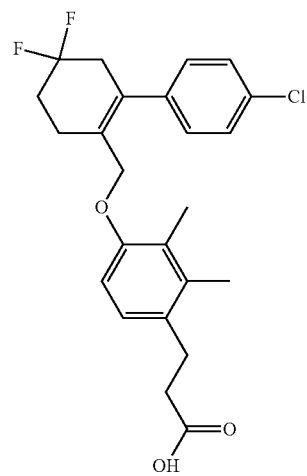 [SMILES: Cc1c(CCC(=O)O)ccc(OCC2=C(c3ccc(Cl)cc3)CC(F)(F)CC2)c1C]

$^1$H NMR (CHLOROFORM-d) δ: 7.28-7.35 (m, 2H), 7.07-7.17 (m, 2H), 6.88 (d, J=8.6 Hz, 1H), 6.42 (d, J=8.6 Hz, 1H), 4.27 (s, 2H), 2.91 (br t, J=7.8 Hz, 2H), 2.81 (br t, J=14.1 Hz, 2H), 2.52-2.70 (m, 4H), 2.10-2.28 (m, 8H). Calculated for $C_{24}H_{25}ClF_2O_3$: 457.1 (M+23); Measured: 457.2.

Example 68: Compound #566

3-[4-[[2-(4-chlorophenyl)-4,4-difluoro-cyclohexen-1-yl]methoxy]-3-methyl-phenyl]Propanoic Acid

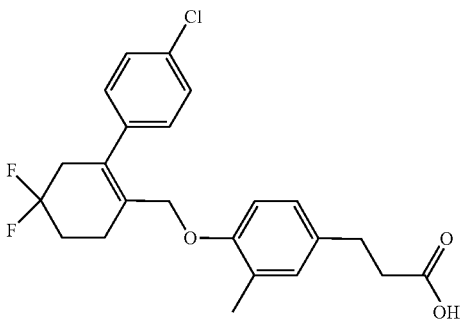 [SMILES: Cc1cc(CCC(=O)O)ccc1OCC1=C(c2ccc(Cl)cc2)CC(F)(F)CC1]

¹H NMR (CHLOROFORM-d) δ: 7.29-7.36 (m, 2H), 7.07-7.17 (m, 2H), 6.97 (s, 1H), 6.89 (br d, J=8.1 Hz, 1H), 6.49 (d, J=8.1 Hz, 1H), 4.28 (s, 2H), 2.74-2.91 (m, 4H), 2.62 (br s, 4H), 2.09-2.27 (m, 5H). Calculated for $C_{23}H_{23}ClF_2O_3$: 443.1 (M+23); Measured: 443.2.

The following representative compounds of formula (I) were prepared according to the process described in Scheme 1 above, selecting appropriate starting materials and reagents, as would be readily recognized by those skilled in the art.

Example 69: Compound #233-(2,3-dimethyl-4-((2-phenylcyclopent-1-en-1-yl)methoxy)phenyl)Propanoic Acid

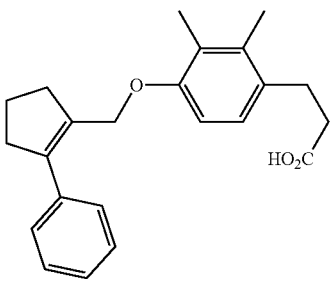 [SMILES: Cc1c(CCC(=O)O)ccc(OCC2=C(c3ccccc3)CCC2)c1C]

¹H NMR (CHLOROFORM-d) δ: 7.26 (s, 7H), 6.86-6.93 (m, 1H), 6.49-6.59 (m, 1H), 4.57-4.68 (m, 2H), 2.88-2.95 (m, 2H), 2.79-2.86 (m, 2H), 2.69-2.76 (m, 2H), 2.57 (s, 2H), 2.22 (s, 3H), 2.19 (s, 3H), 1.92-2.05 (m, 3H).

Example 70: Compound #27

3-(4-((2-(4-ethylphenyl)cyclopent-1-en-1-yl)methoxy)-2,3-dimethylphenyl)Propanoic Acid

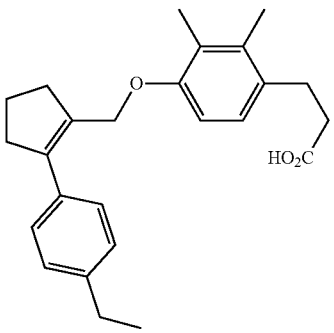 [SMILES: CCc1ccc(C2=C(COc3ccc(CCC(=O)O)c(C)c3C)CCC2)cc1]

Step 1: methyl 2-(4-ethylphenyl)cyclopent-1-ene-1-carboxylate

A suspension of anhydrous potassium phosphate (4.96 g, 23.27 mmol), tetrakis(triphenylphosphine) palladium (655 mg, 0.57 mmol), (4-ethylphenyl)boronic acid (1.19 g, 7.94 mmol) and methyl 2-(((trifluoromethyl)sulfonyl)oxy)cyclopent-1-ene-1-carboxylate (1.8 g, 6.55 mmol) in 1,4-dioxane (50 mL) was sparged with a stream of argon for 20 minutes. The reaction was then placed under an argon atmosphere and heated to 90° C. for 16 hours before cooling to ambient temperature. The mixture was diluted with diethyl ether and filtered through a plug of CELITE®. The filtrate was concentrated in vacuo and purified by flash chromatography (SiO₂, DCM) to yield methyl 2-(4-ethylphenyl)cyclopent-1-ene-1-carboxylate.

Step 2: (2-(4-ethylphenyl)cyclopent-1-en-1-yl)methanol

A solution of methyl 2-(4-ethylphenyl)cyclopent-1-ene-1-carboxylate (850 mg, 3.7 mmol) in dry toluene (40 mL) was cooled to −78° C. under an argon atmosphere. The reaction mixture was treated dropwise with DiBAl-H (8.2 mL, 8.2 mmol in toluene) and stirred, allowing the reaction mixture to reach ambient temperature over 2 hours. After stirred for one additional hour, the mixture was cooled to ~−10° C. and quenched by the dropwise addition of sat. Rochelle's salt (12 mL). The aqueous layer was extracted with diethyl ether and the combined organic layers washed with sat. NaHCO₃ and brine before being dried over MgSO₄. The resulting mixture was concentrated in vacuo, followed by flash chromatography (SiO₂, diethyl ether) to yield (2-(4-ethylphenyl)cyclopent-1-en-1-yl)methanol as a colorless crystalline solid.

Step 3: ethyl 3-(4-((2-(4-ethylphenyl)cyclopent-1-en-1-yl)methoxy)-2,3-dimethylphenyl)Propanoate A solution of (2-(4-ethylphenyl)cyclopent-1-en-1-yl)methanol (89 mg, 0.44 mmol), ADDP (236 mg, 0.93 mmol) and ethyl 3-(4-hydroxy-2,3-dimethylphenyl)propanoate (149 mg, 0.67 mmol) in toluene (20 mL) was placed under an argon atmosphere and treated with neat tri-n-butylphosphine (0.28 mL, 1.1 mmol). The reaction was stirred at 60° C. for ~18 hours and then concentrated in vacuo. The residue was triturated with diethyl ether, the resulting white precipitate was filtered off and the filtrate concentrated. The resulting residue was purified by flash chromatography (SiO₂, 6:7 DCM:heptane) to yield ethyl 3-(4-((2-(4-ethylphenyl)cyclopent-1-en-1-yl)methoxy)-2,3-dimethylphenyl)propanoate.

Step 4: 3-(4-((2-(4-ethylphenyl)cyclopent-1-en-1-yl)methoxy)-2,3-dimethylphenyl)Propanoic Acid A solution of ethyl 3-(4-((2-(4-ethylphenyl)cyclopent-1-en-1-yl)methoxy)-2,3-dimethylphenyl)propanoate (178 mg, 0.44 mmol) was dissolved in THF (12 mL), water (3 mL) and methanol (3 mL) before being treated with a solution of KOH (45%) (0.3 mL, 5.84 mmol). After stirring at ambient temperature overnight, the reaction mixture was adjusted to pH 4 with 1 N HCl before being extracted with ethyl acetate. The organic extracts were dried (MgSO₄) and concentrated in vacuo to yield 3-(4-((2-(4-ethylphenyl)cyclopent-1-en-1-yl)methoxy)-2,3-dimethylphenyl)propanoic acid as solid.

¹H NMR (CHLOROFORM-d) δ: 7.17 (s, 4H), 6.84-6.96 (m, 1H), 6.48-6.62 (m, 1H), 4.57-4.69 (m, 2H), 2.86-2.99 (m, 3H), 2.76-2.86 (m, 2H), 2.49-2.76 (m, 7H), 2.22 (s, 3H), 2.18-2.20 (m, 3H), 1.91-2.06 (m, 2H), 1.24 (s, 4H).

Example 71: Compound #25

3-(4-((2-(4-ethylphenyl)cyclopent-1-en-1-yl)methoxy)-2,3-difluorophenyl)Propanoic Acid

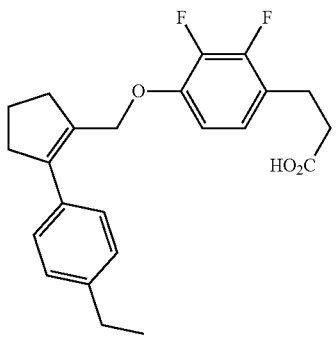 [SMILES: CCc1ccc(C2=C(COc3ccc(CCC(=O)O)c(F)c3F)CCC2)cc1]

¹H NMR (CHLOROFORM-d) δ: 7.17 (brd, J=7.1 Hz, 4H), 6.66-6.85 (m, 1H), 6.38-6.56 (m, 1H), 4.71 (s, 2H), 2.91 (br s, 2H), 2.74-2.85 (m, 2H), 2.57-2.72 (m, 6H), 1.89-2.05 (m, 2H), 1.24 (br t, J=7.6 Hz, 3H).

Example 72: Compound #15

3-(4-((2-(4-chlorophenyl)cyclopent-1-en-1-yl)methoxy)-2,3-dimethylphenyl)Propanoic Acid

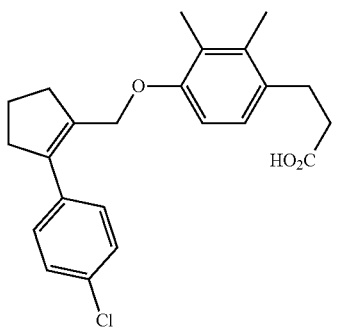 [SMILES: Cc1c(CCC(=O)O)ccc(OCC2=C(c3ccc(Cl)cc3)CCC2)c1C]

¹H NMR (CHLOROFORM-d) δ: 7.27-7.34 (m, 2H), 7.18 (brd, J=8.1 Hz, 2H), 6.91 (br d, J=8.1 Hz, 1H), 6.54 (br d, J=8.6 Hz, 1H), 4.58 (s, 2H), 2.92 (br t, J=7.8 Hz, 2H), 2.65-2.85 (m, 4H), 2.58 (br t, J=7.8 Hz, 2H), 2.22 (s, 3H), 2.18 (s, 3H), 1.92-2.05 (m, 2H).

Example 73: Compound #16

3-(4-((2-(4-ethylphenyl)cyclopent-1-en-1-yl)methoxy)-3,5-difluorophenyl)Propanoic Acid

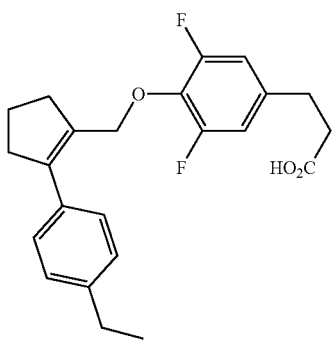 [SMILES: CCc1ccc(C2=C(COc3c(F)cc(CCC(=O)O)cc3F)CCC2)cc1]

¹H NMR (CHLOROFORM-d) δ: 7.17 (d, J=2.5 Hz, 4H), 6.73 (d, J=8.6 Hz, 2H), 4.70 (s, 2H), 2.82-2.92 (m, 2H), 2.71-2.82 (m, 4H), 2.64 (br d, J=7.6 Hz, 4H), 1.92-2.04 (m, 2H), 1.20-1.29 (m, 3H).

Example 74: Compound #19

3-(4-((2-phenylcyclopent-1-en-1-yl)methoxy)phenyl)Propanoic Acid

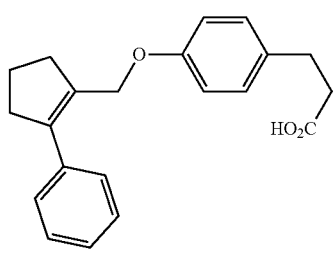 [SMILES: O=C(O)CCc1ccc(OCC2=C(c3ccccc3)CCC2)cc1]

¹H NMR (CHLOROFORM-d) δ: 7.30-7.38 (m, 2H), 7.23-7.28 (m, 3H), 7.07 (d, J=8.6 Hz, 2H), 6.75-6.81 (m, 2H), 4.62 (s, 2H), 2.85-2.91 (m, 2H), 2.82 (br t, J=7.6 Hz, 2H), 2.69 (br t, J=7.6 Hz, 2H), 2.63 (s, 2H), 1.99 (t, J=7.6 Hz, 2H).

Example 75: Compound #20

3-(2,3-dimethyl-4-((2-(4-(trifluoromethoxy)phenyl)cyclopent-1-en-1-yl)methoxy)phenyl)Propanoic Acid

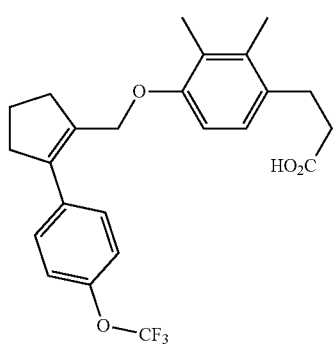 [SMILES: Cc1c(CCC(=O)O)ccc(OCC2=C(c3ccc(OC(F)(F)F)cc3)CCC2)c1C]

¹H NMR (CHLOROFORM-d) δ: 7.26-7.29 (m, 2H), 7.15-7.20 (m, 2H), 6.85-6.97 (m, 1H), 6.49-6.62 (m, 1H), 4.53-4.63 (m, 2H), 2.88-2.97 (m, 2H), 2.77-2.85 (m, 2H), 2.67-2.77 (m, 2H), 2.53-2.63 (m, 2H), 2.22 (s, 3H), 2.17 (s, 3H), 1.96-2.05 (m, 2H).

Example 76: Compound #21

3-(4-((2-(4-methoxyphenyl)cyclopent-1-en-1-yl)methoxy)-2,3-dimethylphenyl)Propanoic Acid

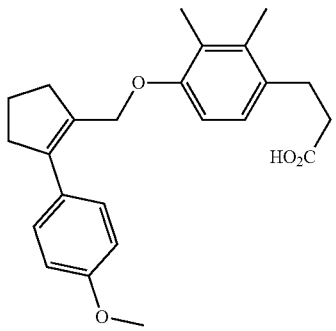 [SMILES: COc1ccc(C2=C(COc3ccc(CCC(=O)O)c(C)c3C)CCC2)cc1]

$^1$H NMR (CHLOROFORM-d) δ: 7.05-7.33 (m, 2H), 6.75-7.03 (m, 3H), 6.57 (d, J=8.1 Hz, 1H), 3.81 (d, J=3.5 Hz, 3H), 3.68 (s, 2H), 2.84-2.95 (m, 2H), 2.47-2.82 (m, 6H), 2.21 (s, 3H), 2.17 (s, 3H), 1.88-2.04 (m, 2H)

Example 77: Compound #22

3-(2,3-dimethyl-4-((2-(thiophen-3-yl)cyclopent-1-en-1-yl)methoxy)phenyl)Propanoic Acid

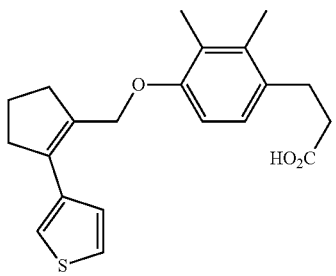 [SMILES: Cc1c(CCC(=O)O)ccc(OCC2=C(c3ccsc3)CCC2)c1C]

$^1$H NMR (CHLOROFORM-d) δ: 7.18-7.40 (m, 2H), 7.06-7.18 (m, 1H), 6.79-6.90 (m, 1H), 6.52-6.60 (m, 1H), 3.68 (s, 2H), 2.46-2.95 (m, 8H), 2.21 (s, 3H), 2.17 (s, 3H), 1.87-1.99 (m, 2H)

Example 78: Compound #72

3-(4-((2-(2,4-dimethylphenyl)cyclopent-1-en-1-yl)methoxy)-2,3-difluorophenyl)Propanoic Acid

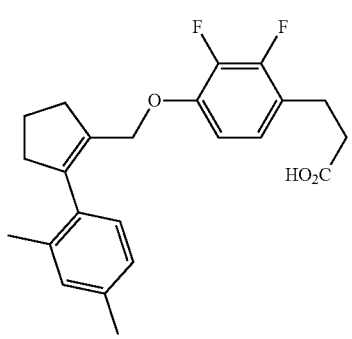 [SMILES: Cc1ccc(C2=C(COc3ccc(CCC(=O)O)c(F)c3F)CCC2)c(C)c1]

$^1$H NMR (CHLOROFORM-d) δ: 7.00-7.05 (m, 1H), 6.94-6.99 (m, 1H), 6.86-6.94 (m, 1H), 6.68-6.78 (m, 1H), 6.37-6.45 (m, 1H), 4.44 (s, 2H), 2.86-2.95 (m, 2H), 2.63 (br s, 6H), 2.31 (s, 3H), 2.15 (s, 3H), 1.92-2.06 (m, 2H)

Example 79: Compound #78

3-(2,3-difluoro-4-((2-(3-fluoro-4-methylphenyl)cyclopent-1-en-1-yl)methoxy)phenyl)Propanoic Acid

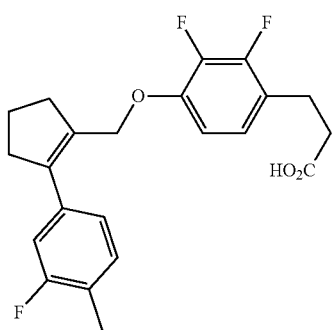 [SMILES: Cc1ccc(C2=C(COc3ccc(CCC(=O)O)c(F)c3F)CCC2)cc1F]

$^1$H NMR (CHLOROFORM-d) δ: 7.09-7.18 (m, 1H), 6.84-6.93 (m, 2H), 6.71-6.82 (m, 1H), 6.44-6.54 (m, 1H), 4.69 (s, 2H), 2.92 (m, 2H), 2.66 (m, J=8.1 Hz, 6H), 2.27 (d, J=1.5 Hz, 3H), 1.97 (m, 2H)

Example 80: Compound #80

3-(4-((2-(3-fluoro-4-methylphenyl)cyclopent-1-en-1-yl)methoxy)-2,3-dimethylphenyl)Propanoic Acid

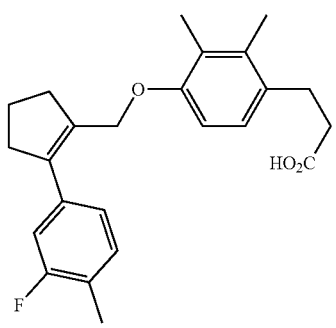 [SMILES: Cc1ccc(C2=C(COc3ccc(CCC(=O)O)c(C)c3C)CCC2)cc1F]

Step 1: methyl 2-(3-fluoro-4-methylphenyl)cyclopent-1-ene-1-carboxylate

A suspension of anhydrous potassium phosphate (2.92 g, 13.76 mmol), tetrakis(triphenylphosphine) palladium (337 mg, 0.29 mmol), (3-fluoro-4-methylphenyl)boronic acid (682 mg, 4.43 mmol) and methyl 2-(((trifluoromethyl)sulfonyl)oxy)cyclopent-1-ene-1-carboxylate (1.04 g, 3.79 mmol) in 1,4-dioxane (50 mL) was sparged with a stream of argon for 20 minutes. The reaction was then placed under an argon atmosphere and heated to 90° C. for 16 hours before cooling to ambient temperature. The mixture was diluted with diethyl ether and filtered through a plug of CELITE®. The filtrate was concentrated in vacuo and purified by flash chromatography (SiO₂, 7:6 DCM/heptane) to yield methyl 2-(3-fluoro-4-methylphenyl)cyclopent-1-ene-1-carboxylate.

Step 2: (2-(3-fluoro-4-methylphenyl)cyclopent-1-en-1-yl)methanol

A solution of methyl 2-(3-fluoro-4-methylphenyl)cyclopent-1-ene-1-carboxylate (676 mg, 2.9 mmol) in dry toluene (50 mL) was cooled to −78° C. under an argon atmosphere. The reaction mixture was treated dropwise with DiBAl-H (6.4 mL, 6.4 mmol in toluene) and stirred, allowing the reaction mixture to reach ambient temperature over 2 hours. After stirred for one additional hour, the mixture was cooled to ~−10° C. and quenched by the dropwise addition of sat. Rochelle's salt (12 mL). The aqueous layer was extracted with diethyl ether and the combined organic layers washed with sat. NaHCO₃ and brine before being dried over MgSO₄. The resulting mixture was concentrated in vacuo, followed by flash chromatography (SiO₂, diethyl ether) to yield (2-(3-fluoro-4-methylphenyl)cyclopent-1-en-1-yl)methanol as a colorless crystalline solid.

Step 3: ethyl 3-(4-((2-(3-fluoro-4-methylphenyl)cyclopent-1-en-1-yl)methoxy)-2,3-dimethylphenyl)Propanoate A solution of (2-(3-fluoro-4-methylphenyl)cyclopent-1-en-1-yl)methanol (99 mg, 0.48 mmol), ADDP (258 mg, 1.01 mmol) and ethyl 3-(4-hydroxy-2,3-dimethylphenyl)propanoate (156 mg, 0.7 mmol) in toluene (15 mL) was placed under an argon atmosphere and treated with neat tri-n-butylphosphine (0.31 mL, 1.22 mmol). The reaction was stirred at 60° C. for ~18 hours and then concentrated in vacuo. The residue was triturated with diethyl ether, the resulting white precipitate was filtered off and the filtrate concentrated. The resulting residue was purified by flash chromatography (SiO₂, 6:7 DCM:heptane) to yield ethyl 3-(4-((2-(3-fluoro-4-methylphenyl)cyclopent-1-en-1-yl)methoxy)-2,3-dimethylphenyl)propanoate.

Step 4: 3-(4-((2-(3-fluoro-4-methylphenyl)cyclopent-1-en-1-yl)methoxy)-2,3-dimethylphenyl)Propanoic Acid A solution of ethyl 3-(4-((2-(3-fluoro-4-methylphenyl)cyclopent-1-en-1-yl)methoxy)-2,3-dimethylphenyl)propanoate (143 mg, 0.35 mmol) was dissolved in THF (6 mL), water (3 mL) and methanol (3 mL) before being treated with a solution of KOH (45%) (0.25 mL, 2.92 mmol). After stirring at ambient temperature overnight, the reaction mixture was adjusted to pH 4 with 1 N HCl before being extracted with ethyl acetate. The organic extracts were dried (MgSO₄) and concentrated in vacuo to yield 3-(4-((2-(3-fluoro-4-methylphenyl)cyclopent-1-en-1-yl)methoxy)-2,3-dimethylphenyl)propanoic acid as solid.

¹H NMR (CHLOROFORM-d) δ: 7.07-7.19 (m, 1H), 6.85-6.97 (m, 3H), 6.48-6.61 (m, 1H), 4.61 (s, 2H), 2.88-2.98 (m, 1H), 2.66-2.81 (m, 4H), 2.54-2.62 (m, 2H), 2.26 (d, J=1.0 Hz, 3H), 2.22 (s, 3H), 2.18 (s, 3H), 1.90-2.04 (m, 2H).

Example 81: Compound #81

3-(4-((2-(2,4-dimethylphenyl)cyclopent-1-en-1-yl)methoxy)-2,3-dimethylphenyl)Propanoic Acid

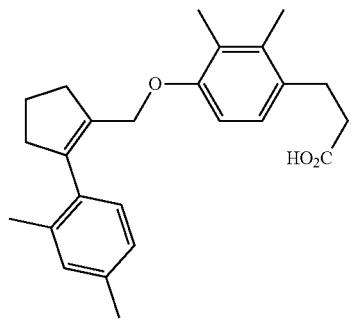 [SMILES: Cc1ccc(C2=C(COc3ccc(CCC(=O)O)c(C)c3C)CCC2)c(C)c1]

¹H NMR (CHLOROFORM-d) δ: 6.90-7.06 (m, 3H), 6.79-6.88 (m, 1H), 6.38-6.51 (m, 1H), 4.28-4.38 (m, 2H), 2.85-2.94 (m, 2H), 2.50-2.75 (m, 6H), 2.30 (s, 3H), 2.19 (s, 3H), 2.17 (s, 3H), 2.15 (s, 3H), 1.94-2.05 (m, 2H)

Example 82: Compound #94

3-(2,3-difluoro-4-((2-(p-tolyl)cyclopent-1-en-1-yl)methoxy)phenyl)Propanoic Acid

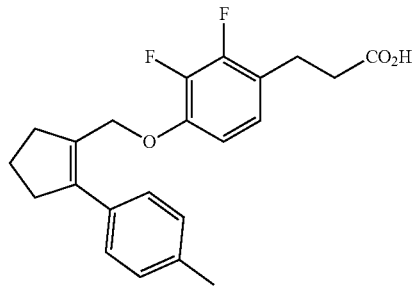 [SMILES: Cc1ccc(C2=C(COc3ccc(CCC(=O)O)c(F)c3F)CCC2)cc1]

¹H NMR (CHLOROFORM-d) δ: 7.11-7.19 (m, 4H), 6.73-6.80 (m, 1H), 6.43-6.51 (m, 1H), 4.65-4.76 (m, 2H), 2.91 (t, J=7.6 Hz, 2H), 2.73-2.84 (m, 2H), 2.65 (br d, J=7.6 Hz, 4H), 2.35 (s, 3H), 1.90-2.03 (m, 2H).

Example 83: Compound #95

3-(3,5-difluoro-4-((2-(p-tolyl)cyclopent-1-en-1-yl)methoxy)phenyl)Propanoic Acid

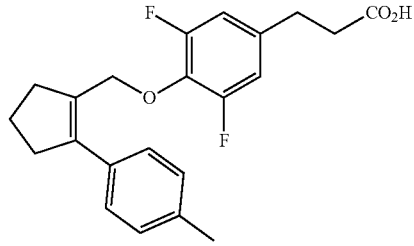 [SMILES: Cc1ccc(C2=C(COc3c(F)cc(CCC(=O)O)cc3F)CCC2)cc1]

$^1$H NMR (CHLOROFORM-d) δ: 7.15 (brs, 4H), 6.65-6.78 (m, 2H), 4.69 (br s, 2H), 2.86 (br d, J=7.1 Hz, 2H), 2.76 (br d, J=7.1 Hz, 4H), 2.66 (br d, J=7.1 Hz, 2H), 2.34 (s, 3H), 1.90-2.05 (m, 2H).

Example 84: Compound #85

3-(2,3-dimethyl-4-((2-(6-methylpyridin-3-yl)cyclopent-1-en-1-yl)methoxy)phenyl)Propanoic Acid

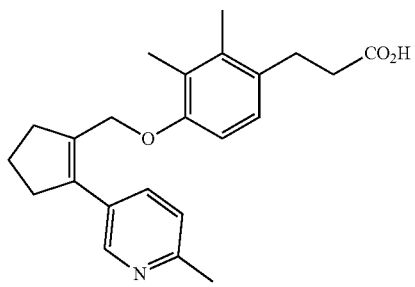 [SMILES: Cc1ccc(C2=C(COc3ccc(CCC(=O)O)c(C)c3C)CCC2)cn1]

The title compound was prepared to the process described in Example 70 above, substituting (6-methylpyridin-3-yl)boronic acid for (4-ethylphenyl)boronic acid in Step 1, and following the procedures in Steps 2 to 4, as described.

$^1$H NMR (MeOD) δ: 8.47-8.61 (m, 1H), 8.21-8.36 (m, 1H), 7.74-7.87 (m, 1H), 6.83-6.94 (m, 1H), 6.53-6.63 (m, 1H), 4.62-4.74 (m, 2H), 2.76-2.94 (m, 6H), 2.74 (s, 3H), 2.42-2.51 (m, 2H), 2.18 (s, 3H), 2.06-2.14 (m, 2H), 2.03 (s, 3H).

Example 85: Compound #87

3-(2,3-difluoro-4-((2-(6-methylpyridin-3-yl)cyclopent-1-en-1-yl)methoxy)phenyl)Propanoic Acid

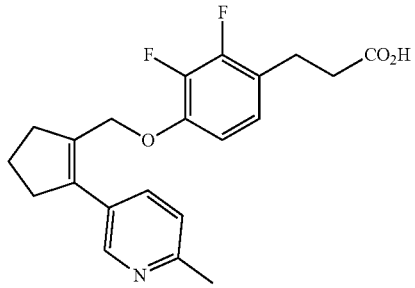

$^1$H NMR (MeOD) δ: 8.34-8.51 (m, 1H), 7.88-7.97 (m, 1H), 7.49-7.60 (m, 1H), 6.86-6.94 (m, 1H), 6.65-6.73 (m, 1H), 4.74 (s, 2H), 2.81-2.91 (m, 4H), 2.70-2.79 (m, 2H), 2.59-2.66 (m, 3H), 2.52-2.59 (m, 2H), 2.02-2.10 (m, 2H).

Example 86: Compound #134

3-(4-((2-(3-amino-4-methylphenyl)cyclopent-1-en-1-yl)methoxy)-2,3-dimethylphenyl)Propanoic Acid

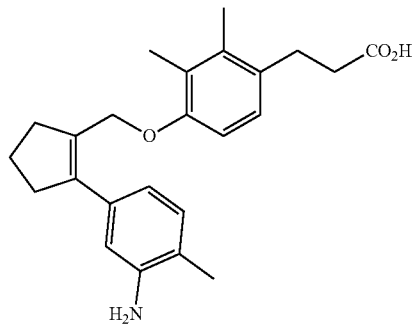 [SMILES: Cc1ccc(C2=C(COc3ccc(CCC(=O)O)c(C)c3C)CCC2)cc1N]

$^1$H NMR (ACETONITRILE-d$_3$) δ: 7.04 (d, J=7.6 Hz, 1H), 6.87 (d, J=8.6 Hz, 1H), 6.69 (s, 2H), 6.51-6.59 (m, 1H), 4.52-4.71 (m, 2H), 2.80-2.86 (m, 5H), 2.42-2.51 (m, 4H), 2.18-2.20 (m, 3H), 2.15 (s, 3H), 2.13-2.14 (m, 3H), 2.07-2.11 (m, 2H).

Example 87: Compound #135

3-(4-((2-(3-amino-4-methylphenyl)cyclopent-1-en-1-yl)methoxy)-3,5-difluorophenyl)Propanoic Acid

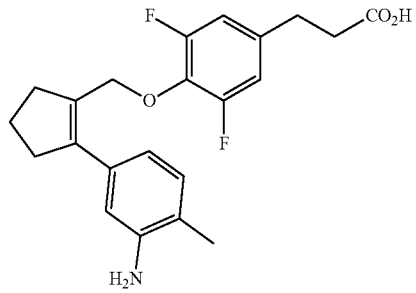 [SMILES: Cc1ccc(C2=C(COc3c(F)cc(CCC(=O)O)cc3F)CCC2)cc1N]

$^1$H NMR (CHLOROFORM-d) δ: 6.99-7.13 (m, 1H), 6.57-6.81 (m, 4H), 4.34 (s, 2H), 2.87 (s, 2H), 2.65 (s, 2H), 2.34-2.45 (m, 2H), 2.24 (d, J=1.0 Hz, 5H), 1.74 (m, 4H).

Example 88: Compound #93

3-(4-((2-(3-amino-4-methylphenyl)cyclopent-1-en-1-yl)methoxy)-2,3-difluorophenyl)Propanoic Acid

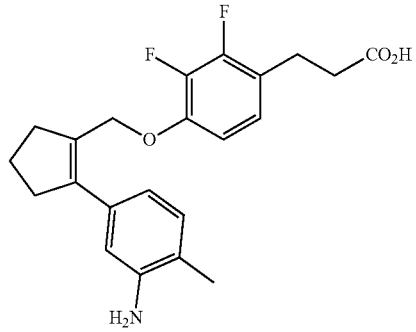 [SMILES: Cc1ccc(C2=C(COc3ccc(CCC(=O)O)c(F)c3F)CCC2)cc1N]

¹H NMR (ACETONITRILE-d₃) δ: 7.11-7.18 (m, 1H), 6.83-6.94 (m, 3H), 6.58-6.67 (m, 1H), 4.68-4.77 (m, 2H), 2.80-2.90 (m, 3H), 2.70-2.80 (m, 2H), 2.60-2.70 (m, 2H), 2.51-2.60 (m, 2H), 2.22 (s, 3H), 2H under solvent peak (1-99-1.90).

Example 89: Compound #113

3-(4-((2-(3-methoxy-4-methylphenyl)cyclopent-1-en-1-yl)methoxy)-2,3-dimethylphenyl)Propanoic Acid

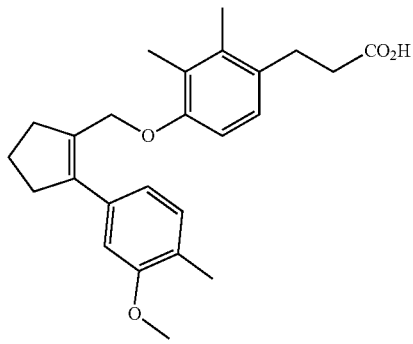 [SMILES: COc1cc(C2=C(COc3ccc(CCC(=O)O)c(C)c3C)CCC2)ccc1C]

¹H NMR (CHLOROFORM-d) δ: 7.04-7.13 (m, 1H), 6.86-6.92 (m, 1H), 6.71-6.79 (m, 2H), 6.51-6.59 (m, 1H), 4.56-4.68 (m, 2H), 3.72 (s, 3H), 2.86-2.99 (m, 2H), 2.76-2.86 (m, 2H), 2.67-2.76 (m, 2H), 2.52-2.63 (m, 2H), 2.14-2.26 (m, 10H), 1.93-2.06 (m, 2H).

Example 90: Compound #115

3-(2,3-dimethyl-4-((2-(4-methyl-3-nitrophenyl)cyclopent-1-en-1-yl)methoxy)phenyl)Propanoic Acid

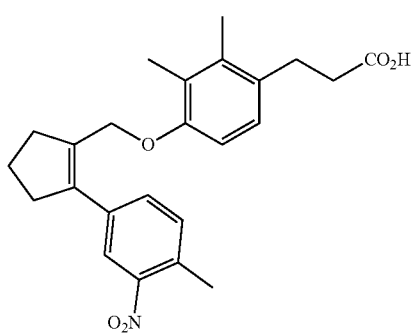

¹H NMR (CHLOROFORM-d) δ: 7.77-7.92 (m, 1H), 7.35-7.43 (m, 1H), 7.27-7.33 (m, 1H), 6.86-6.95 (m, 1H), 6.49-6.59 (m, 1H), 4.59 (s, 2H), 2.88-2.97 (m, 2H), 2.79-2.88 (m, 2H), 2.70-2.79 (m, 3H), 2.59 (s, 6H), 2.22 (s, 3H), 2.17 (s, 3H), 1.96-2.08 (m, 3H), 1.96-2.08 (m, 2H).

Example 91: Compound #106

3-(4-((2-(3,4-dimethylphenyl)cyclopent-1-en-1-yl)methoxy)-2,3-dimethylphenyl)Propanoic Acid

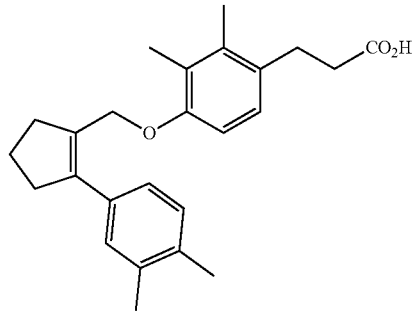 [SMILES: Cc1ccc(C2=C(COc3ccc(CCC(=O)O)c(C)c3C)CCC2)cc1C]

¹H NMR (CHLOROFORM-d) δ: 7.08-7.12 (m, 1H), 6.95-7.05 (m, 2H), 6.84-6.92 (m, 1H), 6.49-6.59 (m, 1H), 4.54-4.69 (m, 2H), 2.85-2.96 (m, 2H), 2.75-2.84 (m, 2H), 2.64-2.74 (m, 2H), 2.52-2.61 (m, 2H), 2.25 (d, J=3.0 Hz, 6H), 2.22 (s, 3H), 2.19 (s, 3H), 1.90-2.03 (m, 2H).

Example 92: Compound #109

3-(3,5-difluoro-4-((2-(4-methyl-3-nitrophenyl)cyclopent-1-en-1-yl)methoxy)phenyl)Propanoic Acid

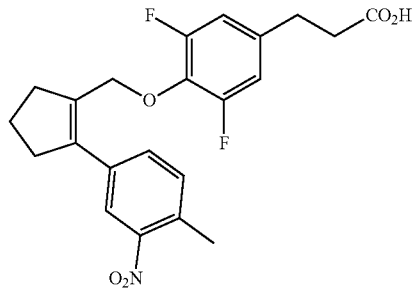

¹H NMR (CHLOROFORM-d) δ: 7.76 (s, 1H), 7.39-7.46 (m, 1H), 7.28-7.32 (m, 1H), 6.74 (d, J=8.6 Hz, 2H), 4.58-4.68 (m, 2H), 2.88 (m, 2H), 2.79 (m, 4H), 2.66 (m, 2H), 2.58 (s, 3H), 1.93-2.09 (m, 2H).

Example 93: Compound #92

3-(2,3-difluoro-4-((2-(4-methyl-3-nitrophenyl)cyclopent-1-en-1-yl)methoxy)phenyl)Propanoic Acid

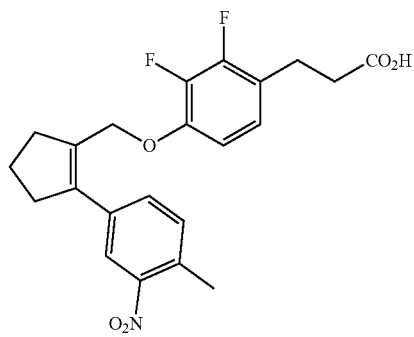 [SMILES: Cc1ccc(C2=C(COc3ccc(CCC(=O)O)c(F)c3F)CCC2)cc1[N+](=O)[O-]]

¹H NMR (CHLOROFORM-d) δ: 7.83 (d, J=1.0 Hz, 1H), 7.35-7.42 (m, 1H), 7.29-7.34 (m, 1H), 6.81 (m, 1H), 6.54

(m, 1H), 4.58-4.73 (m, 2H), 2.93 (br t, J=7.6 Hz, 2H), 2.78-2.86 (m, 2H), 2.70-2.77 (m, 2H), 2.66 (m, 2H), 2.59 (s, 3H), 2.02 (m, J=7.6 Hz, 2H).

Example 94: Compound #83

3-(4-((2-(3,4-dimethylphenyl)cyclopent-1-en-1-yl)methoxy)-2,3-difluorophenyl)Propanoic Acid

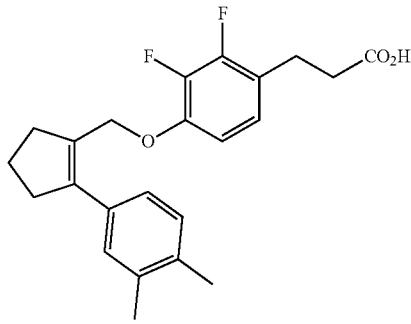 [SMILES: Cc1ccc(C2=C(COc3ccc(CCC(=O)O)c(F)c3F)CCC2)cc1C]

¹H NMR (CHLOROFORM-d) δ: 7.09-7.13 (m, 1H), 6.93-7.04 (m, 2H), 6.70-6.78 (m, 1H), 6.40-6.52 (m, 1H), 4.71 (s, 2H), 2.91 (m, 3H), 2.74-2.83 (m, 2H), 2.65 (m, 3H), 2.23-2.29 (m, 6H), 1.91-2.02 (m, 2H).

Example 95: Compound #84

3-(4-((2-(3,4-dimethylphenyl)cyclopent-1-en-1-yl)methoxy)-3,5-difluorophenyl)Propanoic Acid

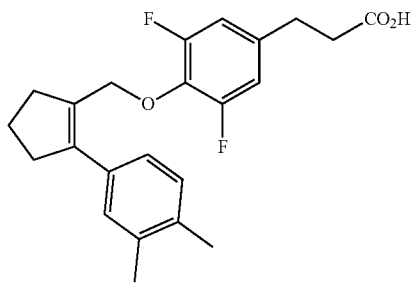 [SMILES: Cc1ccc(C2=C(COc3c(F)cc(CCC(=O)O)cc3F)CCC2)cc1C]

¹H NMR (CHLOROFORM-d) δ: 6.97-7.21 (m, 3H), 6.73 (m, 2H), 4.68 (br s, 2H), 2.55-2.97 (m, 8H), 2.25 (br s, 6H), 1.97 m, 2H).

Example 96: Compound #152

3-(4-((2-(3,4-dimethylphenyl)cyclopent-1-en-1-yl)methoxy)-2,3-difluorophenyl)Propanoic Acid

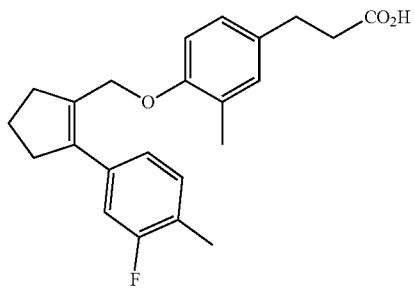 [SMILES: Cc1ccc(C2=C(COc3ccc(CCC(=O)O)cc3C)CCC2)cc1F]

¹H NMR (CHLOROFORM-d) δ: 7.13-7.1 (m, 1H), 7.0-6.85 (m, 4H), 6.61-6.55 (m, 1H), 4.62 (br s, 2H), 2.55-2.91 (series of m, 8H), 2.25 (s, 3H), 2.20 (s, 1H), 1.90-1.97 (m, 2H).

Example 97: Compound #102

3-(3-methyl-4-((2-(6-methylpyridin-3-yl)cyclopent-1-en-1-yl)methoxy)phenyl)Propanoic Acid

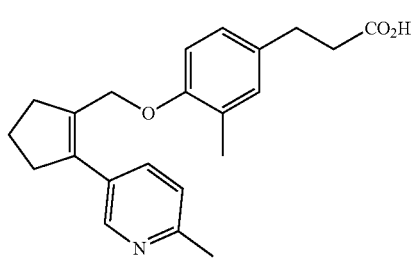 [SMILES: Cc1ccc(C2=C(COc3ccc(CCC(=O)O)cc3C)CCC2)cn1]

¹H NMR (MeOD) δ: 8.52-8.61 (m, 1H), 8.28-8.37 (m, 1H), 7.81-7.88 (m, 1H), 6.88-6.98 (m, 2H), 6.64-6.74 (m, 1H), 4.71 (s, 2H), 2.86-2.95 (m, 2H), 2.72-2.83 (m, 8H), 2.48-2.56 (m, 2H), 2.05 (s, 5H).

Example 98: Compound #158

3-(4-((2-(6-chloropyridin-3-yl)cyclopent-1-en-1-yl)methoxy)-2,3-dimethylphenyl)Propanoic Acid

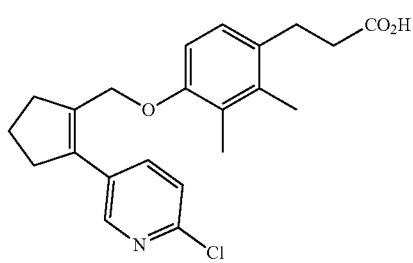 [SMILES: Cc1c(CCC(=O)O)ccc(OCC2=C(c3ccc(Cl)nc3)CCC2)c1C]

¹H NMR (DMSO-d₆) δ: 11.96-12.27 (m, 1H), 8.24-8.40 (m, 1H), 7.70-7.83 (m, 1H), 7.54 (s, 1H), 6.82-6.94 (m, 1H), 6.57-6.72 (m, 1H), 4.62 (s, 2H), 2.61-2.90 (m, 6H), 2.39 (t, J=7.8 Hz, 2H), 2.13 (s, 3H), 2.04 (s, 3H), 1.90-2.00 (m, 2H).

Example 99: Compound #157

3-(4-((2-(4-chloro-3-fluorophenyl)cyclopent-1-en-1-yl)methoxy)-2,3-dimethylphenyl)Propanoic Acid

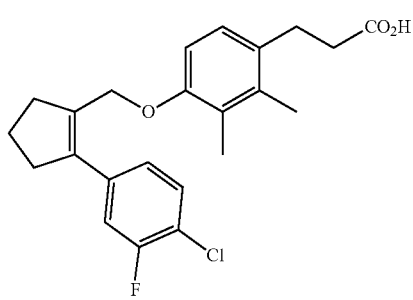 [SMILES: Cc1c(CCC(=O)O)ccc(OCC2=C(c3ccc(Cl)c(F)c3)CCC2)c1C]

¹H NMR (CHLOROFORM-d) δ: 7.29-7.36 (m, 1H), 6.86-7.07 (m, 3H), 6.46-6.60 (m, 1H), 4.58 (s, 2H), 2.92 (br d, J=8.6 Hz, 2H), 2.73 (br s, 4H), 2.59 (br d, J=8.1 Hz, 3H), 2.22 (s, 3H), 2.18 (s, 3H), 2.00 (s, 2H).

Example 100: Compound #159

3-(4-((2-(4-chloro-3-fluorophenyl)cyclopent-1-en-1-yl)methoxy)-3-methylphenyl)Propanoic Acid

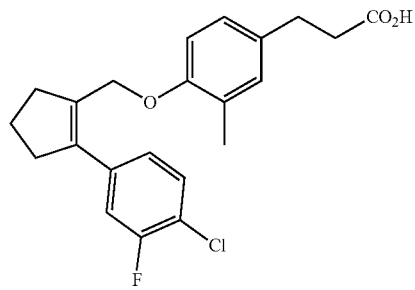

¹H NMR (CHLOROFORM-d) δ: 7.34 (s, 1H), 6.99 (s, 4H), 6.62 (d, J=8.1 Hz, 1H), 4.60 (s, 2H), 2.85 (d, J=8.1 Hz, 2H), 2.75-2.81 (m, 2H), 2.68-2.74 (m, 2H), 2.61-2.67 (m, 2H), 2.20 (s, 3H), 1.94-2.04 (m, 2H).

Example 101: Compound #119

3-(4-((2-(4-chlorophenyl)cyclopent-1-en-1-yl)methoxy)-2,6-dimethylphenyl)Propanoic Acid

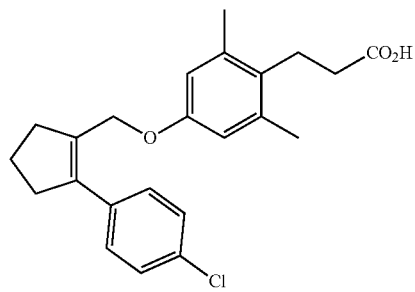 [SMILES: Cc1cc(OCC2=C(c3ccc(Cl)cc3)CCC2)cc(C)c1CCC(=O)O]

¹H NMR (CHLOROFORM-d) δ: 7.28-7.35 (m, 2H), 7.19 (d, J=8.6 Hz, 2H), 6.52 (s, 2H), 4.55 (s, 2H), 2.87-2.98 (m, 2H), 2.79 (br t, J=7.3 Hz, 2H), 2.68 (br t, J=7.3 Hz, 2H), 2.41-2.52 (m, 2H), 2.27 (s, 6H), 1.99 (br t, J=7.3 Hz, 2H).

Example 102: Compound #126-D 3-(4-((2-(4-chlorophenyl)cyclopent-1-en-1-yl)methoxy)-3-methylphenyl)Propanoic-2,3-d2 Acid

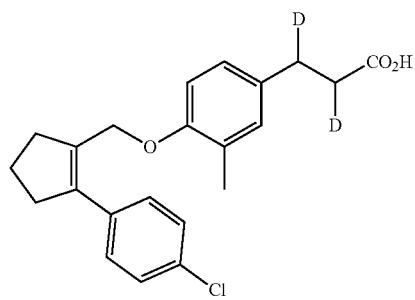 [SMILES: [2H]C(C(=O)O)C([2H])c1ccc(OCC2=C(c3ccc(Cl)cc3)CCC2)c(C)c1]

¹H NMR (CHLOROFORM-d) δ: 7.30 (s, 2H), 7.14-7.23 (m, 2H), 6.96-7.01 (m, 1H), 6.88-6.95 (m, 1H), 6.53-6.65 (m, 1H), 4.51-4.64 (m, 2H), 2.51-2.91 (series of m, 6H), 2.21 (s, 3H), 1.99 (quin, J=7.6 Hz, 2H).

Example 103: Compound #129

3-[3-bromo-4-[[2-(4-chlorophenyl)cyclopenten-1-yl]methoxy]phenyl]Propanoic Acid

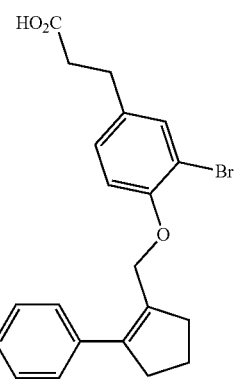

¹H NMR (CHLOROFORM-d) δ: 7.40 (s, 1H), 7.31 (m, 2H), 7.18 (d, J=8.6 Hz, 2H), 7.01-7.07 (m, 1H), 6.60-6.70 (m, 1H), 4.65 (s, 2H), 2.55-2.91 (m, 10H), 2.00 (s, 2H).

Example 104: Compound #130

3-[3-iodo-4-[[2-(4-chlorophenyl)cyclopenten-1-yl]methoxy]phenyl]Propanoic Acid

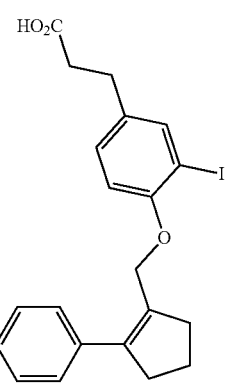

¹H NMR (CHLOROFORM-d) δ: 7.62 (d, J=2.0 Hz, 1H), 7.31 (m, 2H), 7.18 (d, J=8.6 Hz, 2H), 7.01-7.07 (m, 1H), 6.50-6.60 (m, 1H), 4.65 (s, 2H), 2.55-2.91 (m, 10H), 2.00 (s, 2H).

Example 105: Compound #181

3-[4-[[2-(4-chlorophenyl)cyclopenten-1-yl]methoxy]-3-(4-methylsulfonylbutyl)phenyl]Propanoic Acid

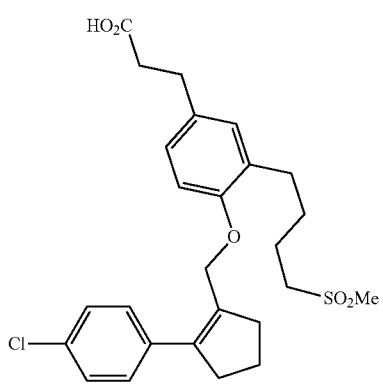 [SMILES: CS(=O)(=O)CCCCc1cc(CCC(=O)O)ccc1OCC1=C(c2ccc(Cl)cc2)CCC1]

$^1$H NMR (CHLOROFORM-d) δ: 7.28-7.35 (m, 2H), 7.17 (d, J=8.6 Hz, 2H), 6.90-6.97 (m, 2H), 6.59-6.65 (m, 1H), 4.60 (s, 2H), 2.96-3.05 (m, 2H), 2.76-2.92 (m, 8H), 2.54-2.72 (m, 7H), 1.93-2.06 (m, 2H), 1.66-1.88 (m, 5H).

Example 106: Compound #198

3-[4-[[2-(4-chlorophenyl)cyclopenten-1-yl]methoxy]-3-(4-methylsulfanylbutyl)phenyl]Propanoic Acid

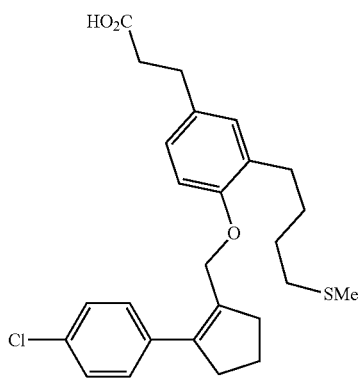 [SMILES: CSCCCCc1cc(CCC(=O)O)ccc1OCC1=C(c2ccc(Cl)cc2)CCC1]

$^1$H NMR (CHLOROFORM-d) δ: 7.31 (d, J=8.1 Hz, 2H), 7.18 (d, J=8.6 Hz, 2H), 6.89-7.01 (m, 2H), 6.62 (d, J=8.1 Hz, 1H), 4.59 (s, 2H), 2.47-2.93 (m, 14H), 2.06-2.13 (m, 3H), 1.99 (s, 2H), 1.57-1.76 (m, 6H).

Example 107: Compound #472

3-[2,3-dimethyl-4-[(2-phenylcyclohexen-1-yl)methoxy]phenyl]Propanoic Acid

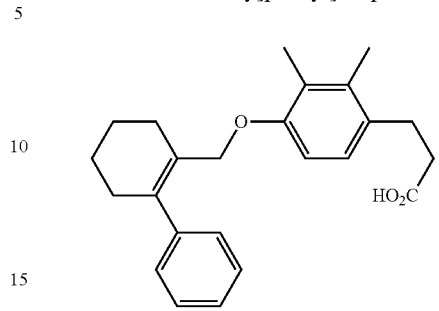

$^1$H NMR (CHLOROFORM-d) δ: 7.29 (d, J=7.6 Hz, 2H), 7.13-7.25 (m, 3H), 6.85 (d, J=8.6 Hz, 1H), 6.44 (s, 1H), 4.27 (s, 2H), 2.85-2.94 (m, 2H), 2.51-2.62 (m, 2H), 2.27-2.40 (m, 4H), 2.21 (s, 3H), 2.19 (s, 3H), 1.76 (br s, 4H).

Example 108: Compound #474

3-[4-[[2-(4-chlorophenyl)cyclohexen-1-yl]methoxy]-2,3-dimethyl-phenyl]Propanoic Acid

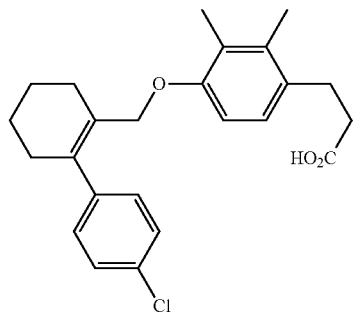 [SMILES: Cc1c(CCC(=O)O)ccc(OCC2=C(c3ccc(Cl)cc3)CCCC2)c1C]

$^1$H NMR (CHLOROFORM-d) δ: 7.26 (d, J=8.6 Hz, 2H), 7.11 (d, J=8.1 Hz, 2H), 6.87 (d, J=8.6 Hz, 1H), 6.43 (d, J=8.6 Hz, 1H), 4.22 (s, 2H), 2.85-2.95 (m, 2H), 2.53-2.60 (m, 2H), 2.30 (br s, 4H), 2.21 (s, 3H), 2.18 (s, 3H), 1.75 (br d, J=2.5 Hz, 4H).

Example 109: Compound #477

3-[3-methyl-4-[[2-(6-methyl-3-pyridyl)cyclohexen-1-yl]methoxy]phenyl]Propanoic Acid

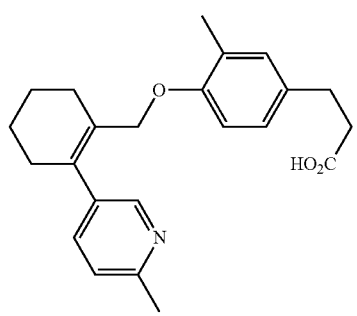 [SMILES: Cc1ccc(C2=C(COc3ccc(CCC(=O)O)cc3C)CCCC2)cn1]

¹H NMR (METHANOL-d₄) δ: 8.43-8.54 (m, 1H), 8.20-8.30 (m, 1H), 7.76-7.87 (m, 1H), 6.94-6.99 (m, 1H), 6.87-6.93 (m, 1H), 6.55-6.60 (m, 1H), 4.30 (s, 2H), 2.76-2.81 (m, 2H), 2.74 (s, 3H), 2.49-2.56 (m, 2H), 2.33-2.44 (m, 4H), 2.10 (s, 3H), 1.76-1.88 (m, 4H).

Example 110: Compound #493

3-[3,5-difluoro-4-[[2-(3-fluoro-4-methyl-phenyl)cyclohexen-1-yl]methoxy]phenyl]Propanoic Acid

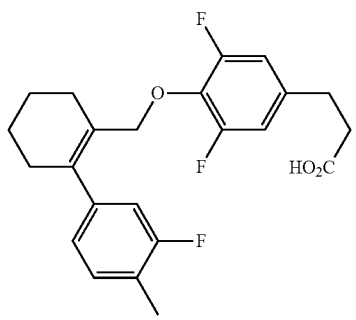 [SMILES: Cc1ccc(C2=C(COc3c(F)cc(CCC(=O)O)cc3F)CCCC2)cc1F]

¹H NMR (CHLOROFORM-d) δ: 6.99-7.11 (m, 1H), 6.70 (d, J=8.6 Hz, 3H), 4.34 (s, 2H), 2.81-2.92 (m, 2H), 2.61-2.72 (m, 2H), 2.40 (br s, 2H), 2.24 (br s, 5H), 1.68-1.82 (m, 4H).

Example 111: Compound #494

3-[2,3-difluoro-4-[[2-(3-fluoro-4-methyl-phenyl)cyclohexen-1-yl]methoxy]phenyl]Propanoic Acid

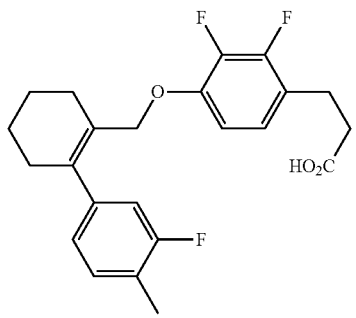 [SMILES: Cc1ccc(C2=C(COc3ccc(CCC(=O)O)c(F)c3F)CCCC2)cc1F]

¹H NMR (CHLOROFORM-d) δ: 7.03-7.16 (m, 1H), 6.70-6.88 (m, 3H), 6.36-6.49 (m, 1H), 4.36 (s, 2H), 2.85-3.00 (m, 2H), 2.57-2.72 (m, 2H), 2.27 (br d, J=15.2 Hz, 7H), 1.73 (br s, 4H).

Example 112: Compound #496

3-[4-[[2-(3-fluoro-4-methyl-phenyl)cyclohexen-1-yl]methoxy]-2,3-dimethyl-phenyl]Propanoic Acid

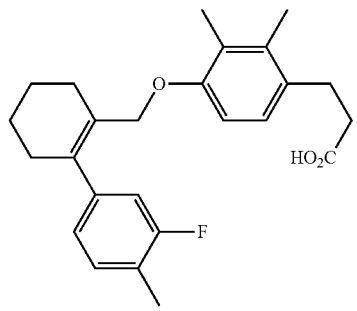 [SMILES: Cc1ccc(C2=C(COc3ccc(CCC(=O)O)c(C)c3C)CCCC2)cc1F]

¹H NMR (CHLOROFORM-d) δ: 7.04-7.13 (m, 1H), 6.77-6.91 (m, 3H), 6.38-6.50 (m, 1H), 4.20-4.30 (m, 2H), 2.85-2.95 (m, 2H), 2.52-2.60 (m, 2H), 2.27-2.35 (m, 4H), 2.23-2.26 (br s, 3H), 2.21 (s, 3H), 2.18 (s, 3H), 1.70-1.77 (m, 4H).

Example 113: Compound #62

3-[4-[[2-(4-chlorophenyl)cyclopenten-1-yl]methoxy]-3-methyl-phenyl]Propanoic Acid

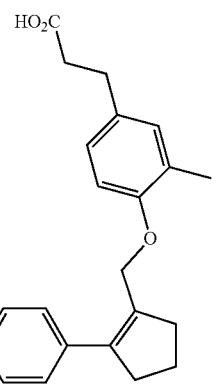

Step 1: methyl 2-(4-chlorophenyl)cyclopent-1-ene-1-carboxylate

A suspension of anhydrous potassium phosphate (2.74 g, 12.88 mmol), tetrakis(triphenylphosphine) palladium (260 mg, 0.22 mmol), (4-chlorophenyl)boronic acid (793 mg, 4.82 mmol) and methyl 2-(((trifluoromethyl)sulfonyl)oxy)cyclopent-1-ene-1-carboxylate (1.07 g, 3.89 mmol) in 1,4-dioxane (24 mL) was sparged with a stream of argon for 20 minutes. The reaction was then placed under an argon atmosphere and heated to 90° C. for 16 hours before cooling to ambient temperature. The mixture was diluted with diethyl ether and filtered through a plug of CELITE®. The filtrate was concentrated in vacuo to yield methyl 2-(4-chlorophenyl)cyclopent-1-ene-1-carboxylate.

Step 2: (2-(4-chlorophenyl)cyclopent-1-en-1-yl)methanol

A solution of methyl 2-(4-chlorophenyl)cyclopent-1-ene-1-carboxylate (210 mg, 0.9 mmol) in dry toluene (15 mL) was cooled to −78° C. under an argon atmosphere. The reaction mixture was treated dropwise with DiBAl-H (2.0 mL, 2.0 mmol in toluene) and stirred, allowing the reaction mixture to reach ambient temperature over 2 hours. After stirred for one additional hour, the mixture was cooled to ∼−10° C. and quenched by the dropwise addition of sat. Rochelle's salt (12 mL). The aqueous layer was extracted with diethyl ether and the combined organic layers washed with sat. $NaHCO_3$ and brine before being dried over $MgSO_4$. The resulting mixture was concentrated in vacuo, followed by flash chromatography ($SiO_2$, diethyl ether) to yield (2-(4-chlorophenyl)cyclopent-1-en-1-yl)methanol as a colorless oil.

Step 3: ethyl 3-(4-((2-(4-chlorophenyl)cyclopent-1-en-1-yl)methoxy)-3-methylphenyl)Propanoate A solution of (2-(4-chlorophenyl)cyclopent-1-en-1-yl)methanol (138 mg, 0.66 mmol), ADDP (338 mg, 1.32 mmol) and ethyl 3-(4-hydroxy-3-methylphenyl)propanoate (162 mg, 0.78 mmol) in toluene (20 mL) was placed under an argon atmosphere and treated with neat tri-n-butylphosphine (0.42 mL, 1.65 mmol). The reaction was stirred at 60° C. for ~18 hours and then concentrated in vacuo. The residue was triturated with diethyl ether, the resulting white precipitate was filtered off and the filtrate concentrated. The resulting residue was purified by flash chromatography ($SiO_2$, 6:7 DCM:heptane) to yield ethyl 3-(4-((2-(4-chlorophenyl)cyclopent-1-en-1-yl)methoxy)-3-methylphenyl)propanoate.

Step 4: 3-[4-[[2-(4-chlorophenyl)cyclopenten-1-yl]methoxy]-3-methyl-phenyl]Propanoic Acid A solution of ethyl 3-(4-((2-(4-chlorophenyl)cyclopent-1-en-1-yl)methoxy)-3-methylphenyl)propanoate (209 mg, 0.52 mmol) was dissolved in THF (8 mL), water (4 mL) and methanol (4 mL) before being treated with a solution of KOH (45%) (0.25 mL, 2.92 mmol). After stirring at ambient temperature overnight, the reaction mixture was adjusted to pH 4 with 1 N HCl before being extracted with ethyl acetate. The organic extracts were dried ($MgSO_4$) and concentrated in vacuo to yield the 3-[4-[[2-(4-chlorophenyl)cyclopenten-1-yl]methoxy]-3-methyl-phenyl]propanoic acid as solid.

$^1$H NMR (CHLOROFORM-d) δ: 7.27-7.35 (m, 2H), 7.15-7.22 (m, 2H), 6.96-7.00 (m, 1H), 6.88-6.94 (m, 1H), 6.57-6.64 (m, 1H), 4.60 (s, 2H), 2.86 (s, 4H), 2.63 (s, 4H), 2.21 (s, 3H), 1.93-2.04 (m, 2H).

The following representative compounds of formula (I) were prepared according to the process described in Scheme 5 above (and as described in more detail hereinafter), selecting appropriate starting materials and reagents, as would be readily recognized by those skilled in the art.

Example 114: Compound #467

3-(4-((4'-chloro-4,4-difluoro-3,4,5,6-tetrahydro-[1,1'-biphenyl]-2-yl)methoxy)-3-methylphenyl)Propanoic Acid

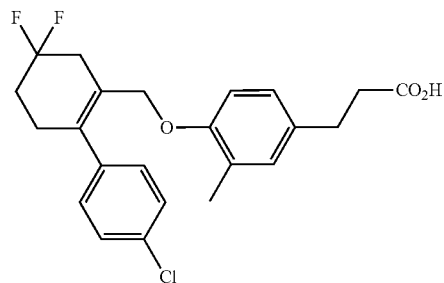 [SMILES: Cc1cc(CCC(=O)O)ccc1OCC1=C(c2ccc(Cl)cc2)CCC(F)(F)C1]

Step 1: ethyl 8-(((trifluoromethyl)sulfonyl)oxy)-1,4-dioxaspiro[4.5]dec-7-ene-7-carboxylate To a suspension of sodium hydride (466 mg, 11.6 mmol) in dry diethyl ether (80 mL) cooled to −10 C under argon was added a solution of 8-oxo-1,4-dioxaspiro[4.5]decane-7-carboxylic acid ethyl ester (2.386 g, 10.45 mmol in 20 mL diethyl ether) dropwise. The reaction mixture was stirred @ −10° C. for 30 minutes post addition and then treated dropwise with neat trifluoromethanesulfonic anhydride (1.8 mL, 10.9 mmol). After stirring the reaction mixture for 1 h @ −10° C., the reaction was quenched by the cautious addition of cold water (11 mL). The reaction mixture was warmed to ambient temperature and diluted with water and diethyl ether. The aqueous layer was extracted with diethyl ether and the combined organic layers washed with sat. $NaHCO_3$ and brine before being dried over $MgSO_4$. The resulting mixture was concentrated in vacuo, followed by flash chromatography ($SiO_2$, DCM) to yield a pale yellow oil.

Step 2: ethyl 8-(4-chlorophenyl)-1,4-dioxaspiro[4.5]dec-7-ene-7-carboxylate

A suspension of anhydrous potassium phosphate (4.3 g, 20.26 mmol), tetrakis(triphenylphosphine) palladium (639.7 mg, 0.554 mmol), 4-chlorophenylboronic acid (1.066 g, 6.474 mmol) and ethyl 8-(((trifluoromethyl)sulfonyl)oxy)-1,4-dioxaspiro[4.5]dec-7-ene-7-carboxylate (2.02 g, 5.606 mmol) in 1,4-dioxane (60 mL) was sparged with a stream of argon for 20 minutes. The reaction was then placed under an argon atmosphere and heated to 90° C. for 16 hours before cooling to ambient temperature. The mixture was diluted with diethyl ether and filtered through a plug of CELITE®. The filtrate was concentrated in vacuo and purified by flash chromatography ($SiO_2$, 0-100% DCM/heptane) to yield a residue.

Step 3: ethyl 4'-chloro-4-oxo-3,4,5,6-tetrahydro-[1,1'-biphenyl]-2-carboxylate A solution of ethyl 8-(4-chlorophenyl)-1,4-dioxaspiro[4.5]dec-7-ene-7-carboxylate (1.47 g, 4.554 mmol) in 1,4-dioxane (20 mL) was treated with a solution of HCl (4 mL, 47.898 mmol) in water (20 mL). The reaction was stirred at ambient temperature for 8 hours and then poured into a sat.

NaHCO₃ solution. The aqueous layer was extracted with diethyl ether and the combined organic layers washed with sat. NaHCO₃ and brine before being dried over MgSO₄. The resulting mixture was concentrated in vacuo followed by flash chromatography (SiO2, DCM) to yield a residue.

Step 4: ethyl 4'-chloro-4,4-difluoro-3,4,5,6-tetra-hydro-[1,1'-biphenyl]-2-carboxylate A solution of ethyl 4'-chloro-4-oxo-3,4,5,6-tetrahydro-[1,1'-biphenyl]-2-carboxylate (542.5 mg, 1.946 mmol) in DCM (20 mL) under an argon atmosphere was treated with neat BAST (1.6 mL, 8.678 mmol) and stirred at ambient temperature for ~18 hours, before being quenched by the cautious addition of sat. NaHCO₃ solution. The aqueous layer was extracted with diethyl ether and the combined organic layers washed with sat. NaHCO₃ and brine before being dried over MgSO₄. The resulting mixture was concentrated in vacuo followed by flash chromatography (SiO₂, DCM) to yield a residue.

Step 5: (4'-chloro-4,4-difluoro-3,4,5,6-tetrahydro-[1,1'-biphenyl]-2-yl)methanol A solution of ethyl 4'-chloro-4,4-difluoro-3,4,5,6-tetrahydro-[1,1'-biphenyl]-2-carboxylate (413 mg, 1.373 mmol) in dry DCM (20 mL) was cooled to −78° C. under an argon atmosphere. The reaction mixture was treated dropwise with DiBAl-H (3.2 mL, 3.2 mmol in toluene) and stirred, allowing the reaction mixture to reach ambient temperature over 2 hours. After stirred for one additional hour, the mixture was cooled to ~−10° C. and quenched by the dropwise addition of sat. Rochelle's salt (12 mL). The aqueous layer was extracted with diethyl ether and the combined organic layers washed with sat. NaHCO₃ and brine before being dried over MgSO₄. The resulting mixture was concentrated in vacuo, followed by flash chromatography (SiO₂, diethyl ether) to yield a colorless crystalline solid.

Step 6: methyl 3-(4-((4'-chloro-4,4-difluoro-3,4,5,6-tetrahydro-[1,1'-biphenyl]-2-yl)methoxy)-3-methylphenyl)Propanoate A solution of (4'-chloro-4,4-difluoro-3,4,5,6-tetrahydro-[1,1'-biphenyl]-2-yl)methanol (0.223 mmol), ADDP (110 mg, 0.432 mmol) and methyl 3-(4-hydroxy-3-methylphenyl)propanoate (0.265 mmol) in toluene (7 mL) was placed under an argon atmosphere and treated with neat tri-n-butylphosphine (0.14 mL, 0.55 mmol). The reaction was stirred at 60° C. for ~18 hours and then concentrated in vacuo. The residue was triturated with diethyl ether, the resulting white precipitate was filtered off and the filtrate concentrated. The resulting residue was purified by flash chromatography (SiO₂, 6:7 DCM:heptane) to yield a residue.

Step 7: 3-(4-((4'-chloro-4,4-difluoro-3,4,5,6-tetra-hydro-[1,1'-biphenyl]-2-yl)methoxy)-3-methylphenyl)Propanoic Acid A solution of methyl 3-(4-((4'-chloro-4,4-difluoro-3,4,5,6-tetrahydro-[1,1'-biphenyl]-2-yl)methoxy)-3-methylphenyl)propanoate (42.7 mg, 0.0982 mmol) was dissolved in THF (7 mL), water (3 mL) and methanol (3 mL) before being treated with a solution of KOH (0.183 mL, 2.142 mmol, 45%). After stirring at ambient temperature overnight, the reaction mixture was adjusted to pH 4 with 1 N HCl before being extracted with ethyl acetate. The organic extracts were dried (MgSO₄) and concentrated in vacuo to yield the title compound.

¹H NMR (CHLOROFORM-d) δ: 7.29-7.34 (m, 2H), 7.08-7.14 (m, 2H), 6.94-7.00 (m, 1H), 6.85-6.91 (m, 1H), 6.43-6.50 (m, 1H), 4.26-4.32 (m, 2H), 2.81-2.88 (m, 2H), 2.59-2.65 (m, 2H), 2.20 (s, 3H)

Example 115: Compound #489

3-[4-[[5,5-difluoro-2-(4-fluorophenyl)cyclohexen-1-yl]methoxy]-2-(trifluoromethyl)phenyl]Propanoic Acid

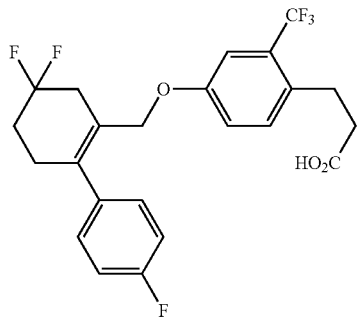 [SMILES: O=C(O)CCc1ccc(OCC2=C(c3ccc(F)cc3)CCC(F)(F)C2)cc1C(F)(F)F]

¹H NMR (CHLOROFORM-d) δ: 7.21 (br d, J=8.6 Hz, 1H), 7.09-7.17 (m, 2H), 6.95-7.08 (m, 3H), 6.80-6.89 (m, 1H), 4.33 (s, 2H), 3.04 (br s, 2H), 2.71-2.87 (m, 2H), 2.54-2.69 (m, 4H), 2.07-2.26 (m, 2H).

Example 116: Compound #491

3-[4-[[2-(4-chlorophenyl)-5,5-difluoro-cyclohexen-1-yl]methoxy]-3,5-difluoro-phenyl]Propanoic Acid

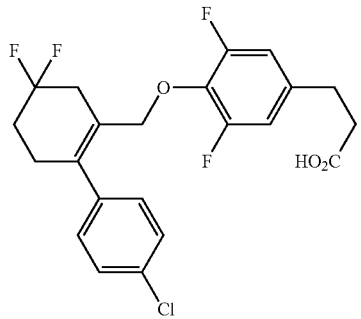 [SMILES: O=C(O)CCc1cc(F)c(OCC2=C(c3ccc(Cl)cc3)CCC(F)(F)C2)c(F)c1]

¹H NMR (CHLOROFORM-d) δ: 7.26 (s, 2H), 7.01 (d, J=8.6 Hz, 2H), 6.71 (d, J=8.6 Hz, 2H), 4.34 (s, 2H), 2.82-3.00 (m, 5H), 2.61-2.70 (m, 3H), 2.57 (br s, 2H), 2.07-2.23 (m, 2H).

Example 117: Compound #497

3-[4-[[5,5-difluoro-2-(4-fluorophenyl)cyclohexen-1-yl]methoxy]-2,3-dimethyl-phenyl]Propanoic Acid

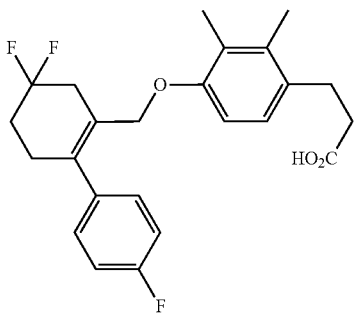 [SMILES: Cc1c(CCC(=O)O)ccc(OCC2=C(c3ccc(F)cc3)CCC(F)(F)C2)c1C]

$^1$H NMR (CHLOROFORM-d) δ: 7.09-7.18 (m, 2H), 6.97-7.06 (m, 2H), 6.79-6.91 (m, 1H), 6.32-6.46 (m, 1H), 4.21-4.32 (m, 2H), 2.74-2.99 (m, 4H), 2.50-2.67 (m, 4H), 2.21 (br s, 3H), 2.17 (br s, 3H), 1.55-1.65 (m, 2H note: buried under water peak).

Example 118: Compound #498

3-[4-[[5,5-difluoro-2-(4-fluorophenyl)cyclohexen-1-yl]methoxy]-3-methyl-phenyl]Propanoic Acid

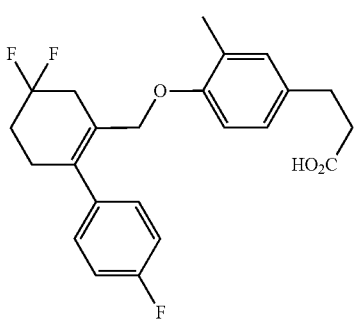 [SMILES: Cc1cc(CCC(=O)O)ccc1OCC1=C(c2ccc(F)cc2)CCC(F)(F)C1]

$^1$H NMR (CHLOROFORM-d) δ: 7.10-7.17 (m, 2H), 6.94-7.08 (m, 3H), 6.83-6.92 (m, 1H), 6.42-6.52 (m, 1H), 4.24-4.33 (m, 2H), 2.80-2.92 (m, 4H), 2.56-2.68 (m, 4H), 2.20 (s, 5H).

Example 119: Compound #499

3-[4-[[5,5-difluoro-2-(4-fluorophenyl)cyclohexen-1-yl]methoxy]phenyl]Propanoic Acid

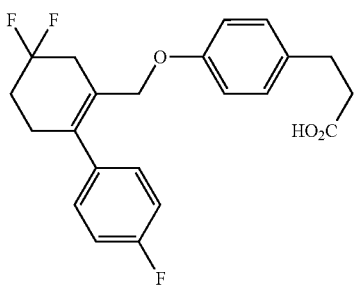 [SMILES: O=C(O)CCc1ccc(OCC2=C(c3ccc(F)cc3)CCC(F)(F)C2)cc1]

$^1$H NMR (CHLOROFORM-d) δ: 7.11-7.16 (m, 2H), 7.00-7.08 (m, 4H), 6.69 (d, J=9.1 Hz, 2H), 4.25-4.31 (m, 2H), 2.74-2.94 (m, 4H), 2.63 (m, 4H), 2.08-2.24 (m, 2H).

Example 120: Compound #503

3-[4-[[2-(4-chlorophenyl)-5,5-difluoro-cyclohexen-1-yl]methoxy]-2,3-difluoro-phenyl]Propanoic Acid

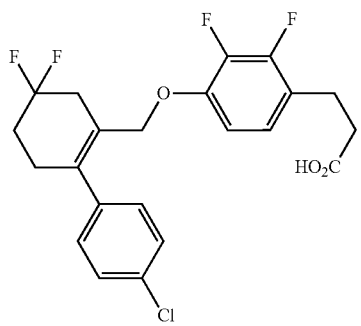 [SMILES: O=C(O)CCc1ccc(OCC2=C(c3ccc(Cl)cc3)CCC(F)(F)C2)c(F)c1F]

$^1$H NMR (CHLOROFORM-d) δ: 7.32 (d, J=8.6 Hz, 2H), 7.08 (d, J=8.1 Hz, 2H), 6.74-6.84 (m, 1H), 6.35-6.47 (m, 1H), 4.34 (s, 2H), 2.77-2.98 (m, 4H), 2.53-2.72 (m, 4H), 2.08-2.28 (m, 2H).

Example 121: Compound #518

3-[4-[[5,5-difluoro-2-(4-fluorophenyl)cyclohexen-1-yl]methoxy]-2-methyl-phenyl]Propanoic Acid

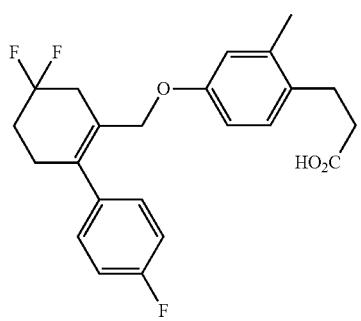 [SMILES: Cc1cc(OCC2=C(c3ccc(F)cc3)CCC(F)(F)C2)ccc1CCC(=O)O]

$^1$H NMR (CHLOROFORM-d) δ: 7.10-7.18 (m, 2H), 7.03 (s, 3H), 6.49-6.61 (m, 2H), 4.28 (s, 2H), 2.74-2.91 (m, 4H), 2.59 (m, 4H), 2.25 (s, 3H), 2.08-2.22 (m, 2H).

Example 122: Compound #519

3-[4-[[2-(4-chlorophenyl)-5,5-difluoro-cyclohexen-1-yl]methoxy]-2-methyl-phenyl]Propanoic Acid

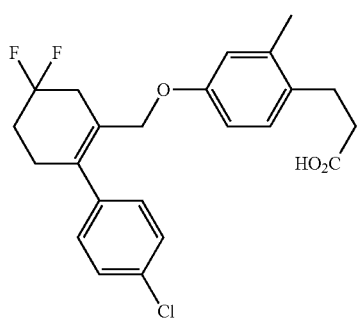 [SMILES: Cc1cc(OCC2=C(c3ccc(Cl)cc3)CCC(F)(F)C2)ccc1CCC(=O)O]

¹H NMR (CHLOROFORM-d) δ: 7.28-7.34 (m, 2H), 7.08-7.14 (m, 2H), 6.97-7.04 (m, 1H), 6.49-6.63 (m, 2H), 4.27 (s, 2H), 2.74-2.92 (m, 4H), 2.51-2.64 (m, 4H), 2.25 (s, 3H), 2.08-2.23 (m, 2H).

Example 123: Compound #551

3-[4-[[2-(4-chlorophenyl)-5,5-difluoro-cyclohexen-1-yl]methoxy]-3-(4-methylsulfonylbutyl)phenyl]Propanoic Acid

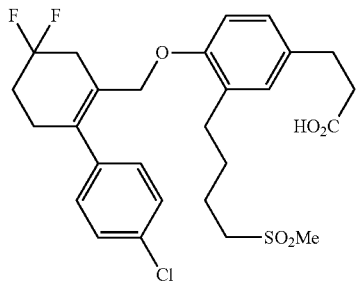 [SMILES: CS(=O)(=O)CCCCc1cc(CCC(=O)O)ccc1OCC1=C(c2ccc(Cl)cc2)CCC(F)(F)C1]

¹H NMR (CHLOROFORM-d) δ: 7.28-7.36 (m, 2H), 7.11 (d, J=8.1 Hz, 2H), 6.87-6.98 (m, 2H), 6.46-6.57 (m, 1H), 4.29 (s, 2H), 3.00-3.09 (m, 2H), 2.92 (s, 3H), 2.85 (s, 4H), 2.56-2.70 (m, 6H), 2.12-2.28 (m, 2H), 1.67-1.90 (m, 4H).

Example 124: Compound #565

3-[4-[[2-(4-chlorophenyl)-5,5-difluoro-cyclohexen-1-yl]methoxy]-3-(4-methylsulfanylbutyl)phenyl]Propanoic Acid

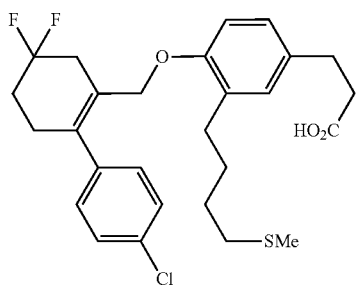 [SMILES: CSCCCCc1cc(CCC(=O)O)ccc1OCC1=C(c2ccc(Cl)cc2)CCC(F)(F)C1]

¹H NMR (CHLOROFORM-d) δ: 7.30 (s, 2H), 7.12 (s, 2H), 6.93-6.99 (m, 1H), 6.85-6.92 (m, 1H), 6.43-6.52 (m, 1H), 4.28 (s, 2H), 2.75-2.90 (m, 4H), 2.61 (br d, J=6.1 Hz, 6H), 2.48-2.56 (m, 2H), 2.12-2.25 (m, 2H), 2.09 (s, 3H), 1.58-1.72 (m, 4H).

Example 125: Compound #567-D

3-[4-[[2-(4-chlorophenyl)-5,5-difluoro-cyclohexen-1-yl]-dideuterio-methoxy]-3-methyl-phenyl]Propanoic Acid

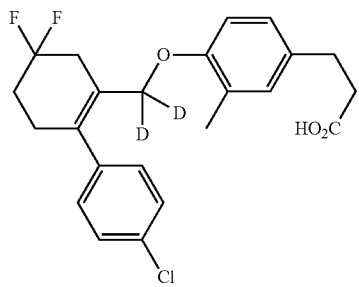 [SMILES: [2H]C([2H])(Oc1ccc(CCC(=O)O)cc1C)C1=C(c2ccc(Cl)cc2)CCC(F)(F)C1]

In the synthesis of this compound, DIBAL-D was used to install the deuterium atoms in the appropriate step.

¹H NMR (CHLOROFORM-d) δ: 7.28-7.36 (m, 2H), 7.12 (s, 2H), 6.94-7.01 (m, 1H), 6.83-6.93 (m, 1H), 6.43-6.52 (m, 1H), 2.74-2.89 (m, 4H), 2.62 (s, 4H), 2.20 (s, 6H).

Example 126: Compound #468

3-[4-[[2-(4-chlorophenyl)-5,5-difluoro-cyclohexen-1-yl]methoxy]-2,3-dimethyl-phenyl]Propanoic Acid

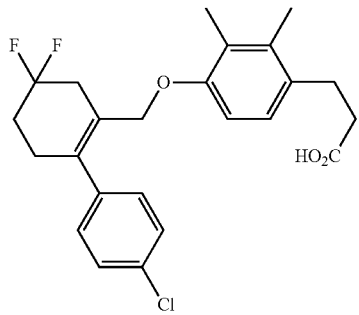

The title compound was prepared according to the process as describe in Example 114, Steps 1 to 5, and then reacting the resulting product as described below.

Step 1: ethyl 3-(4-((4'-chloro-4,4-difluoro-3,4,5,6-tetrahydro-[1,1'-biphenyl]-2-yl)methoxy)-2,3-dimethylphenyl)Propanoate A solution of (4'-chloro-4,4-difluoro-3,4,5,6-tetrahydro-[1,1'-biphenyl]-2-yl)methanol (152 mg, 0.59 mmol), ADDP (300 mg, 1.18 mmol) and ethyl 3-(4-hydroxy-2,3-dimethylphenyl)propanoate (161 mg, 0.73 mmol) in toluene (15 mL) was placed under an argon atmosphere and treated with neat tri-n-butylphosphine (0.38 mL, 1.49 mmol). The reaction was stirred at 60° C. for ~18 hours and then concentrated in vacuo. The residue was triturated with diethyl ether, the resulting white precipitate was filtered off and the filtrate concentrated. The resulting residue was purified by flash chromatography (SiO₂, 25% DCM/heptane) to yield ethyl 3-(4-((4'-chloro-4,4-difluoro-3,4,5,6-tetrahydro-[1,1'-biphenyl]-2-yl)methoxy)-2,3-dimethylphenyl)propanoate.

Step 2: 3-[4-[[2-(4-chlorophenyl)-5,5-difluoro-cyclohexen-1-yl]methoxy]-2,3-dimethyl-phenyl]Propanoic Acid A solution of ethyl 3-(4-((4'-chloro-4,4-difluoro-3,4,5,6-tetrahydro-[1,1'-biphenyl]-2-yl)methoxy)-2,3-dimethylphenyl)propanoate (276 mg, 0.6 mmol) was dissolved in THF (20 mL), water (5 mL) and methanol (5 mL) before being treated with a solution of KOH (45%) (0.5 mL, 5.84 mmol). After stirring at ambient temperature overnight, the reaction mixture was adjusted to pH 4 with 1 N HCl before being extracted with ethyl acetate. The organic extracts were dried (MgSO$_4$) and concentrated in vacuo to yield 3-[4-[[2-(4-chlorophenyl)-5,5-difluoro-cyclohexen-1-yl]methoxy]-2,3-dimethyl-phenyl]propanoic acid as solid.

$^1$H NMR (CHLOROFORM-d) δ: 7.29 (s, 2H), 7.10 (brd, J=8.1 Hz, 2H), 6.84-6.91 (m, 1H), 6.34-6.44 (m, 1H), 4.22-4.33 (m, 2H), 2.75-2.99 (m, 4H), 2.58 (br d, J=8.1 Hz, 4H), 2.21 (s, 3H), 2.16-2.19 (m, 3H).

The following representative compounds of formula (I) were prepared according to the process described in Scheme 6 above (and as described in more detail hereinafter), selecting appropriate starting materials and reagents, as would be readily recognized by those skilled in the art.

Example 127: Compound #574

3-[4-[[5-methoxy-2-(p-tolyl)cyclohexen-1-yl]methoxy]phenyl]Propanoic Acid

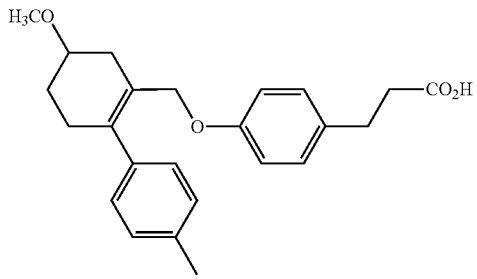 [SMILES: COC1CCC(c2ccc(C)cc2)=C(COc2ccc(CCC(=O)O)cc2)C1]

Step 1: ethyl 4'-methyl-4-oxo-3,4,5,6-tetrahydro-[1,1'-biphenyl]-2-carboxylate The compound was prepared as described in Scheme 5, using appropriate starting materials and reagents, as would be recognized by those skilled in the art.

Step 2: ethyl 4-hydroxy-4'-methyl-3,4,5,6-tetrahydro-[1,1'-biphenyl]-2-carboxylate To a solution of ethyl 4'-methyl-4-oxo-3,4,5,6-tetrahydro-[1,1'-biphenyl]-2-carboxylate (408.6 mg, 1.582 mmol) in dry THF was treated with sodium borohydride (67.8 mg, 1.792 mmol). After stirring overnight at ambient temperature, the mixture was concentrated in vacuo, treated with sat. NaHCO$_3$ solution and extracted with diethyl ether. The organic layer was concentrated in vacuo and the residue purified by flash chromatography (SiO$_2$, 0-100% diethyl ether/DCM).

Step 3: ethyl 4-methoxy-4'-methyl-3,4,5,6-tetrahydro-[1,1'-biphenyl]-2-carboxylate To a suspension of sodium hydride (41.5 mg, 1.038 mmol) in dry THF (10 mL) under argon was added a solution of ethyl 4-hydroxy-4'-methyl-3,4,5,6-tetrahydro-[1,1'-biphenyl]-2-carboxylate (244.6 mg, 0.94 mmol in 10 mL diethyl ether) dropwise. The reaction mixture was stirred ambient temperature for 30 minutes post addition and then treated dropwise with neat methyl iodide (0.06 mL, 0.964 mmol). After stirring the reaction mixture for 1 h the mixture was poured onto sat. NaHCO$_3$ and extracted with diethyl ether. The organic layer was concentrated in vacuo, then purified by flash chromatography (SiO$_2$, DCM→diethyl ether) to yield a residue.

Step 4: (4-methoxy-4'-methyl-3,4,5,6-tetrahydro-[1,1'-biphenyl]-2-yl)methanol A solution of ethyl 4-methoxy-4'-methyl-3,4,5,6-tetrahydro-[1,1'-biphenyl]-2-carboxylate (116.7 mg, 0.425 mmol) in dry toluene (20 mL) was cooled to −78° C. under an argon atmosphere. The reaction mixture was treated dropwise with DIBAL-H (1.2 mL, 1.2 mmol in toluene) and stirred, allowing the reaction mixture to reach ambient temperature over 2 hours. After stirring for one additional hour, the mixture was cooled to ∼−10° C. and quenched by the dropwise addition of sat. Rochelle's salt (12 mL). The aqueous layer was extracted with diethyl ether and the combined organic layers washed with sat. NaHCO$_3$ and brine before being dried over MgSO$_4$. The resulting mixture was concentrated in vacuo, followed by flash chromatography (SiO$_2$, DCM→diethyl ether) to yield a residue.

Step 5: methyl 3-(4-((4-methoxy-4'-methyl-3,4,5,6-tetrahydro-[1,1'-biphenyl]-2-yl)methoxy)phenyl)Propanoate A solution of (4-methoxy-4'-methyl-3,4,5,6-tetrahydro-[1,1'-biphenyl]-2-yl)methanol (39 mg, 0.168 mmol), ADDP (85 mg, 0.336 mmol) and methyl 3-(4-hydroxyphenyl)propanoate (33 mg, 0.185 mmol) in toluene (5 mL) was placed under an argon atmosphere and treated with neat tri-n-butylphosphine (0.11 mL, 0.432 mmol). The reaction was stirred at 60° C. for ∼18 hours and then concentrated in vacuo. The residue was triturated with diethyl ether, the resulting white precipitate was filtered off and the filtrate was concentrated. The resulting residue was purified by flash chromatography (SiO$_2$, DCM→diethyl ether) to yield a residue.

Step 6: 3-(4-((4-methoxy-4'-methyl-3,4,5,6-tetrahydro-[1,1'-biphenyl]-2-yl)methoxy)phenyl)Propanoic Acid A solution of methyl 3-(4-((4-methoxy-4'-methyl-3,4,5,6-tetrahydro-[1,1'-biphenyl]-2-yl)methoxy)phenyl)propanoate (61.2 mg, 0.155 mmol) was dissolved in THF (8 mL), water (4 mL) and methanol (4 mL) before being treated with a solution of KOH (0.30 mL, 3.503 mmol, 45%). After stirring at ambient temperature overnight, the reaction mixture was adjusted to pH 4 with 1 N HCl then extracted with ethyl acetate. The organic extracts were dried (MgSO$_4$) and concentrated in vacuo to yield the title compound.

$^1$H NMR (CHLOROFORM-d) δ: 7.00-7.16 (m, 6H), 6.73 (s, 2H), 4.19-4.40 (m, 2H), 3.56-3.68 (m, 1H), 3.42 (s, 3H), 2.80-2.93 (m, 2H), 2.62 (s, 5H), 2.33 (s, 3H), 2.19-2.29 (m, 1H), 1.96-2.12 (m, 1H), 1.68-1.83 (m, 1H).

Example 128: Compound #575

3-[4-[[5-methoxy-2-(o-tolyl)cyclohexen-1-yl]methoxy]phenyl]Propanoic Acid

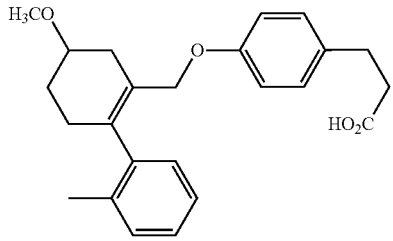 [SMILES: COC1CCC(c2ccccc2C)=C(COc2ccc(CCC(=O)O)cc2)C1]

$^1$H NMR (CHLOROFORM-d) δ: 7.15 (s, 6H), 6.68 (dd, J=8.6, 1.5 Hz, 2H), 4.05-4.21 (m, 2H), 3.61-3.72 (m, 1H), 3.43 (s, 3H), 2.81-2.91 (m, 2H), 2.61 (s, 3H), 2.22-2.41 (m, 3H), 2.19 (d, J=3.0 Hz, 3H), 1.97-2.11 (m, 1H), 1.68-1.87 (m, 1H).

Example 129: Compound #576

3-[4-[[5-methoxy-2-(o-tolyl)cyclohexen-1-yl]methoxy]-2-(trifluoromethyl)phenyl]Propanoic Acid

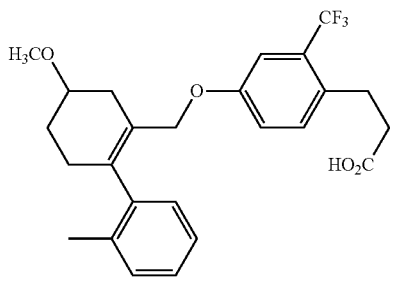 [SMILES: COC1CCC(c2ccccc2C)=C(COc2ccc(CCC(=O)O)c(C(F)(F)F)c2)C1]

$^1$H NMR (CHLOROFORM-d) δ: 7.17 (brs, 4H), 6.95-7.06 (m, 2H), 6.78-6.86 (m, 1H), 4.10-4.21 (m, 2H), 3.61-3.71 (m, 1H), 3.44 (s, 3H), 2.97-3.11 (m, 2H), 2.54-2.74 (m, 3H), 2.21-2.41 (m, 3H), 2.18 (s, 3H), 1.97-2.12 (m, 1H), 1.69-1.87 (m, 1H).

Example 130: Compound #577

3-[4-[[5-methoxy-2-(p-tolyl)cyclohexen-1-yl]methoxy]-2-(trifluoromethyl)phenyl]Propanoic Acid

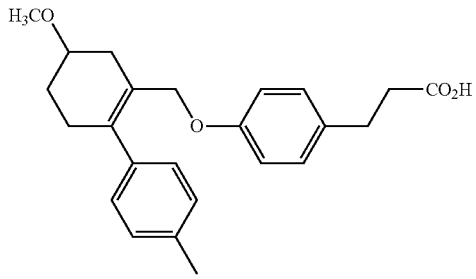 [SMILES: COC1CCC(c2ccc(C)cc2)=C(COc2ccc(CCC(=O)O)cc2)C1]

$^1$H NMR (CHLOROFORM-d) δ: 7.16-7.22 (m, 1H), 7.10-7.16 (m, 2H), 6.99-7.08 (m, 3H), 6.81-6.89 (m, 1H), 4.25-4.44 (m, 2H), 3.56-3.68 (m, 1H), 3.42 (s, 3H), 2.99-3.09 (m, 2H), 2.36-2.73 (m, 5H), 2.34 (s, 3H), 2.16-2.28 (m, 1H), 1.97-2.07 (m, 1H), 1.70-1.83 (m, 1H).

Example 131: Compound #226

3-[4-[[2-(6-ethoxy-3-pyridyl)cyclopenten-1-yl]methoxy]-3,5-difluoro-phenyl]Propanoic Acid

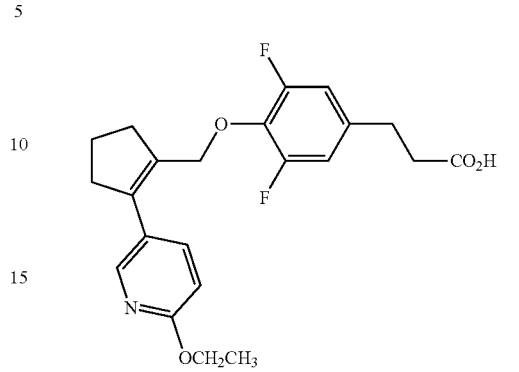

Step 1: methyl 2-(6-ethoxypyridin-3-yl)cyclopent-1-ene-1-carboxylate

A suspension of methyl 2-(((trifluoromethyl)sulfonyl)oxy)cyclopent-1-enecarboxylate (200 mg, 0.73 mmol), (Ph$_3$P)$_2$PdCl$_2$ (51 mg, 0.073 mmol), 6-ethoxypyridine-3-boronic acid (244 mg, 1.46 mmol) and sodium carbonate (1.09 mL of a 2 M aq. solution, 2.18 mmol) in 1,4-dioxane (7 mL) under nitrogen was heated to 80° C. for 2 hrs. The suspension was cooled to room temperature, filtered through CELITE®, washed with ethyl acetate, dried over MgSO$_4$ and concentrated under reduced pressure to yield a residue. The residue was purified by chromatography (12 g), eluting with 2 to 12% EA/heptane to yield methyl 2-(6-ethoxypyridin-3-yl)cyclopent-1-ene-1-carboxylate. Calculated for C$_{1-4}$H$_{17}$NO$_3$: 248.1 (M+1); Measured: 248.3.

Step 2: (2-(6-ethoxypyridin-3-yl)cyclopent-1-en-1-yl)methanol

To a solution of the compound prepared in Step 1 (152 mg, 0.61 mmol) in toluene (14 mL) at −78° C. under nitrogen was added DIBAL (1.23 mL of a 1 M solution in toluene, 1.23 mmol). After 2 hrs, the reaction was not complete, so additional DIBAL (0.7 mL of a 1 M solution in toluene, 0.7 mmol) was added. After 30 min, the reaction was quenched with aqueous sodium potassium tartrate and water, extracted with diethyl ether, washed with brine, dried over MgSO$_4$ and concentrated under reduced pressure to yield a residue. The residue was purified by chromatography (12 g), eluting with 20 to 40% EA/heptane to yield (2-(6-ethoxypyridin-3-yl)cyclopent-1-en-1-yl)methanol. 1H NMR (CHLOROFORM-d) δ: 8.03 (d, J=2.0 Hz, 1H), 7.49 (dd, J=8.6, 2.5 Hz, 1H), 6.71 (d, J=8.6 Hz, 1H), 4.35 (q, J=7.1 Hz, 2H), 4.30 (br d, J=3.5 Hz, 2H), 2.74 (br t, J=7.6 Hz, 2H), 2.67 (br t, J=7.3 Hz, 2H), 1.90-2.03 (m, 2H), 1.67 (br s, 1H), 1.40 (t, J=7.1 Hz, 3H). Calculated for C$_{13}$H$_{17}$NO$_2$: 220.3 (M+1); Measured 220.2.

Step 3: ethyl 3-(4-((2-(6-ethoxypyridin-3-yl)cyclopent-1-en-1-yl)methoxy)-3,5-difluorophenyl)Propanoate A solution of the compound prepared in Step 2 (42 mg, 0.19 mmol) in toluene (4 mL) at room temperature under nitrogen was added ethyl 3-(3,5-difluoro-4-hydroxyphenyl)propanoate (0.058 mL, 0.31 mmol), tri-n-butylphosphine (0.12 mL, 0.48 mmol) and ADDP (100 mg, 0.38 mmol) was warmed to 60° C. for 2 hrs. Heptane (15 mL) was added, the resulting white solid was filtered off, and the filtrate concentrated under reduced pressure to yield a residue. The residue was purified by chromatography (12 g), eluting with 3 to 12% EA/heptane to yield ethyl 3-(4-((2-(6-ethoxypyridin-3-yl)cyclopent-1-en-1-yl)methoxy)-3,5-difluorophenyl)propanoate. $^1$H NMR (CHLOROFORM-d) δ: 8.02 (d, J=2.5 Hz, 1H), 7.50 (dd, J=8.6, 2.0 Hz, 1H), 6.65-6.77 (m, 3H), 4.67 (s, 2H), 4.35 (q, J=7.1 Hz, 2H), 4.13 (q, J=7.2 Hz, 2H), 2.86 (t, J=7.6 Hz, 2H), 2.75 (t, J=7.6 Hz, 4H), 2.58 (t, J=7.6 Hz, 2H), 1.99 (quin, J=7.6 Hz, 2H), 1.40 (t, J=7.1 Hz, 3H), 1.24 (t, J=7.3 Hz, 3H). Calculated for $C_{24}H_{27}F_2NO_4$: 432.2 (M+1); Measured 432.3.

Step 4: 3-(4-((2-(6-ethoxypyridin-3-yl)cyclopent-1-en-1-yl)methoxy)-3,5-difluorophenyl)Propanoic Acid To a solution of the compound prepared in Step 3 (71 mg, 0.16 mmol) in tetrahydrofuran (1 mL) and methanol (1 mL) was added 1 M NaOH (1 mL). After stirring overnight, 1 M HCl (1.5 mL) was added, the solution extracted with DCM, dried over MgSO$_4$ and concentrated under reduced pressure to yield the title compound.
$^1$H NMR (CHLOROFORM-d) δ: 7.82 (d, J=2.0 Hz, 1H), 7.48 (dd, J=8.6, 2.5 Hz, 1H), 6.65-6.79 (m, 3H), 4.64 (s, 2H), 4.33 (q, J=7.1 Hz, 2H), 2.84-2.92 (m, 2H), 2.74 (dt, J=14.3, 7.3 Hz, 4H), 2.61-2.69 (m, 2H), 1.98 (quin, J=7.6 Hz, 2H), 1.40 (t, J=7.1 Hz, 3H); MS Calculated for $C_{22}H_{23}F_2NO_4$: 404.2 (M+1); Measured 404.2.

Additional representative compounds of formula (I) were prepared according to the procedure described in Example 131, selecting and substituting suitable reagents and starting materials, as would be readily recognized by those skilled in the art.

Example 132: Compound #36

3-[4-[[2-(4-chlorophenyl)cyclopenten-1-yl]methoxy]-3-methyl-phenyl]-2-methyl-Propanoic Acid

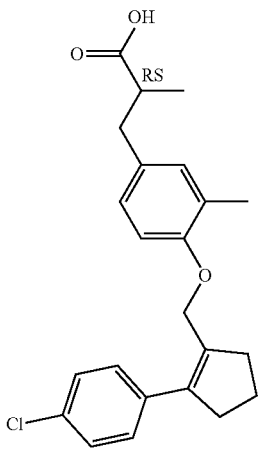 [SMILES: Cc1cc(CC(C)C(=O)O)ccc1OCC1=C(c2ccc(Cl)cc2)CCC1]

$^1$H NMR (CHLOROFORM-d) δ: 7.28-7.34 (m, 2H), 7.14-7.21 (m, 2H), 6.95 (s, 1H), 6.89 (dd, J=8.1, 2.0 Hz, 1H), 6.60 (d, J=8.6 Hz, 1H), 4.59 (s, 2H), 2.97 (dd, J=13.6, 6.6 Hz, 1H), 2.79 (br t, J=7.3 Hz, 2H), 2.65-2.75 (m, 3H), 2.57 (dd, J=13.6, 8.1 Hz, 1H), 2.20 (s, 3H), 1.99 (quin, J=7.5 Hz, 2H), 1.16 (d, J=7.1 Hz, 3H). Calculated for $C_{23}H_{26}ClO_3$: 407.1 (M+23); Measured: 407.1.

Example 133: Compound #160

3-[4-[[2-(4-fluorophenyl)cyclopenten-1-yl]methoxy]-3-methyl-phenyl]-2-methyl-Propanoic Acid

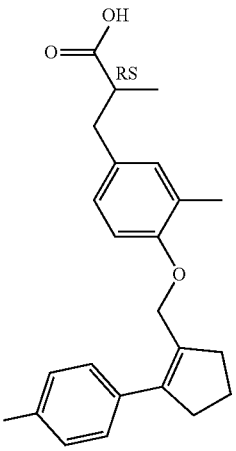

$^1$H NMR (CHLOROFORM-d) δ: 7.18-7.25 (m, 2H), 6.98-7.08 (m, 2H), 6.95 (s, 1H), 6.89 (br d, J=8.1 Hz, 1H), 6.60 (d, J=8.6 Hz, 1H), 4.59 (s, 2H), 2.97 (dd, J=13.4, 6.3 Hz, 1H), 2.79 (br t, J=7.3 Hz, 2H), 2.65-2.75 (m, 3H), 2.56 (dd, J=13.6, 8.1 Hz, 1H), 2.20 (s, 3H), 1.98 (quin, J=7.6 Hz, 2H), 1.15 (d, J=7.1 Hz, 3H). Calculated for $C_{23}H_{25}FO_3$: 391.2 (M+23); Measured: 391.2.

Example 134: Compound #458

3-(3-fluoro-4-((2-(4-fluorophenyl)cyclopent-1-en-1-yl)methoxy)phenyl)-2-methylpropanoic Acid

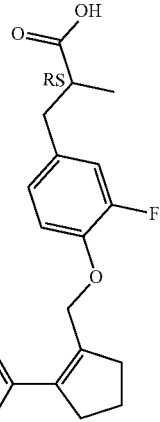

$^1$H NMR (CHLOROFORM-d) δ: 7.18-7.24 (m, 2H), 6.99-7.07 (m, 2H), 6.91 (dd, J=12.1, 2.0 Hz, 1H), 6.76-6.82 (m, 1H), 6.68-6.76 (m, 1H), 4.65 (s, 2H), 2.96 (dd, J=13.6, 6.6 Hz, 1H), 2.78 (br t, J=7.6 Hz, 2H), 2.66-2.75 (m, 3H), 2.56-2.65 (m, 1H), 1.93-2.04 (m, 2H), 1.17 (d, J=7.1 Hz, 3H). Calculated for $C_{22}H_{22}F_2O_3$: 395.2 (M+23); Measured: 395.1.

Example 135: Compound #30

3-[3-bromo-4-[[2-(4-chlorophenyl)cyclopenten-1-yl]methoxy]-5-methyl-phenyl]Propanoic Acid

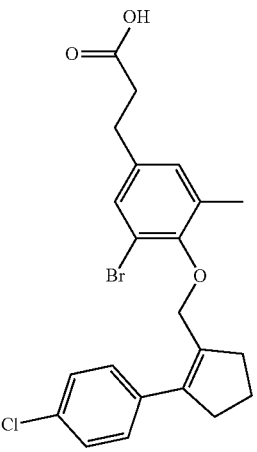 [SMILES: Cc1cc(CCC(=O)O)cc(Br)c1OCC1=C(c2ccc(Cl)cc2)CCC1]

$^1$H NMR (CHLOROFORM-d) δ: 7.18-7.33 (m, 5H), 6.90-6.97 (m, 1H), 6.94 (s, 1H), 4.49 (s, 2H), 2.73-2.92 (m, 6H), 2.59-2.69 (m, 2H), 2.25 (s, 3H), 1.96-2.08 (m, 2H). Calculated for $C_{22}H_{22}BrClO_3$: 471.0 (M+23); Measured: 471.0.

Example 136: Compound #169

3-[3-bromo-4-[[2-(p-tolyl)cyclopenten-1-yl]methoxy]phenyl]Propanoic Acid

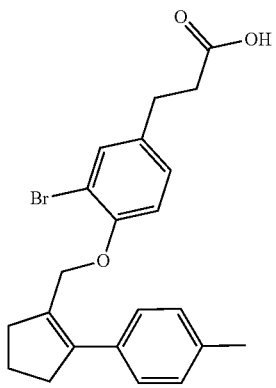 [SMILES: Cc1ccc(C2=C(COc3ccc(CCC(=O)O)cc3Br)CCC2)cc1]

$^1$H NMR (CHLOROFORM-d) δ: 7.37 (d, J=2.0 Hz, 1H), 7.10-7.20 (m, 4H), 6.98 (dd, J=8.3, 2.3 Hz, 1H), 6.63 (d, J=8.1 Hz, 1H), 4.72 (s, 2H), 2.82-2.88 (m, 2H), 2.79 (br t, J=7.3 Hz, 2H), 2.71 (br t, J=7.3 Hz, 2H), 2.58-2.66 (m, 2H), 2.36 (s, 3H), 1.97 (quin, J=7.6 Hz, 2H). Calculated for $C_{21}H_{15}ClF_5NO_3$: 437.1 (M+23); Measured: 437.1.

Example 137: Compound #230

3-[4-[[2-(cyclohexen-1-yl)cyclopenten-1-yl]methoxy]phenyl]Propanoic Acid

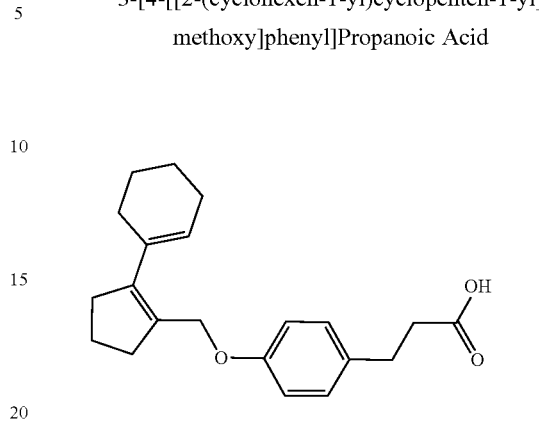

$^1$H NMR (CHLOROFORM-d) δ: 7.10 (brd, J=7.6 Hz, 2H), 6.82 (br d, J=7.6 Hz, 2H), 5.53 (br s, 1H), 4.62 (s, 2H), 2.91 (br s, 2H), 2.70 (br s, 2H), 2.50 (dt, J=14.4, 7.5 Hz, 4H), 2.09 (br d, J=6.1 Hz, 4H), 1.82 (dt, J=15.0, 7.4 Hz, 2H), 1.53-1.72 (m, 4H). Calculated for $C_{21}H_2O_3$: 349.2 (M+23); Measured: 349.0.

Example 138: Compound #218

3-[4-[[2-(6-methoxy-3-pyridyl)cyclopenten-1-yl]methoxy]-3-methyl-phenyl]Propanoic Acid

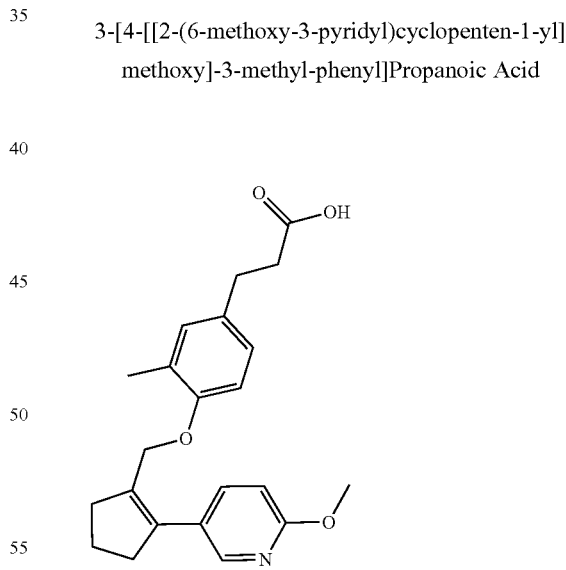

$^1$H NMR (CHLOROFORM-d) δ: 8.04 (d, J=2.5 Hz, 1H), 7.51 (dd, J=8.6, 2.5 Hz, 1H), 6.98 (s, 1H), 6.92 (dd, J=8.1, 2.0 Hz, 1H), 6.74 (d, J=8.6 Hz, 1H), 6.63 (d, J=8.1 Hz, 1H), 4.61 (s, 2H), 3.95 (s, 3H), 2.82-2.89 (m, 2H), 2.78 (br t, J=7.3 Hz, 2H), 2.71 (br t, J=7.3 Hz, 2H), 2.59-2.66 (m, 2H), 2.20 (s, 3H), 1.95-2.05 (m, 2H). Calculated for $C_{22}H_{25}NO_4$: 390.2 (M+23); Measured: 390.3.

Example 139: Compound #220

3-[4-[[2-(6-methoxy-3-pyridyl)cyclopenten-1-yl]methoxy]-2,3-dimethyl-phenyl]Propanoic Acid

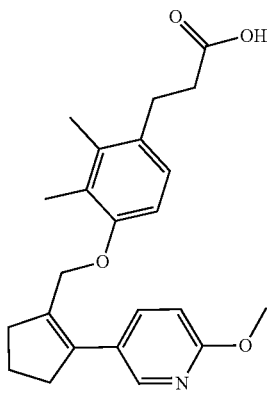 [SMILES: COc1ccc(C2=C(COc3ccc(CCC(=O)O)c(C)c3C)CCC2)cn1]

$^1$H NMR (CHLOROFORM-d) δ: 8.03 (s, 1H), 7.55 (dd, J=8.3, 1.8 Hz, 1H), 6.91 (d, J=8.1 Hz, 1H), 6.76 (d, J=8.6 Hz, 1H), 6.56 (d, J=8.6 Hz, 1H), 4.59 (s, 2H), 3.98 (s, 3H), 2.88-2.97 (m, 2H), 2.68-2.82 (m, 4H), 2.53-2.63 (m, 2H), 2.22 (s, 3H), 2.16 (s, 3H), 2.01 (quin, J=7.6 Hz, 2H). Calculated for $C_{23}H_{27}NO_4$: 404.2 (M+23); Measured: 404.2.

Example 140: Compound #221

3-[3,5-difluoro-4-[[2-(6-methoxy-3-pyridyl)cyclopenten-1-yl]methoxy]phenyl]Propanoic Acid

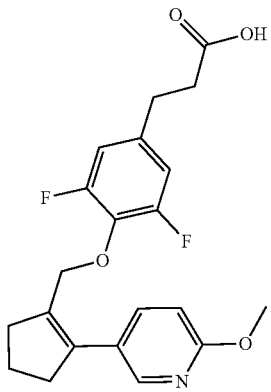 [SMILES: COc1ccc(C2=C(COc3c(F)cc(CCC(=O)O)cc3F)CCC2)cn1]

$^1$H NMR (CHLOROFORM-d) δ: 7.75 (br d, J=2.0 Hz, 1H), 7.47 (dd, J=8.3, 2.3 Hz, 1H), 6.67-6.79 (m, 3H), 4.62 (s, 2H), 3.94 (s, 3H), 2.85-2.93 (m, 2H), 2.74 (dt, J=20.8, 7.5 Hz, 4H), 2.61-2.69 (m, 2H), 1.99 (quin, J=7.5 Hz, 2H). Calculated for $C_{21}H_{21}F_2NO_4$: 412.1 (M+23); Measured: 412.2.

Example 141: Compound #222

3-[4-[[2-(5-fluoro-6-methoxy-3-pyridyl)cyclopenten-1-yl]methoxy]-3-methyl-phenyl]Propanoic Acid

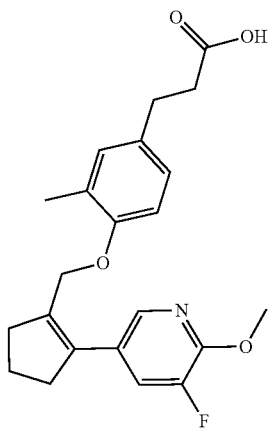 [SMILES: COc1ncc(C2=C(COc3ccc(CCC(=O)O)cc3C)CCC2)cc1F]

$^1$H NMR (CHLOROFORM-d) δ: 7.84 (d, J=2.0 Hz, 1H), 7.23-7.30 (m, 1H), 6.98 (s, 1H), 6.93 (dd, J=8.1, 2.0 Hz, 1H), 6.64 (d, J=8.1 Hz, 1H), 4.61 (s, 2H), 4.03 (s, 3H), 2.82-2.90 (m, 2H), 2.68-2.81 (m, 4H), 2.58-2.66 (m, 2H), 2.20 (s, 3H), 2.00 (quin, J=7.6 Hz, 2H). Calculated for $C_{22}H_{24}FNO_4$: 386.2 (M+1); Measured: 386.2.

Example 142: Compound #223

3-[4-[[2-(5-fluoro-6-methoxy-3-pyridyl)cyclopenten-1-yl]methoxy]-2,3-dimethyl-phenyl]Propanoic Acid

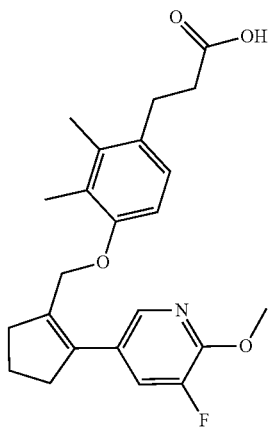 [SMILES: COc1ncc(C2=C(COc3ccc(CCC(=O)O)c(C)c3C)CCC2)cc1F]

$^1$H NMR (CHLOROFORM-d) δ: 7.80 (d, J=1.5 Hz, 1H), 7.21-7.28 (m, 1H), 6.92 (d, J=8.6 Hz, 1H), 6.57 (d, J=8.1 Hz, 1H), 4.59 (s, 2H), 4.03 (s, 3H), 2.88-2.96 (m, 2H), 2.69-2.81 (m, 4H), 2.58 (br t, J=8.1 Hz, 2H), 2.22 (s, 3H), 2.17 (s, 3H), 2.01 (quin, J=7.6 Hz, 3H). Calculated for $C_{23}H_{26}FNO_4$: 422.2 (M+23); Measured: 422.2.

Example 143: Compound #224

3-[3,5-difluoro-4-[[2-(5-fluoro-6-methoxy-3-pyridyl)cyclopenten-1-yl]methoxy]phenyl]Propanoic Acid

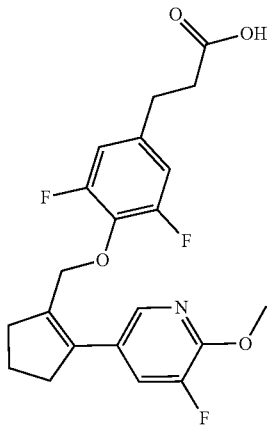 [SMILES: COc1ncc(C2=C(COc3c(F)cc(CCC(=O)O)cc3F)CCC2)cc1F]

$^1$H NMR (CHLOROFORM-d) δ: 7.75 (d, J=2.0 Hz, 1H), 7.22-7.30 (m, 1H), 6.69-6.79 (m, 2H), 4.65 (s, 2H), 4.03 (s, 3H), 2.83-2.92 (m, 2H), 2.69-2.80 (m, 4H), 2.61-2.69 (m, 2H), 1.99 (quin, J=7.5 Hz, 2H). Calculated for $C_{21}H_{20}F_3NO_4$: 430.1 (M+23); Measured: 430.2.

Example 144: Compound #225

3-[4-[[2-(6-ethoxy-3-pyridyl)cyclopenten-1-yl]methoxy]-3-methyl-phenyl]Propanoic Acid

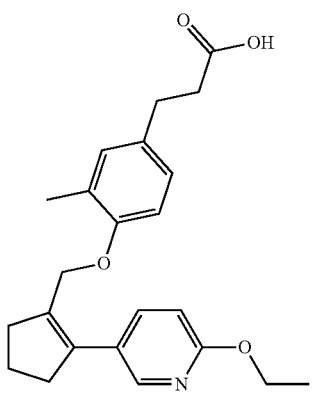 [SMILES: CCOc1ccc(C2=C(COc3ccc(CCC(=O)O)cc3C)CCC2)cn1]

$^1$H NMR (CHLOROFORM-d) δ: 8.04 (br s, 1H), 7.49 (dd, J=8.6, 2.0 Hz, 1H), 6.97 (s, 1H), 6.92 (dd, J=8.3, 1.8 Hz, 1H), 6.71 (br d, J=8.6 Hz, 1H), 6.63 (d, J=8.1 Hz, 1H), 4.61 (s, 2H), 4.34 (q, J=7.1 Hz, 2H), 2.81-2.90 (m, 2H), 2.77 (br t, J=7.3 Hz, 2H), 2.71 (br t, J=7.6 Hz, 2H), 2.63 (br t, J=7.6 Hz, 2H), 2.20 (s, 3H), 1.92-2.07 (m, 2H), 1.40 (t, J=7.1 Hz, 3H). Calculated for $C_{23}H_{27}NO_4$: 382.2 (M+23); Measured: 382.4.

Example 145: Compound #219

3-[4-[[2-(6-ethoxy-3-pyridyl)cyclopenten-1-yl]methoxy]-2,3-dimethyl-phenyl]Propanoic Acid

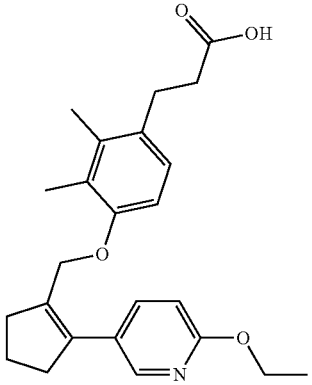 [SMILES: CCOc1ccc(C2=C(COc3ccc(CCC(=O)O)c(C)c3C)CCC2)cn1]

$^1$H NMR (CHLOROFORM-d) δ: 8.02 (d, J=2.5 Hz, 1H), 7.49 (dd, J=8.6, 2.5 Hz, 1H), 6.91 (d, J=8.6 Hz, 1H), 6.70 (d, J=8.6 Hz, 1H), 6.57 (d, J=8.6 Hz, 1H), 4.60 (s, 2H), 4.34 (q, J=7.1 Hz, 2H), 2.87-2.96 (m, 2H), 2.67-2.82 (m, 4H), 2.57 (dd, J=9.1, 7.1 Hz, 2H), 2.22 (s, 3H), 2.17 (s, 3H), 1.99 (quin, J=7.5 Hz, 2H), 1.39 (t, J=7.1 Hz, 3H). Calculated for $C_{24}H_{29}NO_4$: 396.2 (M+1); Measured: 396.3.

Example 146: Compound #208

3-[4-[[2-(2-furyl)cyclopenten-1-yl]methoxy]-3-methyl-phenyl]Propanoic Acid

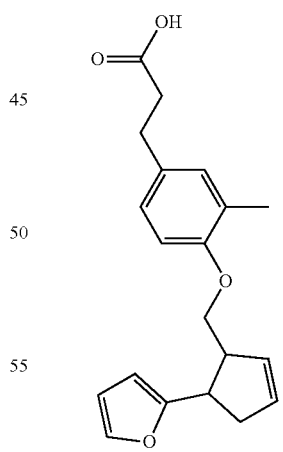

$^1$H NMR (CHLOROFORM-d) δ: 7.43 (d, J=1.5 Hz, 1H), 6.91-7.01 (m, 2H), 6.80 (d, J=8.1 Hz, 1H), 6.40 (dd, J=3.3, 1.8 Hz, 1H), 6.23 (d, J=3.0 Hz, 1H), 5.06 (s, 2H), 2.82-2.92 (m, 2H), 2.59-2.79 (m, 6H), 2.22 (s, 3H), 1.94 (quin, J=7.6 Hz, 2H). Calculated for $C_{20}H_{22}O_4$: 349.2 (M+23); Measured: 349.2.

Example 147: Compound #210

3-[4-[[2-(2-furyl)cyclopenten-1-yl]methoxy]-2,3-dimethyl-phenyl]Propanoic Acid

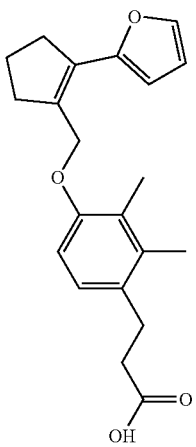 [SMILES: Cc1c(CCC(=O)O)ccc(OCC2=C(c3ccco3)CCC2)c1C]

$^1$H NMR (CHLOROFORM-d) δ: 7.42 (d, J=1.5 Hz, 1H), 6.94 (d, J=8.1 Hz, 1H), 6.73 (d, J=8.6 Hz, 1H), 6.40 (dd, J=3.5, 2.0 Hz, 1H), 6.23 (d, J=3.5 Hz, 1H), 5.04 (s, 2H), 2.89-2.97 (m, 2H), 2.67-2.79 (m, 4H), 2.55-2.63 (m, 2H), 2.23 (s, 3H), 2.19 (s, 3H), 1.95 (quin, J=7.5 Hz, 2H). Calculated for $C_{21}H_{24}O_4$: 363.2 (M+23); Measured: 363.1.

Example 148: Compound #209

3-[3,5-difluoro-4-[[2-(2-furyl)cyclopenten-1-yl]methoxy]phenyl]Propanoic Acid

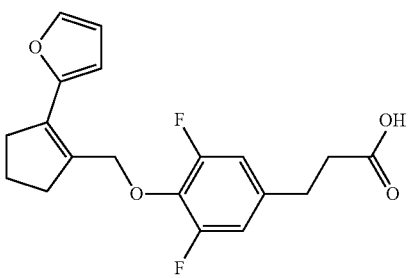 [SMILES: O=C(O)CCc1cc(F)c(OCC2=C(c3ccco3)CCC2)c(F)c1]

$^1$H NMR (CHLOROFORM-d) δ: 7.36 (d, J=2.0 Hz, 1H), 6.67-6.77 (m, 2H), 6.35 (dd, J=3.3, 1.8 Hz, 1H), 6.22 (d, J=3.0 Hz, 1H), 5.11 (s, 2H), 2.82-2.90 (m, 2H), 2.77 (br t, J=7.3 Hz, 2H), 2.71 (br t, J=7.6 Hz, 2H), 2.59-2.67 (m, 2H), 1.96 (quin, J=7.6 Hz, 2H). Calculated for $C_{19}H_{18}F_2O_4$: 371.1 (M+23); Measured: 371.2.

Example 149: Compound #211

3-[3-methyl-4-[[2-(5-methyl-2-furyl)cyclopenten-1-yl]methoxy]phenyl]Propanoic Acid

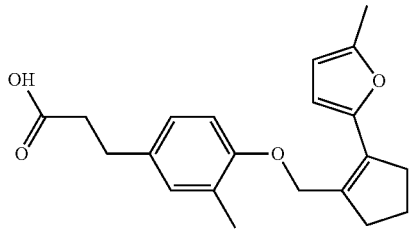 [SMILES: Cc1ccc(C2=C(COc3ccc(CCC(=O)O)cc3C)CCC2)o1]

$^1$H NMR (CHLOROFORM-d) δ: 6.91-7.01 (m, 2H), 6.80 (d, J=8.1 Hz, 1H), 6.12 (d, J=3.5 Hz, 1H), 5.98 (d, J=3.0 Hz, 1H), 5.05 (s, 2H), 2.81-2.91 (m, 2H), 2.60-2.75 (m, 6H), 2.32 (s, 3H), 2.22 (s, 3H), 1.92 (quin, J=7.5 Hz, 2H). Calculated for $C_{21}H_{24}O_4$: 363.2 (M+23); Measured: 363.1.

Example 150: Compound #212

3-[3,5-difluoro-4-[[2-(5-methyl-2-furyl)cyclopenten-1-yl]methoxy]phenyl]Propanoic Acid

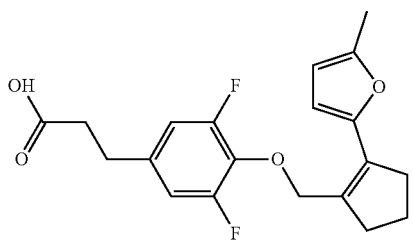 [SMILES: Cc1ccc(C2=C(COc3c(F)cc(CCC(=O)O)cc3F)CCC2)o1]

$^1$H NMR (CHLOROFORM-d) δ: 6.76 (d, J=8.6 Hz, 2H), 6.12 (d, J=3.0 Hz, 1H), 5.97 (d, J=3.0 Hz, 1H), 5.11 (s, 2H), 2.84-2.91 (m, 2H), 2.68 (br t, J=7.6 Hz, 2H), 2.59-2.65 (m, 2H), 2.50 (br t, J=7.3 Hz, 2H), 2.30 (s, 3H), 1.91 (dt, J=15.2, 7.6 Hz, 2H).

Example 151: Compound #238

3-[4-[[2-(3,6-dihydro-2H-pyran-4-yl)cyclopenten-1-yl]methoxy]-3-methyl-phenyl]Propanoic Acid

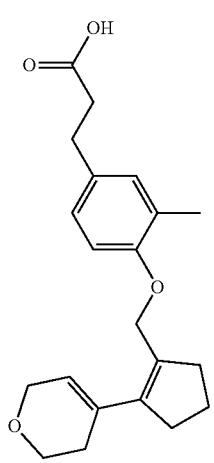 [SMILES: Cc1cc(CCC(=O)O)ccc1OCC1=C(C2=CCOCC2)CCC1]

¹H NMR (CHLOROFORM-d) δ: 6.92-7.01 (m, 2H), 6.71 (d, J=8.1 Hz, 1H), 5.56 (br s, 1H), 4.64 (s, 2H), 4.24 (br d, J=2.5 Hz, 2H), 3.82 (t, J=5.3 Hz, 2H), 2.82-2.91 (m, 2H), 2.56-2.68 (m, 4H), 2.53 (br t, J=7.3 Hz, 2H), 2.23-2.30 (m, 2H), 2.20 (s, 3H), 1.86 (quin, J=7.6 Hz, 2H). Calculated for $C_{21}H_{26}O_4$: 365.2 (M+23); Measured: 365.2.

Example 152: Compound #239

3-[4-[[2-(3,6-dihydro-2H-pyran-4-yl)cyclopenten-1-yl]methoxy]-2,3-dimethyl-phenyl]Propanoic Acid

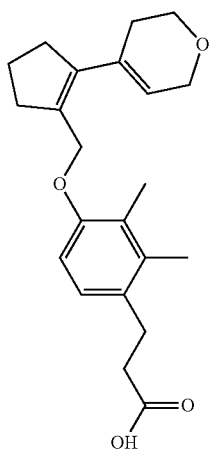 [SMILES: Cc1c(CCC(=O)O)ccc(OCC2=C(C3=CCOCC3)CCC2)c1C]

¹H NMR (CHLOROFORM-d) δ: 6.95 (d, J=8.6 Hz, 1H), 6.64 (d, J=8.1 Hz, 1H), 5.56 (br s, 1H), 4.62 (s, 2H), 4.24 (br s, 2H), 3.82 (t, J=5.6 Hz, 2H), 2.93 (br t, J=8.1 Hz, 2H), 2.48-2.65 (m, 6H), 2.26 (br s, 2H), 2.22 (s, 3H), 2.17 (s, 3H), 1.86 (quin, J=7.5 Hz, 2H). Calculated for $C_{22}H_{28}O_4$: 379.2 (M+23); Measured: 379.2.

Example 153: Compound #319

3-[4-[(2-benzylcyclopenten-1-yl)methoxy]-2-(trifluoromethyl)phenyl]Propanoic Acid

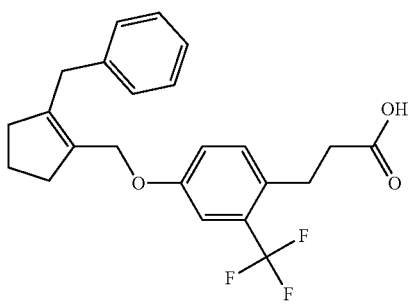 [SMILES: O=C(O)CCc1ccc(OCC2=C(Cc3ccccc3)CCC2)cc1C(F)(F)F]

¹H NMR (CHLOROFORM-d) δ: 7.23-7.31 (m, 3H), 7.16-7.23 (m, 2H), 7.14 (d, J=7.1 Hz, 2H), 7.03 (dd, J=8.6, 2.5 Hz, 1H), 4.66 (s, 2H), 3.50 (s, 2H), 3.08 (br t, J=7.8 Hz, 2H), 2.65 (t, J=8.1 Hz, 2H), 2.53 (br t, J=7.1 Hz, 2H), 2.31 (br t, J=7.1 Hz, 2H), 1.77-1.88 (m, 2H). Calculated for $C_{23}H_{23}F_3O_3$: 427.2 (M+23); Measured: 427.0.

Example 154: Compound #329

3-[4-[(2-benzylcyclopenten-1-yl)methoxy]-2-chloro-phenyl]Propanoic Acid

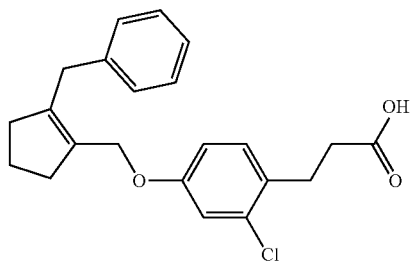 [SMILES: O=C(O)CCc1ccc(OCC2=C(Cc3ccccc3)CCC2)cc1Cl]

¹H NMR (CHLOROFORM-d) δ: 7.24-7.31 (m, 2H), 7.17-7.22 (m, 1H), 7.14 (dd, J=7.8, 4.3 Hz, 3H), 6.97 (d, J=2.5 Hz, 1H), 6.79 (dd, J=8.6, 2.5 Hz, 1H), 4.62 (s, 2H), 3.49 (s, 2H), 2.96-3.05 (m, 2H), 2.68 (t, J=7.6 Hz, 2H), 2.52 (br t, J=7.3 Hz, 2H), 2.30 (br t, J=7.3 Hz, 2H), 1.76-1.86 (m, 2H). Calculated for $C_{22}H_{23}ClO_3$: 393.1 (M+23); Measured: 393.1.

Example 155: Compound #330

3-[4-[(2-benzylcyclopenten-1-yl)methoxy]-3,5-difluoro-phenyl]Propanoic Acid

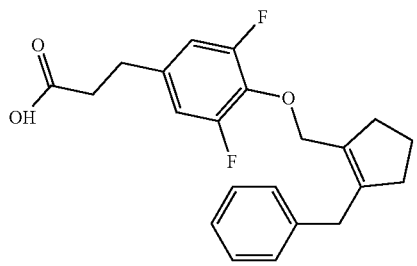 [SMILES: O=C(O)CCc1cc(F)c(OCC2=C(Cc3ccccc3)CCC2)c(F)c1]

¹H NMR (CHLOROFORM-d) δ: 7.19-7.25 (m, 2H), 7.13-7.20 (m, 1H), 7.00-7.07 (m, 2H), 6.70-6.79 (m, 2H), 4.77 (s, 2H), 3.39 (s, 2H), 2.84-2.93 (m, 2H), 2.63-2.70 (m, 2H), 2.61 (br t, J=7.3 Hz, 2H), 2.23 (br t, J=7.6 Hz, 2H), 1.74-1.84 (m, 2H). Calculated for $C_{22}H_{22}F_2O_3$: 395.2 (M+23); Measured: 395.1.

Example 156: Compound #322

3-[4-[(2-benzylcyclopenten-1-yl)methoxy]phenyl]Propanoic Acid

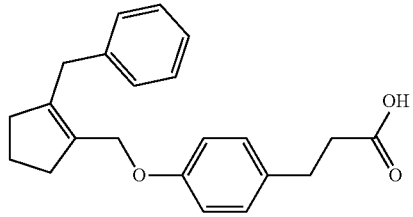 [SMILES: O=C(O)CCc1ccc(OCC2=C(Cc3ccccc3)CCC2)cc1]

¹H NMR (CHLOROFORM-d) δ: 7.62-7.62 (m, 1H), 7.24-7.30 (m, 2H), 7.16-7.22 (m, 1H), 7.10-7.16 (m, 4H), 6.85-6.91 (m, 2H), 4.64 (s, 2H), 3.49 (s, 2H), 2.87-2.94 (m, 2H), 2.62-2.69 (m, 2H), 2.54 (br t, J=7.3 Hz, 2H), 2.29 (br t, J=6.8 Hz, 2H), 1.81 (quin, J=7.5 Hz, 2H). Calculated for $C_{22}H_{24}O_3$: 359.2 (M+23); Measured: 359.1.

Example 157: Compound #314

3-[4-[(2-benzylcyclopenten-1-yl)methoxy]-5-fluoro-2-methyl-phenyl]Propanoic Acid

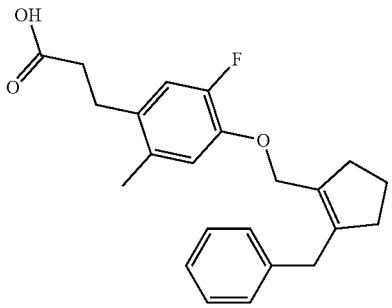 [SMILES: Cc1cc(OCC2=C(Cc3ccccc3)CCC2)c(F)cc1CCC(=O)O]

¹H NMR (CHLOROFORM-d) δ: 7.22-7.30 (m, 2H), 7.15-7.22 (m, 1H), 7.12 (d, J=7.1 Hz, 2H), 6.88 (d, J=12.1 Hz, 1H), 6.80 (d, J=8.6 Hz, 1H), 4.70 (s, 2H), 3.48 (s, 2H), 2.81-2.91 (m, 2H), 2.51-2.65 (m, 4H), 2.27 (br d, J=8.1 Hz, 2H), 2.24 (s, 3H), 1.81 (quin, J=7.6 Hz, 2H). Calculated for $C_{23}H_{25}FO_3$: 391.2 (M+23); Measured: 391.0.

Example 158: Compound #315

3-[4-[(2-benzylcyclopenten-1-yl)methoxy]-3-methyl-phenyl]Propanoic Acid

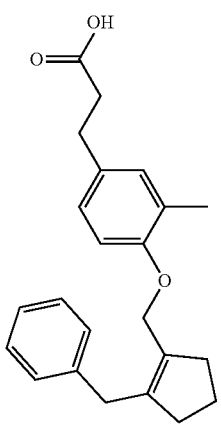 [SMILES: Cc1cc(CCC(=O)O)ccc1OCC1=C(Cc2ccccc2)CCC1]

¹H NMR (CHLOROFORM-d) δ: 7.23-7.30 (m, 2H), 7.11-7.22 (m, 3H), 6.93-7.02 (m, 2H), 6.79 (d, J=8.1 Hz, 1H), 4.64 (s, 2H), 3.50 (s, 2H), 2.83-2.92 (m, 2H), 2.62-2.69 (m, 2H), 2.56 (br t, J=7.3 Hz, 2H), 2.29 (br t, J=7.3 Hz, 2H), 2.22 (s, 3H), 1.75-1.87 (m, 2H). Calculated for $C_{23}H_{26}O_3$: 373.2 (M+23); Measured: 373.2.

Example 159: Compound #345

3-[4-[[2-(p-tolylmethyl)cyclopenten-1-yl]methoxy]-2-(trifluoromethyl)phenyl]Propanoic Acid

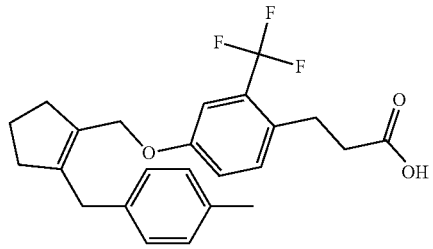 [SMILES: Cc1ccc(CC2=C(COc3ccc(CCC(=O)O)c(C(F)(F)F)c3)CCC2)cc1]

¹H NMR (CHLOROFORM-d) δ: 7.22-7.29 (m, 1H), 7.20 (d, J=2.5 Hz, 1H), 7.06-7.12 (m, 2H), 6.98-7.06 (m, 3H), 4.65 (s, 2H), 3.45 (s, 2H), 3.07 (br t, J=7.8 Hz, 2H), 2.66 (br t, J=7.6 Hz, 2H), 2.52 (br t, J=7.1 Hz, 2H), 2.32 (s, 5H), 1.81 (quin, J=7.5 Hz, 2H). Calculated for $C_{24}H_{25}F_3O_3$: 441.2 (M+23); Measured: 441.1.

Example 160: Compound #348

3-[2-chloro-4-[[2-(p-tolylmethyl)cyclopenten-1-yl]methoxy]phenyl]Propanoic Acid

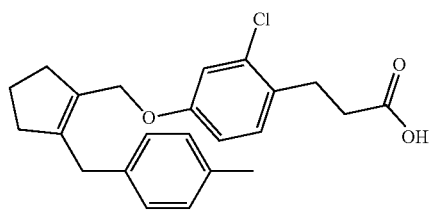 [SMILES: Cc1ccc(CC2=C(COc3ccc(CCC(=O)O)c(Cl)c3)CCC2)cc1]

¹H NMR (CHLOROFORM-d) δ: 7.15 (d, J=8.6 Hz, 1H), 7.06-7.11 (m, 2H), 7.00-7.05 (m, 2H), 6.96 (d, J=2.5 Hz, 1H), 6.79 (dd, J=8.3, 2.8 Hz, 1H), 4.61 (s, 2H), 3.45 (s, 2H), 3.00 (t, J=7.6 Hz, 2H), 2.68 (br t, J=7.6 Hz, 2H), 2.51 (br t, J=7.3 Hz, 2H), 2.25-2.35 (m, 5H), 1.73-1.86 (m, 2H). Calculated for $C_{23}H_{25}ClO_3$: 407.1 (M+23); Measured: 407.1.

Example 161: Compound #346

3-[4-[[2-(p-tolylmethyl)cyclopenten-1-yl]methoxy]phenyl]Propanoic Acid

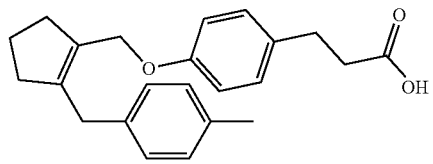 [SMILES: Cc1ccc(CC2=C(COc3ccc(CCC(=O)O)cc3)CCC2)cc1]

¹H NMR (CHLOROFORM-d) δ: 7.05-7.16 (m, 4H), 6.99-7.05 (m, 2H), 6.88 (br d, J=8.6 Hz, 2H), 4.63 (s, 2H), 3.45 (s, 2H), 2.85-2.95 (m, 2H), 2.66 (br t, J=7.3 Hz, 2H), 2.52 (br d, J=6.6 Hz, 2H), 2.23-2.34 (m, 5H), 1.80 (quin, J=7.5 Hz, 2H). Calculated for $C_{23}H_{26}O_3$: 373.2 (M+23); Measured: 373.2.

Example 162: Compound #347

3-[5-fluoro-2-methyl-4-[[2-(p-tolylmethyl)cyclopenten-1-yl]methoxy]phenyl]Propanoic Acid

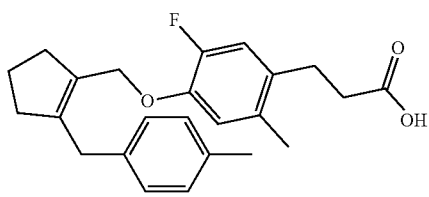 [SMILES: Cc1ccc(CC2=C(COc3cc(C)c(CCC(=O)O)cc3F)CCC2)cc1]

¹H NMR (CHLOROFORM-d) δ: 7.05-7.10 (m, 2H), 6.98-7.04 (m, 2H), 6.88 (d, J=12.1 Hz, 1H), 6.80 (d, J=8.6 Hz, 1H), 4.69 (s, 2H), 3.44 (s, 2H), 2.81-2.90 (m, 2H), 2.58 (dt, J=22.7, 7.6 Hz, 4H), 2.28 (d, J=28.8 Hz, 7H), 1.75-1.85 (m, 2H). Calculated for $C_{24}H_{27}FO_3$: 405.2 (M+23); Measured: 405.1.

Example 163: Compound #34

3-[4-[[2-(4-chlorophenyl)cyclopenten-1-yl]methoxy]-3-fluoro-phenyl]-2-methyl-Propanoic Acid

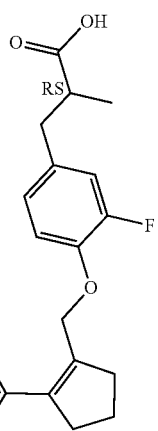

¹H NMR (CHLOROFORM-d) δ: 7.28-7.34 (m, 2H), 7.13-7.21 (m, 2H), 6.91 (dd, J=12.1, 2.0 Hz, 1H), 6.76-6.82 (m, 1H), 6.68-6.76 (m, 1H), 4.64 (s, 2H), 2.97 (dd, J=13.6, 6.6 Hz, 1H), 2.78 (br t, J=7.3 Hz, 2H), 2.65-2.74 (m, 3H), 2.55-2.64 (m, 1H), 1.93-2.04 (m, 2H), 1.17 (d, J=6.6 Hz, 3H). Calculated for $C_{22}H_{22}ClFO_3$: 411.1 (M+23); Measured: 411.1.

Example 164: Compound #351

3-[4-[(2-cyclopropylcyclopenten-1-yl)methoxy]-2-(trifluoromethyl)phenyl]Propanoic Acid

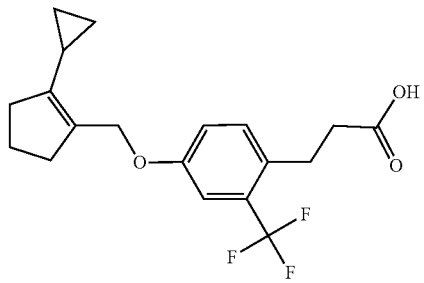 [SMILES: O=C(O)CCc1ccc(OCC2=C(C3CC3)CCC2)cc1C(F)(F)F]

¹H NMR (CHLOROFORM-d) δ: 7.18-7.30 (m, 2H), 7.02-7.08 (m, 1H), 4.70 (s, 2H), 3.07 (br d, J=7.6 Hz, 2H), 2.67 (br s, 2H), 2.48 (br t, J=7.3 Hz, 2H), 2.02-2.13 (m, 2H), 1.67-1.85 (m, 3H), 0.66-0.73 (m, 2H), 0.56-0.64 (m, 2H). Calculated for $C_{19}H_{21}F_3O_3$: 377.1 (M+23); Measured: 377.1.

Example 165: Compound #354

3-[4-[[2-(cyclohexen-1-yl)cyclopenten-1-yl]methoxy]-2-(trifluoromethyl)phenyl]Propanoic Acid

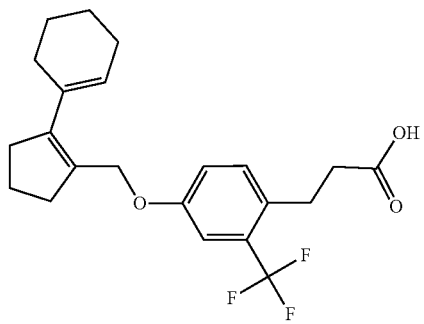 [SMILES: O=C(O)CCc1ccc(OCC2=C(C3=CCCCC3)CCC2)cc1C(F)(F)F]

¹H NMR (CHLOROFORM-d) δ: 7.22 (br s, 1H), 7.11 (d, J=2.0 Hz, 1H), 6.97 (br s, 1H), 5.52 (br s, 1H), 4.66 (s, 2H), 3.06 (br s, 2H), 2.75 (br s, 2H), 2.49 (t, J=7.6 Hz, 4H), 2.04-2.15 (m, 4H), 1.82 (quin, J=7.6 Hz, 2H), 1.56-1.72 (m, 4H). Calculated for $C_{22}H_{25}F_3O_3$: 417.2 (M+23); Measured: 417.1.

Example 166: Compound #355

3-[2-chloro-4-[[2-(cyclohexen-1-yl)cyclopenten-1-yl]methoxy]phenyl]Propanoic Acid

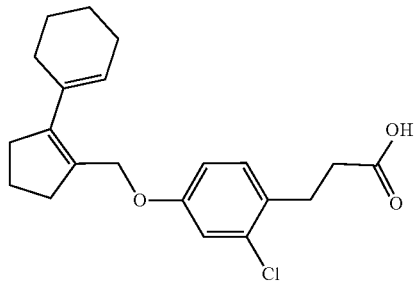 [SMILES: O=C(O)CCc1ccc(OCC2=C(C3=CCCCC3)CCC2)cc1Cl]

¹H NMR (CHLOROFORM-d) δ: 7.11 (br s, 1H), 6.82-6.87 (m, 1H), 6.85 (d, J=2.0 Hz, 1H), 6.72 (br d, J=6.1 Hz,

1H), 5.51 (br s, 1H), 4.61 (s, 2H), 2.99 (br s, 2H), 2.75 (br s, 2H), 2.48 (t, J=7.6 Hz, 4H), 2.05-2.17 (m, 4H), 1.82 (dt, J=14.8, 7.5 Hz, 2H), 1.55-1.73 (m, 4H). Calculated for $C_{21}H_{26}ClO_3$: 383.1 (M+23); Measured: 383.1.

Example 167: Compound #352

3-[4-[[2-(cyclohexen-1-yl)cyclopenten-1-yl]methoxy]-5-fluoro-2-methyl-phenyl]Propanoic Acid

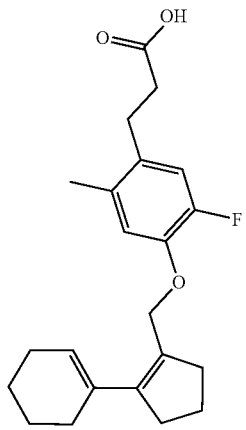 [SMILES: Cc1cc(OCC2=C(C3=CCCCC3)CCC2)c(F)cc1CCC(=O)O]

$^1$H NMR (CHLOROFORM-d) δ: 6.86 (br d, J=10.6 Hz, 1H), 6.67 (d, J=8.6 Hz, 1H), 5.51 (br s, 1H), 4.70 (s, 2H), 2.86 (br s, 2H), 2.40-2.77 (m, 6H), 2.23 (s, 3H), 2.03-2.16 (m, 4H), 1.81 (dt, J=15.2, 7.6 Hz, 2H), 1.54-1.74 (m, 4H). Calculated for $C_{22}H_{27}FO_3$: 381.2 (M+23); Measured: 381.1.

Example 168: Compound #373

3-[4-[(2-cyclopropylcyclopenten-1-yl)methoxy]-5-fluoro-2-methyl-phenyl]Propanoic Acid

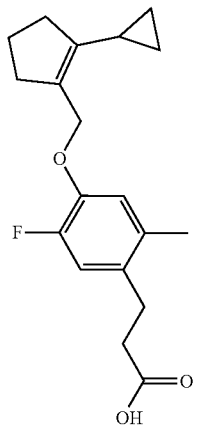 [SMILES: Cc1cc(OCC2=C(C3CC3)CCC2)c(F)cc1CCC(=O)O]

$^1$H NMR (CHLOROFORM-d) δ: 6.78-6.92 (m, 2H), 4.73 (s, 2H), 2.80-2.92 (m, 2H), 2.61 (br s, 2H), 2.50 (br t, J=7.3 Hz, 2H), 2.25 (s, 3H), 2.00-2.12 (m, 2H), 1.67-1.84 (m, 3H), 0.63-0.74 (m, 2H), 0.54-0.63 (m, 2H). Calculated for $C_{19}H_{23}FO_3$: 341.2 (M+23); Measured: 341.1.

Example 169: Compound #4

3-[4-[[2-(4-fluorophenyl)cyclopenten-1-yl]methoxy]-2,3-dimethyl-phenyl]Propanoic Acid

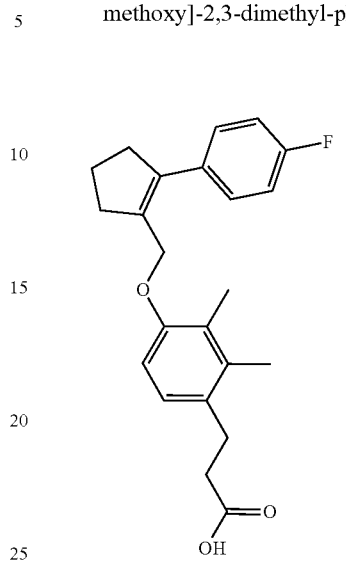

$^1$H NMR (300 MHz, CDCl$_3$) δ: 7.25-7.32 (m, 2H), 7.04-7.11 (m, 2H), 6.87 (d, J=8.4 Hz, 1H), 6.51 (d, J=8.4 Hz, 1H), 4.60 (s, 2H), 2.83-2.90 (m, 4H), 2.68-2.73 (m, 2H), 2.45-2.51 (m, 2H), 2.22 (s, 3H), 2.16 (s, 3H), 1.94-2.05 (m, 2H). Mass spectrum (ESI, m/z): Calculated for $C_{23}H_{25}FO_3$, 367.2 [M–H], Measured: 367.2.

Compound 170: Compound #47

3-[4-[[2-(4-chlorophenyl)cyclopenten-1-yl]methoxy]-2-fluoro-phenyl]Propanoic Acid

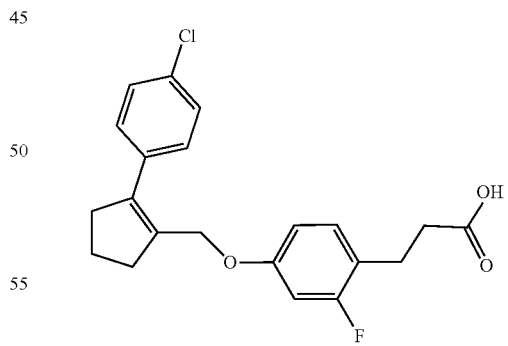

$^1$H NMR (400 MHz, CDCl$_3$) δ: 7.34 (d, J=8.4 Hz, 2H), 7.19 (d, J=8.4 Hz, 2H), 7.09 (t, J=8.4 Hz, 1H), 6.53-6.59 (m, 2H), 4.59 (s, 2H), 2.92 (t, J=7.6 Hz, 2H), 2.79-2.81 (m, 2H), 2.65-2.72 (m, 4H), 1.98-2.05 (m, 2H). Mass spectrum (ESI, m/z): Calculated for $C_{21}H_{20}ClFO_3$, 373.1 [M–H], Measured: 373.1.

Example 171: Compound #50

3-[2,3-dimethyl-4-[[2-(4-methylsulfanylphenyl)cyclopenten-1-yl]methoxy]phenyl]Propanoic Acid

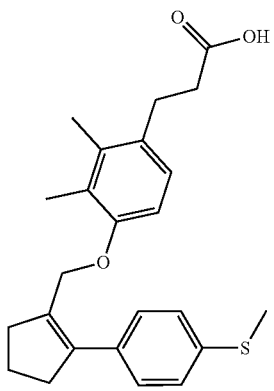 [SMILES: CSc1ccc(C2=C(COc3ccc(CCC(=O)O)c(C)c3C)CCC2)cc1]

$^1$H NMR (300 MHz, CDCl$_3$) δ: 7.17-7.24 (m, 4H), 6.90 (d, J=8.4 Hz, 2H), 6.54 (d, J=8.4 Hz, 2H), 4.61 (s, 2H), 2.90-2.95 (m, 2H), 2.73-2.82 (m, 2H), 2.71-2.69 (m, 2H), 2.61-2.56 (m, 2H), 2.56 (s, 1H), 2.19-2.22 (m, 6H), 1.97-2.07 (m, 2H). Mass spectrum (ESI, m/z): Calculated for C$_{24}$H$_{23}$O$_3$S, 395.2 [M–H], Measured: 395.2

Example 172: Compound #51

3-[4-[[2-(4-acetamidophenyl)cyclopenten-1-yl]methoxy]-2,3-dimethyl-phenyl]Propanoic Acid

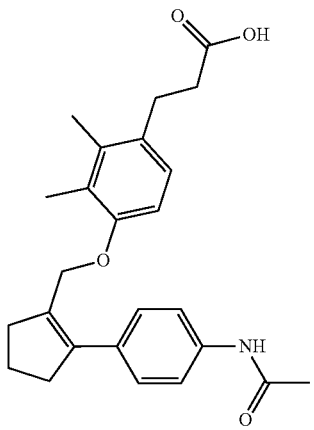 [SMILES: CC(=O)Nc1ccc(C2=C(COc3ccc(CCC(=O)O)c(C)c3C)CCC2)cc1]

$^1$H NMR (300 MHz, CDCl$_3$) δ: 7.44 (d, J=8.1 Hz, 2H), 7.19 (d, J=8.4 Hz, 2H), 6.90 (d, J=8.7 Hz, 1H), 6.54 (d, J=8.7 Hz, 1H), 4.61 (s, 2H), 2.93 (t, J=8.4 Hz, 2H), 2.70-2.79 (m, 4H), 2.58 (t, J=8.4 Hz, 2H), 2.18-2.22 (m, 9H), 1.98 (t, J=7.5 Hz, 2H). Mass spectrum (ESI, m/z): Calculated for C$_{25}$H$_{29}$NO$_4$, 406.2 [M–H], found 406.2.

Example 173: Compound #55

3-[4-[[2-(4-isopropylphenyl)cyclopenten-1-yl]methoxy]-2,3-dimethyl-phenyl]Propanoic Acid

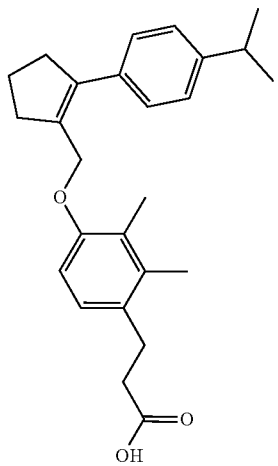 [SMILES: Cc1c(CCC(=O)O)ccc(OCC2=C(c3ccc(C(C)C)cc3)CCC2)c1C]

$^1$H NMR (300 MHz, CDCl$_3$) δ: 7.19 (s, 4H), 6.91 (d, J=8.1 Hz, 1H), 6.57 (d, J=8.4 Hz, 1H), 4.63 (s, 2H), 2.88-2.95 (m, 3H), 2.73-2.87 (m, 2H), 2.61-2.73 (m, 2H), 2.58 (t, J=7.5 Hz, 2H), 2.22 (s, 3H), 2.19 (s, 3H), 1.93-2.03 (m, 2H), 1.25 (d, J=6.9 Hz, 6H). Mass spectrum (ESI, m/z): Calculated for C$_{26}$H$_{32}$O$_3$, 391.2 [M–H], Measured: 391.2.

Example 174: Compound #56

3-[4-[[2-(4-bromophenyl)cyclopenten-1-yl]methoxy]-2,3-dimethyl-phenyl]Propanoic Acid

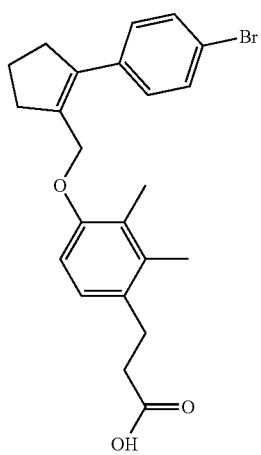 [SMILES: Cc1c(CCC(=O)O)ccc(OCC2=C(c3ccc(Br)cc3)CCC2)c1C]

$^1$H NMR (300 MHz, CDCl$_3$) δ: 7.45 (d, J=8.4 Hz, 2H), 6.92 (d, J=8.4 Hz, 2H), 6.91 (d, J=8.4 Hz, 1H), 6.54 (d, J=8.4 Hz, 1H), 4.58 (s, 2H), 2.93 (t, J=7.5 Hz, 2H), 2.79-2.86 (m, 4H), 2.58 (t, J=7.5 Hz, 2H), 2.18-2.22 (m, 6H), 1.94-2.05 (m, 2H). Mass spectrum (ESI, m/z): Calculated for C$_{23}$H$_{26}$BrO$_3$, 429.1 [M+H], Measured: 429.1.

Example 175: Compound #57

3-[4-[[2-(4-iodophenyl)cyclopenten-1-yl]methoxy]-2,3-dimethyl-phenyl]Propanoic Acid

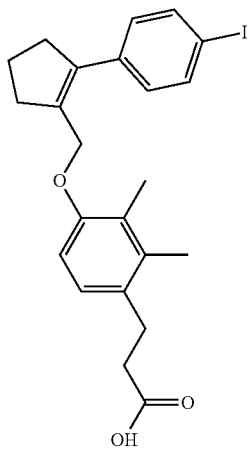 [SMILES: Cc1c(CCC(=O)O)ccc(OCC2=C(c3ccc(I)cc3)CCC2)c1C]

$^1$H NMR (300 MHz, CDCl$_3$) δ: 7.65 (d, J=8.4 Hz, 2H), 7.00 (d, J=8.4 Hz, 2H), 6.91 (d, J=8.4 Hz, 1H), 6.54 (d, J=8.4 Hz, 1H), 4.57 (s, 2H), 2.93 (t, J=7.5 Hz, 2H), 2.79-2.86 (m, 4H), 2.59 (t, J=7.5 Hz, 2H), 2.22 (s, 3H), 2.18 (s, 3H), 1.94-2.05 (m, 2H). Mass spectrum (ESI, m/z): Calculated for C$_{23}$H$_{25}$IO$_3$, 475.1 [M−H], Measured: 475.1.

Example 176: Compound #58

3-[4-[[2-(3-chlorophenyl)cyclopenten-1-yl]methoxy]-2,3-dimethyl-phenyl]Propanoic Acid

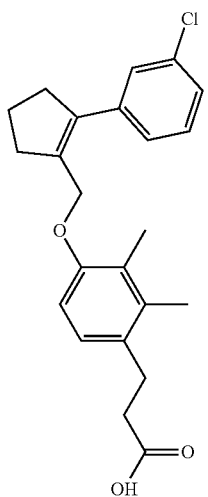 [SMILES: Cc1c(CCC(=O)O)ccc(OCC2=C(c3cccc(Cl)c3)CCC2)c1C]

$^1$H NMR (300 MHz, CDCl$_3$): 7.20-7.29 (m, 3H), 7.12 (d, J=6.6 Hz, 1H), 6.91 (d, J=8.4 Hz, 1H), 6.55 (d, J=8.4 Hz, 1H), 4.60 (s, 2H), 2.89-2.94 (m, 2H), 2.62-2.82 (m, 4H), 2.55-2.60 (m, 2H), 2.22 (s, 3H), 2.18 (s, 3H), 1.94-2.04 (m, 2H). Mass spectrum (ESI, m/z): Calculated for C$_{23}$H$_{25}$ClO$_3$, 383.1 [M−H], Measured: 383.1.

Example 177: Compound #60

3-[4-[[2-(4-chlorophenyl)cyclopenten-1-yl]methoxy]-3,5-difluoro-phenyl]Propanoic Acid

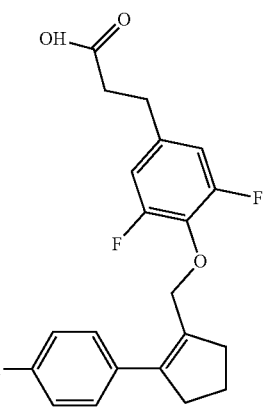

$^1$H NMR (300 MHz, CDCl$_3$) δ: 7.29 (d, J=8.4 Hz, 2H), 7.18 (d, J=8.4 Hz, 2H), 6.73 (d, J=8.7 Hz, 2H), 4.64 (s, 2H), 2.88 (t, J=7.5 Hz, 2H), 2.73-2.78 (m, 4H), 2.65 (t, J=7.5 Hz, 2H), 1.94-2.04 (m, 2H). Mass spectrum (ESI, m/z): Calculated for C$_{21}$H$_{19}$ClF$_2$O$_3$, 391.1 [M−H], Measured: 391.1.

Example 178: Compound #65

3-[4-[[2-(3-fluoro-5-methoxy-phenyl)cyclopenten-1-yl]methoxy]-2,3-dimethyl-phenyl]Propanoic Acid

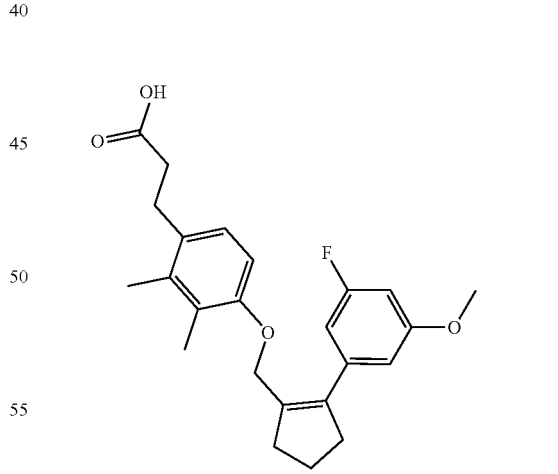

$^1$H NMR (400 MHz, CD$_3$OD) δ: 6.91 (d, J=8.4 Hz, 1H), 6.55-6.64 (m, 4H), 4.63 (s, 2H), 3.76 (s, 3H), 2.87 (t, J=8.4 Hz, 2H), 2.81 (t, J=7.2 Hz, 2H), 2.73 (t, J=7.2 Hz, 2H), 2.49 (t, J=8.4 Hz, 2H), 2.22 (s, 3H), 2.16 (s, 3H), 1.97-2.05 (m, 2H). Mass spectrum (ESI, m/z): Calculated for C$_{24}$H$_{27}$FO$_4$, 397.2 [M−H], Measured: 397.2.

Example 179: Compound #66

3-[4-[[2-(3,4-dichlorophenyl)cyclopenten-1-yl]methoxy]-2,3-dimethyl-phenyl]Propanoic Acid

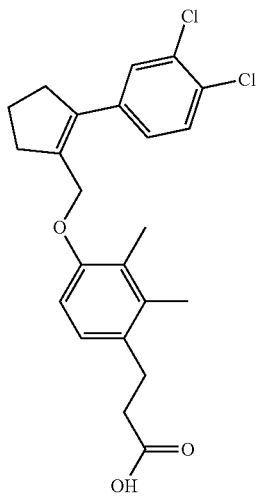 [SMILES: Cc1c(CCC(=O)O)ccc(OCC2=C(c3ccc(Cl)c(Cl)c3)CCC2)c1C]

$^{1}$H NMR (300 MHz, CDCl$_3$) δ: 7.36 (d, J=7.8 Hz, 2H), 7.06 (d, J=6.3 Hz, 1H), 6.91 (d, J=8.4 Hz, 1H), 6.54 (d, J=8.1 Hz, 1H), 4.56 (s, 2H), 2.91 (t, J=7.2 Hz, 2H), 2.70-2.77 (m, 4H), 2.56 (t, J=7.5 Hz, 2H), 2.20 (s, 3H), 2.15 (s, 3H), 1.92-2.02 (m, 2H). Mass spectrum (ESI, m/z): Calculated for C$_{23}$H$_{24}$Cl$_2$O$_3$, 417.1 [M–H], Measured: 417.1

Example 180: Compound #74

3-[2,3-dimethyl-4-[[2-(4-methylsulfonylphenyl)cyclopenten-1-yl]methoxy]phenyl]Propanoic Acid

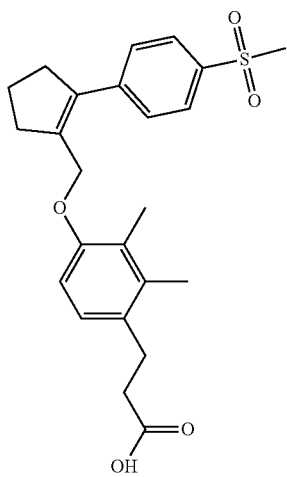 [SMILES: Cc1c(CCC(=O)O)ccc(OCC2=C(c3ccc(S(C)(=O)=O)cc3)CCC2)c1C]

$^{1}$H NMR (300 MHz, CDCl$_3$) δ: 7.89 (d, J=8.7 Hz, 2H), 7.42 (d, J=8.4 Hz, 2H), 6.92 (d, J=8.4 Hz, 1H), 6.55 (d, J=8.7 Hz, 1H), 4.59 (s, 2H), 3.06 (s, 3H), 2.75-2.96 (m, 6H), 2.52-2.62 (m, 2H), 2.22 (s, 3H), 2.17 (s, 3H), 1.99-2.09 (m, 2H). Mass spectrum (ESI, m/z): Calculated for C$_{24}$H$_{28}$O$_5$S, 427.2 [M–H], Measured: 427.2.

Example 181: Compound #75

3-[2,3-dimethyl-4-[[2-[4-(trifluoromethyl)phenyl]cyclopenten-1-yl]methoxy]phenyl]Propanoic Acid

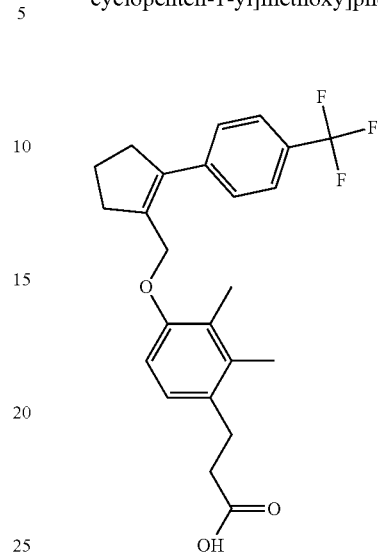

$^{1}$H NMR (300 MHz, CDCl$_3$) δ: 7.58 (d, J=8.1 Hz, 2H), 7.32 (d, J=8.7 Hz, 2H), 6.92 (d, J=8.1 Hz, 1H), 6.54 (d, J=8.4 Hz, 1H), 4.59 (s, 2H), 2.93-2.95 (m, 2H), 2.88-2.90 (m, 2H), 2.73-2.81 (m, 2H), 2.58-2.61 (m, 2H), 2.22 (s, 3H), 2.17 (s, 3H), 1.97-2.07 (m, 2H). Mass spectrum (ESI, m/z): Calculated for C$_{24}$H$_{25}$F$_3$O$_3$, 417.2 [M–H], Measured: 417.2.

Example 182: Compound #76

3-[4-[[2-(2-chlorophenyl)cyclopenten-1-yl]methoxy]-2,3-dimethyl-phenyl]Propanoic Acid

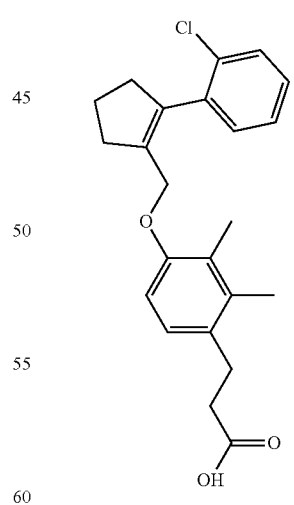

$^{1}$H NMR (300 MHz, CDCl$_3$): 7.39 (d, J=7.2 Hz, 1H), 7.11-7.25 (m, 3H), 6.86 (d, J=8.4 Hz, 1H), 6.49 (d, J=8.4 Hz, 1H), 4.39 (s, 2H), 2.87-2.92 (m, 2H), 2.67-2.78 (m, 4H), 2.53-2.58 (m, 2H), 2.19 (s, 3H), 2.13 (s, 3H), 1.98-2.08 (m, 2H). Mass spectrum (ESI, m/z): Calculated for C$_{23}$H$_{25}$ClO$_3$, 383.2 [M–H], Measured: 383.2.

Example 183: Compound #77

3-[2,3-dimethyl-4-[[2-(2-thienyl)cyclopenten-1-yl]methoxy]phenyl]Propanoic Acid

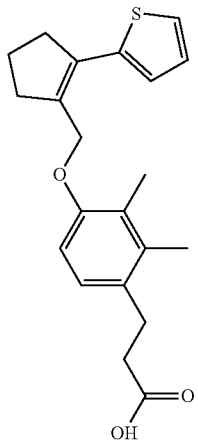 [SMILES: Cc1c(CCC(=O)O)ccc(OCC2=C(c3cccs3)CCC2)c1C]

$^1$H NMR (300 MHz, CDCl$_3$) δ: 7.26 (s, 1H), 7.03-7.05 (m, 1H), 6.96-7.02 (m, 1H), 6.91-6.93 (m, 1H), 6.66 (d, J=8.7 Hz, 1H), 4.86 (s, 2H), 2.87-2.96 (m, 4H), 2.73-2.84 (m, 2H), 2.57-2.62 (m, 2H), 2.23 (s, 3H), 2.19 (s, 3H), 1.93-2.01 (m, 2H). Mass spectrum (ESI, m/z): Calculated for C$_{21}$H$_{24}$O$_3$S, 355.1 [M–H], Measured: 355.2.

Example 184: Compound #79

3-[2,3-dimethyl-4-[(2-thiazol-2-ylcyclopenten-1-yl)methoxy]phenyl]Propanoic Acid

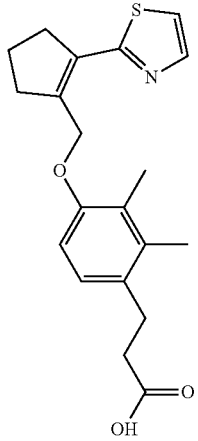 [SMILES: Cc1c(CCC(=O)O)ccc(OCC2=C(c3nccs3)CCC2)c1C]

$^1$H NMR (300 MHz, CDCl$_3$) δ: 7.90 (s, 1H), 7.29 (s, 1H), 6.96 (d, J=8.4 Hz, 1H), 6.75 (d, J=8.0 Hz, 1H), 5.23 (s, 2H), 2.96 (t, J=6.8 Hz, 4H), 2.81-2.85 (m, 2H), 2.61 (t, J=8.4 Hz, 2H), 2.25 (s, 3H), 2.22 (s, 3H), 2.03-2.08 (m, 2H). Mass spectrum (ESI, m/z): Calculated for C$_{20}$H$_{23}$NO$_3$S, 356.1 [M–H], Measured: 356.1.

Example 185: Compound #88

3-[2,3-dimethyl-4-[(2-thiazol-5-ylcyclopenten-1-yl)methoxy]phenyl]Propanoic Acid

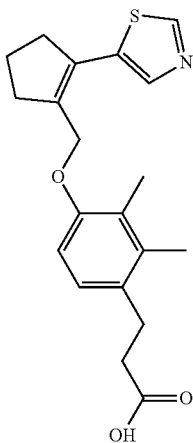 [SMILES: Cc1c(CCC(=O)O)ccc(OCC2=C(c3cncs3)CCC2)c1C]

$^1$H NMR (300 MHz, CDCl$_3$) δ: 8.76 (s, 1H), 7.74 (s, 1H), 6.93 (d, J=8.4 Hz, 1H), 6.62 (d, J=8.4 Hz, 1H), 4.75 (s, 2H), 2.83-2.95 (m, 4H), 2.73-2.78 (m, 2H), 2.57 (t, J=7.5 Hz, 2H), 2.21 (s, 3H), 2.15 (s, 3H), 1.96-2.06 (m, 2H). Mass spectrum (ESI, m/z): Calculated for C$_{20}$H$_{23}$NO$_3$S, 358.1 [M+H], Measured: 358.2.

Example 186: Compound #89

3-[4-[[2-(4-chlorophenyl)cyclopenten-1-yl]methoxy]-2-(1,1,2,2,2-pentafluoroethyl)phenyl]Propanoic Acid

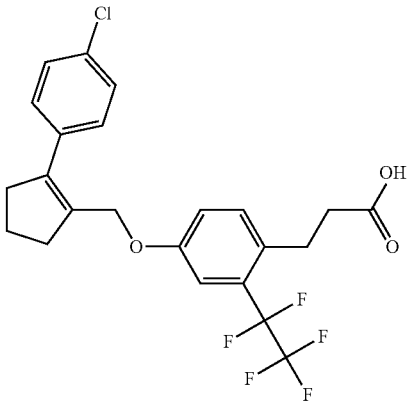 [SMILES: O=C(O)CCc1ccc(OCC2=C(c3ccc(Cl)cc3)CCC2)cc1C(F)(F)C(F)(F)F]

$^1$H NMR (300 MHz, CD$_3$OD) δ: 7.22-7.37 (m, 5H), 6.97 (d, J=7.8 Hz, 1H), 6.91 (s, 1H), 4.71 (s, 2H), 2.98 (t, J=7.8 Hz, 2H), 2.76 (t, J=7.8 Hz, 2H), 2.62 (t, J=8.4 Hz, 2H), 2.64-2.50 (m, 2H), 1.99-2.04 (m, 2H). Mass spectrum (ESI, m/z): Calculated for C$_{23}$H$_{20}$ClF$_5$O$_3$, 473.1 [M–H], Measured: 473.1.

Example 187: Compound #91

3-[4-[[2-(4-chlorophenyl)cyclopenten-1-yl]methoxy]-5-fluoro-2-(trifluoromethyl)phenyl]Propanoic Acid

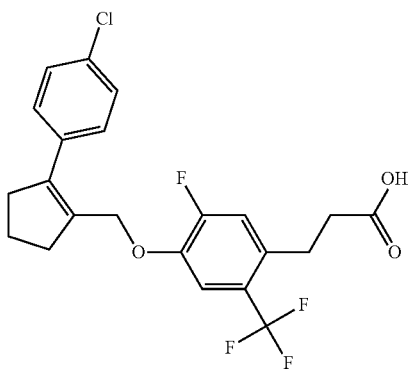 [SMILES: O=C(O)CCc1cc(F)c(OCC2=C(c3ccc(Cl)cc3)CCC2)cc1C(F)(F)F]

$^1$H NMR (300 MHz, CD$_3$OD) δ: 7.25-7.37 (m, 6H), 4.76 (s, 2H), 3.09 (t, J=8.1 Hz, 2H), 2.80-2.82 (m, 4H), 2.47-2.53 (m, 2H), 2.01-2.06 (m, 2H). Mass spectrum (ESI, m/z): Calculated for C$_{22}$H$_{19}$ClF$_4$O$_3$, 441.1 [M–H], Measured: 441.2.

Example 188: Compound #96

3-[4-[[2-(4-chlorophenyl)cyclopenten-1-yl]methoxy]-2-(trifluoromethoxy)phenyl]Propanoic Acid

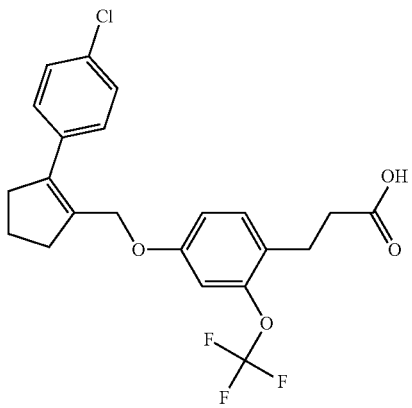 [SMILES: O=C(O)CCc1ccc(OCC2=C(c3ccc(Cl)cc3)CCC2)cc1OC(F)(F)F]

$^1$H NMR (300 MHz, CD$_3$OD) δ: 7.37 (d, J=8.4 Hz, 2H), 7.21-7.27 (m, 3H), 6.68-6.77 (m, 1H), 6.68 (s, 1H), 4.69 (s, 2H), 2.79-2.91 (m, 4H), 2.67 (t, J=7.2 Hz, 2H), 2.54 (t, J=7.5 Hz, 2H), 1.94-2.05 (m, 2H). Mass spectrum (ESI, m/z): Calculated for C$_{22}$H$_{20}$ClF$_3$O$_4$, 439.1 [M–H], Measured: 439.1.

Example 189: Compound #97

3-[4-[[2-(4-chlorophenyl)cyclopenten-1-yl]methoxy]-2-methoxy-phenyl]Propanoic Acid

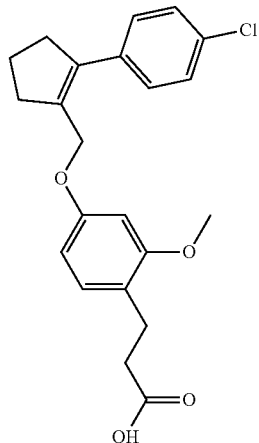 [SMILES: COc1cc(OCC2=C(c3ccc(Cl)cc3)CCC2)ccc1CCC(=O)O]

$^1$H NMR (300 MHz, CD$_3$OD) δ: 7.33 (d, J=8.4 Hz, 2H), 7.21 (d, J=8.4 Hz, 2H), 7.02 (d, J=8.4 Hz, 1H), 6.42 (s, 1H), 6.34 (d, J=8.1 Hz, 1H), 4.61 (s, 2H), 3.76 (s, 3H), 2.61-2.90 (m, 8H), 1.96-2.06 (m, 2H). Mass spectrum (ESI, m/z): Calculated for C$_{22}$H$_{23}$ClO$_4$, 385.1 [M–H], Measured: 385.1.

Example 190: Compound #98

3-[4-[[2-(4-chlorophenyl)cyclopenten-1-yl]methoxy]-5-methyl-2-(trifluoromethyl)phenyl]Propanoic Acid

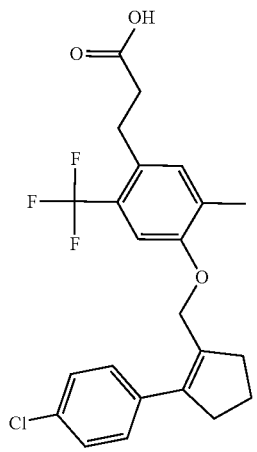 [SMILES: Cc1cc(CCC(=O)O)c(C(F)(F)F)cc1OCC1=C(c2ccc(Cl)cc2)CCC1]

$^1$H NMR (300 MHz, CDCl$_3$) δ: 7.33 (d, J=8.4 Hz, 2H), 7.17 (d, J=8.4 Hz, 2H), 7.09 (s, 1H), 6.85 (s, 1H), 4.64 (s, 2H), 3.02 (t, J=7.8 Hz, 2H), 2.79 (t, J=7.5 Hz, 2H), 2.60-2.69 (m, 4H), 2.23 (s, 3H), 1.94-2.04 (m, 2H). $^{19}$F NMR (300 MHz, CDCl$_3$) δ: −59.24. Mass spectrum (ESI, m/z): Calculated for C$_{23}$H$_{22}$ClF$_3$O$_3$, 437.1 [M–H], Measured: 437.1.

Example 191: Compound #99

3-[2,3-dichloro-4-[[2-(4-chlorophenyl)cyclopenten-1-yl]methoxy]phenyl]Propanoic Acid

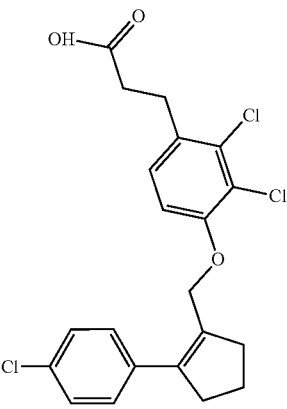 [SMILES: O=C(O)CCc1ccc(OCC2=C(c3ccc(Cl)cc3)CCC2)c(Cl)c1Cl]

$^1$H NMR (300 MHz, CDCl$_3$) δ: 7.40 (d, J=8.7 Hz, 2H), 7.17 (d, J=6.6 Hz, 2H), 7.03 (d, J=8.7 Hz, 1H), 6.60 (d, J=8.4 Hz, 1H), 4.68 (s, 2H), 3.03 (t, J=7.8 Hz, 2H), 2.65-2.81 (m, 6H), 1.94-2.05 (m, 2H). Mass spectrum (ESI, m/z): Calculated for C$_{21}$H$_{19}$C$_{13}$O$_3$, 423.0 [M−H], Measured: 423.0.

Example 192: Compound #101

3-[3,5-dibromo-4-[[2-(4-chlorophenyl)cyclopenten-1-yl]methoxy]-2-(trifluoromethyl)phenyl]Propanoic Acid

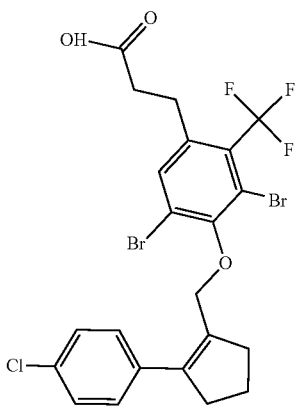 [SMILES: O=C(O)CCc1cc(Br)c(OCC2=C(c3ccc(Cl)cc3)CCC2)c(Br)c1C(F)(F)F]

$^1$H NMR (300 MHz, CD$_3$OD) δ: 7.70 (s, 1H), 7.33 (d, J=8.7 Hz, 2H), 7.28 (d, J=8.7 Hz, 2H), 4.70 (s, 2H), 3.08-3.17 (m, 2H), 2.90-2.99 (m, 2H), 2.80-2.85 (m, 2H), 2.57 (t, J=8.4 Hz, 2H), 2.08-2.03 (m, 2H). Mass spectrum (ESI, m/z): Calculated for C$_{22}$H$_{18}$Br$_2$ClF$_3$O$_3$, 580.9 [M+H], Measured: 581.0.

Example 193: Compound #105

3-[2,3-dimethyl-4-[(2-pyrimidin-2-ylcyclopenten-1-yl)methoxy]phenyl]Propanoic Acid

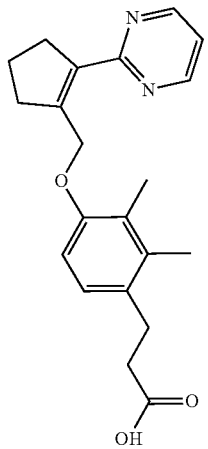 [SMILES: Cc1c(CCC(=O)O)ccc(OCC2=C(c3ncccn3)CCC2)c1C]

$^1$H NMR (300 MHz, CDCl$_3$) δ: 8.78-8.80 (m, 2H), 7.12-7.19 (m, 1H), 6.94 (d, J=8.4 Hz, 1H), 6.73 (d, J=8.4 Hz, 1H), 5.32 (s, 2H), 2.87-3.21 (m, 6H), 2.57-2.63 (m, 2H), 2.24 (s, 3H), 2.21 (s, 3H), 1.98-2.02 (m, 2H). Mass spectrum (ESI, m/z): Calculated for C$_{21}$H$_{24}$N$_2$O$_3$, 351.2 [M−H], Measured: 351.2.

Example 194: Compound #108

3-[2,3-dimethyl-4-[[2-(3-pyridyl)cyclopenten-1-yl]methoxy]phenyl]Propanoic Acid

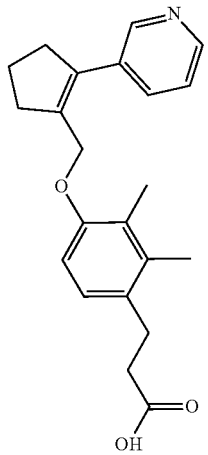 [SMILES: Cc1c(CCC(=O)O)ccc(OCC2=C(c3cccnc3)CCC2)c1C]

$^1$H NMR (300 MHz, CD$_3$OD) δ: 8.43-8.49 (m, 2H), 7.82 (d, J=6.3 Hz, 1H), 7.47 (t, J=6.3 Hz, 1H), 6.87 (d, J=8.4 Hz, 1H), 6.53 (d, J=8.7 Hz, 1H), 4.60 (s, 2H), 2.81-2.86 (m, 4H), 2.76 (t, J=7.5 Hz, 2H), 2.45 (t, J=7.5 Hz, 2H), 2.21 (s, 3H), 2.09 (s, 3H), 1.97-2.02 (m, 2H). Mass spectrum (ESI, m/z): Calculated for C$_{22}$H$_{25}$NO$_3$, 350.2 [M−H], Measured: 350.3.

Example 195: Compound #111

3-[4-[[2-(2-bromophenyl)cyclopenten-1-yl]methoxy]-2,3-dimethyl-phenyl]Propanoic Acid

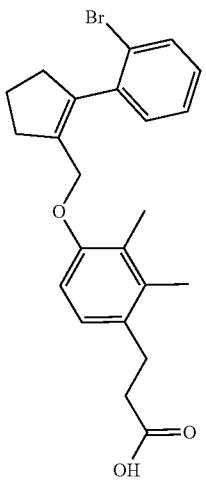 [SMILES: Cc1c(CCC(=O)O)ccc(OCC2=C(c3ccccc3Br)CCC2)c1C]

$^1$H NMR (300 MHz, CDCl$_3$) δ: 7.57 (d, J=7.5 Hz, 1H), 7.25 (s, 1H), 7.11-7.13 (m, 2H), 6.90 (d, J=8.4 Hz, 1H), 6.52 (d, J=8.4 Hz, 1H), 4.39 (s, 2H), 2.92 (t, J=7.5 Hz, 2H), 2.68-2.76 (m, 4H), 2.57 (t, J=7.2 Hz, 2H), 2.21 (s, 3H), 2.14 (s, 3H), 2.02-2.10 (m, 2H). Mass spectrum (ESI, m/z): Calculated for C$_{23}$H$_{25}$BrO$_3$, 427.1 [M−H], Measured: 427.1.

Example 196: Compound #112

3-[4-[[2-(3,5-dichlorophenyl)cyclopenten-1-yl]methoxy]-2,3-dimethyl-phenyl]Propanoic Acid'

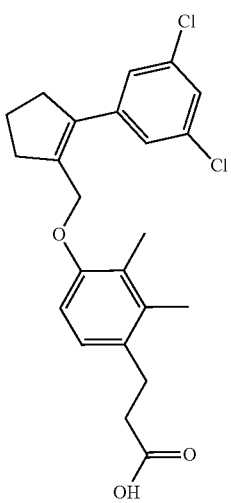 [SMILES: Cc1c(CCC(=O)O)ccc(OCC2=C(c3cc(Cl)cc(Cl)c3)CCC2)c1C]

$^1$H NMR (400 MHz, CDCl$_3$) δ: 7.26 (s, 1H), 7.13 (s, 2H), 7.00 (d, J=8.4 Hz, 1H), 6.58 (d, J=8.4 Hz, 1H), 4.60 (s, 2H), 2.96 (t, J=8.0 Hz, 2H), 2.73-2.80 (m, 4H), 2.61 (t, J=8.0 Hz, 2H), 2.25 (s, 3H), 2.08 (s, 3H), 1.95-2.05 (m, 2H). Mass spectrum (ESI, m/z): Calculated for C$_{23}$H$_{24}$Cl$_2$O$_3$, 417.1 [M−H], Measured: 417.1.

Example 197: Compound #114

3-[4-[[2-[3-(dimethylamino)phenyl]cyclopenten-1-yl]methoxy]-2,3-dimethyl-phenyl]Propanoic Acid

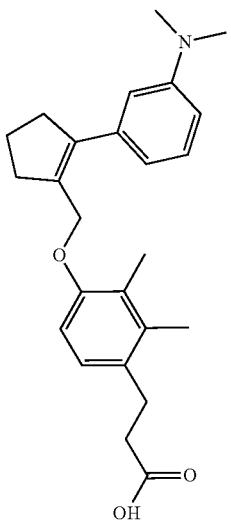 [SMILES: Cc1c(CCC(=O)O)ccc(OCC2=C(c3cccc(N(C)C)c3)CCC2)c1C]

$^1$H NMR (300 MHz, CD$_3$OD) δ: 7.18 (t, J=8.1 Hz, 1H), 6.84 (d, J=8.4 Hz, 1H), 6.68-6.76 (m, 3H), 6.51 (d, J=8.4 Hz, 1H), 4.58 (s, 2H), 2.75-2.86 (m, 10H), 2.67 (t, J=6.9 Hz, 2H), 2.44 (t, J=1.5 Hz, 2H), 2.18 (s, 3H), 2.12 (s, 3H), 1.90-2.00 (m, 2H). Mass spectrum (ESI, m/z): Calculated for C$_{25}$H$_{31}$NO$_3$, 392.2 [M−H], Measured: 392.3.

Example 198: Compound #120

3-[2,3-dimethyl-4-[[2-(4-methylsulfinylphenyl)cyclopenten-1-yl]methoxy]phenyl]Propanoic Acid

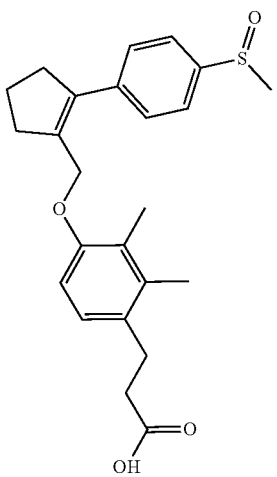 [SMILES: Cc1c(CCC(=O)O)ccc(OCC2=C(c3ccc(S(C)=O)cc3)CCC2)c1C]

$^1$H NMR (300 MHz, CDCl$_3$) δ: 7.59 (d, J=8.4 Hz, 2H), 7.36 (d, J=8.4 Hz, 2H), 6.90 (d, J=8.7 Hz, 1H), 6.54 (d, J=8.7 Hz, 1H), 4.59 (s, 2H), 2.93-2.98 (m, 2H), 2.80-2.90 (m, 4H), 2.75 (s, 3H), 2.55-2.61 (m, 2H), 2.21 (s, 3H), 2.17 (s, 3H), 1.97-2.07 (m, 2H). Mass spectrum (ESI, m/z): Calculated for C$_{24}$H$_{28}$O$_4$S, 411.2 [M−H], Measured: 411.2

Example 199: Compound #122

3-[4-[[2-(4-chlorophenyl)cyclopenten-1-yl]methoxy]-2,3,5,6-tetrafluoro-phenyl]Propanoic Acid

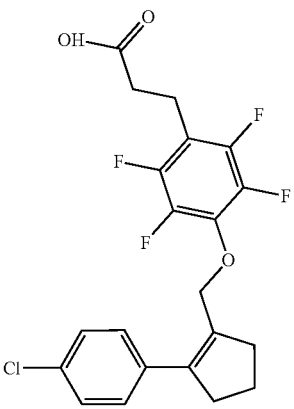 [SMILES: O=C(O)CCc1c(F)c(F)c(OCC2=C(c3ccc(Cl)cc3)CCC2)c(F)c1F]

¹H NMR (400 MHz, CDCl₃) δ: 7.34 (d, J=8.4 Hz, 2H), 7.16 (d, J=8.4 Hz, 2H), 4.80 (s, 2H), 3.00 (t, J=7.2 Hz, 2H), 2.74-2.80 (m, 4H), 2.60 (t, J=7.2 Hz, 2H), 1.99-2.03 (m, 2H). Mass spectrum (ESI, m/z): Calculated for C₂₁H₁₇ClF₄O₃, 427.1 [M−H], Measured: 427.1.

Example 200: Compound #124

3-[4-[[2-(2-fluorophenyl)cyclopenten-1-yl]methoxy]-2,3-dimethyl-phenyl]Propanoic Acid

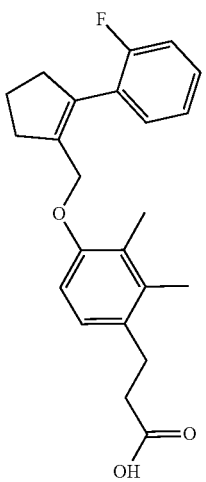 [SMILES: Cc1c(CCC(=O)O)ccc(OCC2=C(c3ccccc3F)CCC2)c1C]

¹H NMR (300 MHz, CDCl₃) δ: 7.16-7.20 (m, 2H), 7.00-7.09 (m, 2H), 6.87 (d, J=8.4 Hz, 1H), 6.51 (d, J=8.4 Hz, 1H), 4.47 (s, 2H), 2.89 (t, J=8.4 Hz, 2H), 2.66-2.76 (m, 4H), 2.54 (t, J=7.2 Hz, 2H), 2.18 (s, 3H), 2.12 (s, 3H), 1.94-2.04 (m, 2H). Mass spectrum (ESI, m/z): Calculated for C₂₃H₂₅FO₃, 367.2 [M−H], Measured: 367.2.

Example 201: Compound #127

4-[4-[[2-(4-chlorophenyl)cyclopenten-1-yl]methoxy]-2,3-dimethyl-phenyl]Butanoic Acid

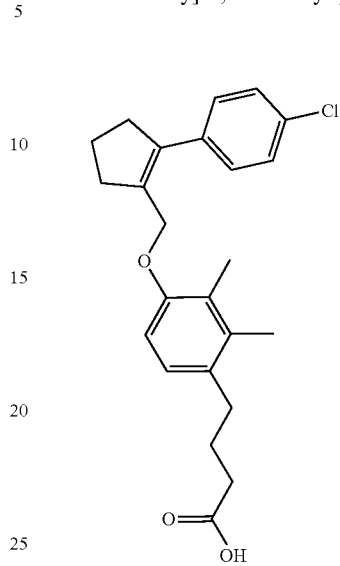

¹H NMR (300 MHz, CD₃OD) δ: 7.31 (d, J=6.6 Hz, 2H), 7.21 (d, J=6.6 Hz, 2H), 6.80 (d, J=5.4 Hz, 1H), 6.47 (d, J=8.1 Hz, 1H), 4.57 (s, 2H), 2.77 (t, J=7.5 Hz, 2H), 2.68 (t, J=7.5 Hz, 2H), 2.56 (t, J=7.5 Hz, 2H), 2.23 (t, J=7.5 Hz, 2H), 2.17 (s, 3H), 2.01 (s, 3H), 1.93-1.98 (m, 2H), 1.73-1.78 (m, 2H). Mass spectrum (ESI, m/z): Calculated for C₂₄H₂₇ClO₃, 397.2 [M−H], Measured: 397.2.

Example 202: Compound #131

3-[4-[[2-(4-chlorophenyl)cyclopenten-1-yl]methoxy]-2-methyl-phenyl]Propanoic Acid

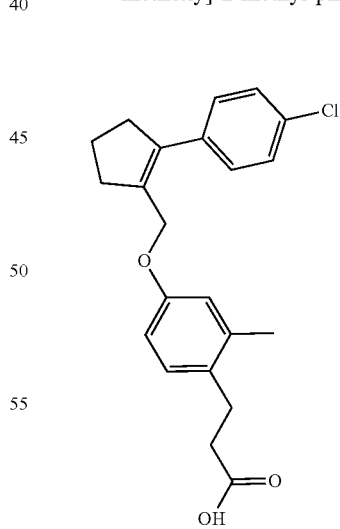

¹H NMR (300 MHz, CDCl₃) δ: 7.30 (d, J=9.0 Hz, 2H), 7.20 (d, J=8.4 Hz, 2H), 7.03 (d, J=8.4 Hz, 1H), 6.61-6.66 (m, 2H), 4.58 (s, 2H), 2.89 (t, J=7.5 Hz, 2H), 2.80 (t, J=7.5 Hz, 2H), 2.70 (t, J=7.2 Hz, 2H), 2.60 (t, J=8.4 Hz, 2H), 2.27 (s, 3H), 1.95-2.05 (m, 2H). Mass spectrum (ESI, m/z): Calculated for C₂₂H₂₃ClO₃, 369.1 [M−H], Measured: 369.1.

Example 203: Compound #132

3-[2,3-dimethyl-4-[[2-(o-tolyl)cyclopenten-1-yl]methoxy]phenyl]Propanoic Acid

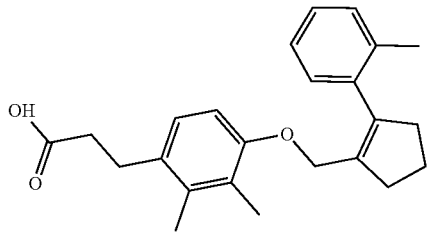 [SMILES: Cc1ccccc1C1=C(COc2ccc(CCC(=O)O)c(C)c2C)CCC1]

$^1$H NMR (300 MHz, CDCl$_3$) δ: 7.12-7.21 (m, 3H), 6.98-7.01 (m, 1H), 6.82 (d, J=8.4 Hz, 1H), 6.40 (d, J=8.4 Hz, 1H), 4.33 (s, 2H), 2.86 (t, J=7.5 Hz, 2H), 2.65-2.70 (m, 4H), 2.46 (t, J=7.5 Hz, 2H), 2.19 (s, 6H), 2.10 (s, 3H), 1.95-2.10 (m, 2H). Mass spectrum (ESI, m/z): Calculated for C$_{24}$H$_{28}$O$_3$, 363.2 [M–H], Measured: 363.2.

Example 204: Compound #133

3-[4-[[2-(2,4-dichlorophenyl)cyclopenten-1-yl]methoxy]-2,3-dimethyl-phenyl]Propanoic Acid

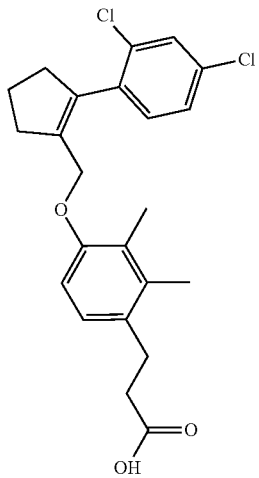 [SMILES: Cc1c(CCC(=O)O)ccc(OCC2=C(c3ccc(Cl)cc3Cl)CCC2)c1C]

$^1$H NMR (300 MHz, CDCl$_3$) δ: 7.46 (s, 1H), 7.27 (d, J=8.4 Hz, 1H), 7.10 (d, J=8.1 Hz, 1H), 6.87 (d, J=8.4 Hz, 1H), 6.44 (d, J=8.4 Hz, 1H), 4.39 (s, 2H), 2.85 (t, J=7.5 Hz, 2H), 2.65-2.75 (m, 4H), 2.38 (t, J=7.5 Hz, 2H), 2.19 (s, 3H), 1.91-2.08 (m, 5H). Mass spectrum (ESI, m/z): Calculated for C$_{23}$H$_{24}$Cl$_2$O$_3$, 417.1 [M–H], Measured: 417.1.

Example 205: Compound #136

3-[4-[[2-(4-chlorophenyl)cyclopenten-1-yl]methoxy]-2-phenyl-phenyl]Propanoic Acid

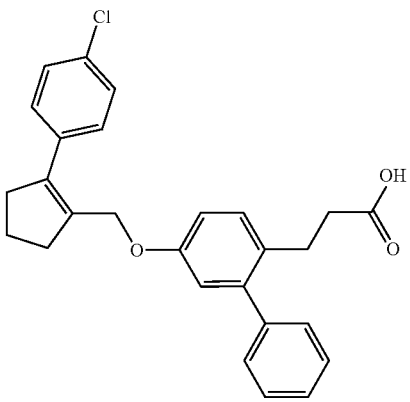 [SMILES: O=C(O)CCc1ccc(OCC2=C(c3ccc(Cl)cc3)CCC2)cc1-c1ccccc1]

$^1$H NMR (300 MHz, CDCl$_3$) δ: 7.32-7.41 (m, 3H), 7.23-7.28 (m, 4H), 7.12-7.17 (m, 3H), 6.80 (d, J=8.4 Hz, 1H), 6.67 (s, 1H), 4.59 (s, 2H), 2.66-2.87 (m, 6H), 2.39 (t, J=7.5 Hz, 2H), 2.03 (t, J=7.8 Hz, 2H). Mass spectrum (ESI, m/z): Calculated for C$_{27}$H$_{25}$ClO$_3$, 431.1 [M–H], Measured: 431.1.

Example 206: Compound #139

3-[2,3-dimethyl-4-[[2-(4-pyridyl)cyclopenten-1-yl]methoxy]phenyl]Propanoic Acid

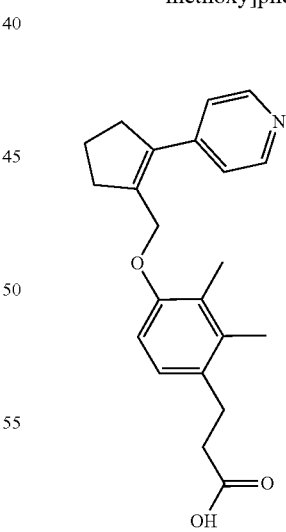

$^1$H NMR (300 MHz, CDCl$_3$) δ: 8.65 (d, J=6.0 Hz, 2H), 7.78 (d, J=6.3 Hz, 2H), 6.91 (d, J=9.6 Hz, 1H), 6.57 (d, J=8.4 Hz, 1H), 4.77 (s, 2H), 2.82-2.93 (m, 6H), 2.41-2.49 (m, 2H), 2.20 (s, 3H), 2.01-2.08 (m, 5H). Mass spectrum (ESI, m/z): Calculated for C$_{22}$H$_{25}$NO$_3$, 350.2 [M–H], Measured: 350.2.

Example 207: Compound #140

3-[2,3-dimethyl-4-[[2-(4-propylphenyl)cyclopenten-1-yl]methoxy]phenyl]Propanoic Acid

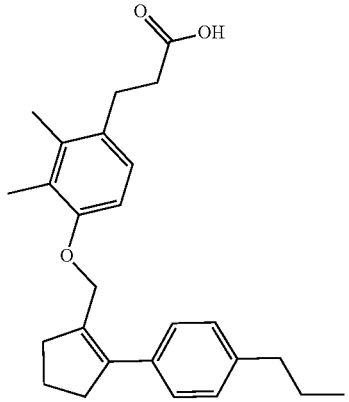 [SMILES: CCCc1ccc(C2=C(COc3ccc(CCC(=O)O)c(C)c3C)CCC2)cc1]

¹H NMR (300 MHz, CDCl₃) δ: 7.10-7.20 (m, 4H), 6.87 (d, J=8.4 Hz, 1H), 6.53 (d, J=8.1 Hz, 1H), 4.61 (s, 2H), 2.87-2.92 (m, 2H), 2.81-2.86 (m, 2H), 2.61-2.71 (m, 2H), 2.53-2.58 (m, 4H), 2.20 (s, 3H), 2.16 (s, 3H), 1.90-2.00 (m, 2H), 1.56-1.68 (m, 2H), 0.92 (t, J=7.5 Hz, 3H). Mass spectrum (ESI, m/z): Calculated for $C_{26}H_{32}O_3$, 391.2 [M–H], Measured: 391.2.

Example 208: Compound #141

3-[4-[[2-(3-methoxyphenyl)cyclopenten-1-yl]methoxy]-2,3-dimethyl-phenyl]Propanoic Acid

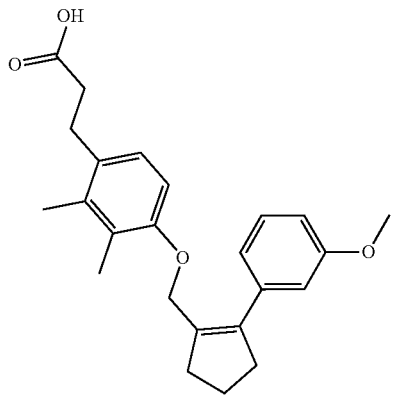 [SMILES: COc1cccc(C2=C(COc3ccc(CCC(=O)O)c(C)c3C)CCC2)c1]

¹H NMR (300 MHz, CD₃OD) δ: 7.25 (t, J=7.8 Hz, 1H), 6.84-7.18 (m, 4H), 6.51 (d, J=8.4 Hz, 1H), 4.61 (s, 2H), 3.73 (s, 3H), 2.83-2.99 (m, 4H), 2.71-2.78 (m, 2H), 2.36-2.41 (m, 2H), 2.22 (s, 3H), 2.16 (s, 3H), 1.93-2.09 (m, 2H). Mass spectrum (ESI, m/z): Calculated for $C_{24}H_{28}O_4$, 379.2 [M–H], Measured: 379.2

Example 209: Compound #142

3-[4-[[2-(4-chlorophenyl)cyclopenten-1-yl]methoxy]-5-ethyl-2-(trifluoromethyl)phenyl]Propanoic Acid

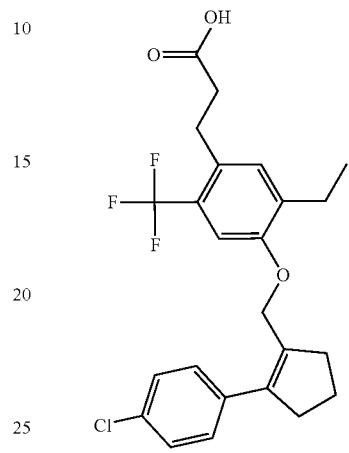

¹H NMR (300 MHz, CD3OD) δ: 7.50 (d, J=8.4 Hz, 2H), 7.21-7.40 (m, 3H), 6.86 (s, 1H), 4.76 (s, 2H), 2.96-3.09 (m, 2H), 2.74-2.82 (m, 2H), 2.51-2.67 (m, 6H), 1.95-2.05 (m, 2H), 1.23 (t, J=7.2 Hz, 3H). ¹⁹F NMR (300 MHz, CD3OD) δ: –60.58. Mass spectrum (ESI, m/z): Calculated for $C_{24}H_{24}ClF_3O_3$, 451.1 [M–H], Measured: 451.1.

Example 210: Compound #143

3-[2-chloro-4-[[2-(4-chlorophenyl)cyclopenten-1-yl]methoxy]phenyl]Propanoic Acid

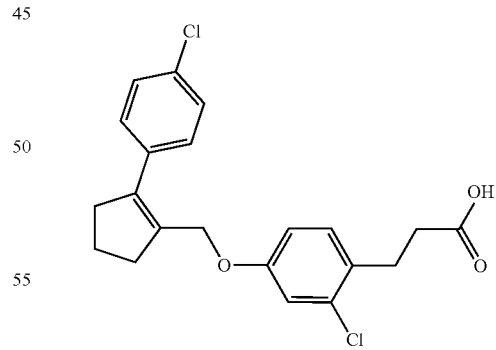

¹H NMR (300 MHz, CDCl₃) δ: 7.37 (d, J=8.4 Hz, 2H), 7.26 (d, J=8.7 Hz, 2H), 7.16 (d, J=8.7 Hz, 1H), 6.80 (s, 1H), 6.70 (d, J=8.7 Hz, 1H), 4.64 (s, 2H), 2.94 (t, J=7.5 Hz, 2H), 2.80 (t, J=7.5 Hz, 2H), 2.66 (t, J=7.2 Hz, 2H), 2.55 (t, J=7.8 Hz, 2H), 1.95-2.04 (m, 2H). Mass spectrum (ESI, m/z): Calculated for $C_{21}H_{20}Cl_2O_3$, 389.1[M–H], Measured: 389.1

Example 211: Compound #144

3-[4-[[2-(4-chlorophenyl)cyclopenten-1-yl]methoxy]-3,5-difluoro-phenyl]-2-methyl-Propanoic Acid

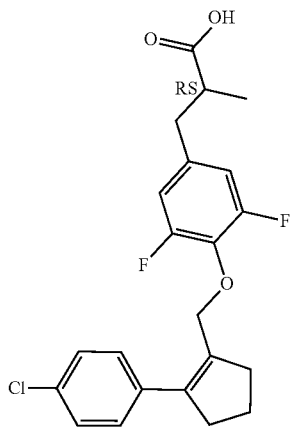 [SMILES: CC(Cc1cc(F)c(OCC2=C(c3ccc(Cl)cc3)CCC2)c(F)c1)C(=O)O]

$^1$H NMR (300 MHz, CD$_3$OD) δ: 7.17 (d, J=8.4 Hz, 2H), 7.32 (d, J=8.4 Hz, 2H), 6.82 (d, J=9.3 Hz, 2H), 4.65 (s, 2H), 2.86-3.01 (m, 1H), 2.59-2.76 (m, 6H), 1.95-2.05 (m, 2H), 1.15 (d, J=5.4 Hz, 3H). Mass spectrum (ESI, m/z): Calculated for C$_{22}$H$_{21}$ClF$_2$O$_3$, 405.1 [M−H], Measured: 405.1.

Example 212: Compound #146

3-[4-[[2-(4-cyanophenyl)cyclopenten-1-yl]methoxy]-2,3-dimethyl-phenyl]Propanoic Acid

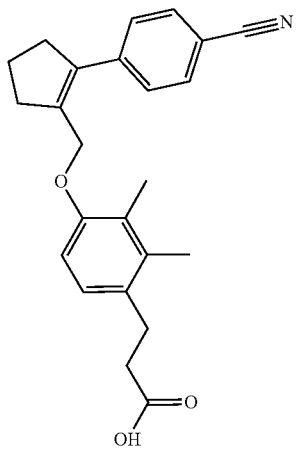 [SMILES: Cc1c(CCC(=O)O)ccc(OCC2=C(c3ccc(C#N)cc3)CCC2)c1C]

$^1$H NMR (300 MHz, CDCl$_3$) δ: 7.64 (d, J=8.1 Hz, 2H), 7.37 (d, J=8.1 Hz, 2H), 6.94 (d, J=8.4 Hz, 1H), 6.56 (d, J=8.4 Hz, 1H), 4.61 (s, 2H), 2.93-2.98 (m, 2H), 2.76-2.88 (m, 4H), 2.58-2.69 (m, 2H), 2.25 (s, 3H), 2.19 (s, 3H), 2.00-2.13 (m, 2H). Mass spectrum (ESI, m/z): Calculated for C$_{24}$H$_{25}$NO$_3$, 374.2[M−H], Measured: 374.2.

Example 213: Compound #147

3-[2,3-dimethyl-4-[[2-(2-pyridyl)cyclopenten-1-yl]methoxy]phenyl]Propanoic Acid

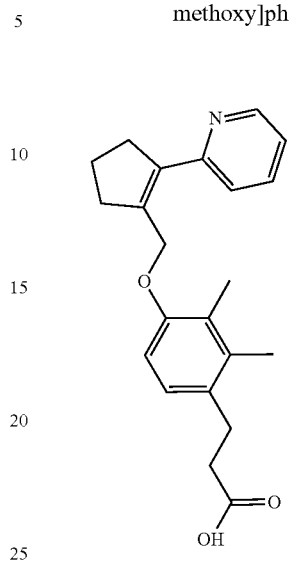

$^1$H NMR (300 MHz, CDCl$_3$) δ: 11.77 (s, 1H), 8.84 (d, J=4.6 Hz, 1H), 7.95 (t, J=7.8 Hz, 1H), 7.39-7.49 (m, 2H), 6.93 (d, J=8.4 Hz, 1H), 6.58 (d, J=8.4 Hz, 1H), 4.87 (s, 2H), 2.90-3.01 (m, 4H), 2.80-2.85 (m, 2H), 2.55-2.60 (m, 2H), 2.20 (s, 3H), 2.04-2.14 (m, 5H). Mass spectrum (ESI, m/z): Calculated for C$_{22}$H$_{26}$NO$_3$, 352.2 [M+H], Measured: 352.2.

Example 214: Compound #149

3-[4-[[2-(4-chlorophenyl)cyclopenten-1-yl]methoxy]-3-fluoro-phenyl]Propanoic Acid

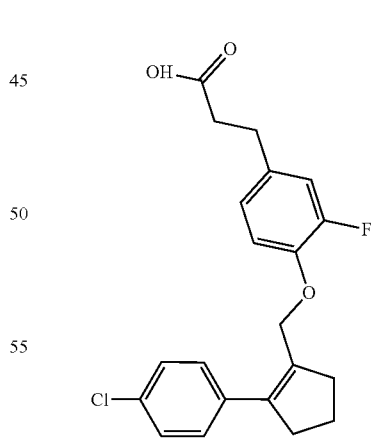

$^1$H NMR (300 MHz, CDCl$_3$) δ: 7.32 (d, J=8.4 Hz, 2H), 7.18 (d, J=8.4 Hz, 2H), 6.94 (d, J=12.0 Hz, 1H), 6.83 (d, J=8.7 Hz, 1H), 6.75 (d, J=8.1 Hz, 1H), 4.66 (s, 2H), 2.89 (t, J=7.5 Hz, 2H), 2.64-2.82 (m, 6H), 1.95-2.05 (m, 2H). Mass spectrum (ESI, m/z): Calculated for C$_{21}$H$_{20}$ClFO$_3$, 373.1 [M−H], Measured: 373.1

Example 215: Compound #151

3-[4-[[2-(4-ethoxyphenyl)cyclopenten-1-yl]methoxy]-2,3-dimethyl-phenyl]Propanoic Acid

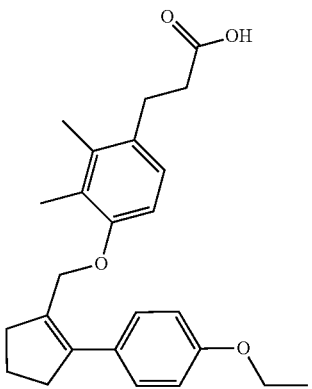 [SMILES: CCOc1ccc(C2=C(COc3ccc(CCC(=O)O)c(C)c3C)CCC2)cc1]

$^1$H NMR (300 MHz, CD$_3$OD) δ: 7.20 (d, J=9.0 Hz, 2H), 6.86-6.91 (m, 3H), 6.52 (d, J=8.1 Hz, 1H), 4.63 (s, 2H), 4.01-4.08 (m, 2H), 2.77-2.91 (m, 4H), 2.66-2.71 (m, 2H), 2.45-2.50 (m, 2H), 2.20 (s, 3H), 2.17 (s, 3H), 2.93-2.00 (m, 2H), 1.31-1.42 (m, 3H). Mass spectrum (ESI, m/z): Calculated for C$_{25}$H$_{30}$O$_4$, 393.2 [M−H], Measured: 393.2.

Example 216: Compound #153

3-[4-[[2-(4-chlorophenyl)cyclopenten-1-yl]methoxy]phenyl]Propanoic Acid

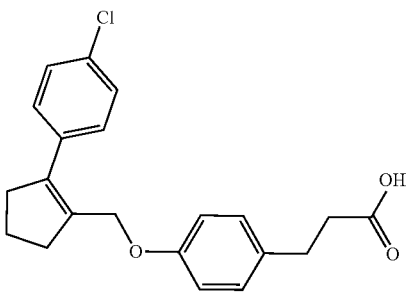 [SMILES: O=C(O)CCc1ccc(OCC2=C(c3ccc(Cl)cc3)CCC2)cc1]

$^1$H NMR (300 MHz, CDCl$_3$) δ: 7.32 (d, J=8.4 Hz, 2H), 7.19 (d, J=8.4 Hz, 2H), 7.10 (d, J=8.4 Hz, 2H), 6.79 (d, J=8.7 Hz, 2H), 4.59 (s, 2H), 2.91 (t, J=7.5 Hz, 2H), 2.78-2.80 (m, 2H), 2.63-2.72 (m, 4H), 2.05-1.95 (m, 2H). Mass spectrum (ESI, m/z): Calculated for C$_{21}$H$_{21}$ClO$_3$, 355.1 [M−H], Measured: 355.1.

Example 217: Compound #161

3-[4-[[2-(4-chlorophenyl)cyclopenten-1-yl]methoxy]-2-ethyl-phenyl]Propanoic Acid

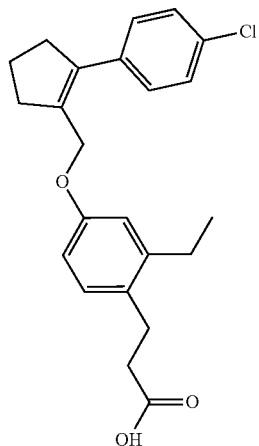 [SMILES: CCc1cc(OCC2=C(c3ccc(Cl)cc3)CCC2)ccc1CCC(=O)O]

$^1$H NMR (300 MHz, CD$_3$OD) δ: 7.36 (d, J=8.7 Hz, 2H), 7.26 (d, J=8.7 Hz, 2H), 7.02 (d, J=8.1 Hz, 1H), 6.56-6.61 (m, 2H), 4.63 (s, 2H), 2.77-2.88 (m, 4H), 2.48-2.69 (m, 6H), 1.95-2.02 (m, 2H), 1.15 (t, J=7.5 Hz, 3H). Mass spectrum (ESI, m/z): Calculated for C$_{23}$H$_{25}$ClO$_3$, 383.2 [M−H], Measured: 383.3.

Example 218: Compound #167

3-[4-[[2-(4-chlorophenyl)cyclopenten-1-yl]methoxy]-2-isopropyl-phenyl]Propanoic Acid

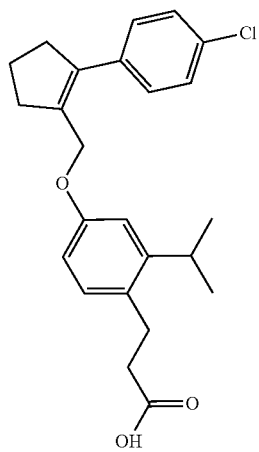 [SMILES: CC(C)c1cc(OCC2=C(c3ccc(Cl)cc3)CCC2)ccc1CCC(=O)O]

$^1$H NMR (300 MHz, CD$_3$OD) δ: 7.37 (d, J=7.6 Hz, 2H), 7.27 (d, J=8.7 Hz, 2H), 7.01 (d, J=8.4 Hz, 1H), 6.68 (s, 1H), 6.55 (d, J=8.4 Hz, 1H), 4.66 (s, 2H), 3.08-3.17 (m, 1H), 2.88-2.91 (m, 4H), 2.67 (t, J=7.8 Hz, 2H), 2.46 (t, J=7.8 Hz, 2H), 1.93-2.05 (m, 2H), 1.16 (d, J=6.4 Hz, 6H). Mass spectrum (ESI, m/z): Calculated for C$_{24}$H$_{27}$ClO$_3$, 397.2 [M−H], Measured: 397.3.

Example 219: Compound #168

3-[2-tert-butyl-4-[[2-(4-chlorophenyl)cyclopenten-1-yl]methoxy]phenyl]Propanoic Acid

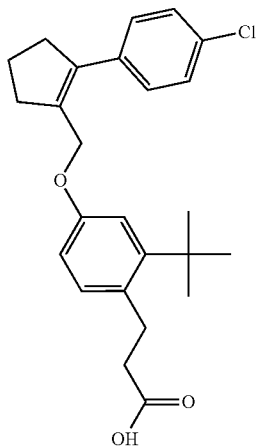 [SMILES: CC(C)(C)c1cc(OCC2=C(c3ccc(Cl)cc3)CCC2)ccc1CCC(=O)O]

¹H NMR (300 MHz, CD₃OD) δ: 7.35 (d, J=8.4 Hz, 2H), 7.25 (d, J=6.9 Hz, 2H), 7.05 (d, J=8.4 Hz, 1H), 6.82 (s, 1H), 6.59 (d, J=8.4 Hz, 1H), 4.91 (s, 2H), 3.09 (t, J=8.1 Hz, 2H), 2.80 (t, J=7.5 Hz, 2H), 2.67 (t, J=7.5 Hz, 2H), 2.54 (t, J=8.7 Hz, 2H), 1.93-2.03 (m, 2H), 1.36 (s, 9H). Mass spectrum (ESI, m/z): Calculated for $C_{25}H_{29}ClO_3$, 411.2 [M–H], Measured: 411.2.

Example 220: Compound #227

3-[3-fluoro-4-[[2-(4-fluorophenyl)cyclopenten-1-yl]methoxy]-5-methyl-phenyl]Propanoic Acid

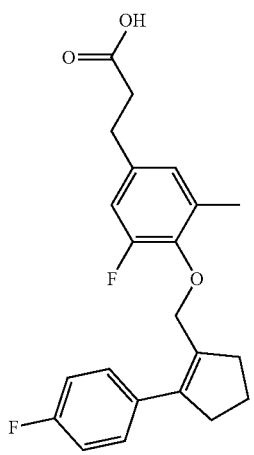 [SMILES: Cc1cc(CCC(=O)O)cc(F)c1OCC1=C(c2ccc(F)cc2)CCC1]

¹H NMR (300 MHz, CDCl₃) δ: 7.23-7.28 (m, 2H), 6.98-7.05 (m, 2H), 6.74-6.77 (m, 2H), 4.55 (s, 2H), 2.75-2.88 (m, 6H), 2.64 (t, J=7.8 Hz, 2H), 2.24 (s, 3H), 1.94-2.05 (m, 2H). ¹⁹F NMR (300 MHz, CDCl₃) δ: −115.13, −130.06. Mass spectrum (ESI, m/z): Calculated for $C_{22}H_{22}F_2O_3$, 371.2 [M–H], Measured: 371.0

Example 221: Compound #235

3-[3,5-dichloro-4-[[2-(4-fluorophenyl)cyclopenten-1-yl]methoxy]phenyl]Propanoic Acid

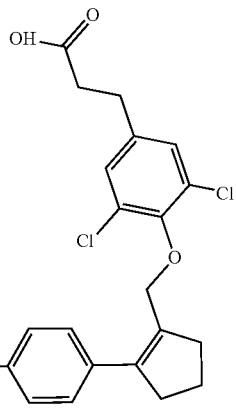

¹H NMR (300 MHz, CDCl₃) δ: 7.30-7.41 (m, 2H), 7.13 (s, 2H), 6.97-7.07 (m, 2H), 4.58 (s, 2H), 2.76-2.89 (m, 6H), 2.63-2.68 (m, 2H), 1.96-2.06 (m, 2H). ¹⁹F NMR (300 MHz, CDCl₃) δ: −115.06. Mass spectrum (ESI, m/z): Calculated for $C_{21}H_{19}Cl_2FO_3$, 407.1 [M–H], Measured: 406.9.

Example 222: Compound #236

3-[3-chloro-4-[[2-(4-fluorophenyl)cyclopenten-1-yl]methoxy]-5-methyl-phenyl]Propanoic Acid

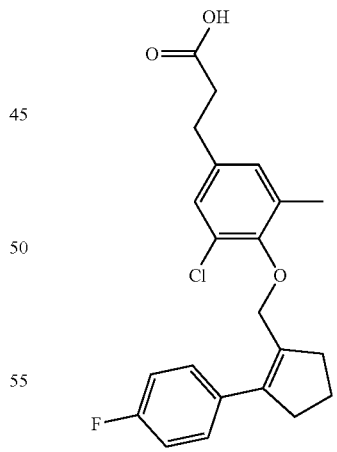

¹H NMR (300 MHz, CDCl₃) δ: 7.26-7.31 (m, 2H), 6.97-7.05 (m, 3H), 6.89 (s, 1H), 4.48 (s, 2H), 2.76-2.87 (m, 6H), 2.61-2.66 (m, 2H), 2.25 (s, 3H), 1.96-2.06 (m, 2H). ¹⁹F NMR (300 MHz, CDCl₃) δ: −115.12. Mass spectrum (ESI, m/z): Calculated for $C_{22}H_{22}ClFO_3$, 387.1 [M–H], Measured: 387.0

Example 223: Compound #237

3-[2-cyano-4-[[2-(4-fluorophenyl)cyclopenten-1-yl]methoxy]phenyl]Propanoic Acid

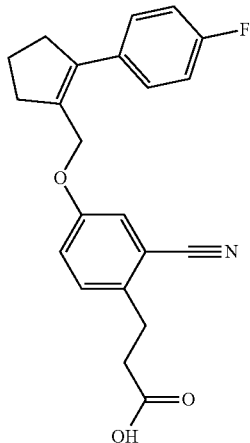 [SMILES: N#Cc1cc(OCC2=C(c3ccc(F)cc3)CCC2)ccc1CCC(=O)O]

$^1$H NMR (300 MHz, CDCl$_3$) δ: 7.16-7.26 (m, 3H), 6.95-7.09 (m, 4H), 4.60 (s, 2H), 3.09 (t, J=7.5 Hz, 2H), 2.62-2.81 (m, 6H), 1.93-2.03 (m, 2H). $^{19}$F NMR (300 MHz, CDCl$_3$) δ: −114.38. Mass spectrum (ESI, m/z): Calculated for C$_{22}$H$_{20}$FNO$_3$, 364.1 [M−H], Measured: 364.0.

Example 224: Compound #240

3-[4-[[2-(4-fluorophenyl)cyclopenten-1-yl]methoxy]-2-(trifluoromethyl)phenyl]Propanoic Acid

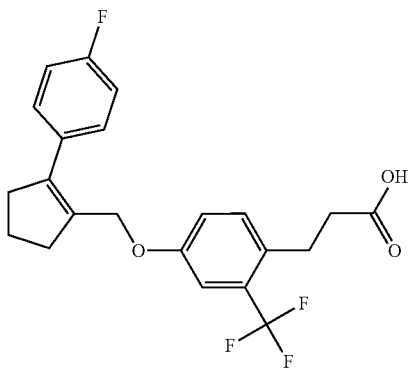 [SMILES: O=C(O)CCc1ccc(OCC2=C(c3ccc(F)cc3)CCC2)cc1C(F)(F)F]

$^1$H NMR (400 MHz, CD$_3$OD) δ: 7.28-7.35 (m, 3H), 7.08-7.13 (m, 2H), 6.94-7.00 (m, 2H), 4.70 (s, 2H), 3.00 (t, J=8.0 Hz, 2H), 2.81 (t, J=7.2 Hz, 2H), 2.67 (t, J=7.2 Hz, 2H), 2.41 (t, J=8.0 Hz, 2H), 1.95-2.03 (m, 2H). $^{19}$F NMR (400 MHz, CD$_3$OD) δ: −60.06, −114.65. Mass spectrum (ESI, m/z): Calculated for C$_{22}$H$_{20}$F$_4$O$_3$, 407.1 [M−H], Measured: 407.0

Example 225: Compound #243

3-[4-[[2-(4-chloro-2-methyl-phenyl)cyclopenten-1-yl]methoxy]-2-(trifluoromethyl)phenyl]Propanoic Acid

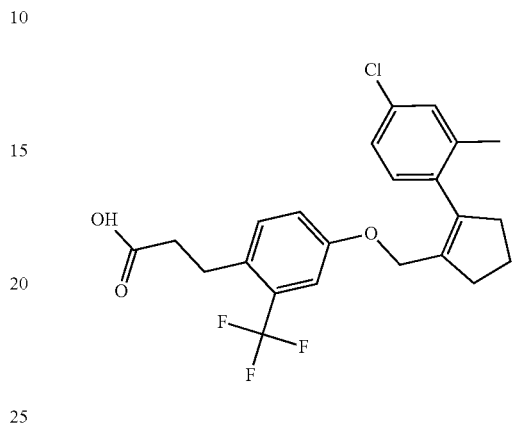

$^1$H NMR (300 MHz, CD$_3$OD) δ: 7.28 (d, J=8.4 Hz, 1H), 7.22 (s, 1H), 7.12-7.15 (m, 1H), 6.94-6.98 (m, 2H), 6.87-6.91 (m, 1H), 4.87 (s, 2H), 2.99 (t, J=7.8 Hz, 2H), 2.61-2.66 (m, 4H), 2.53 (t, J=7.5 Hz, 2H), 2.16 (s, 3H), 1.97-2.06 (m, 2H). Mass spectrum (ESI, m/z): Calculated for C$_{23}$H$_{22}$ClF$_3$O$_3$, 437.1 [M−H], Measured: 437.0

Example 226: Compound #244

3-[4-[[2-(2,4-dimethylphenyl)cyclopenten-1-yl]methoxy]-5-fluoro-2-methyl-phenyl]Propanoic Acid

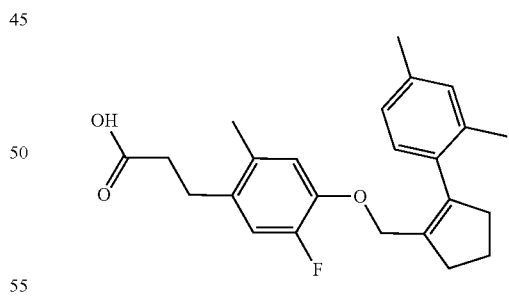

$^1$H NMR (300 MHz, CD$_3$OD) δ: 7.03 (s, 1H), 6.97 (d, J=7.5 Hz, 1H), 6.87-6.93 (m, 2H), 6.19 (d, J=8.1 Hz, 1H), 4.15 (s, 2H), 2.81 (t, J=7.2 Hz, 2H), 2.62-2.66 (m, 4H), 2.51 (t, J=7.5 Hz, 2H), 2.31 (s, 3H), 2.16 (s, 3H), 2.12 (s, 3H), 1.94-2.01 (m, 2H). $^{19}$F NMR (300 MHz, CD$_3$OD) δ: −140.73. Mass spectrum (ESI, m/z): Calculated for C$_{24}$H$_{27}$FO$_3$, 381.2 [M−H], Measured: 381.1

Example 227: Compound #245

3-[4-[[2-(2,4-dimethylphenyl)cyclopenten-1-yl]methoxy]phenyl]Propanoic Acid

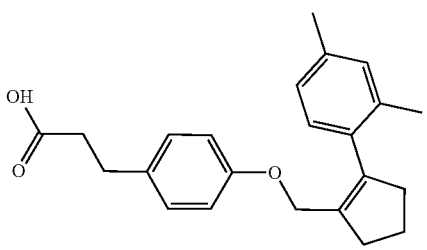 [SMILES: Cc1ccc(C2=C(COc3ccc(CCC(=O)O)cc3)CCC2)c(C)c1]

$^1$H NMR (400 MHz, CD$_3$OD) δ: 7.04-7.07 (m, 3H), 6.97 (d, J=7.6 Hz, 1H), 6.90 (d, J=7.6 Hz, 1H), 6.65 (d, J=8.7 Hz, 2H), 4.34 (s, 2H), 2.82 (t, J=7.6 Hz, 2H), 2.64 (t, J=7.2 Hz, 4H), 2.45 (t, J=7.2 Hz, 2H), 2.28 (s, 3H), 2.16 (s, 3H), 1.96-2.02 (m, 2H). Mass spectrum (ESI, m/z): Calculated for C$_{23}$H$_{26}$O$_3$, 349.2[M−H], Measured: 349.1.

Example 228: Compound #246

3-[2-chloro-4-[[2-(2,4-dimethylphenyl)cyclopenten-1-yl]methoxy]phenyl]Propanoic Acid

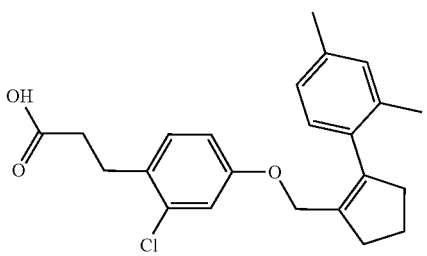 [SMILES: Cc1ccc(C2=C(COc3ccc(CCC(=O)O)c(Cl)c3)CCC2)c(C)c1]

$^1$H NMR (400 MHz, CD$_3$OD) δ 7.14 (d, J=8.4 Hz, 1H), 7.05 (s, 1H), 6.99 (d, J=7.6 Hz, 1H), 6.91 (d, J=7.6 Hz, 1H), 6.70 (s, 1H), 6.61-6.63 (m, 1H), 4.38 (s, 2H), 2.91 (t, J=7.6 Hz, 2H), 2.59-2.66 (m, 4H), 2.45 (t, J=8.0 Hz, 2H), 2.31 (s, 3H), 2.17 (s, 3H), 1.96-2.04 (m, 2H). Mass spectrum (ESI, m/z): Calculated for C$_{23}$H$_{25}$ClO$_3$, 383.1[M−H], Measured: 383.1

Example 229: Compound #247

3-[4-[[2-(2,4-dimethylphenyl)cyclopenten-1-yl]methoxy]-2-(trifluoromethyl)phenyl]Propanoic Acid

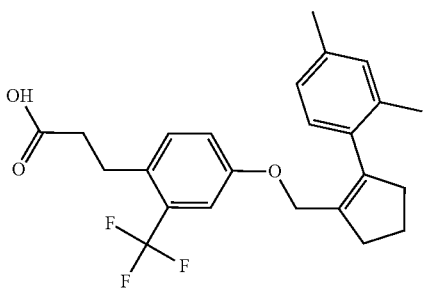 [SMILES: Cc1ccc(C2=C(COc3ccc(CCC(=O)O)c(C(F)(F)F)c3)CCC2)c(C)c1]

$^1$H NMR (400 MHz, CD$_3$OD) δ: 7.18 (d, J=8.4 Hz, 1H), 6.92 (s, 1H), 6.81-6.87 (m, 2H), 6.74-6.78 (m, 2H), 4.32 (s, 2H), 2.87 (t, J=8.0 Hz, 2H), 2.49-2.52 (m, 4H), 2.27-2.31 (m, 2H), 2.19 (s, 3H), 2.03 (s, 3H), 1.85-1.92 (m, 2H). $^{19}$F NMR (400 MHz, CD$_3$OD) δ: −61.20. Mass spectrum (ESI, m/z): Calculated for C$_{24}$H$_{25}$F$_3$O$_3$, 417.2 [M−H], Measured: 417.1

Example 230: Compound #254

3-[5-fluoro-4-[[2-(4-fluorophenyl)cyclopenten-1-yl]methoxy]-2,3-dimethyl-phenyl]Propanoic Acid

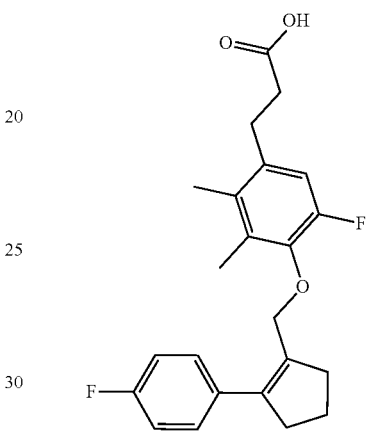

$^1$H NMR (300 MHz, CDCl$_3$) δ: 7.24-7.28 (m, 2H), 6.98-7.04 (m, 2H), 6.75 (d, J=12.0 Hz, 1H), 4.52 (s, 2H), 2.91 (t, J=7.8 Hz, 2H), 2.76-2.81 (m, 4H), 2.59 (t, J=7.8 Hz, 2H), 2.17 (s, 3H), 2.15 (s, 3H), 1.95-2.05 (m, 2H). $^{19}$F NMR (300 MHz, CDCl$_3$) δ: −115.19, −133.17. Mass spectrum (ESI, m/z): Calculated for C$_{23}$H$_{24}$F$_2$O$_3$, 385.2 [M−H], Measured: 385.1

Example 231: Compound #257

3-[4-[[2-(o-tolyl)cyclopenten-1-yl]methoxy]-2-(trifluoromethyl)phenyl]Propanoic Acid

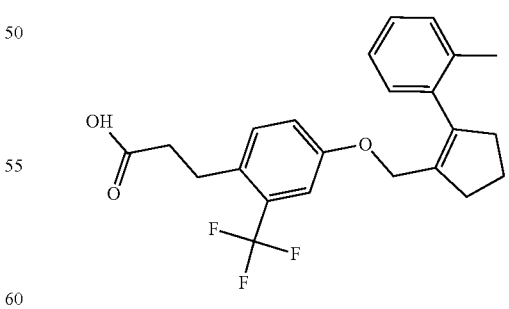

$^1$H NMR (300 MHz, CD$_3$OD) δ: 7.26 (d, J=8.4 Hz, 1H), 7.10-7.21 (m, 3H), 6.95-7.00 (m, 2H), 6.86-6.89 (m, 1H), 4.43 (s, 2H), 2.97 (t, J=7.8 Hz, 2H), 2.61-2.65 (m, 4H), 2.52 (t, J=7.5 Hz, 2H), 2.17 (s, 3H), 1.95-2.05 (m, 2H). $^{19}$F NMR (300 MHz, CD$_3$OD) δ: −61.13. Mass spectrum (ESI, m/z): Calculated for C$_{23}$H$_{23}$F$_3$O$_3$, 403.2 [M−H], Measured: 403.1

Example 232: Compound #258

3-[4-[(2-phenylcyclopenten-1-yl)methoxy]-2-(trifluoromethyl)phenyl]Propanoic Acid

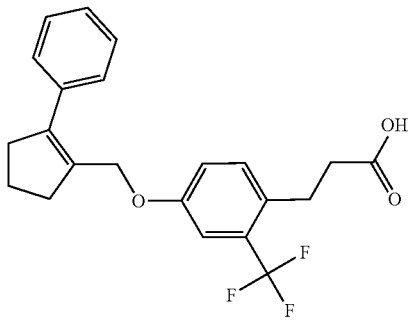 [SMILES: O=C(O)CCc1ccc(OCC2=C(c3ccccc3)CCC2)cc1C(F)(F)F]

$^1$H NMR (300 MHz, CD$_3$OD) δ: 7.34-7.39 (m, 2H), 7.24-7.30 (m, 3H), 7.16 (d, J=8.4 Hz, 1H), 6.75 (s, 1H), 6.64-6.68 (m, 1H), 4.61 (s, 2H), 2.92 (t, J=7.5 Hz, 2H), 2.79-2.84 (m, 2H), 2.63-2.67 (m, 2H), 2.39-2.44 (m, 2H), 1.93-2.03 (m, 2H). Mass spectrum (ESI, m/z): Calculated for C$_{22}$H$_{21}$F$_3$O$_3$, 389.1 [M–H], Measured: 389.1

Example 233: Compound #259

3-[2-chloro-4-[(2-phenylcyclopenten-1-yl)methoxy]phenyl]Propanoic Acid

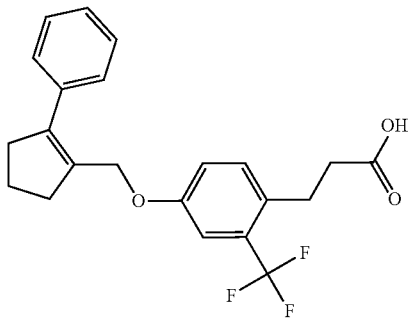 [SMILES: O=C(O)CCc1ccc(OCC2=C(c3ccccc3)CCC2)cc1C(F)(F)F]

$^1$H NMR (300 MHz, CD$_3$OD) δ: 7.25-7.61 (m, 6H), 6.88-7.00 (m, 2H), 4.72 (s, 2H), 2.99 (t, J=7.5 Hz, 2H), 2.82 (t, J=7.5 Hz, 2H), 2.64 (t, J=7.8 Hz, 2H), 2.41 (t, J=7.8 Hz, 2H), 1.99-2.04 (m, 2H). Mass spectrum (ESI, m/z): Calculated for C$_{21}$H$_{21}$ClO$_3$, 355.1 [M–H], Measured: 355.0

Example 234: Compound #260

3-[2-chloro-4-[[2-(4-fluorophenyl)cyclopenten-1-yl]methoxy]phenyl]Propanoic Acid

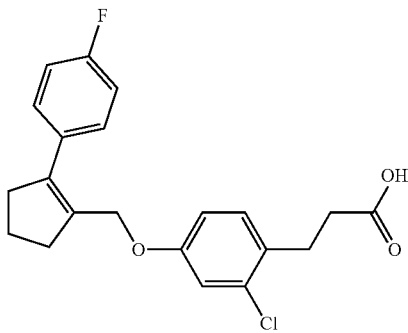 [SMILES: O=C(O)CCc1ccc(OCC2=C(c3ccc(F)cc3)CCC2)cc1Cl]

$^1$H NMR (300 MHz, CDCl$_3$) δ: 7.18-7.26 (m, 2H), 7.01-7.12 (m, 3H), 6.82 (s, 1H), 6.66-6.69 (m, 1H), 4.56 (s, 2H), 2.98 (t, J=7.8 Hz, 2H), 2.78 (t, J=7.5 Hz, 2H), 2.63-2.68 (m, 4H), 1.93-2.03 (m, 2H). $^{19}$F NMR (300 MHz, CDCl$_3$) δ: –114.71. Mass spectrum (ESI, m/z): Calculated for C$_{21}$H$_{20}$ClFO$_3$, 373.1 [M–H], Measured: 373.1

Example 235: Compound #262

3-[5-fluoro-2-methyl-4-[[2-(o-tolyl)cyclopenten-1-yl]methoxy]phenyl]Propanoic Acid

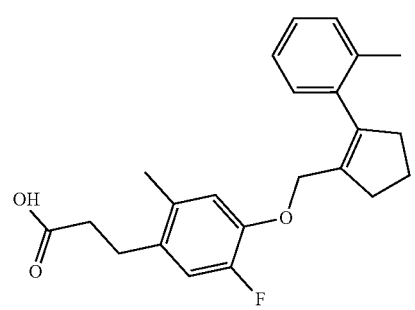 [SMILES: Cc1cc(OCC2=C(c3ccccc3C)CCC2)c(F)cc1CCC(=O)O]

$^1$H NMR (300 MHz, CD$_3$OD) δ: 7.11-7.22 (m, 3H), 6.96 (d, J=5.7 Hz, 1H), 6.87 (d, J=12.3 Hz, 1H), 6.50 (d, J=9.0 Hz, 1H), 4.41 (s, 2H), 2.82 (t, J=7.6 Hz, 2H), 2.63-2.77 (m, 4H), 2.50 (t, J=7.6 Hz, 2H), 2.15 (s, 6H), 1.95-2.05 (m, 2H). $^{19}$F NMR (300 MHz, CD$_3$OD) δ: –140.67. Mass spectrum (ESI, m/z): Calculated for C$_{23}$H$_{25}$FO$_3$, 367.2 [M–H], Measured: 367.2

Example 236: Compound #263

3-[4-[[2-(3-fluorophenyl)cyclopenten-1-yl]methoxy]-2-(trifluoromethyl)phenyl]Propanoic Acid

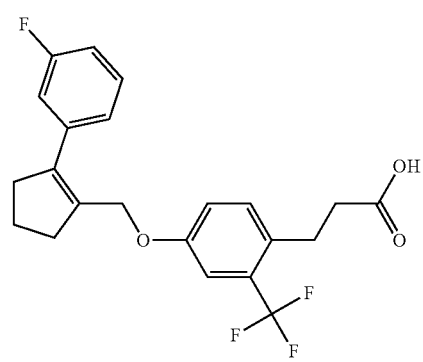 [SMILES: O=C(O)CCc1ccc(OCC2=C(c3cccc(F)c3)CCC2)cc1C(F)(F)F]

$^1$H NMR (400 MHz, CD$_3$OD) δ: 7.31-7.41 (m, 2H), 6.98-7.09 (m, 5H), 4.80 (s, 2H), 3.01 (t, J=7.6 Hz, 2H), 2.82 (t, J=7.2 Hz, 2H), 2.68 (t, J=7.2 Hz, 2H), 2.56 (m, J=8.0 Hz, 2H), 1.98-2.05 (m, 2H). $^{19}$F NMR (400 MHz, CD$_3$OD) δ: –61.38, –115.34. Mass spectrum (ESI, m/z): Calculated for C$_{22}$H$_{20}$F$_4$O$_3$, 407.1 [M–H], Measured: 407.1

Example 237: Compound #264

3-[5-fluoro-4-[[2-(3-fluoro-4-methyl-phenyl)cyclopenten-1-yl]methoxy]-2-methyl-phenyl]Propanoic Acid

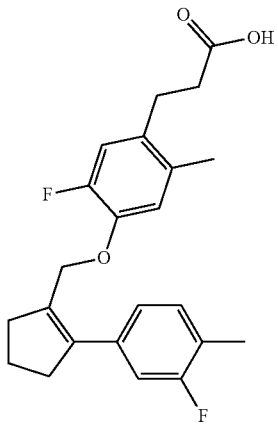 [SMILES: Cc1ccc(C2=C(COc3cc(C)c(CCC(=O)O)cc3F)CCC2)cc1F]

$^1$H NMR (300 MHz, CD$_3$OD) δ: 7.22 (t, J=7.9 Hz, 1H), 7.04-6.81 (m, 3H), 6.61 (d, J=8.6 Hz, 1H), 4.68 (s, 2H), 2.88-2.75 (m, 4H), 2.67 (t, J=7.2 Hz, 2H), 2.52 (t, J=7.5 Hz, 2H), 2.27 (s, 3H), 2.16 (s, 3H), 2.05-1.89 (m, 2H). $^{19}$F NMR (300 MHz, CD$_3$OD) δ: −119.83, −140.57. Mass spectrum (ESI, m/z): Calculated for C$_{23}$H$_{24}$F$_2$O$_3$, 385.2 [M−H], Measured: 385.1

Example 238: Compound #265

3-[4-[[2-(2-chlorophenyl)cyclopenten-1-yl]methoxy]-5-fluoro-2-methyl-phenyl]Propanoic Acid

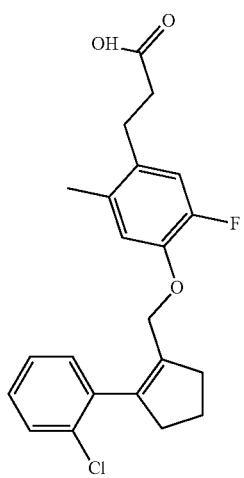 [SMILES: Cc1cc(OCC2=C(c3ccccc3Cl)CCC2)c(F)cc1CCC(=O)O]

$^1$H NMR (300 MHz, CD$_3$OD) δ: 7.43 (d, J=5.8 Hz, 1H), 7.35-7.22 (m, 2H), 7.11 (d, J=5.8 Hz, 1H), 6.85 (d, J=12.4 Hz, 1H), 6.54 (d, J=8.7 Hz, 1H), 4.47 (s, 2H), 2.59-2.87 (m, 6H), 2.51 (d, J=7.5 Hz, 2H), 2.17 (s, 3H), 1.96-2.06 (m, 2H). $^{19}$F NMR (300 MHz, CD$_3$OD) δ: −140.58. Mass spectrum (ESI, m/z): Calculated for C$_{22}$H$_{22}$ClFO$_3$, 387.1 [M−H], Measured: 387.1.

Example 239: Compound #268-D

3-[4-[[2-[4-(trideuteriomethyl)phenyl]cyclopenten-1-yl]methoxy]-2-(trifluoromethyl)phenyl]Propanoic Acid

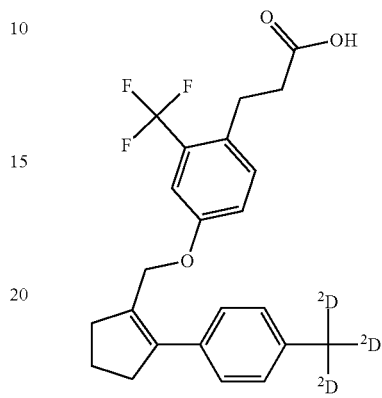

$^1$H NMR (400 MHz, CD$_3$OD) δ: 7.33 (d, J=8.4 Hz, 1H), 7.08-7.18 (m, 3H), 7.03 (s, 1H), 6.96 (d, J=8.4 Hz, 2H), 4.87 (s, 2H), 3.00 (t, J=7.6 Hz, 2H), 2.79 (t, J=7.6 Hz, 2H), 2.65 (t, J=7.2 Hz, 2H), 2.53-2.57 (m, 2H), 1.95-2.03 (m, 2H). $^{19}$F NMR (400 MHz, CD$_3$OD) δ: −61.34. Mass spectrum (ESI, m/z): Calculated for C$_{23}$H$_{20}$D3F$_3$O$_3$, 406.2 [M−H], Measured: 406.1

Example 240: Compound #269

3-[4-[[2-(4-bromophenyl)cyclopenten-1-yl]methoxy]-2-(trifluoromethyl)phenyl]Propanoic Acid

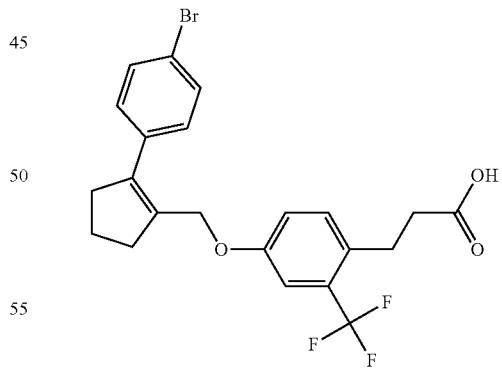

$^1$H NMR (400 MHz, CD$_3$OD) δ: 7.51-7.53 (m, 2H), 7.31 (d, J=8.8 Hz, 1H), 7.18-7.23 (m, 2H), 7.04 (s, 1H), 6.97-6.99 (m, 1H), 4.72 (s, 2H), 3.01 (t, J=8.0 Hz, 2H), 2.81 (t, J=7.6 Hz, 2H), 2.67 (t, J=7.6 Hz, 2H), 2.54-2.57 (m, 2H), 1.95-2.05 (m, 2H). $^{19}$F NMR (400 MHz, CD$_3$OD) δ: −61.32. Mass spectrum (ESI, m/z): Calculated for C$_{22}$H$_{20}$BrF$_3$O$_3$, 467.1 [M−H], Measured: 467.0

Example 241: Compound #270

3-[5-fluoro-4-[[2-(2-fluoro-4-methyl-phenyl)cyclo-penten-1-yl]methoxy]-2-methyl-phenyl]Propanoic Acid

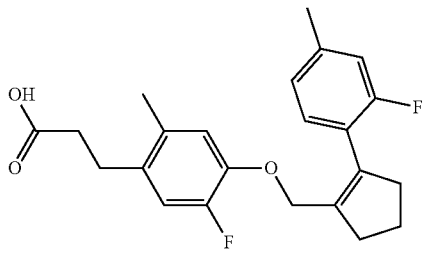 [SMILES: Cc1ccc(C2=C(COc3cc(C)c(CCC(=O)O)cc3F)CCC2)c(F)c1]

$^1$H NMR (300 MHz, CD$_3$OD) δ: 6.94-7.09 (m, 3H), 6.82 (d, J=12.3 Hz, 1H), 6.75 (d, J=8.1 Hz, 1H), 4.56 (s, 2H), 2.73-2.83 (m, 4H), 2.60-2.64 (m, 2H), 2.51 (t, J=7.5 Hz, 2H), 2.36 (s, 3H), 2.15 (s, 3H), 1.93-2.03 (m, 2H). $^{19}$F NMR (300 MHz, CD$_3$OD) δ: −116.71, −140.76. Mass spectrum (ESI, m/z): Calculated for C$_{23}$H$_{24}$F$_2$O$_3$, 385.2 [M−H], Measured: 385.1

Example 242: Compound #272

3-[2-chloro-4-[[2-[4-(trifluoromethyl)phenyl]cyclo-penten-1-yl]methoxy]phenyl]Propanoic Acid

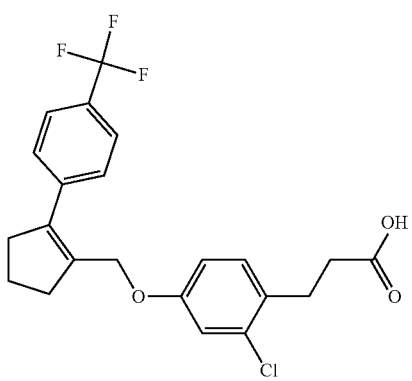 [SMILES: O=C(O)CCc1ccc(OCC2=C(c3ccc(C(F)(F)F)cc3)CCC2)cc1Cl]

$^1$H NMR (400 MHz, CD$_3$OD) δ: 7.67 (d, J=8.4 Hz, 2H), 7.46 (d, J=8.0 Hz, 2H), 7.17 (d, J=8.8 Hz, 1H), 6.81 (s, 1H), 6.72 (d, J=8.8 Hz, 1H), 4.67 (s, 2H), 2.95 (t, J=8.0 Hz, 2H), 2.86 (t, J=7.6 Hz, 2H), 2.71 (t, J=7.6 Hz, 2H), 2.56 (t, J=8.0 Hz, 2H), 1.99-2.06 (m, 2H). $^{19}$F NMR (400 MHz, CD$_3$OD) δ: −63.99. Mass spectrum (ESI, m/z): Calculated for C$_{22}$H$_{20}$ClF$_3$O$_3$, 423.1 [M−H], Measured: 423.0

Example 243: Compound #273

3-[2-chloro-4-[[2-(2-fluoro-4-methyl-phenyl)cyclo-penten-1-yl]methoxy]phenyl]Propanoic Acid

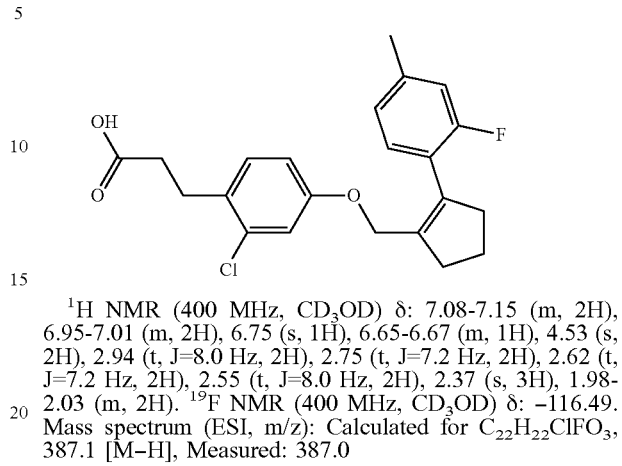

$^1$H NMR (400 MHz, CD$_3$OD) δ: 7.08-7.15 (m, 2H), 6.95-7.01 (m, 2H), 6.75 (s, 1H), 6.65-6.67 (m, 1H), 4.53 (s, 2H), 2.94 (t, J=8.0 Hz, 2H), 2.75 (t, J=7.2 Hz, 2H), 2.62 (t, J=7.2 Hz, 2H), 2.55 (t, J=8.0 Hz, 2H), 2.37 (s, 3H), 1.98-2.03 (m, 2H). $^{19}$F NMR (400 MHz, CD$_3$OD) δ: −116.49. Mass spectrum (ESI, m/z): Calculated for C$_{22}$H$_{22}$ClFO$_3$, 387.1 [M−H], Measured: 387.0

Example 244: Compound #274

3-[2-chloro-4-[[2-(4-chloro-3-fluoro-phenyl)cyclo-penten-1-yl]methoxy]phenyl]Propanoic Acid

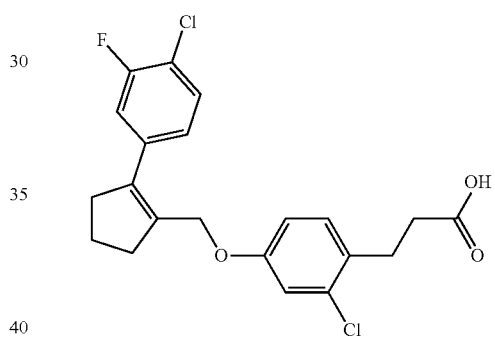

$^1$H NMR (400 MHz, CD$_3$OD) δ: 7.46 (t, J=8.0 Hz, 1H), 7.08-7.26 (m, 3H), 6.82 (s, 1H), 6.71-6.74 (m, 1H), 4.66 (s, 2H), 2.95 (t, J=7.6 Hz, 2H), 2.79 (t, J=7.6 Hz, 2H), 2.68 (t, J=7.6 Hz, 2H), 2.57 (t, J=7.6 Hz, 2H), 1.98-2.08 (m, 2H). $^{19}$F NMR (400 MHz, CD$_3$OD) δ: −117.78. Mass spectrum (ESI, m/z): Calculated for C$_{21}$H$_{19}$Cl$_2$FO$_3$, 407.1 [M−H], Measured: 407.0

Example 245: Compound #275

3-[2-chloro-4-[[2-(4-chloro-2-fluoro-phenyl)cyclo-penten-1-yl]methoxy]phenyl]Propanoic Acid

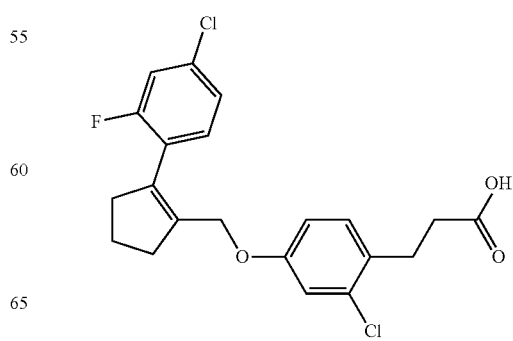

¹H NMR (400 MHz, CD₃OD) δ: 7.14-7.24 (m, 4H), 6.75 (s, 1H), 7.64-6.67 (m, 1H), 4.53 (s, 2H), 2.94 (t, J=7.6 Hz, 2H), 2.76 (t, J=7.2 Hz, 2H), 2.64 (t, J=7.6 Hz, 2H), 2.55 (t, J=7.2 Hz, 2H), 1.98-2.05 (m, 2H). ¹⁹F NMR (400 MHz, CD₃OD) δ: −112.66. Mass spectrum (ESI, m/z): Calculated for C₂₁H₁₉Cl₂FO₃, 407.1 [M−H], Measured: 407.0

Example 246: Compound #276

3-[4-[[2-(4-bromophenyl)cyclopenten-1-yl]methoxy]-2-chloro-phenyl]Propanoic Acid

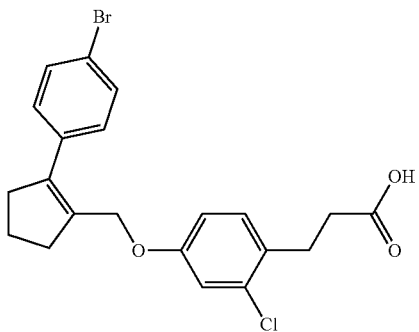 [SMILES: O=C(O)CCc1ccc(OCC2=C(c3ccc(Br)cc3)CCC2)cc1Cl]

¹H NMR (400 MHz, CD₃OD) δ: 7.52 (d, J=8.2 Hz, 2H), 7.15-7.18 (m, 3H), 6.81 (s, 1H), 6.70 (d, J=8.4 Hz, 1H), 4.64 (s, 2H), 2.95 (t, J=8.0 Hz, 2H), 2.81 (t, J=7.2 Hz, 2H), 2.67 (t, J=7.2 Hz, 2H), 2.57 (t, J=8.0 Hz, 2H), 1.95-2.05 (m, 2H). Mass spectrum (ESI, m/z): Calculated for C₂₁H₂₀BrClO₃, 433.0 [M−H], Measured: 433.0

Example 247: Compound #277

3-[5-fluoro-2-methyl-4-[(2-phenylcyclopenten-1-yl)methoxy]phenyl]Propanoic Acid

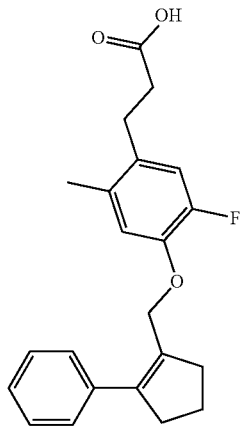 [SMILES: Cc1cc(OCC2=C(c3ccccc3)CCC2)c(F)cc1CCC(=O)O]

¹H NMR (400 MHz, CD₃OD) δ: 7.31-7.39 (m, 2H), 7.26-7.31 (m, 3H), 6.89 (d, J=12.4 Hz, 1H), 6.57 (d, J=8.4 Hz, 1H), 4.70 (s, 2H), 2.80-2.84 (m, 4H), 2.69 (t, J=7.2 Hz, 2H), 2.52 (t, J=8.8 Hz, 2H), 2.15 (s, 3H), 1.95-2.03 (m, 2H). ¹⁹F NMR (400 MHz, CD₃OD) δ: −140.77. Mass spectrum (ESI, m/z): Calculated for C₂₂H₂₃FO₃, 353.2 [M−H], Measured: 353.1

Example 248: Compound #278

3-[5-fluoro-4-[[2-(4-methoxy-2-methyl-phenyl)cyclopenten-1-yl]methoxy]-2-methyl-phenyl]Propanoic Acid

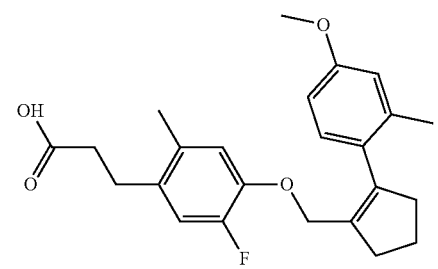 [SMILES: COc1ccc(C2=C(COc3cc(C)c(CCC(=O)O)cc3F)CCC2)c(C)c1]

¹H NMR (300 MHz, CD₃OD) δ: 6.71-6.90 (m, 4H), 6.70 (d, J=8.4 Hz, 1H), 4.41 (s, 2H), 3.78 (s, 3H), 2.82 (t, J=7.6 Hz, 2H), 2.34-2.63 (m, 6H), 2.34 (s, 3H), 2.13 (s, 3H), 1.95-2.13 (m, 2H). ¹⁹F NMR (300 MHz, CD₃OD) δ: −140.64. Mass spectrum (ESI, m/z): Calculated for C₂₄H₂₇FO₄, 397.2 [M−H], Measured: 397.1

Example 249: Compound #279

3-[5-fluoro-4-[[2-(4-methoxyphenyl)cyclopenten-1-yl]methoxy]-2-methyl-phenyl]Propanoic Acid

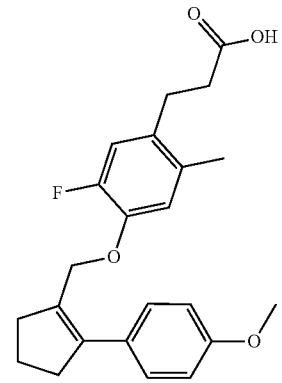 [SMILES: COc1ccc(C2=C(COc3cc(C)c(CCC(=O)O)cc3F)CCC2)cc1]

¹H NMR (300 MHz, CD₃OD) δ: 7.21 (d, J=6.0 Hz, 2H), 6.84-6.95 (m, 3H), 6.59 (d, J=6.3 Hz, 1H), 4.70 (s, 2H), 3.82 (s, 3H), 2.76-2.84 (m, 4H), 2.66 (t, J=5.1 Hz, 2H), 2.53 (t, J=7.6 Hz, 2H), 2.16 (s, 3H), 1.93-2.01 (m, 2H). ¹⁹F NMR (300 MHz, CD₃OD) δ: −140.79. Mass spectrum (ESI, m/z): Calculated for C₂₃H₂₅FO₄, 383.2 [M−H], Measured: 383.1

Example 250: Compound #280

3-[4-[[2-(4-chloro-3-fluoro-phenyl)cyclopenten-1-yl]methoxy]-5-fluoro-2-methyl-phenyl]Propanoic Acid

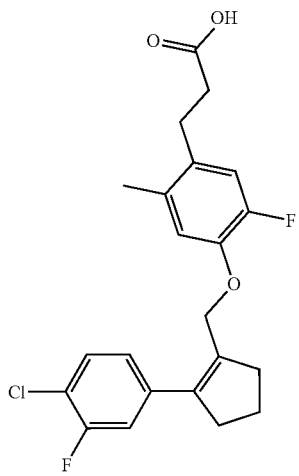 [SMILES: Cc1cc(OCC2=C(c3ccc(Cl)c(F)c3)CCC2)c(F)cc1CCC(=O)O]

$^1$H NMR (300 MHz, CD$_3$OD) δ: 7.42-7.71 (m, 1H), 7.06-7.15 (m, 2H), 6.82 (d, J=12.3 Hz, 1H), 6.60 (d, J=9.0 Hz, 1H), 4.87 (s, 2H), 2.55-2.85 (m, 6H), 2.29-2.53 (m, 2H), 2.18 (s, 3H), 1.73-2.11 (m, 2H). $^{19}$F NMR (300 MHz, CD$_3$OD) δ: −117.87, −140.39. Mass spectrum (ESI, m/z): Calculated for C$_{22}$H$_{21}$ClF$_2$O$_3$, 405.1 [M−H], Measured: 405.1

Example 251: Compound #281

3-[4-[[2-(4-chloro-2-fluoro-phenyl)cyclopenten-1-yl]methoxy]-5-fluoro-2-methyl-phenyl]Propanoic Acid

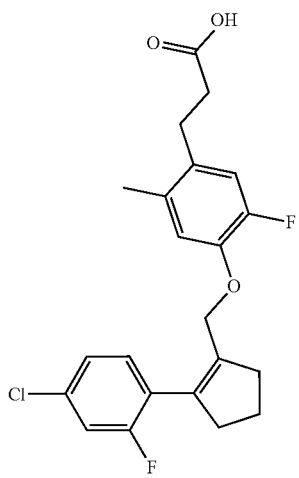 [SMILES: Cc1cc(OCC2=C(c3ccc(Cl)cc3F)CCC2)c(F)cc1CCC(=O)O]

$^1$H NMR (300 MHz, CD$_3$OD) δ: 7.07-7.45 (m, 3H), 6.82 (d, J=12.3 Hz, 1H), 6.58 (d, J=8.1 Hz, 1H), 4.67 (s, 2H), 2.67-2.89 (m, 6H), 2.39-2.54 (m, 2H), 2.17 (s, 3H), 1.89-2.03 (m, 2H). $^{19}$F NMR (300 MHz, CD$_3$OD) δ: −76.98, −112.96, −140.55. Mass spectrum (ESI, m/z): Calculated for C$_{21}$H$_{21}$FO$_5$, 405.1 [M−0.29CF$_3$COOH−H], Measured: 405.1

Example 252: Compound #282

3-[4-[[2-(3-fluoro-4-methyl-phenyl)cyclopenten-1-yl]methoxy]-2-(trifluoromethyl)phenyl]Propanoic Acid

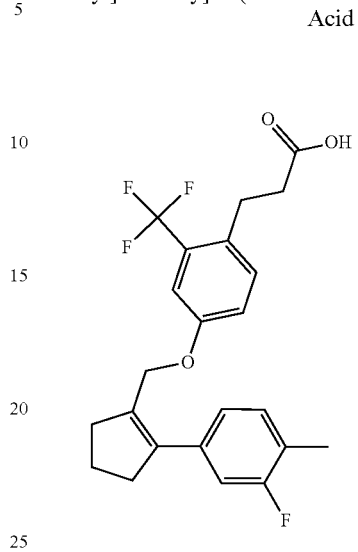

$^1$H NMR (400 MHz, CD$_3$OD) δ: 7.32 (d, J=8.8 Hz, 1H), 7.21-7.25 (m, 1H), 6.93-7.03 (m, 4H), 4.78 (s, 2H), 3.01 (t, J=8.0 Hz, 2H), 2.79 (t, J=7.6 Hz, 2H), 2.66 (t, J=7.6 Hz, 2H), 2.56 (t, J=8.0 Hz, 2H), 2.27 (s, 3H), 1.95-2.03 (m, 2H). $^{19}$F NMR (400 MHz, CD$_3$OD) δ-61.35, −119.80. Mass spectrum (ESI, m/z): Calculated for C$_{23}$H$_{22}$F$_4$O$_3$, 421.2 [M−H], Measured: 421.1

Example 253: Compound #283

3-[4-[[2-(2-fluoro-4-methyl-phenyl)cyclopenten-1-yl]methoxy]-2-(trifluoromethyl)phenyl]Propanoic Acid

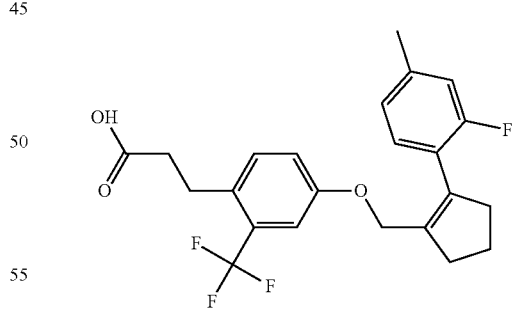

$^1$H NMR (400 MHz, CD$_3$OD) δ: 7.29 (d, J=8.8 Hz, 1H), 7.03-7.12 (m, 1H), 6.92-7.00 (m, 4H), 4.61 (s, 2H), 3.00 (t, J=8.0 Hz, 2H), 2.76 (t, J=7.2 Hz, 2H), 2.63 (t, J=7.6 Hz, 2H), 2.53-2.57 (m, 2H), 2.37 (s, 3H), 1.95-2.03 (m, 2H). $^{19}$F NMR (400 MHz, CD$_3$OD) δ-61.37, −116.77. Mass spectrum (ESI, m/z): Calculated for C$_{23}$H$_{22}$F$_4$O$_3$, 421.2 [M−H], Measured: 421.0

Example 254: Compound #284

3-[4-[[2-(4-chloro-3-fluoro-phenyl)cyclopenten-1-yl]methoxy]-2-(trifluoromethyl)phenyl]Propanoic Acid

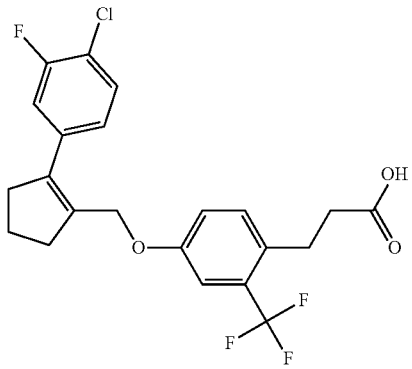 [SMILES: O=C(O)CCc1ccc(OCC2=C(c3ccc(Cl)c(F)c3)CCC2)cc1C(F)(F)F]

¹H NMR (400 MHz, CD₃OD) δ: 7.47 (d, J=8.0 Hz, 1H), 7.35 (d, J=12.0 Hz, 1H), 7.16 (d, J=8.4 Hz, 1H), 7.09 (d, J=8.4 Hz, 1H), 6.99-7.04 (m, 2H), 4.74 (s, 2H), 3.02 (t, J=8.0 Hz, 2H), 2.73 (t, J=8.0 Hz, 2H), 2.69 (t, J=7.2 Hz, 2H), 2.54-2.58 (m, 2H), 1.98-2.05 (m, 2H). ¹⁹F NMR (400 MHz, CD₃OD) δ: −61.37, −117.84. Mass spectrum (ESI, m/z): Calculated for $C_{22}H_{19}ClF_4O_3$, 441.1 [M−H], Measured: 441.0

Example 255: Compound #285

3-[4-[[2-(4-chloro-2-fluoro-phenyl)cyclopenten-1-yl]methoxy]-2-(trifluoromethyl)phenyl]Propanoic Acid

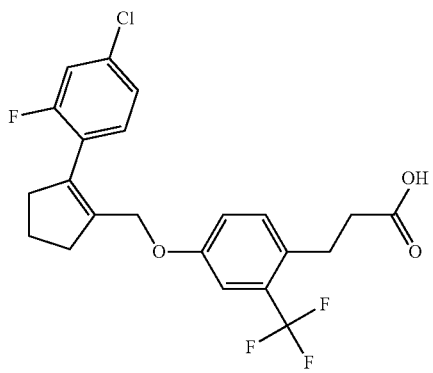 [SMILES: O=C(O)CCc1ccc(OCC2=C(c3ccc(Cl)cc3F)CCC2)cc1C(F)(F)F]

¹H NMR (400 MHz, CD₃OD) A: 7.47 (d, J=8.0 Hz, 1H), 7.35 (d, J=12.0 Hz, 1H), 7.16 (d, J=8.4 Hz, 1H), 7.09 (d, J=8.4 Hz, 1H), 6.99-7.04 (m, 2H), 4.74 (s, 2H), 3.02 (t, J=8.0 Hz, 2H), 2.73 (t, J=8.0 Hz, 2H), 2.69 (t, J=7.2 Hz, 2H), 2.54-2.58 (m, 2H), 1.98-2.05 (m, 2H). ¹⁹F NMR (400 MHZ, CD₃OD) A: −1561.37, −112.96. MASS SPECTRUM (ESI, M/Z): CALCULATED FOR $C_{22}H_{19}ClF_4O_3$, 441.1 [M−H], MEASURED: 441.0.

Example 256: Compound #286

3-[4-[[2-(4-chloro-2-methyl-phenyl)cyclopenten-1-yl]methoxy]-5-fluoro-2-methyl-phenyl]Propanoic Acid

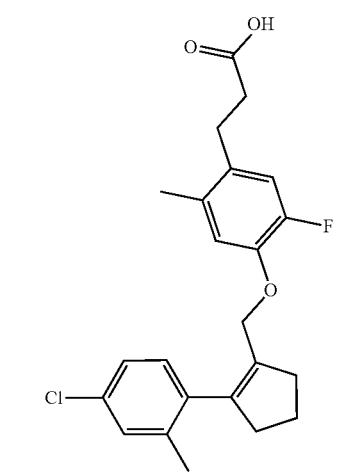 [SMILES: Cc1cc(OCC2=C(c3ccc(Cl)cc3C)CCC2)c(F)cc1CCC(=O)O]

¹H NMR (300 MHz, CD₃OD) δ: 7.23 (s, 1H), 7.15 (d, J=7.8 Hz, 1H), 6.92 (d, J=8.1 Hz, 1H), 6.82 (d, J=12.3 Hz, 1H), 6.70 (d, J=9.0 Hz, 1H), 4.41 (s, 2H), 2.82 (t, J=7.6 Hz, 2H) 2.64-2.79 (m, 4H), 2.53 (t, J=7.6 Hz, 2H), 2.17 (s, 3H), 2.14 (s, 3H), 1.96-2.01 (m, 2H). ¹⁹F NMR (300 MHz, CD₃OD) δ: −140.38. Mass spectrum (ESI, m/z): Calculated for $C_{23}H_{24}ClFO_3$, 401.1 [M−H], Measured: 401.1

Example 257: Compound #287

3-[4-[[2-(4-methoxy-2-methyl-phenyl)cyclopenten-1-yl]methoxy]-2-(trifluoromethyl)phenyl]Propanoic Acid

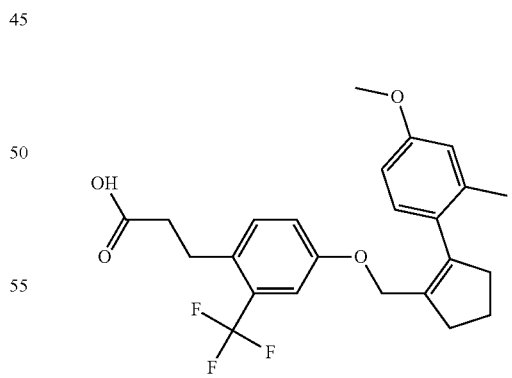

¹H NMR (300 MHz, CD₃OD) δ: 7.26 (d, J=8.4 Hz, 1H), 6.86-6.96 (m, 3H), 6.69-6.77 (m, 2H), 4.44 (s, 2H), 3.77 (s, 3H), 2.98 (t, J=7.5 Hz, 2H), 2.58-2.64 (m, 4H), 2.52 (t, J=7.5 Hz, 2H), 2.15 (s, 3H), 1.95-2.00 (m, 2H). ¹⁹F NMR (300 MHz, CD₃OD) δ: −61.30. Mass spectrum (ESI, m/z): Calculated for $C_{24}H_{25}F_3O_4$, 433.2 [M−H], Measured: 433.1

Example 258: Compound #288

3-[2-chloro-4-[[2-(4-methoxyphenyl)cyclopenten-1-yl]methoxy]phenyl]Propanoic Acid

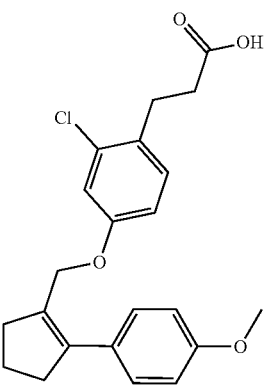 [SMILES: COc1ccc(C2=C(COc3ccc(CCC(=O)O)c(Cl)c3)CCC2)cc1]

¹H NMR (400 MHz, CD₃OD) δ: 7.15-7.22 (m, 3H), 6.93 (d, J=8.4 Hz, 2H), 6.81 (s, 1H), 6.70 (d, J=8.4 Hz, 1H), 4.66 (s, 2H), 3.81 (s, 3H), 2.94 (t, J=7.6 Hz, 2H), 2.79 (t, J=7.2 Hz, 2H), 2.64 (t, J=7.6 Hz, 2H), 2.56 (t, J=7.6 Hz, 2H), 1.93-2.00 (m, 2H). Mass spectrum (ESI, m/z): Calculated for $C_{22}H_{23}ClO_4$, 385.1 [M–H], Measured: 385.0

Example 259: Compound #289

3-[4-[[2-(4-chlorophenyl)cyclopenten-1-yl]methoxy]-5-fluoro-2-methyl-phenyl]Propanoic Acid

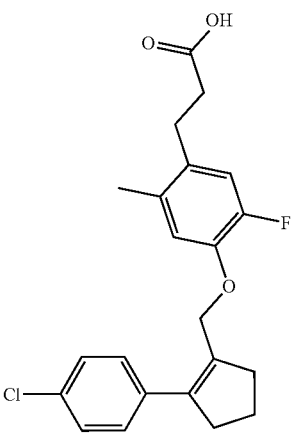 [SMILES: Cc1cc(OCC2=C(c3ccc(Cl)cc3)CCC2)c(F)cc1CCC(=O)O]

¹H NMR (300 MHz, CD₃OD) δ: 7.37 (d, J=6.6 Hz, 2H), 7.24 (d, J=6.6 Hz, 2H), 6.88 (d, J=12.3 Hz, 1H), 6.61 (d, J=9.7 Hz, 1H), 4.67 (s, 2H), 2.77-2.84 (m, 4H), 2.68 (t, J=7.2 Hz, 2H), 2.51 (t, J=9.1 Hz, 2H), 2.16 (s, 3H), 1.93-2.03 (m, 2H). ¹⁹F NMR (300 MHz, CD₃OD) δ: –140.59. Mass spectrum (ESI, m/z): Calculated for $C_{22}H_{22}ClFO_3$, 387.1 [M–H], Measured: 387.1

Example 260: Compound #290

3-[4-[[2-(4-ethylphenyl)cyclopenten-1-yl]methoxy]-5-fluoro-2-methyl-phenyl]Propanoic Acid

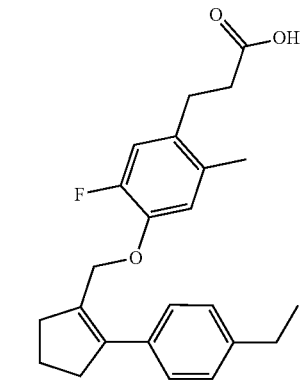 [SMILES: CCc1ccc(C2=C(COc3cc(C)c(CCC(=O)O)cc3F)CCC2)cc1]

¹H NMR (400 MHz, CD₃OD) δ: 7.17-7.23 (m, 4H), 6.88 (d, J=12.4 Hz, 1H), 6.56 (d, J=8.1 Hz, 1H), 4.70 (s, 2H), 2.79-2.83 (m, 4H), 2.64-2.69 (m, 4H), 2.47 (t, J=8.1 Hz, 2H), 2.14 (s, 3H), 1.93-2.01 (m, 2H), 1.26 (t, J=7.6 Hz, 3H). ¹⁹F NMR (400 MHz, CD₃OD) δ-140.88. Mass spectrum (ESI, m/z): Calculated for $C_{24}H_{27}FO_3$, 381.2 [M–H], Measured: 381.1

Example 261: Compound #291

3-[4-[[2-(4-methyl-2-phenyl-phenyl)cyclopenten-1-yl]methoxy]-2-(trifluoromethyl)phenyl]Propanoic Acid

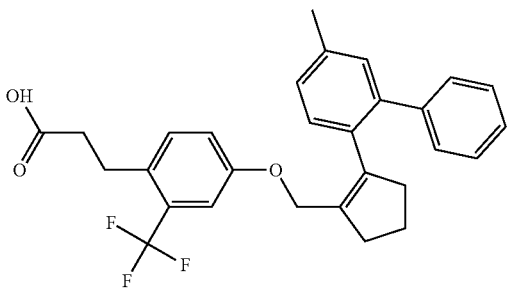 [SMILES: Cc1ccc(C2=C(COc3ccc(CCC(=O)O)c(C(F)(F)F)c3)CCC2)c(-c2ccccc2)c1]

¹H NMR (300 MHz, CD₃OD) δ: 7.28-7.39 (m, 6H), 7.13-7.21 (m, 3H), 6.92 (s, 1H), 6.84-6.88 (m, 1H), 4.14 (s, 2H), 3.00 (t, J=7.22 Hz, 2H), 2.42-2.54 (m, 9H), 1.81-1.86 (m, 2H). ¹⁹F NMR (300 MHz, CD₃OD) δ: –61.34. Mass spectrum (ESI, m/z): Calculated for $C_{29}H_{27}F_3O_3$, 479.2 [M–H], Measured: 479.1

Example 262: Compound #292

3-[4-[[2-(4-methyl-3-phenyl-phenyl)cyclopenten-1-yl]methoxy]-2-(trifluoromethyl)phenyl]Propanoic Acid

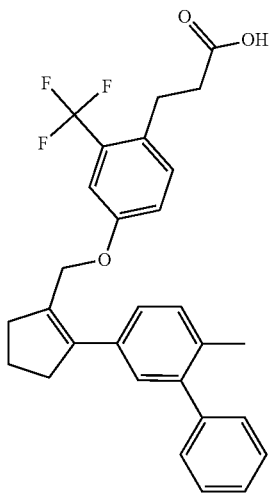 [SMILES: Cc1ccc(C2=C(COc3ccc(CCC(=O)O)c(C(F)(F)F)c3)CCC2)cc1-c1ccccc1]

$^1$H NMR (300 MHz, CD$_3$OD) δ: 7.25-7.38 (m, 7H), 7.17-7.23 (m, 1H), 7.09 (s, 1H), 6.93-7.01 (m, 2H), 4.73 (s, 2H), 2.97-3.08 (m, 2H), 2.80-2.82 (m, 2H), 2.67-2.69 (m, 2H), 2.38-2.44 (m, 2H), 2.24 (s, 3H), 1.87-2.04 (m, 2H). $^{19}$F NMR (300 MHz, CD$_3$OD) δ: −61.22. Mass spectrum (ESI, m/z): Calculated for C$_{29}$H$_{27}$F$_3$O$_3$, 479.2 [M−H], Measured: 479.0

Example 263: Compound #293

3-[2-chloro-4-[[2-(4-ethylphenyl)cyclopenten-1-yl]methoxy]phenyl]Propanoic Acid

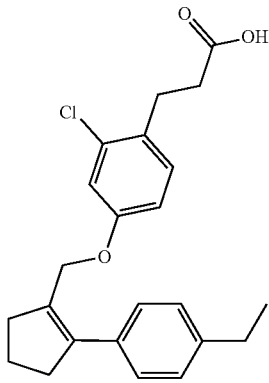 [SMILES: CCc1ccc(C2=C(COc3ccc(CCC(=O)O)c(Cl)c3)CCC2)cc1]

$^1$H NMR (400 MHz, CD$_3$OD) δ: 7.15-7.23 (m, 5H), 6.80 (s, 1H), 6.70 (d, J=8.4 Hz, 1H), 4.88 (s, 2H), 2.94 (t, J=7.6 Hz, 2H), 2.81 (t, J=7.6 Hz, 2H), 2.63-2.69 (m, 4H), 2.56 (t, J=8.0 Hz, 2H), 1.94-2.01 (m, 2H), 1.27 (t, J=8.1 Hz, 3H). Mass spectrum (ESI, m/z): Calculated for C$_{23}$H$_{25}$ClO$_3$, 383.1 [M−H], Measured: 383.1

Example 264: Compound #294

3-[4-[[2-(4-ethylphenyl)cyclopenten-1-yl]methoxy]-2-(trifluoromethyl)phenyl]Propanoic Acid

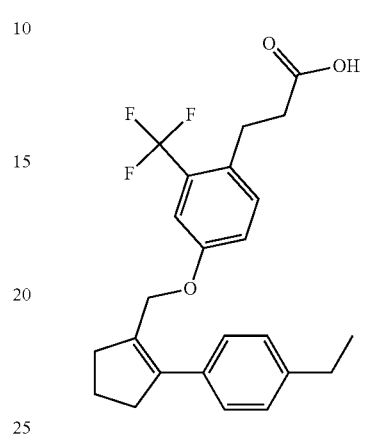

$^1$H NMR (400 MHz, CD$_3$OD) δ: 7.30 (d, J=8.4 Hz, 1H), 7.17-7.23 (m, 4H), 7.03 (s, 1H), 6.97 (d, J=8.8 Hz, 1H), 4.74 (s, 2H), 3.00 (t, J=8.0 Hz, 2H), 2.81 (t, J=7.6 Hz, 2H), 2.63-2.69 (m, 4H), 2.55 (t, J=8.4 Hz, 2H), 1.96-2.02 (m, 2H), 1.25 (t, J=7.6 Hz, 3H). $^{19}$F NMR (400 MHz, CD$_3$OD) δ: −64.10. Mass spectrum (ESI, m/z): Calculated for C$_{24}$H$_{25}$F$_3$O$_3$, 417.2 [M−H], Measured: 417.1

Example 265: Compound #295

3-[2-chloro-4-[[2-(2-chlorophenyl)cyclopenten-1-yl]methoxy]phenyl]Propanoic Acid

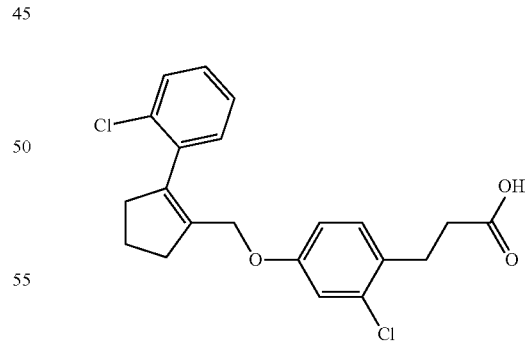

$^1$H NMR (400 MHz, CD$_3$OD) δ: 7.42-7.47 (m, 1H), 7.27-7.32 (m, 2H), 7.12-7.21 (m, 2H), 6.73 (s, 1H), 6.62-6.65 (m, 1H), 4.44 (s, 2H), 2.93 (t, J=7.6 Hz, 2H), 2.69-2.76 (m, 2H), 2.63 (t, J=7.2 Hz, 2H), 2.55 (t, J=7.6 Hz, 2H), 1.99-2.06 (m, 2H). Mass spectrum (ESI, m/z): Calculated for C$_{21}$H$_{20}$Cl$_2$O$_3$, 389.1 [M−H], Measured: 389.0

Example 266: Compound #296

3-[2-chloro-4-[[2-(3-fluoro-4-methyl-phenyl)cyclopenten-1-yl]methoxy]phenyl]Propanoic Acid

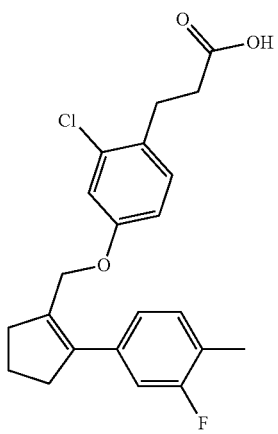 [SMILES: Cc1ccc(C2=C(COc3ccc(CCC(=O)O)c(Cl)c3)CCC2)cc1F]

$^1$H NMR (400 MHz, CD$_3$OD) δ: 7.04-7.13 (m, 2H), 6.81-6.87 (m, 2H), 6.68 (s, 1H), 6.58-6.60 (m, 1H), 4.53 (s, 2H), 2.83 (t, J=7.6 Hz, 2H), 2.67 (t, J=6.8 Hz, 2H), 2.54 (t, J=7.2 Hz, 2H), 2.44 (t, J=7.6 Hz, 2H), 2.16 (s, 3H), 1.82-1.93 (m, 2H). $^{19}$F NMR (400 MHz, CD$_3$OD) δ: −119.74. Mass spectrum (ESI, m/z): Calculated for C$_{22}$H$_{22}$ClFO$_3$, 387.1 [M−H], Measured: 387.1

Example 267: Compound #297

3-[2-chloro-4-[[2-(3-fluorophenyl)cyclopenten-1-yl]methoxy]phenyl]Propanoic Acid

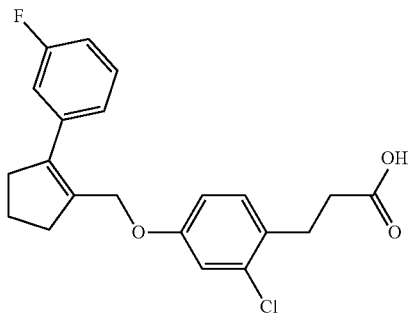 [SMILES: O=C(O)CCc1ccc(OCC2=C(c3cccc(F)c3)CCC2)cc1Cl]

$^1$H NMR (300 MHz, CD$_3$OD) δ: 7.33-7.41 (m, 1H), 7.16 (d, J=8.4 Hz, 1H), 6.99-7.09 (m, 3H), 6.80 (s, 1H), 6.69-6.72 (m, 1H), 4.65 (s, 2H), 2.94 (t, J=7.5 Hz, 2H), 2.81 (t, J=7.2 Hz, 2H), 2.66 (t, J=7.5 Hz, 2H), 2.55 (t, J=7.2 Hz, 2H), 1.93-2.04 (m, 2H). $^{19}$F NMR (300 MHz, CD$_3$OD) δ: −115.32. Mass spectrum (ESI, m/z): Calculated for C$_{21}$H$_{20}$ClFO$_3$, 373.1 [M−H], Measured: 373.0

Example 268: Compound #298

3-[2-chloro-4-[[2-(m-tolyl)cyclopenten-1-yl]methoxy]phenyl]Propanoic Acid

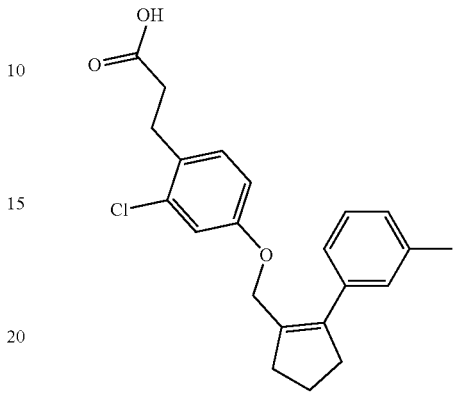

$^1$H NMR (300 MHz, CD$_3$OD) δ: 7.21-7.26 (m, 1H), 7.01-7.15 (m, 4H), 6.76 (s, 1H), 6.65-6.77 (m, 1H), 4.62 (s, 2H), 2.93 (t, J=7.5 Hz, 2H), 2.78 (t, J=7.5 Hz, 2H), 2.63 (t, J=7.2 Hz, 2H), 2.54 (t, J=7.2 Hz, 2H), 2.32 (s, 3H), 1.90-2.00 (m, 2H). Mass spectrum (ESI, m/z): Calculated for C$_{22}$H$_{23}$ClO$_3$, 369.1 [M−H], Measured: 369.1

Example 269: Compound #299

3-[4-[[2-(4-bromophenyl)cyclopenten-1-yl]methoxy]-5-fluoro-2-methyl-phenyl]Propanoic Acid

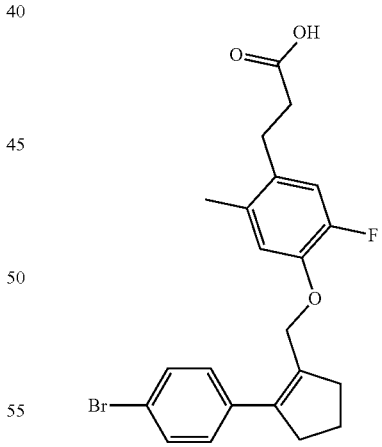

$^1$H NMR (400 MHz, CD$_3$OD) δ: 7.52 (d, J=8.4 Hz, 2H), 7.19 (d, J=8.4 Hz, 2H), 6.89 (d, J=12.4 Hz, 1H), 6.62 (d, J=8.8 Hz, 1H), 4.67 (s, 2H), 2.78-2.84 (m, 4H), 2.69 (t, J=7.6 Hz, 2H), 2.51 (t, J=8.0 Hz, 2H), 2.17 (s, 3H), 1.95-1.99 (m, 2H). $^{19}$F NMR (300 MHz, CD$_3$OD) δ: −140.59. Mass spectrum (ESI, m/z): Calculated for C$_{22}$H$_{22}$BrFO$_3$, 431.1 [M−H], Measured: 431.0

Example 270: Compound #300

3-[2-(trifluoromethyl)-4-[[2-[4-(trifluoromethyl)phenyl]cyclopenten-1-yl]methoxy]phenyl]Propanoic Acid

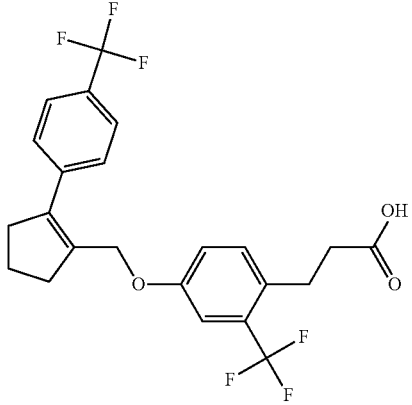 [SMILES: O=C(O)CCc1ccc(OCC2=C(c3ccc(C(F)(F)F)cc3)CCC2)cc1C(F)(F)F]

$^1$H NMR (400 MHz, CD$_3$OD) δ: 7.67 (d, J=8.0 Hz, 2H), 7.45 (d, J=8.0 Hz, 2H), 7.32 (d, J=8.4 Hz, 1H), 6.98-3.03 (m, 2H), 4.75 (s, 2H), 3.01 (t, J=7.2 Hz, 2H), 2.86 (t, J=7.2 Hz, 2H), 2.71 (t, J=7.2 Hz, 2H), 2.53-2.57 (m, 2H), 1.98-2.06 (m, 2H). $^{19}$F NMR (400 MHz, CD$_3$OD) δ: −61.38, −64.02. Mass spectrum (ESI, m/z): Calculated for C$_{23}$H$_{20}$F$_6$O$_3$, 457.1 [M−H], Measured: 457.1

Example 271: Compound #301

3-[4-[[2-(4-methoxyphenyl)cyclopenten-1-yl]methoxy]-2-(trifluoromethyl)phenyl]Propanoic Acid

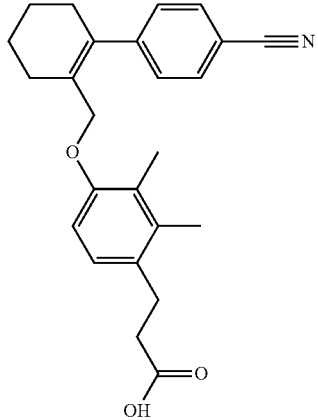

$^1$H NMR (400 MHz, CD$_3$OD) δ: 7.30 (d, J=8.4 Hz, 1H), 7.20 (d, J=8.0 Hz, 2H), 7.04 (s, 1H), 6.92-6.97 (m, 3H), 4.73 (s, 2H), 3.81 (s, 3H), 3.01 (t, J=7.6 Hz, 2H), 2.78 (t, J=7.2 Hz, 2H), 2.64 (t, J=7.6 Hz, 2H), 2.55 (t, J=8.0 Hz, 2H), 1.93-2.00 (m, 2H). $^{19}$F NMR (400 MHz, CD$_3$OD) δ: −61.38. Mass spectrum (ESI, m/z): Calculated for C$_{23}$H$_{23}$F$_3$O$_4$, 419.2 [M−H], Measured: 419.1

Example 272: Compound #302-D

3-[2-chloro-4-[[2-[4-(trideuteriomethyl)phenyl]cyclopenten-1-yl]methoxy]phenyl]Propanoic Acid

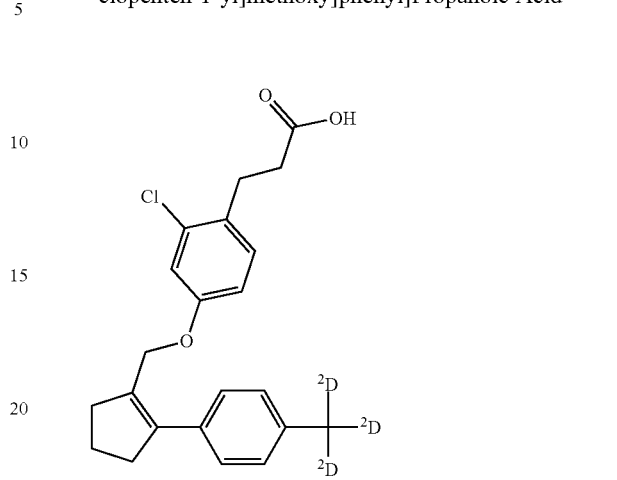

$^1$H NMR (400 MHz, CD$_3$OD) δ: 7.14-7.20 (m, 5H), 6.79 (s, 1H), 6.68-6.71 (m, 1H), 4.66 (s, 2H), 2.95 (t, J=7.6 Hz, 2H), 2.78 (t, J=7.2 Hz, 2H), 2.64 (t, J=7.2 Hz, 2H), 2.56 (t, J=8.0 Hz, 2H), 1.94-2.05 (m, 2H). Mass spectrum (ESI, m/z): Calculated for C$_{22}$H$_{20}$D3ClO$_3$, 372.2 [M−H], Measured: 372.1

Example 273: Compound #303-D

3-[5-fluoro-2-methyl-4-[[2-[4-(trideuteriomethyl)phenyl]cyclopenten-1-yl]methoxy]phenyl]Propanoic Acid

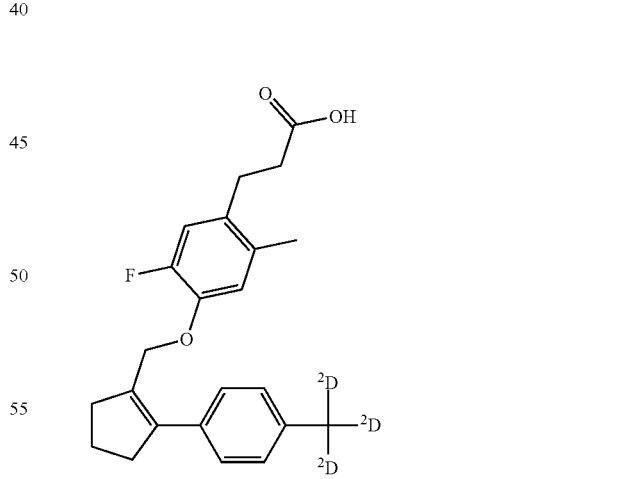

$^1$H NMR (400 MHz, CD$_3$OD) δ: 7.14-7.20 (m, 4H), 6.88 (d, J=12.4 Hz, 1H), 6.56 (d, J=8.0 Hz, 1H), 4.69 (s, 2H), 2.77-2.84 (m, 4H), 2.66 (t, J=7.2 Hz, 2H), 2.52 (t, J=8.0 Hz, 2H), 2.14 (s, 3H), 1.93-2.01 (m, 2H). $^{19}$F NMR (400 MHz, CD$_3$OD) −140.75. Mass spectrum (ESI, m/z): Calculated for C$_{23}$H$_{21}$D3FO$_3$, 370.2 [M−H], Measured: 370.1

Example 274: Compound #304

3-[5-fluoro-4-[[2-(4-fluorophenyl)cyclopenten-1-yl]methoxy]-2-methyl-phenyl]Propanoic Acid

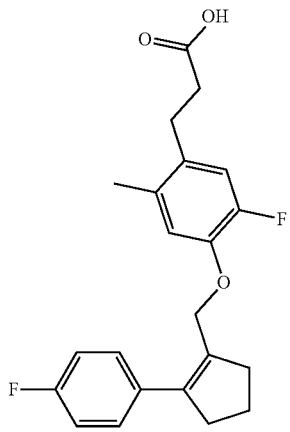 [SMILES: Cc1cc(OCC2=C(c3ccc(F)cc3)CCC2)c(F)cc1CCC(=O)O]

$^1$H NMR (300 MHz, CD$_3$OD) δ: 7.26-7.71 (m, 2H), 7.10-7.26 (m, 2H), 6.88 (d, J=12.3 Hz, 1H), 6.61 (d, J=8.7 Hz, 1H), 4.87 (s, 2H), 2.70-2.85 (m, 4H), 2.68 (t, J=7.5 Hz, 2H), 2.52 (t, J=7.5 Hz, 2H), 2.16 (s, 3H), 1.93-2.16 (m, 2H). $^{19}$F NMR (300 MHz, CD$_3$OD) δ: −117.03, −140.61. Mass spectrum (ESI, m/z): Calculated for C$_{22}$H$_{22}$F$_2$O$_3$, 371.2 [M−H], Measured: 371.1

Example 275: Compound #305

3-[5-fluoro-4-[[2-(3-fluorophenyl)cyclopenten-1-yl]methoxy]-2-methyl-phenyl]Propanoic Acid

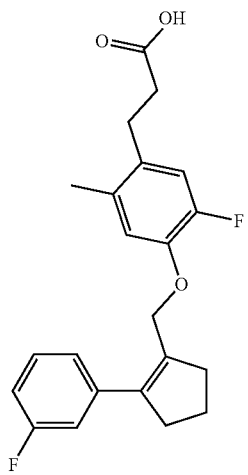 [SMILES: Cc1cc(OCC2=C(c3cccc(F)c3)CCC2)c(F)cc1CCC(=O)O]

$^1$H NMR (300 MHz, CD$_3$OD) δ: 7.34-7.41 (m, 2H), 6.97-7.09 (m, 3H), 6.89 (d, J=12.3 Hz, 1H), 6.62 (d, J=8.7 Hz, 1H), 4.87 (s, 2H), 2.79-2.85 (m, 4H), 2.69 (t, J=7.2 Hz, 2H), 2.52 (t, J=7.5 Hz, 2H), 2.17 (s, 3H), 1.94-2.04 (m, 2H). $^{19}$F NMR (300 MHz, CD$_3$OD) δ-115.39, −140.55. Mass spectrum (ESI, m/z): Calculated for C$_{22}$H$_{22}$F$_2$O$_3$, 371.2 [M−H], Measured: 371.1

Example 276: Compound #307

3-[4-[[2-(p-tolyl)cyclopenten-1-yl]methoxy]-2-(trifluoromethyl)phenyl]Propanoic Acid

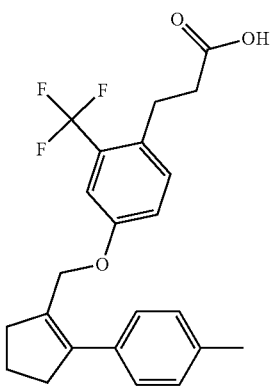 [SMILES: Cc1ccc(C2=C(COc3ccc(CCC(=O)O)c(C(F)(F)F)c3)CCC2)cc1]

$^1$H NMR (300 MHz, CD$_3$OD) δ: 7.12-7.41 (m, 5H), 6.92-6.95 (m, 2H), 4.70 (s, 2H), 2.99 (t, J=7.2 Hz, 2H), 2.77-2.89 (m, 2H), 2.50-2.63 (m, 4H), 2.33 (s, 3H), 1.90-2.03 (m, 2H). $^{19}$F NMR (300 MHz, CD$_3$OD) δ: −61.32. Mass spectrum (ESI, m/z): Calculated for C$_{23}$H$_{23}$F$_3$O$_3$, 403.2 [M−H], Measured: 403.1

Example 277: Compound #308

3-[4-[[2-[4-(trifluoromethoxy)phenyl]cyclopenten-1-yl]methoxy]-2-(trifluoromethyl)phenyl]Propanoic Acid

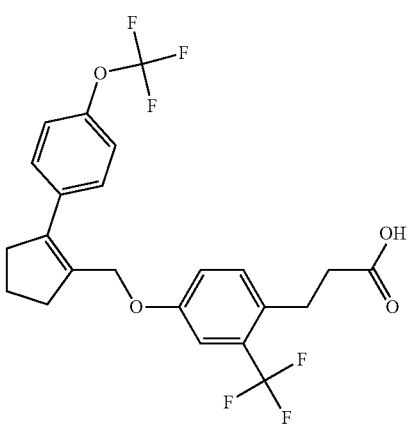 [SMILES: O=C(O)CCc1ccc(OCC2=C(c3ccc(OC(F)(F)F)cc3)CCC2)cc1C(F)(F)F]

$^1$H NMR (300 MHz, CD$_3$OD) δ: 7.14-7.26 (m, 5H), 6.84-6.91 (m, 2H), 4.60 (s, 2H), 2.88 (t, J=7.8 Hz, 2H), 2.70 (t, J=7.5 Hz, 2H), 2.56 (t, J=7.2 Hz, 2H), 2.42 (t, J=7.5 Hz, 2H), 1.83-1.93 (m, 2H). $^{19}$F NMR (300 MHz, CD$_3$OD) δ: −59.45, −61.36. Mass spectrum (ESI, m/z): Calculated for C$_{23}$H$_{20}$F$_6$O$_4$, 473.1 [M−H], Measured: 473.1

Example 278: Compound #310

3-[2-chloro-4-[[2-(p-tolyl)cyclopenten-1-yl]methoxy]phenyl]Propanoic Acid

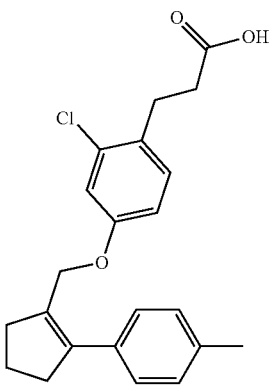 [SMILES: Cc1ccc(C2=C(COc3ccc(CCC(=O)O)c(Cl)c3)CCC2)cc1]

$^1$H NMR (300 MHz, CD$_3$OD) δ: 7.13-7.19 (m, 5H), 6.78 (s, 1H), 6.68 (d, J=8.4 Hz, 1H), 4.64 (s, 2H), 2.93 (t, J=7.5 Hz, 2H), 2.78 (t, J=7.8 Hz, 2H), 2.52-2.65 (m, 4H), 2.34 (s, 3H), 1.91-2.01 (m, 2H). Mass spectrum (ESI, m/z): Calculated for C$_{22}$H$_{23}$ClO$_3$, 369.1 [M−H], Measured: 369.1

Example 279: Compound #311

3-[2-chloro-4-[[2-[4-(trifluoromethoxy)phenyl]cyclopenten-1-yl]methoxy]phenyl]Propanoic Acid

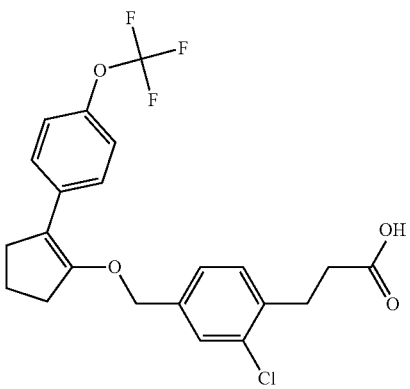 [SMILES: O=C(O)CCc1ccc(COC2=C(c3ccc(OC(F)(F)F)cc3)CCC2)cc1Cl]

$^1$H NMR (300 MHz, CD$_3$OD) δ: 7.34-7.37 (m, 2H), 7.25-7.28 (m, 2H), 7.16 (d, J=8.4 Hz, 1H), 6.80 (s, 1H), 6.72 (d, J=8.4 Hz, 1H), 4.64 (s, 2H), 2.94 (t, J=7.5 Hz, 2H), 2.82 (t, J=7.2 Hz, 2H), 2.67 (t, J=7.5 Hz, 2H), 2.55 (t, J=7.5 Hz, 2H), 1.94-2.04 (m, 2H). $^{19}$F NMR (300 MHz, CD$_3$OD) δ: −59.45. Mass spectrum (ESI, m/z): Calculated for C$_{22}$H$_{20}$ClF$_3$O$_4$, 439.1 [M−H], Measured: 439.0

Example 280: Compound #312

3-[4-[[2-(m-tolyl)cyclopenten-1-yl]methoxy]-2-(trifluoromethyl)phenyl]Propanoic Acid

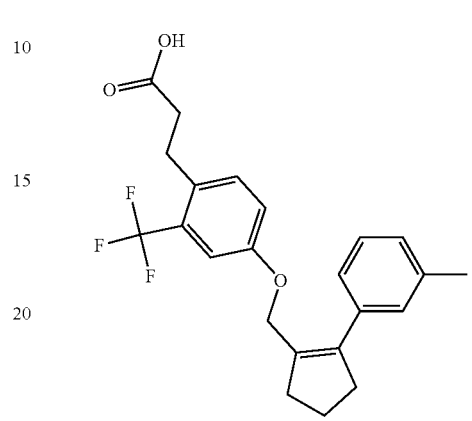

$^1$H NMR (400 MHz, CD$_3$OD) δ: 7.23-7.31 (m, 2H), 6.95-7.11 (m, 5H), 4.89 (s, 2H), 3.01 (t, J=8.0 Hz, 2H), 2.80 (t, J=7.6 Hz, 2H), 2.65 (t, J=7.2 Hz, 2H), 2.55 (d, J=8.0 Hz, 2H), 2.34 (s, 3H), 1.98-2.00 (m, 2H). $^{19}$F NMR (400 MHz, CD$_3$OD) δ: −61.34. Mass spectrum (ESI, m/z): Calculated for C$_{23}$H$_{23}$F$_3$O$_3$, 403.2 [M−H], Measured: 403.1.

Example 281: Compound #313

3-[4-[[2-(2-chlorophenyl)cyclopenten-1-yl]methoxy]-2-(trifluoromethyl)phenyl]Propanoic Acid

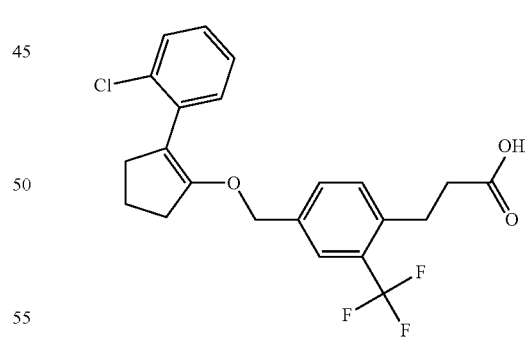

$^1$H NMR (400 MHz, CD$_3$OD) δ: 7.48 (d, J=8.4 Hz, 1H), 7.41-7.45 (m, 3H), 7.28-7.33 (m, 1H), 6.90-6.97 (m, 2H), 4.51 (s, 2H), 3.00 (t, J=7.6 Hz, 2H), 2.76 (t, J=7.6 Hz, 2H), 2.65 (t, J=7.2 Hz, 2H), 2.55 (t, J=8.0 Hz, 2H), 2.00-2.07 (m, 2H). $^{19}$F NMR (400 MHz, CD$_3$OD) δ: −61.34. Mass spectrum (ESI, m/z): Calculated for C$_{22}$H$_{20}$ClF$_3$O$_3$, 423.1 [M−H], Measured: 423.1.

Example 282: Compound #318

3-[5-fluoro-2-methyl-4-[[2-(m-tolyl)cyclopenten-1-yl]methoxy]phenyl]Propanoic Acid

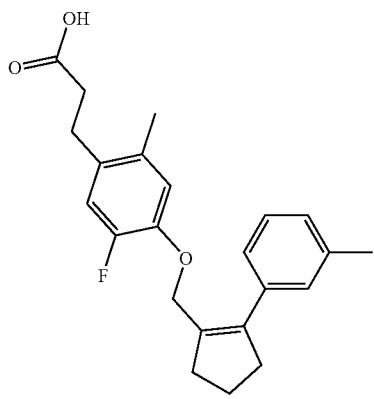 [SMILES: Cc1cccc(C2=C(COc3cc(C)c(CCC(=O)O)cc3F)CCC2)c1]

$^1$H NMR (300 MHz, CD$_3$OD) δ: 7.25-7.27 (m, 1H), 7.02-7.22 (m, 3H), 6.87 (d, J=12.6 Hz, 1H), 6.54 (d, J=8.7 Hz, 1H), 4.68 (s, 2H), 2.76-2.84 (m, 4H), 2.66 (t, J=7.4 Hz, 2H), 2.51 (t, J=7.6 Hz, 2H), 2.33 (s, 3H), 2.19 (s, 3H), 1.94-1.99 (m, 2H). $^{19}$F NMR (300 MHz, CD$_3$OD) δ: −140.71. Mass spectrum (ESI, m/z): Calculated for C$_{23}$H$_{25}$FO$_3$, 367.2 [M−H], Measured: 367.1

Example 283: Compound #325

3-[5-fluoro-2-methyl-4-[[2-[4-(trifluoromethoxy)phenyl]cyclopenten-1-yl]methoxy]phenyl]Propanoic Acid

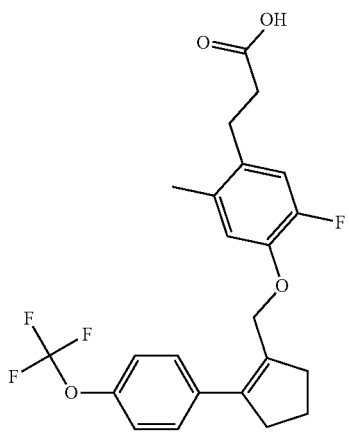 [SMILES: Cc1cc(OCC2=C(c3ccc(OC(F)(F)F)cc3)CCC2)c(F)cc1CCC(=O)O]

$^1$H NMR (300 MHz, CD$_3$OD) δ: 7.36 (d, J=6.6 Hz, 2H), 7.27 (d, J=8.1 Hz, 2H), 6.88 (d, J=12.3 Hz, 1H), 6.61 (d, J=8.7 Hz, 1H), 4.67 (s, 2H), 2.81 (t, J=7.5 Hz, 4H), 2.70 (t, J=7.2 Hz, 2H), 2.51 (t, J=7.2 Hz, 2H), 2.16 (s, 3H), 1.94-2.04 (m, 2H). $^{19}$F NMR (300 MHz, CD$_3$OD) δ: −59.46, −140.54. Mass spectrum (ESI, m/z): Calculated for C$_{23}$H$_{22}$F$_4$O$_4$, 437.1 [M−H], Measured: 437.1

Example 284: Compound #326

3-[5-fluoro-2-methyl-4-[[2-(p-tolyl)cyclopenten-1-yl]methoxy]phenyl]Propanoic Acid

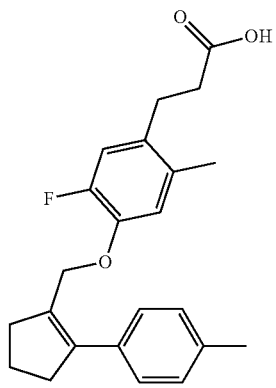 [SMILES: Cc1ccc(C2=C(COc3cc(C)c(CCC(=O)O)cc3F)CCC2)cc1]

$^1$H NMR (300 MHz, CD$_3$OD) δ: 7.12-7.20 (m, 4H), 6.87 (d, J=12.3 Hz, 1H), 6.55 (d, J=8.7 Hz, 1H), 4.68 (s, 2H), 2.75-2.83 (m, 4H), 2.65 (t, J=8.1 Hz, 2H), 2.50 (t, J=8.1 Hz, 2H), 2.34 (s, 3H), 2.13 (s, 3H), 1.91-2.01 (m, 2H). $^{19}$F NMR (300 MHz, CD$_3$OD) δ: −140.78. Mass spectrum (ESI, m/z): Calculated for C$_{23}$H$_{25}$FO$_3$, 367.2 [M−H], Measured: 367.1

Example 285: Compound #331

3-[4-[[2-(2-isopropyl-4-methyl-phenyl)cyclopenten-1-yl]methoxy]-2-(trifluoromethyl)phenyl]Propanoic Acid

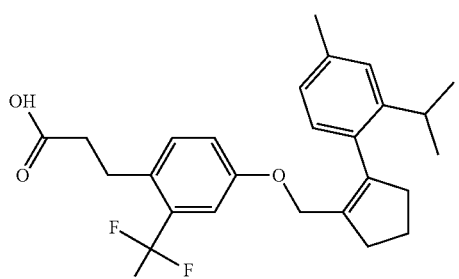

$^1$H NMR (400 MHz, CD$_3$OD) δ: 7.32 (d, J=8.4 Hz, 1H), 7.12 (d, J=7.2 Hz, 2H), 7.01 (s, 1H), 6.97-6.99 (m, 2H), 4.70 (s, 2H), 3.12-3.18 (m, 1H), 3.02 (t, J=7.6 Hz, 2H), 2.82 (t, J=7.2 Hz, 2H), 2.68 (t, J=7.4 Hz, 2H), 2.55 (t, J=8.0 Hz, 2H), 2.33 (s, 3H), 1.96-2.04 (m, 2H), 1.33 (d, J=3.2 Hz, 6H). $^{19}$F NMR (400 MHz, CD$_3$OD) δ: −61.35. Mass spectrum (ESI, m/z): Calculated for C$_{26}$H$_{29}$F$_3$O$_3$, 445.2 [M−H], Measured: 445.1

Example 286: Compound #339

3-[4-[[2-(5-chloro-2-fluoro-phenyl)cyclopenten-1-yl]methoxy]-5-fluoro-2-methyl-phenyl]Propanoic Acid

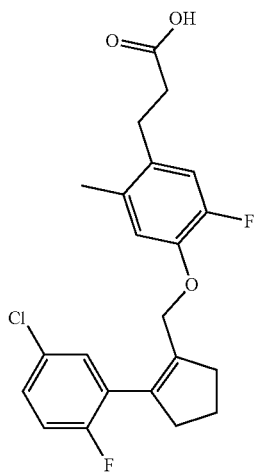 [SMILES: Cc1cc(OCC2=C(c3cc(Cl)ccc3F)CCC2)c(F)cc1CCC(=O)O]

$^1$H NMR (300 MHz, CD$_3$OD) δ: 7.28-7.31 (m, 1H), 7.09-7.17 (m, 2H), 6.86 (d, J=12.3 Hz, 1H), 6.59 (d, J=8.7 Hz, 1H), 4.55 (s, 2H), 2.64-2.84 (m, 6H), 2.51 (t, J=8.1 Hz, 2H), 2.17 (s, 3H), 1.98-2.03 (m, 2H). $^{19}$F NMR (300 MHz, CD$_3$OD) δ: −116.94, −137.78. Mass spectrum (ESI, m/z): Calculated for C$_{22}$H$_{21}$ClF$_2$O$_3$, 405.1 [M−H], Measured: 405.0

Example 287: Compound #340

3-[5-fluoro-4-[[2-(2-fluoro-5-methyl-phenyl)cyclopenten-1-yl]methoxy]-2-methyl-phenyl]Propanoic Acid

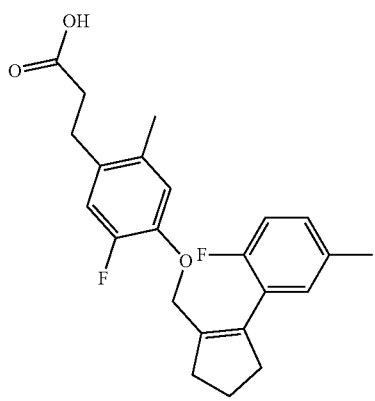 [SMILES: Cc1ccc(F)c(C2=C(COc3cc(C)c(CCC(=O)O)cc3F)CCC2)c1]

$^1$H NMR (400 MHz, CD$_3$OD) δ: 7.11-7.15 (m, 1H), 6.98-7.03 (m, 2H), 6.88 (d, J=12.4 Hz, 1H), 6.54 (d, J=8.4 Hz, 1H), 4.56 (s, 2H), 2.81 (t, J=8.4 Hz, 2H), 2.75 (t, J=7.6 Hz, 2H), 2.65 (t, J=7.6 Hz, 2H), 2.46 (t, J=7.6 Hz, 2H), 2.30 (s, 3H), 2.16 (s, 3H), 1.95-2.03 (m, 2H). 15 $^{19}$F NMR (400 MHz, CD$_3$OD) δ: −121.07, −140.77. Mass spectrum (ESI, m/z): Calculated for C$_{23}$H$_{24}$F$_2$O$_3$, 385.2 [M−H], Measured: 385.1

Example 288: Compound #341

3-[4-[[2-(2-fluoro-5-methyl-phenyl)cyclopenten-1-yl]methoxy]-2-(trifluoromethyl)phenyl]Propanoic Acid

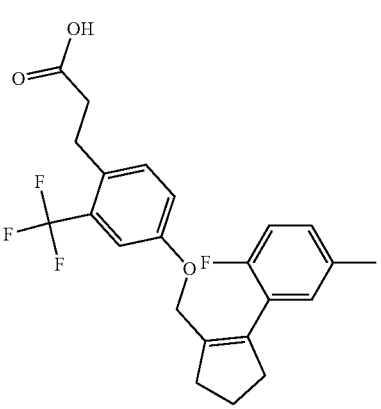 [SMILES: Cc1ccc(F)c(C2=C(COc3ccc(CCC(=O)O)c(C(F)(F)F)c3)CCC2)c1]

$^1$H NMR (400 MHz, CD$_3$OD) δ: 7.30 (d, J=8.4 Hz, 1H), 7.10-7.14 (m, 1H), 6.93-7.02 (m, 4H), 4.61 (s, 2H), 3.00 (t, J=7.6 Hz, 2H), 2.76 (t, J=7.6 Hz, 2H), 2.63 (t, J=7.6 Hz, 2H), 2.54 (t, J=7.6 Hz, 2H), 2.30 (s, 3H), 1.97-2.04 (m, 2H). $^{19}$F NMR (400 MHz, CD$_3$OD) δ: −61.36, −121.38. Mass spectrum (ESI, m/z): Calculated for C$_{23}$H$_{22}$F$_4$O$_3$, 421.2 [M−H], Measured: 421.0

Example 289: Compound #342

3-[2-chloro-4-[[2-(5-chloro-2-fluoro-phenyl)cyclopenten-1-yl]methoxy]phenyl]Propanoic Acid

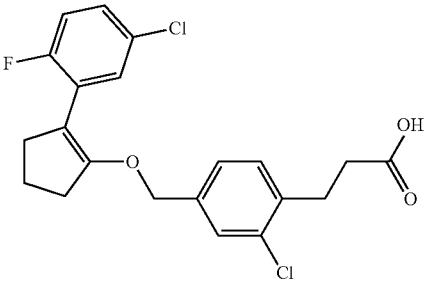 [SMILES: O=C(O)CCc1ccc(COC2=C(c3cc(Cl)ccc3F)CCC2)cc1Cl]

$^1$H NMR (300 MHz, CD$_3$OD) δ: 7.28-7.33 (m, 1H), 7.21 (d, J=6.0 Hz, 1H), 7.09-7.16 (m, 2H), 6.73 (s, 1H), 6.66 (d, J=8.4 Hz, 1H), 4.53 (s, 2H), 2.93 (t, J=7.5 Hz, 2H), 2.75 (t, J=7.2 Hz, 2H), 2.64 (t, J=7.5 Hz, 2H), 2.54 (t, J=7.5 Hz, 2H), 1.98-2.03 (m, 2H). $^{19}$F NMR (300 MHz, CD$_3$OD) δ: −116.90. Mass spectrum (ESI, m/z): Calculated for C$_{21}$H$_{19}$Cl$_2$FO$_3$, 407.1 [M−H], Measured: 407.0

Example 290: Compound #343

3-[2-chloro-4-[[2-(2-fluoro-5-methyl-phenyl)cyclo-penten-1-yl]methoxy]phenyl]Propanoic Acid

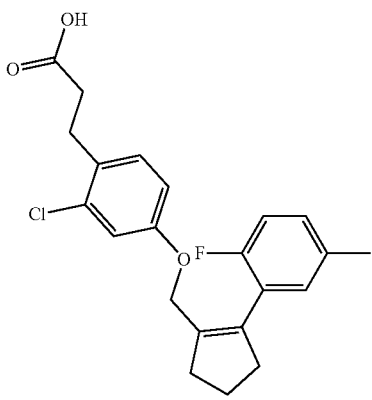 [SMILES: Cc1ccc(F)c(C2=C(COc3ccc(CCC(=O)O)c(Cl)c3)CCC2)c1]

$^1$H NMR (400 MHz, CD$_3$OD) δ: 7.11-7.16 (m, 2H), 6.98-7.03 (m, 2H), 6.74 (s, 1H), 6.67 (d, J=8.4 Hz, 1H), 4.53 (s, 2H), 2.94 (t, J=7.2 Hz, 2H), 2.76 (t, J=7.6 Hz, 2H), 2.63 (t, J=7.2 Hz, 2H), 2.55 (t, J=7.6 Hz, 2H), 2.31 (s, 3H), 1.96-2.04 (m, 2H). $^{19}$F NMR (400 MHz, CD$_3$OD) δ: −121.38. Mass spectrum (ESI, m/z): Calculated for C$_{22}$H$_{22}$ClFO$_3$, 387.1 (M−H), Measured: 387.0

Example 291: Compound #344

3-[4-[[2-(5-chloro-2-fluoro-phenyl)cyclopenten-1-yl]methoxy]-2-(trifluoromethyl)phenyl]Propanoic Acid

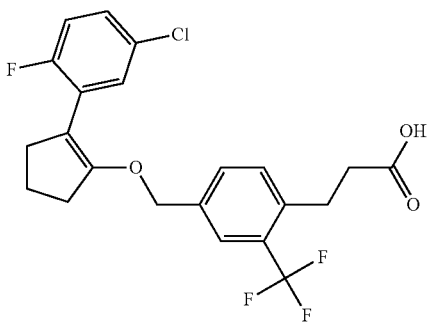 [SMILES: O=C(O)CCc1ccc(COC2=C(c3cc(Cl)ccc3F)CCC2)cc1C(F)(F)F]

$^1$H NMR (300 MHz, CD$_3$OD) δ: 7.33-7.38 (m, 2H), 7.26 (d, J=6.0 Hz, 1H), 7.17 (t, J=9.3 Hz, 2H), 6.97-7.00 (m, 2H), 4.66 (s, 2H), 3.05 (t, J=7.8 Hz, 2H), 2.81 (t, J=6.9 Hz, 2H), 2.70 (t, J=7.2 Hz, 2H), 2.59 (t, J=8.4 Hz, 2H), 2.02-2.12 (m, 2H). $^{19}$F NMR (300 MHz, CD$_3$OD) δ: −61.36, −118.44. Mass spectrum (ESI, m/z): Calculated for C$_{22}$H$_{19}$ClF$_4$O$_3$, 441.1 [M−H], Measured: 441.0

Example 292: Compound #349

3-[2-chloro-4-[[2-[(4-fluorophenyl)methyl]cyclo-penten-1-yl]methoxy]phenyl]Propanoic Acid

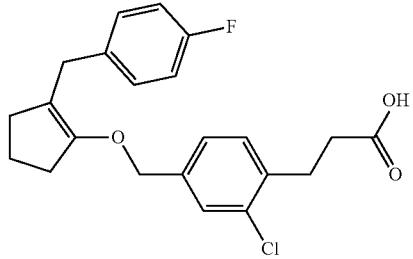 [SMILES: O=C(O)CCc1ccc(COC2=C(Cc3ccc(F)cc3)CCC2)cc1Cl]

$^1$H NMR (300 MHz, CD$_3$OD) δ: 7.10-7.19 (m, 3H), 6.82-6.97 (m, 3H), 6.78-6.82 (m, 1H), 4.65 (s, 2H), 3.29 (s, 2H), 2.93 (t, J=7.8 Hz, 2H), 2.45-2.56 (m, 4H), 2.12-2.24 (m, 2H), 1.73-1.81 (m, 2H). $^{19}$F NMR (300 MHz, CD$_3$OD) δ: −119.63. Mass spectrum (ESI, m/z): Calculated for C$_{22}$H$_{22}$ClFO$_3$, 387.1 [M−H], Measured: 387.0

Example 293: Compound #350

3-[5-fluoro-4-[[2-[(4-fluorophenyl)methyl]cyclo-penten-1-yl]methoxy]-2-methyl-phenyl]Propanoic Acid

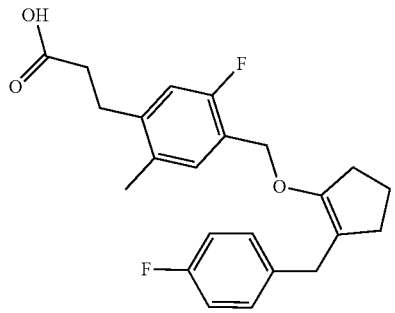 [SMILES: Cc1cc(COC2=C(Cc3ccc(F)cc3)CCC2)c(F)cc1CCC(=O)O]

$^1$H NMR (300 MHz, CD$_3$OD) δ: 7.04-7.09 (m, 2H), 6.85-6.95 (m, 4H), 4.69 (s, 2H), 3.43 (s, 2H), 2.81 (t, J=7.8 Hz, 2H), 2.47-2.53 (m, 4H), 2.18-2.21 (m, 5H), 1.71-1.81 (m, 2H). $^{19}$F NMR (300 MHz, CD$_3$OD) δ: −119.72, −140.21. Mass spectrum (ESI, m/z): Calculated for C$_{23}$H$_{24}$F$_2$O$_3$, 385.2 [M−H], Measured: 385.1.

Example 294: Compound #353

3-[4-[[2-[(4-fluorophenyl)methyl]cyclopenten-1-yl]methoxy]-2-(trifluoromethyl)phenyl]Propanoic Acid

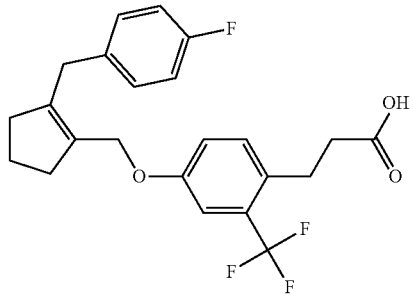

¹H NMR (300 MHz, CD₃OD) δ:7.24 (d, J=8.4 Hz, 1H), 7.01-7.08 (m, 4H), 6.85 (t, J=8.7 Hz, 2H), 4.75 (s, 2H), 3.39 (s, 2H), 3.21 (t, J=7.8 Hz, 2H), 2.43-2.48 (m, 4H), 2.15 (bs, 2H), 1.67-1.74 (m, 2H). Mass spectrum (ESI, m/z): Calculated for $C_{23}H_{22}F_4O_3$, 421.1 [M−H], Measured: 421.0

Example 295: Compound #356

3-[2-chloro-4-[[2-[(4-chlorophenyl)methyl]cyclopenten-1-yl]methoxy]phenyl]Propanoic Acid

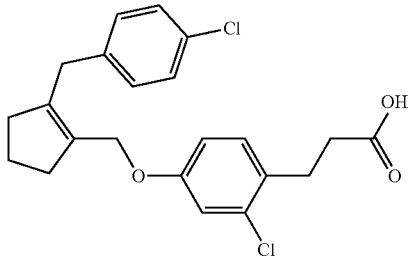 [SMILES: O=C(O)CCc1ccc(OCC2=C(Cc3ccc(Cl)cc3)CCC2)cc1Cl]

¹H NMR (400 MHz, CD₃OD) δ: 7.21-7.33 (m, 3H), 7.14 (d, J=8.4 Hz, 2H), 7.00 (s, 1H), 6.85 (d, J=8.4 Hz, 1H), 4.70 (s, 2H), 3.56 (s, 2H), 2.98 (t, J=7.6 Hz, 2H), 2.59 (t, J=8.0 Hz, 2H), 2.53 (t, J=6.4 Hz, 2H), 2.27 (t, J=7.6 Hz, 2H), 1.78-1.85 (m, 2H). Mass spectrum (ESI, m/z): Calculated for $C_{22}H_{22}Cl_2O_3$, 403.1 [M−H], Measured: 403.0

Example 296: Compound #359

3-[4-[[2-[(4-chlorophenyl)methyl]cyclopenten-1-yl]methoxy]-2-(trifluoromethyl)phenyl]Propanoic Acid

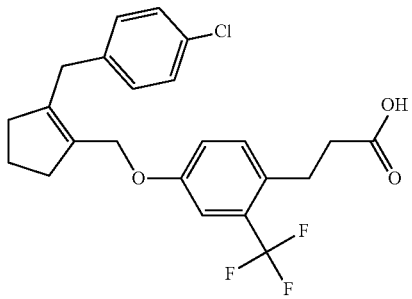 [SMILES: O=C(O)CCc1ccc(OCC2=C(Cc3ccc(Cl)cc3)CCC2)cc1C(F)(F)F]

¹H NMR (400 MHz, CD₃OD) δ: 7.26 (d, J=8.4 Hz, 1H), 7.14 (d, J=8.4 Hz, 2H), 7.08 (s, 1H), 7.01-7.03 (m, 3H), 4.64 (s, 2H), 3.41 (s, 2H), 2.92 (t, J=7.6 Hz, 2H), 2.40-2.47 (m, 4H), 2.16 (t, J=7.6 Hz, 2H), 1.62-1.77 (m, 2H). ¹⁹F NMR (400 MHz, CD₃OD) δ: −61.09. Mass spectrum (ESI, m/z): Calculated for $C_{23}H_{22}ClF_3O_3$, 437.1 [M−H], Measured: 437.0

Example 297: Compound #360

3-[4-[[2-[(4-chlorophenyl)methyl]cyclopenten-1-yl]methoxy]-5-fluoro-2-methyl-phenyl]Propanoic Acid

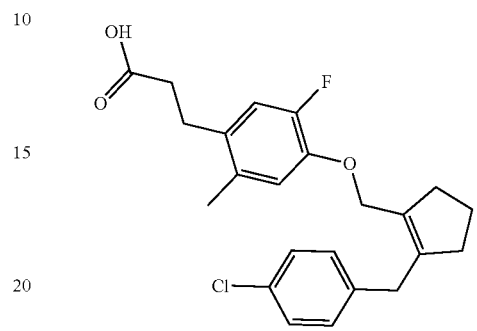

¹H NMR (400 MHz, CD₃OD) δ: 7.12 (d, J=8.4 Hz, 2H), 6.98 (d, J=8.4 Hz, 2H), 6.79-6.82 (m, 2H), 4.61 (s, 2H), 3.37 (s, 2H), 2.74 (t, J=7.6 Hz, 2H), 2.41-2.45 (m, 4H), 2.11-2.14 (m, 5H), 1.66-1.73 (m, 2H). ¹⁹F NMR (400 MHz, CD₃OD) δ: −140.25. Mass spectrum (ESI, m/z): Calculated for $C_{23}H_{24}ClFO_3$, 401.1 [M−H], Measured: 401.1

Example 298: Compound #361

3-[4-[[2-[(3-fluorophenyl)methyl]cyclopenten-1-yl]methoxy]-2-(trifluoromethyl)phenyl]Propanoic Acid

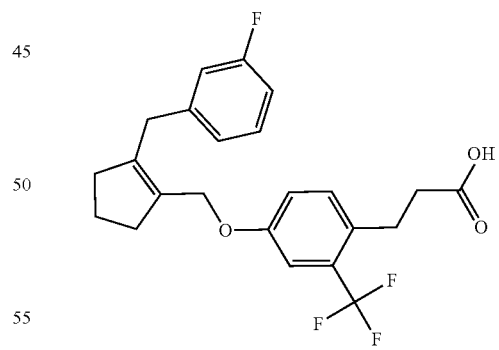

¹H NMR (400 MHz, CD₃OD) δ: 7.38 (d, J=8.4 Hz, 1H), 7.21-7.30 (m, 1H), 7.20 (s, 1H), 7.16-7.20 (m, 1H), 6.98 (d, J=7.6 Hz, 1H), 6.87-6.93 (m, 2H), 4.76 (s, 2H), 3.56 (s, 2H), 3.04 (t, J=7.6 Hz, 2H), 2.53-2.60 (m, 4H), 2.29 (t, J=7.2 Hz, 2H), 1.80-1.87 (m, 2H). ¹⁹F NMR (400 MHz, CD₃OD) δ: −61.34, −115.83. Mass spectrum (ESI, m/z): Calculated for $C_{23}H_{22}F_4O_3$, 421.1 [M−H], Measured: 421.0

Example 299: Compound #362

3-[2-chloro-4-[[2-[(3-fluorophenyl)methyl]cyclopenten-1-yl]methoxy]phenyl]Propanoic Acid

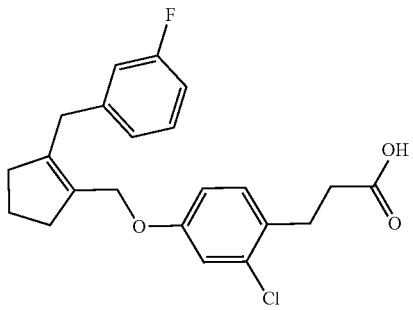 [SMILES: O=C(O)CCc1ccc(OCC2=C(Cc3cccc(F)c3)CCC2)cc1Cl]

¹H NMR (400 MHz, CD₃OD) δ: 7.22-7.30 (m, 2H), 6.98-7.08 (m, 2H), 6.85-6.94 (m, 3H), 4.71 (s, 2H), 3.55 (s, 2H), 2.98 (t, J=7.2 Hz, 2H), 2.52-2.61 (m, 4H), 2.29 (t, J=7.2 Hz, 2H), 1.80-1.87 (m, 2H). ¹⁹F NMR (400 MHz, CD₃OD) δ: −115.85. Mass spectrum (ESI, m/z): Calculated for $C_{22}H_{22}ClFO_3$, 387.1 [M−H] Measured: 387.0

Example 300: Compound #363

3-[5-fluoro-4-[[2-[(3-fluorophenyl)methyl]cyclopenten-1-yl]methoxy]-2-methyl-phenyl]Propanoic Acid

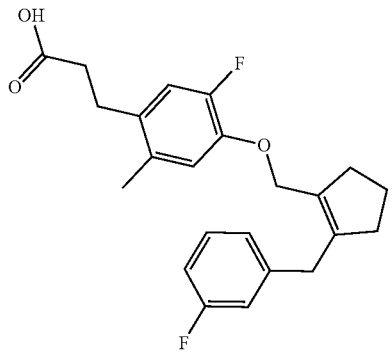 [SMILES: Cc1cc(OCC2=C(Cc3cccc(F)c3)CCC2)c(F)cc1CCC(=O)O]

¹H NMR (400 MHz, CD₃OD) δ: 7.23-7.28 (m, 1H), 6.88-6.96 (m, 4H), 6.81 (d, J=10.0 Hz, 1H), 4.75 (s, 2H), 3.52 (s, 2H), 2.86 (t, J=7.2 Hz, 2H), 2.53-2.59 (m, 4H), 2.24-2.28 (m, 5H), 1.79-1.86 (m, 2H). ¹⁹F NMR (400 MHz, CD₃OD) δ: −115.86, 140.11. Mass spectrum (ESI, m/z): Calculated for $C_{23}H_{24}F_2O_3$, 385.2 [M−H], Measured: 385.1

Example 301: Compound #404

3-[4-[[2-[(2-fluorophenyl)methyl]cyclopenten-1-yl]methoxy]-2-(trifluoromethyl)phenyl]Propanoic Acid

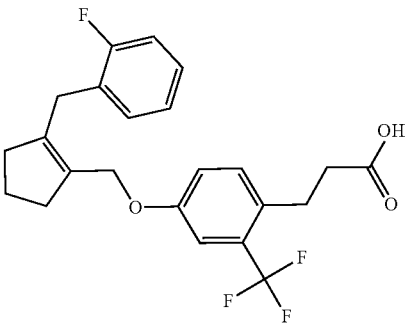 [SMILES: O=C(O)CCc1ccc(OCC2=C(Cc3ccccc3F)CCC2)cc1C(F)(F)F]

¹H NMR (300 MHz, CD₃OD) δ: 7.37 (d, J=8.7 Hz, 1H), 7.00-7.24 (m, 6H), 4.76 (s, 2H), 3.62 (s, 2H), 3.03 (t, J=7.8 Hz, 2H), 2.49-2.59 (m, 4H), 2.30 (t, J=6.9 Hz, 2H), 1.78-1.86 (m, 2H). ¹⁹F NMR (300 MHz, CD₃OD) δ: −61.40, −120.46. Mass spectrum (ESI, m/z): Calculated for $C_{23}H_{22}F_4O_3$, 421.2 [M−H], Measured: 421.1

Example 302: Compound #405

3-[4-[[2-(m-tolylmethyl)cyclopenten-1-yl]methoxy]-2-(trifluoromethyl)phenyl]Propanoic Acid

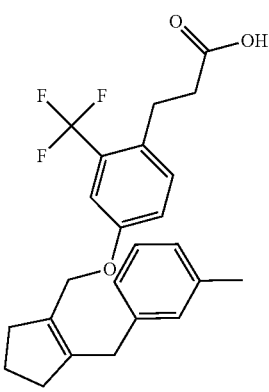 [SMILES: Cc1cccc(CC2=C(COc3ccc(CCC(=O)O)c(C(F)(F)F)c3)CCC2)c1]

¹H NMR (300 MHz, CD₃OD) δ: 7.31 (d, J=8.4 Hz, 1H), 7.06-7.15 (m, 3H), 6.87-6.95 (m, 3H), 4.69 (s, 2H), 3.42 (s, 2H), 2.98 (t, J=7.6 Hz, 2H), 2.45-2.55 (m, 4H), 2.21-2.23 (m, 5H), 1.70-1.80 (m, 2H). ¹⁹F NMR (300 MHz, CD₃OD) δ: −61.28. Mass spectrum (ESI, m/z): Calculated for $C_{24}H_{25}F_3O_3$, 417.2 [M−H], Measured: 417.1.

Example 303: Compound #406

3-[2-chloro-4-[[2-(m-tolylmethyl)cyclopenten-1-yl]methoxy]phenyl]Propanoic Acid

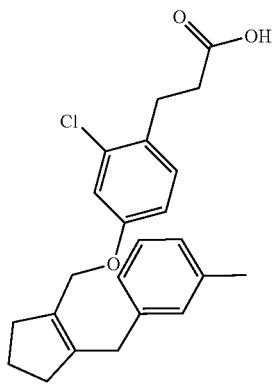 [SMILES: Cc1cccc(CC2=C(COc3ccc(CCC(=O)O)c(Cl)c3)CCC2)c1]

$^1$H NMR (300 MHz, CD$_3$OD) δ: 7.16 (d, J=8.4 Hz, 1H), 7.06-7.11 (m, 1H), 6.81-6.94 (m, 4H), 6.78-6.81 (m, 1H), 4.63 (s, 2H), 3.42 (s, 2H), 2.93 (t, J=7.6 Hz, 2H), 2.44-2.56 (m, 4H), 2.20-2.40 (m, 5H), 1.70-1.80 (m, 2H). Mass spectrum (ESI, m/z): Calculated for C$_{23}$H$_{25}$C$_1$O$_3$, 383.1 [M−H], Measured: 383.1.

Example 304: Compound #43

3-[4-[[2-(4-fluorophenyl)cyclopenten-1-yl]methoxy]phenyl]Propanoic Acid

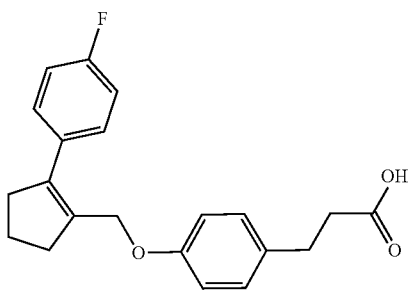 [SMILES: O=C(O)CCc1ccc(OCC2=C(c3ccc(F)cc3)CCC2)cc1]

$^1$H NMR (300 MHz, CDCl$_3$) δ: 7.18-7.23 (m, 2H), 7.00-7.16 (m, 4H), 6.75-6.80 (m, 2H), 4.57 (s, 2H), 2.84-2.89 (m, 2H), 2.76-2.81 (m, 2H), 2.59-2.71 (m, 4H), 1.93-2.03 (m, 2H). $^{19}$F NMR (300 MHz, CDCl$_3$) δ: −114.94. Mass spectrum (ESI, m/z): Calculated for C$_{21}$H$_{21}$FO$_3$, 339.1 [M−H], Measured: 339.0

Example 305: Compound #52

3-[2,3-dimethyl-4-[[2-(p-tolyl)cyclopenten-1-yl]methoxy]phenyl]Propanoic Acid

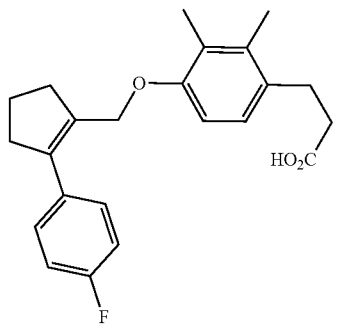 [SMILES: Cc1c(CCC(=O)O)ccc(OCC2=C(c3ccc(F)cc3)CCC2)c1C]

The title compound was prepared according to the process as described above in Example 70 substituting (4-methylphenyl)boronic acid for (4-ethylphenyl)boronic acid in Step 1, and following the procedures in Steps 2 to 4, as described.

$^1$H NMR (300 MHz, CDCl$_3$) δ: 7.15 (s, 4H), 6.90 (d, J=8.4 Hz, 1H), 6.54 (d, J=8.1 Hz, 1H), 4.62 (s, 2H), 2.95-2.90 (m, 2H), 2.78-2.83 (m, 2H), 2.69-2.73 (m, 2H), 2.58 (t, J=7.5 Hz, 2H), 2.35 (s, 3H), 2.22 (s, 3H), 2.19 (s, 3H), 1.88-2.03 (m, 2H). Mass spectrum (ESI, m/z): Calculated for C$_{24}$H$_{28}$O$_3$, 363.2 [M−H], Measured: 363.2.

Example 306: Compound #70

3-[4-[[2-(4-chlorophenyl)cyclopenten-1-yl]methoxy]-2,3-difluoro-phenyl]Propanoic Acid

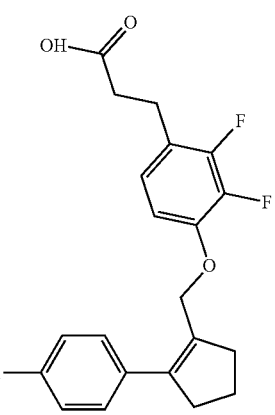

$^1$H NMR (CDCl$_3$, 300 MHz) δ: 7.17-7.26 (m, 4H), 6.90 (d, J=8.4 Hz, 1H), 6.55 (d, J=8.4 Hz, 1H), 4.61 (s, 2H), 2.92-3.18 (m, 2H), 2.76-2.87 (m, 2H), 2.64-2.73 (m, 4H), 1.95-2.05 (m, 2H). Mass spectrum (ESI, m/z): Calculated for C$_{21}$H$_{19}$ClF$_2$O$_3$, 391.1 [M−H], Measured: 391.1.

Example 307: Compound #524

3-[5-iodo-4-[[2-(4-iodophenyl)cyclohexen-1-yl]methoxy]-2,3-dimethyl-phenyl]Propanoic Acid

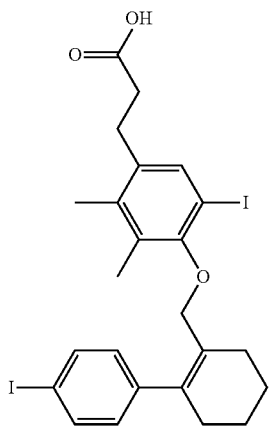 [SMILES: Cc1c(CCC(=O)O)cc(I)c(OCC2=C(c3ccc(I)cc3)CCCC2)c1C]

$^1$H NMR (CHLOROFORM-d) δ: 7.59 (d, J=8.6 Hz, 2H), 7.37 (s, 1H), 6.86 (d, J=8.6 Hz, 2H), 4.11 (s, 2H), 2.79-2.88 (m, 2H), 2.49-2.64 (m, 5H), 2.28 (br s, 2H), 2.10 (s, 3H), 1.97 (s, 3H), 1.71-1.85 (m, 5H). Calculated for $C_{24}H_{26}I_2O_3$: 639.0 (M+23); Measured: 638.8.

Example 308: Compound #39

3-[4-[[2-(4-chlorophenyl)cyclopenten-1-yl]methoxy]-2-(trifluoromethyl)phenyl]Propanoic Acid

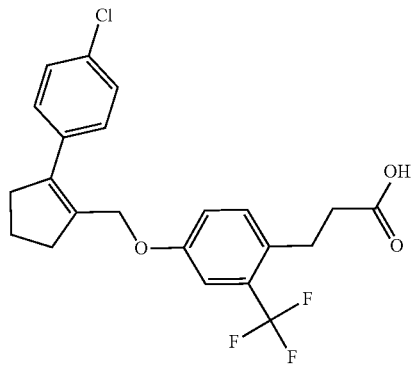 [SMILES: O=C(O)CCc1ccc(OCC2=C(c3ccc(Cl)cc3)CCC2)cc1C(F)(F)F]

$^1$H NMR (CHLOROFORM-d) δ: 7.29-7.35 (m, 2H), 7.22 (d, J=8.6 Hz, 1H), 7.14-7.20 (m, 2H), 7.08 (d, J=2.5 Hz, 1H), 6.91 (dd, J=8.3, 2.8 Hz, 1H), 4.62 (s, 2H), 3.05 (t, J=7.8 Hz, 2H), 2.79 (br t, J=7.3 Hz, 2H), 2.58-2.72 (m, 4H), 1.92-2.05 (m, 2H). Calculated for $C_{22}H_{20}ClF_3O_3$: 447.1 (M+23); Measured: 447.1.

Example 309: Compound #514

3-[7-[[2-(4-chlorophenyl)cyclohexen-1-yl]methoxy]indan-4-yl]Propanoic Acid

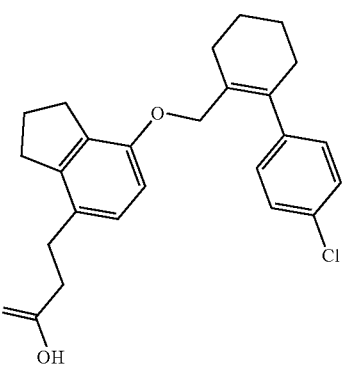

$^1$H NMR (300 MHz, CDCl$_3$) δ: 7.25 (d, J=8.4 Hz, 2H), 7.10 (d, J=8.1 Hz, 2H), 6.85 (d, J=8.4 Hz, 1H), 6.40 (d, J=8.1 Hz, 1H), 4.26 (s, 2H), 2.82-2.89 (m, 6H), 2.58 (t, J=8.1 Hz, 2H), 2.29 (br s, 4H), 2.07 (t, J=7.5 Hz, 2H), 1.74 (br s, 4H). Mass spectrum (ESI, m/z): Calculated for $C_{25}H_{27}ClO_3$, 409.2 [M−H], Measured: 409.3

Example 310: Compound #460

3-[2,3-dimethyl-4-[[2-[4-(trifluoromethyl)phenyl]cyclohexen-1-yl]methoxy]phenyl]Propanoic Acid

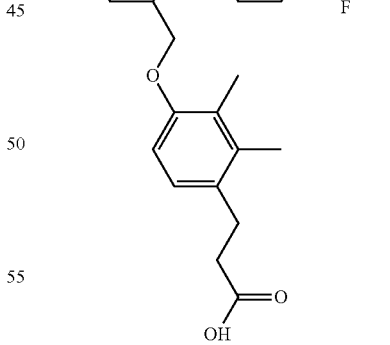

$^1$H NMR (300 MHz, CDCl$_3$) δ 7.55 (d, J=8.1 Hz, 2H), 7.30 (d, J=8.1 Hz, 2H), 6.43 (d, J=8.4 Hz, 1H), 6.33 (d, J=8.1 Hz, 1H), 4.23 (s, 2H), 3.45 (t, J=6.3 Hz, 2H), 2.57 (t, J=7.5 Hz, 2H), 2.43-2.49 (m, 4H), 2.27 (s, 3H), 2.19 (s, 3H), 2.01-2.22 (m, 4H). Mass spectrum (ESI, m/z): Calculated for $C_{25}H_{27}F_3O_3$, 431.2 [M−H], Measured: 431.2.

Example 311: Compound #461

3-[4-[[2-(4-ethoxyphenyl)cyclohexen-1-yl]methoxy]-2,3-dimethyl-phenyl]Propanoic Acid

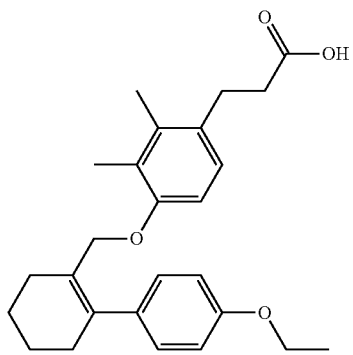

$^1$H NMR (300 MHz, CDCl$_3$) δ: 7.11 (d, J=6.9 Hz, 2H), 6.82-6.89 (m, 3H), 6.45 (d, J=8.4 Hz, 1H), 4.29 (s, 2H), 3.99-4.06 (m, 2H), 2.92 (t, J=7.5 Hz, 2H), 2.55-2.60 (t, J=7.5 Hz, 2H), 2.32 (s, 4H), 2.22 (d, J=6.3 Hz, 6H), 1.75 (s, 4H), 1.41 (t, J=6.9 Hz, 3H). Mass spectrum (ESI, m/z): Calculated for C$_{26}$H$_{32}$O$_4$, 407.2 [M–H], Measured: 407.3.

Example 312: Compound #462

3-[2,3-dimethyl-4-[[2-(p-tolyl)cyclohexen-1-yl]methoxy]phenyl]Propanoic Acid

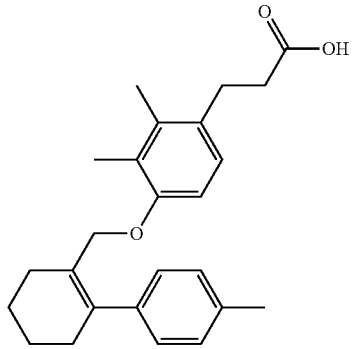 [SMILES: Cc1ccc(C2=C(COc3ccc(CCC(=O)O)c(C)c3C)CCCC2)cc1]

$^1$H NMR (300 MHz, CDCl$_3$) δ: 7.06-7.13 (m, 4H), 6.87 (d, J=8.4 Hz, 1H), 6.45 (d, J=8.4 Hz, 1H), 4.29 (s, 2H), 2.89 (t, J=7.5 Hz, 2H), 2.58 (t, J=7.5 Hz, 2H), 2.43 (br s, 7H), 2.21 (s, 3H), 2.13 (s, 3H), 1.76 (br s, 4H). Mass spectrum (ESI, m/z): Calculated for C$_{25}$H$_{30}$O$_3$, 377.2 [M–H], Measured: 377.1.

Example 313: Compound #463

3-[2,3-dimethyl-4-[[2-(4-propylphenyl)cyclohexen-1-yl]methoxy]phenyl]Propanoic Acid

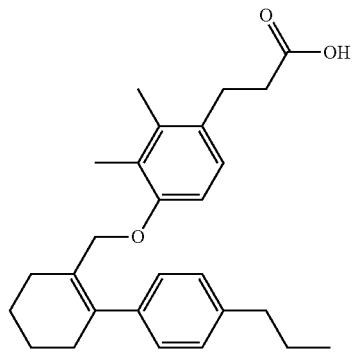 [SMILES: CCCc1ccc(C2=C(COc3ccc(CCC(=O)O)c(C)c3C)CCCC2)cc1]

$^1$H NMR (300 MHz, CDCl$_3$) δ: 7.12-7.05 (m, 4H), 6.85 (d, J=8.4 Hz, 1H), 6.44 (d, J=8.4 Hz, 1H), 4.28 (s, 2H), 2.90 (t, J=7.5 Hz, 2H), 2.53-2.58 (m, 4H), 2.30-2.41 (m, 4H), 2.20 (s, 3H), 2.18 (s, 3H), 2.19 (d, J=6.3 Hz, 6H), 1.75 (br s, 4H), 1.57-1.70 (m, 2H), 0.94 (t, J=7.2 Hz, 3H). Mass spectrum (ESI, m/z): Calculated for C$_{27}$H$_{34}$O$_3$, 405.3 (M–H), Measured: 405.4.

Example 314: Compound #464

3-[4-[[2-(2-chlorophenyl)cyclohexen-1-yl]methoxy]-2,3-dimethyl-phenyl]Propanoic Acid

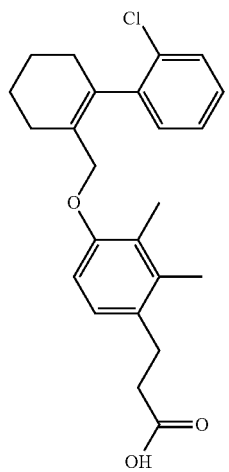 [SMILES: Cc1c(CCC(=O)O)ccc(OCC2=C(c3ccccc3Cl)CCCC2)c1C]

$^1$H NMR (300 MHz, CDCl$_3$) δ: 7.33-7.39 (m, 2H), 7.11-7.22 (m, 3H), 6.86 (d, J=8.4 Hz, 1H), 6.45 (d, J=8.4 Hz, 1H), 4.15 (s, 2H), 2.91 (t, J=7.5 Hz, 2H), 2.58 (t, J=7.5 Hz, 2H), 2.29-2.42 (m, 3H), 2.02-2.16 (m, 7H), 1.63-1.83 (m, 4H). Mass spectrum (ESI, m/z): Calculated for C$_{24}$H$_{27}$ClO$_3$, 397.2 [M–H], Measured: 397.2.

Example 315: Compound #465

3-[2,3-dimethyl-4-[[2-(4-pyridyl)cyclohexen-1-yl]methoxy]phenyl]Propanoic Acid

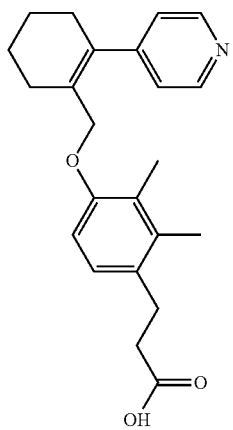 [SMILES: Cc1c(CCC(=O)O)ccc(OCC2=C(c3ccncc3)CCCC2)c1C]

$^1$H NMR (300 MHz, CDCl$_3$) δ 8.60 (d, J=6.4 Hz, 2H), 7.38 (d, J=6.6 Hz, 2H), 6.88 (d, J=8.4 Hz, 1H), 6.38 (d, J=8.4 Hz, 1H), 4.21 (s, 2H), 2.93 (t, J=7.5 Hz, 2H), 2.59 (t, J=7.7 Hz, 2H), 2.32-2.40 (m, 4H), 2.22 (s, 3H), 2.14 (s, 3H), 1.79 (br s, 4H). Mass spectrum (ESI, m/z): Calculated for C$_{23}$H$_{27}$NO$_3$, 366.2 [M+H], Measured: 366.2.

Example 316: Compound #466

3-[2,3-dimethyl-4-[[2-[4-(trifluoromethoxy)phenyl]cyclohexen-1-yl]methoxy]phenyl]Propanoic Acid

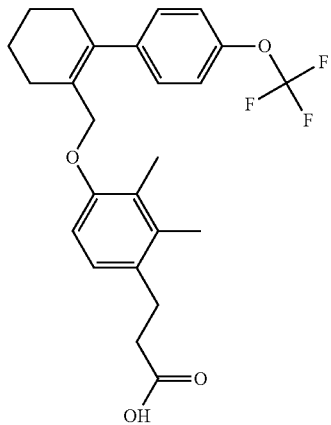 [SMILES: Cc1c(CCC(=O)O)ccc(OCC2=C(c3ccc(OC(F)(F)F)cc3)CCCC2)c1C]

$^1$H NMR (300 MHz, CDCl$_3$) δ: 7.13-7.21 (m, 4H), 6.58 (d, J=8.4 Hz, 1H), 6.44 (d, J=8.4 Hz, 1H), 4.24 (s, 2H), 2.92 (t, J=7.5 Hz, 2H), 2.58 (t, J=7.5 Hz, 2H), 2.33 (br s, 4H), 2.22 (s, 3H), 2.18 (s, 3H), 1.77 (br s, 4H). Mass spectrum (ESI, m/z): Calculated for C$_{25}$H$_{27}$F$_3$O$_4$, 447.2 [M−H], Measured: 447.3.

Example 317: Compound #475

3-[2,3-dimethyl-4-[(2-pyrimidin-2-ylcyclohexen-1-yl)methoxy]phenyl]Propanoic Acid

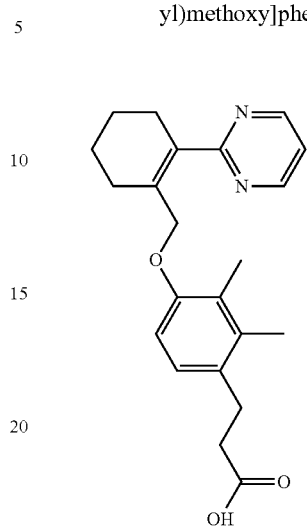

$^1$H NMR (300 MHz, CD$_3$OD) δ: 8.79 (d, J=5.1 Hz, 2H), 7.35 (t, J=5.1 Hz, 1H), 6.84 (d, J=8.4 Hz, 1H), 6.46 (d, J=8.1 Hz, 1H), 4.57 (s, 2H), 2.83-3.09 (m, 2H), 2.40-2.54 (m, 6H), 2.27 (s, 3H), 2.06 (s, 3H), 1.81 (br s, 4H). Mass spectrum (ESI, m/z): Calculated for C$_{22}$H$_{26}$N$_2$O$_3$, 365.2 [M−H], Measured: 365.1.

Example 318: Compound #476

3-[4-[[2-(4-iodophenyl)cyclohexen-1-yl]methoxy]-2,3-dimethyl-phenyl]Propanoic Acid

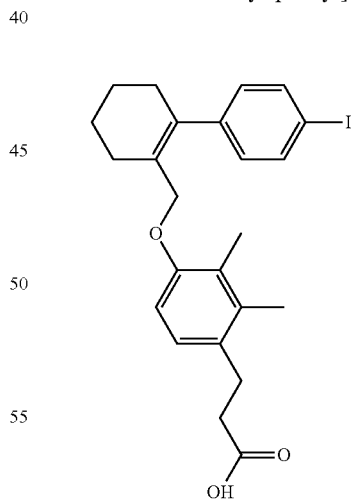

$^1$H NMR (300 MHz, CD$_3$OD) δ: 7.65 (d, J=6.3 Hz, 2H), 6.94 (d, J=6.3 Hz, 2H), 6.88 (d, J=6.3 Hz, 2H), 6.40 (d, J=6.3 Hz, 2H), 4.247 (s, 2H), 2.86 (t, J=6.2 Hz, 2H), 2.38-2.33 (m, 6H), 2.29 (s, 3H), 2.23 (s, 3H), 1.78 (s, 4H). Mass spectrum (ESI, m/z): Calculated for C$_{24}$H$_{27}$IO$_3$, 489.1 [M−H], Measured: 489.2.

Example 319: Compound #479

3-[4-[[2-(4-chlorophenyl)cyclohexen-1-yl]methoxy]-2,3,5,6-tetrafluoro-phenyl]Propanoic Acid

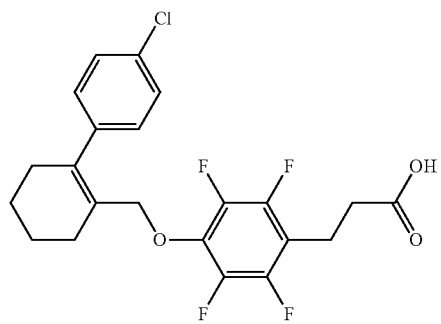 [SMILES: O=C(O)CCc1c(F)c(F)c(OCC2=C(c3ccc(Cl)cc3)CCCC2)c(F)c1F]

$^1$H NMR (300 MHz, CD$_3$OD) δ: 7.22 (d, J=8.7 Hz, 1H), 6.88 (d, J=8.7 Hz, 2H), 4.43 (s, 2H), 2.90 (t, J=7.5 Hz, 2H), 2.58 (t, J=7.5 Hz, 2H), 2.37 (br s, 2H), 2.24 (br s, 2H), 1.60-1.80 (m, 4H). Mass spectrum (ESI, m/z): Calculated for C$_{22}$H$_{19}$ClF$_4$O$_3$, 441.1 [M−H], Measured: 441.2

Example 320: Compound #480

3-[4-[[2-(4-fluorophenyl)cyclohexen-1-yl]methoxy]-2,3-dimethyl-phenyl]Propanoic Acid

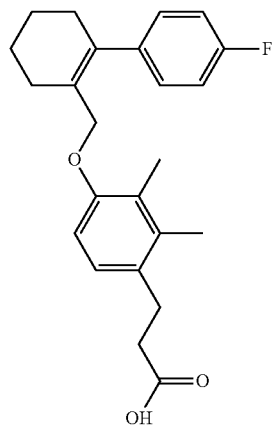 [SMILES: Cc1c(CCC(=O)O)ccc(OCC2=C(c3ccc(F)cc3)CCCC2)c1C]

$^1$H NMR (300 MHz, CDCl$_3$) δ: 7.13 (d, J=6.9 Hz, 2H), 6.97 (t, J=8.7 Hz, 2H), 6.88 (d, J=8.7 Hz, 1H), 6.43 (d, J=8.4 Hz, 1H), 4.23 (s, 2H), 2.91 (t, J=7.5 Hz, 2H), 2.56 (t, J=7.5 Hz, 2H), 2.31 (s, 4H), 2.19 (d, J=6.3 Hz, 6H), 1.75 (br s, 4H). Mass spectrum (ESI, m/z): Calculated for C$_{24}$H$_{27}$FO$_3$, 381.2 [M−H], Measured: 381.6.

Example 321: Compound #481

3-[4-[[2-(4-bromophenyl)cyclohexen-1-yl]methoxy]-2,3-dimethyl-phenyl]Propanoic Acid

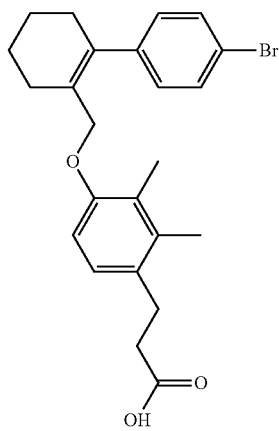 [SMILES: Cc1c(CCC(=O)O)ccc(OCC2=C(c3ccc(Br)cc3)CCCC2)c1C]

$^1$H NMR (300 MHz, CDCl$_3$) δ: 7.42 (d, J=7.8 Hz, 2H), 7.04-7.08 (t, J=8.4 Hz, 2H), 6.91 (d, J=8.4 Hz, 1H), 6.42 (d, J=8.4 Hz, 1H), 4.24 (s, 2H), 2.93 (t, J=7.5 Hz, 2H), 2.58 (t, J=7.5 Hz, 2H), 2.32 (br s, 5H), 2.22 (s, 3H), 2.19 (s, 3H), 1.77 (br s, 4H). Mass spectrum (ESI, m/z): Calculated for C$_{24}$H$_{27}$BrO$_3$, 441.1 [M−H], Measured: 441.3.

Example 322: Compound #482

3-[2,3-dimethyl-4-[[2-(2-thienyl)cyclohexen-1-yl]methoxy]phenyl]Propanoic Acid

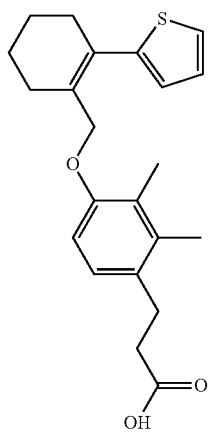 [SMILES: Cc1c(CCC(=O)O)ccc(OCC2=C(c3cccs3)CCCC2)c1C]

$^1$H NMR (300 MHz, CDCl3) δ: 7.24 (d, J=8.1 Hz, 1H), 6.90-6.98 (m, 3H), 6.55 (d, J=8.4 Hz, 1H), 4.51 (s, 2H), 2.94 (t, J=7.5 Hz, 2H), 2.59 (t, J=7.5 Hz, 2H), 2.44 (br s, 2H), 2.35 (br s, 2H), 2.19 (s, 3H), 2.11 (s, 3H), 1.74-1.76 (m, 4H). Mass spectrum (ESI, m/z): Calculated for C$_{22}$H$_{26}$O$_3$S, 393.2 [M+Na], Measured: 393.4.

Example 323: Compound #490

3-[2,3-dimethyl-4-[[2-(2-pyridyl)cyclohexen-1-yl]methoxy]phenyl]Propanoic Acid

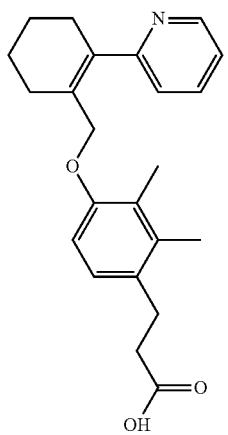 [SMILES: Cc1c(CCC(=O)O)ccc(OCC2=C(c3ccccn3)CCCC2)c1C]

$^1$H NMR (300 MHz, CD$_3$OD) δ: 8.52 (d, J=5.4 Hz, 1H), 7.76-7.81 (m, 1H), 7.28-7.34 (m, 2H), 6.85 (d, J=8.4 Hz, 1H), 6.40 (d, J=8.4 Hz, 1H), 4.29 (s, 2H), 2.87 (t, J=7.8 Hz, 2H), 2.39-2.49 (m, 6H), 2.21 (s, 3H), 2.12 (s, 3H), 1.82 (br s, 4H). Mass spectrum (ESI, m/z): Calculated for C$_{23}$H$_{27}$NO$_3$, 364.2 [M−H], Measured: 364.1.

Example 324: Compound #492

3-[2,3-dimethyl-4-[[2-(4-methylsulfanylphenyl)cyclohexen-1-yl]methoxy]phenyl]Propanoic Acid

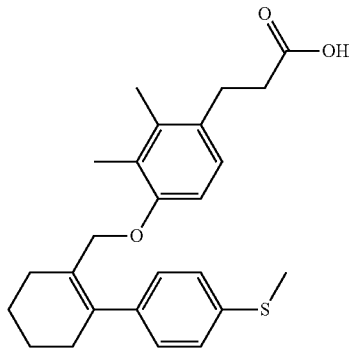 [SMILES: CSc1ccc(C2=C(COc3ccc(CCC(=O)O)c(C)c3C)CCCC2)cc1]

$^1$H NMR (300 MHz, CD$_3$OD) δ: 7.27 (d, J=8.4 Hz, 2H), 7.20 (d, J=8.1 Hz, 2H), 6.84 (d, J=8.4 Hz, 1H), 6.39 (d, J=8.4 Hz, 1H), 4.27 (s, 2H), 2.87 (t, J=8.4 Hz, 2H), 2.42-2.50 (m, 5H), 2.32 (br s, 4H), 2.21 (s, 3H), 2.14 (s, 3H), 1.30 (br s, 4H). Mass spectrum (ESI, m/z): Calculated for C$_{25}$H$_{30}$O$_3$S, 409.2[M−H], Measured: 409.2

Example 325: Compound #495

3-[4-[[2-(4-acetamidophenyl)cyclohexen-1-yl]methoxy]-2,3-dimethyl-phenyl]Propanoic Acid

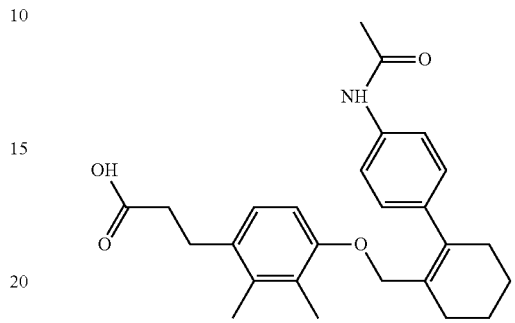

$^1$H NMR (300 MHz, CD$_3$OD) δ: 7.38 (d, J=8.4 Hz, 2H), 7.01 (d, J=8.4 Hz, 2H), 6.74 (d, J=8.4 Hz, 1H), 6.30 (d, J=8.4 Hz, 1H), 4.18 (s, 2H), 2.77 (t, J=7.8 Hz, 2H), 2.37 (t, J=7.8 Hz, 2H), 2.23 (br s, 4H), 2.23 (s, 3H), 2.05 (s, 3H), 2.02 (s, 3H), 1.67 (s, 4H). Mass spectrum (ESI, m/z): Calculated for C$_{26}$H$_{31}$NO$_4$, 420.2 [M−H], Measured: 420.2.

Example 326: Compound #504

3-[4-[[2-(4-chlorophenyl)cyclohexen-1-yl]methoxy]-2-fluoro-phenyl]Propanoic Acid

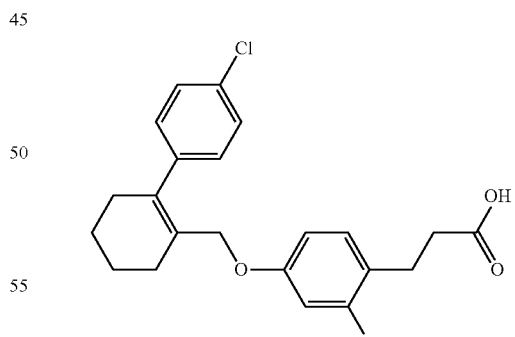

$^1$H NMR (300 MHz, CDCl$_3$) δ: 7.28 (t, J=7.2 Hz, 2H), 7.02-7.09 (m, 3H), 6.42-6.49 (m, 2H), 4.23 (s, 2H), 2.88 (t, J=7.8 Hz, 2H), 2.63 (t, J=7.8 Hz, 2H), 2.26-2.30 (m, 4H), 1.74-1.75 (m, 4H). Mass spectrum (ESI, m/z): Calculated for C$_{22}$H$_{22}$ClFO$_3$, 387.1 [M−H], Measured: 387.2

Example 327: Compound #506

3-[4-[[2-(4-chlorophenyl)cyclohexen-1-yl]methoxy]-2-methyl-phenyl]Propanoic Acid

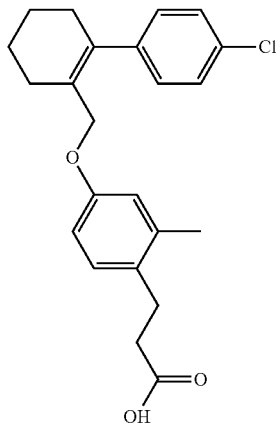 [SMILES: Cc1cc(OCC2=C(c3ccc(Cl)cc3)CCCC2)ccc1CCC(=O)O]

¹H NMR (300 MHz, CDCl₃) δ: 7.28 (d, J=6.6 Hz, 2H), 7.12 (d, J=8.4 Hz, 2H), 7.01 (d, J=8.4 Hz, 1H), 6.55-6.61 (m, 2H), 4.24 (s, 2H), 2.88 (t, J=7.8 Hz, 2H), 2.60 (t, J=7.8 Hz, 2H), 2.30 (br s, 4H), 2.26 (s, 3H), 1.76 (br s, 4H). Mass spectrum (ESI, m/z): Calculated for $C_{23}H_{25}ClO_3$, 383.1 [M−H], Measured: 383.3

Example 328: Compound #507

3-[2,3-dimethyl-4-[[2-(4-methylsulfinylphenyl)cyclohexen-1-yl]methoxy]phenyl]Propanoic Acid

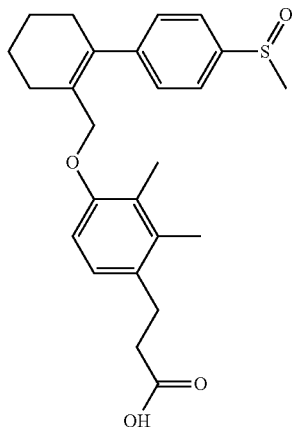 [SMILES: Cc1c(CCC(=O)O)ccc(OCC2=C(c3ccc(S(C)=O)cc3)CCCC2)c1C]

¹H NMR (300 MHz, CDCl₃) δ 7.55 (d, J=8.1 Hz, 2H), 7.27 (d, J=8.1 Hz, 2H), 6.87 (d, J=8.4 Hz, 1H), 6.39 (d, J=8.4 Hz, 1H), 4.23 (s, 2H), 2.96 (t, J=7.5 Hz, 2H), 2.90 (s, 3H), 2.74 (t, J=7.8 Hz, 2H), 2.37-2.58 (m, 4H), 2.34 (s, 3H), 2.23 (s, 3H), 1.79 (br s, 4H). Mass spectrum (ESI, m/z): Calculated for $C_{25}H_{30}O_4S$, 427.2 [M+H], Measured: 427.1.

Example 329: Compound #509

3-[4-[[2-(3-chlorophenyl)cyclohexen-1-yl]methoxy]-2,3-dimethyl-phenyl]Propanoic Acid

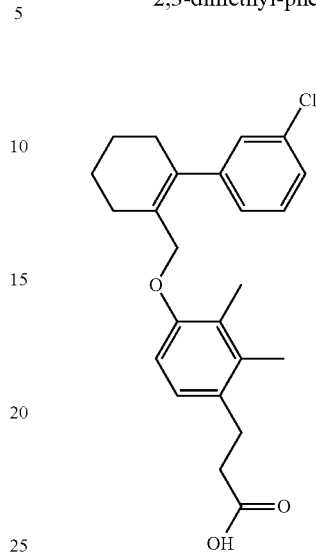

¹H NMR (300 MHz, CDCl₃) δ: 7.17-7.30 (m, 3H), 7.04-7.08 (m, 1H), 6.88 (d, J=6.6 Hz, 1H), 6.45 (d, J=8.4 Hz, 1H), 4.25 (s, 2H), 2.92 (t, J=7.5 Hz, 2H), 2.58 (t, J=7.5 Hz, 2H), 2.32 (br s, 4H), 2.22 (s, 3H), 2.19 (s, 3H), 1.27 (br s, 4H). Mass spectrum (ESI, m/z): Calculated for $C_{24}H_{27}ClO_3$, 397.2 [M−H], Measured: 397.2.

Example 330: Compound #510

3-[4-[[2-(4-chlorophenyl)cyclohexen-1-yl]methoxy]-3,5-difluoro-phenyl]Propanoic Acid

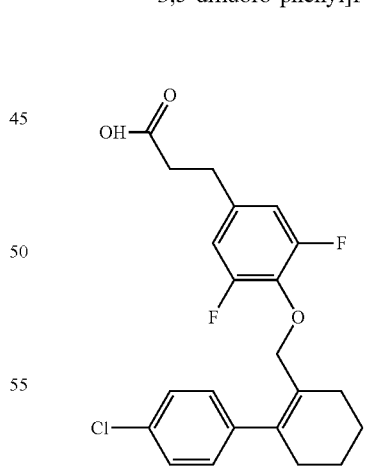

¹H NMR (300 MHz, CDCl₃) δ: 7.25 (d, J=8.4 Hz, 2H), 7.02 (d, J=6.6 Hz, 2H), 6.70 (d, J=8.7 Hz, 2H), 4.31 (s, 2H), 2.87 (t, J=7.5 Hz, 2H), 2.64 (t, J=7.5 Hz, 2H), 2.40 (br s, 2H), 2.27 (br s, 2H), 1.70-1.75 (m, 4H). Mass spectrum (ESI, m/z): Calculated for $C_{22}H_{21}ClF_2O_3$, 405.1 [M−H], Measured: 405.3

Example 331: Compound #511

3-[4-[[2-(4-chlorophenyl)cyclohexen-1-yl]methoxy]-3-fluoro-phenyl]Propanoic Acid

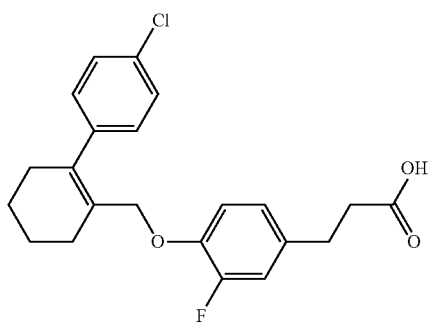 [SMILES: O=C(O)CCc1ccc(OCC2=C(c3ccc(Cl)cc3)CCCC2)c(F)c1]

¹H NMR (300 MHz, CDCl₃) δ 7.28 (d, J=9.3 Hz, 2H), 7.10 (d, J=8.3 Hz, 2H), 6.91 (d, J=12.0 Hz, 1H), 6.80 (d, J=8.4 Hz, 1H), 6.63-6.69 (m, 1H), 4.30 (s, 2H), 2.86 (t, J=7.5 Hz, 2H), 2.63 (t, J=7.5 Hz, 2H), 2.30 (br s, 4H), 1.74 (br s, 4H). Mass spectrum (ESI, m/z): Calculated for $C_{22}H_{22}ClFO_3$, 387.1 [M−H], Measured: 387.1

Example 332: Compound #512

3-[4-[[2-(4-dimethylaminophenyl)cyclohexen-1-yl]methoxy]-2,3-dimethyl-phenyl]Propanoic Acid

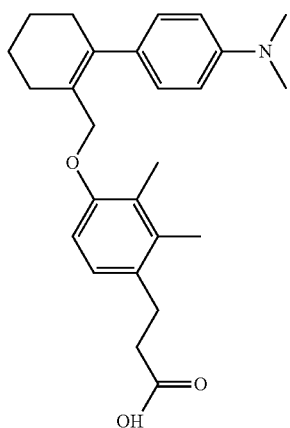 [SMILES: Cc1c(CCC(=O)O)ccc(OCC2=C(c3ccc(N(C)C)cc3)CCCC2)c1C]

¹H NMR (400 MHz, CD₃OD) δ: 7.04 (d, J=5.7 Hz, 2H), 6.84 (d, J=5.7 Hz, 1H), 6.74 (d, J=5.7 Hz, 2H), 6.40 (d, J=8.3 Hz, 1H), 4.32 (s, 2H), 2.92 (s, 6H), 2.87 (t, J=8.0 Hz, 2H), 2.472 (t, J=8.0 Hz, 2H), 2.30-2.32 (m, 4H), 2.27 (s, 3H), 2.16 (s, 3H), 1.75 (br s, 4H). Mass spectrum (ESI, m/z): Calculated for $C_{26}H_{33}NO_3$, 408.2 [M+H], Measured: 408.3.

Example 333: Compound #513

3-[4-[[2-(4-chlorophenyl)cyclohexen-1-yl]methoxy]-2,3-difluoro-phenyl]Propanoic Acid

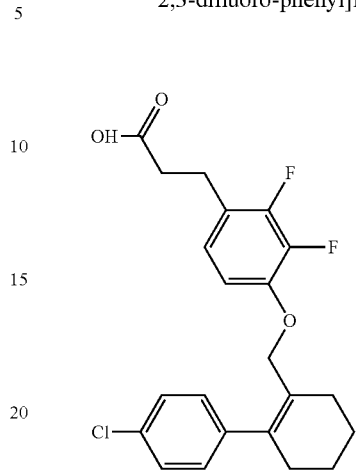

¹H NMR (400 MHz, CDCl₃) δ: 7.30 (d, J=9.6 Hz, 2H), 7.11 (d, J=8.0 Hz, 2H), 6.80 (t, J=7.6 Hz, 1H), 6.45 (t, J=8.0 Hz, 1H), 4.33 (s, 2H), 2.94 (t, J=7.6 Hz, 2H), 2.65 (t, J=7.2 Hz, 2H), 2.32 (br s, 4H), 1.77 (br s, 4H). Mass spectrum (ESI, m/z): Calculated for $C_{22}H_{21}ClF_2O_3$, 405.1 [M−H], Measured: 405.3

Example 334: Compound #515

3-[2,3-dimethyl-4-[[2-(4-methylsulfonylphenyl)cyclohexen-1-yl]methoxy]phenyl]Propanoic Acid

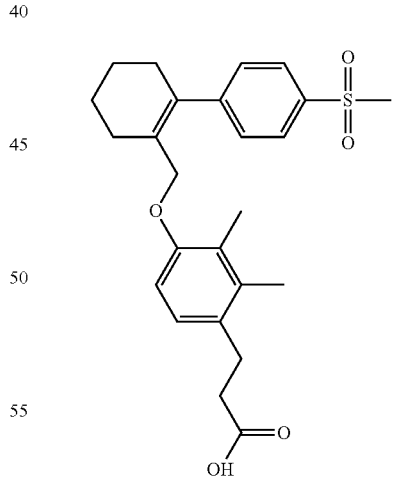

¹H NMR (400 MHz, CDCl₃) δ: 7.86 (d, J=8.4 Hz, 2H), 7.36 (d, J=8.4 Hz, 2H), 6.90 (d, J=8.0 Hz, 1H), 6.43 (d, J=8.0 Hz, 1H), 4.22 (s, 2H), 3.08 (s, 3H), 2.94 (t, J=8.0 Hz, 2H), 2.60 (t, J=8.4 Hz, 2H), 2.35-2.38 (m, 4H), 2.24 (s, 3H), 2.20 (s, 3H), 1.70-1.81 (m, 4H). Mass spectrum (ESI, m/z): Calculated for $C_{25}H_{30}O_5S$, 441.2 [M−H], Measured: 441.2.

Example 335: Compound #516

3-[4-[[2-(4-isopropylphenyl)cyclohexen-1-yl]methoxy]-2,3-dimethyl-phenyl]Propanoic Acid

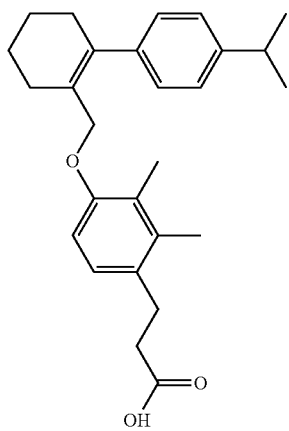 [SMILES: Cc1c(CCC(=O)O)ccc(OCC2=C(c3ccc(C(C)C)cc3)CCCC2)c1C]

$^1$H NMR (300 MHz, CDCl$_3$) δ: 7.07-7.16 (m, 4H), 6.85 (d, J=8.1 Hz, 1H), 6.44 (d, J=8.4 Hz, 1H), 4.28 (s, 2H), 2.83-2.92 (m, 3H), 2.55 (t, J=8.1 Hz, 2H), 2.31-2.32 (m, 4H), 2.18-2.20 (m, 6H), 1.74 (br s, 4H), 1.23 (s, 3H), 1.25 (s, 3H). Mass spectrum (ESI, m/z): Calculated for C$_{27}$H$_{34}$O$_3$, 405.3 [M−H], Measured: 405.2.

Example 336: Compound #517

3-[4-[[2-(4-chlorophenyl)cyclohexen-1-yl]methoxy]phenyl]Propanoic Acid

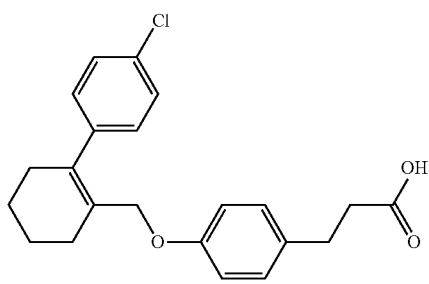 [SMILES: O=C(O)CCc1ccc(OCC2=C(c3ccc(Cl)cc3)CCCC2)cc1]

$^1$H NMR (400 MHz, CDCl$_3$) δ 7.30 (d, J=10.0 Hz, 2H), 7.13-7.18 (m, 3H), 6.79 (d, J=7.6 Hz, 1H), 6.64-6.66 (m, 2H), 4.29 (s, 2H), 2.91 (t, J=8.0 Hz, 2H), 2.66 (t, J=7.6 Hz, 2H), 2.33 (br s, 4H), 1.77 (br s, 4H). Mass spectrum (ESI, m/z): Calculated for C$_{22}$H$_{23}$ClO$_3$, 369.1 [M−H], Measured: 369.3

Example 337: Compound #520

3-[4-[[2-(4-cyanophenyl)cyclohexen-1-yl]methoxy]-2,3-dimethyl-phenyl]Propanoic Acid

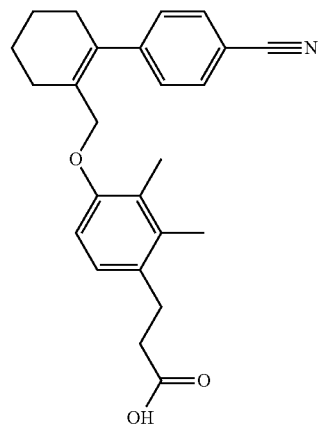 [SMILES: Cc1c(CCC(=O)O)ccc(OCC2=C(c3ccc(C#N)cc3)CCCC2)c1C]

$^1$H NMR (300 MHz, MeOD) δ: 7.67 (d, J=8.4 Hz, 2H), 7.34 (d, J=8.7 Hz, 2H), 6.88 (d, J=8.4 Hz, 1H), 6.38 (d, J=8.4 Hz, 1H), 4.23 (s, 2H), 2.83-2.88 (m, 2H), 2.32-2.43 (m, 6H), 2.22 (s, 3H), 2.17 (s, 3H), 1.84 (br s, 4H). Mass spectrum (ESI, m/z): Calculated for C$_{25}$H$_{27}$NO$_3$, 388.2 [M−H], Measured: 388.1.

Example 338: Compound #385

3-(4-((2-isobutylcyclopent-1-en-1-yl)methoxy)-2-(trifluoromethyl)phenyl)Propanoic Acid

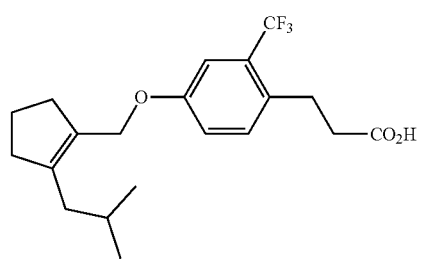 [SMILES: CC(C)CC1=C(COc2ccc(CCC(=O)O)c(C(F)(F)F)c2)CCC1]

Step 1: 2-bromocyclopent-1-ene-1-carbaldehyde

To a mixture of dimethylformamide (13.7 ml, 178.3 mmol) and chloroform (80 ml) was added phosphorus tribromide (16.2 ml, 160.5 mmol) dropwise at 0° C., and the mixture was stirred for 60 min before the addition of cyclopentanone (5.0 g, 59.5 mol). The resulting solution was stirred overnight, then poured into water (300 mL), neutralized with solid NaHCO$_3$, and extracted with dichloromethane, then dried over anhydrous MgSO$_4$, and concentrated under reduced pressure to yield a residue. The residue was purified by chromatography (120 g) eluting with 0 to 10% EA/heptane to yield 2-bromocyclopent-1-ene-1-carbaldehyde. $^1$H NMR (CHLOROFORM-d) δ: 9.91 (s, 1H), 2.91 (tt, J=7.7, 2.4 Hz, 2H), 2.48-2.59 (m, 2H), 2.03 (quin, J=7.6 Hz, 2H). Calculated for C$_6$H$_7$BrO: 175.0 (M+1); Measured: 174.9.

Step 2: (2-bromocyclopent-1-en-1-yl)methanol

To a solution of the compound prepared in Step 1 (6.80 g, 38.9 mmol) in methanol (30 mL) at 0° C. was added sodium borohydride (2.94 g, 77.7 mmol) portionwise over 10 min. After 5 min, the reaction was allowed to warm to room temperature. After 2 hrs, water was added, methanol was removed under reduced pressure, aqueous $NH_4Cl$ was added, the solution was extracted with diethyl ether and ethyl acetate, then washed with brine, dried over $MgSO_4$ and concentrated under reduced pressure to yield (2-bromocyclopent-1-en-1-yl)methanol. 1H NMR (CHLOROFORM-d) δ: 4.26 (br s, 2H), 2.61-2.72 (m, 2H), 2.41-2.54 (m, 2H), 1.91-2.04 (m, 2H), 1.52 (br s, 1H).

Step 3: ethyl 3-(4-((2-bromocyclopent-1-en-1-yl)methoxy)-2-(trifluoromethyl)phenyl)Propanoate A solution of the compound prepared in Step 2 (500 mg, 2.82 mmol) in toluene (40 mL) at room temperature under nitrogen was added ethyl 3-(4-hydroxy-2-(trifluoromethyl)phenyl)propanoate (741 mg, 2.82 mmol), tri-n-butylphosphine (1.53 mL, 6.21 mmol) and ADDP (1.82 g, 5.08 mmol) was warmed to 60° C. overnight. Heptane (60 mL) was added, the resulting white solid was filtered off, and the filtrate concentrated under reduced pressure to yield a residue. The residue was purified by chromatography (40 g) eluting with 1 to 10% EA/heptane to yield ethyl 3-(4-((2-bromocyclopent-1-en-1-yl)methoxy)-2-(trifluoromethyl)phenyl)propanoate. $^1$H NMR (CHLOROFORM-d) δ: 7.23-7.29 (m, 2H), 7.18 (d, J=3.0 Hz, 1H), 7.00 (dd, J=8.6, 2.5 Hz, 1H), 4.66 (s, 2H), 4.14 (q, J=7.1 Hz, 2H), 3.05 (t, J=8.1 Hz, 2H), 2.66-2.75 (m, 2H), 2.53-2.63 (m, 2H), 2.39-2.49 (m, 2H), 1.90-2.04 (m, 2H), 1.25 (t, J=7.1 Hz, 3H).

Step 4: ethyl 3-(4-((2-isobutylcyclopent-1-en-1-yl)methoxy)-2-(trifluoromethyl)phenyl)Propanoate A suspension of the compound prepared in Step 3 (40 mg, 0.095 mmol), isobutylboronic acid (15 mg, 0.14 mmol), $Pd_2dba_3$ (2 mg, 0.002 mmol), Q-Phos (2.7 mg, 0.004 mmol) and $K_3PO_4$ (40 mg, 0.19 mmol) in toluene (3 mL) under nitrogen in a vial was heated to 100° C. overnight. The suspension was cooled to room temperature, filtered through CELITE® washed with ethyl acetate, and concentrated under reduced pressure to yield a residue. The residue was purified by chromatography (12 g) eluting with 1 to 8% EA/heptane to yield ethyl 3-(4-((2-isobutylcyclopent-1-en-1-yl)methoxy)-2-(trifluoromethyl)phenyl)propanoate. Calculated for $C_{22}H_{29}F_3O_3$: 421.1 (M+23); Measured: 421.2.

Step 5: 3-(4-((2-isobutylcyclopent-1-en-1-yl)methoxy)-2-(trifluoromethyl)phenyl)Propanoic Acid To a solution of the compound prepared in Step 4 (20 mg, 0.05 mmol) in tetrahydrofuran (2 mL) and methanol (0.25 mL) was added 1 M NaOH (1 mL). After stirring overnight, 1 M HCl (1.5 mL) was added, the solution extracted with DCM, dried over $MgSO_4$ and concentrated under reduced pressure to yield a residue. The residue was purified by HPLC (30×100 mm column, $C_{18}$) eluting with 20 to 100% acetonitrile/water+0.1% TFA to yield the title compound.
$^1$H NMR (CHLOROFORM-d) δ: 7.23-7.28 (m, 1H), 7.17 (d, J=2.5 Hz, 1H), 7.01 (dd, J=8.6, 2.5 Hz, 1H), 4.54 (s, 2H), 3.07 (br t, J=7.8 Hz, 2H), 2.67 (br d, J=7.6 Hz, 2H), 2.47 (br t, J=7.3 Hz, 2H), 2.36 (br t, J=7.3 Hz, 2H), 2.03 (d, J=7.1 Hz, 2H), 1.70-1.89 (m, 3H), 0.87 (d, J=6.6 Hz, 6H). Calculated for $C_{20}H_{25}F_3O_3$: 393.2 (M+23); Measured: 393.1.

Alternative Step 4: ethyl 3-(4-((2-isobutylcyclopent-1-en-1-yl)methoxy)-2-(trifluoromethyl)phenyl)Propanoate (Used, for Example, in the Preparation of a Separate Batch of the Title Compound Above)

A suspension of the compound prepared in Step 3 (24 mg, 0.057 mmol), 1-ethylpropylzinc bromide (0.23 mL of a 0.5 M solution in THF, 0.11 mmol), $Pd_2dba_3$ (2 mg, 0.002 mmol), Q-Phos (3 mg, 0.004 mmol) in toluene (3 mL) under nitrogen in a vial was heated to 100° C. for 3 hrs. The solution was cooled to room temperature, water was added, extracted with DCM, and concentrated under reduced pressure to yield a residue. The residue was purified by chromatography (12 g) eluting with 0 to 4% EA/heptane to yield ethyl 3-(4-((2-isobutylcyclopent-1-en-1-yl)methoxy)-2-(trifluoromethyl)phenyl)propanoate. Calculated for $C_{23}H_{31}F_3O_3$: 435.2 (M+23); Measured: 435.1.

Additional representative compounds of formula (I) were prepared according to the procedure described in Example 338, selecting and substituting suitable reagents and starting materials, and using Step 4 or alternative Step 4, as would be readily recognized by those skilled in the art.

Example 339: Compound #384

3-[4-[(2-isobutylcyclopenten-1-yl)methoxy]phenyl]Propanoic Acid

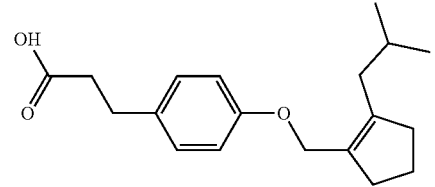 [SMILES: CC(C)CC1=C(COc2ccc(CCC(=O)O)cc2)CCC1]

$^1$H NMR (CHLOROFORM-d) δ: 7.11 (d, J=8.1 Hz, 2H), 6.86 (d, J=8.1 Hz, 2H), 4.51 (s, 2H), 2.86-2.94 (m, 2H), 2.60-2.69 (m, 2H), 2.49 (br t, J=7.1 Hz, 2H), 2.35 (br t, J=7.1 Hz, 2H), 2.02 (d, J=7.1 Hz, 2H), 1.69-1.88 (m, 3H), 0.86 (d, J=6.6 Hz, 6H). Calculated for $C_{19}H_{26}O_3$: 325.2 (M+23); Measured: 325.2.

Example 340: Compound #369

3-[4-[[2-(cyclohexylmethyl)cyclopenten-1-yl]methoxy]-2-(trifluoromethyl)phenyl]Propanoic Acid

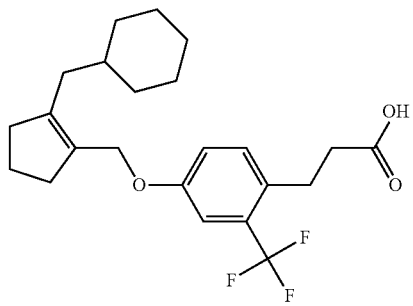 [SMILES: O=C(O)CCc1ccc(OCC2=C(CC3CCCCC3)CCC2)cc1C(F)(F)F]

¹H NMR (CHLOROFORM-d) δ: 7.21-7.30 (m, 1H), 7.17 (d, J=2.5 Hz, 1H), 7.01 (dd, J=8.6, 2.5 Hz, 1H), 4.53 (s, 2H), 3.07 (br t, J=7.8 Hz, 2H), 2.65 (t, J=7.8 Hz, 2H), 2.47 (br t, J=7.1 Hz, 2H), 2.36 (br t, J=7.3 Hz, 2H), 2.03 (d, J=7.1 Hz, 2H), 1.83 (quin, J=7.5 Hz, 2H), 1.58-1.75 (m, 5H), 1.33-1.49 (m, 1H), 1.05-1.29 (m, 3H), 0.77-0.93 (m, 2H). Calculated for $C_{23}H_{29}F_3O_3$: 433.2 (M+23); Measured: 433.2.

Example 341: Compound #374

3-[4-[(2-isopentylcyclopenten-1-yl)methoxy]-2-(trifluoromethyl)phenyl]Propanoic Acid

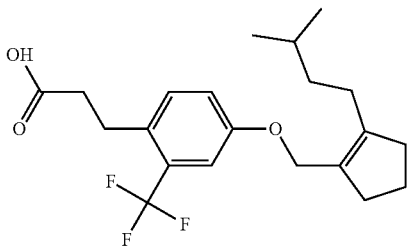 [SMILES: CC(C)CCC1=C(COc2ccc(CCC(=O)O)c(C(F)(F)F)c2)CCC1]

¹H NMR (CHLOROFORM-d) δ: 7.21-7.30 (m, 1H), 7.18 (d, J=2.5 Hz, 1H), 7.01 (dd, J=8.3, 2.3 Hz, 1H), 4.55 (s, 2H), 3.07 (br s, 2H), 2.70 (br s, 2H), 2.45 (br t, J=7.3 Hz, 2H), 2.38 (br t, J=7.3 Hz, 2H), 2.10-2.20 (m, 2H), 1.76-1.88 (m, 2H), 1.51 (d quin, J=13.2, 6.7 Hz, 1H), 1.22-1.33 (m, 2H), 0.89 (d, J=7.1 Hz, 6H). Calculated for $C_{21}H_{27}F_3O_3$: 407.2 (M+23); Measured: 407.2.

Example 342: Compound #370

3-[4-[(2-butylcyclopenten-1-yl)methoxy]-2-(trifluoromethyl)phenyl]Propanoic Acid

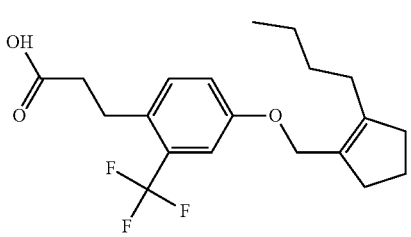 [SMILES: CCCCC1=C(COc2ccc(CCC(=O)O)c(C(F)(F)F)c2)CCC1]

¹H NMR (CHLOROFORM-d) δ: 7.22-7.29 (m, 1H), 7.17 (d, J=2.5 Hz, 1H), 7.01 (dd, J=8.6, 2.5 Hz, 1H), 4.55 (s, 2H), 3.07 (t, J=8.1 Hz, 2H), 2.60-2.68 (m, 2H), 2.46 (br t, J=7.3 Hz, 2H), 2.38 (br t, J=7.3 Hz, 2H), 2.16 (t, J=7.3 Hz, 2H), 1.77-1.88 (m, 2H), 1.27-1.44 (m, 4H), 0.90 (t, J=7.1 Hz, 3H). Calculated for $C_{20}H_{25}F_3O_3$: 393.2 (M+23); Measured: 393.1.

Example 343: Compound #372

3-[4-[(2-phenethylcyclopenten-1-yl)methoxy]-2-(trifluoromethyl)phenyl]Propanoic Acid

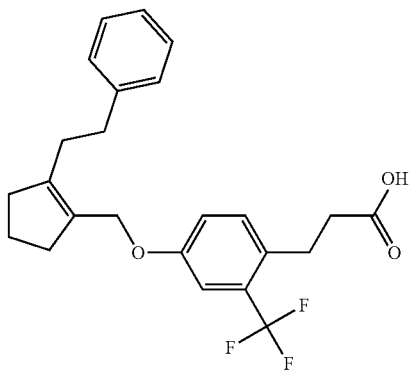 [SMILES: O=C(O)CCc1ccc(OCC2=C(CCc3ccccc3)CCC2)cc1C(F)(F)F]

¹H NMR (CHLOROFORM-d) δ: 7.25-7.32 (m, 2H), 7.17-7.24 (m, 2H), 7.11-7.16 (m, 2H), 7.06 (d, J=2.5 Hz, 1H), 6.90 (dd, J=8.6, 2.5 Hz, 1H), 4.20 (s, 2H), 3.06 (br s, 2H), 2.59-2.76 (m, 4H), 2.37-2.51 (m, 6H), 1.85 (quin, J=7.5 Hz, 2H). Calculated for $C_{24}H_{25}F_3O_3$: 441.2 (M+23); Measured: 441.1.

Example 344: Compound #395

3-[4-[(2-cyclopentylcyclopenten-1-yl)methoxy]phenyl]Propanoic Acid

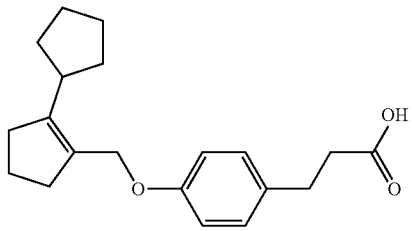 [SMILES: O=C(O)CCc1ccc(OCC2=C(C3CCCC3)CCC2)cc1]

¹H NMR (CHLOROFORM-d) δ: 7.11 (d, J=8.6 Hz, 2H), 6.82-6.90 (m, 2H), 4.55 (s, 2H), 2.80-2.95 (m, 3H), 2.65 (t, J=7.6 Hz, 2H), 2.48 (br t, J=7.3 Hz, 2H), 2.38 (br t, J=7.3 Hz, 2H), 1.76-1.87 (m, 2H), 1.52-1.73 (m, 6H), 1.36-1.49 (m, 2H). Calculated for $C_{20}H_{26}O_3$: 337.2 (M+23); Measured: 337.2.

Example 345: Compound #397

3-[4-[(2-cyclobutylcyclopenten-1-yl)methoxy]phenyl]Propanoic Acid

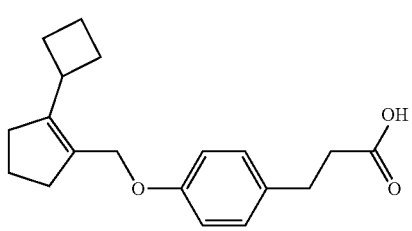 [SMILES: O=C(O)CCc1ccc(OCC2=C(C3CCC3)CCC2)cc1]

$^1$H NMR (CHLOROFORM-d) δ: 7.11 (d, J=8.1 Hz, 2H), 6.84 (d, J=8.6 Hz, 2H), 4.50 (s, 2H), 3.36 (quin, J=8.6 Hz, 1H), 2.84-2.94 (m, 2H), 2.59-2.71 (m, 2H), 2.49 (q, J=6.6 Hz, 4H), 1.98-2.11 (m, 4H), 1.69-1.98 (m, 4H). Calculated for $C_{19}H_{24}O_3$: 323.2 (M+23); Measured: 323.3.

Example 346: Compound #398

3-[4-[(2-cyclopentylcyclopenten-1-yl)methoxy]-2-(trifluoromethyl)phenyl]Propanoic Acid

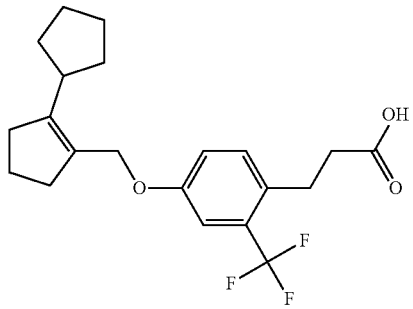

$^1$H NMR (CHLOROFORM-d) δ: 7.22-7.29 (m, 1H), 7.18 (d, J=2.5 Hz, 1H), 7.02 (dd, J=8.3, 1.8 Hz, 1H), 4.58 (s, 2H), 3.06 (br s, 2H), 2.80-2.92 (m, 1H), 2.67 (br s, 2H), 2.45 (br t, J=7.3 Hz, 2H), 2.38 (br t, J=7.1 Hz, 2H), 1.82 (quin, J=7.5 Hz, 2H), 1.52-1.75 (m, 6H), 1.43 (br d, J=10.1 Hz, 2H). Calculated for $C_{21}H_{25}F_3O_3$: 405.2 (M+23); Measured: 405.0.

Example 347: Compound #399

3-[4-[(2-cyclobutylcyclopenten-1-yl)methoxy]-2-(trifluoromethyl)phenyl]Propanoic Acid

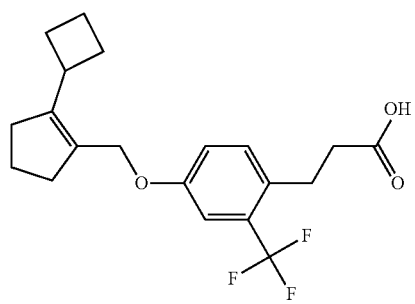 [SMILES: O=C(O)CCc1ccc(OCC2=C(C3CCC3)CCC2)cc1C(F)(F)F]

$^1$H NMR (CHLOROFORM-d) δ: 7.21-7.27 (m, 1H), 7.16 (d, J=2.5 Hz, 1H), 7.00 (dd, J=8.3, 2.8 Hz, 1H), 4.54 (s, 2H), 3.36 (quin, J=8.6 Hz, 1H), 3.00-3.10 (m, 2H), 2.65 (br t, J=7.8 Hz, 2H), 2.40-2.55 (m, 4H), 1.98-2.10 (m, 4H), 1.71-1.98 (m, 4H). Calculated for $C_{20}H_{23}F_3O_3$: 391.2 (M+23); Measured: 391.0.

Example 348: Compound #386

3-[4-[(2-cyclohexylcyclopenten-1-yl)methoxy]-2-(trifluoromethyl)phenyl]Propanoic Acid

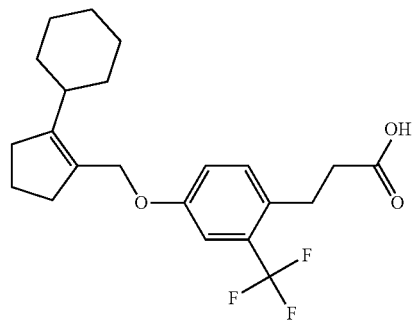 [SMILES: O=C(O)CCc1ccc(OCC2=C(C3CCCCC3)CCC2)cc1C(F)(F)F]

$^1$H NMR (CHLOROFORM-d) δ: 7.22-7.28 (m, 1H), 7.18 (d, J=2.5 Hz, 1H), 7.02 (dd, J=8.3, 2.8 Hz, 1H), 4.57 (s, 2H), 3.07 (br t, J=7.8 Hz, 2H), 2.65 (brt, J=7.8 Hz, 2H), 2.31-2.49 (m, 5H), 1.63-1.87 (m, 5H), 1.44-1.56 (m, 1H), 1.22-1.34 (m, 5H), 1.08-1.22 (m, 1H). Calculated for $C_{22}H_{27}F_3O_3$: 419.2 (M+23); Measured: 419.1.

Example 349: Compound #387

3-[4-[[2-(2,2-dimethylpropyl)cyclopenten-1-yl]methoxy]-2-(trifluoromethyl)phenyl]Propanoic Acid

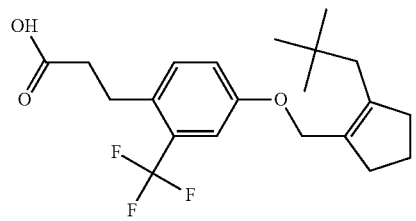 [SMILES: CC(C)(C)CC1=C(COc2ccc(CCC(=O)O)c(C(F)(F)F)c2)CCC1]

$^1$H NMR (CHLOROFORM-d) δ: 7.22-7.28 (m, 1H), 7.16 (d, J=2.5 Hz, 1H), 6.99 (dd, J=8.6, 2.5 Hz, 1H), 4.52 (s, 2H), 3.07 (br t, J=7.6 Hz, 2H), 2.66 (br s, 2H), 2.40-2.51 (m, 4H), 2.08 (s, 2H), 1.81 (quin, J=7.5 Hz, 2H), 0.92 (s, 9H). Calculated for $C_{21}H_{27}F_3O_3$: 407.2 (M+23); Measured: 407.1.

Example 350: Compound #389

3-[4-[(2-propylcyclopenten-1-yl)methoxy]-2-(trifluoromethyl)phenyl]Propanoic Acid

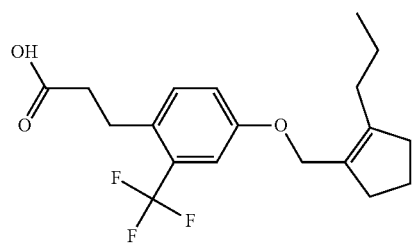 [SMILES: CCCC1=C(COc2ccc(CCC(=O)O)c(C(F)(F)F)c2)CCC1]

¹H NMR (CHLOROFORM-d) δ: 7.22-7.28 (m, 1H), 7.17 (d, J=2.0 Hz, 1H), 7.01 (br d, J=7.6 Hz, 1H), 4.55 (s, 2H), 3.07 (br s, 2H), 2.68 (br s, 2H), 2.46 (br t, J=7.3 Hz, 2H), 2.38 (br t, J=7.1 Hz, 2H), 2.14 (br t, J=7.6 Hz, 2H), 1.83 (quin, J=7.5 Hz, 2H), 1.43 (sxt, J=7.4 Hz, 2H), 0.88 (t, J=7.3 Hz, 3H). Calculated for $C_{19}H_{23}F_3O_3$: 379.2 (M+23); Measured: 379.2.

Example 351: Compound #390

3-[4-[(2-norbornan-2-ylcyclopenten-1-yl)methoxy]-2-(trifluoromethyl)phenyl]Propanoic Acid

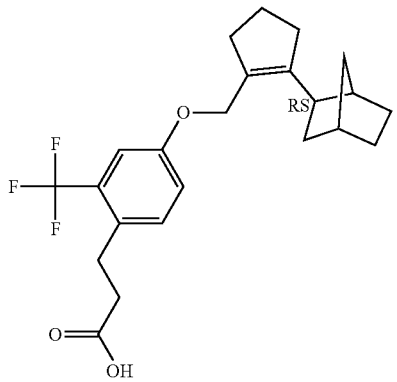 [SMILES: O=C(O)CCc1ccc(OCC2=C(C3CC4CCC3C4)CCC2)cc1C(F)(F)F]

¹H NMR (CHLOROFORM-d) δ: 7.22-7.30 (m, 1H), 7.17 (d, J=2.0 Hz, 1H), 7.02 (br d, J=8.6 Hz, 1H), 4.47-4.68 (m, 2H), 3.07 (br t, J=7.8 Hz, 2H), 2.80-2.92 (m, 1H), 2.65 (br t, J=7.8 Hz, 2H), 2.31-2.58 (m, 4H), 2.15-2.30 (m, 2H), 2.06 (br s, 1H), 1.67-1.89 (m, 3H), 1.11-1.59 (m, 6H). Calculated for $C_{23}H_{27}F_3O_3$: 431.2 (M+23); Measured: 431.3.

Example 352: Compound #377

3-[4-[(2-isopropylcyclopenten-1-yl)methoxy]-2-(trifluoromethyl)phenyl]Propanoic Acid

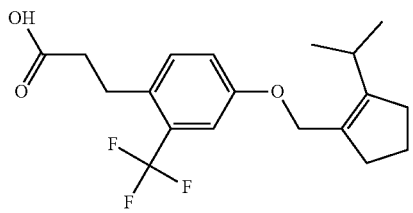 [SMILES: CC(C)C1=C(COc2ccc(CCC(=O)O)c(C(F)(F)F)c2)CCC1]

¹H NMR (CHLOROFORM-d) δ: 7.22-7.30 (m, 1H), 7.18 (d, J=3.0 Hz, 1H), 7.02 (dd, J=8.6, 2.5 Hz, 1H), 4.57 (s, 2H), 3.07 (br t, J=7.6 Hz, 2H), 2.75-2.89 (m, 1H), 2.66 (br s, 2H), 2.45 (br t, J=7.6 Hz, 2H), 2.37 (br t, J=7.3 Hz, 2H), 1.75-1.87 (m, 2H), 1.01 (d, J=7.1 Hz, 6H). Calculated for $C_{19}H_{23}F_3O_3$: 379.2 (M+23); Measured: 379.2.

Example 353: Compound #380

3-[4-[[2-(1-ethylpropyl)cyclopenten-1-yl]methoxy]-2-(trifluoromethyl)phenyl]Propanoic Acid

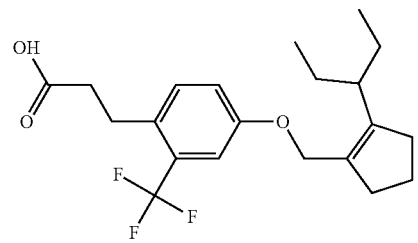 [SMILES: CCC(CC)C1=C(COc2ccc(CCC(=O)O)c(C(F)(F)F)c2)CCC1]

¹H NMR (CHLOROFORM-d) δ: 7.22-7.30 (m, 1H), 7.17 (d, J=2.5 Hz, 1H), 6.97-7.05 (m, 1H), 4.48-4.63 (m, 2H), 3.07 (br s, 2H), 2.57-2.75 (m, 2H), 2.41-2.53 (m, 2H), 2.21-2.30 (m, 2H), 2.16-2.30 (m, 1H), 1.77-1.88 (m, 2H), 1.37-1.51 (m, 2H), 1.26-1.37 (m, 2H), 0.78 (t, J=7.6 Hz, 6H). Calculated for $C_{21}H_{27}F_3O_3$: 407.2 (M+23); Measured: 407.1.

Example 354: Compound #394

3-[2-chloro-4-[(2-isobutylcyclopenten-1-yl)methoxy]phenyl]Propanoic Acid

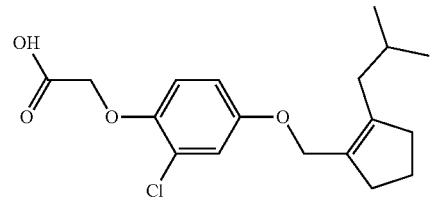 [SMILES: CC(C)CC1=C(COc2ccc(OCC(=O)O)c(Cl)c2)CCC1]

¹H NMR (CHLOROFORM-d) δ: 7.14 (d, J=8.6 Hz, 1H), 6.93 (d, J=2.5 Hz, 1H), 6.76 (dd, J=8.6, 2.5 Hz, 1H), 4.50 (s, 2H), 3.00 (t, J=7.6 Hz, 2H), 2.67 (br t, J=7.6 Hz, 2H), 2.47 (br t, J=7.1 Hz, 2H), 2.35 (br t, J=7.3 Hz, 2H), 2.02 (d, J=7.1 Hz, 2H), 1.69-1.90 (m, 3H), 0.86 (d, J=6.6 Hz, 6H). Calculated for $C_{19}H_{25}ClO_3$: 359.1 (M+23); Measured: 359.1.

Example 355: Compound #400

3-[2-chloro-4-[(2-cyclobutylcyclopenten-1-yl)methoxy]phenyl]Propanoic Acid

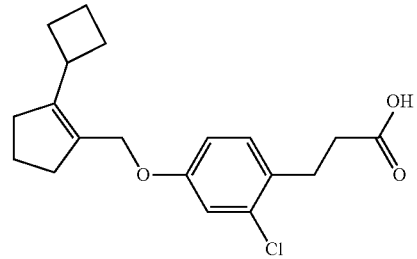 [SMILES: O=C(O)CCc1ccc(OCC2=C(C3CCC3)CCC2)cc1Cl]

¹H NMR (CHLOROFORM-d) δ: 7.13 (d, J=8.6 Hz, 1H), 6.91 (d, J=2.5 Hz, 1H), 6.75 (dd, J=8.6, 2.5 Hz, 1H), 4.50 (s, 2H), 3.36 (quin, J=8.6 Hz, 1H), 2.99 (t, J=7.8 Hz, 2H), 2.67 (br t, J=7.6 Hz, 2H), 2.39-2.54 (m, 4H), 1.99-2.12 (m, 4H), 1.69-1.99 (m, 4H). Calculated for $C_{19}H_{23}ClO_3$: 357.1 (M+23); Measured: 357.1.

Example 356: Compound #388

3-[4-[(2-sec-butylcyclopenten-1-yl)methoxy]-2-(trifluoromethyl)phenyl]Propanoic Acid

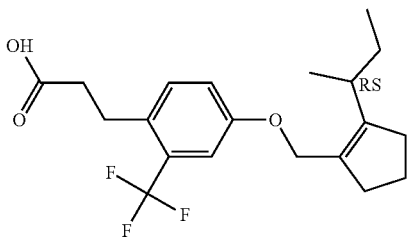 [SMILES: CCC(C)C1=C(COc2ccc(CCC(=O)O)c(C(F)(F)F)c2)CCC1]

¹H NMR (CHLOROFORM-d) δ: 7.21-7.29 (m, 1H), 7.17 (d, J=2.5 Hz, 1H), 7.02 (dd, J=8.3, 2.8 Hz, 1H), 4.49-4.65 (m, 2H), 3.07 (t, J=7.8 Hz, 2H), 2.60-2.70 (m, 2H), 2.41-2.58 (m, 3H), 2.21-2.41 (m, 2H), 1.75-1.87 (m, 2H), 1.28-1.46 (m, 2H), 1.00 (d, J=7.1 Hz, 3H), 0.80 (t, J=7.3 Hz, 3H). Calculated for $C_{20}H_{25}F_3O_3$: 393.2 (M+23); Measured: 393.1.

Example 357: Compound #415

3-[4-[(2-tetrahydropyran-4-ylcyclopenten-1-yl)methoxy]-2-(trifluoromethyl)phenyl]Propanoic Acid

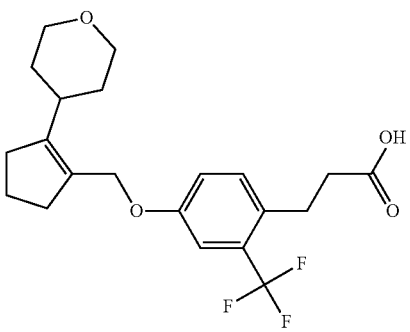 [SMILES: O=C(O)CCc1ccc(OCC2=C(C3CCOCC3)CCC2)cc1C(F)(F)F]

¹H NMR (CHLOROFORM-d) δ: 7.23-7.30 (m, 1H), 7.17 (d, J=2.5 Hz, 1H), 7.02 (dd, J=8.6, 2.5 Hz, 1H), 4.58 (s, 2H), 4.00 (dd, J=11.1, 4.0 Hz, 2H), 3.39-3.50 (m, 2H), 3.07 (t, J=7.8 Hz, 2H), 2.59-2.76 (m, 3H), 2.47 (br t, J=7.3 Hz, 2H), 2.40 (br t, J=7.1 Hz, 2H), 1.79-1.89 (m, 2H), 1.72 (qd, J=12.7, 4.3 Hz, 2H), 1.39 (br dd, J=12.9, 1.8 Hz, 2H). Calculated for $C_{21}H_{25}F_3O_4$: 421.2 (M+23); Measured: 421.2.

Example 358: Compound #418

3-[2-chloro-4-[(2-tetrahydropyran-4-ylcyclopenten-1-yl)methoxy]phenyl]Propanoic Acid

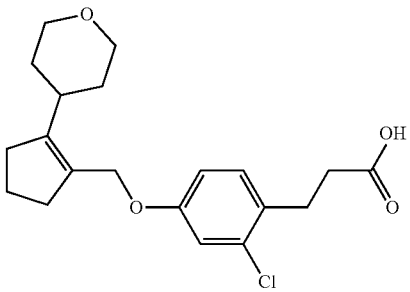 [SMILES: O=C(O)CCc1ccc(OCC2=C(C3CCOCC3)CCC2)cc1Cl]

¹H NMR (CHLOROFORM-d) δ: 7.15 (d, J=8.6 Hz, 1H), 6.93 (d, J=2.5 Hz, 1H), 6.77 (dd, J=8.3, 2.8 Hz, 1H), 4.54 (s, 2H), 4.00 (dd, J=11.1, 4.0 Hz, 2H), 3.39-3.49 (m, 2H), 3.00 (t, J=7.6 Hz, 2H), 2.62-2.74 (m, 3H), 2.47 (br t, J=7.3 Hz, 2H), 2.39 (br t, J=7.3 Hz, 2H), 1.78-1.89 (m, 2H), 1.72 (qd, J=12.6, 4.5 Hz, 2H), 1.39 (br dd, J=12.9, 1.8 Hz, 2H). Calculated for $C_{20}H_{25}ClO_4$: 387.1 (M+23); Measured: 387.1.

Example 359: Compound #436

3-(4-(2-([1,1'-bi(cyclopentan)]-3-en-2-yl)ethyl)-3,5-difluorophenyl)Propanoic Acid

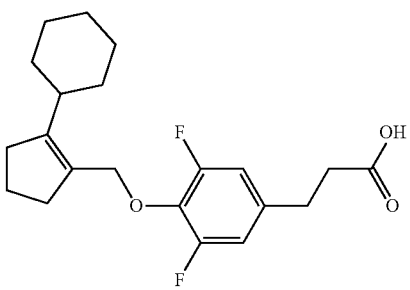 [SMILES: O=C(O)CCc1cc(F)c(OCC2=C(C3CCCCC3)CCC2)c(F)c1]

¹H NMR (CHLOROFORM-d) δ: 6.68-6.77 (m, 2H), 4.66 (s, 2H), 2.83-2.91 (m, 2H), 2.69-2.81 (m, 1H), 2.60-2.69 (m, 2H), 2.53 (br t, J=7.3 Hz, 2H), 2.30 (br t, J=7.3 Hz, 2H), 1.74-1.84 (m, 2H), 1.38-1.66 (m, 6H), 1.21-1.35 (m, 2H). Calculated for $C_{20}H_{24}F_2O_3$: 373.2 (M+23); Measured: 373.2.

Example 360: Compound #427

3-[4-[[2-(cyclopentylmethyl)cyclopenten-1-yl]methoxy]-2,3-dimethyl-phenyl]Propanoic Acid

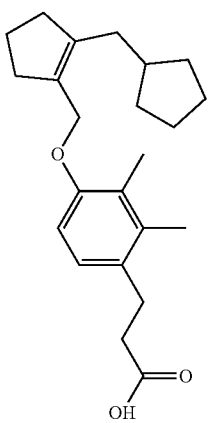 [SMILES: Cc1c(CCC(=O)O)ccc(OCC2=C(CC3CCCC3)CCC2)c1C]

$^1$H NMR (CHLOROFORM-d) δ: 6.96 (d, J=8.6 Hz, 1H), 6.70 (d, J=8.6 Hz, 1H), 4.50 (s, 2H), 2.88-2.98 (m, 2H), 2.56-2.64 (m, 2H), 2.50 (br t, J=7.1 Hz, 2H), 2.39 (br t, J=7.3 Hz, 2H), 2.22 (s, 3H), 2.10-2.20 (m, 5H), 1.88-2.03 (m, 1H), 1.77-1.88 (m, 2H), 1.42-1.76 (m, 6H), 1.09 (dq, J=12.1, 7.4 Hz, 2H). Calculated for $C_{23}H_{32}O_3$: 379.2 (M+23); Measured: 379.2.

Example 361: Compound #420

3-[4-[[2-(cyclopentylmethyl)cyclopenten-1-yl]methoxy]-2-(trifluoromethyl)phenyl]Propanoic Acid

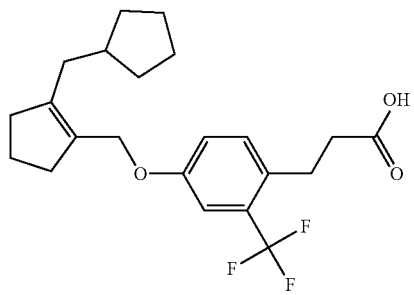 [SMILES: O=C(O)CCc1ccc(OCC2=C(CC3CCCC3)CCC2)cc1C(F)(F)F]

$^1$H NMR (CHLOROFORM-d) δ: 7.21-7.29 (m, 1H), 7.18 (d, J=2.5 Hz, 1H), 7.01 (dd, J=8.6, 2.5 Hz, 1H), 4.55 (s, 2H), 3.07 (t, J=8.1 Hz, 2H), 2.61-2.70 (m, 2H), 2.46 (br t, J=7.3 Hz, 2H), 2.39 (br t, J=7.3 Hz, 2H), 2.15 (d, J=7.6 Hz, 2H), 1.96 (d quin, J=15.3, 7.5 Hz, 1H), 1.78-1.89 (m, 2H), 1.45-1.76 (m, 6H), 1.02-1.15 (m, 2H). Calculated for $C_{22}H_{27}F_3O_3$: 419.2 (M+23); Measured: 419.2.

Example 362: Compound #410

3-[4-[(2-cyclopentylcyclopenten-1-yl)methoxy]-2-isopropyl-phenyl]Propanoic Acid

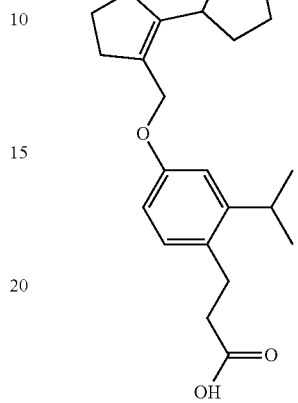

$^1$H NMR (300 MHz, CD$_3$OD) δ: 7.04 (d, J=8.4 Hz, 1H), 6.80 (d, J=2.7 Hz, 1H), 6.60-6.68 (m, 1H), 4.58 (s, 2H), 3.11-3.20 (m, 1H), 2.87-2.99 (m, 3H), 2.36-2.52 (m, 6H), 1.80-1.85 (m, 2H), 1.61-1.71 (m, 6H), 1.42-1.47 (m, 2H), 1.23 (d, J=4.0 Hz, 6H). Mass spectrum (ESI, m/z): Calculated for $C_{23}H_{32}O_3$, 355.2 [M−H], Measured: 355.2

Example 363: Compound #414

3-[2-cyano-4-[(2-cyclopentylcyclopenten-1-yl)methoxy]phenyl]Propanoic Acid

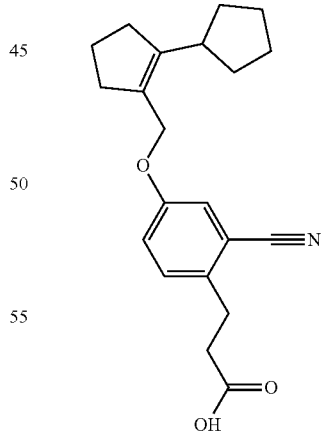

$^1$H NMR (300 MHz, CD$_3$OD) δ: 7.35 (d, J=8.6 Hz, 1H), 7.09-7.24 (m, 2H), 4.65 (s, 2H), 2.90-3.13 (m, 3H), 2.65 (t, J=7.6 Hz, 2H), 2.30-2.49 (m, 4H), 1.55-1.90 (m, 8H), 1.37-1.53 (m, 2H). Mass spectrum (ESI, m/z): Calculated for $C_{21}H_{25}NO_3$, 338.2 [M−H], Measured: 338.1.

Example 364: Compound #421

3-[2-bromo-4-[(2-cyclopentylcyclopenten-1-yl)methoxy]phenyl]Propanoic Acid

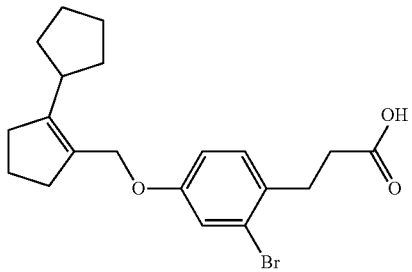 [SMILES: O=C(O)CCc1ccc(OCC2=C(C3CCCC3)CCC2)cc1Br]

$^1$H NMR (300 MHz, CD$_3$OD) δ: 7.22 (d, J=8.4 Hz, 1H), 7.14 (s, 1H), 6.88 (d, J=8.4 Hz, 1H), 4.63 (s, 2H), 2.96-3.10 (m, 3H), 2.58 (t, J=7.6 Hz, 2H), 2.41-2.44 (m, 4H), 1.60-1.87 (m, 8H), 1.40-1.55 (m, 2H). Mass spectrum (ESI, m/z): Calculated for C$_{20}$H$_{25}$BrO$_3$, 391.1 [M−H], Measured: 391.0.

Example 365: Compound #422

3-[4-[(2-cyclopentylcyclopenten-1-yl)methoxy]-2-methyl-phenyl]Propanoic Acid

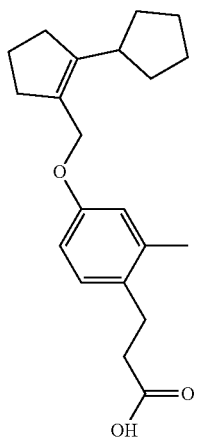 [SMILES: Cc1cc(OCC2=C(C3CCCC3)CCC2)ccc1CCC(=O)O]

$^1$H NMR (400 MHz, CD$_3$OD) δ: 7.04 (d, J=8.4 Hz, 1H), 6.73 (s, 1H), 6.71 (d, J=8.4 Hz, 1H), 4.58 (s, 2H), 2.93-2.99 (m, 1H), 2.86 (t, J=7.6 Hz, 2H), 2.37-2.54 (m, 6H), 2.30 (s, 3H), 1.80-1.85 (m, 2H), 1.62-1.77 (m, 6H), 1.40-1.52 (m, 2H). Mass spectrum (ESI, m/z): Calculated for C$_{21}$H$_{28}$O$_3$, 327.2 [M−H], Measured: 327.2

Example 366: Compound #423

3-[4-[(2-cyclopentylcyclopenten-1-yl)methoxy]-2-ethyl-phenyl]Propanoic Acid

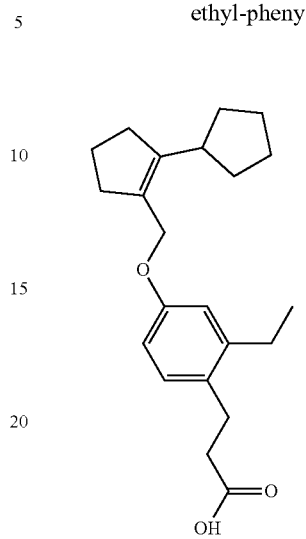

$^1$H NMR (400 MHz, CD$_3$OD) δ: 7.06 (d, J=8.4 Hz, 1H), 6.68-6.75 (m, 2H), 4.88 (s, 2H), 2.86-2.98 (m, 3H), 2.62-2.67 (m, 2H), 2.37-2.55 (m, 6H), 1.81-1.85 (m, 2H), 1.61-1.73 (m, 6H), 1.41-1.50 (m, 2H), 1.22 (t, J=7.6 Hz, 3H). Mass spectrum: Calculated for C$_{22}$H$_{30}$O$_3$, 341.2 [M−H], Measured: 341.1.

Example 367: Compound #424

3-[4-[(2-cyclopentylcyclopenten-1-yl)methoxy]-5-fluoro-2-methyl-phenyl]Propanoic Acid

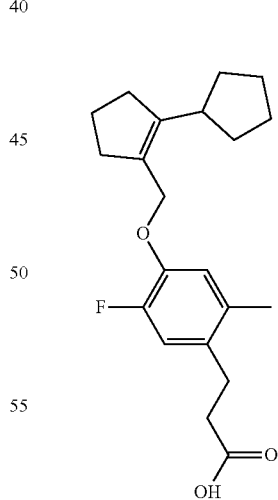

$^1$H NMR (400 MHz, CD$_3$OD) δ: 6.86-6.92 (m, 2H), 4.88 (s, 2H), 2.89-2.96 (m, 1H), 2.84 (t, J=7.6 Hz, 2H), 2.42-2.53 (m, 4H), 2.38 (t, J=7.6 Hz, 2H), 2.27 (s, 3H), 1.81-1.85 (m, 2H), 1.57-1.77 (m, 6H), 1.35-1.45 (m, 2H). Mass spectrum (ESI, m/z): Calculated for C$_{21}$H$_{27}$FO$_3$, 345.2 [M−H], Measured: 345.1.

Example 368: Compound #425

3-[4-[(2-cyclopentylcyclopenten-1-yl)methoxy]-3-fluoro-phenyl]Propanoic Acid

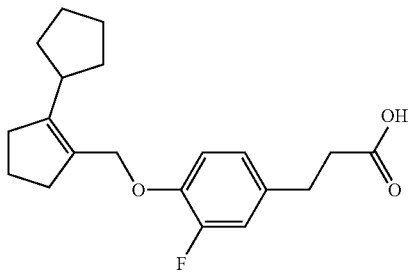 [SMILES: O=C(O)CCc1ccc(OCC2=C(C3CCCC3)CCC2)c(F)c1]

$^1$H NMR (300 MHz, CD$_3$OD) δ: 6.90-6.99 (m, 3H), 4.64 (s, 2H), 2.82-2.97 (m, 3H), 2.57 (t, J=7.5 Hz, 2H), 2.47 (t, J=7.5 Hz, 2H), 2.37 (t, J=7.5 Hz, 2H), 1.75-1.85 (m, 2H), 1.56-1.72 (m, 6H), 1.33-1.48 (m, 2H). $^{19}$F NMR (300 MHz, CD$_3$OD) δ: −136.00. Mass spectrum (ESI, m/z): Calculated for C$_{20}$H$_{25}$FO$_3$, 331.2 [M−H], Measured: 331.1.

Example 369: Compound #426

3-[4-[(2-cyclopentylcyclopenten-1-yl)methoxy]-2-fluoro-phenyl]Propanoic Acid

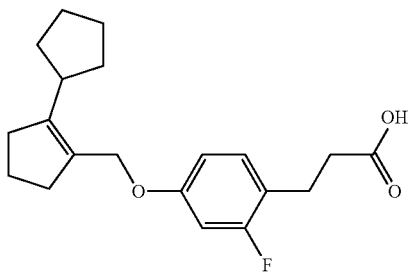 [SMILES: O=C(O)CCc1ccc(OCC2=C(C3CCCC3)CCC2)cc1F]

$^1$H NMR (300 MHz, CD$_3$OD) δ: 7.14 (t, J=8.9 Hz, 1H), 6.62-6.69 (m, 2H), 4.59 (s, 2H), 2.84-2.97 (m, 3H), 2.55 (t, J=7.7 Hz, 2H), 2.37-2.46 (m, 4H), 1.64-1.86 (m, 8H), 1.54-1.34 (m, 2H). $^{19}$F NMR (300 MHz, CD$_3$OD) δ: −119.01. Mass spectrum (ESI, m/z): Calculated for C$_{20}$H$_{25}$FO$_3$, 331.2[M−H], Measured: 331.1.

Example 370: Compound #428

3-[2-chloro-4-[(2-cyclopentylcyclopenten-1-yl)methoxy]phenyl]Propanoic Acid

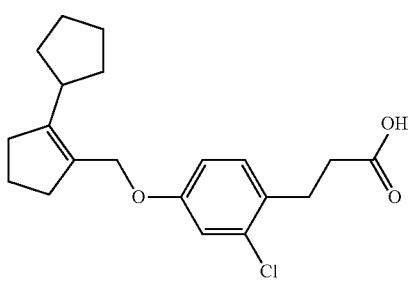 [SMILES: O=C(O)CCc1ccc(OCC2=C(C3CCCC3)CCC2)cc1Cl]

$^1$H NMR (300 MHz, CD$_3$OD,) δ: 7.20 (d, J=8.5 Hz, 1H), 6.94 (s, 1H), 6.74-6.87 (m, 1H), 4.60 (s, 2H), 2.91-2.98 (m, 3H), 2.56 (t, J=7.5 Hz, 2H), 2.31-2.50 (m, 4H), 1.57-1.89 (m, 8H), 1.38-1.55 (m, 2H). Mass spectrum (ESI, m/z): Calculated for C$_{20}$H$_{25}$ClO$_3$, 347.1 [M−H], Measured: 347.1.

Example 371: Compound #431

3-[4-[(2-cyclopentylcyclopenten-1-yl)methoxy]-3-fluoro-2-methyl-phenyl]Propanoic Acid

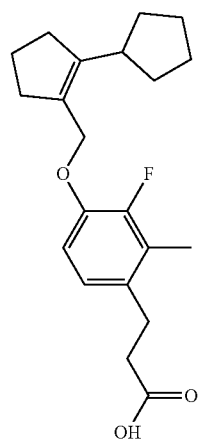 [SMILES: Cc1c(CCC(=O)O)ccc(OCC2=C(C3CCCC3)CCC2)c1F]

$^1$H NMR (300 MHz, CD$_3$OD) δ: 6.83-6.86 (m, 2H), 4.62 (s, 2H), 2.85-2.90 (m, 3H), 2.47-2.53 (m, 4H), 2.37 (t, J=7.2 Hz, 2H), 2.22 (s, 3H), 1.78-1.83 (m, 2H), 1.60-1.65 (m, 6H), 1.30-1.50 (m, 2H). $^{19}$F NMR (300 MHz, CD$_3$OD) δ: −139.04. Mass spectrum (ESI, m/z): Calculated for C$_{21}$H$_{27}$FO$_3$, 345.2 [M−H], Measured: 345.1.

Example 372: Compound #432

3-[4-[(2-cyclopentylcyclopenten-1-yl)methoxy]-2,3-dimethyl-phenyl]Propanoic Acid

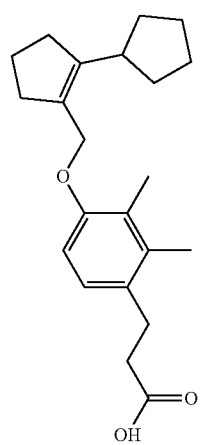 [SMILES: Cc1c(CCC(=O)O)ccc(OCC2=C(C3CCCC3)CCC2)c1C]

¹H NMR (300 MHz, CD₃OD) δ: 6.93 (d, J=8.4 Hz, 1H), 6.71 (d, J=8.4 Hz, 1H), 4.56 (s, 2H), 2.86-2.97 (m, 3H), 2.46 (t, J=7.2 Hz, 4H), 2.37 (t, J=7.2 Hz, 2H), 2.15 (s, 3H), 2.22 (s, 3H), 1.79-1.86 (m, 2H), 1.61-1.77 (m, 6H), 1.45-1.50 (m, 2H). Mass spectrum (ESI, m/z): Calculated for $C_{22}H_{30}O_3$, 341.2 [M−H], Measured: 341.2.

Example 373: Compound #433

3-[4-[(2-cyclopentylcyclopenten-1-yl)methoxy]-5-fluoro-2-(trifluoromethyl)phenyl]Propanoic Acid

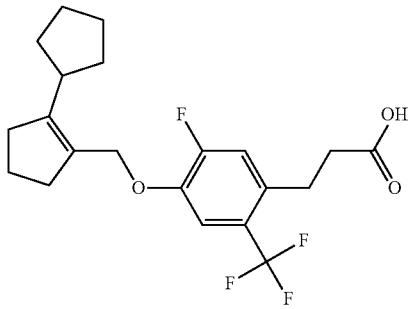 [SMILES: O=C(O)CCc1cc(F)c(OCC2=C(C3CCCC3)CCC2)cc1C(F)(F)F]

¹H NMR (300 MHz, CD₃OD) δ: 7.39-7.43 (m, 1H), 7.20 (t, J=7.6 Hz, 1H), 4.73 (s, 2H), 3.05 (t, J=8.1 Hz, 2H), 2.80-2.85 (m, 1H), 2.36-2.57 (m, 6H), 1.81-1.90 (m, 2H), 1.33-1.79 (m, 8H). Mass spectrum: Calculated for $C_{21}H_{24}F_4O_3$, 399.2 [M−H], Measured: 399.1.

Example 374: Compound #434

3-[4-[(2-cyclopentylcyclopenten-1-yl)methoxy]-2-methoxy-phenyl]Propanoic Acid

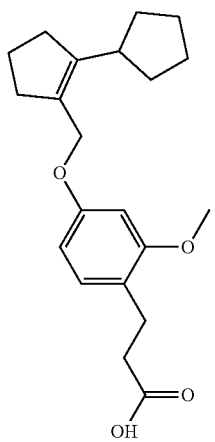

¹H NMR (400 MHz, CD₃OD) δ: 7.01 (d, J=8.0 Hz, 1H), 6.50 (s, 1H), 6.41-6.44 (m, 1H), 4.87 (s, 2H), 3.80 (s, 3H), 2.92-2.98 (m, 1H), 2.81 (t, J=7.6 Hz, 2H), 2.36-2.52 (m, 6H), 1.81-1.86 (m, 2H), 1.76-1.79 (m, 6H), 1.67-1.71 (m, 2H). Mass spectrum (ESI, m/z): Calculated for $C_{21}H_{28}O_4$, 343.2 [M−H], Measured: 343.1

Example 375: Compound #435

3-[4-[(2-cyclopentylcyclopenten-1-yl)methoxy]-3-fluoro-2-(trifluoromethyl)phenyl]Propanoic Acid

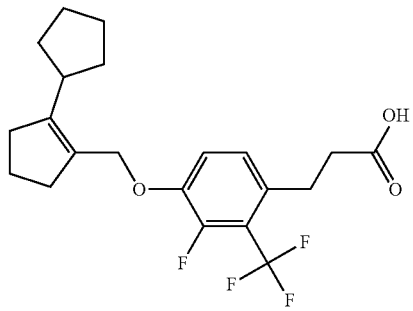 [SMILES: O=C(O)CCc1ccc(OCC2=C(C3CCCC3)CCC2)c(F)c1C(F)(F)F]

¹H NMR (300 MHz, CD₃OD) δ: 7.25-7.33 (m, 1H), 7.19 (d, J=8.3 Hz, 1H), 4.72 (s, 2H), 2.99 (t, J=7.8 Hz, 2H), 2.77-2.86 (m, 1H), 2.50-2.66 (m, 4H), 2.37 (t, J=7.5 Hz, 2H), 1.78-1.88 (m, 2H), 1.25-1.71 (m, 8H). 19F NMR (300 MHz, CD₃OD) δ: −62.48, −133.30. Mass spectrum (ESI, m/z): Calculated for $C_{21}H_{24}F_4O_3$, 399.2 [M−H], Measured: 399.1

Example 376: Compound #438

3-[2-chloro-4-[[2-[(2-fluorophenyl)methyl]cyclopenten-1-yl]methoxy]phenyl]Propanoic Acid

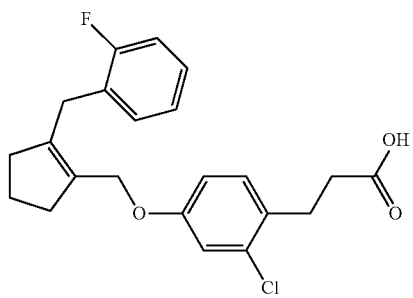 [SMILES: O=C(O)CCc1ccc(OCC2=C(Cc3ccccc3F)CCC2)cc1Cl]

¹H NMR (300 MHz, CD₃OD) δ: 7.15-7.25 (m, 3H), 6.97-7.10 (m, 3H), 6.82-6.97 (m, 1H), 4.70 (s, 2H), 3.55 (s, 2H), 2.97 (t, J=7.8 Hz, 2H), 2.48-2.60 (m, 4H), 2.27-2.32 (m, 2H), 1.75-1.85 (m, 2H). ¹⁹F NMR (300 MHz, CD₃OD) δ: −120.43. Mass spectrum (ESI, m/z): Calculated for $C_{22}H_{22}ClFO_3$, 387.1 (M−H) Measured: 387.0.

Example 377: Compound #439

3-[4-[(2-cyclopentylcyclopenten-1-yl)methoxy]-2-fluoro-6-(trifluoromethyl)phenyl]Propanoic Acid

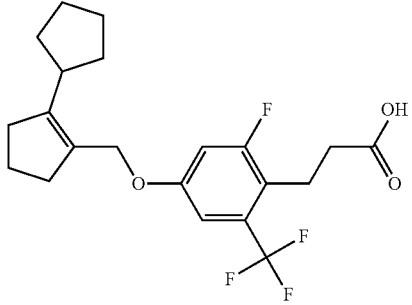 [SMILES: O=C(O)CCc1c(F)cc(OCC2=C(C3CCCC3)CCC2)cc1C(F)(F)F]

¹H NMR (300 MHz, CD₃OD) δ: 7.02 (s, 1H), 6.97 (d, J=9.3 Hz, 1H), 4.74 (s, 2H), 2.91-2.99 (m, 3H), 2.35-2.51 (m, 6H), 1.81-1.84 (m, 2H), 1.60-1.78 (m, 6H), 1.43-1.46 (m, 2H). ¹⁹F NMR (300 MHz, CD₃OD) δ: −64.11,−116.56. Mass spectrum (ESI, m/z): Calculated for $C_{21}H_{24}F_4O_3$, 399.2 [M−H], Measured: 399.1

Example 378: Compound #440

3-[4-[[2-(thiazol-2-ylmethyl)cyclopenten-1-yl]methoxy]-2-(trifluoromethyl)phenyl]Propanoic Acid

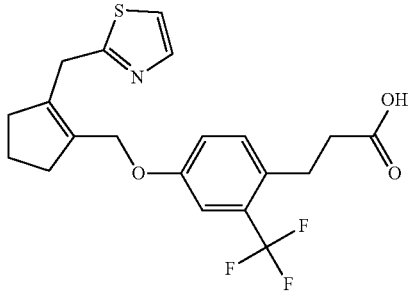 [SMILES: O=C(O)CCc1ccc(OCC2=C(Cc3nccs3)CCC2)cc1C(F)(F)F]

¹H NMR (400 MHz, CD₃OD) δ: 7.68 (d, J=3.2 Hz, 1H), 7.48 (d, J=3.6 Hz, 1H), 7.40 (d, J=8.4 Hz, 1H), 7.12-7.16 (m, 2H), 4.76 (s, 2H), 3.97 (s, 2H), 3.03 (t, J=8.2 Hz, 2H), 2.55 (t, J=7.6 Hz, 2H), 2.42-2.56 (m, 4H), 1.85-1.92 (m, 2H). ¹⁹F NMR (400 MHz, CD₃OD) δ: −61.26. Mass spectrum (ESI, m/z): Calculated for $C_{20}H_{20}F_3NO_3S$, 410.1 [M−H], Measured: 410.0.

Example 379: Compound #442

3-[4-[(2-cyclopentylcyclopenten-1-yl)methoxy]-2-vinyl-phenyl]Propanoic Acid

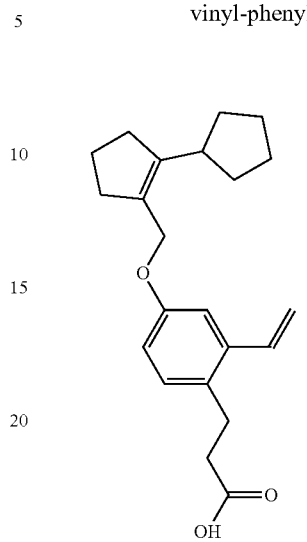

¹H NMR (400 MHz, CD₃OD) δ: 7.08 (d, J=8.4 Hz, 1H), 7.04-7.05 (m, 1H), 6.98-7.03 (m, 1H), 6.78-6.81 (m, 1H), 5.64-5.69 (m, 1H), 5.31-5.34 (m, 1H), 4.63 (s, 2H), 2.92-2.98 (m, 3H), 2.42-2.52 (m, 4H), 2.38-2.40 (m, 2H), 1.80-1.86 (m, 2H), 1.61-1.78 (m, 6H), 1.43-1.48 (m, 2H). Mass spectrum (ESI, m/z): Calculated for $C_{22}H_{23}O_3$, 339.2 [M−H], Measured: 339.1.

Example 380: Compound #443

3-[4-[(2-cyclopentylcyclopenten-1-yl)methoxy]-2-(1-hydroxyethyl)phenyl]Propanoic Acid

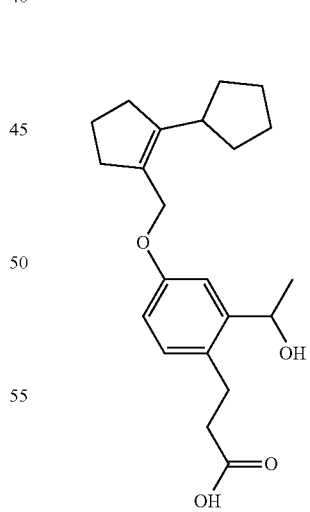

¹H NMR (400 MHz, CD₃OD) δ: 7.07-7.09 (m, 2H), 6.75-6.78 (m, 1H), 5.08-5.13 (m, 1H), 4.61 (s, 2H), 2.89-2.97 (m, 3H), 2.54-2.60 (m, 2H), 2.47 (t, J=7.6 Hz, 2H), 2.40 (t, J=7.6 Hz, 2H), 1.80-1.86 (m, 2H), 1.61-1.75 (m, 6H), 1.43-1.48 (m, 5H). Mass spectrum (ESI, m/z): Calculated for $C_{22}H_{30}O_4$, 357.2 [M−H], Measured: 357.1.

Example 381: Compound #444

3-[4-[(2-cyclopentylcyclopenten-1-yl)methoxy]-2-cyclopropyl-phenyl]Propanoic Acid

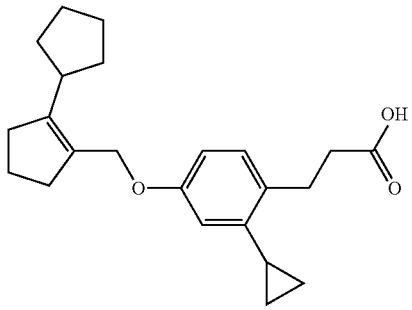 [SMILES: O=C(O)CCc1ccc(OCC2=C(C3CCCC3)CCC2)cc1C1CC1]

$^1$H NMR (300 MHz, CD$_3$OD) δ: 7.00 (d, J=8.4 Hz, 1H), 6.61-6.65 (m, 1H), 6.47 (s, 1H), 4.52 (s, 2H), 3.01 (t, J=7.5 Hz, 2H), 2.85-2.95 (m, 1H), 2.56 (t, J=7.5 Hz, 2H), 2.31-2.41 (m, 4H), 1.85-1.95 (m, 1H), 1.70-1.80 (m, 2H), 1.50-1.70 (m, 6H), 1.30-1.42 (m, 2H), 0.88-0.95 (m, 2H), 0.56-0.61 (m, 2H). Mass spectrum (ESI, m/z): Calculated for C$_{23}$H$_{30}$O$_3$, 353.2 [M−H], Measured: 353.1.

Example 382: Compound #445

3-[2-chloro-4-[[2-(thiazol-2-ylmethyl)cyclopenten-1-yl]methoxy]phenyl]Propanoic Acid

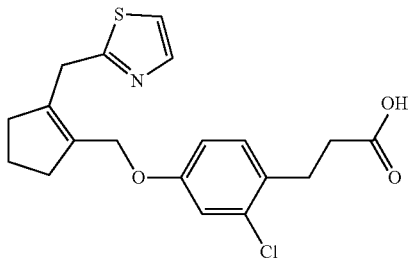 [SMILES: O=C(O)CCc1ccc(OCC2=C(Cc3nccs3)CCC2)cc1Cl]

$^1$H NMR (400 MHz, CD$_3$OD) δ: 7.71 (d, J=4.0 Hz, 1H), 7.48 (d, J=3.2 Hz, 1H), 7.23 (d, J=8.4 Hz, 1H), 6.95 (d, J=2.8 Hz, 1H), 6.82 (d, J=8.4 Hz, 1H), 4.70 (s, 2H), 3.96 (s, 2H), 2.96 (t, J=7.6 Hz, 2H), 2.53-2.57 (m, 2H), 2.31-2.48 (m, 4H), 1.84-1.92 (m, 2H). Mass spectrum (ESI, m/z): Calculated for C$_{19}$H$_{20}$ClNO$_3$S, 376.1 [M−H], Measured: 376.0.

Example 383: Compound #446

3-[4-[(2-cyclopentylcyclopenten-1-yl)methoxy]-2-(1,1,2,2,2-pentafluoroethyl)phenyl]Propanoic Acid

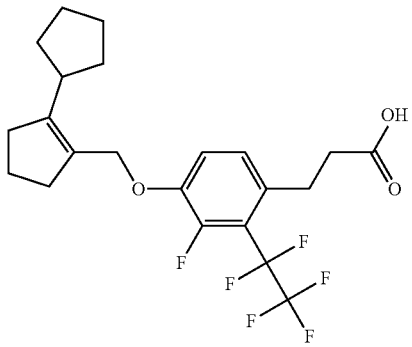 [SMILES: O=C(O)CCc1ccc(OCC2=C(C3CCCC3)CCC2)c(F)c1C(F)(F)C(F)(F)F]

$^1$H NMR (400 MHz, CD$_3$OD) δ: 7.37 (d, J=8.4 Hz, 1H), 7.15 (d, J=8.4 Hz, 1H), 7.06 (s, 1H), 4.68 (s, 2H), 2.92-3.03 (m, 3H), 2.56 (t, J=8.4 Hz, 2H), 2.38-2.46 (m, 3H), 1.80-1.85 (m, 3H), 1.61-1.79 (m, 6H), 1.42-1.50 (m, 2H). $^{19}$F NMR (400 MHz, CD$_3$OD) δ: −85.73, −110.34. Mass spectrum (EI, m/z): Calculated for C$_{22}$H$_{25}$F$_5$O$_3$, 431.2 [M−H], Measured: 431.1.

Example 384: Compound #448

3-[2-(1-bromovinyl)-4-[(2-cyclopentylcyclopenten-1-yl)methoxy]phenyl]Propanoic Acid

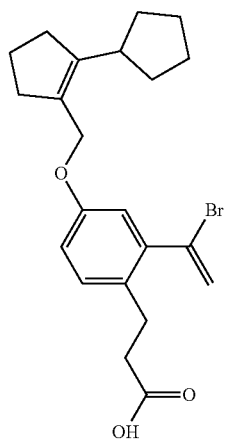 [SMILES: C=C(Br)c1cc(OCC2=C(C3CCCC3)CCC2)ccc1CCC(=O)O]

$^1$H NMR (300 MHz, CD$_3$OD) δ: 7.13 (d, J=8.4 Hz, 1H), 6.73-6.82 (m, 1H), 6.72 (s, 1H), 5.84 (s, 1H), 5.74 (s, 1H), 4.56 (s, 2H), 2.87-2.95 (m, 3H), 2.32-2.43 (m, 6H), 1.72-1.81 (m, 2H), 1.55-1.71 (m, 6H), 1.38-1.55 (m, 2H). Mass spectrum (ESI, m/z): Calculated for C$_{22}$H$_{27}$BrO$_3$, 417.1 [M−H], Measured: 417.0.

Example 385: Compound #450

3-[2-chloro-4-[(2-cyclopentylcyclopenten-1-yl)methoxy]-5-fluoro-phenyl]Propanoic Acid

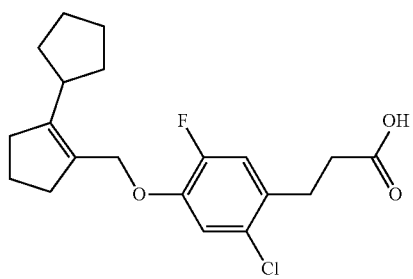 [SMILES: O=C(O)CCc1cc(F)c(OCC2=C(C3CCCC3)CCC2)cc1Cl]

$^1$H NMR (400 MHz, CD$_3$OD) δ: 7.08-7.13 (m, 2H), 4.70 (s, 2H), 2.93-3.01 (m, 3H), 2.59 (t, J=8.0 Hz, 2H), 2.38-2.47 (m, 4H), 1.81-1.85 (m, 3H), 1.63-1.80 (m, 6H), 1.42-1.49 (m, 2H). $^{19}$F NMR (400 MHz, CD$_3$OD) δ: −137.67. Mass spectrum (EI, m/z): Calculated for C$_{20}$H$_{24}$ClFO$_3$, 365.1 [M−H], Measured: 365.1.

Example 386: Compound #451

3-[2-chloro-4-[(2-cyclopent-2-en-1-ylcyclopenten-1-yl)methoxy]phenyl]Propanoic Acid

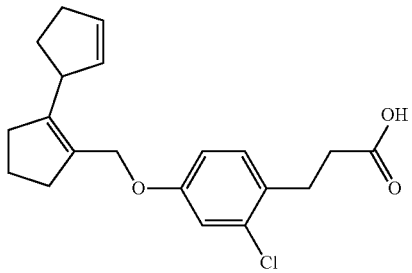 [SMILES: O=C(O)CCc1ccc(OCC2=C(C3C=CCC3)CCC2)cc1Cl]

¹H NMR (400 MHz, CD₃OD) δ: 7.21 (d, J=8.4 Hz, 1H), 6.97 (s, 1H), 6.81-6.84 (m, 1H), 5.84-5.86 (m, 1H), 5.52-5.54 (m, 1H), 4.65 (s, 2H), 3.86-3.87 (m, 1H), 2.97 (t, J=7.6 Hz, 2H), 2.58 (t, J=7.6 Hz, 2H), 2.29-2.48 (m, 6H), 2.07-2.10 (m, 1H), 1.78-1.84 (m, 2H), 1.66-1.70 (m, 1H). Mass spectrum (EI, m/z): Calculated for $C_{20}H_{23}ClO_3$, 345.1 [M–H], Measured: 345.1.

Example 387: Compound #452

3-[4-[(2-cyclopent-2-en-1-ylcyclopenten-1-yl)methoxy]phenyl]Propanoic Acid

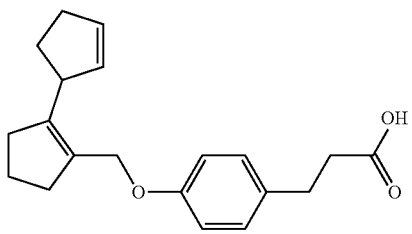 [SMILES: O=C(O)CCc1ccc(OCC2=C(C3C=CCC3)CCC2)cc1]

¹H NMR (400 MHz, CD₃OD) δ: 7.12 (d, J=6.4 Hz, 2H), 6.85 (d, J=6.4 Hz, 2H), 5.82-5.84 (m, 1H), 5.50-5.52 (m, 1H), 4.62 (s, 2H), 3.84-3.85 (m, 1H), 2.86 (t, J=7.6 Hz, 2H), 2.57 (t, J=7.6 Hz, 2H), 2.46-2.50 (m, 2H), 2.33-2.40 (m, 4H), 2.05-2.08 (m, 1H), 1.78-1.84 (m, 2H), 1.65-1.69 (m, 1H). Mass spectrum (EI, m/z): Calculated for $C_{20}H_{24}O_3$, 311.2 [M–H], Measured: 311.1.

Example 388: Compound #453

3-[4-[(2-cyclopent-2-en-1-ylcyclopenten-1-yl)methoxy]-2-(trifluoromethyl)phenyl]Propanoic Acid

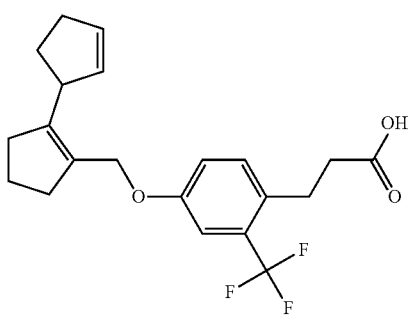 [SMILES: O=C(O)CCc1ccc(OCC2=C(C3C=CCC3)CCC2)cc1C(F)(F)F]

¹H NMR (400 MHz, CD₃OD) δ: 7.36 (d, J=8.4 Hz, 1H), 7.18 (s, 1H), 7.11-7.14 (m, 1H), 5.84-5.86 (m, 1H), 5.51-5.53 (m, 1H), 4.71 (s, 2H), 3.86-3.87 (m, 1H), 3.04 (t, J=7.6 Hz, 2H), 2.57 (t, J=7.6 Hz, 2H), 2.30-2.49 (m, 6H), 2.05-2.10 (m, 1H), 1.78-1.84 (m, 2H), 1.65-1.69 (m, 1H). ¹⁹F NMR (400 MHz, CD₃OD) δ: –61.30. Mass spectrum (EI, m/z): Calculated for $C_{21}H_{23}F_3O_3$, 379.2 (M–H), Measured: 379.1.

Example 389: Compound #454

3-[4-[(2-cyclopentylcyclopenten-1-yl)methoxy]-2-ethynyl-phenyl]Propanoic Acid

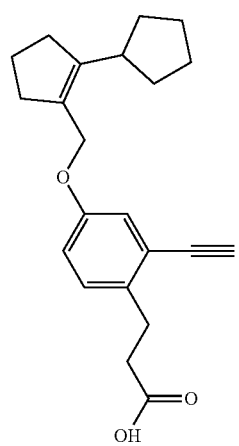 [SMILES: C#Cc1cc(OCC2=C(C3CCCC3)CCC2)ccc1CCC(=O)O]

¹H NMR (300 MHz, CD₃OD) δ: 7.14 (d, J=8.4 Hz, 1H), 6.82 (d, J=2.7 Hz, 1H), 6.79-6.83 (m, 1H), 4.55 (s, 2H), 3.59 (s, 1H), 2.88-3.04 (m, 3H), 2.32-2.45 (m, 6H), 1.73-1.81 (m, 2H), 1.60-1.71 (m, 6H), 1.30-1.50 (m, 2H). Mass spectrum (ESI, m/z): Calculated for $C_{22}H_{26}O_3$, 337.2 [M–H], Measured: 337.1.

Example 390: Compound #455

3-[4-[[2-(4-bicyclo[3.1.0]hexanyl)cyclopenten-1-yl]methoxy]phenyl]Propanoic Acid

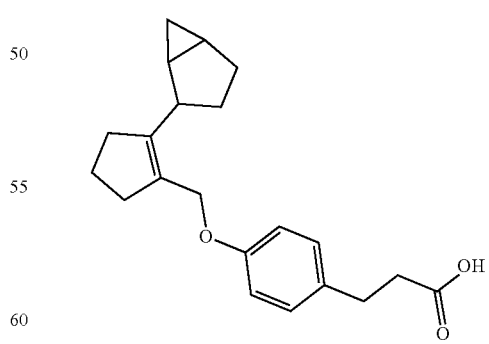

¹H NMR (400 MHz, CD₃OD) δ: 7.12 (d, J=6.8 Hz, 2H), 6.86 (d, J=6.8 Hz, 2H), 4.62 (s, 2H), 3.15 (d, J=8.0 Hz, 1H), 2.86 (t, J=7.6 Hz, 2H), 2.57 (t, J=7.6 Hz, 2H), 2.43-2.47 (m, 3H), 2.30-2.40 (m, 1H), 1.81-1.87 (m, 3H), 1.72-1.80 (m, 1H), 1.51-1.54 (m, 1H), 1.34-1.40 (m, 2H), 1.07-1.09 (m,

1H), 0.43-0.45 (m, 1H), 0.13-0.16 (m, 1H). Mass spectrum (EI, m/z): Calculated for $C_{21}H_{26}O_3$, 325.2 [M−H], Measured: 325.1.

Example 391: Compound #456

3-[4-[[2-(4-bicyclo[3.1.0]hexanyl)cyclopenten-1-yl]methoxy]-2-(trifluoromethyl)phenyl]Propanoic Acid

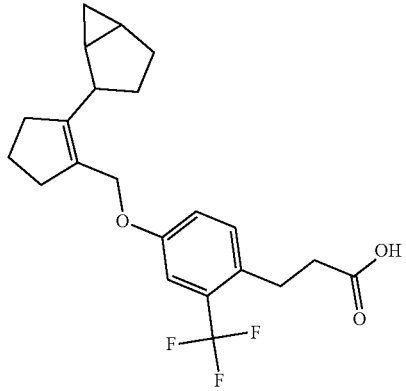 [SMILES: O=C(O)CCc1ccc(OCC2=C(C3CCC4CC43)CCC2)cc1C(F)(F)F]

$^1$H NMR (400 MHz, $CD_3OD$) δ: 7.35 (d, J=8.4 Hz, 1H), 7.18 (s, 1H), 7.11-7.14 (d, J=8.4 Hz, 1H), 4.71 (s, 2H), 3.17 (d, J=8.4 Hz, 1H), 3.03 (t, J=7.6 Hz, 2H), 2.25-2.59 (m, 6H), 1.70-1.87 (m, 4H), 1.50-1.60 (m, 1H), 1.34-1.40 (m, 2H), 1.05-1.09 (m, 1H), 0.44-0.46 (m, 1H), 0.14-0.18 (m, 1H). $^{19}$FNMR (400 MHz, $CD_3OD$) δ: −61.30. Mass spectrum (EI, m/z): Calculated for $C_{22}H_{25}F_3O_3$, 393.2 [M−H], Measured: 393.1.

Example 392: Compound #578

3-[4-[(2-isobutylcyclohexen-1-yl)methoxy]phenyl]Propanoic Acid

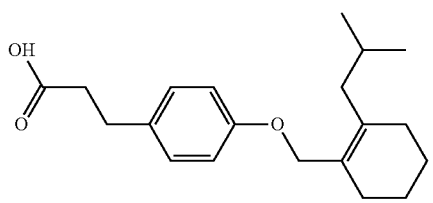 [SMILES: CC(C)CC1=C(COc2ccc(CCC(=O)O)cc2)CCCC1]

$^1$H NMR (300 MHz, Methanol-$d_4$) δ: 7.08 (d, J=8.7 Hz, 2H), 6.68-6.86 (m, 2H), 4.40 (s, 2H), 2.81 (t, J=7.6 Hz, 2H), 2.52 (t, J=7.7 Hz, 2H), 2.13 (s, 2H), 1.90-2.06 (m, 4H), 1.66-1.86 (m, 1H), 1.57-1.62 (m, 4H), 0.85 (d, J=6.4 Hz, 6H). Mass spectrum (ESI, m/z): Calculated for $C_{20}H_{28}O_3$, 315.2 [M−H], Measured: 315.2

Example 393: Compound #579

3-[4-[(2-isobutylcyclohexen-1-yl)methoxy]-2-(trifluoromethyl)phenyl]Propanoic Acid

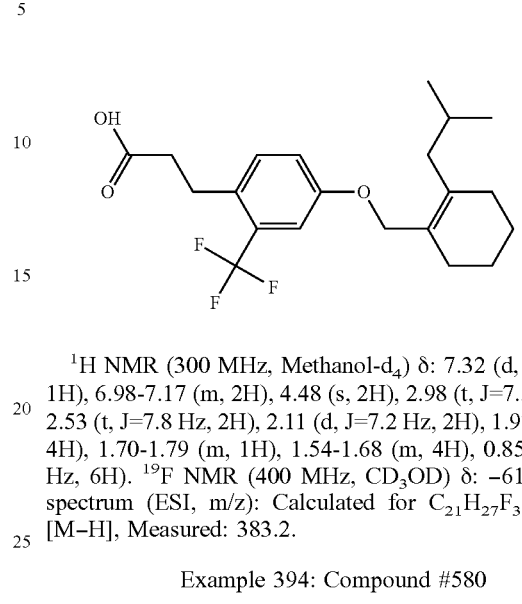

$^1$H NMR (300 MHz, Methanol-$d_4$) δ: 7.32 (d, J=8.4 Hz, 1H), 6.98-7.17 (m, 2H), 4.48 (s, 2H), 2.98 (t, J=7.5 Hz, 2H), 2.53 (t, J=7.8 Hz, 2H), 2.11 (d, J=7.2 Hz, 2H), 1.97-2.01 (m, 4H), 1.70-1.79 (m, 1H), 1.54-1.68 (m, 4H), 0.85 (d, J=6.3 Hz, 6H). $^{19}$F NMR (400 MHz, $CD_3OD$) δ: −61.31. Mass spectrum (ESI, m/z): Calculated for $C_{21}H_{27}F_3O_3$, 383.2 [M−H], Measured: 383.2.

Example 394: Compound #580

3-[2-chloro-4-[(2-isobutylcyclohexen-1-yl)methoxy]phenyl]Propanoic Acid

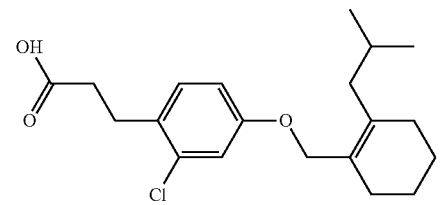 [SMILES: CC(C)CC1=C(COc2ccc(CCC(=O)O)c(Cl)c2)CCCC1]

$^1$H NMR (300 MHz, Methanol-$d_4$) δ: 7.57 (d, J=8.5 Hz, 1H), 7.30 (d, J=2.6 Hz, 1H), 7.17 (dd, J=8.5, 2.6 Hz, 1H), 4.83 (s, 2H), 3.33 (t, J=7.6 Hz, 2H), 2.94 (t, J=7.6 Hz, 2H), 2.11-2.20 (m, 2H), 1.96-2.00 (m, 4H), 1.72-1.79 (m, 1H), 1.56-1.61 (m, 4H), 0.80 (d, J=6.3 Hz, 6H). Mass spectrum (ESI, m/z): Calculated for $C_{20}H_{27}ClO_3$, 349.2 [M−H], Measured: 349.2

Example 395: Compound #581

3-[4-[(2-benzylcyclohexen-1-yl)methoxy]phenyl]Propanoic Acid

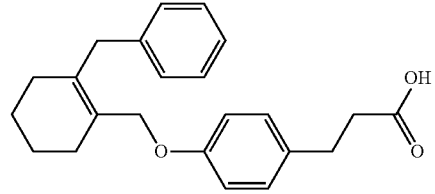 [SMILES: O=C(O)CCc1ccc(OCC2=C(Cc3ccccc3)CCCC2)cc1]

$^1$H NMR (400 MHz, $CD_3OD$) δ: 7.23-7.27 (m, 2H), 7.12-7.18 (m, 5H), 6.86 (d, J=8.8 Hz, 2H), 4.58 (s, 2H), 3.47

(s, 2H), 2.86 (t, J=7.6 Hz, 2H), 2.57 (t, J=7.6 Hz, 2H), 2.23-2.25 (m, 2H), 1.97-2.00 (m, 2H), 1.59-1.69 (m, 4H). Mass spectrum (ESI, m/z): Calculated for $C_{23}H_{26}O_3$, 349.2 [M–H], Measured: 349.1

Example 396: Compound #582

3-[4-[(2-benzylcyclohexen-1-yl)methoxy]-2-chlorophenyl]Propanoic Acid

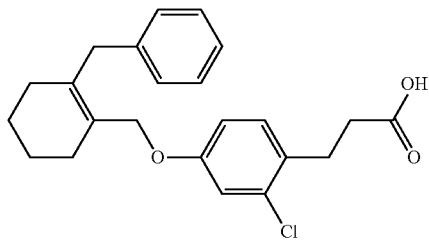 [SMILES: O=C(O)CCc1ccc(OCC2=C(Cc3ccccc3)CCCC2)cc1Cl]

$^1$H NMR (400 MHz, CD$_3$OD) δ: 7.21-7.27 (m, 3H), 7.14-7.18 (m, 3H), 6.86 (s, 1H), 6.81 (d, J=8.4 Hz, 1H), 4.58 (s, 2H), 3.47 (s, 2H), 2.96 (t, J=7.6 Hz, 2H), 2.44 (t, J=7.6 Hz, 2H), 2.23-2.25 (m, 2H), 1.97-1.99 (m, 2H), 1.59-1.69 (m, 4H). Mass spectrum (ESI, m/z): Calculated for $C_{23}H_{25}ClO_3$, 383.1 [M–H], Measured: 383.1

Example 397: Compound #583

3-[4-[(2-butylcyclohexen-1-yl)methoxy]-2-chlorophenyl]Propanoic Acid

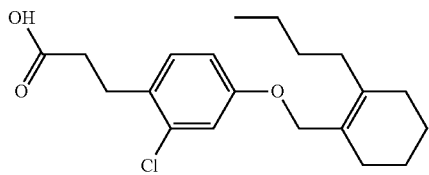 [SMILES: CCCCC1=C(COc2ccc(CCC(=O)O)c(Cl)c2)CCCC1]

$^1$H NMR (300 MHz, CD$_3$OD) δ 7.20 (d, J=8.5 Hz, 1H), 6.94 (d, J=2.5 Hz, 1H), 6.80 (dd, J=8.5, 2.6 Hz, 1H), 4.45 (s, 2H), 2.96 (t, J=7.8 Hz, 2H), 2.57 (t, J=7.8 Hz, 2H), 2.00-2.19 (m, 6H), 1.55-1.71 (br s, 4H), 1.22-1.46 (m, 4H), 0.90 (t, J=7.0 Hz, 3H). Mass spectrum (ESI, m/z): Calculated for $C_{20}H_{27}ClO_3$, 349.2 [M–H], Measured: 349.2

Example 398: Compound #584

3-[4-[(2-benzylcyclohexen-1-yl)methoxy]-2-(trifluoromethyl)phenyl]Propanoic Acid

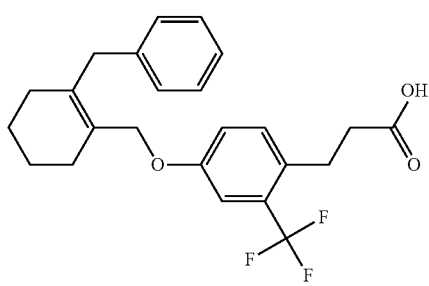 [SMILES: O=C(O)CCc1ccc(OCC2=C(Cc3ccccc3)CCCC2)cc1C(F)(F)F]

$^1$H NMR (400 MHz, CD$_3$OD) δ: 7.36 (d, J=8.4 Hz, 1H), 7.23-7.27 (m, 2H), 7.11-7.18 (m, 5H), 4.65 (s, 2H), 3.49 (s, 2H), 3.03 (t, J=7.6 Hz, 2H), 2.57 (t, J=8.4 Hz, 2H), 2.23-2.25 (m, 2H), 1.98-2.00 (m, 2H), 1.61-1.70 (m, 4H). $^{19}$F NMR (400 MHz, CD$_3$OD) δ: −61.31. Mass spectrum (ESI, m/z): Calculated for $C_{24}H_{25}F_3O_3$, 417.2 [M–H], Measured: 417.1

Example 399: Compound #585

3-[4-[(2-isopropylcyclohexen-1-yl)methoxy]phenyl]Propanoic Acid

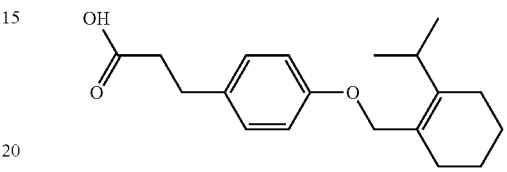

$^1$H NMR (400 MHz, CD$_3$OD) δ:7.01 (d, J=8.8 Hz, 2H), 6.71-6.74 (m, 2H), 4.34 (s, 2H), 2.82-2.88 (m, 1H), 2.74 (t, J=7.6 Hz, 2H), 2.45 (t, J=7.6 Hz, 2H), 2.04 (d, J=2.8 Hz, 2H), 1.92 (d, J=2.8 Hz, 2H), 1.48-1.54 (m, 4H), 0.88 (d, J=6.9 Hz, 6H). Mass spectrum (ESI, m/z): Calculated for $C_{19}H_{26}O_3$, 301.2 [M–H], Measured: 301.2

Example 400: Compound #586

3-[4-[(2-isopropylcyclohexen-1-yl)methoxy]-2-(trifluoromethyl)phenyl]Propanoic Acid

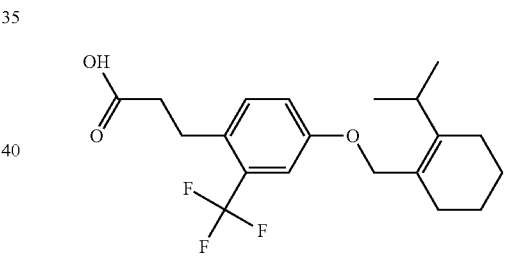

$^1$H NMR (400 MHz, CD$_3$OD) δ: 7.37 (d, J=8.5 Hz, 1H), 7.17 (s, 1H), 7.12 (d, J=8.4 Hz, 1H), 4.55 (s, 2H), 2.94-3.05 (m, 3H), 2.57 (t, J=8.0 Hz, 2H), 2.16 (br s, 2H), 2.04 (br s, 2H), 1.61-1.64 (m, 4H), 1.00 (d, J=6.8 Hz, 6H). $^{19}$F NMR (400 MHz, CD$_3$OD) δ: −61.32. Mass spectrum (ESI, m/z): Calculated for $C_{20}H_{25}F_3O_3$, 369.2 [M–H], Measured: 369.2.

Example 401: Compound #587

3-[2-chloro-4-[(2-isopropylcyclohexen-1-yl)methoxy]phenyl]Propanoic Acid

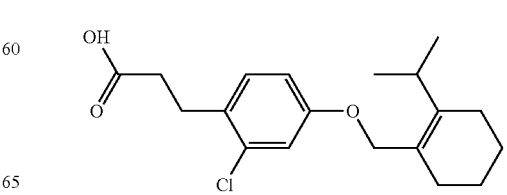

¹H NMR (400 MHz, CD₃OD) δ7.22 (d, J=8.5 Hz, 1H), 6.96 (s, 1H), 6.82 (d, J=8.4 Hz, 1H), 4.49 (s, 2H), 2.89-3.08 (m, 3H), 2.58 (t, J=7.2 Hz, 2H), 2.15 (br s, 2H), 2.04 (br s, 2H), 1.60-1.65 (m, 4H), 1.01 (d, J=6.9 Hz, 6H). Mass spectrum (ESI, m/z): Calculated for $C_{19}H_{25}ClO_3$, 335.1 [M−H], Measured: 335.2

Example 402: Compound #588

3-[4-[(2-butylcyclohexen-1-yl)methoxy]phenyl]Propanoic Acid

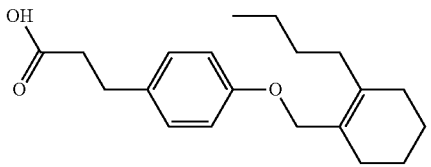 [SMILES: CCCCC1=C(COc2ccc(CCC(=O)O)cc2)CCCC1]

¹H NMR (300 MHz, CD₃OD) δ 7.08 (d, J=8.4 Hz, 2H), 6.79 (d, J=8.4 Hz, 2H), 4.39 (s, 2H), 2.81 (t, J=7.7 Hz, 2H), 2.52 (t, J=7.6 Hz, 2H), 1.93-2.19 (m, 6H), 1.57-1.59 (br s, 4H), 1.16-1.40 (m, 4H), 0.86 (t, J=7.0 Hz, 3H). Mass spectrum (ESI, m/z): Calculated for $C_{20}H_{23}O_3$, 315.2 [M−H], Measured: 315.2

Example 403: Compound #589

3-[4-[(2-propylcyclohexen-1-yl)methoxy]phenyl]Propanoic Acid

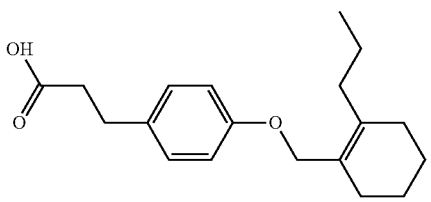 [SMILES: CCCC1=C(COc2ccc(CCC(=O)O)cc2)CCCC1]

¹H NMR (400 MHz, CD₃OD) δ: 7.13 (d, J=8.8 Hz, 2H), 6.83 (d, J=8.8 Hz, 2H), 4.44 (s, 2H), 2.85 (t, J=7.6 Hz, 2H), 2.47 (t, J=7.6 Hz, 2H), 2.07-2.15 (m, 6H), 1.61-1.67 (m, 4H), 1.41-1.49 (m, 2H), 0.91 (t, J=7.3 Hz, 3H). Mass spectrum (ESI, m/z): Calculated for $C_{19}H_{26}O_3$, 301.2 [M−H], Measured: 301.1

Example 404: Compound #590

3-[4-[(2-propylcyclohexen-1-yl)methoxy]-2-(trifluoromethyl)phenyl]Propanoic Acid

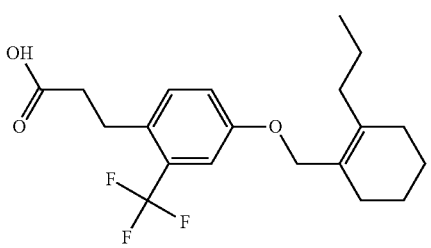

¹H NMR (400 MHz, CD₃OD) δ: 7.27 (d, J=8.4 Hz, 1H), 6.95-7.01 (m, 2H), 4.40 (s, 2H), 2.91 (t, J=7.6 Hz, 2H), 2.33 (t, J=8.0 Hz, 2H), 1.95-2.02 (m, 6H), 1.50-1.55 (m, 4H), 1.31-1.37 (m, 2H), 0.91 (t, J=7.4 Hz, 3H). ¹⁹F NMR (400 MHz, CD₃OD) δ: −61.23. Mass spectrum (ESI, m/z): Calculated for $C_{20}H_{25}F_3O_3$, 369.2 [M−H], Measured: 369.1

Example 405: Compound #591

3-[2-chloro-4-[(2-propylcyclohexen-1-yl)methoxy]phenyl]Propanoic Acid

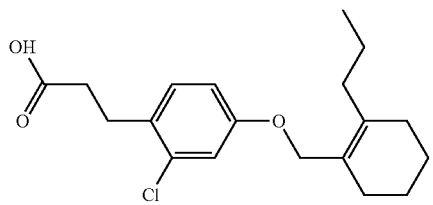 [SMILES: CCCC1=C(COc2ccc(CCC(=O)O)c(Cl)c2)CCCC1]

¹H NMR (400 MHz, CD₃OD) δ: 7.23 (d, J=8.4 Hz, 1H), 6.92 (s, 1H), 6.80 (d, J=8.4 Hz, 1H), 4.46 (s, 2H), 2.96 (t, J=8.0 Hz, 2H), 2.46 (t, J=7.6 Hz, 2H), 2.07-2.13 (m, 6H), 1.62-1.67 (m, 4H), 1.42-1.49 (m, 2H), 0.92 (t, J=7.6 Hz, 3H). Mass spectrum (ESI, m/z): Calculated for $C_{19}H_{25}ClO_3$, 335.1 [M−H], Measured: 335.1

Example 406: Compound #592

3-[4-[(2-norbornan-2-ylcyclohexen-1-yl)methoxy]-2-(trifluoromethyl)phenyl]Propanoic Acid

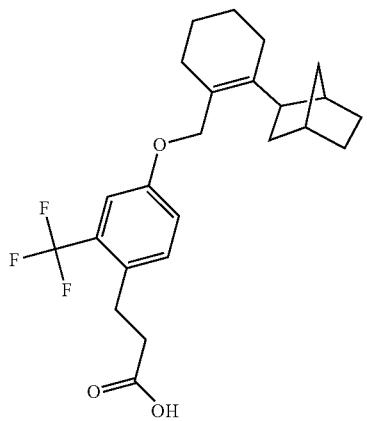 [SMILES: O=C(O)CCc1ccc(OCC2=C(C3CC4CCC3C4)CCCC2)cc1C(F)(F)F]

¹H NMR (300 MHz, CD₃OD) δ: 7.35 (d, J=8.7 Hz, 1H), 7.11-7.16 (m, 2H), 4.60 (d, J=10.8 Hz, 1H), 4.49 (d, J=11.1 Hz, 1H), 3.03 (t, J=8.1 Hz, 2H), 2.53-2.67 (m, 3H), 2.09-2.23 (m, 6H), 1.17-1.66 (m, 12H). Mass spectrum (ESI, m/z): Calculated for $C_{24}H_{29}F_3O_3$, 421.2 [M−H], Measured: 421.1.

Example 407: Compound #593

3-[2-chloro-4-[(2-norbornan-2-ylcyclohexen-1-yl)methoxy]phenyl]Propanoic Acid

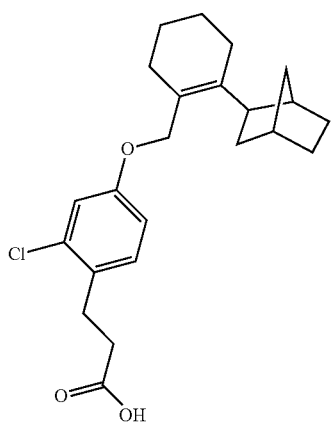 [SMILES: O=C(O)CCc1ccc(OCC2=C(C3CC4CCC3C4)CCCC2)cc1Cl]

$^1$H NMR (300 MHz, CD$_3$OD) δ: 7.21 (d, J=8.7 Hz, 1H), 6.94 (d, J=2.7 Hz, 1H), 6.78-6.82 (m, 1H), 4.54 (d, J=11.4 Hz, 1H), 4.43 (d, J=11.1 Hz, 1H), 2.96 (t, J=7.8 Hz, 2H), 2.64 (t, J=8.1 Hz, 1H), 2.54 (t, J=7.8 Hz, 2H), 2.23 (br s, 1H), 2.09 (br s, 5H), 1.44-1.61 (m, 9H), 1.15-1.21 (m, 3H). Mass spectrum (ESI, m/z): Calculated for C$_{23}$H$_{29}$ClO$_3$, 387.2 [M−H], Measured: 387.1.

Example 408: Compound #594

3-[2-chloro-4-[(2-cyclopentylcyclohexen-1-yl)methoxy]phenyl]Propanoic Acid

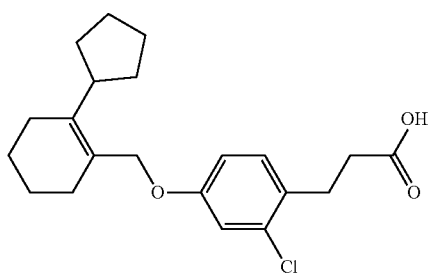 [SMILES: O=C(O)CCc1ccc(OCC2=C(C3CCCC3)CCCC2)cc1Cl]

$^1$H NMR (300 MHz, CD$_3$OD) δ: 7.24 (s, 1H), 7.10 (d, J=8.4 Hz, 1H), 6.97 (d, J=8.4 Hz, 1H), 4.55 (s, 2H), 2.97-3.12 (m, 1H), 2.84 (t, J=7.5 Hz, 2H), 2.53 (t, J=7.5 Hz, 2H), 2.20 (br s, 2H), 2.03 (br s, 2H), 1.59-1.64 (m, 1 OH), 1.35-1.49 (m, 2H). Mass spectrum (ESI, m/z): Calculated for C$_{21}$H$_{27}$ClO$_3$, 361.2 [M−H], Measured: 361.0.

Example 409: Compound #595

3-[2-chloro-4-[[2-(thiazol-5-ylmethyl)cyclohexen-1-yl]methoxy]phenyl]Propanoic Acid

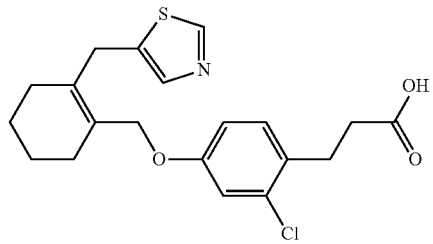 [SMILES: O=C(O)CCc1ccc(OCC2=C(Cc3cncs3)CCCC2)cc1Cl]

$^1$H NMR (400 MHz, CD$_3$OD) δ: 8.86 (s, 1H), 7.64 (s, 1H), 7.23 (d, J=8.5 Hz, 1H), 6.98 (d, J=2.6 Hz, 1H), 6.83-6.86 (m, 1H), 4.58 (s, 2H), 3.71 (s, 2H), 2.97 (t, J=8.0 Hz, 2H), 2.58 (t, J=8.0 Hz, 2H), 2.23-2.27 (m, 2H), 2.07 (br s, 2H), 1.66-1.70 (m, 4H). Mass spectrum (ESI, m/z): Calculated for C$_{20}$H$_{22}$ClNO$_3$S, 392.1 [M+H], Measured: 392.1

Example 410: Compound #596

3-[4-[[2-(thiazol-5-ylmethyl)cyclohexen-1-yl]methoxy]-2-(trifluoromethyl)phenyl]Propanoic Acid

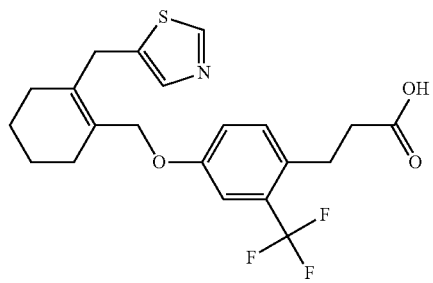 [SMILES: O=C(O)CCc1ccc(OCC2=C(Cc3cncs3)CCCC2)cc1C(F)(F)F]

$^1$H NMR: (400 MHz, CD$_3$OD) δ: 8.93 (s, 1H), 7.67 (s, 1H), 7.38 (d, J=8.2 Hz, 1H), 7.19 (s, 1H), 7.13-1.16 (m, 2H), 4.64 (s, 2H), 3.73 (s, 2H), 3.04 (t, J=7.6 Hz, 2H), 2.57 (t, J=7.6 Hz, 2H), 2.20-2.26 (m, 2H), 2.06-2.10 (m, 2H), 1.64-1.71 (m, 4H). $^{19}$F NMR: (400 MHz, CD$_3$OD) δ: −61.36. Mass spectrum (ESI, m/z): Calculated for C$_{21}$H$_{22}$F$_3$NO$_3$S, 426.1 [M+H], Measured: 426.0

Example 411: Compound #598

3-[4-[(2-butylcyclohexen-1-yl)methoxy]-2-(trifluoromethyl)phenyl]Propanoic Acid

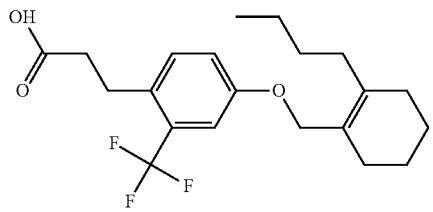 [SMILES: CCCCC1=C(COc2ccc(CCC(=O)O)c(C(F)(F)F)c2)CCCC1]

¹H NMR (300 MHz, CD₃OD) δ 7.32 (d, J=8.4 Hz, 1H), 7.16-7.02 (m, 2H), 4.48 (s, 2H), 2.99 (t, J=7.8 Hz, 2H), 2.52 (t, J=7.0 Hz, 2H), 1.95-2.16 (m, 6H), 1.58-1.60 (m, 4H), 1.16-1.44 (m, 4H), 0.86 (t, J=7.0 Hz, 3H). Mass spectrum (ESI, m/z): Calculated for $C_{21}H_{27}F_3O_3$, 383.2 [M−H], Measured: 383.1

Example 412: Compound #599

3-[4-[(2-cyclobutylcyclohexen-1-yl)methoxy]-2-(trifluoromethyl)phenyl]Propanoic Acid

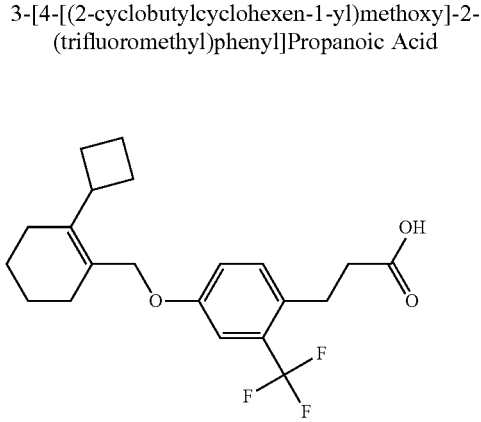

¹H NMR (300 MHz, CD₃OD) δ: 7.31 (d, J=8.5 Hz, 1H), 7.10 (d, J=2.6 Hz, 1H), 7.07-6.98 (m, 1H), 4.44 (s, 2H), 3.35-3.54 (m, 1H), 2.98 (t, J=7.8 Hz, 2H), 2.52 (t, J=7.5 Hz, 2H), 2.01-2.18 (m, 5H), 1.76-2.01 (m, 4H), 1.63-1.73 (m, 1H), 1.49-1.62 (m, 4H). ¹⁹F NMR (300 MHz, CD₃OD) δ: −61.30. Mass spectrum (ESI, m/z): Calculated for $C_{21}H_{25}F_3O_3$, 381.2 [M−H], Measured: 381.1.

Example 413: Compound #600

3-[2-chloro-4-[(2-cyclobutylcyclohexen-1-yl)methoxy]phenyl]Propanoic Acid

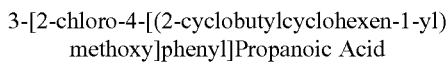

¹H NMR (300 MHz, CD₃OD) δ: 7.16 (d, J=8.5 Hz, 1H), 6.89 (d, J=2.5 Hz, 1H), 6.73-6.77 (m, 1H), 4.38 (s, 2H), 3.33-3.52 (m, 1H), 2.92 (d, J=7.8 Hz, 2H), 2.53 (t, J=7.8 Hz, 2H), 1.73-2.09 (m, 9H), 1.63-1.71 (m, 1H), 1.49-1.62 (m, 4H). Mass spectrum (ESI, m/z): Calculated for $C_{20}H_{25}ClO_3$, 347.1 [M−H], Measured: 347.1.

Example 414: Compound #601

3-[4-[(2-cyclohexylcyclohexen-1-yl)methoxy]-2-(trifluoromethyl)phenyl]Propanoic Acid

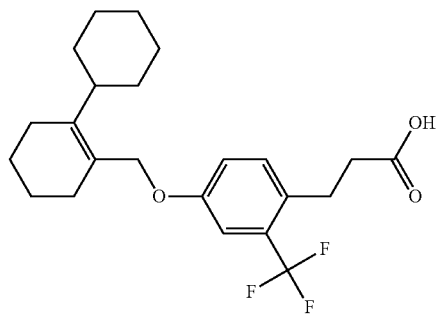 [SMILES: O=C(O)CCc1ccc(OCC2=C(C3CCCCC3)CCCC2)cc1C(F)(F)F]

¹H NMR (400 MHz, CD₃OD) δ: 7.37-7.39 (m, 1H), 7.10-7.16 (m, 2H), 4.54 (s, 2H), 3.03 (t, J=8.0 Hz, 2H), 2.47-2.63 (m, 3H), 2.15 (br s, 2H), 2.03 (br s, 2H), 1.71-1.87 (m, 2H), 1.55-1.72 (m, 5H), 1.47-1.50 (m, 2H), 1.24-1.46 (m, 4H), 1.13-1.24 (m, 1H). ¹⁹F NMR (300 MHz, CD₃OD) δ: −61.32. Mass spectrum (ESI, m/z): Calculated for $C_{23}H_{29}F_3O_3$, 409.2 [M−H], Measured: 409.2.

Example 415: Compound #602

3-[2-chloro-4-[(2-cyclohexylcyclohexen-1-yl)methoxy]phenyl]Propanoic Acid

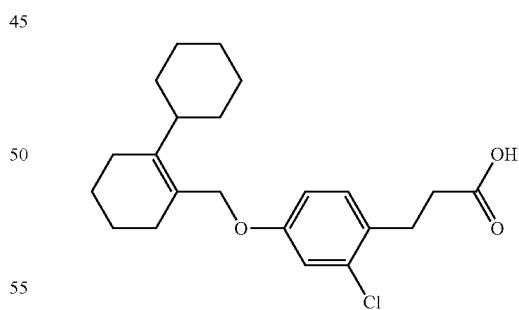

¹H NMR (400 MHz, CD₃OD) δ: 7.21-7.26 (m, 1H), 6.95 (d, J=2.5 Hz, 1H), 6.80-6.82 (m, 1H), 4.48 (s, 2H), 2.97 (t, J=7.9 Hz, 2H), 2.47-2.64 (m, 3H), 2.14 (br s, 2H), 2.03 (br s, 2H), 1.72-1.83 (m, 2H), 1.55-1.73 (m, 5H), 1.48-1.51 (m, 2H), 1.26-1.46 (m, 4H), 1.13-1.24 (m, 1H). Mass spectrum (ESI, m/z): Calculated for $C_{22}H_{29}ClO_3$, 375.2 [M−H], Measured: 375.2

Example 416: Compound #603

3-[4-[(2-cyclopentylcyclohexen-1-yl)methoxy]-2-(trifluoromethyl)phenyl]Propanoic Acid

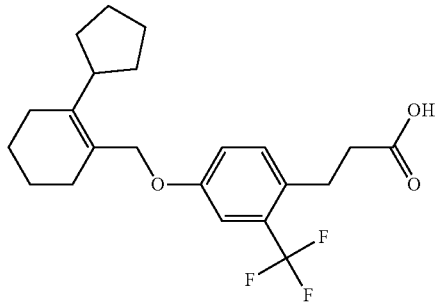 [SMILES: O=C(O)CCc1ccc(OCC2=C(C3CCCC3)CCCC2)cc1C(F)(F)F]

$^1$H NMR (400 MHz, CD$_3$OD) δ: 7.38 (d, J=8.5 Hz, 1H), 7.16 (s, J=2.6 Hz, 1H), 7.11 (d, J=8.5 Hz, 1H), 4.56 (s, 2H), 2.92-3.14 (m, 3H), 2.53 (t, J=8.0 Hz, 2H), 2.16 (br s, 2H), 2.04 (br s, 2H), 1.56-1.75 (m, 10H), 1.53-1.39 (m, 2H). Mass spectrum (ESI, m/z): Calculated for C$_{22}$H$_{27}$F$_3$O$_3$, 395.2[M–H], Measured: 395.2.

Example 417

Synthesis of 4,4-difluorocyclohexanecyclopentenes

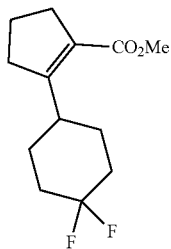 [SMILES: COC(=O)C1=C(C2CCC(F)(F)CC2)CCC1]

To a solution methyl 2-(((trifluoromethyl)sulfonyl)oxy)cyclopent-1-enecarboxylate (0.44 mL, 2.25 mmol), Pd(OAc)$_2$ (20 mg, 0.09 mmol), C-Phos (79 mg, 0.18 mmol) in THF (11 mL) at room temperature under nitrogen was added (4,4-difluorocyclohexyl)zinc(II) bromide (6.9 mL of a 0.65 M solution in THF prepared according to HAN, C., et al., "Negishi Coupling of Secondary Alkylzinc Halides with Aryl Bromides and Chlorides", *JACS,* 2009, pp 7532, Vol 131(22), 4.50 mmol). After 2 hrs, the reaction was filtered through CELITE® and washed with DCM. Water and 2 N HCl were added, the solution was extracted with DCM, dried over MgSO$_4$ and concentrated under reduced pressure to yield a residue. The residue was purified by chromatography (40 g) eluting with 2 to 10% EA/heptane to yield the title compound.

$^1$H NMR (CHLOROFORM-d) δ: 3.72 (s, 3H), 3.45 (brt, J=11.9 Hz, 1H), 2.55-2.65 (m, 2H), 2.41-2.52 (m, 2H), 2.04-2.21 (m, 2H), 1.51-1.94 (m, 8H).

Example 418: Compound #416

3-[4-[[2-(4,4-difluorocyclohexyl)cyclopenten-1-yl]methoxy]-2-(trifluoromethyl)phenyl]Propanoic Acid

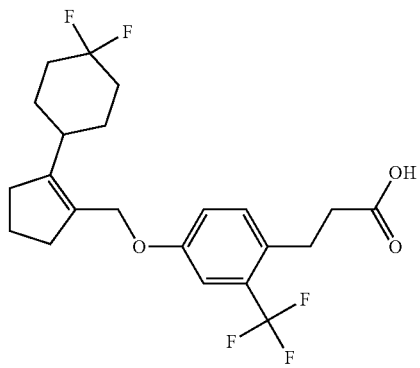 [SMILES: O=C(O)CCc1ccc(OCC2=C(C3CCC(F)(F)CC3)CCC2)cc1C(F)(F)F]

$^1$H NMR (CHLOROFORM-d) δ: 7.23-7.30 (m, 1H), 7.16 (d, J=2.5 Hz, 1H), 7.02 (dd, J=8.6, 2.5 Hz, 1H), 4.57 (s, 2H), 3.07 (br t, J=7.6 Hz, 2H), 2.65 (br t, J=7.8 Hz, 2H), 2.42-2.56 (m, 3H), 2.37 (br t, J=7.1 Hz, 2H), 2.07-2.20 (m, 2H), 1.51-1.89 (m, 8H). Calculated for C$_{22}$H$_{25}$F$_6$O$_3$: 455.2 (M+23); Measured: 455.3.

Example 419: Compound #411

3-[2-chloro-4-[[2-(4,4-difluorocyclohexyl)cyclopenten-1-yl]methoxy]phenyl]Propanoic Acid

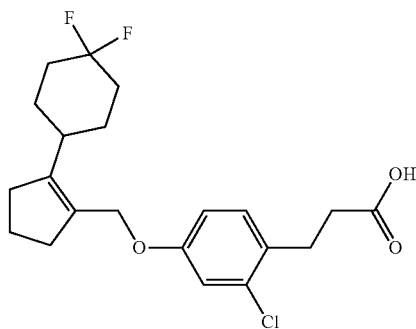 [SMILES: O=C(O)CCc1ccc(OCC2=C(C3CCC(F)(F)CC3)CCC2)cc1Cl]

$^1$H NMR (CHLOROFORM-d) δ: 7.16 (d, J=8.1 Hz, 1H), 6.93 (d, J=2.5 Hz, 1H), 6.76 (dd, J=8.6, 2.5 Hz, 1H), 4.52 (s, 2H), 2.95-3.04 (m, 2H), 2.67 (t, J=7.8 Hz, 2H), 2.42-2.57 (m, 3H), 2.37 (br t, J=7.3 Hz, 2H), 2.07-2.20 (m, 2H), 1.52-1.89 (m, 8H). Calculated for C$_{21}$H$_{25}$ClF$_2$O$_3$: 421.1 (M+23); Measured: 421.2.

Example 420: Compound #412

3-[4-[[2-(4,4-difluorocyclohexyl)cyclopenten-1-yl]methoxy]phenyl]Propanoic Acid

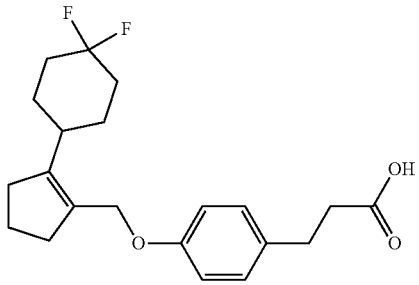 [SMILES: O=C(O)CCc1ccc(OCC2=C(C3CCC(F)(F)CC3)CCC2)cc1]

¹H NMR (CHLOROFORM-d) δ: 7.08-7.17 (m, 2H), 6.81-6.90 (m, 2H), 4.52 (s, 2H), 2.85-2.96 (m, 2H), 2.61-2.70 (m, 2H), 2.43-2.57 (m, 3H), 2.36 (br t, J=7.3 Hz, 2H), 2.06-2.18 (m, 2H), 1.53-1.90 (m, 8H). Calculated for $C_{21}H_{28}F_2O_3$: 387.2 (M+23); Measured: 387.1.

Example 421: Compound #419

3-[4-[[2-(4,4-difluorocyclohexyl)cyclopenten-1-yl]methoxy]-3,5-difluoro-phenyl]Propanoic Acid

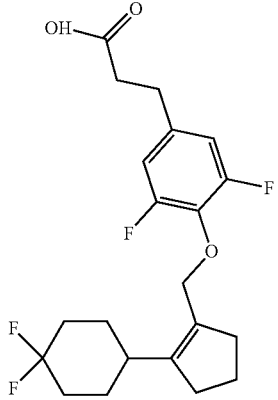 [SMILES: O=C(O)CCc1cc(F)c(OCC2=C(C3CCC(F)(F)CC3)CCC2)c(F)c1]

¹H NMR (CHLOROFORM-d) δ: 6.69-6.79 (m, 2H), 4.65 (s, 2H), 2.82-2.92 (m, 2H), 2.60-2.69 (m, 2H), 2.53 (br t, J=7.6 Hz, 2H), 2.33-2.45 (m, 1H), 2.29 (br t, J=7.3 Hz, 2H), 1.99-2.14 (m, 2H), 1.47-1.85 (m, 6H), 1.24-1.35 (m, 2H). Calculated for $C_{21}H_{24}F_4O_3$: 423.2 (M+23); Measured: 423.1.

Example 422: Compound #417

3-[4-[[2-(4,4-difluorocyclohexyl)cyclopenten-1-yl]methoxy]-5-fluoro-2-methyl-phenyl]Propanoic Acid

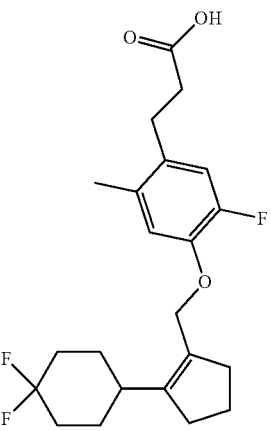 [SMILES: Cc1cc(OCC2=C(C3CCC(F)(F)CC3)CCC2)c(F)cc1CCC(=O)O]

¹H NMR (CHLOROFORM-d) δ: 6.88 (d, J=12.6 Hz, 1H), 6.77 (d, J=8.6 Hz, 1H), 4.59 (s, 2H), 2.81-2.90 (m, 2H), 2.56-2.64 (m, 2H), 2.44-2.56 (m, 3H), 2.34 (br t, J=7.3 Hz, 2H), 2.25 (s, 3H), 2.05-2.18 (m, 2H), 1.47-1.87 (m, 8H). Calculated for $C_{22}H_{27}F_3O_3$: 419.2 (M+23); Measured: 419.2.

Example 423: Compound #413

3-[4-[[2-(4,4-difluorocyclohexyl)cyclopenten-1-yl]methoxy]-2,3-dimethyl-phenyl]Propanoic Acid

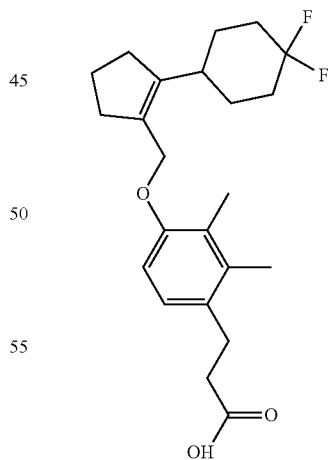

¹H NMR (CHLOROFORM-d) δ: 6.97 (d, J=8.6 Hz, 1H), 6.69 (d, J=8.1 Hz, 1H), 4.51 (s, 2H), 2.89-2.99 (m, 2H), 2.60 (t, J=8.1 Hz, 2H), 2.51 (br t, J=7.1 Hz, 3H), 2.36 (br t, J=7.3 Hz, 2H), 2.22 (s, 3H), 2.05-2.20 (m, 5H), 1.53-1.89 (m, 8H). Calculated for $C_{23}H_{30}F_2O_3$: 415.2 (M+23); Measured: 415.2.

Example 424: Compound #69

3-[4-[[2-(4-chlorophenyl)-5-hydroxy-5-(trifluoromethyl)cyclopenten-1-yl]methoxy]-2,3-dimethyl-phenyl]Propanoic Acid

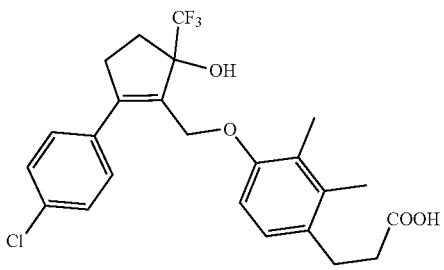 [SMILES: Cc1c(CCC(=O)O)ccc(OCC2=C(c3ccc(Cl)cc3)CCC2(O)C(F)(F)F)c1C]

Step 1: 3-(4-chlorophenyl)-2-(hydroxymethyl)cyclopent-2-en-1-one

To a solution of 6,7-dihydrocyclopenta[d][1,3]dioxin-5(4H)-one (prepared as described in SMITH III, A.B., et al., "Preparation, reactivity, and spectral properties of 1,3-dioxin vinyloqous esters: versatile beta.-ketovinyl cation equivalents", JOC, 1988, pp 4314-4325, Vol. 53, 3.0 g, 21.4 mmol) in THF (100 mL) cooled to −78° C. under nitrogen was added a solution of 4-chlorophenylmagnesium bromide (42.8 mL of a 1 M solution in THF, 42.8 mmol) dropwise over 5 min. After 1 hr at −78° C., the solution was warmed to room temperature and after 1 hr, LCMS indicated the reaction was complete. 1 N HCl was added, the solution was extracted with diethyl ether, dried over MgSO$_4$ and concentrated under reduced pressure to yield a residue. The residue was purified by chromatography (120 g) eluting with 20 to 80% EA/heptane to yield 3-(4-chlorophenyl)-2-(hydroxymethyl)cyclopent-2-en-1-one. $^1$H NMR (CHLOROFORM-d) δ: 7.40-7.52 (m, 4H), 4.47 (d, J=6.1 Hz, 2H), 2.93-3.00 (m, 2H), 2.86 (t, J=6.3 Hz, 1H), 2.55-2.62 (m, 2H). Calculated for $C_{12}H_{11}ClO_2$: 223.0 (M+1); Measured: 223.1.

Step 2: 3-(4-chlorophenyl)-2-((methoxymethoxy)methyl)cyclopent-2-en-1-one

To a solution of the compound prepared in Step 1 (856 mg, 3.84 mmol) in DCM (20 mL) and DIEA (20 mL) was added MOMCl (1.46 mL, 19.22 mmol). After 2 hrs, LCMS indicated the reaction was not complete so more MOMCl (1.0 mL) was added. After stirring overnight, the reaction was complete by LCMS. Water was added, the solution extracted with DCM, washed with 1 N HCl, saturated NaHCO$_3$, and brine, dried over MgSO$_4$ and concentrated under reduced pressure to yield a residue. The residue was purified by chromatography (50 g) eluting with 20 to 40% EA/heptane to yield 3-(4-chlorophenyl)-2-((methoxymethoxy)methyl)cyclopent-2-en-1-one. $^1$H NMR (CHLOROFORM-d) δ: 7.58-7.66 (m, 2H), 7.44 (d, J=8.6 Hz, 2H), 4.72 (s, 2H), 4.25 (s, 2H), 3.41 (s, 3H), 2.96 (dt, J=4.9, 2.3 Hz, 2H), 2.57 (dt, J=5.1, 2.5 Hz, 2H). Calculated for $C_{14}H_{15}ClO_3$: 267.1 (M+1); Measured: 267.0.

Step 3: 3-(4-chlorophenyl)-2-((methoxymethoxy)methyl)-1-(trifluoromethyl)cyclopent-2-en-1-ol To a solution of the compound prepared in Step 2 (715 mg, 2.68 mmol) in THF (10 mL) at 0° C. was added (trifluoromethyl)trimethylsilane (2.0 mL of a 2 M solution in THF, 4 mmol) followed by TBAF (1.34 mL of a 1 M solution in THF, 1.34 mmol). After 2 hrs, the reaction appeared done by LCMS. Water and 1 N HCl were added, the solution was extracted with EA, washed with water, brine, dried over MgSO$_4$ and concentrated under reduced pressure to yield a residue. The residue was purified by chromatography (40 g) eluting with 5 to 50% EA/heptane to yield 3-(4-chlorophenyl)-2-((methoxymethoxy)methyl)-1-(trifluoromethyl)cyclopent-2-en-1-ol. $^1$H NMR (CHLOROFORM-d) δ: 7.32-7.40 (m, 2H), 7.18-7.24 (m, 2H), 4.61-4.69 (m, 2H), 4.48 (s, 1H), 4.39-4.45 (m, 1H), 4.26-4.34 (m, 1H), 3.36 (s, 3H), 2.84-2.97 (m, 1H), 2.68-2.79 (m, 1H), 2.44-2.56 (m, 1H), 2.15 (ddd, J=14.0, 8.2, 5.6 Hz, 1H). Calculated for $C_{15}H_{18}ClF_3O_3$: 359.1 (M+23); Measured: 359.0.

Step 4: 3-(4-chlorophenyl)-2-(hydroxymethyl)-1-(trifluoromethyl)cyclopent-2-en-1-ol To a solution of the compound prepared in Step 3 (207 mg, 0.61 mmol) in methanol (5 mL) was added conc. HCl (0.1 mL, 1.2 mmol). After 2 hrs at room temperature, only starting material was present by TLC. The solution was then heated to 55° C. overnight. The reaction appeared done by TLC and LCMS. Water was added, the solution extracted with DCM, dried over MgSO$_4$ and concentrated under reduced pressure to yield a residue. The residue was purified by chromatography (24 g) eluting with 20 to 40% EA/heptane to yield 3-(4-chlorophenyl)-2-(hydroxymethyl)-1-(trifluoromethyl)cyclopent-2-en-1-ol. $^1$H NMR (CHLOROFORM-d) δ: 7.32-7.40 (m, 2H), 7.15-7.23 (m, 2H), 4.47-4.58 (m, 2H), 4.41 (br s, 1H), 2.86-2.98 (m, 1H), 2.66-2.78 (m, 1H), 2.45-2.55 (m, 1H), 2.15 (dddd, J=14.3, 9.0, 5.6, 1.0 Hz, 1H), 2.05 (br s, 1H). Calculated for $C_{13}H_{12}ClF_3O_2$: 315.1 (M+23); Measured: 315.0.

Step 5: ethyl 3-(4-((2-(4-chlorophenyl)-5-hydroxy-5-(trifluoromethyl)cyclopent-1-en-1-yl)methoxy)-2,3-dimethylphenyl)Propanoate A solution of the product of Step 4 (58 mg, 0.20 mmol) in toluene (5 mL) at room temperature under nitrogen was added ethyl 3-(4-hydroxy-2,3-dimethylphenyl)propanoate (70 mg, 0.32 mmol), tri-n-butylphosphine (0.13 mL, 0.50 mmol) and ADDP (103 mg, 0.40 mmol) was warmed to 60° C. for 1 hr. Heptane (10 mL) was added, the resulting white solid was filtered off, and the filtrate concentrated under reduced pressure to yield a residue. The residue was purified by chromatography (24 g) eluting with 10 to 30% EA/heptane to yield ethyl 3-(4-((2-(4-chlorophenyl)-5-hydroxy-5-(trifluoromethyl)cyclopent-1-en-1-yl)methoxy)-2,3-dimethylphenyl)propanoate, which was determined to be contaminated with some phenol starting material. Calculated for $C_{28}H_{28}ClF_3O_4$: 519.2 (M+23); Measured: 519.2.

Step 6: 3-(4-((2-(4-chlorophenyl)-5-hydroxy-5-(trifluoromethyl)cyclopent-1-en-1-yl)methoxy)-2,3-dimethylphenyl)Propanoic Acid To a solution of the compound prepared in Step 5 (26 mg, 0.04 mmol) in tetrahydrofuran (2 mL) and methanol (2 mL) was added 1 M LiOH (1 mL). After stirring 3 hrs, saturated NH$_4$Cl was added, the solution extracted with DCM, dried over MgSO$_4$ and concentrated under reduced pressure to yield a residue. The residue was purified by chromatography (4 g) eluting with 40 to 80% EA/heptane+0.5% HOAc yield the title compound, 3-(4-((2-(4-chlorophenyl)-5-hydroxy-5-(trifluoromethyl)cyclopent-1-en-1-yl)methoxy)-2,3-dimethylphenyl)propanoic acid.

$^1$H NMR (CHLOROFORM-d) δ: 7.32-7.38 (m, 2H), 7.18-7.24 (m, 2H), 6.95 (d, J=8.6 Hz, 1H), 6.62 (d, J=8.1 Hz, 1H), 4.64-4.76 (m, 2H), 4.03 (br s, 1H), 2.88-3.04 (m, 3H), 2.75-2.86 (m, 1H), 2.49-2.63 (m, 3H), 2.18-2.28 (m, 4H), 2.15 (s, 3H). Calculated for $C_{24}H_{24}ClF_3O_4$: 491.1 (M+23); Measured: 491.1.

Example 425: Compound #12

3-[4-[[2-(4-chlorophenyl)-5-(trifluoromethyl)cyclopenten-1-yl]methoxy]-2,3-dimethyl-phenyl]Propanoic Acid

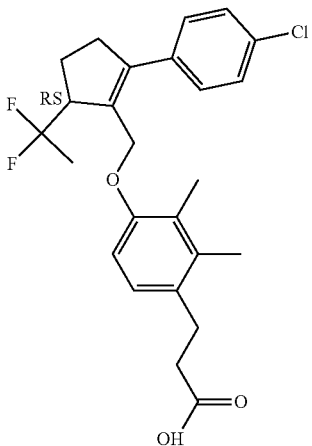 [SMILES: Cc1c(CCC(=O)O)ccc(OCC2=C(c3ccc(Cl)cc3)CCC2C(C)(F)F)c1C]

Step 1: 3-(4-chlorophenyl)-2-((methoxymethoxy)methyl)-1-(trifluoromethyl)cyclopent-2-en-1-yl 2-oxo-2-phenylacetate To a solution of the product of prepared in Example 424, Step 3 (184 mg, 0.55 mmol) in toluene (5 mL) at room temperature under nitrogen was added pyridine (0.05 mL, 1.15 eq) and 2-oxo-2-phenylacetyl chloride (121 mg, 0.66 mmol). After 1 day, the toluene was pipetted away from the solid, the solid washed with toluene, and the toluene extracts concentrated under reduced pressure to yield 3-(4-chlorophenyl)-2-((methoxymethoxy)methyl)-1-(trifluoromethyl)cyclopent-2-en-1-yl 2-oxo-2-phenylacetate, which was determined to be contaminated with 25% of the compound prepared in Example 424, Step 3. Calculated for $C_{23}H_{20}ClF_3O_6$: 507.1 (M+23); Measured: 507.0.

Step 2: 1-chloro-4-(2-((methoxymethoxy)methyl)-3-(trifluoromethyl)cyclopent-1-en-1-yl)benzene To a solution of Bu$_3$SnH (0.70 mL, 2.57 mmol) in toluene (5 mL) at 100° C. under nitrogen was added a solution dropwise of the compound prepared in Step 1 (332 mg, 0.51 mmol) and AIBN (27 mg, 0.16 mmol) in toluene (5 mL) that was saturated with nitrogen. After 1 hr, the solution was concentrated under reduced pressure to yield a residue. The residue was purified by chromatography (40 g) eluting with 3 to 20% EA/heptane to yield 1-chloro-4-(2-((methoxymethoxy)methyl)-3-(trifluoromethyl)cyclopent-1-en-1-yl)benzene. $^1$H NMR (CHLOROFORM-d) δ: 7.31-7.40 (m, 2H), 7.18-7.25 (m, 2H), 4.62 (s, 2H), 4.21-4.29 (m, 1H), 4.10-4.20 (m, 1H), 3.70 (br t, J=9.3 Hz, 1H), 3.35 (s, 3H), 2.68-2.94 (m, 2H), 2.08-2.33 (m, 2H). Calculated for $C_{15}H_{18}ClF_3O_2$: 259.1 (M–59, loss of OMOM); Measured: 259.0.

Step 3: (2-(4-chlorophenyl)-5-(trifluoromethyl)cyclopent-1-en-1-yl)methanol

A solution of the compound prepared in Step 2 (96 mg, 0.3 mmol), lithium tetrafluoroborate (3.0 mL of a 1 M solution in acetonitrile, 3.0 mmol) and water (0.15 mL) were heated to 75° C. under nitrogen for 4 hrs. Saturated NH$_4$Cl was added, the solution extracted with ethyl acetate, dried over MgSO$_4$ and concentrated under reduced pressure to yield a residue. The residue was purified by chromatography (12 g) eluting with 10 to 50% EA/heptane to yield (2-(4-chlorophenyl)-5-(trifluoromethyl)cyclopent-1-en-1-yl)methanol. $^1$H NMR (CHLOROFORM-d) δ: 7.34 (br d, J=8.1 Hz, 2H), 7.20-7.28 (m, 2H), 4.21-4.42 (m, 2H), 3.72 (br s, 1H), 2.73-2.93 (m, 2H), 2.19-2.34 (m, 1H), 2.07-2.19 (m, 1H). Calculated for $C_{13}H_{12}ClF_3O$: 259.1 (M–17); Measured: 259.0.

Step 4: ethyl 3-(4-((2-(4-chlorophenyl)-5-(trifluoromethyl)cyclopent-1-en-1-yl)methoxy)-2,3-dimethylphenyl)Propanoate A solution of the compound prepared in Step 3 (18 mg, 0.07 mmol) in toluene (5 mL) at room temperature under nitrogen was added ethyl 3-(4-hydroxy-2,3-dimethylphenyl)propanoate (23 mg, 0.1 mmol), tri-n-butylphosphine (0.04 mL, 0.16 mmol) and ADDP (34 mg, 0.13 mmol) was warmed to 60° C. for 2 hrs. Heptane (10 mL) was added, the resulting white solid was filtered off, and the filtrate concentrated under reduced pressure to yield a residue. The residue was purified by chromatography (12 g) eluting with 10 to 20% EA/heptane to yield ethyl 3-(4-((2-(4-chlorophenyl)-5-(trifluoromethyl)cyclopent-1-en-1-yl)methoxy)-2,3-dimethylphenyl)propanoate, which was determined to be contaminated with some phenol starting material. $^1$H NMR (CHLOROFORM-d) δ: 7.30-7.37 (m, 2H), 7.19-7.25 (m, 2H), 6.89 (d, J=8.1 Hz, 1H), 6.49 (d, J=8.6 Hz, 1H), 4.59-4.66 (m, 1H), 4.50-4.57 (m, 1H), 4.08-4.18 (m, 2H), 3.66-3.82 (m, 1H), 2.76-2.96 (m, 4H), 2.46-2.56 (m, 2H), 2.12-2.35 (m, 6H), 1.21-1.29 (m, 3H). Calculated for $C_{28}H_{28}ClF_3O_3$: 503.2 (M+23); Measured: 503.1.

Step 5: 3-[4-[[2-(4-chlorophenyl)-5-(trifluoromethyl)cyclopenten-1-yl]methoxy]-2,3-dimethyl-phenyl]Propanoic Acid To a solution of the compound prepared in Step 4 (17 mg, 0.04 mmol) in methanol (2 mL) was added 1 M NaOH (2 mL). After stirring overnight, 1 N HCl was added, the solution extracted with DCM, dried over MgSO$_4$ and concentrated under reduced pressure to yield a residue. The residue was purified by HPLC (30×100 mm column, $C_{18}$) eluting with 50 to 80% acetonitrile/water+0.1% TFA to yield the title compound, 3-[4-[[2-(4-chlorophenyl)-5-(trifluoromethyl)cyclopenten-1-yl]methoxy]-2,3-dimethyl-phenyl] propanoic acid.

$^1$H NMR (CHLOROFORM-d) δ: 7.33 (brd, J=8.1 Hz, 2H), 7.18-7.25 (m, 2H), 6.90 (br d, J=8.1 Hz, 1H), 6.50 (br d, J=8.1 Hz, 1H), 4.50-4.73 (m, 2H), 3.75 (br s, 1H), 2.75-3.04 (m, 4H), 2.53-2.69 (m, 2H), 2.12-2.40 (m, 8H). Calculated for $C_{24}H_{24}ClF_3O_3$: 475.1 (M+23); Measured: 475.0.

Example 426: Compound #32

3-[4-[[2-(4-chlorophenyl)-5-(trifluoromethyl)cyclopenten-1-yl]methoxy]-2,3-difluoro-phenyl]Propanoic Acid

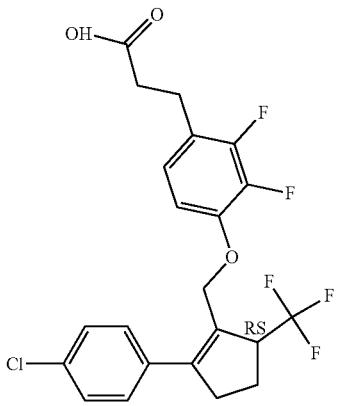 [SMILES: O=C(O)CCc1ccc(OCC2=C(c3ccc(Cl)cc3)CCC2C(F)(F)F)c(F)c1F]

$^1$H NMR (CHLOROFORM-d) δ: 7.31-7.49 (m, 2H), 7.16-7.31 (m, 2H), 6.75-6.95 (m, 1H), 6.49-6.68 (m, 1H), 4.57-4.83 (m, 2H), 3.80 (br s, 1H), 2.59-3.13 (m, 6H), 2.12-2.44 (m, 2H). Calculated for $C_{22}H_1ClF_5O_3$: 483.1 (M+23); Measured: 483.1.

Example 427: Compound #33

3-[4-[[2-(4-chlorophenyl)-5-(trifluoromethyl)cyclopenten-1-yl]methoxy]-3,5-difluoro-phenyl]Propanoic Acid

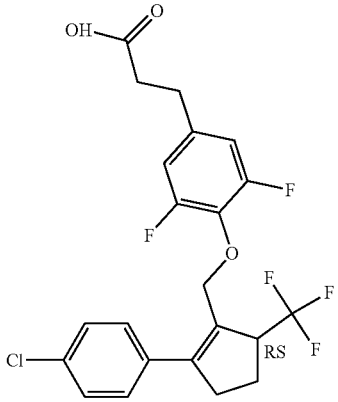 [SMILES: O=C(O)CCc1cc(F)c(OCC2=C(c3ccc(Cl)cc3)CCC2C(F)(F)F)c(F)c1]

$^1$H NMR (CHLOROFORM-d) δ: 7.28-7.35 (m, 2H), 7.14-7.20 (m, 2H), 6.67-6.77 (m, 2H), 4.77 (d, J=11.1 Hz, 1H), 4.62 (brd, J=11.1 Hz, 1H), 3.78-3.94 (m, 1H), 2.81-2.98 (m, 3H), 2.59-2.77 (m, 3H), 2.11-2.36 (m, 2H). Calculated for $C_{22}H_{18}ClF_5O_3$: 483.1 (M+23); Measured: 483.1.

Example 428: Compound #145

3-[4-[[2-(4-chlorophenyl)-5-oxo-cyclopenten-1-yl]methoxy]-2,3-dimethyl-phenyl]Propanoic Acid

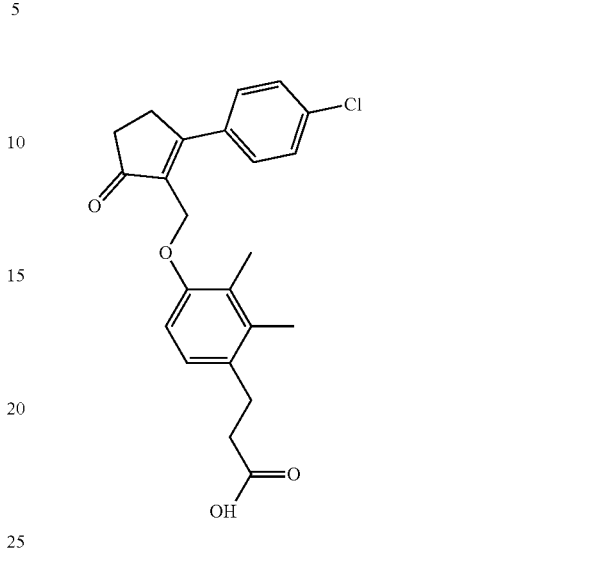

Step 1: ethyl 3-(4-((2-(4-chlorophenyl)-5-oxocyclopent-1-en-1-yl)methoxy)-2,3-dimethylphenyl)Propanoate A solution of 3-(4-chlorophenyl)-2-(hydroxymethyl)cyclopent-2-enone (40 mg, 0.14 mmol) in toluene (3 mL) at room temperature under nitrogen was added ethyl 3-(4-hydroxy-2,3-dimethylphenyl)propanoate (42 mg, 0.19 mmol), tri-n-butylphosphine (0.09 mL, 0.36 mmol) and ADDP (75 mg, 0.29 mmol) was warmed to 60° C. for 2 hrs. Heptane (10 mL) was added, the resulting white solid was filtered off, and the filtrate concentrated under reduced pressure to yield a residue. The residue was purified by chromatography (12 g) eluting with 10 to 30% EA/heptane to yield ethyl 3-(4-((2-(4-chlorophenyl)-5-oxocyclopent-1-en-1-yl)methoxy)-2,3-dimethylphenyl)propanoate. $^1$H NMR (CHLOROFORM-d) δ: 7.59-7.65 (m, 2H), 7.37-7.45 (m, 2H), 6.96 (d, J=8.1 Hz, 1H), 6.78 (d, J=8.6 Hz, 1H), 4.69 (s, 2H), 4.14 (q, J=7.2 Hz, 2H), 2.99-3.06 (m, 2H), 2.88-2.96 (m, 2H), 2.60-2.68 (m, 2H), 2.48-2.56 (m, 2H), 2.21 (s, 3H), 2.07 (s, 3H), 1.26 (t, J=7.1 Hz, 3H). Calculated for $C_{25}H_{27}ClO_4$: 427.2 (M+1); Measured: 427.2.

Step 2, 3-[4-[[2-(4-chlorophenyl)-5-oxo-cyclopenten-1-yl]methoxy]-2,3-dimethyl-phenyl]Propanoic Acid A solution of the compound prepared in Step 1 (46 mg, 0.11 mmol) in 1,4-dioxane (3.5 mL) and 1 N HCl (2.1 mL, 2.1 mmol) was heated overnight to 60° C. Water was added, the solution extracted with DCM, dried over $MgSO_4$ and concentrated under reduced pressure to yield a residue. Methanol was added and a solid fell out of solution. Water was added to precipitate more solid, and the solid collected by filtration to yield the title compound, 3-(4-((2-(4-chlorophenyl)-5-oxocyclopent-1-en-1-yl)methoxy)-2,3-dimethylphenyl)propanoic acid. $^1$H NMR (CHLOROFORM-d) δ: 7.63 (d, J=8.6 Hz, 2H), 7.38-7.46 (m, 2H), 6.97 (d, J=8.1 Hz, 1H), 6.79 (d, J=8.6 Hz, 1H), 4.70 (s, 2H), 3.00-3.07 (m, 2H), 2.90-2.98 (m, 2H), 2.64 (dt, J=4.9, 2.3 Hz, 2H), 2.55-2.62 (m, 2H), 2.21 (s, 3H), 2.07 (s, 3H). Calculated for C$_{23}$H$_{23}$ClO$_4$: 399.1 (M+1); Measured: 399.1.

Example 429: Compound #409

3-[2-chloro-4-[(2-cyclopentyl-4,4-difluoro-cyclopenten-1-yl)methoxy]phenyl]Propanoic Acid

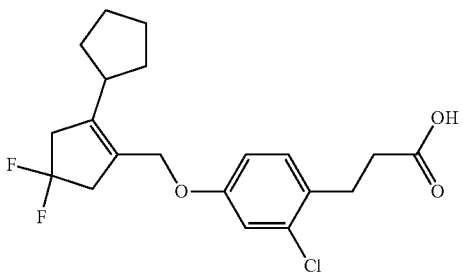

Step 1: ethyl 4-(benzyloxy)-2-oxocyclopentane-1-carboxylate

To a solution of 3-(benzyloxy)cyclobutanone (1 mL, 6.24 mmol) and ethyl diazoacetate (1.51 mL, 12.48 mmol) at −78° C. under nitrogen was added borontrifluoride etherate (0.78 mL, 6.24 mmol). After 30 min at −78° C., the solution was warmed to −20° C. over 1 hr. Saturated NaHCO$_3$ was added, and the solution stirred 20 min as it warmed to room temperature. The solution was extracted with DCM, dried over MgSO$_4$ and concentrated under reduced pressure to yield a residue. The residue was purified by chromatography (40 g) eluting with 10 to 20% EA/heptane to yield ethyl 4-(benzyloxy)-2-oxocyclopentane-1-carboxylate as a mix of diastereomers. Calculated for C$_{15}$H$_{18}$O$_4$: 285.1 (M+23); Measured: 285.1.

Step 2: ethyl 4-(benzyloxy)-2-(((trifluoromethyl)sulfonyl)oxy)cyclopent-1-ene-1-carboxylate To a suspension of sodium hydride (843 mg of a 60% suspension in mineral oil, 21.1 mmol) in diethyl ether (40 mL) at 0° C. under nitrogen was added a solution of the compound prepared in Step 1 (4.61 g, 17.6 mmol) in diethyl ether (25 mL) dropwise over 10 min. After 30 min, a solution of triflic anhydride (3.18 mL, 19.3 mmol) in diethyl ether (25 mL) was added dropwise over 10 min. After 1 hr, water was carefully added. The solution was warmed to room temperature, extracted with diethyl ether, washed with saturated NaHCO$_3$ and brine, dried over MgSO$_4$ and concentrated under reduced pressure to yield a residue. The residue was purified by chromatography (80 g) eluting with 5 to 10% EA/heptane to yield ethyl 4-(benzyloxy)-2-(((trifluoromethyl)sulfonyl)oxy)cyclopent-1-ene-1-carboxylate. $^1$H NMR (CHLOROFORM-d) δ: 7.27-7.41 (m, 5H), 4.46-4.57 (m, 2H), 4.21-4.31 (m, 3H), 2.94-3.09 (m, 2H), 2.77-2.91 (m, 2H), 1.32 (t, J=7.1 Hz, 3H). Calculated for C$_{16}$H$_{17}$F$_3$O$_6$S: 417.1 (M+23); Measured: 417.0.

Step 3: ethyl 4-hydroxy-2-(((trifluoromethyl)sulfonyl)oxy)cyclopent-1-ene-1-carboxylate To a solution of the compound prepared in Step 2 (9.34 g, 23.7 mmol) in DCM (150 mL) at 0° C. under nitrogen was added boron tribromide (4.67 mL, 48.5 mmol) dropwise over 5 min. After 30 min, the reaction was done by LCMS. Anhydrous ethanol was carefully added and the solution stirred 15 min as it warmed to room temperature. The solution was then neutralized by the addition of saturated NaHCO$_3$, followed by solid K$_2$CO$_3$. The solution was extracted with DCM, dried over MgSO$_4$ and concentrated under reduced pressure to yield ethyl 4-hydroxy-2-(((trifluoromethyl)sulfonyl)oxy)cyclopent-1-ene-1-carboxylate, which was used in the next step without further purification. Calculated for C$_{16}$H$_{17}$F$_3$O$_6$S: 305.0 (M+1); Measured: 305.0.

Step 4: ethyl 4-((tert-butyldimethylsilyl)oxy)-2-(((trifluoromethyl)sulfonyl)oxy)cyclopent-1-ene-1-carboxylate To a solution of the compound prepared in Step 3 (10.45 g, 23.4 mmol) in DMF (60 mL) at rt was added TBDMSCl (12.32 g, 81.8 mmol) and imidazole (5.57 g, 81.8 mmol). The solution was stirred overnight. Diethyl ether was added, the solution was washed with 1 N HCl, water, brine, dried over MgSO$_4$ and concentrated under reduced pressure to yield a residue. The residue was purified chromatography (220 g) eluting with 0 to 5% EA/heptane to yield ethyl 4-((tert-butyldimethylsilyl)oxy)-2-(((trifluoromethyl)sulfonyl)oxy)cyclopent-1-ene-1-carboxylate. $^1$H NMR (CHLOROFORM-d) δ: 4.50 (tt, J=7.1, 3.5 Hz, 1H), 4.27 (q, J=7.1 Hz, 2H), 2.91-3.06 (m, 2H), 2.59-2.73 (m, 2H), 1.33 (t, J=7.1 Hz, 3H), 0.89 (s, 9H), 0.08 (d, J=1.5 Hz, 6H). Calculated for C$_{15}$H$_{25}$F$_3$O$_6$SSi: 419.1 (M+1); Measured: 419.1.

Step 5: ethyl 4-((tert-butyldimethylsilyl)oxy)-[1,1'-bi(cyclopentan)]-1-ene-2-carboxylate A solution of the compound prepared in Step 4 (1.5 mL, 4.23 mmol), Pd(PPh$_3$)$_4$ (244 mg, 0.21 mmol) and cyclopentylzinc bromide (12.7 mL of a 0.5 M solution in THF, 6.34 mmol) in THF (20 mL) under nitrogen was warmed to 60° C. for 2 hrs. Water and 1 N HCl were added, the solution was extracted with DCM, dried over MgSO$_4$ and concentrated under reduced pressure to yield a residue. The residue was purified by chromatography (80 g) eluting with 0 to 15 to 80% EA/heptane to yield ethyl 4-((tert-butyldimethylsilyl)oxy)-[1,1'-bi(cyclopentan)]-1-ene-2-carboxylate, in a mixture with ethyl 4-hydroxy-[1,1'-bi(cyclopentan)]-1-ene-2-carboxylate.

Ethyl 4-((tert-butyldimethylsilyl)oxy)-[1,1'-bi(cyclopentan)]-1-ene-2-carboxylate: $^1$H NMR (CHLOROFORM-d) δ: 5.07-5.07 (m, 1H), 4.36-4.46 (m, 1H), 4.17 (q, J=7.1 Hz, 2H), 3.76 (quin, J=8.8 Hz, 1H), 2.85 (dd, J=15.9, 6.8 Hz, 1H), 2.71 (dd, J=17.7, 6.6 Hz, 1H), 2.56 (br dd, J=16.4, 3.3 Hz, 1H), 2.43 (br dd, J=17.7, 3.5 Hz, 1H), 1.74-1.89 (m, 2H), 1.59-1.74 (m, 4H), 1.26-1.47 (m, 5H), 0.89 (s, 9H), 0.07 (s, 6H). Calculated for C$_{19}$H$_{34}$O$_3$Si: 339.2 (M+1); Measured: 339.3.

Ethyl 4-hydroxy-[1,1'-bi(cyclopentan)]-1-ene-2-carboxylate: 1H NMR (CHLOROFORM-d) δ: 4.43 (br d, J=5.1 Hz, 1H), 4.18 (q, J=7.1 Hz, 2H), 3.78 (quin, J=8.8 Hz, 1H), 2.94 (dd, J=16.7, 6.1 Hz, 1H), 2.79 (dd, J=18.2, 6.1 Hz, 1H), 2.62 (br d, J=16.7 Hz, 1H), 2.49 (br d, J=18.2 Hz, 1H), 1.74-1.92 (m, 2H), 1.51-1.74 (m, 6H), 1.32-1.49 (m, 2H), 1.23-1.32 (m, 3H). Calculated for C$_{13}$H$_{20}$O$_3$: 225.1 (M+1); Measured: 225.3.

Step 6: (4-((tert-butyldimethylsilyl)oxy)-[1,1'-bi(cyclopentan)]-1-en-2-yl)methanol To a solution of the compound prepared in Step 5 (1.08 g, 3.2 mmol) in DCM (30 mL) at −78° C. was added DIBAL (6.4 mL of a 1 M solution in toluene, 6.4 mmol). After 1 hr, 2 N HCl was added carefully and the solution gradually warmed to room temperature. The solution was extracted with DCM, dried over MgSO$_4$ and concentrated under reduced pressure to yield (4-((tert-butyldimethylsilyl)oxy)-[1,1'-bi(cyclopentan)]-1-en-2-yl)methanol. H NMR (CHLOROFORM-d) δ: 4.42-4.52 (m, 1H), 4.18 (d, J=5.6 Hz, 2H), 2.78-2.91 (m, 1H), 2.73 (dd, J=15.9, 7.3 Hz, 1H), 2.59 (dd, J=16.2, 7.1 Hz, 1H), 2.41 (br dd, J=15.7, 4.0 Hz, 1H), 2.29 (br dd, J=16.2, 3.5 Hz, 1H), 1.48-1.74 (m, 6H), 1.28-1.47 (m, 2H), 1.16 (t, J=5.6 Hz, 1H), 0.89 (s, 9H), 0.07 (s, 6H). Calculated for $C_{17}H_{32}O_2Si$: 279.2 (M−17); Measured: 279.3.

Step 7: ethyl 3-(4-((4-((tert-butyldimethylsilyl)oxy)-[1,1'-bi(cyclopentan)]-1-en-2-yl)methoxy)-2-chlorophenyl)Propanoate A solution of the product of Step 6 (558 mg, 1.88 mmol) in THF (30 mL) at room temperature under nitrogen was added ethyl 3-(2-chloro-4-hydroxyphenyl)propanoate (452 mg, 1.98 mmol), tri-n-butylphosphine (10.88 mL of a 10% solution in hexane, 3.76 mmol) and ADDP (950 mg, 3.76 mmol) was warmed to 60° C. for 2 hrs. Heptane (50 mL) was added, the resulting white solid was filtered off, and the filtrate concentrated under reduced pressure to yield a residue. The residue was purified by chromatography (40 g) eluting with 0 to 5% EA/heptane to yield ethyl 3-(4-((4-((tert-butyldimethylsilyl)oxy)-[1,1'-bi(cyclopentan)]-1-en-2-yl)methoxy)-2-chlorophenyl)propanoate. $^1$H NMR (CHLOROFORM-d) δ: 7.12 (d, J=8.1 Hz, 1H), 6.92 (d, J=2.5 Hz, 1H), 6.75 (dd, J=8.3, 2.3 Hz, 1H), 4.42-4.60 (m, 3H), 4.13 (q, J=7.1 Hz, 2H), 2.98 (t, J=7.8 Hz, 2H), 2.79-2.93 (m, 1H), 2.72 (dd, J=16.2, 7.1 Hz, 1H), 2.56-2.67 (m, 3H), 2.25-2.42 (m, 2H), 1.53-1.79 (m, 6H), 1.40 (br d, J=8.6 Hz, 2H), 1.24 (t, J=7.1 Hz, 3H), 0.88 (s, 9H), 0.05 (s, 6H). Calculated for $C_{26}H_{43}ClO_4Si$: 529.3 (M+23); Measured: 529.2.

Step 8: ethyl 3-(2-chloro-4-((4-hydroxy-[1,1'-bi(cyclopentan)]-1-en-2-yl)methoxy)phenyl)Propanoate To a solution of the compound prepared in Step 7 (781 mg, 1.54 mmol) in THF (8 mL) at room temperature was added TBAF (3.7 mL of a 1 M solution in THF, 3.7 mmol) and stirred overnight. Water was added, the solution extracted with DCM, dried over MgSO$_4$ and concentrated under reduced pressure to yield a residue. The residue was purified by chromatography (12 g) eluting with 15 to 30% EA/heptane to yield ethyl 3-(2-chloro-4-((4-hydroxy-[1,1'-bi(cyclopentan)]-1-en-2-yl)methoxy)phenyl)propanoate. $^1$H NMR (CHLOROFORM-d) δ: 7.13 (d, J=8.6 Hz, 1H), 6.92 (d, J=2.5 Hz, 1H), 6.75 (dd, J=8.1, 2.5 Hz, 1H), 4.51-4.62 (m, 2H), 4.46 (br s, 1H), 4.13 (q, J=7.1 Hz, 2H), 2.98 (t, J=7.8 Hz, 2H), 2.77-2.94 (m, 2H), 2.71 (br dd, J=16.7, 6.1 Hz, 1H), 2.60 (t, J=7.6 Hz, 2H), 2.29-2.47 (m, 2H), 1.51-1.80 (m, 7H), 1.32-1.51 (m, 2H), 1.24 (t, J=7.1 Hz, 3H). Calculated for $C_{22}H_{29}ClO_4$: 393.2 (M+1); Measured: 393.3.

Step 9: ethyl 3-(2-chloro-4-((4-oxo-[1,1'-bi(cyclopentan)]-1-en-2-yl)methoxy)phenyl)Propanoate To a solution of the compound prepared in Step 8 (481 mg, 1.22 mmol) in DCM (20 mL) at 0° C. was added Dess-Martin periodinane (1.04 g, 2.45 mmol) and stirred 2 hrs as the reaction warmed to room temperature. A solution of sodium thiosulfate was added, followed by saturated NaHCO$_3$, and the solution stirred 30 min. The solution was extracted with DCM, dried over MgSO$_4$ and concentrated under reduced pressure to yield ethyl 3-(2-chloro-4-((4-oxo-[1,1'-bi(cyclopentan)]-1-en-2-yl)methoxy)phenyl)propanoate. $^1$H NMR (CHLOROFORM-d) δ: 7.15 (d, J=8.6 Hz, 1H), 6.93 (d, J=2.5 Hz, 1H), 6.76 (dd, J=8.6, 2.5 Hz, 1H), 4.65 (s, 2H), 4.13 (q, J=7.1 Hz, 2H), 2.90-3.10 (m, 7H), 2.60 (t, J=7.6 Hz, 2H), 1.52-1.85 (m, 6H), 1.33-1.48 (m, 2H), 1.24 (t, J=7.1 Hz, 3H). Calculated for $C_{22}H_{27}ClO_4$: 391.2 (M+1); Measured: 391.4.

Step 10: ethyl 3-(2-chloro-4-((4,4-difluoro-[1,1'-bi(cyclopentan)]-1-en-2-yl)methoxy)phenyl)Propanoate To a solution of the compound prepared in Step 9 (469 mg, 1.2 mmol) in DCM (10 mL) at room temperature was added Deoxo-Fluor® (3.32 mL, 18 mmol) and ethanol (0.1 mL, 1.71 mmol) and the solution warmed to 40° C. overnight. The solution was poured slowly into water, then saturated NaHCO$_3$ was added, the solution extracted with DCM, dried over MgSO$_4$ and concentrated under reduced pressure to yield a residue. The residue was purified by chromatography (40 g) eluting with 0 to 5% EA/heptane to yield ethyl 3-(2-chloro-4-((4,4-difluoro-[1,1'-bi(cyclopentan)]-1-en-2-yl)methoxy)phenyl)propanoate. $^1$H NMR (CHLOROFORM-d) δ: 7.15 (d, J=8.1 Hz, 1H), 6.91 (d, J=2.5 Hz, 1H), 6.74 (dd, J=8.6, 2.0 Hz, 1H), 4.54 (s, 2H), 4.13 (q, J=7.1 Hz, 2H), 2.78-3.04 (m, 7H), 2.60 (t, J=7.8 Hz, 2H), 1.58-1.81 (m, 6H), 1.30-1.45 (m, 2H), 1.24 (t, J=7.1 Hz, 3H). Calculated for $C_{22}H_{27}ClF_2O_3$: 435.2 (M+23); Measured: 435.3.

Step 11. 3-[2-chloro-4-[(2-cyclopentyl-4,4-difluoro-cyclopenten-1-yl)methoxy]phenyl]Propanoic Acid To a solution of the compound prepared in Step 10 (354 mg, 0.86 mmol) in THF (10 mL) and methanol (1 mL) was added 1 M NaOH (4.3 mL, 4.3 mmol). After stirring overnight, 2 N HCl was added to acidify the solution, the solution extracted with DCM, dried over MgSO$_4$ and concentrated under reduced pressure to yield give 3-[2-chloro-4-[(2-cyclopentyl-4,4-difluoro-cyclopenten-1-yl)methoxy]phenyl]propanoic acid.

$^1$H NMR (CHLOROFORM-d) δ: 7.16 (d, J=8.6 Hz, 1H), 6.92 (d, J=2.0 Hz, 1H), 6.71-6.79 (m, 1H), 4.54 (s, 2H), 2.80-3.05 (m, 7H), 2.67 (t, J=7.8 Hz, 2H), 1.53-1.82 (m, 6H), 1.31-1.43 (m, 2H). Calculated for $C_{20}H_{23}ClF_2O_3$: 407.1 (M+23); Measured: 407.1.

Alternative Step 5: ethyl 4-((tert-butyldimethylsilyl)oxy)-2-(2,4-difluorophenyl)cyclopent-1-ene-1-carboxylate (used, for example, in the preparation of a separate batch)

A solution of the compound prepared in Step 4 above, (4.6 mL, 12.7 mmol), Pd(PPh$_3$)$_2$Cl$_2$ (500 mg, 0.71 mmol), Na$_2$CO$_3$ (18.9 mL of a 2M aq. solution, 37.8 mmol) and 2,4-difluorophenylboronic acid (2.98 g, 18.9 mmol) in 1,4-dioxane (100 mL) under nitrogen was warmed to 80° C. for 2 hrs. The solution was cooled to room temperature, filtered through CELITE® washed with ethyl acetate, the filtrate dried over MgSO$_4$ and concentrated under reduced pressure to yield a residue. The residue was purified by chromatography (120 g) eluting with 1 to 15% EA/heptane to yield ethyl 4-((tert-butyldimethylsilyl)oxy)-2-(2,4-difluorophenyl)cyclopent-1-ene-1-carboxylate. $^1$H NMR (CHLOROFORM-d) δ: 7.21 (td, J=8.3, 6.6 Hz, 1H), 6.75-6.90 (m, 2H), 4.55-4.63 (m, 1H), 4.07 (q, J=7.1 Hz, 2H), 2.98-3.11 (m, 2H), 2.71-2.82 (m, 2H), 1.11 (t, J=7.1 Hz, 3H), 0.90 (s, 9H), 0.08 (d, J=3.0 Hz, 6H). Calculated for C$_{20}$H$_{28}$F$_2$O$_3$Si: 383.2 (M+1); Measured: 383.2.

Additional representative compounds of formula (I) were prepared according to the procedure described in Example 429, selecting and substituting suitable reagents and starting materials, and using Step 5 or alternative Step 5, as would be readily recognized by those skilled in the art.

Example 430: Compound #137

3-[4-[[2-(4-chlorophenyl)-4,4-difluoro-cyclopenten-1-yl]methoxy]-2,3-dimethyl-phenyl]Propanoic Acid

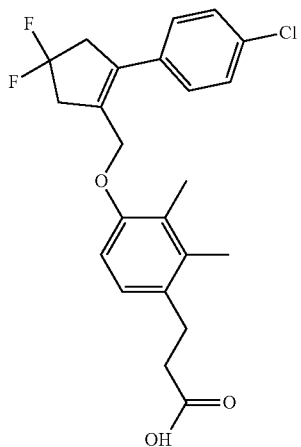 [SMILES: Cc1c(CCC(=O)O)ccc(OCC2=C(c3ccc(Cl)cc3)CC(F)(F)C2)c1C]

$^1$H NMR (CHLOROFORM-d) δ: 7.31-7.38 (m, 2H), 7.13-7.20 (m, 2H), 6.92 (d, J=8.6 Hz, 1H), 6.52 (d, J=8.1 Hz, 1H), 4.60 (s, 2H), 3.24 (dt, J=25.8, 15.2 Hz, 4H), 2.88-2.97 (m, 2H), 2.53-2.62 (m, 2H), 2.22 (s, 3H), 2.17 (s, 3H). Calculated for C$_{22}$H$_{23}$BrO$_3$: 443.1 (M+23); Measured: 443.0.

Example 431: Compound #166

3-[4-[[2-(4-chlorophenyl)-4,4-difluoro-cyclopenten-1-yl]methoxy]-3-methyl-phenyl]Propanoic Acid

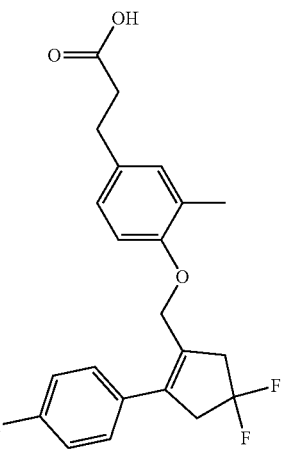

$^1$H NMR (CHLOROFORM-d) δ: 7.32-7.39 (m, 2H), 7.13-7.20 (m, 2H), 6.99 (d, J=2.0 Hz, 1H), 6.93 (dd, J=8.1, 2.0 Hz, 1H), 6.59 (d, J=8.1 Hz, 1H), 4.62 (s, 2H), 3.24 (dt, J=29.6, 15.0 Hz, 4H), 2.81-2.90 (m, 2H), 2.58-2.67 (m, 2H), 2.20 (s, 3H). Calculated for C$_{22}$H$_{21}$ClF$_2$O$_3$: 429.1 (M+23); Measured: 429.1.

Example 432: Compound #177

3-[4-[[2-(3,4-difluorophenyl)-4,4-difluoro-cyclopenten-1-yl]methoxy]-2,3-dimethyl-phenyl]Propanoic Acid

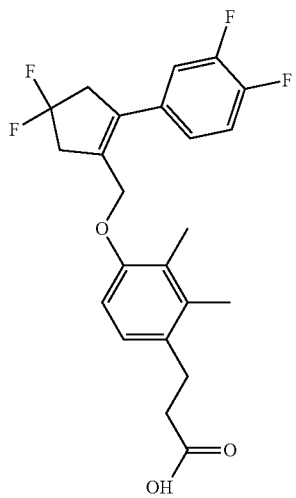 [SMILES: Cc1c(CCC(=O)O)ccc(OCC2=C(c3ccc(F)c(F)c3)CC(F)(F)C2)c1C]

$^1$H NMR (CHLOROFORM-d) δ: 7.16 (dt, J=10.1, 8.3 Hz, 1H), 7.05 (ddd, J=11.0, 7.5, 2.3 Hz, 1H), 6.90-7.00 (m, 2H), 6.53 (d, J=8.6 Hz, 1H), 4.59 (s, 2H), 3.16-3.31 (m, 4H), 2.89-2.97 (m, 2H), 2.55-2.62 (m, 2H), 2.23 (s, 3H), 2.17 (s, 3H). Calculated for C$_{23}$H$_{22}$F$_4$O$_3$: 445.2 (M+23); Measured: 445.1.

Example 433: Compound #171

3-[4-[[2-(4-chloro-3-fluoro-phenyl)-4,4-difluoro-cyclopenten-1-yl]methoxy]-2,3-dimethyl-phenyl]Propanoic Acid

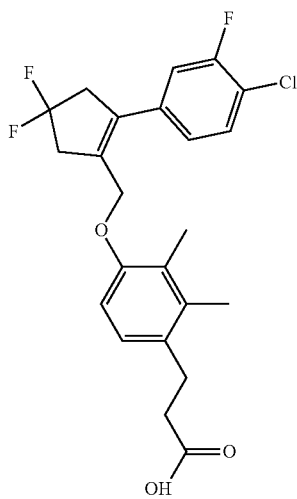 [SMILES: Cc1c(CCC(=O)O)ccc(OCC2=C(c3ccc(Cl)c(F)c3)CC(F)(F)C2)c1C]

$^1$H NMR (CHLOROFORM-d) δ: 7.34-7.43 (m, 1H), 7.06-7.14 (m, 2H), 6.91 (br d, J=8.6 Hz, 1H), 6.50 (br d, J=8.6 Hz, 1H), 4.50 (s, 2H), 3.24 (dt, J=28.7, 14.7 Hz, 4H), 2.92 (br t, J=7.8 Hz, 2H), 2.52-2.63 (m, 2H), 2.21 (s, 3H), 2.14 (s, 3H). Calculated for $C_{23}H_{22}ClF_3O_3$: 461.1 (M+23); Measured: 461.1.

Example 434: Compound #172

3-[4-[[4,4-difluoro-2-(3-fluoro-4-methyl-phenyl)cyclopenten-1-yl]methoxy]-2,3-dimethyl-phenyl]Propanoic Acid

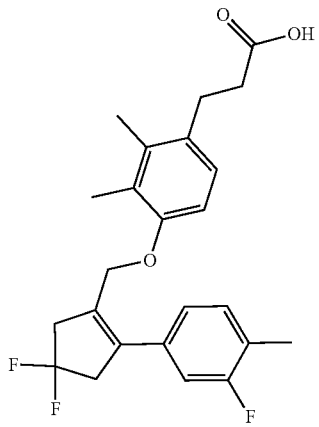 [SMILES: Cc1ccc(C2=C(COc3ccc(CCC(=O)O)c(C)c3C)CC(F)(F)C2)cc1F]

$^1$H NMR (CHLOROFORM-d) δ: 7.17 (br t, J=7.8 Hz, 1H), 6.84-6.97 (m, 3H), 6.53 (br d, J=8.6 Hz, 1H), 4.64 (s, 2H), 3.14-3.34 (m, 4H), 2.93 (br t, J=7.8 Hz, 2H), 2.54-2.63 (m, 2H), 2.28 (s, 3H), 2.22 (s, 3H), 2.17 (s, 3H). Calculated for $C_{24}H_{25}F_3O_3$: 441.2 (M+23); Measured: 441.1.

Example 435: Compound #173

3-[4-[[2-(2,4-difluorophenyl)-4,4-difluoro-cyclopenten-1-yl]methoxy]-2,3-dimethyl-phenyl]Propanoic Acid

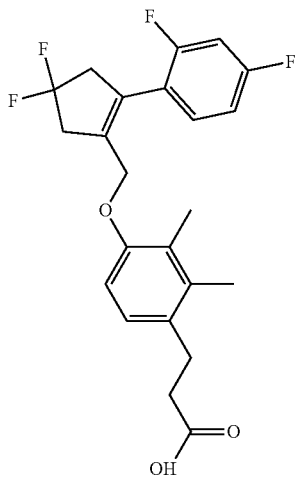 [SMILES: Cc1c(CCC(=O)O)ccc(OCC2=C(c3ccc(F)cc3F)CC(F)(F)C2)c1C]

$^1$H NMR (CHLOROFORM-d) δ: 7.17 (td, J=8.5, 6.3 Hz, 1H), 6.82-6.94 (m, 3H), 6.50 (d, J=8.6 Hz, 1H), 4.48 (s, 2H), 3.13-3.33 (m, 4H), 2.88-2.96 (m, 2H), 2.53-2.61 (m, 2H), 2.21 (s, 3H), 2.14 (s, 3H). Calculated for $C_{23}H_{22}F_4O_3$: 445.2 (M+23); Measured: 445.1.

Example 436: Compound #179

3-[4-[[2-(3,4-difluorophenyl)-4,4-difluoro-cyclopenten-1-yl]methoxy]-3-methyl-phenyl]Propanoic Acid

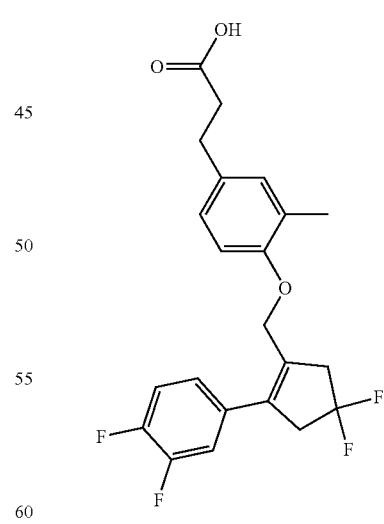

$^1$H NMR (CHLOROFORM-d) δ: 7.17 (dt, J=10.1, 8.3 Hz, 1H), 7.06 (ddd, J=11.1, 7.6, 2.0 Hz, 1H), 6.91-7.02 (m, 3H), 6.60 (d, J=8.1 Hz, 1H), 4.61 (s, 2H), 3.23 (dt, J=20.7, 15.2 Hz, 4H), 2.82-2.90 (m, 2H), 2.64 (br t, J=7.3 Hz, 2H), 2.20 (s, 3H). Calculated for $C_{22}H_{20}F_4O_3$: 431.1 (M+23); Measured: 431.2.

Example 437: Compound #184

3-[4-[[2-(3,4-difluorophenyl)-4,4-difluoro-cyclopenten-1-yl]methoxy]-3,5-difluoro-phenyl]Propanoic Acid

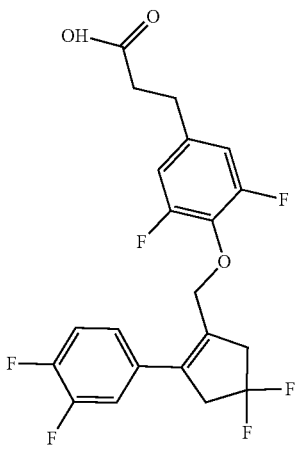 [SMILES: O=C(O)CCc1cc(F)c(OCC2=C(c3ccc(F)c(F)c3)CC(F)(F)C2)c(F)c1]

$^1$H NMR (CHLOROFORM-d) δ: 7.15 (dt, J=10.1, 8.3 Hz, 1H), 7.03 (ddd, J=11.1, 7.6, 2.0 Hz, 1H), 6.93-6.99 (m, 1H), 6.76 (d, J=9.1 Hz, 2H), 4.64 (s, 2H), 3.16-3.33 (m, 4H), 2.84-2.94 (m, 2H), 2.62-2.72 (m, 2H). Calculated for $C_{21}H_{16}F_6O_3$: 453.1 (M+23); Measured: 453.2.

Example 438: Compound #182

3-[4-[[2-(2,4-difluorophenyl)-4,4-difluoro-cyclopenten-1-yl]methoxy]-3-methyl-phenyl]Propanoic Acid

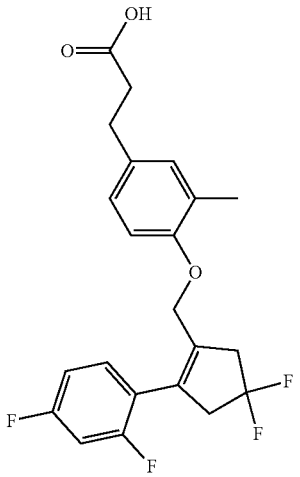 [SMILES: Cc1cc(CCC(=O)O)ccc1OCC1=C(c2ccc(F)cc2F)CC(F)(F)C1]

$^1$H NMR (CHLOROFORM-d) δ: 7.12-7.23 (m, 1H), 6.98 (br s, 1H), 6.82-6.95 (m, 3H), 6.57 (br d, J=8.1 Hz, 1H), 4.50 (br s, 2H), 3.22 (dt, J=31.1, 15.3 Hz, 4H), 2.85 (br t, J=7.1 Hz, 2H), 2.64 (br s, 2H), 2.17 (s, 3H). Calculated for $C_{22}H_{20}F_4O_3$: 431.1 (M+23); Measured: 431.3.

Example 439: Compound #191

3-[4-[[4,4-difluoro-2-(3-fluorophenyl)cyclopenten-1-yl]methoxy]-3-methyl-phenyl]Propanoic Acid

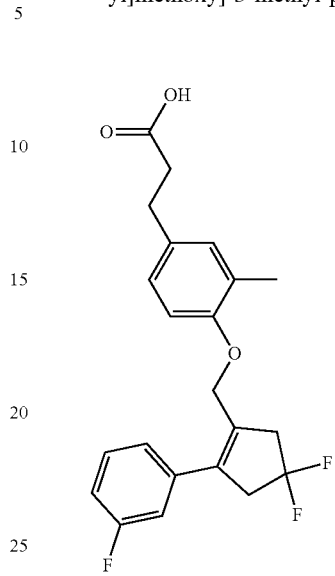

$^1$H NMR (CHLOROFORM-d) δ: 7.30-7.40 (m, 1H), 6.97-7.07 (m, 3H), 6.93 (br d, J=8.1 Hz, 2H), 6.60 (d, J=8.1 Hz, 1H), 4.65 (s, 2H), 3.14-3.36 (m, 4H), 2.86 (t, J=7.8 Hz, 2H), 2.58-2.70 (m, 2H), 2.20 (s, 3H), Calculated for $C_{22}H_{21}F_3O_3$: 413.1 (M+23); Measured: 413.3.

Example 440: Compound #192

3-[4-[[4,4-difluoro-2-(3-fluorophenyl)cyclopenten-1-yl]methoxy]-2,3-dimethyl-phenyl]Propanoic Acid

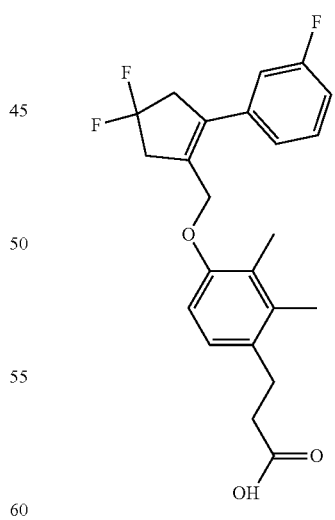

$^1$H NMR (CHLOROFORM-d) δ: 7.34 (td, J=8.0, 5.8 Hz, 1H), 6.98-7.06 (m, 2H), 6.88-6.96 (m, 2H), 6.53 (d, J=8.6 Hz, 1H), 4.64 (s, 2H), 3.25 (dt, J=24.4, 15.1 Hz, 4H), 2.87-2.97 (m, 2H), 2.53-2.62 (m, 2H), 2.22 (s, 3H), 2.17 (s, 3H). Calculated for $C_{23}H_{23}F_3O_3$: 427.2 (M+23); Measured: 427.2.

Example 441: Compound #193

3-[4-[(4,4-difluoro-2-phenyl-cyclopenten-1-yl)methoxy]-3-methyl-phenyl]Propanoic Acid

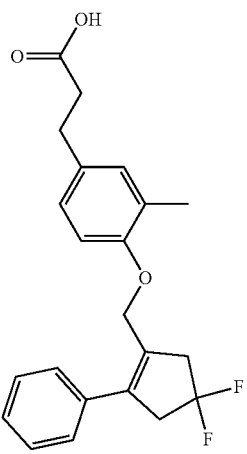 [SMILES: Cc1cc(CCC(=O)O)ccc1OCC1=C(c2ccccc2)CC(F)(F)C1]

$^1$H NMR (CHLOROFORM-d) δ: 7.35-7.42 (m, 2H), 7.29-7.35 (m, 1H), 7.20-7.25 (m, 2H), 6.98 (d, J=2.0 Hz, 1H), 6.91 (dd, J=8.6, 2.0 Hz, 1H), 6.59 (d, J=8.1 Hz, 1H), 4.66 (s, 2H), 3.31 (br t, J=15.2 Hz, 2H), 3.21 (t, J=15.4 Hz, 2H), 2.79-2.90 (m, 2H), 2.58-2.68 (m, 2H), 2.21 (s, 3H). Calculated for $C_{22}H_{22}F_2O_3$: 395.2 (M+23); Measured: 395.2.

Example 442: Compound #194

3-[4-[(4,4-difluoro-2-phenyl-cyclopenten-1-yl)methoxy]-2,3-dimethyl-phenyl]Propanoic Acid

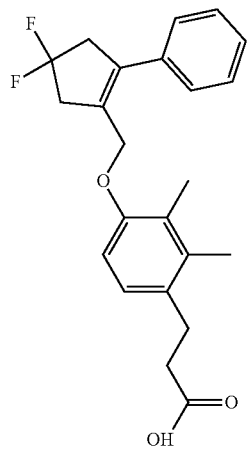 [SMILES: Cc1c(CCC(=O)O)ccc(OCC2=C(c3ccccc3)CC(F)(F)C2)c1C]

$^1$H NMR (CHLOROFORM-d) δ: 7.35-7.41 (m, 2H), 7.29-7.35 (m, 1H), 7.20-7.25 (m, 2H), 6.91 (d, J=8.1 Hz, 1H), 6.52 (d, J=8.6 Hz, 1H), 4.65 (s, 2H), 3.31 (br t, J=15.2 Hz, 2H), 3.22 (t, J=15.2 Hz, 2H), 2.88-2.96 (m, 2H), 2.54-2.62 (m, 2H), 2.22 (s, 3H), 2.18 (s, 3H). Calculated for $C_{23}H_{24}F_2O_3$: 409.2 (M+23); Measured: 409.2.

Example 443: Compound #180

3-[4-[[4,4-difluoro-2-(4-fluorophenyl)cyclopenten-1-yl]methoxy]-3-methyl-phenyl]Propanoic Acid

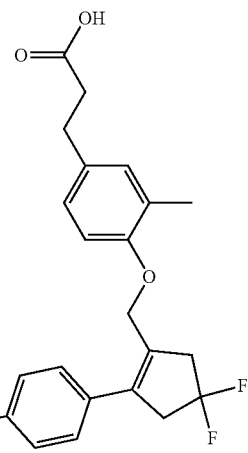

$^1$H NMR (CHLOROFORM-d) δ: 7.17-7.24 (m, 2H), 7.03-7.11 (m, 2H), 6.99 (s, 1H), 6.93 (br d, J=8.1 Hz, 1H), 6.59 (d, J=8.1 Hz, 1H), 4.62 (s, 2H), 3.24 (dt, J=30.7, 15.2 Hz, 4H), 2.85 (br d, J=6.6 Hz, 2H), 2.67 (br s, 2H), 2.20 (s, 3H). Calculated for $C_{22}H_{21}F_3O_3$: 413.1 (M+23); Measured: 413.3.

Example 444: Compound #183

3-[4-[[4,4-difluoro-2-(4-fluorophenyl)cyclopenten-1-yl]methoxy]-3,5-difluoro-phenyl]Propanoic Acid

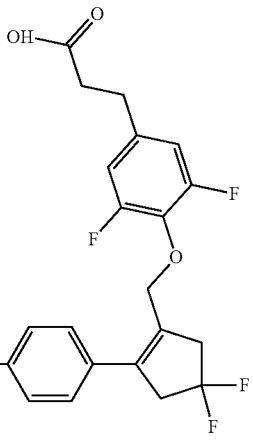

$^1$H NMR (CHLOROFORM-d) δ: 7.16-7.24 (m, 2H), 7.00-7.11 (m, 2H), 6.75 (br d, J=8.6 Hz, 2H), 4.66 (s, 2H), 3.25 (br t, J=15.2 Hz, 4H), 2.89 (br s, 1H), 2.82-2.96 (m, 1H), 2.70 (br s, 2H). Calculated for $C_{21}H_{17}F_5O_3$: 435.1 (M+23); Measured: 435.1.

Example 445: Compound #199

3-[4-[[4,4-difluoro-2-(2-methylthiazol-5-yl)cyclopenten-1-yl]methoxy]-3-methyl-phenyl]Propanoic Acid

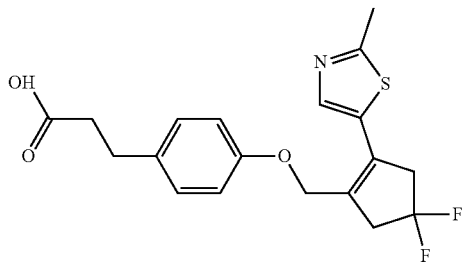 [SMILES: Cc1ncc(C2=C(COc3ccc(CCC(=O)O)cc3)CC(F)(F)C2)s1]

¹H NMR (CHLOROFORM-d) δ: 7.47 (s, 1H), 6.95-7.04 (m, 2H), 6.70 (d, J=8.1 Hz, 1H), 4.78 (s, 2H), 3.16-3.37 (m, 4H), 2.85-2.92 (m, 2H), 2.72 (s, 3H), 2.61-2.69 (m, 2H), 2.20 (s, 3H). Calculated for C₂₀H₂₁F₂NO₃S: 394.1 (M+1); Measured: 394.2.

Example 446: Compound #202

3-[4-[[4,4-difluoro-2-(2-thienyl)cyclopenten-1-yl]methoxy]-3-methyl-phenyl]Propanoic Acid

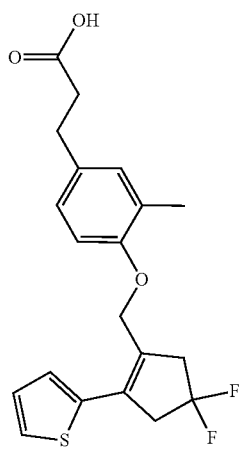 [SMILES: Cc1cc(CCC(=O)O)ccc1OCC1=C(c2cccs2)CC(F)(F)C1]

¹H NMR (CHLOROFORM-d) δ: 7.36 (d, J=5.1 Hz, 1H), 7.07 (dd, J=5.1, 3.5 Hz, 1H), 6.95-7.04 (m, 3H), 6.72 (d, J=8.1 Hz, 1H), 4.88 (s, 2H), 3.35 (br t, J=15.2 Hz, 2H), 3.24 (br t, J=15.4 Hz, 2H), 2.84-2.92 (m, 2H), 2.61-2.68 (m, 2H), 2.21 (s, 3H). Calculated for C₂₀H₂₀F₂O₃S: 401.1 (M+23); Measured: 401.1.

Example 447: Compound #200

3-[4-[[4,4-difluoro-2-(2-thienyl)cyclopenten-1-yl]methoxy]-2,3-dimethyl-phenyl]Propanoic Acid

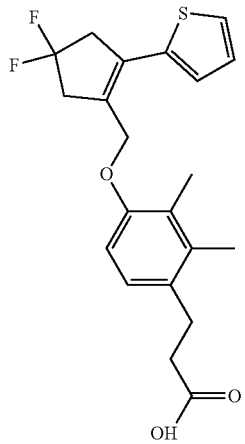 [SMILES: Cc1c(CCC(=O)O)ccc(OCC2=C(c3cccs3)CC(F)(F)C2)c1C]

¹H NMR (CHLOROFORM-d) δ: 7.35 (br d, J=5.1 Hz, 1H), 7.04-7.14 (m, 1H), 6.92-7.04 (m, 2H), 6.65 (br d, J=8.1 Hz, 1H), 4.87 (br s, 2H), 3.35 (br t, J=14.9 Hz, 2H), 3.25 (br t, J=14.9 Hz, 2H), 2.94 (br s, 2H), 2.72 (br s, 2H), 2.23 (s, 3H), 2.18 (s, 3H). Calculated for C₂₁H₂₂F₂O₃S: 415.1 (M+23); Measured: 415.1.

Example 448: Compound #201

3-[4-[[4,4-difluoro-2-(2-thienyl)cyclopenten-1-yl]methoxy]-3,5-difluoro-phenyl]Propanoic Acid

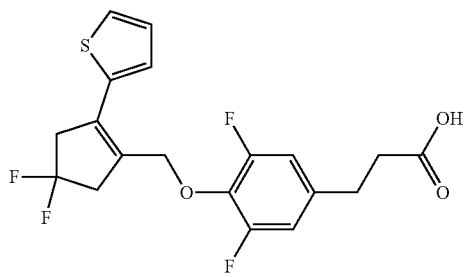 [SMILES: O=C(O)CCc1cc(F)c(OCC2=C(c3cccs3)CC(F)(F)C2)c(F)c1]

¹H NMR (CHLOROFORM-d) δ: 7.32 (d, J=5.1 Hz, 1H), 7.04 (dd, J=5.1, 3.5 Hz, 1H), 6.97-7.02 (m, 1H), 6.76 (br d, J=8.6 Hz, 2H), 4.95 (s, 2H), 3.31 (td, J=15.0, 6.8 Hz, 4H), 2.90 (br s, 4H). Calculated for C₁₉H₁₆F₄O₃S: 423.1 (M+23); Measured: 423.1.

Example 449: Compound #190

3-[4-[(4,4-difluoro-2-thiazol-5-yl-cyclopenten-1-yl)methoxy]-3-methyl-phenyl]Propanoic Acid

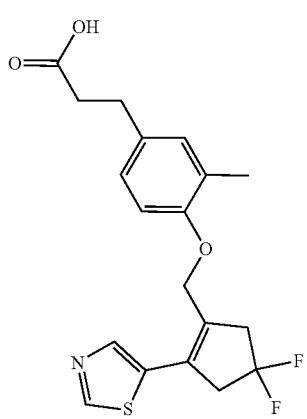 [SMILES: Cc1cc(CCC(=O)O)ccc1OCC1=C(c2cncs2)CC(F)(F)C1]

$^1$H NMR (CHLOROFORM-d) δ: 8.88 (br s, 1H), 7.81 (br s, 1H), 6.93-7.05 (m, 2H), 6.70 (d, J=8.6 Hz, 1H), 4.80 (s, 2H), 3.31 (dt, J=37.5, 14.8 Hz, 4H), 2.83-2.94 (m, 2H), 2.67 (br s, 2H), 2.20 (s, 3H). Calculated for $C_{19}H_{19}F_2NO_3S$: 402.1 (M+23); Measured: 402.1.

Example 450: Compound #232

3-[4-[[4,4-difluoro-2-(2-furyl)cyclopenten-1-yl]methoxy]-3-methyl-phenyl]Propanoic Acid

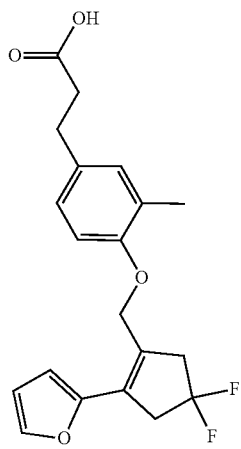 [SMILES: Cc1cc(CCC(=O)O)ccc1OCC1=C(c2ccco2)CC(F)(F)C1]

$^1$H NMR (CHLOROFORM-d) δ: 7.47 (s, 1H), 6.94-7.02 (m, 2H), 6.78 (d, J=8.1 Hz, 1H), 6.44 (dd, J=3.5, 2.0 Hz, 1H), 6.27 (d, J=3.5 Hz, 1H), 5.04 (s, 2H), 3.14-3.30 (m, 4H), 2.84-2.92 (m, 2H), 2.66 (br s, 2H), 2.21 (s, 3H). Calculated for $C_{20}H_{20}F_2O_4$: 385.1 (M+23); Measured: 385.2.

Example 451: Compound #364

3-[4-[(2-benzyl-4,4-difluoro-cyclopenten-1-yl)methoxy]-2-chloro-phenyl]Propanoic Acid

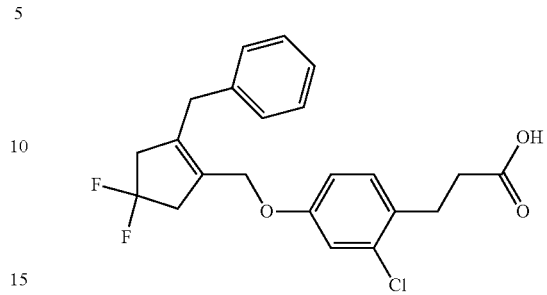

$^1$H NMR (CHLOROFORM-d) δ: 7.28-7.35 (m, 2H), 7.20-7.25 (m, 1H), 7.17 (d, J=8.6 Hz, 1H), 7.12 (d, J=7.1 Hz, 2H), 6.95 (d, J=2.5 Hz, 1H), 6.77 (dd, J=8.6, 2.5 Hz, 1H), 4.62 (s, 2H), 3.51 (s, 2H), 2.96-3.10 (m, 4H), 2.77 (br t, J=15.2 Hz, 2H), 2.68 (br t, J=7.3 Hz, 2H). Calculated for $C_{22}H_{21}ClF_2O_3$: 429.1 (M+23); Measured: 429.0.

Example 452: Compound #358

3-[4-[(2-benzyl-4,4-difluoro-cyclopenten-1-yl)methoxy]-2-(trifluoromethyl)phenyl]Propanoic Acid

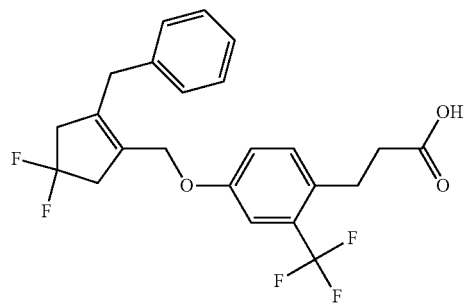 [SMILES: O=C(O)CCc1ccc(OCC2=C(Cc3ccccc3)CC(F)(F)C2)cc1C(F)(F)F]

$^1$H NMR (CHLOROFORM-d) δ: 7.20-7.34 (m, 4H), 7.18 (d, J=2.5 Hz, 1H), 7.12 (d, J=7.6 Hz, 2H), 7.02 (dd, J=8.6, 2.5 Hz, 1H), 4.66 (s, 2H), 3.52 (s, 2H), 2.97-3.13 (m, 4H), 2.78 (br t, J=15.2 Hz, 2H), 2.66 (br t, J=7.6 Hz, 2H). Calculated for $C_{23}H_{21}F_5O_3$: 463.1 (M+23); Measured: 463.0.

Example 453: Compound #357

3-[4-[(2-benzyl-4,4-difluoro-cyclopenten-1-yl)methoxy]-5-fluoro-2-methyl-phenyl]Propanoic Acid

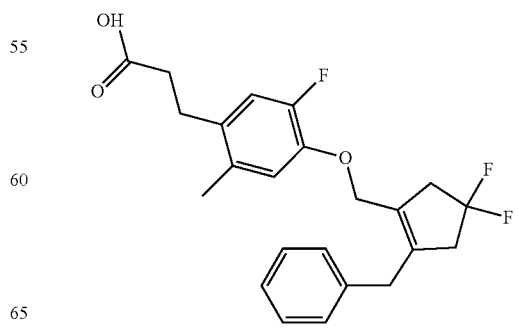

$^1$H NMR (CHLOROFORM-d) δ: 7.26-7.32 (m, 2H), 7.17-7.25 (m, 1H), 7.09 (d, J=7.1 Hz, 2H), 6.90 (d, J=12.1 Hz, 1H), 6.78 (d, J=8.1 Hz, 1H), 4.70 (s, 2H), 3.50 (s, 2H), 3.07 (br t, J=15.2 Hz, 2H), 2.83-2.92 (m, 2H), 2.75 (br t, J=15.2 Hz, 2H), 2.56-2.67 (m, 2H), 2.25 (s, 3H). Calculated for $C_{23}H_{23}F_3O_3$: 427.2 (M+23); Measured: 427.0.

Example 454: Compound #381

3-[4-[(4,4-difluoro-2-isobutyl-cyclopenten-1-yl)methoxy]-2-(trifluoromethyl)phenyl]Propanoic Acid

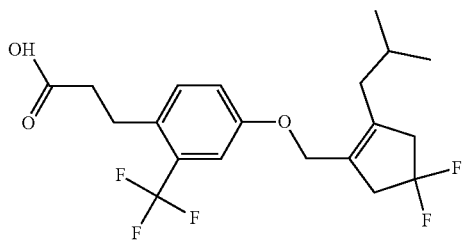 [SMILES: CC(C)CC1=C(COc2ccc(CCC(=O)O)c(C(F)(F)F)c2)CC(F)(F)C1]

$^1$H NMR (CHLOROFORM-d) δ: 7.22-7.30 (m, 1H), 7.15 (d, J=3.0 Hz, 1H), 7.00 (dd, J=8.6, 2.5 Hz, 1H), 4.55 (s, 2H), 3.08 (t, J=7.6 Hz, 2H), 2.98 (br t, J=15.4 Hz, 2H), 2.85 (br t, J=15.2 Hz, 2H), 2.65 (t, J=7.8 Hz, 2H), 2.05 (br d, J=7.6 Hz, 2H), 1.75 (tt, J=13.6, 6.6 Hz, 1H), 0.89 (d, J=6.6 Hz, 6H). Calculated for $C_{20}H_{23}F_5O_3$: 429.2 (M+23); Measured: 429.1.

Example 455: Compound #382

3-[4-[(2-cyclobutyl-4,4-difluoro-cyclopenten-1-yl)methoxy]-2-(trifluoromethyl)phenyl]Propanoic Acid

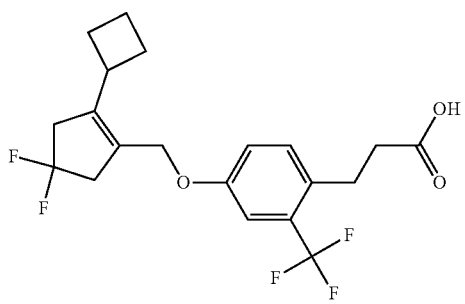 [SMILES: O=C(O)CCc1ccc(OCC2=C(C3CCC3)CC(F)(F)C2)cc1C(F)(F)F]

$^1$H NMR (CHLOROFORM-d) δ: 7.23-7.29 (m, 1H), 7.14 (d, J=2.5 Hz, 1H), 6.98 (dd, J=8.6, 3.0 Hz, 1H), 4.54 (s, 2H), 3.30-3.43 (m, 1H), 3.07 (br t, J=7.8 Hz, 2H), 2.90-3.04 (m, 4H), 2.65 (t, J=7.8 Hz, 2H), 1.74-2.15 (m, 6H). Calculated for $C_{20}H_{21}F_5O_3$: 427.1 (M+23); Measured: 427.2.

Example 456: Compound #407

3-[4-[(2-cyclopentyl-4,4-difluoro-cyclopenten-1-yl)methoxy]-2-(trifluoromethyl)phenyl]Propanoic Acid

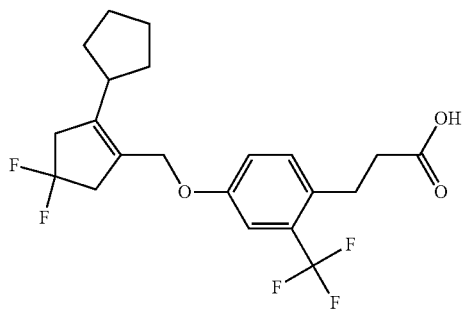 [SMILES: O=C(O)CCc1ccc(OCC2=C(C3CCCC3)CC(F)(F)C2)cc1C(F)(F)F]

$^1$H NMR (CHLOROFORM-d) δ: 7.24-7.30 (m, 1H), 7.16 (d, J=2.5 Hz, 1H), 7.01 (dd, J=8.6, 2.5 Hz, 1H), 4.59 (s, 2H), 3.07 (t, J=7.8 Hz, 2H), 2.80-3.02 (m, 5H), 2.60-2.69 (m, 2H), 1.54-1.80 (m, 6H), 1.32-1.43 (m, 2H). Calculated for $C_{21}H_{23}F_5O_3$: 441.2 (M+23); Measured: 441.1.

Example 457: Compound #429

3-[4-[[4,4-difluoro-2-(1-fluorocyclobutyl)cyclopenten-1-yl]methoxy]-2-(trifluoromethyl)phenyl]Propanoic Acid

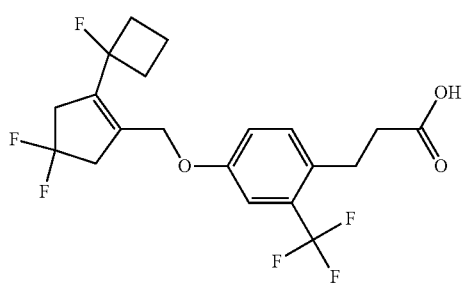 [SMILES: O=C(O)CCc1ccc(OCC2=C(C3(F)CCC3)CC(F)(F)C2)cc1C(F)(F)F]

$^1$H NMR (CHLOROFORM-d) δ: 7.23-7.30 (m, 1H), 7.16 (d, J=2.5 Hz, 1H), 7.00 (dd, J=8.6, 2.5 Hz, 1H), 4.76 (s, 2H), 2.96-3.12 (m, 6H), 2.66 (br s, 2H), 2.34-2.60 (m, 4H), 1.98-2.13 (m, 1H), 1.63-1.78 (m, 1H). Calculated for $C_{20}H_{20}F_6O_3$: 445.1 (M+23); Measured: 445.2.

Example 458: Compound #430

3-[2-chloro-4-[(2-cyclobutyl-4,4-difluoro-cyclopenten-1-yl)methoxy]phenyl]Propanoic Acid

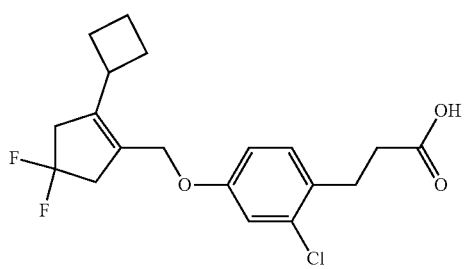 [SMILES: O=C(O)CCc1ccc(OCC2=C(C3CCC3)CC(F)(F)C2)cc1Cl]

¹H NMR (CHLOROFORM-d) δ: 7.15 (d, J=8.1 Hz, 1H), 6.89 (d, J=2.5 Hz, 1H), 6.73 (dd, J=8.3, 2.8 Hz, 1H), 4.49 (s, 2H), 3.36 (quin, J=8.5 Hz, 1H), 2.89-3.04 (m, 6H), 2.67 (br t, J=7.3 Hz, 2H), 1.90-2.17 (m, 5H), 1.75-1.85 (m, 1H). Calculated for $C_{19}H_{21}ClF_2O_3$: 393.1 (M+23); Measured: 393.0.

Example 459: Compound #188

3-[4-[[4,4-difluoro-2-(4-fluorophenyl)cyclopenten-1-yl]methoxy]-2-(trifluoromethyl)phenyl]Propanoic Acid

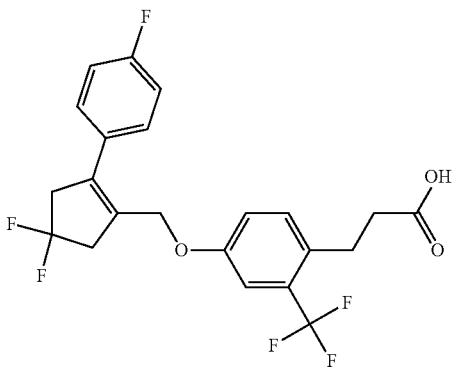 [SMILES: O=C(O)CCc1ccc(OCC2=C(c3ccc(F)cc3)CC(F)(F)C2)cc1C(F)(F)F]

¹H NMR (300 MHz, CD₃OD) δ: 7.33-7.36 (m, 3H), 7.12-7.18 (m, 2H), 6.98-7.05 (m, 2H), 4.74 (s, 2H), 3.32-3.34 (m, 1H), 3.03-3.19 (m, 3H), 2.97 (t, J=7.5 Hz, 2H), 2.45 (t, J=7.5 Hz, 2H). ¹⁹F NMR (300 MHz, CD₃OD) δ: −61.34, −91.94, −115.36. Mass spectrum (ESI, m/z): Calculated for $C_{22}H_{18}F_6O_3$, 443.1[M−H], Measured: 443.0.

Example 460: Compound #203

3-[3-chloro-4-[[4,4-difluoro-2-(4-fluorophenyl)cyclopenten-1-yl]methoxy]phenyl]Propanoic Acid

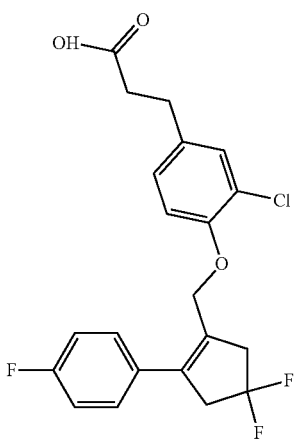 [SMILES: O=C(O)CCc1ccc(OCC2=C(c3ccc(F)cc3)CC(F)(F)C2)c(Cl)c1]

¹H NMR (300 MHz, CD₃OD) δ 7.31-7.36 (m, 2H), 7.25-7.26 (m, 1H), 7.09-7.18 (m, 2H), 7.03-7.07 (m, 1H), 7.81 (d, J=8.4 Hz, 1H), 4.61 (s, 2H), 3.15-3.35 (m, 4H), 2.85 (t, J=7.5 Hz, 2H), 2.53 (t, J=7.5 Hz, 2H). ¹⁹F NMR (300 MHz, CD₃OD) δ: −99.74, −115.47. Mass spectrum (ESI, m/z): Calculated for $C_{21}H_{18}ClF_3O_3$, 409.1 [M−H], Measured: 409.0

Example 461: Compound #204

3-[4-[[4,4-difluoro-2-(4-fluorophenyl)cyclopenten-1-yl]methoxy]-3-fluoro-5-methyl-phenyl]Propanoic Acid

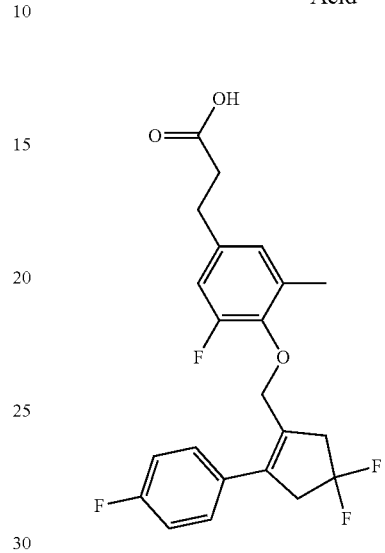

¹H NMR (300 MHz, CD₃OD) δ: 7.26-7.32 (m, 2H), 7.05-7.13 (m, 2H), 6.81-6.85 (m, 2H), 4.58 (s, 2H), 3.80-2.85 (m, 4H), 2.82 (t, J=7.5 Hz, 2H), 2.52 (t, J=7.5 Hz, 2H), 2.22 (s, 3H). ¹⁹F NMR (300 MHz, CD₃OD) δ: −72.79, −115.67, −133.12. Mass spectrum (ESI, m/z): Calculated for $C_{22}H_{20}F_4O_3$, 407.1 [M−H], Measured: 407.0.

Example 462: Compound #205

3-[3,5-dichloro-4-[[4,4-difluoro-2-(4-fluorophenyl)cyclopenten-1-yl]methoxy]phenyl]Propanoic Acid

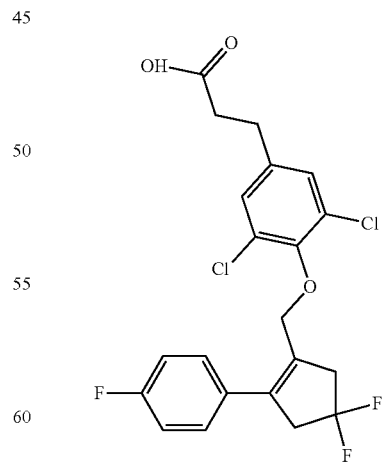

¹H NMR (300 MHz, CD₃OD) δ: 7.34-7.40 (m, 2H), 7.27 (s, 2H), 7.08-7.14 (m, 2H), 4.61 (s, 2H), 3.33-3.39 (m, 2H), 3.25-3.32 (m, 2H), 2.86 (t, J=7.5 Hz, 2H), 2.59 (t, J=7.5 Hz, 2H). ¹⁹F NMR (300 MHz, CD3OD) δ: −92.23, −115.54.

Mass spectrum (ESI, m/z): Calculated for $C_{21}H_{17}Cl_2F_3O_3$, 443.1 [M–H], Measured: 443.0

Example 463: Compound #207

3-[2-cyano-4-[[4,4-difluoro-2-(4-fluorophenyl)cyclopenten-1-yl]methoxy]phenyl]Propanoic Acid

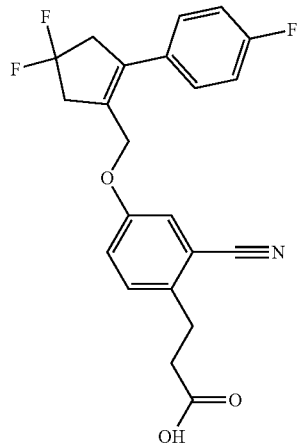 [SMILES: N#Cc1cc(OCC2=C(c3ccc(F)cc3)CC(F)(F)C2)ccc1CCC(=O)O]

$^1$H NMR (300 MHz, $CD_3OD$) δ: 7.31-7.37 (m, 3H), 7.06-7.19 (m, 4H), 4.71 (s, 2H), 3.15-3.34 (m, 4H), 3.06 (t, J=7.5 Hz, 2H), 2.51 (t, J=7.5 Hz, 2H). $^{19}$F NMR (300 MHz, $CD_3OD$) δ: −92.87, −115.25. Mass spectrum (ESI, m/z): Calculated for $C_{22}H_{18}F_3NO_3$, 400.1 [M–H], Measured: 400.0

Example 464: Compound #214

3-[4-[[4,4-difluoro-2-(4-fluorophenyl)cyclopenten-1-yl]methoxy]-3-fluoro-phenyl]Propanoic Acid

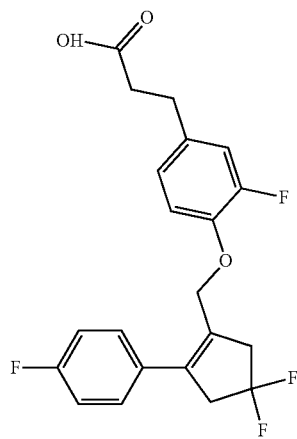 [SMILES: O=C(O)CCc1ccc(OCC2=C(c3ccc(F)cc3)CC(F)(F)C2)c(F)c1]

$^1$H NMR (300 MHz, $CD_3OD$) δ: 7.28-7.44 (m, 2H), 7.10-7.17 (m, 2H), 6.91-7.01 (m, 1H), 6.78-6.88 (m, 2H), 4.69 (s, 2H), 3.12-3.32 (m, 4H), 2.83 (t, J=8.4 Hz, 2H), 2.40 (t, J=8.4 Hz, 2H). $^{19}$F NMR (300 MHz, $CD_3OD$) δ: −92.82, −115.53, −136.51. Mass spectrum (ESI, m/z): Calculated for $C_{21}H_{18}F_4O_3$, 393.1 [M–H], Measured: 393.0

Example 465: Compound #215

3-[4-[[4,4-difluoro-2-(3-fluorophenyl)cyclopenten-1-yl]methoxy]-3,5-difluoro-phenyl]Propanoic Acid

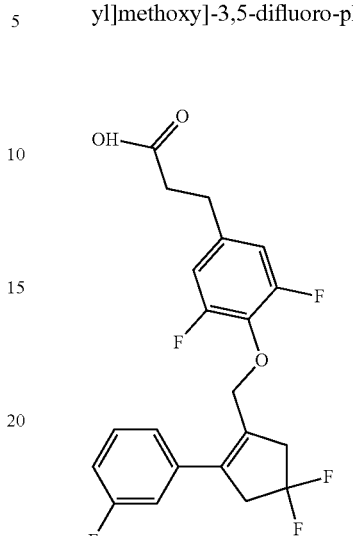

$^1$H NMR (300 MHz, $CD_3OD$) δ: 7.35-7.42 (m, 1H), 6.94-7.11 (m, 3H), 6.86-6.91 (m, 2H), 4.71 (s, 2H), 3.21-3.34 (m, 4H), 2.88 (t, J=7.5 Hz, 2H), 2.61 (t, J=7.5 Hz, 2H). $^{19}$F NMR (300 MHz, $CD_3OD$) δ: −92.76, −114.82, −130.01. Mass spectrum (ESI, m/z): Calculated for $C_{21}H_{17}F_5O_3$, 411.1 [M–H], Measured: 411.0

Example 466: Compound #216

3-[4-[[2-(2,4-difluorophenyl)-4,4-difluoro-cyclopenten-1-yl]methoxy]-3,5-difluoro-phenyl]Propanoic Acid

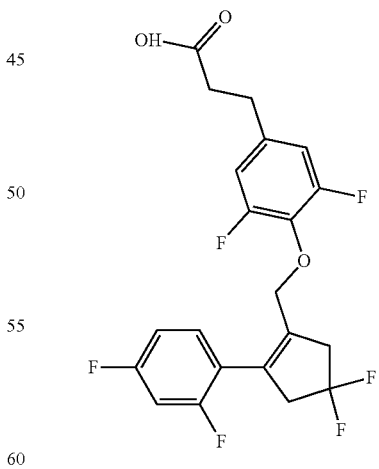

$^1$H NMR (300 MHz, $CD_3OD$) δ: 7.07-7.15 (m, 1H), 6.91-6.97 (m, 2H), 6.79-6.87 (m, 2H), 4.59 (s, 2H), 3.14-3.32 (m, 4H), 2.85 (t, J=7.5 Hz, 2H), 2.59 (t, J=7.5 Hz, 2H). $^{19}$F NMR (300 MHz, $CD_3OD$) δ: −92.68, −111.47, −130.10. Mass spectrum (ESI, m/z): Calculated for $C_{21}H_{16}F_6O_3$, 429.1 [M–H], Measured: 429.0

Example 467: Compound #228

3-[4-[[4,4-difluoro-2-(4-fluorophenyl)cyclopenten-1-yl]methoxy]phenyl]Propanoic Acid

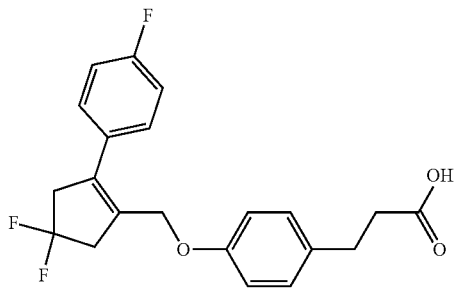 [SMILES: O=C(O)CCc1ccc(OCC2=C(c3ccc(F)cc3)CC(F)(F)C2)cc1]

$^1$H NMR (300 MHz, CD$_3$OD) A: 7.30-7.37 (m, 2H), 7.04-7.17 (m, 4H), 6.73-6.78 (m, 2H), 4.65 (s, 2H), 3.20-3.31 (m, 4H), 2.83 (t, J=7.5 Hz, 2H), 2.53 (t, J=7.5 Hz, 2H). $^{19}$F NMR (300 MHZ, CD$_3$OD) A: −92.87, −115.59. MASS SPECTRUM (ESI, M/Z): CALCULATED FOR C$_{21}$H$_{19}$F$_3$O$_3$, 375.1 [M−H], MEASURED: 375.0

Example 468: Compound #229

3-[3-chloro-4-[[4,4-difluoro-2-(4-fluorophenyl)cyclopenten-1-yl]methoxy]-5-methyl-phenyl]Propanoic Acid

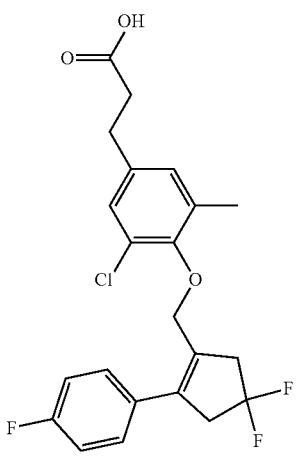 [SMILES: Cc1cc(CCC(=O)O)cc(Cl)c1OCC1=C(c2ccc(F)cc2)CC(F)(F)C1]

$^1$H NMR (300 MHz, CD$_3$OD) δ: 7.31-7.37 (m, 2H), 7.06-7.14 (m, 3H), 6.99 (s, 1H), 4.53 (s, 2H), 3.31-3.35 (m, 2H), 3.25-3.30 (m, 2H), 2.80 (t, J=7.5 Hz, 2H), 2.41 (t, J=7.5 Hz, 2H), 2.22 (s, 3H). $^{19}$F NMR (300 MHz, CD$_3$OD) δ: −92.65, −115.65. Mass spectrum (ESI, m/z): Calculated for C$_{22}$H$_{20}$ClF$_3$O$_3$, 423.1 [M−H], Measured: 423.0

Example 469: Compound #24

3-[4-[(4,4-difluoro-2-phenyl-cyclopenten-1-yl)methoxy]-2-(trifluoromethyl)phenyl]Propanoic Acid

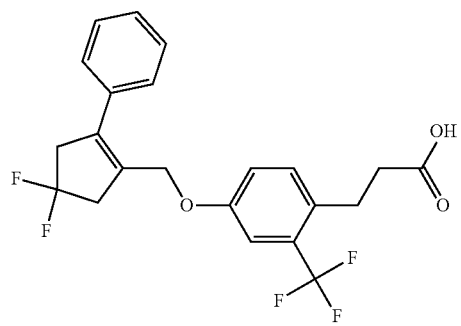 [SMILES: O=C(O)CCc1ccc(OCC2=C(c3ccccc3)CC(F)(F)C2)cc1C(F)(F)F]

$^1$H NMR (300 MHz, CD$_3$OD) δ: 7.31-7.46 (m, 6H), 7.08 (s, 1H), 7.01-7.05 (m, 1H), 4.78 (s, 2H), 3.27-3.37 (m, 2H), 3.12-3.22 (m, 2H), 3.02 (t, J=8.1 Hz, 2H), 2.56 (t, J=8.4 Hz, 2H). $^{19}$F NMR (300 MHz, CD$_3$OD) δ: −61.46, −92.95. Mass spectrum (ESI, m/z): Calculated for C$_{22}$H$_{19}$F$_5$O$_3$, 425.1 [M−H], Measured: 425.0

Example 470: Compound #242

3-[2-chloro-4-[(4,4-difluoro-2-phenyl-cyclopenten-1-yl)methoxy]phenyl]Propanoic Acid

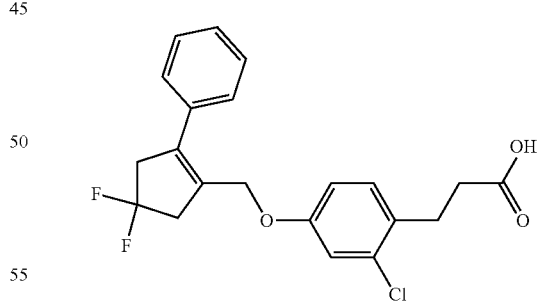

$^1$H NMR (300 MHz, CD$_3$OD) δ: 7.30-7.44 (m, 5H), 7.16 (d, J=6.0 Hz, 1H), 6.84 (s, 1H), 6.73 (d, J=8.4 Hz, 1H), 4.69 (s, 2H), 3.30-3.64 (m, 2H), 3.09-3.25 (m, 2H), 2.94 (t, J=7.5 Hz, 2H), 2.55 (t, J=7.2 Hz, 2H). $^{19}$F NMR (300 MHz, CD$_3$OD) δ: −92.86. Mass spectrum (ESI, m/z): Calculated for C$_{21}$H$_{19}$ClF$_2$O$_3$, 391.1 [M−H], Measured: 391.0

Example 471: Compound #248

3-[4-[[2-(4-chlorophenyl)-4,4-difluoro-cyclopenten-1-yl]methoxy]-2-(trifluoromethyl)phenyl]Propanoic Acid

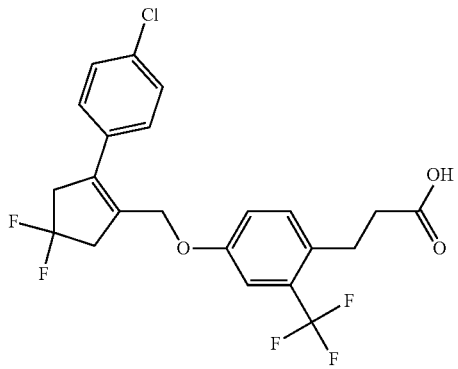 [SMILES: O=C(O)CCc1ccc(OCC2=C(c3ccc(Cl)cc3)CC(F)(F)C2)cc1C(F)(F)F]

$^1$H NMR (400 MHz, CD$_3$OD) δ: 7.30-7.32 (m, 2H), 7.25 (d, J=8.4 Hz, 1H), 7.19-7.21 (m, 2H), 6.87-6.93 (m, 2H), 4.63 (s, 2H), 3.19-3.20 (m, 2H), 3.05 (t, J=15.2 Hz, 2H), 2.87 (t, J=7.6 Hz, 2H), 2.30 (t, J=8.0 Hz, 2H). $^{19}$F NMR (400 MHz, CD$_3$OD) δ: −61.20, −92.96. Mass spectrum (ESI, m/z): Calculated for C$_{22}$H$_{18}$ClF$_5$O$_3$, 459.0 [M−H], Measured: 459.0

Example 472: Compound #249

3-[4-[[4,4-difluoro-2-(p-tolyl)cyclopenten-1-yl]methoxy]-2-(trifluoromethyl)phenyl]Propanoic Acid

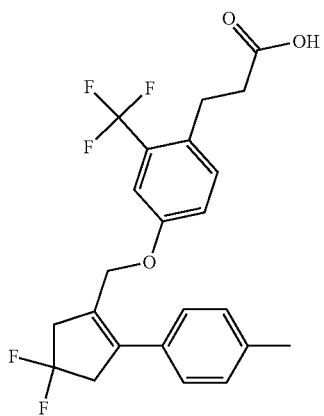 [SMILES: Cc1ccc(C2=C(COc3ccc(CCC(=O)O)c(C(F)(F)F)c3)CC(F)(F)C2)cc1]

$^1$H NMR (300 MHz, CD$_3$OD) δ: 7.32 (d, J=9.0 Hz, 1H), 7.17-7.24 (m, 4H), 6.98-7.06 (m, 2H), 4.75 (s, 2H), 3.12-3.31 (m, 4H), 3.00 (t, J=7.8 Hz, 2H), 2.54 (t, J=7.5 Hz, 2H), 2.36 (s, 3H). $^{19}$F NMR (300 MHz, CD$_3$OD) δ: −61.45, −93.02. Mass spectrum (ESI, m/z): Calculated for C$_{23}$H$_{21}$F$_5$O$_3$, 439.1 [M−H], Measured: 439.1

Example 473: Compound #250

3-[2-chloro-4-[[4,4-difluoro-2-(p-tolyl)cyclopenten-1-yl]methoxy]phenyl]Propanoic Acid

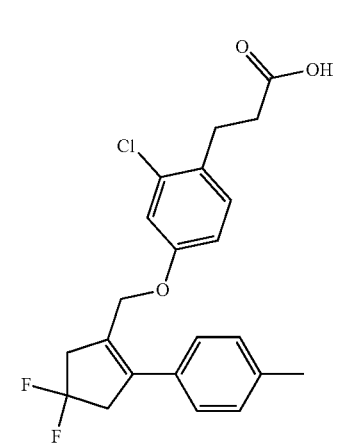 [SMILES: Cc1ccc(C2=C(COc3ccc(CCC(=O)O)c(Cl)c3)CC(F)(F)C2)cc1]

$^1$H NMR (300 MHz, CD$_3$OD) δ: 7.16-7.26 (m, 5H), 6.84 (s, 1H), 6.72 (d, J=8.4 Hz, 1H), 4.68 (s, 2H), 3.07-3.32 (m, 4H), 2.97 (t, J=7.5 Hz, 2H), 2.55 (t, J=7.8 Hz, 2H), 2.36 (s, 3H). $^{19}$F NMR (300 MHz, CD$_3$OD) δ: −92.88. Mass spectrum (ESI, m/z): Calculated for C$_{22}$H$_{21}$ClF$_2$O$_3$, 405.1 [M−H], Measured: 405.1

Example 474: Compound #251

3-[2-chloro-4-[[2-(4-chlorophenyl)-4,4-difluoro-cyclopenten-1-yl]methoxy]phenyl]Propanoic Acid

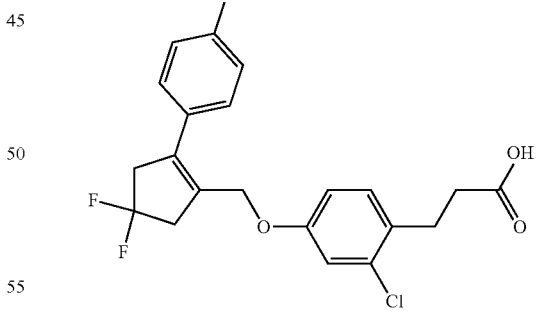

$^1$H NMR (400 MHz, CD$_3$OD) δ: 7.31 (d, J=8.4 Hz, 2H), 7.19 (d, J=8.4 Hz, 2H), 7.08 (d, J=4.4 Hz, 1H), 6.75 (s, 1H), 6.62-6.65 (m, 1H), 4.57 (s, 2H), 3.19-3.20 (m, 2H), 3.00-3.15 (m, 2H), 2.84 (t, J=7.6 Hz, 2H), 2.42 (t, J=8.0 Hz, 2H). $^{19}$F NMR (400 MHz, CD$_3$OD) δ: −92.96. Mass spectrum (ESI, m/z): Calculated for C$_{21}$H$_{18}$Cl$_2$F$_2$O$_3$, 425.1 [M−H], Measured: 425.0.

Example 475: Compound #252

3-[2-chloro-4-[[2-(4-chlorophenyl)-4-fluoro-cyclopenten-1-yl]methoxy]phenyl]Propanoic Acid

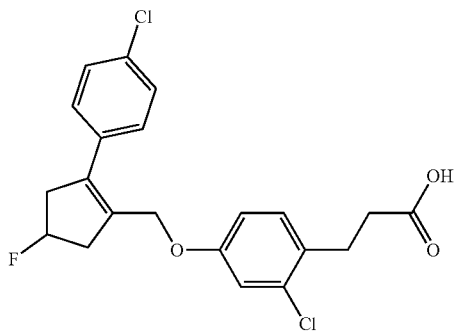 [SMILES: O=C(O)CCc1ccc(OCC2=C(c3ccc(Cl)cc3)CC(F)C2)cc1Cl]

$^1$H NMR (400 MHz, CD$_3$OD) δ: 7.29 (d, J=8.4 Hz, 2H), 7.18 (d, J=8.4 Hz, 2H), 7.08 (d, J=8.4 Hz, 1H), 6.69 (s, 1H), 6.58-6.61 (m, 1H), 5.13-5.29 (m, 1H), 4.58 (s, 2H), 2.76-3.20 (m, 6H), 32 (t, J=8.0 Hz, 2H). $^{19}$F NMR (400 MHz, CD$_3$OD) δ: −171.11. Mass spectrum (ESI, m/z): Calculated for C$_{21}$H$_{19}$Cl$_2$FO$_3$, 407.1 [M−0.06CF$_3$COOH—H], Measured: 407.0

Example 476: Compound #275

3-[4-[[2-(4-chlorophenyl)-4,4-difluoro-cyclopenten-1-yl]methoxy]-5-fluoro-2-methyl-phenyl]Propanoic Acid

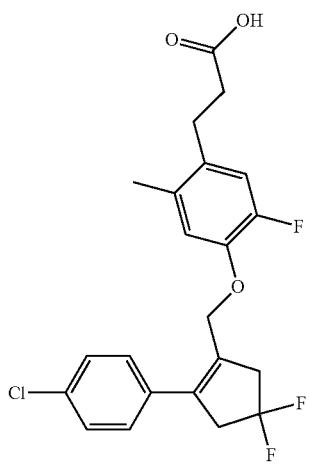 [SMILES: Cc1cc(OCC2=C(c3ccc(Cl)cc3)CC(F)(F)C2)c(F)cc1CCC(=O)O]

$^1$H NMR (400 MHz, CD$_3$OD) δ: 7.42 (d, J=8.8 Hz, 2H), 7.29 (d, J=8.8 Hz, 2H), 6.92 (d, J=12.4 Hz, 1H), 6.68 (d, J=8.4 Hz, 1H), 4.71 (s, 2H), 3.18-3.33 (m, 4H), 2.83 (t, J=8.0 Hz, 2H), 2.53 (t, J=8.0 Hz, 2H), 2.19 (s, 3H). $^{19}$F NMR (400 MHz, CD$_3$OD) δ: −92.83, −140.39. Mass spectrum (ESI, m/z): Calculated for C$_{22}$H$_{20}$ClF$_3$O$_3$, 423.1 [M−H], Measured: 423.0

Example 477: Compound #392

3-[4-[[2-(4-bromophenyl)-4,4-difluoro-cyclopenten-1-yl]methoxy]-5-fluoro-2-methyl-phenyl]Propanoic Acid

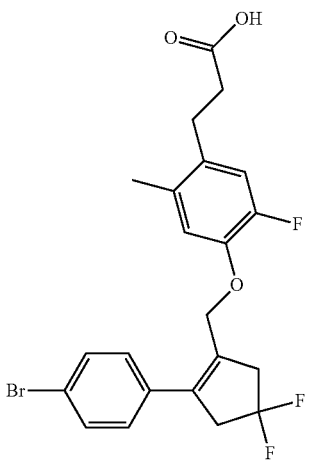 [SMILES: Cc1cc(OCC2=C(c3ccc(Br)cc3)CC(F)(F)C2)c(F)cc1CCC(=O)O]

$^1$H NMR (400 MHz, CD$_3$OD) δ: 7.57 (d, J=8.4 Hz, 2H), 7.23 (d, J=8.4 Hz, 2H), 6.92 (d, J=12.4 Hz, 1H), 6.68 (d, J=8.8 Hz, 1H), 4.72 (s, 2H), 3.13-3.33 (m, 4H), 2.83 (t, J=7.6 Hz, 2H), 2.53 (t, J=7.6 Hz, 2H), 2.19 (s, 3H). $^{19}$F NMR (400 MHz, CD$_3$OD) δ: −92.86, −140.42. Mass spectrum (ESI, m/z): Calculated for C$_{22}$H$_{20}$BrF$_3$O$_3$, 467.0 [M−H], Measured: 466.9

Example 478: Compound #393

3-[4-[[2-(4-bromophenyl)-4,4-difluoro-cyclopenten-1-yl]methoxy]-2-chloro-phenyl]Propanoic Acid

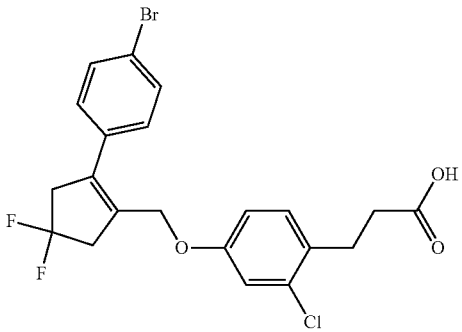 [SMILES: O=C(O)CCc1ccc(OCC2=C(c3ccc(Br)cc3)CC(F)(F)C2)cc1Cl]

$^1$H NMR (400 MHz, CD$_3$OD) δ: 7.58 (d, J=8.4 Hz, 2H), 7.25 (d, J=8.4 Hz, 2H), 7.20 (d, J=8.4 Hz, 1H), 6.87 (s, 1H), 6.74-6.76 (m, 1H), 4.69 (s, 2H), 3.27-3.33 (m, 2H), 3.15 (t, J=15.2 Hz, 2H), 2.96 (t, J=7.2 Hz, 2H), 2.57 (t, J=7.6 Hz, 2H). $^{19}$F NMR (400 MHz, CD$_3$OD) δ: −92.89. Mass spectrum (ESI, m/z): Calculated for C$_{21}$H$_{18}$BrClF$_2$O$_3$, 469.0 [M−H], Measured: 468.9

Example 479: Compound #401

3-[2-chloro-4-[[4,4-difluoro-2-(4-fluorophenyl)cyclopenten-1-yl]methoxy]phenyl]Propanoic Acid

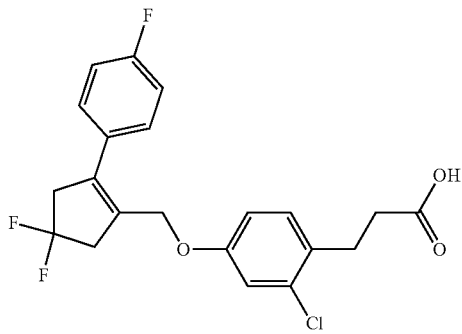

$^1$H NMR (400 MHz, CD$_3$OD) δ: 7.33-7.41 (m, 2H), 7.14-7.21 (m, 3H), 6.87 (s, 1H), 6.75 (d, J=8.4 Hz, 1H), 4.68 (s, 2H), 3.27-3.32 (m, 2H), 3.16 (t, J=14.8 Hz, 2H), 2.96 (t, J=7.6 Hz, 2H), 2.57 (t, J=7.6 Hz, 52H). $^{19}$F NMR (400 MHz, CD$_3$OD) δ: −92.86, −115.37. Mass spectrum (ESI, m/z): Calculated for C$_{21}$H$_{18}$ClF$_3$O$_3$, 409.1 [M−H], Measured: 409.0

Example 480: Compound #402

3-[4-[[4,4-difluoro-2-(4-fluorophenyl)cyclopenten-1-yl]methoxy]-5-fluoro-2-methyl-phenyl]Propanoic Acid

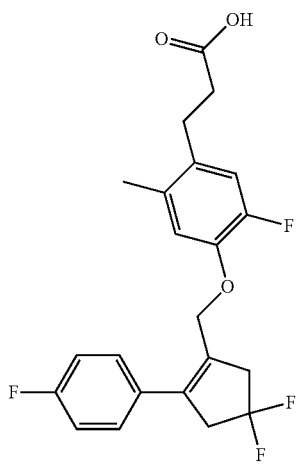 [SMILES: Cc1cc(OCC2=C(c3ccc(F)cc3)CC(F)(F)C2)c(F)cc1CCC(=O)O]

$^1$H NMR (400 MHz, CD$_3$OD) δ: 7.31-7.35 (m, 2H), 7.13-7.18 (m, 2H), 6.91 (d, J=12.4 Hz, 1H), 6.68 (d, J=8.4 Hz, 1H), 4.71 (s, 2H), 3.17-3.33 (m, 4H), 2.83 (t, J=7.2 Hz, 2H), 2.53 (t, J=7.2 Hz, 2H), 2.19 (s, 3H). $^{19}$F NMR (400 MHz, CD$_3$OD) δ: −92.83, −115.46, −140.39. Mass spectrum (ESI, m/z): Calculated for C$_{22}$H$_{20}$F$_4$O$_3$, 407.1 [M−H], Measured: 407.0

Example 481: Compound #441

3-[4-[(2-cyclopentyl-4,4-difluoro-cyclopenten-1-yl)methoxy]-2-methyl-phenyl]Propanoic Acid

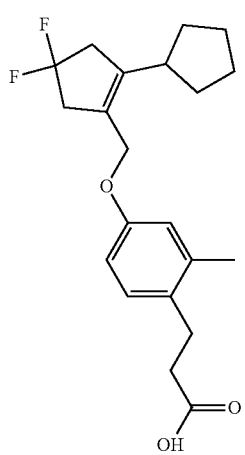 [SMILES: Cc1cc(OCC2=C(C3CCCC3)CC(F)(F)C2)ccc1CCC(=O)O]

$^1$H NMR (400 MHz, CD$_3$OD) δ: 7.17-7.19 (m, 1H), 6.64-6.69 (m, 2H), 4.62 (s, 2H), 2.84-3.04 (m, 7H), 2.43 (t, J=8.4 Hz, 2H), 1.63-1.81 (m, 6H), 1.31-1.47 (m, 2H). $^{19}$F NMR (400 MHz, CD$_3$OD) δ: −93.01, −118.82. Mass spectrum (ESI, m/z): Calculated for C$_{20}$H$_{23}$F$_3$O$_3$, 363.2[M−H], Measured: 363.1

Example 482: Compound #457

3-[4-[(2-cyclopentyl-4,4-difluoro-cyclopenten-1-yl)methoxy]-2-fluoro-phenyl]Propanoic Acid

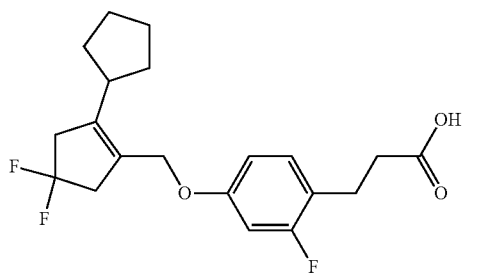 [SMILES: O=C(O)CCc1ccc(OCC2=C(C3CCCC3)CC(F)(F)C2)cc1F]

$^1$H NMR (400 MHz, CD$_3$OD) δ: 7.17-7.19 (m, 1H), 6.64-6.69 (m, 2H), 4.62 (s, 2H), 2.84-3.04 (m, 7H), 2.43 (t, J=8.4 Hz, 2H), 1.63-1.81 (m, 6H), 1.31-1.47 (m, 2H). $^{19}$F NMR (400 MHz, CD3OD) δ: −93.01, −118.82. Mass spectrum (ESI, m/z): Calculated for C$_{20}$H$_{23}$F$_3$O$_3$, 367.2[M−H], Measured: 367.1

Example 483: Compound #186

3-[4-[[4-fluoro-2-(4-fluorophenyl)cyclopenten-1-yl]methoxy]-2-(trifluoromethyl)phenyl]Propanoic Acid

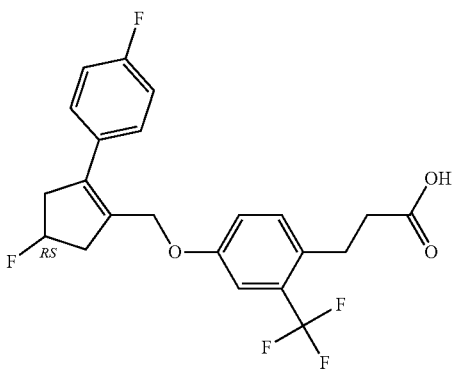 [SMILES: O=C(O)CCc1ccc(OCC2=C(c3ccc(F)cc3)CC(F)C2)cc1C(F)(F)F]

¹H NMR (300 MHz, CD₃OD) δ: 7.28-7.34 (m, 3H), 7.09-7.16 (m, 2H), 6.98-7.05 (m, 2H), 5.40 (t, J=5.4 Hz, 0.5H), 5.23 (t, J=5.4 Hz, 0.5H), 4.75 (s, 2H), 3.03-3.31 (m, 1H), 2.84-2.99 (m, 5H), 2.50 (t, J=7.5 Hz, 2H). ¹⁹F NMR (300 MHz, CD₃OD) δ: −61.34, −116.19, −171.07. Mass spectrum (ESI, m/z): Calculated for $C_{22}H_{19}F_5O_3$, 425.1 [M−H], Measured: 425.0.

Example 484: Compound #306

3-[4-[(3-methyl-2-phenyl-cyclopenten-1-yl)methoxy]-2-(trifluoromethyl)phenyl]Propanoic Acid

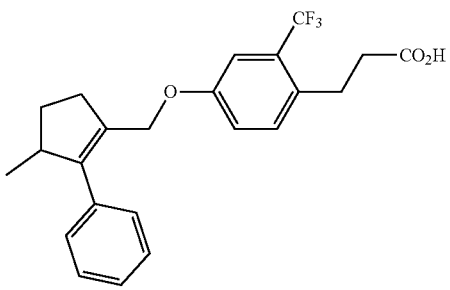 [SMILES: CC1CCC(COc2ccc(CCC(=O)O)c(C(F)(F)F)c2)=C1c1ccccc1]

Step 1: 3-[4-[(3-methyl-2-phenyl-cyclopenten-1-yl)methoxy]-2-(trifluoromethyl)phenyl]Propanoic Acid To a suspension of sodium hydride (254 mg of a 60% suspension in mineral oil, 6.35 mmol) in diethyl ether (10 mL) at 0° C. under nitrogen was added a solution of ethyl 3-methyl-2-oxocyclopentanecarboxylate (0.90 g, 5.29 mmol) in diethyl ether (10 mL) dropwise over 10 min. After 30 min, a solution of triflic anhydride (1.64 g, 5.82 mmol) in diethyl ether (10 mL) was added dropwise over 10 min. The solution was allowed to warmed to room temperature. After 4 hrs, water was carefully added followed by saturated NaHCO₃. The solution was extracted with diethyl ether, dried over MgSO₄ and concentrated under reduced pressure to yield a residue. The residue was purified by chromatography (40 g) eluting with 2 to 5% EA/heptane to yield 3-[4-[(3-methyl-2-phenyl-cyclopenten-1-yl)methoxy]-2-(trifluoromethyl)phenyl]propanoic acid.

¹H NMR (CHLOROFORM-d) δ: 7.32-7.40 (m, 2H), 7.24-7.31 (m, 1H), 7.12-7.21 (m, 3H), 7.06 (d, J=2.5 Hz, 1H), 6.87 (dd, J=8.1, 2.5 Hz, 1H), 4.58 (s, 2H), 3.14-3.29 (m, 1H), 3.04 (br t, J=7.6 Hz, 2H), 2.58-2.72 (m, 3H), 2.46-2.58 (m, 1H), 2.26 (dtd, J=12.8, 8.5, 4.5 Hz, 1H), 1.56 (ddt, J=12.9, 9.1, 6.7 Hz, 1H), 0.98 (d, J=7.1 Hz, 3H). Calculated for $C_{23}H_{23}F_3O_3$: 427.2 (M+23); Measured: 427.0.

Example 485: Compound #320

3-[2-chloro-4-[(3-methyl-2-phenyl-cyclopenten-1-yl)methoxy]phenyl]Propanoic Acid

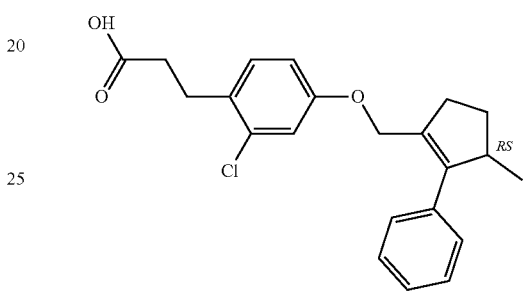

¹H NMR (CHLOROFORM-d) δ: 7.32-7.40 (m, 2H), 7.24-7.31 (m, 1H), 7.12-7.19 (m, 2H), 7.08 (d, J=8.6 Hz, 1H), 6.79 (d, J=2.5 Hz, 1H), 6.64 (dd, J=8.6, 2.5 Hz, 1H), 4.52 (s, 2H), 3.15-3.28 (m, 1H), 2.96 (t, J=7.6 Hz, 2H), 2.65 (br t, J=7.3 Hz, 3H), 2.46-2.59 (m, 1H), 2.25 (dtd, J=12.8, 8.5, 4.5 Hz, 1H), 1.55 (ddt, J=12.9, 9.1, 6.7 Hz, 1H), 0.97 (d, J=7.1 Hz, 3H). Calculated for $C_{22}H_{23}ClO_3$: 393.1 (M+23); Measured: 393.1.

Example 486: Compound #321

3-[4-[(3-methyl-2-phenyl-cyclopenten-1-yl)methoxy]phenyl]Propanoic Acid

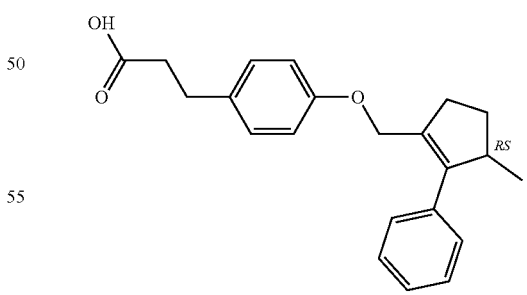

¹H NMR (CHLOROFORM-d) δ: 7.30-7.38 (m, 2H), 7.21-7.29 (m, 1H), 7.12-7.20 (m, 2H), 7.05 (d, J=8.6 Hz, 2H), 6.74 (d, J=8.6 Hz, 2H), 4.48-4.58 (m, 2H), 3.16-3.29 (m, 1H), 2.86 (br t, J=7.6 Hz, 2H), 2.48-2.76 (m, 4H), 2.25 (dtd, J=12.7, 8.6, 4.5 Hz, 1H), 1.55 (ddt, J=12.9, 9.1, 6.7 Hz, 1H), 0.98 (d, J=6.6 Hz, 3H). Calculated for $C_{22}H_{24}O_3$: 359.2 (M+23); Measured: 359.1.

Example 487: Compound #323

3-[5-fluoro-2-methyl-4-[(3-methyl-2-phenyl-cyclopenten-1-yl)methoxy]phenyl]Propanoic Acid

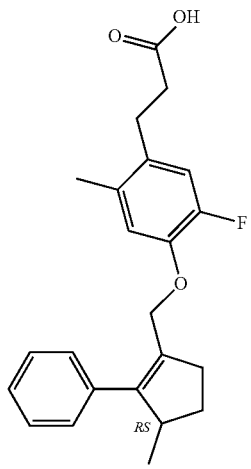 [SMILES: Cc1cc(OCC2=C(c3ccccc3)C(C)CC2)c(F)cc1CCC(=O)O]

$^1$H NMR (CHLOROFORM-d) δ: 7.33-7.42 (m, 2H), 7.23-7.32 (m, 1H), 7.12-7.21 (m, 2H), 6.83 (d, J=12.1 Hz, 1H), 6.47 (d, J=8.6 Hz, 1H), 4.61 (s, 2H), 3.14-3.28 (m, 1H), 2.82 (br t, J=7.8 Hz, 2H), 2.63-2.75 (m, 1H), 2.50-2.63 (m, 3H), 2.24 (dtd, J=12.8, 8.5, 4.5 Hz, 1H), 2.12 (s, 3H), 1.54 (ddt, J=13.0, 9.0, 6.7 Hz, 1H), 0.97 (d, J=7.1 Hz, 3H). Calculated for $C_{23}H_{25}FO_3$: 391.2 (M+23); Measured: 391.2.

Example 488: Compound #316

3-[4-[[2-(4-chlorophenyl)-3-methyl-cyclopenten-1-yl]methoxy]-2-(trifluoromethyl)phenyl]Propanoic Acid

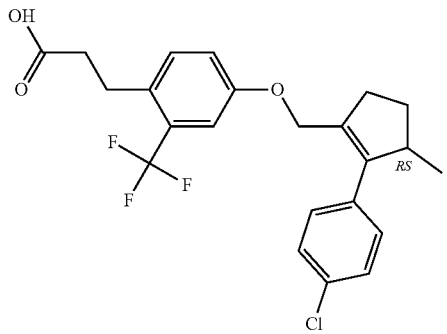 [SMILES: CC1CCC(COc2ccc(CCC(=O)O)c(C(F)(F)F)c2)=C1c1ccc(Cl)cc1]

$^1$H NMR (CHLOROFORM-d) δ: 7.29-7.37 (m, 2H), 7.20 (brd, J=8.6 Hz, 1H), 7.07-7.13 (m, 2H), 7.05 (d, J=2.5 Hz, 1H), 6.88 (dd, J=8.3, 2.3 Hz, 1H), 4.54 (s, 2H), 3.12-3.25 (m, 1H), 3.05 (br t, J=7.1 Hz, 2H), 2.65 (br d, J=7.1 Hz, 3H), 2.46-2.57 (m, 1H), 2.26 (dtd, J=12.8, 8.5, 4.5 Hz, 1H), 1.55 (ddt, J=12.9, 9.1, 6.7 Hz, 1H), 0.96 (d, J=7.1 Hz, 3H). Calculated for $C_{23}H_{22}ClF_3O_3$: 461.1 (M+23); Measured: 461.1.

Example 489: Compound #327

3-[2-chloro-4-[[2-(4-chlorophenyl)-3-methyl-cyclopenten-1-yl]methoxy]phenyl]Propanoic Acid

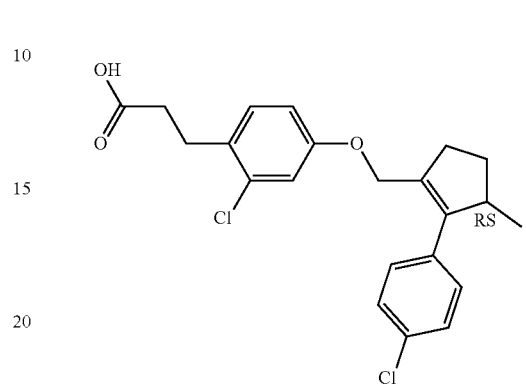

$^1$H NMR (CHLOROFORM-d) δ: 7.28-7.37 (m, 2H), 7.09 (d, J=8.6 Hz, 3H), 6.79 (d, J=2.5 Hz, 1H), 6.64 (dd, J=8.6, 2.5 Hz, 1H), 4.43-4.53 (m, 2H), 3.12-3.25 (m, 1H), 2.97 (br t, J=7.6 Hz, 2H), 2.65 (br d, J=2.5 Hz, 3H), 2.46-2.58 (m, 1H), 2.25 (dtd, J=12.8, 8.5, 4.5 Hz, 1H), 1.49-1.60 (m, 1H), 0.96 (d, J=6.6 Hz, 3H). Calculated for $C_{22}H_{22}Cl_2O_3$: 427.1 (M+23); Measured: 427.0.

Example 490: Compound #328

3-[4-[[2-(4-chlorophenyl)-3-methyl-cyclopenten-1-yl]methoxy]phenyl]Propanoic Acid

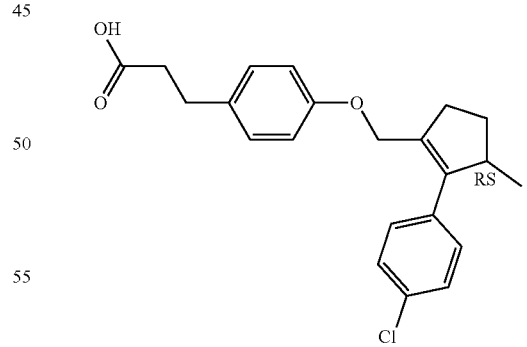

$^1$H NMR (CHLOROFORM-d) δ: 7.27-7.35 (m, 2H), 7.01-7.14 (m, 4H), 6.74 (d, J=8.6 Hz, 2H), 4.44-4.54 (m, 2H), 3.12-3.26 (m, 1H), 2.82-2.94 (m, 2H), 2.60-2.75 (m, 3H), 2.47-2.60 (m, 1H), 2.25 (dtd, J=12.8, 8.5, 4.5 Hz, 1H), 1.49-1.61 (m, 1H), 0.96 (d, J=7.1 Hz, 3H). Calculated for $C_{22}H_{23}ClO_3$: 393.1 (M+23); Measured: 393.0.

Example 491: Compound #317

3-[4-[[2-(4-chlorophenyl)-3-methyl-cyclopenten-1-yl]methoxy]-5-fluoro-2-methyl-phenyl]Propanoic Acid

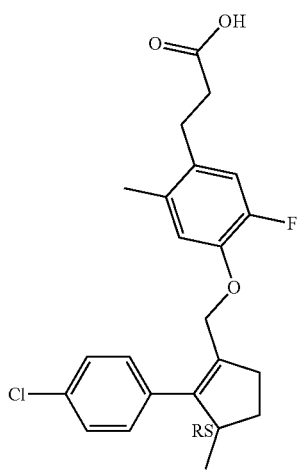 [SMILES: Cc1cc(OCC2=C(c3ccc(Cl)cc3)C(C)CC2)c(F)cc1CCC(=O)O]

$^1$H NMR (CHLOROFORM-d) δ: 7.28-7.37 (m, 2H), 7.05-7.14 (m, 2H), 6.84 (br d, J=12.1 Hz, 1H), 6.50 (d, J=8.6 Hz, 1H), 4.56 (s, 2H), 3.09-3.24 (m, 1H), 2.83 (br s, 2H), 2.50-2.74 (m, 4H), 2.25 (dtd, J=12.8, 8.5, 4.5 Hz, 1H), 2.15 (s, 3H), 1.48-1.60 (m, 1H), 0.95 (d, J=7.1 Hz, 3H). Calculated for $C_{23}H_{24}ClFO_3$: 15425.1 (M+23); Measured: 425.1.

Example 492: Compound #367

3-[4-[(5-methyl-2-phenyl-cyclopenten-1-yl)methoxy]-2-(trifluoromethyl)phenyl]Propanoic Acid

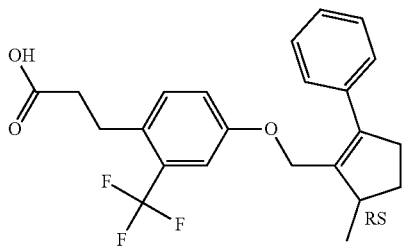 [SMILES: CC1CCC(c2ccccc2)=C1COc1ccc(CCC(=O)O)c(C(F)(F)F)c1]

$^1$H NMR (CHLOROFORM-d) δ: 7.31-7.39 (m, 2H), 7.17-7.31 (m, 4H), 7.09 (d, J=2.5 Hz, 1H), 6.92 (dd, J=8.6, 2.0 Hz, 1H), 4.55-4.69 (m, 2H), 2.97-3.10 (m, 3H), 2.56-2.86 (m, 4H), 2.18-2.29 (m, 1H), 1.48-1.61 (m, 1H), 1.19 (d, J=6.6 Hz, 3H). Calculated for $C_{23}H_{23}F_3O_3$: 427.2 (M+23); Measured: 426.9.

Example 493: Compound #334

3-[2-chloro-4-[(5-methyl-2-phenyl-cyclopenten-1-yl)methoxy]phenyl]Propanoic Acid

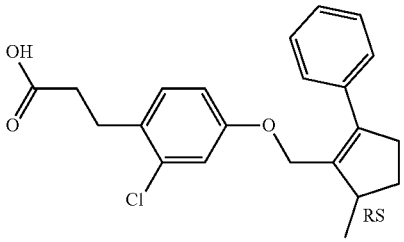 [SMILES: CC1CCC(c2ccccc2)=C1COc1ccc(CCC(=O)O)c(Cl)c1]

$^1$H NMR (CHLOROFORM-d) δ: 7.31-7.38 (m, 2H), 7.21-7.31 (m, 3H), 7.11 (d, J=8.1 Hz, 1H), 6.84 (d, J=2.5 Hz, 1H), 6.69 (dd, J=8.6, 2.5 Hz, 1H), 4.51-4.63 (m, 2H), 2.92-3.08 (m, 3H), 2.60-2.86 (m, 4H), 2.23 (dtd, J=12.6, 8.2, 4.8 Hz, 1H), 1.47-1.59 (m, 1H), 1.18 (d, J=6.6 Hz, 3H). Calculated for $C_{22}H_{23}C_1O_3$: 393.1 (M+23); Measured: 393.0.

Example 494: Compound #366

3-[4-[(5-methyl-2-phenyl-cyclopenten-1-yl)methoxy]phenyl]Propanoic Acid

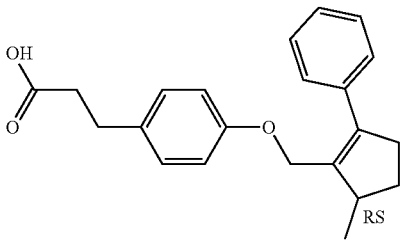 [SMILES: CC1CCC(c2ccccc2)=C1COc1ccc(CCC(=O)O)cc1]

$^1$H NMR (CHLOROFORM-d) δ: 7.30-7.37 (m, 2H), 7.22-7.30 (m, 3H), 7.09 (d, J=8.6 Hz, 2H), 6.79 (d, J=8.6 Hz, 2H), 4.51-4.65 (m, 2H), 2.99-3.12 (m, 1H), 2.85-2.93 (m, 1H), 2.85-2.85 (m, 1H), 2.58-2.85 (m, 4H), 2.18-2.29 (m, 1H), 1.48-1.60 (m, 1H), 1.18 (d, J=7.1 Hz, 3H). Calculated for $C_{22}H_{24}O_3$: 359.2 (M+23); Measured: 359.0.

Example 495: Compound #338

3-[5-fluoro-2-methyl-4-[(5-methyl-2-phenyl-cyclopenten-1-yl)methoxy]phenyl]Propanoic Acid

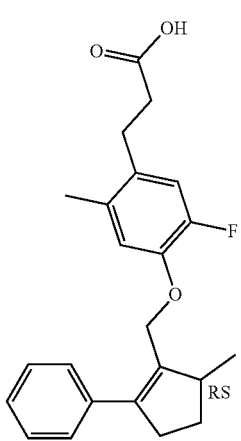 [SMILES: Cc1cc(OCC2=C(c3ccccc3)CCC2C)c(F)cc1CCC(=O)O]

¹H NMR (CHLOROFORM-d) δ: 7.32-7.40 (m, 2H), 7.22-7.32 (m, 3H), 6.86 (d, J=12.1 Hz, 1H), 6.55 (d, J=8.6 Hz, 1H), 4.58-4.73 (m, 2H), 3.00-3.13 (m, 1H), 2.66-2.87 (m, 4H), 2.60 (br d, J=7.6 Hz, 2H), 2.23 (dtd, J=12.6, 8.2, 4.8 Hz, 1H), 2.15 (s, 3H), 1.46-1.59 (m, 1H), 1.21 (d, J=6.6 Hz, 3H). Calculated for $C_{23}H_{25}FO_3$: 391.2 (M+23); Measured: 391.0.

Example 496: Compound #336

3-[4-[[2-(4-chlorophenyl)-5-methyl-cyclopenten-1-yl]methoxy]-2-(trifluoromethyl)phenyl]Propanoic Acid

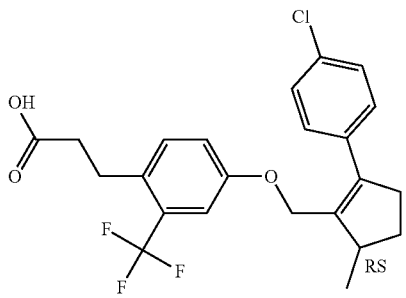 [SMILES: CC1CCC(c2ccc(Cl)cc2)=C1COc1ccc(CCC(=O)O)c(C(F)(F)F)c1]

¹H NMR (CHLOROFORM-d) δ: 7.31 (d, J=8.6 Hz, 2H), 7.22 (d, J=8.6 Hz, 1H), 7.18 (d, J=8.1 Hz, 2H), 7.09 (d, J=2.0 Hz, 1H), 6.92 (dd, J=8.6, 2.5 Hz, 1H), 4.51-4.62 (m, 2H), 2.94-3.11 (m, 3H), 2.59-2.83 (m, 4H), 2.18-2.29 (m, 1H), 1.48-1.60 (m, 1H), 1.18 (d, J=6.6 Hz, 3H). Calculated for $C_{23}H_{22}ClF_3O_3$: 461.1 (M+23); Measured: 461.0.

Example 497: Compound #337

3-[2-chloro-4-[[2-(4-chlorophenyl)-5-methyl-cyclopenten-1-yl]methoxy]phenyl]Propanoic Acid

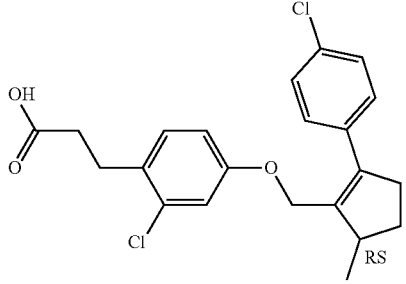 [SMILES: CC1CCC(c2ccc(Cl)cc2)=C1COc1ccc(CCC(=O)O)c(Cl)c1]

¹H NMR (CHLOROFORM-d) δ: 7.31 (d, J=8.1 Hz, 2H), 7.18 (d, J=8.6 Hz, 2H), 7.12 (d, J=8.1 Hz, 1H), 6.84 (d, J=2.5 Hz, 1H), 6.69 (dd, J=8.6, 2.5 Hz, 1H), 4.47-4.57 (m, 2H), 2.92-3.08 (m, 3H), 2.60-2.83 (m, 4H), 2.23 (dtd, J=12.6, 8.2, 4.8 Hz, 1H), 1.47-1.60 (m, 1H), 1.17 (d, J=7.1 Hz, 3H). Calculated for $C_{22}H_{22}Cl_2O_3$: 427.1 (M+23); Measured: 426.9.

Example 498: Compound #332

3-[4-[[2-(4-chlorophenyl)-5-methyl-cyclopenten-1-yl]methoxy]phenyl]Propanoic Acid

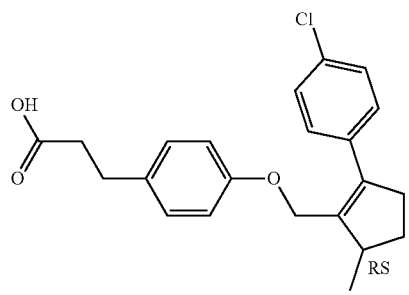 [SMILES: CC1CCC(c2ccc(Cl)cc2)=C1COc1ccc(CCC(=O)O)cc1]

¹H NMR (CHLOROFORM-d) δ: 7.27-7.33 (m, 2H), 7.15-7.24 (m, 2H), 7.10 (d, J=8.6 Hz, 2H), 6.79 (d, J=8.6 Hz, 2H), 4.47-4.59 (m, 2H), 2.98-3.11 (m, 1H), 2.85-2.94 (m, 2H), 2.69-2.83 (m, 2H), 2.59-2.69 (m, 2H), 2.16-2.30 (m, 1H), 1.48-1.60 (m, 1H), 1.18 (d, J=7.1 Hz, 3H). Calculated for $C_{22}H_{23}ClO_3$: 393.1 (M+23); Measured: 393.0.

Example 499: Compound #333

3-[4-[[2-(4-chlorophenyl)-5-methyl-cyclopenten-1-yl]methoxy]-5-fluoro-2-methyl-phenyl]Propanoic Acid

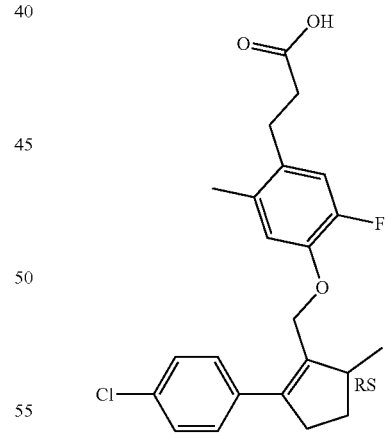

¹H NMR (CHLOROFORM-d) δ: 7.32 (d, J=8.6 Hz, 2H), 7.20 (d, J=8.6 Hz, 2H), 6.87 (d, J=12.1 Hz, 1H), 6.59 (d, J=8.6 Hz, 1H), 4.52-4.65 (m, 2H), 2.99-3.13 (m, 1H), 2.81-2.88 (m, 2H), 2.64-2.81 (m, 2H), 2.54-2.64 (m, 2H), 2.14-2.29 (m, 4H), 1.48-1.60 (m, 1H), 1.20 (d, J=6.6 Hz, 3H). Calculated for $C_{23}H_{24}ClFO_3$: 425.1 (M+23); Measured: 425.0.

Example 500: Compound #6

3-[4-[[2-(4-chlorophenyl)-3-ethyl-cyclopenten-1-yl]methoxy]-2,3-dimethyl-phenyl]Propanoic Acid

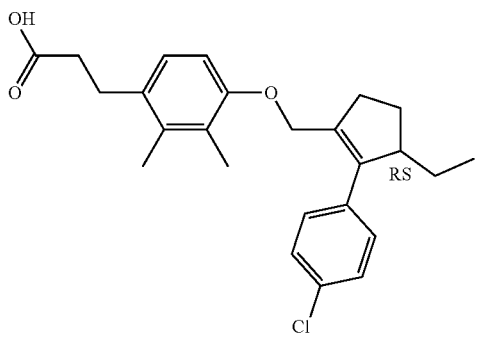 [SMILES: CCC1CCC(COc2ccc(CCC(=O)O)c(C)c2C)=C1c1ccc(Cl)cc1]

$^1$H NMR (300 MHz, CD$_3$OD) δ: 7.34 (d, J=8.7 Hz, 2H), 7.17 (d, J=8.7 Hz, 2H), 6.88 (d, J=8.1 Hz, 1H), 6.45 (d, J=8.4 Hz, 1H), 4.52 (s, 2H), 3.14-3.34 (m, 1H), 2.85-2.89 (m, 2H), 2.50-2.70 (m, 2H), 2.33-2.37 (m, 2H), 2.20-2.31 (m, 4H), 2.15 (s, 3H), 1.67-1.70 (m, 1H), 1.46-1.66 (m, 1H), 1.16-1.23 (m, 1H), 0.84 (t, J=7.5 Hz, 3H). Mass spectrum (ESI, m/z): Calculated for C$_{25}$H$_{29}$ClO$_3$, 411.2 [M−H], Measured: 411.2

Example 501: Compound #46

3-[4-[[2-(4-chlorophenyl)-3-isopropyl-cyclopenten-1-yl]methoxy]-2,3-dimethyl-phenyl]Propanoic Acid

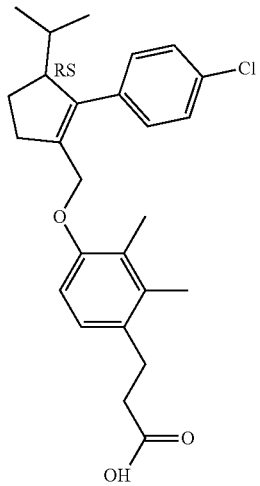 [SMILES: Cc1c(CCC(=O)O)ccc(OCC2=C(c3ccc(Cl)cc3)C(C(C)C)CC2)c1C]

$^1$H NMR (400 MHz, CD$_3$OD) δ: 7.36 (d, J=8.4 Hz, 2H), 7.19 (d, J=8.4 Hz, 2H), 6.86 (d, J=8.4 Hz, 1H), 6.47 (d, J=8.4 Hz, 1H), 4.54 (s, 2H), 3.32-3.34 (m, 1H), 2.86 (t, J=7.5 Hz, 2H), 2.59-2.62 (m, 2H), 2.48 (t, J=7.5 Hz, 2H), 2.22 (s, 3H), 2.14 (s, 3H), 1.95-2.03 (m, 1H), 1.73-1.86 (m, 2H), 0.91 (d, J=8.4 Hz, 3H), 0.68 (d, J=6.8 Hz, 3H). Mass spectrum (ESI, m/z): Calculated for C$_{26}$H$_{31}$ClO$_3$, 425.2 [M−H], Measured: 425.2.

Example 502: Compound #403

3-[4-[(2-benzoylcyclopenten-1-yl)methoxy]-2-(trifluoromethyl)phenyl]Propanoic Acid

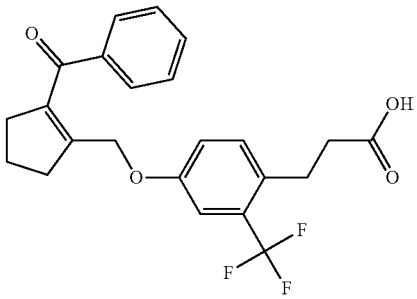 [SMILES: O=C(O)CCc1ccc(OCC2=C(C(=O)c3ccccc3)CCC2)cc1C(F)(F)F]

$^1$H NMR (CHLOROFORM-d) δ: 7.76-7.84 (m, 2H), 7.50-7.58 (m, 1H), 7.39-7.48 (m, 2H), 7.18 (d, J=8.6 Hz, 1H), 6.99 (d, J=2.5 Hz, 1H), 6.84 (dd, J=8.3, 2.8 Hz, 1H), 4.63 (s, 2H), 3.03 (br t, J=7.6 Hz, 2H), 2.78-2.87 (m, 2H), 2.73 (br t, J=7.6 Hz, 2H), 2.62 (br s, 2H), 2.03 (quin, J=7.5 Hz, 2H). Calculated for C$_{23}$H$_{21}$F$_3$O$_4$: 441.1 (M+23); Measured: 441.1.

Biological Example 1: In Vitro Assay

Human GPR120 DiscoveRx PathHunter® Beta-Arrestin Assay Assay Principle:

The binding of an agonist (medium/long chain fatty acids or small molecule agonists) to the G-protein-coupled receptor GPR120 activates phospholipase C, leading to release of intracellular Ca$^{+2}$ through the generation of inositol 1,4,5-trisphosphate (InsP3 or IP3). GPR120 activation can also trigger intracellular signaling via recruitment of Beta-Arrestin. In the present method, agonist-induced activation of the human GPR120 receptor is monitored through the use of PathHunter® CHO-K1 GPR120 Beta-Arrestin Cell Line engineered by DiscoveRx, as detailed below. The cell lines are designed to co-express both the ProLink/Enzyme Donor (PK)-tagged GPCR and the Enzyme Activator (EA)-tagged Beta-Arrestin fusion proteins. Upon GPR120 receptor stimulation/activation, the EA-tagged Beta-Arrestin portion is translocated to the tagged receptor, where the two enzyme fragments are brought within close proximity. Under these conditions, these fragments can interact and form an active Beta-gal enzyme complex through Enzyme Fragment Complementation (EFC). This active Beta-gal complex can enzymatically hydrolyse the substrate to produce a detectable light signal; therefore, activation as a function of agonist concentration can be expressed as an EC$_{50}$ value to determine relative compound activities. This in vitro assay therefore serves to assess compound agonist activity of the GPR120.

Procedure β-Arrestin A:

In Procedure β-arrestin A, the cell used were PathHunter® CHO-K1 GPR120 β-Arrestin Cell Line, expressing the long form of human GPR120 (Genbank accession number NM_181745), with 3000 cells per well.

Procedure β-arrestin B:

In Procedure β-arrestin B the cells used were PathHunter® CHO-K1 GPR120S β-Arrestin Cell Line, expressing the short form of the GPR120 receptor (Accession #NM_181745), with 5000 cells/well.

Assay Procedure:

The selected CHO-K1 GPR120 β-Arrestin cells were cultured in Ham's F12 media supplemented with 10% fetal bovine serum (FBS), 1% Glutamine, 1×p/s, 800 µg/mL G418 and 300 µg/mL Hygromycin B (for selection). Cell stocks were maintained and grown in a sub-confluent state using standard cell culture procedures. The day before the experiment, the cells were harvested with non-enzymatic cell dissociation buffer and re-suspended in complete growth media at the desired concentration. A Corning 384-plate was then seeded with the proper number of cells in a volume of 25 µL, per well. The seeded plates were incubated overnight at 37° C.

On the day of the experiment, the Assay Buffer containing (a) HBSS with $Ca^{++}$ and $Mg^{++}$, (b) 20 mM HEPES, and (c) 0.1% BSA stabilizer (pH 7.4) was prepared. The growth medium was gently removed from the cell plates and 20 µL of Assay Buffer added to each well. The plate was then incubated at 37° C. for 60 min. Test compounds were serially diluted in Assay Buffer to desired concentrations (more particularly to one or more of the following µM concentrations: 25, 12.5, 6.25, 3.12, 1.56, 0.78, 0.39, 0.19, 0.10, 0.05, 0.02, 0.01). Five µL of compound dilution was then added to each well and the plate incubated at 37° C. for 90 min. The detection reagents were prepared according to the manufacture's instruction. Twelve µL of the detection reagents were added to each well and the plate incubated at room temperature for 60 min.

The plates were read on an EnVision instrument, using Protocol name: Luminescence, Plate type: 384 Costar, Measurement height: 3 mm, Measurement time: 1 s, Aperture: 384 Plate aperture. The % Activity relative to the positive control was calculated using the following equation:

$$\% \text{ Activity} = \frac{Count_{compound} - Count_{vehicle}}{Count_{postivite\ control} - Count_{vehicle}} \times 100\%$$

The % Activity values were plotted versus the concentration of test compound and fitted to a sigmoidal dose-response curve with a Hill slope=1 (fixed value) using nonlinear regression with GraphPad Prism 5.0 to calculate the $EC_{50}$ values. The Fitting Equation was: Y=Bottom+(Top-Bottom)/(1+10^((Log $EC_{50}$-X)*HillSlope)), where X is the log of the concentration and Y is the response.

Biological Example 2: in Vitro Assay

Human GPR120 in Calcium Flux Assay

Assay Principle

This in vitro assay serves to assess test compound agonist activity against the short splice variant (SVS with Accession number NM_001195755.1 confirmed by sequencing data) of the GPR120 receptor. The Human Short splice variant #2 (NM_001195755.1) is missing an in-frame coding exon compared to variant 1 (the Human Long splice variant NM_181745.3), resulting in a shorter isoform (GPR120-S) lacking a 16 aa protein segment compared to isoform GPR120-L. The assay platform utilizes HEK-293 cells stably transfected to express the Human GPR120 short form. These cells are first loaded with the $Ca^{+2}$ sensitive dye, Fluo-4 NW. Upon stimulation, intracellular released $Ca^{+2}$ can bind to the dye and alter its fluorescence intensity. This increase in fluorescence signal, and thus the flux in intracellular $[Ca^{2+}]$, is detected and quantitated by fluorescence imaging using a FLIPR reader. The effect of the agonist is measured as a function of concentration and used to calculate an $EC_{50}$ based upon a response curve.

Procedure Calcium A:

In this procedure 2500 cells/well were employed.

Procedure Calcium B:

In this procedure 4200 cells/well were employed.

Assay Procedure:

A Human GPR120 clone (Genbank accession number NM_001195755.1) was placed into the pcDNA3.1 mammalian expression vector carrying the neomycin resistance gene. A stable mammalian cell was generated by placing the above clone into a HEK293 background. Clonal cells responding to long chain fatty acids had expression levels of GPR120 confirmed by RT-qPCR. Human HEK-GPR120 cells were cultured in Dulbecco's Modified Eagle's Medium (DMEM)/F12 medium supplemented with 10% fetal bovine serum (FBS), 1% L-Glutamine and 1% penicillin/streptomycin and 0.5 mg/ml G-418. Cells were split 2 times a week to keep the cells in the log-phase growth.

In preparation for the assay, HEK cells stably transfected with Human GPR120 (2.5K cells per well in 25 uL growth medium) were seeded into 384-well plates and then incubated overnight (37° C., 5% $CO_2$). The next day, the media was changed to 20 µL assay buffer and the cell starved for 1 h at 37° C. The dye loading solution (2× dye) was prepared using 10 mL assay buffer, 100 µL of 250 mM probenecid, 1 bottle of Component A, and 20 µl of dye in DMSO. Twenty µL of the 2× dye loading buffer was then added to each well. The plates were incubated at 37° C. for 30 min, then at room temperature for an additional 15 minutes, before performing the assay on FLIPR.

Test compounds were prepared in assay buffer (2 µL of compound+198 µL assay buffer, final DMSO in assay plate is 0.2%) at the desired concentration, more particularly at 100, 50, 25, 12.5, 6.25, 3.125, 1.562, 0.781, 0.391, 0.195, 0.098, 0.049, 0.024 and 0.012 µM.

The assay was performed on a FLIPR plate reader using the following parameters. Baseline was read for 10 seconds at 1 sec intervals. The program was set to transfer 10 µL of ligand from compound plate to cell plate after baseline reading. Aspiration was executed at: 10 µL/sec speed, 4.6 µL height, Dispensing was executed at: 30 µL/sec speed, 45 µL height. After compound addition, each well was read for 300 sec, with measurements collected at 1 sec intervals.

The kinetic data from the FLIPR was based upon a 5 minute window for data collection. The fluorescence of each sample well was used for individual calculations of a normalized RFU value, which was defined as maximum response minus the minimum response. The normalized fluorescence reading (RFU) was calculated as follows:

$$RFU = F\text{max} - F\text{min}$$

The data were fitted to a sigmoidal dose-response curve with a variable Hill slope (<2) using nonlinear regression with GraphPad Prism 5.0 to calculate the $EC_{50}$ values. The Fitting Equation was: Y=Bottom+(Top-Bottom)/(1+10^((Log $EC_{50}$-X)*HillSlope)), where X is the log of the concentration and Y is the response.

Biological Example 3: In Vitro Assay

GPR40 Calcium Flux Assay

Compounds were tested in a calcium flux assay using transfected HEK293 cells stably expressing either human GPR40 or rat GPR40. Human GPR40 expressing cells were cultured in DMEM–High Glucose media supplemented with 10% fetal bovine serum, 1×L-Glutamine, 1×Penicillin/Streptomycin and 500 μg/mL G418. Rat GPR40 expressing cells were cultured in DMEM–High Glucose media supplemented with 10% fetal bovine serum and 1 μg/mL puromycin. Cells were plated into poly-D-lysine coated 384-well plates and cultured overnight in a 37° C. humidified tissue culture incubator under 5% $CO_2$/90% $O_2$ atmosphere.

On the day of the experiment, the culture media was replaced with assay buffer (HBSS, 20 mM HEPES, 0.1% BSA) and the cells incubated at 37° C. for 1 h. Calcium-sensitive fluorescent dye (Fluo 8 No-Wash Calcium Dye, ABD Bioquest) was then added and the cells incubated for another 30 min at 37° C. followed by 15 min at room temperature while protected from the light. The cell plate and a plate of diluted compounds of Formula (I) were loaded into a fluorescent plate reader that added compounds onto the cells while measuring the fluorescence intensity of each well. The plate reader recorded fluorescence intensity at 1 second intervals for 8 min and provided the data for analysis in an Excel format. $EC_{50}$ values were calculated using Prism (GraphPad) software.

Representative compounds of the present invention were tested according to the Biological Example procedures described above, with results as listed in Table 4 below. Wherein a compound was tested more than once, each measured value is listed individually in the table below.

TABLE 4

GPR40 and GPR120 Assay Results

| ID No. | GPR40 Calcium Flux Assay $EC_{50}$ (μM) | Human GPR120 Beta-Arrestin Assay Procedure A $EC_{50}$ (μM) | Human GPR120 Beta-Arrestin Assay Procedure B $EC_{50}$ (μM) | Human GPR120 Calcium Flux Assay Procedure A $EC_{50}$ (μM) | Human GPR120 Calcium Flux Assay Procedure B $EC_{50}$ (μM) |
|---|---|---|---|---|---|
| 4 | >5 | | 0.164 | 0.294 | 0.044 |
| 6 | >5 | | | | >5 |
| 10 | >5 | 0.155 | | | 0.024 |
| 12 | >5 | | 0.093 | | 0.481 |
| 15 | >5 | | 0.122 | 0.206 | 0.070 |
| 16 | >5 | | 0.149 | 0.198 | 0.049 |
| 19 | >5 | | | 1.933 | 0.603 |
| 20 | >5 | | >5 | >20 | |
| 21 | >5 | | | >20 | |
| 22 | >5 | | | >20 | |
| 23 | >5 | | 0.337 | 0.301 | 0.114 |
| 25 | >5 | | 0.089 | 0.129 | |
| 27 | >5 | | 0.077 | 0.256 | 0.058 |
| 30 | >5 | 0.512 | | | 0.461 |
| 32 | >5 | 0.341 | 0.203 | | 0.311 |
| 33 | >5 | 0.312 | 0.180 | | 0.288 |
| 34 | >5 | 0.680 | | | |
| 36 | >5 | 0.235 | | | 0.193 |
| 39 | 0.131, 0.182 | 0.491 | | | 0.215 |
| 42 | >5 | 0.340 | | | 0.061 |
| 43 | 3.028 | 0.208 | | | 0.207 |
| 45 | >5 | | | >20 | |
| 46 | >5 | | | | >5 |
| 47 | 0.932 | | 0.273 | 0.582 | 0.103 |
| 49 | >5 | 0.123 | | | 0.136 |
| 50 | | | 0.709 | 0.409 | 0.183 |
| 51 | | | | >20 | |
| 52 | >10 | | 0.063 | 0.173 | 0.024 |
| 55 | | | 0.246 | 0.793 | 0.282 |
| 56 | | | 0.085 | 0.324 | 0.037 |
| 57 | | | 0.258 | 0.527 | 0.050 |
| 58 | >10 | | 0.275 | 0.546 | 0.159 |
| 60 | >5 | | 0.359 | 0.550 | 0.103 |
| 62 | >5 | | 0.075 | 0.136 | 0.027 |
| 65 | >5 | | 1.635 | 2.489 | 0.614 |
| 66 | >5 | | 0.629 | 0.658 | 0.205 |
| 67 | >5 | 0.167 | | | 0.073 |
| 68 | >5 | 1.937 | | | 0.517 |
| 69 | >5 | | | >5 | 2.455 |
| 70 | >5 | | 0.073 | 0.344 | 0.023 |
| 72 | >5 | | 0.648 | 0.658 | 0.245 |
| 74 | >10 | | | >20 | |
| 75 | | | 0.171 | 0.591 | 0.195 |
| 76 | >10 | | 0.281 | 0.542 | 0.136 |
| 77 | >10 | | 0.369 | 0.508 | 0.122 |
| 78 | >5 | | 0.075 | 0.094 | 0.034 |
| 79 | >5 | | 0.596 | 0.760 | 0.192 |
| 80 | >5 | 0.073 | 0.139 | 0.081 | 0.019 |
| 82 | >5 | | 1.090 | 0.372 | 0.242 |
| 83 | >5 | | 0.630 | 0.590 | 0.143 |
| 84 | >5 | | 0.533 | 1.738 | 0.290 |
| 85 | >5 | | 0.725 | 0.605 | 0.234 |
| 87 | >5 | | 0.493 | | |
| 88 | >5 | | 0.588 | 0.461 | 0.233 |
| 89 | | | | | 1.413 |
| 91 | >5 | | | | >5 |
| 92 | >5 | | | 1.257 | 0.373 |
| 93 | >5 | | 0.587 | 0.427 | 0.643 |
| 94 | >5 | | 0.047 | 0.400 | 0.023 |
| 95 | >5 | | 0.076 | 0.378 | 0.032 |
| 96 | 1.778 | 0.981 | | | 0.875 |
| 97 | 0.834 | 0.754 | | | 0.237 |
| 98 | >5 | | | | 2.035 |
| 99 | >5 | 0.147 | | | 0.044 |
| 100 | >5 | 0.168 | | | 0.081 |
| 101 | >5 | | | | 1.227 |
| 102 | >5 | | 0.365 | 0.781 | 0.134 |
| 103 | >5 | | | | >5 |
| 105 | >5 | | 0.445 | 1.627 | 0.183 |
| 106 | >5 | | 0.853 | 0.572 | 0.567 |
| 107 | >5 | | | | >5 |
| 108 | >5 | | 0.807 | 1.050 | 0.233 |
| 109 | >5 | | 2.464 | 0.959 | 1.289 |
| 111 | >5 | | 2.708 | 0.777 | 0.687 |
| 112 | >5 | | | 2.464 | 3.068 |
| 113 | >5 | | | >5 | |
| 114 | >5 | | | >5 | |
| 115 | >5 | | | 1.121 | 0.852 |
| 117 | >5 | 0.256 | 0.190 | | 0.110 |
| 119 | >5 | | | 0.895 | 0.327 |
| 120 | | | | >5 | |
| 122 | >5 | | 0.397 | 0.453 | 0.247 |
| 123 | | | 0.257 | 0.248 | 0.084 |
| 124 | >5 | | 0.235 | 0.308 | 0.067 |
| 126-D | >5 | 0.035 | 0.045 | | 0.010 |
| 127 | >5 | | | 2.780 | 0.668 |
| 129 | >5 | | 0.047 | | 0.021 |
| 130 | >5 | 0.087 | 0.041 | | 0.034 |
| 131 | 1.993 | | 0.566 | 0.533 | 0.118 |
| 132 | >5 | | 1.803 | 1.090 | 0.409 |
| 133 | >5 | | 1.128 | 0.682 | 0.344 |
| 134 | >5 | | 0.740 | 2.002 | 1.429 |
| 135 | >5 | | 1.254 | | |
| 136 | >5 | 0.788 | | | |
| 137 | >5 | 0.043 | | | 0.065 |
| 139 | | | | 2.446 | 2.468 |
| 140 | >5 | | | >5 | |
| 141 | >5 | | 1.229 | 1.060 | 0.256 |
| 142 | >5 | | | | |
| 143 | 0.365 | 0.466 | | | |
| 144 | >5 | | | | |
| 145 | >5 | | | | 1.999 |
| 146 | >5 | | | 1.558 | 0.208 |
| 147 | >5 | | 0.923 | 1.013 | 0.336 |
| 149 | >10 | | 0.090 | 0.128 | 0.024 |
| 151 | >5 | | | >5 | |
| 152 | >5 | | 0.060 | 0.123 | 0.011 |

TABLE 4-continued

GPR40 and GPR120 Assay Results

| ID No. | GPR40 Calcium Flux Assay EC$_{50}$ (μM) | Human GPR120 Beta-Arrestin Assay | | Human GPR120 Calcium Flux Assay | |
|---|---|---|---|---|---|
| | | Procedure A EC$_{50}$ (μM) | Procedure B EC$_{50}$ (μM) | Procedure A EC$_{50}$ (μM) | Procedure B EC$_{50}$ (μM) |
| 153 | 2.946 | | 0.093 | 0.319 | 0.023 |
| 157 | >5 | | | 0.097 | 0.067 |
| 158 | >5 | | 0.324 | 0.234 | 0.133 |
| 159 | >5 | | 0.056 | 0.044 | 0.026 |
| 160 | >5 | 0.528 | | | 0.215 |
| 161 | 0.401 | 0.680 | | | |
| 166 | 4.002 | 0.029 | | | 0.024 |
| 167 | 1.254 | 0.727 | | | 0.503 |
| 168 | | | | | >5 |
| 169 | | 0.035 | | | 0.049 |
| 171 | | 0.211 | | | 0.106 |
| 172 | >5 | 0.032 | | | 0.042 |
| 173 | >5 | 0.040 | | | 0.049 |
| 177 | | 0.073 | | | 0.053 |
| 179 | >5 | 0.289 | | | 0.031 |
| 180 | >5 | 0.078 | | | 0.026 |
| 181 | | | | | >5 |
| 182 | >5 | 0.104 | | | 0.032 |
| 183 | >5 | 0.185 | | | 0.051 |
| 184 | >5 | 0.431 | | | 0.091 |
| 185 | 3.435 | 1.436 | | | 0.360 |
| 186 | 0.382 | 1.786 | | | 0.453 |
| 187 | 3.318 | 0.596 | | | 0.137 |
| 188 | 0.142 | 0.548 | | | 0.411 |
| 189 | | 0.245 | | | 0.063 |
| 190 | | 1.054 | | | 0.442 |
| 191 | >5 | 0.259 | | | 0.027 |
| 192 | | 0.320 | | | 0.062 |
| 193 | >5 | 0.133 | | | 0.030 |
| 194 | | 0.161 | | | 0.036 |
| 195 | | 0.466 | | | 0.228 |
| 196 | | 0.996 | | | 0.743 |
| 198 | 2.136 | | | | 1.294 |
| 199 | 1.466 | 0.369 | | | 0.210 |
| 200 | | 0.435 | | | 0.184 |
| 201 | | 0.408 | | | 0.792 |
| 202 | | 0.303 | | | 0.114 |
| 203 | >5 | 0.056 | | | 0.080 |
| 204 | >5 | 0.359 | | | 0.125 |
| 205 | >5 | | | | 0.465 |
| 207 | 1.196 | | | | 2.096 |
| 208 | >5 | | | | 0.185 |
| 209 | >5 | | | | 4.636 |
| 210 | >5 | 0.110 | | | 0.137 |
| 211 | >5 | | | | 0.304 |
| 212 | >5 | | | | >5 |
| 213 | >5 | | | | 0.776 |
| 214 | >5 | 0.084 | | | 0.078 |
| 215 | >5 | 0.282 | | | 0.075 |
| 216 | >5 | 0.169 | | | 0.075 |
| 218 | >5 | | | | 0.089 |
| 219 | >5 | | | | 1.120 |
| 220 | >5 | | | | 0.160 |
| 221 | >5 | | | | 0.160 |
| 222 | >5 | 0.132 | | | 0.057 |
| 223 | >5 | 0.227 | | | 0.156 |
| 224 | >5 | 0.231 | | | 0.285 |
| 225 | >5 | 0.588 | | | 0.530 |
| 226 | >5 | 1.292 | | | 0.724 |
| 227 | >5 | | | | 0.356 |
| 228 | 4.933 | 0.238 | | | 0.124 |
| 229 | >5 | | | | 1.053 |
| 230 | >5 | | | | 1.869 |
| 232 | >5 | | | | >5 |
| 233 | 2.930 | | | | 0.752 |
| 234 | >5 | | | | 1.139 |
| 235 | >5 | | | | 0.668 |
| 236 | >5 | | | | 1.267 |
| 237 | 0.923 | | | | >5 |
| 238 | >5 | | | | 0.435 |
| 239 | >5 | | | | 0.403 |
| 240 | 0.187 | | | | 0.388 |
| 241 | 0.222 | | | | 0.173 |
| 242 | 0.836 | | | | 0.146 |
| 243 | 0.090 | | | | >5 |
| 244 | 0.799 | | | | 2.238 |
| 245 | 1.911 | | | | 2.003 |
| 246 | 0.358 | | | | 3.133 |
| 247 | 0.388 | | | | 3.056 |
| 248 | 0.188 | | | | 0.361 |
| 249 | 0.463 | | | | 0.173 |
| 250 | 1.480 | | | | 0.076 |
| 251 | 0.579 | | | | 0.195 |
| 252 | | | | | 0.265 |
| 254 | >5 | | | | 0.594 |
| 255 | 1.302 | | | | >5 |
| 257 | 0.337 | | | | 2.642 |
| 258 | 0.481 | | | | 0.614 |
| 259 | 1.570 | | | | 1.217 |
| 260 | 0.488 | | | | 0.541 |
| 261 | 1.624 | | | | 1.535 |
| 262 | 1.287 | | | | >5 |
| 263 | 0.134 | | | | 0.262 |
| 264 | 1.589 | | | | 0.103 |
| 265 | 1.137 | | | | 1.213 |
| 268-D | 0.992 | | | | 0.685 |
| 269 | 0.604 | | | | 2.243 |
| 270 | 1.496 | | | | 0.189 |
| 272 | 0.265 | | | | 2.236 |
| 273 | 1.037 | | | | 0.213 |
| 274 | 0.215 | | | | 0.518 |
| 275 | 0.286 | | | | 0.307 |
| 276 | 0.193 | | | | 0.427 |
| 277 | 2.682 | | | | 0.799 |
| 278 | 0.302 | | | | >5 |
| 279 | 3.518 | | | | 0.495 |
| 280 | 0.471 | | | | 0.346 |
| 281 | 0.474 | | | | 0.314 |
| 282 | 0.247 | | | | 0.192 |
| 283 | 0.355 | | | | 0.236 |
| 284 | 0.101 | | | | 0.442 |
| 285 | 0.108 | | | | 0.328 |
| 286 | 0.245 | | | | 2.901 |
| 287 | 0.153 | | | | >5 |
| 288 | 1.083 | | | | 0.847 |
| 289 | 1.005 | | | | 0.219 |
| 290 | >5 | | | | 0.418 |
| 291 | 1.417 | | | | >5 |
| 292 | 1.716 | | | | >5 |
| 293 | 4.244 | | | | 2.175 |
| 294 | 3.509 | | | | >5 |
| 295 | 0.234 | | | | 1.647 |
| 296 | 1.073 | | | | 0.157 |
| 297 | 0.588 | | | | 0.422 |
| 298 | 1.590 | | | | 1.629 |
| 299 | 0.661 | | | | 0.251 |
| 300 | 0.197 | | | | 1.550 |
| 301 | 0.448 | | | | 1.530 |
| 302-D | 0.952 | | | | 0.160 |
| 303-D | 2.370 | | | | 0.124 |
| 304 | 1.109 | | | | 0.502 |
| 305 | | | | | 0.378 |
| 306 | | 0.347 | | | 1.120 |
| 307 | 0.516 | | | | 0.288 |
| 308 | 0.899 | | | | >5 |
| 310 | 1.118 | | | | 0.209 |
| 311 | 0.792 | | | | >5 |
| 312 | 0.402 | | | | 0.612 |
| 313 | 0.191 | | | | 0.855 |
| 314 | 0.461 | | | | 0.765 |
| 315 | >5 | | | | 0.185 |
| 316 | 0.164 | | | | 2.429 |

TABLE 4-continued

GPR40 and GPR120 Assay Results

| ID No. | GPR40 Calcium Flux Assay EC$_{50}$ (μM) | Human GPR120 Beta-Arrestin Assay | | Human GPR120 Calcium Flux Assay | |
|---|---|---|---|---|---|
| | | Procedure A EC$_{50}$ (μM) | Procedure B EC$_{50}$ (μM) | Procedure A EC$_{50}$ (μM) | Procedure B EC$_{50}$ (μM) |
| 317 | 0.746 | | | | 0.866 |
| 318 | | | | | 0.957 |
| 319 | 0.055 | | | | 0.623 |
| 320 | 0.543 | | | | 0.998 |
| 321 | 2.638 | | | | 0.733 |
| 322 | 0.328 | | | | 1.138 |
| 323 | 2.227 | | | | 1.071 |
| 325 | 2.773 | | | | >5 |
| 326 | 4.779 | | | | 0.157 |
| 327 | 0.205 | | | | 0.983 |
| 328 | 0.639 | | | | 0.307 |
| 329 | 0.101 | | | | 1.596 |
| 330 | >5 | | | | 0.492 |
| 331 | 3.340 | | | | >5 |
| 332 | 1.298 | | | | 0.191 |
| 333 | 1.006 | | | | 0.427 |
| 334 | 2.127 | | | | 1.733 |
| 336 | 0.428 | | | | 0.562 |
| 337 | 0.519 | | | | 0.336 |
| 338 | 2.856 | | | | 0.725 |
| 339 | 0.356 | | | | 0.803 |
| 340 | 0.944 | | | | 0.743 |
| 341 | 0.281 | | | | 0.447 |
| 342 | 0.322 | | | | 0.515 |
| 343 | 1.097 | | | | 1.385 |
| 344 | 0.137 | | | | 0.520 |
| 345 | 0.067 | | | | 3.022 |
| 346 | 0.228 | | | | 1.297 |
| 347 | 0.897 | | | | 1.797 |
| 348 | 0.057 | | | | 2.358 |
| 349 | 0.060 | | | | 1.902 |
| 350 | 0.669 | | | | 1.769 |
| 351 | 1.231 | | | | >5 |
| 352 | >10 | | | | >5 |
| 353 | 0.046 | | | | 1.333 |
| 354 | 0.825 | | | | 1.767 |
| 355 | 3.693 | | | | >5 |
| 356 | 0.068 | | | | 2.539 |
| 357 | 0.653 | | | | 0.664 |
| 358 | 0.065 | | | | 0.951 |
| 359 | 0.081 | | | | 3.113 |
| 360 | 0.972 | | | | >5 |
| 361 | 0.131 | | | | 3.301 |
| 362 | 0.159 | | | | >5 |
| 363 | 1.700 | | | | >5 |
| 364 | 0.049 | | | | 0.891 |
| 365 | 0.991 | | | | 0.496 |
| 366 | >10 | | | | 1.140 |
| 367 | 1.509 | | | | 1.139 |
| 369 | 0.125 | | | | >5 |
| 370 | 0.133 | | | | 1.148 |
| 372 | 0.197 | | | | 2.352 |
| 373 | 2.380 | | | | 1.452 |
| 374 | 0.199 | | | | 1.427 |
| 375 | 0.962 | | | | 0.088 |
| 377 | 0.042 | | | | 0.493 |
| 380 | 0.084 | | | | >5 |
| 381 | 0.150 | | | | 1.654 |
| 382 | 0.046 | | | | 0.635 |
| 384 | 0.635 | | | | 0.677 |
| 385 | 0.012 | | | | 0.708 |
| 386 | 0.092 | | | | 1.699 |
| 387 | 0.071 | | | | >5 |
| 388 | 0.086 | | | | 1.633 |
| 389 | 0.051 | | | | 0.750 |
| 390 | 0.023 | | | | 1.191 |
| 392 | 1.405 | | | | 0.223 |
| 393 | 0.420 | | | | 0.291 |
| 394 | 0.129 | | | | 1.412 |
| 395 | 0.188 | | | | 0.255 |
| 397 | 0.418 | | | | 0.592 |
| 398 | 0.008 | | | | 0.556 |
| 399 | 0.015 | | | | 0.671 |
| 400 | 0.135 | | | | 0.995 |
| 401 | 0.311 | | | | 0.304 |
| 402 | 1.087 | | | | 0.278 |
| 403 | 1.139 | | | | 1.489 |
| 404 | 0.105 | | | | 1.912 |
| 405 | 0.205 | | | | 1.823 |
| 406 | 0.152 | | | | >5 |
| 407 | 0.030 | | | | 0.150 |
| 409 | 0.025 | | | | 0.086 |
| 410 | 0.128 | | | | 0.996 |
| 411 | 0.133 | | | | >5 |
| 412 | 0.513 | | | | 4.647 |
| 413 | >10 | | | | 1.804 |
| 414 | | | | | 2.585 |
| 415 | 0.132 | | | | >5 |
| 416 | 0.094 | | | | >5 |
| 417 | 1.011 | | | | >5 |
| 418 | 0.171 | | | | >5 |
| 419 | >10 | | | | 3.172 |
| 420 | | | | | 1.188 |
| 421 | 0.025 | | | | 0.222 |
| 422 | 0.048 | | | | 0.177 |
| 423 | 0.061 | | | | 0.272 |
| 424 | 0.248 | | | | 0.245 |
| 425 | 3.230 | | | | 0.143 |
| 426 | 0.082 | | | | 0.200 |
| 427 | | | | | 0.231 |
| 428 | 0.048 | | | | 0.256 |
| 429 | 0.089 | | | | 0.844 |
| 430 | 0.046 | | | | 0.335 |
| 431 | >10 | | | | 0.059 |
| 432 | >10 | | | | 0.044 |
| 433 | >10 | | | | >5 |
| 434 | 0.059 | | | | 0.387 |
| 435 | >10 | | | | >5 |
| 436 | >10 | | | | 0.159 |
| 438 | 0.138 | | | | 3.343 |
| 439 | >10 | | | | >5 |
| 440 | 0.382 | | | | 2.797 |
| 441 | 0.035 | | | | 0.100 |
| 442 | 0.048 | | | | 0.334 |
| 443 | 1.577 | | | | >5 |
| 444 | 0.174 | | | | 0.319 |
| 445 | 0.266 | | | | 3.539 |
| 446 | 0.458 | | | | 0.828 |
| 448 | 2.036 | | | | >5 |
| 450 | 0.118 | | | | 0.273 |
| 451 | 0.032 | | | | 0.249 |
| 452 | 0.170 | | | | 0.127 |
| 453 | 0.010 | | | | 0.181 |
| 454 | 0.513 | | | | 2.247 |
| 455 | 0.403 | | | | 0.340 |
| 456 | 0.042 | | | | 0.924 |
| 457 | 0.046 | | | | 0.126 |
| 458 | | | 0.371 | | 0.331 |
| 460 | | | 0.625 | | 0.385 |
| 461 | | | | 2.255 | 1.363 |
| 462 | | | 0.478 | 0.462 | 0.066 |
| 463 | >5 | | | 4.813 | 1.620 |
| 464 | | | | 1.338 | 1.248 |
| 465 | >5 | | | 2.165 | 1.452 |
| 466 | | | | 4.445 | 1.454 |
| 467 | >5 | | 0.104 | 0.199 | 0.040 |
| 468 | >5 | 0.168 | 0.244 | 0.261 | 0.056, 0.054 |
| 472 | >5 | | 0.488 | 0.406 | 0.032 |
| 474 | >5 | 0.354 | 1.034 | 0.428 | 0.079 |
| 475 | >5 | | | 4.483 | 2.269 |
| 476 | >5 | | | 1.330 | 0.475 |
| 477 | >5 | | | 1.180 | 0.256 |

TABLE 4-continued

GPR40 and GPR120 Assay Results

| ID No. | GPR40 Calcium Flux Assay EC$_{50}$ (µM) | Human GPR120 Beta-Arrestin Assay | | Human GPR120 Calcium Flux Assay | |
|---|---|---|---|---|---|
| | | Procedure A EC$_{50}$ (µM) | Procedure B EC$_{50}$ (µM) | Procedure A EC$_{50}$ (µM) | Procedure B EC$_{50}$ (µM) |
| 478 | >5 | | | | >5 |
| 479 | >5 | | 0.682 | 0.958 | 0.073 |
| 480 | | | 0.385 | 0.234 | 0.079 |
| 481 | | | 0.475 | 0.250 | 0.134 |
| 482 | | | 0.126 | 0.406 | 0.091 |
| 483 | 3.532 | | 0.155 | 0.255 | 0.052 |
| 489 | 0.825 | 0.312 | | | 0.173 |
| 490 | >5 | | | 2.192 | 0.743 |
| 491 | >5 | | | 0.532 | 0.097 |
| 492 | | | 0.717 | 0.576 | 0.185 |
| 493 | >5 | | 0.356 | 0.123 | 0.037 |
| 494 | >5 | | 0.401 | 0.117 | 0.037 |
| 495 | >5 | | | >5 | |
| 496 | >5 | | 0.352 | 0.297 | 0.081 |
| 497 | >5 | 0.122 | | | 0.075 |
| 498 | >5 | 0.219 | | | 0.096 |
| 499 | >5 | 0.132 | | | 0.215 |
| 500 | >5 | | | | 1.527 |
| 501 | >5 | 0.155 | | | 0.364 |
| 502 | >5 | 0.192 | | | 0.147 |
| 503 | >5 | | 0.191 | 0.493 | 0.097 |
| 504 | 4.017 | | | 2.820 | 0.330 |
| 506 | >5 | | | 1.586 | 0.182 |
| 507 | >10 | | | >5 | |
| 509 | >10 | | 1.787 | 0.963 | 0.414 |
| 510 | >10 | | 0.210 | 0.561 | 0.033 |
| 511 | >10 | | 0.187 | 0.572 | 0.035 |
| 512 | >5 | | 0.803 | 0.808 | 0.140 |
| 513 | >5 | | 0.137 | 0.331 | 0.042 |
| 514 | >5 | | 0.252 | 0.340 | 0.053 |
| 515 | >5 | | | >5 | |
| 516 | >5 | | | 4.607 | 0.755 |
| 517 | >5 | | | >5 | |
| 518 | 3.751 | 0.639 | | | 0.255 |
| 519 | 3.314 | 0.772 | | | 0.222 |
| 520 | >5 | | | 2.357 | 1.453 |
| 521 | >5 | | | 1.281 | 0.626 |
| 522 | >5 | 0.853 | | | 0.714 |
| 523 | >5 | | | | >5 |
| 524 | | | | | 1.572 |
| 525 | 4.035 | 0.121 | | | 0.165 |
| 526 | | 3.843 | | | 0.873 |
| 527 | | 0.498 | | | 0.885 |
| 528 | | | | | 1.072 |
| 529 | >5 | 0.136 | | | 0.156 |
| 530 | >5 | 0.073 | | | 0.068 |
| 531 | | 0.287 | | | 0.117 |
| 532 | >5 | 0.187 | | | 0.133 |
| 533 | >5 | 0.532 | | | 0.309 |
| 534 | >5 | 0.157 | | | 0.096 |
| 535 | >5 | 0.108 | | | 0.120 |
| 536 | >5 | 0.215 | | | 0.207 |
| 537 | >5 | 0.161 | | | 0.083 |
| 538 | | 0.159 | | | 0.089 |
| 539 | >5 | 0.292 | | | 0.192 |
| 540 | | 0.222 | | | 0.151 |
| 541 | 4.756 | | | | 1.499 |
| 542 | 2.862 | 0.182 | | | 0.094 |
| 543 | >5 | 0.287 | | | 0.191 |
| 544 | >5 | | | | 1.353 |
| 545 | | 1.655 | | | 0.977 |
| 546 | 2.354 | 1.652 | | | 0.754 |
| 547 | | 1.801 | | | 0.388 |
| 548 | 3.488 | 1.338 | | | 0.500 |
| 549 | | | | | 1.285 |
| 550 | 0.642 | 0.437 | | | 0.482 |
| 551 | | | | | >5 |
| 552 | | 0.476 | | | 0.155 |
| 553 | 2.337 | 0.727 | | | 0.525 |
| 554 | | 1.022 | | | 0.727 |
| 555 | | 0.358 | | | 0.164 |
| 557 | | 0.302 | | | 0.149 |
| 558 | >5 | 1.311 | | | 0.381 |
| 559 | | 0.409 | | | 0.238 |
| 560 | 4.105 | 0.175 | | | 0.118 |
| 561 | | 0.120 | | | 0.071 |
| 562 | >5 | 0.245 | | | 0.119 |
| 563 | | 0.237 | | | 0.120 |
| 564 | | 0.176 | | | 0.090 |
| 565 | | | | | 3.895 |
| 566 | 3.335 | 0.209 | | | 0.165 |
| 568 | | 0.363 | | | 0.202 |
| 569 | >5 | 0.519 | | | 0.299 |
| 572 | >5 | 1.010 | | | 0.641 |
| 573 | 4.503 | 0.643 | | | 0.444 |
| 574 | 4.409 | | | | 2.126 |
| 575 | >5 | | | | >5 |
| 576 | 1.568 | | | | >5 |
| 577 | 3.009 | | | | 1.100 |
| 578 | 2.140 | | | | 1.780 |
| 579 | 0.075 | | | | 0.585 |
| 580 | 0.202 | | | | 1.328 |
| 581 | 0.591 | | | | 2.108 |
| 582 | 0.077 | | | | 1.209 |
| 583 | 0.294 | | | | 0.765 |
| 584 | 0.091 | | | | 0.756 |
| 585 | 2.423 | | | | 1.645 |
| 586 | 0.052 | | | | 0.908 |
| 587 | 0.099 | | | | 1.145 |
| 588 | 1.920 | | | | 1.135 |
| 589 | 2.386 | | | | 3.152 |
| 590 | 0.316 | | | | 1.362 |
| 591 | 0.431 | | | | 2.389 |
| 592 | 1.555 | | | | >5 |
| 593 | 1.301 | | | | >5 |
| 594 | >10 | | | | 0.362 |
| 595 | 0.218 | | | | 1.107 |
| 596 | 0.324 | | | | 2.370 |
| 598 | 0.177 | | | | 0.399 |
| 599 | 0.098 | | | | 1.349 |
| 600 | 0.024 | | | | 1.200 |
| 601 | 0.577 | | | | 2.126 |
| 602 | 1.060 | | | | 2.405 |
| 603 | 0.185 | | | | 1.966 |
| 604 | 1.501 | | | | 2.009 |
| 605 | 0.852 | | | | 1.173 |
| 606 | 0.247 | | | | 0.166 |
| 607 | 0.325 | | | | 0.148 |
| 610 | 0.267 | | | | 0.302 |
| 611 | 0.733 | | | | 0.312 |
| 612 | 0.107 | | | | 0.233 |
| 613 | 0.225 | | | | 0.436 |
| 614 | 0.560 | | | | 0.376 |
| 615 | >10 | | | | 0.172 |
| 616 | 3.552 | | | | 0.166 |
| 617 | 0.103 | | | | 0.215 |
| 618 | >10 | | | | 0.188 |

Biological Example 4: In Vivo Assay

GPR120 C57b16 Mouse IPGTT

Male, C57bl/6J Mice were ordered in at 8 weeks of age from Jackson Labs. Individual mice weighed anywhere in the range of 25-30 grams on study day. The mice were fasted, with removal of food occurring at 7 am on the morning of the study. Animals were moved into the room at 10:00 am, to give them time to acclimate. Glucose (insulin syringes) was drawn up either the night before or the morning of the study. Glucose was dosed (IP) at 1.5 g/kg at 7.5 ml/kg (20% glucose straight TEKNOVA, 250 ml sterile bottle w/catalogue number G0525). Test compounds were kept spinning and were only drawn into the syringes prior to study commencement. Animals were bled via tail snip to determine basal glucose levels prior to dosing of treatments. An Ascensia BREEZE Blood Glucose Monitoring System by Bayer (using unique 10-test disks) was used for determining glucose levels. The bleeds started at approximately 12:45 pm and dosing started, at 1-minute intervals, immediately after. All groups were dosed 30 minutes prior to glucose administration at a dose volume of 10 ml/kg (the dose volume was calculated separately for each individual animal). Thirty minutes after the first dose animals were bled again for a second baseline, or T=0, and immediately dosed with glucose via an i.p. injection. The exact dose volume for glucose was also calculated separately for each individual animal. Glucose measurements were taken at −30 min prior to compound dose, at t=0 (immediately prior to glucose dose), and at 15, 30, 45, 60, 90 min post glucose dose.

Glucose values were entered into an Excel sheet and graphed in GraphPad Prism. The following were calculated from Prism: Change from −30 to 0 Baseline Glucose, Raw Glucose AUC −30 to 90 min, Delta Glucose AUC −30 to 90 min, Raw Glucose AUC 0 to 90 min, Delta Glucose AUC 0 to 90 min.

Representative compounds of the present invention were tested according to the procedure described above, with results as listed in Table 5 and Table 6, below. Wherein a compound was tested multiple times, each set of results is listed separately.

TABLE 5

C57 IPGTT Results

| ID No. | 3 mg/kg | 10 mg/kg | 30 mg/kg |
| --- | --- | --- | --- |
| 4 | −9 | | |
| 10 | −29 | | |
| 15 | | −33 | |
| 16 | | −22 | |
| 23 | | | −42 |
| 25 | | | −41 |
| 27 | | | −54 |
| 27 | | −43 | |
| 39 | −22 | | |
| 52 | | −40 | |
| 62 | | −54 | |
| 78 | | −24 | |
| 80 | | −42 | |
| 85 | | −46 | |
| 126-D | −8 | | |
| 129 | −27 | | |
| 149 | −17 | | |
| 149 | −25 | | |
| 157 | −18 | | |
| 159 | −23 | | |
| 468 | −41 | | |
| 472 | | | −54 |
| 472 | −17 | −24 | |
| 483 | | −49 | |

TABLE 6

C57 IPGTT, Dose Response Results

| | Dose Response | | | |
| --- | --- | --- | --- | --- |
| ID No. | 1 mg/kg | 3 mg/kg | 10 mg/kg | 30 mg/kg |
| 25 | | 17% | 22% | 39% |
| 27 | 15% | 23% | 37% | |

TABLE 6-continued

C57 IPGTT, Dose Response Results

| | Dose Response | | | |
| --- | --- | --- | --- | --- |
| ID No. | 1 mg/kg | 3 mg/kg | 10 mg/kg | 30 mg/kg |
| 52 | | 11% | 30% | 92% |
| 62 | 10% | 35% | 56% | |
| 80 | | 10% | 55% | 81% |
| 85 | 13% | 24% | 19% | |
| 483 | 23% | 33% | 51% | |

Biological Example 5: In Vivo Assay

GPR120 DIO Mice OGTT Screening

Procedure 18-22 week old, $C_57B16$ mice on a high fat diet (60% HFD) for 12-16 weeks (ave. body weight ~ 37-41 g) were fasted for 6 hr, with removal of food occurring at 7 am on the morning of the study. The animals were sorted into treatment groups the day before the study by body weight. Animals outside the bounds of ~30-50 g were left out of the study. The animals had been handled and shammed a total of 5-8 days (1-3 days immediately prior to the study). Glucose (in 1 mL syringes) was drawn up the morning of the study. Test compounds were kept spinning and were only drawn into 1 ml syringes prior to study commencement. Animals were bled via tail snip to determine basal glucose levels prior to dosing of treatments. An Ascensia BREEZE Blood Glucose Monitoring System by Bayer was used for determining glucose levels.

Animals were moved into the testing room at ~9-11 am, to yield them time to acclimate. The bleeds and dosing started at approximately 1 pm in 30-second intervals per animal. All groups were dosed 30 minutes prior to glucose administration at a dose volume of 10 ml/kg (the dose volume was calculated separately for each individual animal). Test compounds were administered at one or more of the following dosages: 0.1 mg/kg, 0.3 mg/kg, 1 mg/kg, 3 mg/kg and 10 mg/kg.

Thirty minutes after the first dose (with test compound) animals were bled again for a second baseline, or T=0, and immediately dosed with glucose (20% solution, TEKNOVA, 250 ml sterile bottle w/catalogue number G0525) via a PO injection. The exact dose volume for glucose was also calculated separately for each individual animal.

Blood glucose was measured at 15, 30, 45, 60, and 90 minutes post-glucose administration via the snipped tail. If an animal reached a value of "HI", the upper limit of the glucometer (600 mg/dl) was substituted as the blood glucose value and the study was analyzed as normal with no exclusions. If 50% or more of any treatment group reaches a "HI" value at least once, the study was considered invalid and repeated. Glucose values were typed into an EXCEL spreadsheet where they were used to calculate glucose AUC and delta AUC post-compound and post-glucose. The glucose excursion curves and the different versions of the AUC's were graphed in GraphPad Prism 5.

Statistical Methods:

Note: All statistics completed in this study were completed using the statistical software package GraphPad Prism 5. Standard procedures for analyzing data sets from screening GPR120 compounds in DIO mouse OGTT's were as listed here below. In addition to the statistics that were run using GraphPad Prism 5, Microsoft Excel was used to calculate the percent changes in AUC from vehicle groups as detailed below.

Change from −30 to 0 Baseline Glucose, Raw Glucose AUC −30 to 90 min, Delta Glucose AUC −30 to 90 min, Raw Glucose AUC 0 to 90 min, Delta Glucose AUC 0 to 90 min were analyzed using Column Statistics Analysis, with mean values used to calculate % change from the vehicle mean group, as well as mean, SEM and/or % change from vehicle, where appropriate, and using One-Way ANOVA w/a Tukey Post-Test (Comparing All Pairs of Columns) with each treatment group examined to see if it was statistically significant compared to vehicle (*=P<0.05, =P<0.01, *=P<0.001).

Representative compounds of the present invention were tested according to the procedure as described above, with results as listed in Table 7, below.

TABLE 7

| | DIO Lowering Results | |
|---|---|---|
| | DIO Lowering (−30 to 90) | |
| ID No. | 10 mg/kg | 3 mg/kg |
| 52 | −86% | |
| 80 | −60% | −33% |
| 94 | −11% | |
| 137 | −56% | |
| 468 | −85% | |
| 494 | −28% | |

Formulation Example 1: (Prophetic Example)

Solid, Oral Dosage Form

As a specific embodiment of an oral composition, 100 mg of the Compound #80, prepared as in Example 80, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

What is claimed:
1. A compound of formula (I)

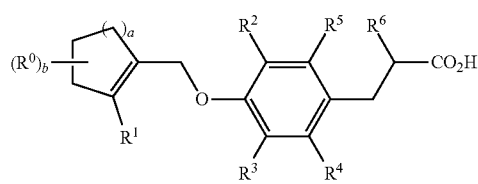

(I)

wherein
a is an integer from 1 to 3;
b is an integer from 0 to 2;
each $R^0$ is independently selected from the group consisting of halogen, oxo, hydroxy, -cyano, $C_{1-4}$alkyl, fluorinated $C_{1-2}$alkyl, $C_{1-4}$alkoxy, and fluorinated $C_{1-2}$alkoxy;
$R^1$ is selected from the group consisting of $C_{1-6}$alkyl, $C_{2-6}$alkynyl, $C_{3-6}$cycloalkyl, —($C_{1-2}$alkyl)-$C_{3-6}$cycloalkyl, $C_{5-6}$cycloalkenyl, bicyclo[3.1.0]hexy-2-yl, (1S,4S)-2-methyl-bicyclo[2.2.1]hept-2-yl, (1R,2R,4S)-bicyclo[2.2.1]heptan-2-yl, 2,2-difluoro-benzo[d][1,3]dioxol-4-yl, phenyl, —($C_{1-2}$alkyl)-phenyl, C(O)-phenyl, tetrahydropyranyl, furanyl, pyrimidinyl, pyridyl, thienyl, thiazolyl, —($C_{1-2}$alkyl)-thiazolyl, 3,6-dihydro-pyran-4-yl and 1-methyl-imidazol-4-yl;
wherein the $C_{3-6}$cycloalkyl or $C_{5-6}$cycloalkenyl, whether alone or as part of a substituent group is optionally substituted with one or more substituents independently selected from the group consisting of halogen, $C_{1-4}$alkyl and fluorinated $C_{1-2}$alkyl;
and wherein the phenyl, furanyl, pyrimidinyl, pyridyl, thienyl, thiazolyl, or 3,6-dihydro-pyran-4-yl, whether alone or as part of a substituent group is optionally substituted with one or more substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$alkyl), —SO$_2$—($C_{1-2}$alkyl), nitro, —NR$^A$R$^B$, —NH—C(O)—($C_{1-4}$alkyl) and phenyl; wherein R$^A$ and R$^B$ are each independently selected from the group consisting of hydrogen and $C_{1-4}$alkyl;
$R^2$ is selected from the group consisting of hydrogen, halogen, $C_{1-4}$alkyl, fluorinated $C_{1-2}$alkyl, —($C_{1-4}$alkyl)-S—($C_{1-2}$alkyl), —($C_{1-4}$alkyl)-SO—($C_{1-2}$alkyl) and —($C_{1-4}$alkyl)-SO$_2$—($C_{1-2}$alkyl);
$R^3$ is selected from the group consisting of hydrogen, halogen, $C_{1-4}$alkyl and fluorinated $C_{1-2}$alkyl;
$R^4$ is selected from the group consisting of hydrogen, halogen, $C_{1-4}$alkyl and fluorinated $C_{1-2}$alkyl;
$R^5$ is selected from the group consisting of hydrogen, cyano, halogen, $C_{1-4}$alkyl, fluorinated $C_{1-2}$alkyl, vinyl, halogen substituted vinyl, ethynyl, hydroxy substituted $C_{1-2}$alkyl, $C_{1-4}$alkoxy, fluorinated $C_{1-2}$alkoxy, cyclopropyl, cyclopropyl-methyl and phenyl, and
alternatively, $R^2$ and $R^5$ or $R^3$ and $R^4$ are taken together with the carbon atoms to which they are bound to form cyclopenten-1-yl;
provided that at least one of $R^2$, $R^3 R^4$ or $R^5$ is other than hydrogen;
$R^6$ is selected from the group consisting of hydrogen and methyl;
or an isotopologue or pharmaceutically acceptable salt thereof.
2. The compound of claim 1, wherein
a is an integer from 1 to 3;
b is an integer from 0 to 2;
each $R^0$ is independently selected from the group consisting of halogen, oxo, hydroxy, cyano, $C_{1-4}$alkyl, fluorinated $C_{1-2}$alkyl, $C_{1-4}$alkoxy, and fluorinated $C_{1-2}$alkoxy;
$R^1$ is selected from the group consisting of $C_{1-6}$alkyl, $C_{2-6}$alkynyl, $C_{3-6}$cycloalkyl, —($C_{1-2}$alkyl)-$C_{3-6}$cycloalkyl, $C_{5-6}$cycloalkenyl, bicyclo[3.1.0]hexy-2-yl, (1S,4S)-2-methyl-bicyclo[2.2.1]hept-2-yl, (1R,2R,4S)-bicyclo[2.2.1]heptan-2-yl, phenyl, —($C_{1-2}$alkyl)-phenyl, —C(O)-phenyl, tetrahydropyran-4-yl, furanyl, pyrimidinyl, pyridyl, thienyl, thiazolyl, —($C_{1-2}$alkyl)-thiazolyl, 3,6-dihydro-pyran-4-yl and 1-methyl-imidazol-4-yl;

wherein the $C_{3-6}$cycloalkyl or $C_{5-6}$cycloalkenyl, whether alone or as part of a substituent group is optionally substituted with one to two substituents independently selected from the group consisting of halogen, $C_{1-2}$alkyl and fluorinated $C_{1-2}$alkyl;

and wherein the phenyl, furanyl, pyrimidinyl, pyridyl, thienyl, thiazolyl, or 3,6-dihydro-pyran-4-yl, whether alone or as part of a substituent group is optionally substituted with one to three substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$ alkyl), —SO$_2$—($C_{1-2}$alkyl), nitro, —NR$^A$R$^B$, —NH—C(O)—($C_{1-4}$alkyl) and phenyl; wherein R$^A$ and R$^B$ are each independently selected from the group consisting of hydrogen and $C_{1-2}$alkyl;

R$^2$ is selected from the group consisting of hydrogen, halogen, $C_{1-4}$alkyl, fluorinated $C_{1-2}$alkyl, —($C_{1-4}$alkyl)-S—($C_{1-2}$alkyl) and —($C_{1-4}$alkyl)-SO$_2$—($C_{1-2}$alkyl);

R$^3$ is selected from the group consisting of hydrogen, halogen, $C_{1-2}$alkyl and fluorinated $C_{1-2}$alkyl;

R$^4$ is selected from the group consisting of hydrogen, halogen, $C_{1-2}$alkyl and fluorinated $C_{1-2}$alkyl;

R$^5$ is selected from the group consisting of hydrogen, halogen, cyano, $C_{1-4}$alkyl, fluorinated $C_{1-2}$alkyl, vinyl, halogen substituted vinyl, ethynyl, hydroxy substituted $C_{1-2}$alkyl, $C_{1-4}$alkoxy, fluorinated $C_{1-2}$alkoxy, cyclopropyl and phenyl;

alternatively, R$^2$ and R$^5$ are taken together with the carbon atoms to which they are bound to form cyclopenten-1-yl;

provided that when a is 3, then R$^1$ is selected from the group consisting of cyclopentyl and 4-chlorophenyl;

R$^6$ is selected from the group consisting of hydrogen and methyl;

or an isotopologue or pharmaceutically acceptable salt thereof.

3. The compound of claim 2, wherein
a is an integer from 1 to 3;
b is an integer from 0 to 2;
each R$^0$ is independently selected from the group consisting of halogen, hydroxy, oxo, cyano, $C_{1-4}$alkyl, fluorinated $C_{1-2}$alkyl and $C_{1-4}$alkoxy;
R$^1$ is selected from the group consisting of $C_{1-6}$alkyl, $C_{2-6}$alkynyl, $C_{3-6}$ cycloalkyl, —($C_{1-2}$alkyl)-$C_{3-6}$cycloalkyl, $C_{5-6}$cycloalkenyl, bicyclo[3.1.0]hex-2-yl, (1R,2R,4S)-bicyclo[2.2.1]heptan-2-yl, (1S,4S)-2-methyl-bicyclo[2.2.21]hept-2-yl, phenyl, —($C_{1-2}$alkyl)-phenyl, —C(O)-phenyl, pyridyl, pyrimidinyl, furanyl, thienyl, thiazolyl, —($C_{1-2}$alkyl)-thiazolyl, 1-methyl-imidazol-4-yl, 3,6-dihydro-pyran-4-yl and tetrahydro-pyran-4-yl;
wherein the $C_{3-6}$cycloalkyl or $C_{5-6}$cycloalkenyl, whether alone or as part of a substituent group is optionally substituted with one to two substituents independently selected from the group consisting of halogen and $C_{1-2}$alkyl;
wherein the phenyl, pyridyl, furanyl, thienyl or thiazolyl, whether alone or as part of a substituent group is optionally substituted with one to three substituents independently selected from the group consisting of halogen, hydroxy, $C_{1-4}$alkyl, fluorinated $C_{1-2}$alkyl, $C_{1-4}$alkoxy, fluorinated $C_{1-2}$alkoxy, —S—($C_{1-2}$alkyl), —SO—($C_{1-2}$alkyl), —SO$_2$—($C_{1-2}$alkyl), cyano, nitro, —NR$^A$R$^B$, —NH—C(O)—($C_{1-4}$alkyl) and phenyl;

wherein R$^A$ and R$^B$ are each independently selected from the group consisting of hydrogen and $C_{1-2}$alkyl;

R$^2$ is selected from the group consisting of hydrogen, halogen, $C_{1-4}$alkyl, —($C_{1-4}$alkyl)-S—($C_{1-2}$alkyl) and —($C_{1-4}$alkyl)-SO$_2$—($C_{1-2}$alkyl);

R$^3$ is selected from the group consisting of hydrogen, halogen and $C_{1-2}$alkyl;

R$^4$ is selected from the group consisting of hydrogen, halogen and fluorinated $C_{1-2}$alkyl;

R$^5$ is selected from the group consisting of hydrogen, halogen, cyano, $C_{1-4}$alkyl, hydroxy substituted $C_{1-2}$alkyl, fluorinated $C_{1-2}$alkyl, $C_{1-4}$alkoxy, fluorinated $C_{1-2}$alkoxy, vinyl, halogen substituted vinyl, ethynyl, cyclopropyl and phenyl;

alternatively, R$^2$ and R$^5$ are taken together with the carbon atoms to which they are bound to form cyclopenten-1-yl;

R$^6$ is selected from the group consisting of hydrogen and methyl;

or an isotopologue or pharmaceutically acceptable salt thereof.

4. The compound of claim 3, wherein
a is an integer from 1 to 3;
b is an integer from 0 to 2;
each R$^0$ is independently selected from the group consisting of 4-fluoro, 5-fluoro, 4-chloro, 5-hydroxy, 5-oxo, 3-methyl, 5-methyl, 3-ethyl, 4-ethyl, 5-ethyl, 3-isopropyl, 4-isopropyl, 5-isopropyl, 5-trifluoromethyl, 4-methoxy, 5-methoxy and 4-cyano;
R$^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, n-pentyn-1-yl, cyclopropyl, cyclobutyl, 1-fluoro-cyclobut-1-yl, cyclopentyl, cyclopentyl-methyl-, cyclohexyl, cyclohexyl-methyl-, bicyclo[3.1.0]hex-2-yl, (1R,2R,4S)-bicyclo[2.2.1]heptan-2-yl, (1 S,4S)-2-methyl-bicyclo[2.2.21]hept-2-yl, cyclopenten-3-yl, cyclohex-1-en-1-yl, 4,4-difluoro-cyclohex-1-yl, phenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 2-iodophenyl, 4-iodophenyl, 2-methylphenyl, 3-methylphenyl, 4-methylphenyl, 4-ethylphenyl, 4-isopropyl-phenyl, 4-n-propyl-phenyl, 4-isopropyl-phenyl, 4-trifluoromethylphenyl, 3-methoxyphenyl, 4-methoxyphenyl, 4-ethoxyphenyl, 4-trifluoromethoxy-phenyl, 2,4-difluorophenyl, 3,4-difluorophenyl, 2,4-dichlorophenyl, 3,4-dichlorophenyl, 3,5-dichlorophenyl, 2-fluoro-4-chloro-phenyl, 2-fluoro-4-methyl-phenyl, 2-fluoro-5-chloro-phenyl, 2-fluoro-5-methyl-phenyl, 3-fluoro-4-chloro-phenyl, 3-fluoro-4-methyl-phenyl, 3-fluoro-5-methoxy-phenyl, 2-methyl-4-chloro-phenyl, 2-methyl-4-methoxy-phenyl, 2,4-dimethylphenyl, 3,4-dimethylphenyl, 2-isopropyl-4-methyl-phenyl, 2-methoxy-4-methyl-phenyl, 3-methoxy-4-methyl-phenyl, 2-hydroxy-4-methyl-phenyl, 3-hydroxy-4-methyl-phenyl, 4-cyanophenyl, 3-nitro-4-methyl-phenyl, 3-amino-4-methyl-phenyl, 3-(dimethylamino)-phenyl, 4-dimethylamino-phenyl, 4-(methyl-thio)-phenyl, 4-(methyl-sulfinyl)-phenyl, 4-(methylsulfonyl)-phenyl, 4-(methyl-carbonyl-amino)-phenyl, 2-phenyl-4-methyl-phenyl, 3-phenyl-4-methyl-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, phenyl-carbonyl-, pyrid-2-yl, pyrid-3-yl, pyrid-4-yl, 6-chloro-pyrid-3-yl, 6-methyl-pyrid-3-yl, 6-methoxy-pyrid-3-yl, 6-ethoxy-pyrid-3-yl, 5-fluoro-6-methoxy-pyrid-3-yl, pyrimidin-2-yl, furan-2-yl, 5-methyl-furan-2-yl, thien-2-yl, thien-3-yl, 5-chloro-thien-2-yl, 5-cyano-thien-2-yl, 5-methyl-thien-2-yl, thiazol-2-yl, thiazol-5-yl, 2-methyl-thiazol-5-yl, thiazol-2-yl-methyl-, thiazol-5-yl-methyl-, 1-methyl-imidazol-4-yl, 3,6-dihydro-pyran-4-yl and tetrahydro-pyran-4-yl;

$R^2$ is selected from the group consisting of hydrogen, fluoro, chloro, bromo, iodo, methyl, ethyl, 4-(methyl-thio)-n-butyl, and 4-(methyl-sulfonyl)-n-butyl;

$R^3$ is selected from the group consisting of hydrogen, fluoro, chloro, bromo, iodo, and methyl;

$R^4$ is selected from the group consisting of hydrogen, fluoro, chloro, and trifluoromethyl;

$R^5$ is selected from the group consisting of hydrogen, fluoro, chloro, bromo, methyl, ethyl, isopropyl, t-butyl, 1-hydroxy-ethyl, trifluoromethyl, 1,1,2,2,2-pentafluor-ethyl, methoxy, trifluoromethoxy, vinyl, 1-bromo-vinyl, ethynyl, cyano, cyclopropyl and phenyl;

alternatively, $R^2$ and $R^5$ are taken together with the carbon atoms to which they are bound to form cyclopenten-1-yl;

$R^6$ is selected from the group consisting of hydrogen and methyl;

or an isotopologue or pharmaceutically acceptable salt thereof.

5. The compound of claim 4, wherein a is an integer from 1 to 2;

b is an integer from 0 to 2;

each $R^0$ is independently selected from the group consisting of 4-fluoro, 5-fluoro, 4-chloro, 5-hydroxy, 5-oxo,-3-methyl, 5-methyl, 3-ethyl, 4-ethyl, 5-ethyl, 3-isopropyl, 4-isopropyl, 5-isopropyl, 5-trifluoromethyl, 4-methoxy, 5-methoxy and 4-cyano;

$R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, n-pentyn-1-yl, cyclopropyl, cyclobutyl, 1-fluoro-cyclobut-1-yl, cyclopentyl, cyclopentyl-methyl-, cyclohexyl, cyclohexyl-methyl-, bicyclo[3.1.0]hex-2-yl, (1R,2R,4S)-bicyclo[2.2.1]heptan-2-yl, (1S,4S)-2-methyl-bicyclo[2.2.21]hept-2-yl, cyclopenten-3-yl, cyclohex-1-en-1-yl, 4,4-difluoro-cyclohex-1-yl, phenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 2-iodophenyl, 4-iodophenyl, 2-methylphenyl, 3-methylphenyl, 4-methylphenyl, 4-ethylphenyl, 4-isopropyl-phenyl, 4-n-propyl-phenyl, 4-isopropyl-phenyl, 4-trifluoromethyl-phenyl, 3-methoxyphenyl, 4-methoxyphenyl, 4-ethoxyphenyl, 4-trifluoromethoxy-phenyl, 2,4-difluorophenyl, 3,4-difluorophenyl, 2,4-dichlorophenyl, 3,4-dichlorophenyl, 3,5-dichlorophenyl, 2-fluoro-4-chloro-phenyl, 2-fluoro-4-methyl-phenyl, 2-fluoro-5-chloro-phenyl, 2-fluoro-5-methyl-phenyl, 3-fluoro-4-chloro-phenyl, 3-fluoro-4-methyl-phenyl, 3-fluoro-5-methoxy-phenyl, 2-methyl-4-chloro-phenyl, 2-methyl-4-methoxy-phenyl, 2,4-dimethylphenyl, 3,4-dimethylphenyl, 2-isopropyl-4-methyl-phenyl, 2-methoxy-4-methyl-phenyl, 3-methoxy-4-methyl-phenyl, 2-hydroxy-4-methyl-phenyl, 3-hydroxy-4-methyl-phenyl, 4-cyanophenyl, 3-nitro-4-methyl-phenyl, 3-amino-4-methyl-phenyl, 3-(dimethylamino)-phenyl, 4-dimethylamino-phenyl, 4-(methyl-thio)-phenyl, 4-(methyl-sulfinyl)-phenyl, 4-(methyl-sulfonyl)-phenyl, 4-(methyl-carbonyl-amino)-phenyl, 2-phenyl-4-methyl-phenyl, 3-phenyl-4-methyl-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, phenyl-carbonyl-, pyrid-2-yl, pyrid-3-yl, pyrid-4-yl, 6-chloro-pyrid-3-yl, 6-methyl-pyrid-3-yl, 6-methoxy-pyrid-3-yl, 6-ethoxy-pyrid-3-yl, 5-fluoro-6-methoxy-pyrid-3-yl, pyrimidin-2-yl, furan-2-yl, 5-methyl-furan-2-yl, thien-2-yl, thien-3-yl, 5-chloro-thien-2-yl, 5-cyano-thien-2-yl, 5-methyl-thien-2-yl, thiazol-2-yl, thiazol-5-yl, 2-methyl-thiazol-5-yl, thiazol-2-yl-methyl-, thiazol-5-yl-methyl-, 1-methyl-imidazol-4-yl, and tetrahydro-pyran-4-yl;

$R^2$ is selected from the group consisting of hydrogen, fluoro, chloro, bromo, iodo, methyl, ethyl, 4-(methyl-thio)-n-butyl, and 4-(methyl-sulfonyl)-n-butyl;

$R^3$ is selected from the group consisting of hydrogen, fluoro, chloro, bromo, iodo, and methyl;

$R^4$ is selected from the group consisting of hydrogen, fluoro, chloro, and trifluoromethyl;

$R^5$ is selected from the group consisting of hydrogen, fluoro, chloro, bromo, methyl, ethyl, isopropyl, t-butyl, 1-hydroxy-ethyl, trifluoromethyl, 1,1,2,2,2-pentafluor-ethyl, methoxy, trifluoromethoxy, vinyl, 1-bromo-vinyl, ethynyl, cyano, cyclopropyl and phenyl;

alternatively, $R^2$ and $R^5$ are taken together with the carbon atoms to which they are bound to form cyclopenten-1-yl;

$R^6$ is selected from the group consisting of hydrogen and methyl;

or an isotopologue or pharmaceutically acceptable salt thereof.

6. The compound of claim 4, wherein a is 1;

b is an integer from 0 to 2;

each $R^0$ is independently selected from the group consisting of 4-fluoro, 4-chloro, 5-hydroxy, 5-oxo, 3-methyl, 5-methyl, ethyl, 3-isopropyl, 5-trifluoromethyl, 4-methoxy and 4-cyano;

$R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, n-pentyn-1-yl, cyclopropyl, cyclobutyl, 1-fluoro-cyclobut-1-yl, cyclopentyl, cyclopentyl-methyl-, cyclohexyl-methyl-, bicyclo[3.1.0]hex-2-yl, (1S,4S)-2-methyl-bicyclo[2.2.21]hept-2-yl, cyclopenten-3-yl, cyclohex-1-en-1-yl, 4,4-difluoro-cyclohex-1-yl, phenyl, 2-fluorophenyl, 3-fluorophenyl, 4-fluorophenyl, 2-chlorophenyl, 3-chlorophenyl, 4-chlorophenyl, 2-bromophenyl, 4-bromophenyl, 4-iodophenyl, 2-methylphenyl, 3-methylphenyl, 4-methylphenyl, 4-ethylphenyl, 4-isopropyl-phenyl, 4-n-propyl-phenyl, 4-trifluoromethyl-phenyl, 3-methoxyphenyl, 4-methoxyphenyl, 4-ethoxyphenyl, 4-trifluoromethoxy-phenyl, 2,4-difluorophenyl, 3,4-difluorophenyl, 2,4-dichlorophenyl, 3,4-dichlorophenyl, 3,5-dichlorophenyl, 2-fluoro-4-chloro-phenyl, 2-fluoro-4-methyl-phenyl, 2-fluoro-5-chloro-phenyl, 2-fluoro-5-methyl-phenyl, 3-fluoro-4-chloro-phenyl, 3-fluoro-4-methyl-phenyl, 3-fluoro-5-methoxy-phenyl, 2-methyl-4-chloro-phenyl, 2-methyl-4-methoxy-phenyl, 2,4-dimethylphenyl, 3,4-dimethylphenyl, 2-isopropyl-4-methyl-phenyl, 2-methoxy-4-methyl-phenyl, 3-methoxy-4-methyl-phenyl, 2-hydroxy-4-methyl-phenyl, 3-hydroxy-4-methyl-phenyl, 4-cyanophenyl, 3-nitro-4-methyl-phenyl, 3-amino-4-methyl-phenyl, 3-(dimethylamino)-phenyl, 4-(methyl-thio)-phenyl, 4-(methyl-sulfinyl)-phenyl, 4-(methyl-sulfonyl)-phenyl, 4-(methyl-carbonyl-amino)-phenyl, 2-phenyl-4- methyl-phenyl, 3-phenyl-4-methyl-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, phenyl-carbonyl-, pyrid-2-yl, pyrid-3-yl, pyrid-4-yl, 6-chloro-pyrid-3-yl, 6-methyl-pyrid-3-yl, 6-methoxy-pyrid-3-yl, 6-ethoxy-pyrid-3-yl, 5-fluoro-6-methoxy-pyrid-3-yl, pyrimidin-2-yl, furan-2-yl, 5-methyl-furan-2-yl, thien-2-yl, thien-3-yl, thiazol-2-yl, thiazol-5-yl, 2-methyl-thiazol-5-yl, thiazol-2-yl-methyl-, 3,6-dihydro-pyran-4-yl and tetrahydro-pyran-4-yl;

$R^2$ is selected from the group consisting of hydrogen, fluoro, chloro, bromo, iodo, methyl, ethyl 4-(methyl-thio)-n-butyl, and 4-(methyl-sulfonyl)-n-butyl;

$R^3$ is selected from the group consisting of hydrogen, fluoro, chloro, bromo, and methyl;

$R^4$ is selected from the group consisting of hydrogen, fluoro, chloro, and trifluoromethyl;

$R^5$ is selected from the group consisting of hydrogen, fluoro, chloro, bromo, methyl, ethyl, isopropyl, t-butyl, 1-hydroxy-ethyl, trifluoromethyl, 1,1,2,2,2-pentafluor-ethyl, methoxy, trifluoromethoxy, vinyl, 1-bromo-vinyl, ethynyl, cyano, cyclopropyl and phenyl;

alternatively, $R^2$ and $R^5$ are taken together with the carbon atoms to which they are bound to form cyclopenten-1-yl;

$R^6$ is selected from the group consisting of hydrogen and methyl;

or an isotopologue or pharmaceutically acceptable salt thereof.

7. The compound of claim 4, wherein
a is 2;
b is an integer from 0 to 2;
each $R^0$ is independently selected from the group consisting of 4-fluoro, 5-fluoro, 5-methyl, 3-ethyl, 4-ethyl, 5-ethyl, 3-isopropyl, 4-isopropyl, 5-isopropyl, and 5-methoxy;

$R^1$ is selected from the group consisting of n-propyl, isopropyl, n-butyl, isobutyl, cyclobutyl, cyclopentyl, cyclohexyl, (1R,2R,4S)-bicyclo[2.2.1]heptan-2-yl, phenyl, 4-cyanophenyl, 4-fluorophenyl, 2-chlorophenyl, 3-chlorophenyl, 4-chlorophenyl, 4-bromophenyl, 2-iodophenyl, 2-methylphenyl, 4-methylphenyl, 4-n-propy-phenyl, 4-isopropyl-phenyl, 4-trifluoromethyl-phenyl, 4-ethoxyphenyl, 4-trifluoromethoxy-phenyl, 2,4-difluorophenyl, 3,4-difluorophenyl, 3-fluoro-4-chloro-phenyl, 3-fluoro-4-methyl-phenyl, 4-(methyl-thio)-phenyl, 4-(methyl-sulfinyl)-phenyl, 4-(methyl-sulfonyl)-phenyl, 4-dimethylamino-phenyl, 4-(methyl-carbonyl-amino)-phenyl, benzyl, pyrid-2-yl, pyrid-4-yl, 6-methyl-pyrid-3-yl, pyrimidin-2-yl, furan-2-yl, thien-2-yl, 5-chloro-thien-2-yl, 5-cyano-thien-2-yl, 5-methyl-thien-2-yl, thiazol-5-yl, 2-methyl-thiazol-5-yl, 1-methyl-imidazol-4-yl and thiazol-5-yl-methyl-;

$R^2$ is selected from the group consisting of hydrogen, fluoro, methyl, 4-(methyl-thio)-n-butyl and 4-(methyl-sulfonyl)-n-butyl;

$R^3$ is selected from the group consisting of hydrogen, fluoro and iodo;

$R^4$ is selected from the group consisting of hydrogen and fluoro;

$R^5$ is selected from the group consisting of hydrogen, fluoro, chloro, methyl and trifluoromethyl;

alternatively, $R^2$ and $R^5$ are taken together with the carbon atoms to which they are bound to form cyclopenten-1-yl;

$R^6$ is hydrogen;

or an isotopologue or pharmaceutically acceptable salt thereof.

8. The compound of claim 4, wherein
a is 3;
b is 0, alternatively b is 2 and each $R^0$ is 5-fluoro;
$R^1$ is selected from the group consisting of cyclopentyl and 4-chlorophenyl;
$R^2$ is selected from the group consisting of hydrogen and methyl;
$R^3$ is hydrogen;
$R^4$ is hydrogen;
$R^5$ is selected from the group consisting of hydrogen, fluoro, methyl and trifluoromethyl;
provided that at least one of $R^2$ or $R^5$ is other than hydrogen;
$R^6$ is hydrogen;
or an isotopologue or pharmaceutically acceptable salt thereof.

9. The compound of claim 4, wherein
a is an integer from 1 to 2;
b is an integer from 0 to 2;
each $R^0$ is independently selected from the group consisting of 4-fluoro, 5-fluoro and 5-methyl;
$R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, cyclobutyl, 1-fluoro-cyclobut-1-yl, cyclopentyl, cyclopentyl-methyl-, cyclohexyl, cyclohexyl-methyl-, bicyclo[3.1.0]hex-2-yl, (1S,4S)-2-methyl-bicyclo[2.2.21]hept-2-yl, cyclopenten-3-yl, cyclohex-1-en-1-yl, 4,4-difluoro-cyclohex-1-yl, 4-fluorophenyl, 4-chlorophenyl, 4-bromophenyl, 2-fluoro-5-chloro-phenyl, 2-fluoro-5-methyl-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, thiazol-2-yl-methyl- and tetrahydro-pyran-4-yl;

$R^2$ is selected from the group consisting of hydrogen, fluoro and methyl;

$R^3$ is selected from the group consisting of hydrogen and fluoro;

$R^4$ is selected from the group consisting of hydrogen and chloro;

$R^5$ is selected from the group consisting of hydrogen, fluoro, chloro, bromo, methyl, ethyl, isopropyl, trifluoromethyl, 1,1,2,2,2-pentafluorethyl, methoxy, vinyl, ethynyl and cyclopropyl;

$R^6$ is hydrogen;

or an isotopologue or pharmaceutically acceptable salt thereof.

10. The compound of claim 4, wherein
a is an integer from 1 to 2;
b is an integer from 0 and 2;
the two $R^0$ groups are the same and are selected from the group consisting of 4-fluoro and 5-fluoro;
$R^1$ is selected from the group consisting of n-propyl, isopropyl, 1-methyl-n-propyl, 2,2-dimethyl-n-propyl, n-butyl, isobutyl, 3-methyl-n-butyl, n-pent-3-yl, cyclobutyl, 1-fluoro-cyclobut-1-yl, cyclopentyl, cyclopentyl-methyl-, cyclohexyl-methyl-, bicyclo[3.1.0]hex-2-yl, (1S,4S)-2-methyl-bicyclo[2.2.21]hept-2-yl, cyclopenten-3-yl, 4,4-difluoro-cyclohex-1-yl, 4-chlorophenyl, 2-fluoro-5-chloro-phenyl, benzyl, 2-fluoro-benzyl, 3-fluoro-benzyl, 4-fluoro-benzyl, 4-chloro-benzyl, 3-methyl-benzyl, 4-methyl-benzyl, phenyl-ethyl-, thiazol-2-yl-methyl- and tetrahydro-pyran-4-yl;

$R^2$ is selected from the group consisting of hydrogen, fluoro and methyl;

$R^3$ is selected from the group consisting of hydrogen and fluoro;
$R^4$ is selected from the group consisting of hydrogen and chloro;
$R^5$ is selected from the group consisting of hydrogen, fluoro, chloro, bromo, methyl, ethyl, isopropyl, trifluoromethyl, methoxy, vinyl and cyclopropyl;
$R^6$ is hydrogen;
or an isotopologue or pharmaceutically acceptable salt thereof.

11. The compound of claim 4, wherein
a is an integer from 1 to 2;
b is 0; alternatively b is 2 and each $R^0$ is 4-fluoro;
$R^1$ is selected from the group consisting of n-propyl, isopropyl, 1-methyl-n-propyl, 2,2-dimethyl-n-propyl, isobutyl, n-pent-3-yl, cyclobutyl, 1-fluoro-cyclobut-1-yl, cyclopentyl, cyclopentyl-methyl-, cyclohexyl-methyl-, bicyclo[3.1.0]hex-2-yl, (1S,4S)-2-methyl-bicyclo[2.2.21]hept-2-yl, cyclopenten-3-yl, 4,4-difluoro-cyclohex-1-yl, benzyl, 4-fluoro-benzyl, 4-chloro-benzyl and 4-methyl-benzyl;
$R^2$ is selected from the group consisting of hydrogen and methyl;
$R^3$ is hydrogen;
$R^4$ is hydrogen;
$R^5$ is selected from the group consisting of fluoro, chloro, bromo, methyl, ethyl, trifluoromethyl, methoxy and vinyl;
$R^6$ is hydrogen;
or an isotopologue or pharmaceutically acceptable salt thereof.

12. The compound of claim 4, wherein
a is an integer from 1 to 2;
b is 0; alternatively b is 2 and each $R^0$ is 4-fluoro;
$R^1$ is selected from the group consisting of isopropyl, isobutyl, cyclobutyl, cyclopentyl, cyclopentyl-methyl-, bicyclo[3.1.0]hex-2-yl, (1S,4S)-2-methyl-bicyclo[2.2.21]hept-2-yl, cyclopenten-3-yl and 4-fluoro-benzyl;
$R^2$ is selected from the group consisting of hydrogen and methyl;
$R^3$ is hydrogen;
$R^4$ is hydrogen;
$R^5$ is selected from the group consisting of fluoro, chloro, bromo, methyl, trifluoromethyl and vinyl;
$R^6$ is hydrogen;
or an isotopologue or pharmaceutically acceptable salt thereof.

13. The compound of claim 4, wherein
a is an integer from 1 to 3;
b is an integer from 0 to 2;
each $R^0$ is independently selected from the group consisting of 4-fluoro, 5-fluoro, 4-chloro, 3-methyl, 5-methyl, 5-ethyl, 5-isopropyl, 5-trifluoromethyl, 4-methoxy, 5-methoxy and 4-cyano;
$R^1$ is selected from the group consisting of isopropyl, n-butyl, cyclobutyl, cyclopentyl, cyclopentyl-methyl-, bicyclo[3.1.0]hex-2-yl, cyclopenten-3-yl, phenyl, 2-fluorophenyl, 3-fluorophenyl, 4-fluorophenyl, 2-chlorophenyl, 3-chlorophenyl, 4-chlorophenyl, 4-bromophenyl, 4-iodophenyl, 4-methylphenyl, 4-ethylphenyl, 4-trifluoromethyl-phenyl, 4-methoxyphenyl, 2,4-difluorophenyl, 3,4-difluorophenyl, 3,4-dichlorophenyl, 2-fluoro-4-chloro-phenyl, 2-fluoro-4-methyl-phenyl, 2-fluoro-5-methyl-phenyl, 3-fluoro-4-chloro-phenyl, 3-fluoro-4-methyl-phenyl, 3-amino-4-methyl-phenyl, 4-dimethylamino-phenyl, 4-(methyl-thio)-phenyl, benzyl, 6-chloro-pyrid-3-yl, 6-methyl-pyrid-3-yl, 6-methoxy-pyrid-3-yl, 5-fluoro-6-methoxy-pyrid-3-yl, furan-2-yl, 5-methyl-furan-2-yl, thien-2-yl, 5-chloro-thien-2-yl, 5-cyano-thien-2-yl, 5-methyl-thien-2-yl, thiazol-2-yl, thiazol-5-yl, 2-methyl-thiazol-5-yl, and 3,6-dihydro-pyran-4-yl;
$R^2$ is selected from the group consisting of hydrogen, fluoro, chloro, bromo, iodo and methyl;
$R^3$ is selected from the group consisting of hydrogen, fluoro, chloro and bromo;
$R^4$ is selected from the group consisting of hydrogen, fluoro, and chloro;
$R^5$ is selected from the group consisting of hydrogen, fluoro, chloro, bromo, methyl, ethyl, isopropyl, trifluoromethyl, methoxy, vinyl, and cyclopropyl;
alternatively, $R^2$ and $R^5$ are taken together with the carbon atoms to which they are bound to form cyclopenten-1-yl;
$R^6$ is selected from the group consisting of hydrogen and methyl;
or an isotopologue or pharmaceutically acceptable salt thereof.

14. The compound of claim 4, wherein
a is an integer from 1 to 3;
b is an integer from 0 to 2;
each $R^0$ is independently selected from the group consisting of 4-fluoro, 5-fluoro, 4-chloro, 5-methyl, 5-ethyl, 4-methoxy and 5-methoxy;
$R^1$ is selected from the group consisting of cyclopentyl, cyclopentyl-methyl-cyclopenten-3-yl, phenyl, 2-fluorophenyl, 3-fluorophenyl, 4-fluorophenyl, 3-chlorophenyl, 4-chlorophenyl, 4-bromophenyl, 4-iodophenyl, 4-methylphenyl, 4-ethylphenyl, 2,4-difluorophenyl, 3,4-difluorophenyl, 2-fluoro-4-methyl-phenyl, 3-fluoro-4-chloro-phenyl, 3-fluoro-4-methyl-phenyl, 4-dimethylamino-phenyl, 4-(methyl-thio)-phenyl, benzyl, 6-chloro-pyrid-3-yl, 6-methoxy-pyrid-3-yl, 5-fluoro-6-methoxy-pyrid-3-yl, furan-2-yl, thien-2-yl, 5-chloro-thien-2-yl, 5-methyl-thien-2-yl and 2-methyl-thiazol-5-yl;
$R^2$ is selected from the group consisting of hydrogen, fluoro, chloro, bromo, iodo and methyl;
$R^3$ is selected from the group consisting of hydrogen, fluoro and bromo;
$R^4$ is hydrogen;
$R^5$ is selected from the group consisting of hydrogen, fluoro, chloro, bromo, methyl, trifluoromethyl and methoxy;
alternatively, $R^2$ and $R^5$ are taken together with the carbon atoms to which they are bound to form cyclopenten-1-yl;
$R^6$ is selected from the group consisting of hydrogen and methyl;
or an isotopologue or pharmaceutically acceptable salt thereof.

15. The compound of claim 4, wherein
a is an integer from 1 to 2;
b is an integer from 0 to 2;
each $R^0$ is independently selected from the group consisting of 4-fluoro, 5-fluoro and 4-methoxy;
$R^1$ is selected from the group consisting of cyclopentyl, phenyl, 2-fluorophenyl, 3-fluorophenyl, 4-fluorophenyl, 4-chlorophenyl, 4-bromophenyl, 4-iodophenyl, 4-methylphenyl, 4-ethylphenyl, 2,4-difluorophenyl, 3,4-difluorophenyl, 3-fluoro-4-chloro-phenyl, 3-fluoro- 4-methyl-phenyl, 6-methoxy-pyrid-3-yl, 5-fluoro-6-methoxy-pyrid-3-yl, thien-2-yl, 5-chloro-thien-2-yl and 5-methyl-thien-2-yl;

$R^2$ is selected from the group consisting of hydrogen, fluoro, chloro, bromo, iodo and methyl;

$R^3$ is selected from the group consisting of hydrogen, fluoro and bromo;

$R^4$ is hydrogen;

$R^5$ is selected from the group consisting of hydrogen, fluoro, chloro and methyl;

alternatively, $R^2$ and $R^5$ are taken together with the carbon atoms to which they are bound to form cyclopenten-1-yl;

$R^6$ is hydrogen;

or an isotopologue or pharmaceutically acceptable salt thereof.

16. The compound of claim 4, wherein a is an integer from 1 to 2;

b is an integer from 0 to 2;

each $R^0$ is independently selected from the group consisting of 4-fluoro and 5-fluoro;

$R^1$ is selected from the group consisting of cyclopentyl, phenyl, 3-fluorophenyl, 4-fluorophenyl, 4-chlorophenyl, 4-bromophenyl, 4-iodophenyl, 4-methylphenyl, 4-ethylphenyl, 2,4-difluorophenyl, 3,4-difluorophenyl, 3-fluoro-4-chloro-phenyl and 3-fluoro-4-methyl-phenyl;

$R^2$ is selected from the group consisting of hydrogen, fluoro, chloro, bromo, iodo and methyl;

$R^3$ is selected from the group consisting of hydrogen and fluoro;

$R^4$ is hydrogen;

$R^5$ is selected from the group consisting of hydrogen, fluoro, chloro and methyl;

alternatively, $R^2$ and $R^5$ are taken together with the carbon atoms to which they are bound to form cyclopenten-1-yl;

$R^6$ is hydrogen;

or an isotopologue or pharmaceutically acceptable salt thereof.

17. The compound of claim 4, selected from the group consisting of 3-(4-{[2-(4-Ethylphenyl)cyclopent-1-en-1-yl]methoxy}-2,3-dimethylphenyl)propanoic acid;

3-(2,3-Dimethyl-4-{[2-(4-methylphenyl)cyclopent-1-en-1-yl]methoxy}phenyl)propanoic acid;

3-(4-{[2-(3-Fluoro-4-methylphenyl)cyclopent-1-en-1-yl]methoxy}-2,3-dimethylphenyl)propanoic acid;

3-(4-{[2-(4-Chlorophenyl)cyclopent-1-en-1-yl]methoxy}-3-methylphenyl)propanoic acid;

3-(4-{[2-(4-Chlorophenyl)cyclohex-1-en-1-yl]methoxy}-3-methylphenyl)propanoic acid;

3-(2,3-Dimethyl-4-{[2-(6-methylpyridin-3-yl)cyclopent-1-en-1-yl]methoxy}phenyl)propanoic acid;

3-(4-{[2-(4-Chlorophenyl)-5,5-difluorocyclohex-1-en-1-yl]methoxy}-2,3-dimethylphenyl)propanoic acid;

3-[4-{[2-(4-Chlorophenyl)cyclopent-1-en-1-yl]methoxy}-2-(trifluoromethyl)phenyl]propanoic acid;

3-(4-{[4,4-Difluoro-2-(4-fluorophenyl)cyclopent-1-en-1-yl]methoxy}-2,3-dimethylphenyl)propanoic acid;

3-(4-{[2-(4-Chlorophenyl)-4,4-difluorocyclopent-1-en-1-yl]methoxy}-2,3-dimethylphenyl)propanoic acid;

and pharmaceutically acceptable salts thereof.

18. The compound of claim 4, selected from the group consisting of

3-[4-{[2-(4-Chlorophenyl)cyclopent-1-en-1-yl]methoxy}-2-(trifluoromethyl)phenyl]propanoic acid;

3-(4-([1,1'-bi(cyclopentan)]-1-en-2-ylmethoxy)-2-(trifluoromethyl)phenyl)propanoic acid;

3-(4-([1,1'-bi(cyclopentane)]-1,2'-dien-2-ylmethoxy)-2-chlorophenyl)propanoic acid;

3-(4-((4,4-difluoro-[1,1'-bi(cyclopentan)]-1-en-2-yl)methoxy)-2-(trifluoromethyl)phenyl)propanoic acid;

3-(2-chloro-4-((4,4-difluoro-[1,1'-bi(cyclopentan)]-1-en-2-yl)methoxy)phenyl)propanoic acid;

3-(4-((4,4-difluoro-[1,1'-bi(cyclopentan)]-1-en-2-yl)methoxy)-2-methylphenyl)propanoic acid;

3-(4-((2-cyclobutylcyclopent-1-en-1-yl)methoxy)-2-(trifluoromethyl)phenyl)propanoic acid;

and pharmaceutically acceptable salts thereof.

19. A pharmaceutical composition comprising a pharmaceutically acceptable carrier and a compound of claim 1.

20. A method of treating a disorder which (a) is modulated by the GPR120 receptor, (b) is modulated by the GPR40 receptor, or (c) responds to dual agonism of the GPR120 and GPR40 receptors comprising administering to a subject in need thereof a therapeutically effective amount of the compound of claim 1.

21. The method of claim 20, wherein the disorder is selected from the group consisting of obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia, non-alcoholic steatohepatitis (NASH), non-alcoholic fatty liver disease (NAFLD), liver fibrosis and cardiovascular disorders.

22. The method of claim 20, wherein the disorder is selected from the group consisting of obesity, impaired glucose tolerance, elevated fasting glucose, insulin resistance, hyperglycemia, hyperinsulinemia, Type II Diabetes Mellitus, metabolic syndrome (also known as Syndrome X), diabetic retinopathy, diabetic nephropathy, dyslipidemia, elevated LDL, hyperlipidemia, hypertriglyceridemia, non-alcoholic steatohepatitis (NASH) and non-alcoholic fatty liver disease (NAFLD).

23. The method of claim 20, wherein the disorder is selected from the group consisting of obesity, Type II diabetes, metabolic syndrome (also known as Syndrome X), dyslipidemia, hypertriglyceridemia (i.e. elevated triglycerides), non-alcoholic steatohepatitis (NASH) and non-alcoholic fatty liver disease (NAFLD).

24. The method of claim 20, wherein the disorder is selected from the group consisting of obesity, Type II diabetes, metabolic syndrome (also known as Syndrome X), dyslipidemia and hypertriglyceridemia.

25. A method of treating a disorder selected from the group consisting of obesity, obesity induced inflammation, impaired glucose tolerance, elevated fasting glucose, insulin resistance, hyperglycemia, hyperinsulinemia, Type II Diabetes Mellitus, metabolic syndrome (also known as Syndrome X), gestational diabetes, diabetic retinopathy, kidney disease, ketoacidosis, diabetic nephropathy, dyslipidemia, elevated LDL, hyperlipidemia, hyperlipoproteinemia, hypertriglyceridemia, non-alcoholic steatohepatitis (NASH), non-alcoholic fatty liver disease (NAFLD), liver fibrosis and cardiovascular disorders comprising administering to a subject in need thereof a therapeutically effective amount of the compound of claim 1.

* * * * *